US012522587B2

(12) United States Patent
Crimmins et al.

(10) Patent No.: US 12,522,587 B2
(45) Date of Patent: Jan. 13, 2026

(54) CANCER TREATMENTS TARGETING CANCER STEM CELLS

(71) Applicant: Remedy Plan, Inc., Gaithersburg, MD (US)

(72) Inventors: Gregory Thomas Crimmins, Washington, DC (US); Dennise Alexandra De Jesús Diaz, Washington, DC (US); Yushma Bhurruth-Alcor, Ashburn, VA (US)

(73) Assignee: Remedy Plan, Inc., Gaithersburg, MD (US)

( * ) Notice: Subject to any disclaimer, the term of this patent is extended or adjusted under 35 U.S.C. 154(b) by 1058 days.

(21) Appl. No.: 17/052,775

(22) PCT Filed: May 3, 2019

(86) PCT No.: PCT/US2019/030664
§ 371 (c)(1),
(2) Date: Nov. 3, 2020

(87) PCT Pub. No.: WO2019/213570
PCT Pub. Date: Nov. 7, 2019

(65) Prior Publication Data

US 2022/0324842 A1 Oct. 13, 2022

Related U.S. Application Data

(60) Provisional application No. 62/815,251, filed on Mar. 7, 2019, provisional application No. 62/667,412, filed on May 4, 2018.

(51) Int. Cl.
*A01N 37/00* (2006.01)
*A01N 25/00* (2006.01)
(Continued)

(52) U.S. Cl.
CPC ............ *C07D 403/12* (2013.01); *A61K 45/06* (2013.01); *C07D 209/08* (2013.01); (Continued)

(58) Field of Classification Search
CPC ............................ C07D 401/12; C07D 403/12
See application file for complete search history.

(56) References Cited

U.S. PATENT DOCUMENTS 4,278,681 A 7/1981 Haskell et al.
4,315,014 A 2/1982 Mich et al.
(Continued)

FOREIGN PATENT DOCUMENTS

CN 108314677 B 6/2020
EP 0015771 A1 9/1980
(Continued)

OTHER PUBLICATIONS

Golub et al. Science, vol. 286, 1999, pp. 531-537.*
(Continued)

*Primary Examiner* — Layla Soroush
(74) *Attorney, Agent, or Firm* — Wolf, Greenfield & Sacks, P.C.

(57) ABSTRACT

Disclosed are compounds, methods, compositions, and kits that allow for treating cancer by, e.g., targeting cancer stem cells. In some embodiments, the cancer is colorectal cancer, gastric cancer, gastrointestinal stromal tumor, ovarian cancer, lung cancer, breast cancer, pancreatic cancer, prostate cancer, testicular cancer, or lymphoma. In some embodiments, the cancer is liver cancer, endometrial cancer, leukemia, or multiple myeloma. The compounds utilized in the disclosure are of Formula (0), (O'), and (I):

(0)

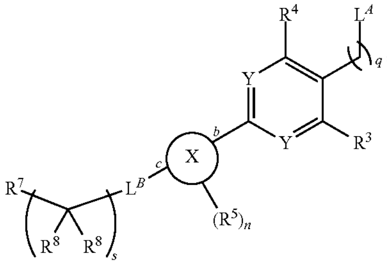

(0')

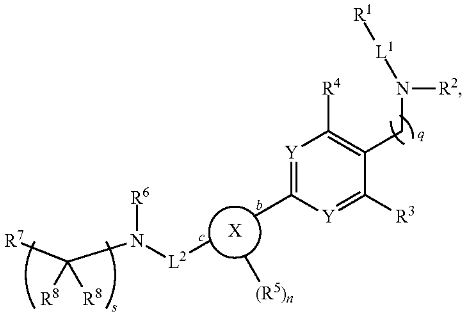

and (I)

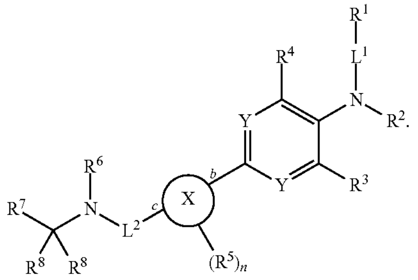

25 Claims, 4 Drawing Sheets

(51) Int. Cl.

| | |
|---|---|
| ***A01N 37/12*** | (2006.01) |
| ***A01N 37/44*** | (2006.01) |
| ***A61K 31/215*** | (2006.01) |
| ***A61K 31/24*** | (2006.01) |
| ***A61K 45/06*** | (2006.01) |
| ***C07D 209/08*** | (2006.01) |
| ***C07D 213/56*** | (2006.01) |
| ***C07D 401/12*** | (2006.01) |
| ***C07D 401/14*** | (2006.01) |
| ***C07D 403/12*** | (2006.01) |
| ***C07D 405/12*** | (2006.01) |
| ***C07D 413/14*** | (2006.01) |
| ***C07D 487/04*** | (2006.01) |

(52) U.S. Cl.
CPC ......... *C07D 213/56* (2013.01); *C07D 401/12* (2013.01); *C07D 401/14* (2013.01); *C07D 405/12* (2013.01); *C07D 413/14* (2013.01); *C07D 487/04* (2013.01)

(56) References Cited

U.S. PATENT DOCUMENTS

| | | | |
|---|---|---|---|
| 4,315,858 A | 2/1982 | Doub et al. | |
| 8,461,342 B2 | 6/2013 | Siesel | |
| 8,524,767 B2 | 9/2013 | Miller et al. | |
| 2009/0131640 A1 | 5/2009 | Berkelman | |
| 2009/0233934 A1 | 9/2009 | Oda et al. | |
| 2010/0222319 A1 | 9/2010 | Bernhart et al. | |
| 2015/0231142 A1 | 8/2015 | Van Goor et al. | |
| 2018/0370909 A1* | 12/2018 | Buchwald | C07C 237/42 |
| 2023/0023124 A1 | 1/2023 | Bhurruth-Alcor et al. | |
| 2024/0376074 A1 | 11/2024 | Bhurruth-Alcor et al. | |

FOREIGN PATENT DOCUMENTS

| | | | |
|---|---|---|---|
| EP | 0015773 A2 | 9/1980 | |
| EP | 0706795 A2 | 4/1996 | |
| EP | 2589292 A1 | 5/2013 | |
| FR | 2904827 B1 | 9/2008 | |
| FR | 2921657 A1 | 4/2009 | |
| GB | 2273930 A * | 7/1994 | C07D 213/40 |
| JP | S56-115784 A | 9/1981 | |
| JP | H02-127429 A | 5/1990 | |
| JP | H02-127512 A | 5/1990 | |
| JP | H10-152462 A | 6/1998 | |
| JP | H11-302173 A | 11/1999 | |
| JP | 2000-256194 A | 9/2000 | |
| JP | 2008-510726 A | 4/2008 | |
| JP | 2013-530199 A | 7/2013 | |
| JP | 2014-518223 A | 7/2014 | |
| JP | 5799117 B2 | 10/2015 | |
| JP | 2017-516774 A | 6/2017 | |
| JP | 2019-512503 A | 5/2019 | |
| KR | 102210267 B1 | 2/2021 | |
| WO | WO 97/48397 A1 | 12/1997 | |
| WO | WO 97/48696 A1 | 12/1997 | |
| WO | WO 2001/011965 A1 | 2/2001 | |
| WO | WO 02/060875 A1 | 8/2002 | |
| WO | WO 2003/003008 A1 | 1/2003 | |
| WO | WO 2003/003009 A1 | 1/2003 | |
| WO | WO 2003/055477 A1 | 7/2003 | |
| WO | WO 2003/059913 A1 | 7/2003 | |
| WO | WO 03/80054 A1 | 10/2003 | |
| WO | WO 2004/058234 A2 | 7/2004 | |
| WO | WO 2005/012299 A1 | 2/2005 | |
| WO | WO 2006/023844 A2 | 3/2006 | |
| WO | WO 2006/028958 A2 | 3/2006 | |
| WO | WO 2006/067445 A2 | 6/2006 | |
| WO | WO 2006/067446 A1 | 6/2006 | |
| WO | WO 2006/130403 A1 | 12/2006 | |
| WO | WO 2007/024922 A1 | 3/2007 | |
| WO | WO 2007/062028 A2 | 5/2007 | |
| WO | WO 2007/072999 A1 | 6/2007 | |
| WO | WO 2007/076055 A2 | 7/2007 | |
| WO | WO 2007/125331 A2 | 11/2007 | |
| WO | WO 2008/016643 A2 | 2/2008 | |
| WO | WO 2008/024963 A1 | 2/2008 | |
| WO | WO 2008/025857 A2 | 3/2008 | |
| WO | WO 2009/053694 A1 | 4/2009 | |
| WO | WO 2009/076142 A2 | 6/2009 | |
| WO | WO 2009/109610 A1 | 9/2009 | |
| WO | WO 2009/126863 A2 | 10/2009 | |
| WO | WO 2012/006475 A1 | 1/2012 | |
| WO | WO 2012/014994 A1 | 2/2012 | |
| WO | WO 2012/024179 A1 | 2/2012 | |
| WO | WO 2012/031197 A1 | 3/2012 | |
| WO | WO 2012/043891 A1 | 4/2012 | |
| WO | WO 2012/054110 A2 | 4/2012 | |
| WO | WO 2012/143415 A1 | 10/2012 | |
| WO | WO 2012/156919 A1 | 11/2012 | |
| WO | WO 2012/158784 A2 | 11/2012 | |
| WO | WO 2013/028445 A1 | 2/2013 | |
| WO | WO 2013/064460 A1 | 5/2013 | |
| WO | WO 2013/083991 A1 | 6/2013 | |
| WO | WO 2014/008214 A1 | 1/2014 | |
| WO | WO 2014/081299 A1 | 5/2014 | |
| WO | WO 2014/081300 A1 | 5/2014 | |
| WO | WO 2014/081301 A1 | 5/2014 | |
| WO | WO 2014/081303 A1 | 5/2014 | |
| WO | WO 2014/145642 A2 | 9/2014 | |
| WO | WO 2014/145873 A2 | 9/2014 | |
| WO | WO 2014/203217 A1 | 12/2014 | |
| WO | WO 2015/040424 A1 | 3/2015 | |
| WO | WO 2015/117053 A1 | 8/2015 | |
| WO | WO 2015/154820 A1 | 10/2015 | |
| WO | WO 2017/009650 A1 | 1/2017 | |
| WO | WO 2017/141036 A1 | 8/2017 | |
| WO | WO 2017/150209 A1 | 9/2017 | |
| WO | WO 2018/075842 A1 | 4/2018 | |
| WO | WO 2018/101424 A1 | 6/2018 | |
| WO | WO 2018/133795 A1 | 7/2018 | |
| WO | WO 2018/190352 A1 | 10/2018 | |
| WO | WO 2018/216640 A1 | 11/2018 | |
| WO | WO 2019/148125 A1 | 8/2019 | |
| WO | WO 2019/213570 A1 | 11/2019 | |
| WO | WO 2020/054712 A1 | 3/2020 | |
| WO | WO 2021/092322 A1 | 5/2021 | |
| WO | WO 2022/050286 A1 | 3/2022 | |

OTHER PUBLICATIONS

Extended European Search Report, mailed Oct. 19, 2021, in connection with Application No. 19796696.3

International Search Report and Written Opinion, mailed Feb. 11, 2021, in connection with Application No. PCT/US2020/059329.

Asciutti et al., Diverse mechanisms of Wnt activation and effects of pathway inhibition on proliferation of human gastric carcinoma cells. Oncogene. Feb. 24, 2011;30(8):956-66. doi: 10.1038/onc.2010.475. Epub Nov. 1, 2010.

Ben-Porath et al., An embryonic stem cell-like gene expression signature in poorly differentiated aggressive human tumors. Nat Genet. May 2008;40(5):499-507. doi: 10.1038/ng.127.

Bonnet et al., Human acute myeloid leukemia is organized as a hierarchy that originates from a primitive hematopoietic cell. Nat Med. Jul. 1997;3(7):730-7. doi: 10.1038/nm0797-730.

Chen et al., A restricted cell population propagates glioblastoma growth after chemotherapy. Nature. Aug. 23, 2012;488(7412):522-6. doi: 10.1038/nature11287.

Galli et al., Recent Advances in NAMPT Inhibitors: A Novel Immunotherapic Strategy. Front Pharmacol. May 12, 2020;11:656. doi: 10.3389/fphar.2020.00656. 20 pages.

Guinney et al., The consensus molecular subtypes of colorectal cancer. Nat Med. Nov. 2015;21(11):1350-6. doi: 10.1038/nm.3967. Epub Oct. 12, 2015.

Laranjeira et al., Therapeutic target discovery and drug development in cancer stem cells for leukemia and lymphoma: from bench to the clinic. Expert Opin Drug Discov. Nov. 2016;11(11):1071-1080. doi: 10.1080/17460441.2016.1236785. Epub Sep. 25, 2016.

(56) References Cited

OTHER PUBLICATIONS

Saunders et al., A DLL3-targeted antibody-drug conjugate eradicates high-grade pulmonary neuroendocrine tumor-initiating cells in vivo. Sci Transl Med. Aug. 26, 2015;7(302):302ra136. doi: 10.1126/scitranslmed.aac9459.
Invitation to Pay Additional Fees, mailed Jun. 13, 2019, in connection with Application No. PCT/US2019/030664
International Search Report and Written Opinion, mailed Aug. 19, 2019, in connection with Application No. PCT/US2019/030664.
International Preliminary Report on Patentability, mailed Nov. 19, 2020, in connection with Application No. PCT/US2019/030664.
U.S. Appl. No. 18/560,228, filed Nov. 10, 2023, Bhurruth-Alcor et al.
PCT/US2020/059329, May 19, 2022, International Preliminary Report on Patentability.
PCT/US2022/029259, Aug. 1, 2022, International Search Report and Written Opinion.
PCT/US2022/029259, Nov. 23, 2023, International Preliminary Report on Patentability.
International Preliminary Report on Patentability, mailed May 19, 2022, in connection with Application No. PCT/US2020/059329.
International Search Report and Written Opinion, mailed Aug. 1, 2022, in connection with Application No. PCT/US2022/029259.
International Preliminary Report on Patentability, mailed Nov. 23, 2023, in connection with Application No. PCT/US2022/029259.
Audrito et al., NAMPT and NAPRT: Two Metabolic Enzymes With Key Roles in Inflammation. Front Oncol. Mar. 19, 2020;10:358. doi: 10.3389/fonc.2020.00358.
Benito-Martin et al., Endogenous NAMPT dampens chemokine expression and apoptotic responses in stressed tubular cells. Biochim Biophys Acta. Feb. 2014;1842(2):293-303. doi: 10.1016/j.bbadis.2013.11.022. Epub Nov. 25, 2013.
Bermudez et al., Leukocyte Overexpression of Intracellular NAMPT Attenuates Atherosclerosis by Regulating PPAR ?-Dependent Monocyte Differentiation and Function. Arterioscler Thromb Vasc Biol. Jun. 2017;37(6):1157-1167. doi: 10.1161/ATVBAHA.116.308187. Epub Apr. 13, 2017.
Busso et al., Pharmacological inhibition of nicotinamide phosphoribosyltransferase/visfatin enzymatic activity identifies a new inflammatory pathway linked to NAD. PLoS One. May 21, 2008;3(5):e2267. doi: 10.1371/journal.pone.0002267.
Chen et al., Endogenous Nampt upregulation is associated with diabetic nephropathy inflammatory-fibrosis through the NF-?B p65 and Sirtl pathway; NMN alleviates diabetic nephropathy inflammatory-fibrosis by inhibiting endogenous Nampt. Exp Ther Med. Nov. 2017;14(5):4181-4193. doi: 10.3892/etm.2017.5098. Epub Sep. 1, 2017.
Chen et al., NAMPT inhibitor protects ischemic neuronal injury in rat brain via anti-neuroinflammation. Neuroscience. Jul. 25, 2017;356:193-206. doi: 10.1016/j.neuroscience.2017.05.022. Epub May 19, 2017.
Colombo et al., Neutralization of extracellular NAMPT (nicotinamide phosphoribosyltransferase) ameliorates experimental murine colitis. J Mol Med (Berl). Apr. 2020;98(4):595-612. doi: 10.1007/s00109-020-01892-0. Epub Apr. 27, 2020.
Esposito et al., The NAMPT inhibitor FK866 reverts the damage in spinal cord injury. J Neuroinflammation. Apr. 10, 2012;9:66. doi: 10.1186/1742-2094-9-66.
Evans et al., Suppression of leukocyte infiltration and cartilage degradation by selective inhibition of pre-B cell colony-enhancing factor/visfatin/nicotinamide phosphoribosyltransferase: Apo866-mediated therapy in human fibroblasts and murine collagen-induced arthritis. Arthritis Rheum. Jul. 2011;63(7):1866-77. doi: 10.1002/art.30338.
Gerner et al., NAD metabolism fuels human and mouse intestinal inflammation. Gut. Oct. 2018;67(10):1813-1823. doi: 10.1136/gutjnl-2017-314241. Epub Sep. 6, 2017.
Gerner et al., Targeting NAD immunometabolism limits severe graft-versus-host disease and has potent antileukemic activity. Leukemia. Jul. 2020;34(7):1885-1897. doi: 10.1038/s41375-020-0709-0. Epub Jan. 23, 2020.
Hadjimichael et al., Common stemness regulators of embryonic and cancer stem cells. World J Stem Cells. Oct. 26, 2015;7(9):1150-84. doi: 10.4252/wjsc.v7.i9.1150.
Kim et al., NAMPT Is an Essential Regulator of RA-Mediated Periodontal Inflammation. J Dent Res. Jun. 2017;96(6):703-711. doi: 10.1177/0022034517690389. Epub Feb. 6, 2017.
Le et al., Inhibition of lactate dehydrogenase A induces oxidative stress and inhibits tumor progression. Proc Natl Acad Sci U S A. Feb. 2, 2010;107(5):2037-42. doi: 10.1073/pnas.0914433107. Epub Jan. 19, 2010.
Li et al., Epigenetic regulation of NfatC1 transcription and osteoclastogenesis by nicotinamide phosphoribosyl transferase in the pathogenesis of arthritis. Cell Death Discov. Feb. 6, 2019;5:62. doi: 10.1038/s41420-018-0134-6.
Moreno-Vinasco et al., Nicotinamide phosphoribosyltransferase inhibitor is a novel therapeutic candidate in murine models of inflammatory lung injury. Am J Respir Cell Mol Biol. Aug. 2014;51(2):223-8. doi: 10.1165/rcmb.2012-0519OC.
Moschen et al., A key role for Pre-B cell colony-enhancing factor in experimental hepatitis. Hepatology. Aug. 2011;54(2):675-86. doi: 10.1002/hep.24416. Epub Jun. 26, 2011.
Moschen et al., Visfatin, an adipocytokine with proinflammatory and immunomodulating properties. J Immunol. Feb. 1, 2007;178(3):1748-58. doi: 10.4049/jimmunol.178.3.1748.
O'Brien et al., A human colon cancer cell capable of initiating tumour growth in immunodeficient mice. Nature. Jan. 4, 2007;445(7123):106-10. doi: 10.1038/nature05372. Epub Nov. 19, 2006.
Romacho et al., Extracellular PBEF/NAMPT/visfatin activates pro-inflammatory signalling in human vascular smooth muscle cells through nicotinamide phosphoribosyltransferase activity. Diabetologia. Nov. 2009;52(11):2455-2463. doi: 10.1007/s00125-009-1509-2. Epub Aug. 29, 2009.
Roulsten et al., New strategies to maximize therapeutic opportunities for NAMPT inhibitors in oncology. Mol Cell Oncol. Jun. 10, 2015;3(1):e1052180. doi: 10.1080/23723556.2015.1052180.
Seyfried et al., On the origin of cancer metastasis. Crit Rev Oncog. 2013;18(1-2):43-73. doi: 10.1615/critrevoncog.v18.il-2.40.
Singh et al., Small Molecule Inhibitor of NRF2 Selectively Intervenes Therapeutic Resistance in KEAP1-Deficient NSCLC Tumors. ACS Chem Biol. Nov. 18, 2016;11(11):3214-3225. doi: 10.1021/acschembio.6b00651. Epub Oct. 17, 2016.
Stromsdorfer et al., NAMPT-Mediated NAD(+) Biosynthesis in Adipocytes Regulates Adipose Tissue Function and Multi-organ Insulin Sensitivity in Mice. Cell Rep. Aug. 16, 2016;16(7):1851-60. doi: 10.1016/j.celrep.2016.07.027. Epub Aug. 4, 2016.
Taniguchi et al., Cancer stem cells in human gastrointestinal cancer. Cancer Sci. Nov. 2016;107(11):1556-1562. doi: 10.1111/cas.13069.
Travelli et al., Nicotinamide Phosphoribosyltransferase Acts as a Metabolic Gate for Mobilization of Myeloid-Derived Suppressor Cells. Cancer Res. Apr. 15, 2019;79(8):1938-1951. doi: 10.1158/0008-5472.CAN-18-1544. Epub Feb. 18, 2019.
Vallejo et al., Visfatin impairs endothelium-dependent relaxation in rat and human mesenteric microvessels through nicotinamide phosphoribosyltransferase activity. PLoS One. 2011;6(11):e27299. doi: 10.1371/journal.pone.0027299. Epub Nov. 3, 2011.
Wang et al., Nicotinamide phosphoribosyltransferase protects against ischemic stroke through SIRT1-dependent adenosine monophosphate-activated kinase pathway. Ann Neurol. Feb. 2011;69(2):360-74. doi: 10.1002/ana.22236. Epub Jan. 19, 2011.
Wu et al., Targeting of nicotinamide phosphoribosyltransferase enzymatic activity ameliorates lung damage induced by ischemia/reperfusion in rats. Respir Res. Apr. 24, 2017;18(1):71. doi: 10.1186/s12931-017-0557-2.
Yerxa et al., New Visions in Ophthalmic Drug Development. Drug Discovery World. Dec. 14, 2002. 18 pages. Retrieved from <https://www.ddw-online.com/new-visions-in-ophthalmic-drug-development-1091-200212/>.

(56) References Cited

OTHER PUBLICATIONS

Zhang et al., Visfatin is regulated by interleukin-6 and affected by the PPAR-γ pathway in BeWo cells. Mol Med Rep. Jan. 2019;19(1):400-406. doi: 10.3892/mmr.2018.9671. Epub Nov. 20, 2018.
Zheng et al., FK866 attenuates sepsis-induced acute lung injury through c-jun-N-terminal kinase (JNK)-dependent autophagy. Life Sci. Jun. 1, 2020;250:117551. doi: 10.1016/j.lfs.2020.117551. Epub Mar. 13, 2020.
[No Author Listed], Benzamide, 3-(1-acetyl-1,2,3,4-tetrahydro-6-quinolinyl)-N-(3-isoxazolylmethyl)-N-methyl-. CAS Registry File RN 2109509-83-1. STN Entry Date Aug. 7, 2017. 1 page.
[No Author Listed], Benzamide, 4-(1-acetyl-2,3-dihydro-1H-indol-5-yl)-N-(1-phenylethyl)-. CAS Registry File RN 1359334-09-0. STN Entry Date Mar. 2, 2012. 1 page.
[No Author Listed], Benzamide, 4-(1-acetyl-2,3-dihydro-1H-indol-5-yl)-N-(2-furanylmethyl)-. CAS Registry File RN 1358036-86-8. STN Entry Date Feb. 28, 2012. 1 page.
[No Author Listed], Benzamide, 4-(1-acetyl-2,3-dihydro-1H-indol-5-yl)-N-(2-thienylmethyl)-. CAS Registry File RN 1358948-71-6. STN Entry Date Mar. 1, 2012. 1 page.
[No Author Listed], Benzamide, 4-(1-acetyl-2,3-dihydro-1H-indol-5-yl)-N-[(1,3,5-trimethyl-1H-pyrazol-4-yl)methyl]-. CAS Registry File RN 1189708-01-7. STN Entry Date Oct. 23, 2009. 1 page.
[No Author Listed], Benzamide, 4-(1-acetyl-2,3-dihydro-1H-indol-5-yl)-N-[(5-methyl-2-furanyl)methyl]-. CAS Registry File RN 1358617-91-0. STN Entry Date Feb. 29, 2012. 1 page.
[No Author Listed], Benzamide, 4-[2,3-dihydro-1-(1-oxopropyl)-1H-indol-5-yl]-N-(2-thienylmethyl)-. CAS Registry File RN 1358617-23-8. STN Entry Date Feb. 29, 2012. 1 page.
[No Author Listed], Benzamide, 4-[2,3-dihydro-1-(1-oxopropyl)-1H-indol-5-yl]-N-[(1,3,5-trimethyl-1H-pyrazol-4-yl)methyl]-. CAS Registry File RN 1189881-08-0. STN Entry Date Oct. 25, 2009. 1 page.
[No Author Listed], Benzamide, 4-[2,3-dihydro-1-(1-oxopropyl)-1H-indol-5-yl]-N-[(5-methyl-2-furanyl)methyl]-. CAS Registry File RN 1358562-49-8. STN Entry Date Feb. 29, 2012. 1 page.
Brucoli et al., Efficient solid-phase synthesis of a library of distamycin analogs containing novel biaryl motifs on SynPhase Lanterns. J Comb Chem. Jul.-Aug. 2009;11(4):576-86. doi: 10.1021/cc900009r.
Honma et al., Antiallergic agents. 2. N-(1H-tetrazol-5-yl)-6-phenyl-2-pyridinecarboxamides. J Med Chem. Oct. 1983;26(10):1499-504. doi: 10.1021/jm00364a026.
Canadian Office Action, mailed Nov. 14, 2024, in connection with Application No. 3,135,740.
[No Author Listed], CAS Registry File RN 1359381-51-3. STN Entry Date Mar. 2, 2012.
[No Author Listed], CAS Registry File RN 1359381-43-3. STN Entry Date Mar. 2, 2012.
[No Author Listed], CAS Registry File RN 1359381-05-7. STN Entry Date Mar. 2, 2012.
[No Author Listed], CAS Registry File RN 1359369-01-9. STN Entry Date Mar. 2, 2012.
[No Author Listed], CAS Registry File RN 1359351-05-5. STN Entry Date Mar. 2, 2012.
[No Author Listed], CAS Registry File RN 1359202-70-2. STN Entry Date Mar. 1, 2012.
[No Author Listed], CAS Registry File RN 1358948-48-7. STN Entry Date Mar. 1, 2012.
[No Author Listed], CAS Registry File RN 1358948-13-6. STN Entry Date Mar. 1, 2012.
[No Author Listed], CAS Registry File RN 1358942-68-3. STN Entry Date Mar. 1, 2012.
[No Author Listed], CAS Registry File RN 1358931-36-8. STN Entry Date Mar. 1, 2012.
[No Author Listed], CAS Registry File RN 1358814-41-1. STN Entry Date Feb. 29, 2012.
[No Author Listed], CAS Registry File RN 1358814-23-9. STN Entry Date Feb. 29, 2012.
[No Author Listed], CAS Registry File RN 1358807-11-0. STN Entry Date Feb. 29, 2012.
[No Author Listed], CAS Registry File RN 1358668-90-2. STN Entry Date Feb. 29, 2012.
[No Author Listed], CAS Registry File RN 1358618-13-9. STN Entry Date Feb. 29, 2012.
[No Author Listed], CAS Registry File RN 1358617-31-8. STN Entry Date Feb. 29, 2012.
[No Author Listed], CAS Registry File RN 1358617-00-1. STN Entry Date Feb. 29, 2012.
[No Author Listed], CAS Registry File RN 1358481-23-8. STN Entry Date Feb. 29, 2012.
[No Author Listed], CAS Registry File RN 1358481-15-8. STN Entry Date Feb. 29, 2012.
[No Author Listed], CAS Registry File RN 1358480-80-4. STN Entry Date Feb. 29, 2012.
[No Author Listed], CAS Registry File RN 1358384-20-9. STN Entry Date Feb. 29, 2012.
[No Author Listed], CAS Registry File RN 1358384-07-2. STN Entry Date Feb. 29, 2012.
[No Author Listed], CAS Registry File RN 1358383-89-7. STN Entry Date Feb. 29, 2012.
[No Author Listed], CAS Registry File RN 1358383-49-9. STN Entry Date Feb. 29, 2012.
[No Author Listed], CAS Registry File RN 1358368-86-1. STN Entry Date Feb. 29, 2012.
[No Author Listed], CAS Registry File RN 1358302-05-2. STN Entry Date Feb. 29, 2012.
[No Author Listed], CAS Registry File RN 1358036-89-1. STN Entry Date Feb. 28, 2012.
[No Author Listed], CAS Registry File RN 1358036-74-4. STN Entry Date Feb. 28, 2012.
[No Author Listed], CAS Registry File RN 1358017-42-1. STN Entry Date Feb. 28, 2012.
[No Author Listed], CAS Registry File RN 1357757-07-3. STN Entry Date Feb. 28, 2012.
[No Author Listed], CAS Registry File RN 1357756-25-2. STN Entry Date Feb. 28, 2012.

* cited by examiner

Compound I-1 inhibited *nanog* expression

No drug (compound I-1) With drug (compound I-1)

Compound I-1 exhibited no toxicity to healthy hepatocytes

No drug (compound I-1) With drug (compound I-1)

| Compound I-1 | Result |
|---|---|
| Molecular Weight | 385.47 |
| ClogP | 2.97 |
| tPSA | 61.77 |
| Solubility (pH 2; 7.4) (μM) | 249; 3.27 |
| Mouse Microsomal Stability ($t_{1/2}$) (min) | 38.08 |
| Mouse Plasma Stability (% remain @ 4 h) | 95.44 |

CANCER TREATMENTS TARGETING CANCER STEM CELLS

RELATED APPLICATIONS

This application claims priority under 35 U.S.C. § 119(e) to U.S. Provisional applications, U.S. Ser. No. 62/667,412, filed May 4, 2018, and U.S. Ser. No. 62/815,251, filed Mar. 7, 2019, each of which is incorporated herein by reference.

BACKGROUND OF THE INVENTION

Cancer is ubiquitous and despite medical advanced, remains among the leading cause of death worldwide. In 2017, an estimated 1.7 million new cases of cancer were diagnosed and 600,000 people died from the disease.[1] Cancer is the second leading cause of death globally and nearly 1 in 6 deaths is due to cancer. The number of new cases is expected to rise by about 70% over the next 2 decades. The economic impact of cancer is significant and is increasing. The total annual economic cost of cancer in 2010 was estimated at approximately 1.16 trillion US dollars.[2]

Cancer is a generic term for a large group of diseases that can affect any part of the body. Other terms used are malignant tumors and neoplasms. Cancer arises from the transformation of normal cells into tumor cells in multistage process that generally progresses from a pre-cancerous lesion to a malignant tumor. One defining feature of cancer is the rapid creation of abnormal cells that grow beyond their usual boundaries, and which can then invade adjoining parts of the body and spread to other organs, the latter process referred to as metastasizing. Metastases are a major cause of death from cancer. The most common cause of cancer death are cancers of lung, liver, colorectal, stomach, and breast.

While there has been some progress in treating subsets of cancer types, the average cancer death rate is still extremely high, with little overall improvement in the ongoing cancer crisis. Nearly all modern cancer treatments, including chemotherapy, targeted therapy, and immunotherapy, focus on de-bulking tumors without targeting the most dangerous cells in the tumor: cancer stem cells. Cancer stem cells are responsible for the spread of cancer cells throughout the body, the growth of tumors, cancer's resistance to chemotherapy, and the recurrence of tumors after treatment or surgical removal.[3,4] Because current treatments do not target the cancer stem cell population, they frequently lead to the rise of resistant tumors and continued cancer spread.

SUMMARY OF THE INVENTION

The discovery of cancer stem cells provides an opportunity to merge the fields of oncology and embryonic stem cell biology.[5,6] By targeting what makes cancer so dangerous—the embryonic properties of cancer stem cells that form the basis for cancer growth, spread, and resistance—the development of effective and non-toxic therapies can be achieved via a strategy called cancer containment therapy. Therapies that can both diminish tumor bulk and disrupt cancer stem cells will revolutionize cancer treatment.[7]

Described herein are compounds that force differentiation of cancer stem cells, inhibiting the signaling pathways required for metastasis, which are the same pathways used by embryonic stem cells during differentiation and development.[8,9] These properties can be safely targeted because they only occur in embryonic stem cells and not healthy adult tissue.

These compounds will be more effective than traditional cancer treatments in decreasing tumor growth, prolonging life, and preventing metastasis and recurrence. And because the reactivation of embryonic properties is a property shared by many kinds of tumors, cancer containment therapy is expected to be effective on many different types of cancer, including cancer of the colon, stomach, prostate, testicles, and breast.

Compounds, methods, compositions, uses, and kits that allow for treating proliferative diseases, benign neoplasms, and cancer are disclosed herein.

In one aspect, the compounds of the disclosure are of Formula (0):

(0)

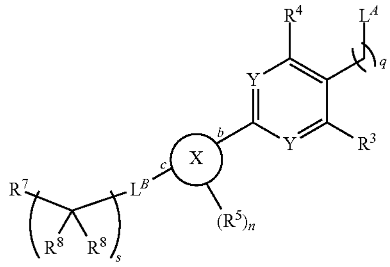

or a pharmaceutically acceptable salt, solvate, hydrate, polymorph, co-crystal, tautomer, stereoisomer, isotopically labeled derivative, or prodrug thereof, wherein the variables recited in Formula (0) are as described herein. In another aspect, the present disclosure provides methods for treating cancer comprising administering to a subject a therapeutically effective amount of a compound of Formula (0), or a pharmaceutically acceptable salt, solvate, hydrate, polymorph, co-crystal, tautomer, stereoisomer, isotopically labeled derivative, or prodrug thereof, wherein the variables recited in Formula (0) are as described herein.

In one aspect, the compounds of the disclosure are of Formula (0'):

(0')

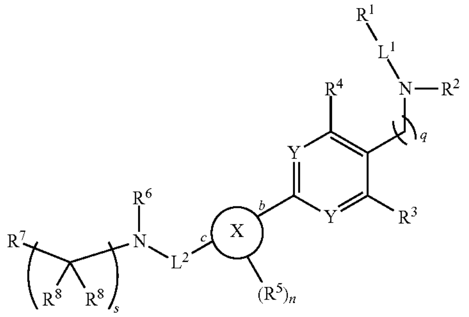

or a pharmaceutically acceptable salt, solvate, hydrate, polymorph, co-crystal, tautomer, stereoisomer, isotopically labeled derivative, or prodrug thereof, wherein the variables recited in Formula (0') are as described herein. In another aspect, the present disclosure provides methods for treating cancer comprising administering to a subject a therapeutically effective amount of a compound of Formula (0'), or a pharmaceutically acceptable salt, solvate, hydrate, polymorph, co-crystal, tautomer, stereoisomer, isotopically labeled derivative, or prodrug thereof, wherein the variables recited in Formula (0') are as described herein.

In one aspect, the compounds of the disclosure are of Formula (I):

(I)

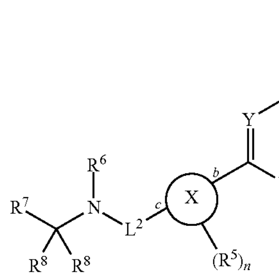

or a pharmaceutically acceptable salt, solvate, hydrate, polymorph, co-crystal, tautomer, stereoisomer, isotopically labeled derivative, or prodrug thereof, wherein the variables recited in Formula (I) are as described herein. In another aspect, the present disclosure provides methods for treating cancer comprising administering to a subject a therapeutically effective amount of a compound of Formula (I), or a pharmaceutically acceptable salt, solvate, hydrate, polymorph, co-crystal, tautomer, stereoisomer, isotopically labeled derivative, or prodrug thereof, wherein the variables recited in Formula (I) are as described herein.

In certain embodiments, the cancer comprises cancer stem cells. In certain embodiments, the cancer involves or is associated with cancer stem cells. In certain embodiments, the cancer is colorectal cancer, gastric cancer, gastrointestinal stromal tumor, ovarian cancer, lung cancer, breast cancer, pancreatic cancer, testicular cancer, or prostate cancer. In certain embodiments, the cancer is liver cancer or endometrial cancer. In certain embodiments, the cancer is leukemia. In certain embodiments, the cancer is lymphoma. In certain embodiments, the cancer is multiple myeloma. In certain embodiments, the subject is in need of a regenerative medicine or therapy.

In yet another aspect, the present disclosure provides methods comprising contacting a cell with an effective amount of Formula (0) or (0'), or a pharmaceutically acceptable salt, solvate, hydrate, polymorph, co-crystal, tautomer, stereoisomer, isotopically labeled derivative, or prodrug thereof.

In yet another aspect, the present disclosure provides methods and uses comprising contacting a cell with an effective amount of Formula (I), or a pharmaceutically acceptable salt, solvate, hydrate, polymorph, co-crystal, tautomer, stereoisomer, isotopically labeled derivative, or prodrug thereof.

In certain embodiments, a compound of Formula (I) is of Formula (I-A):

(I-A)

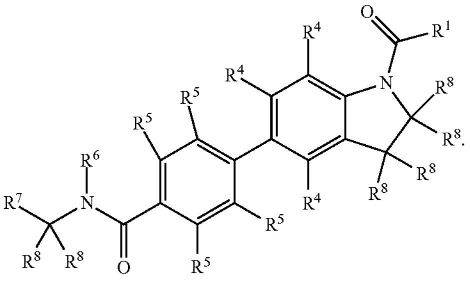

In certain embodiments, Formula (I) is of Formula (I-B), wherein:

(I-B)

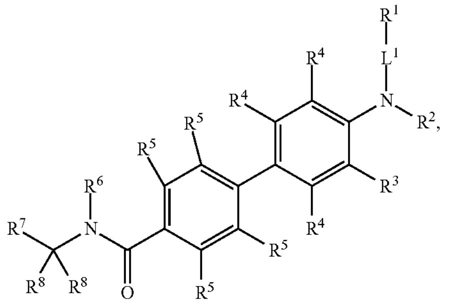

wherein $R^7$ is substituted or unsubstituted, 3-pyridinyl. In certain embodiments, Formula (I) is of Formula (I-C), wherein:

(I-C)

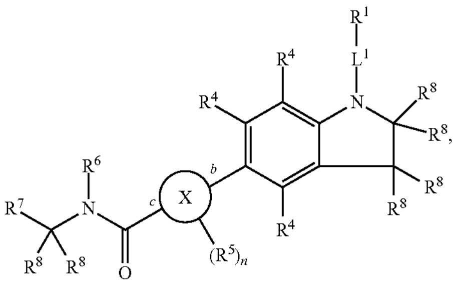

wherein

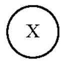

is pyridinyl, pyridazinyl, pyrimidinyl, or pyrazinyl. In certain embodiments, Formula (I) is of Formula (I-C), wherein:

(I-C)

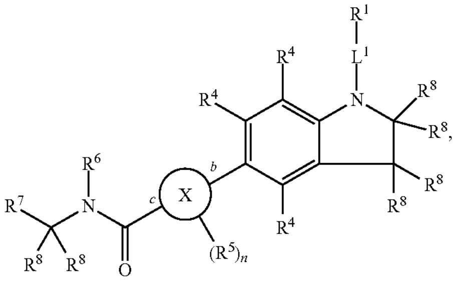

wherein

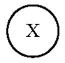

is imidazolyl, oxazolyl, azetidinyl, —C≡C—, or

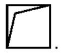.

In certain embodiments, Formula (I) is of Formula (I-D), wherein:

(I-D)

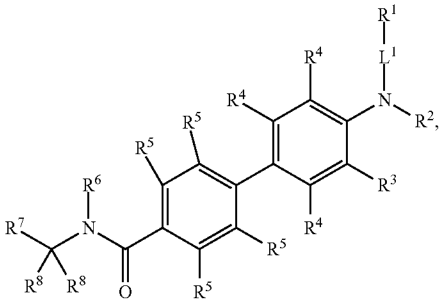

wherein $R^7$ is substituted or unsubstituted, 3- to 7-membered, monocyclic heterocyclyl or substituted or unsubstituted, 5- or 6-membered, monocyclic heteroaryl.

In some embodiments, the present disclosure provides compositions comprising a compound of Formula (0) or (0'), or a pharmaceutically acceptable salt, solvate, hydrate, polymorph, co-crystal, tautomer, stereoisomer, isotopically labeled derivative, or prodrug thereof; and optionally a pharmaceutically acceptable excipient. In certain embodiments, the composition is a pharmaceutical composition. In certain embodiments, the composition further comprises an additional pharmaceutical agent.

In some embodiments, the present disclosure provides compositions comprising a compound of Formula (I), or a pharmaceutically acceptable salt, solvate, hydrate, polymorph, co-crystal, tautomer, stereoisomer, isotopically labeled derivative, or prodrug thereof; and optionally a pharmaceutically acceptable excipient. In certain embodiments, the composition is a pharmaceutical composition. In certain embodiments, the composition further comprises an additional pharmaceutical agent.

In certain embodiments, the present disclosure provides kits comprising a compound of Formula (0) or (0'), or a pharmaceutically acceptable salt, solvate, hydrate, polymorph, co-crystal, tautomer, stereoisomer, isotopically labeled derivative, or prodrug thereof; or a composition as described herein; and instructions for using the compound, pharmaceutically acceptable salt, solvate, hydrate, polymorph, co-crystal, tautomer, stereoisomer, isotopically labeled derivative, prodrug, or pharmaceutical composition.

In further embodiments, the present disclosure provides kits comprising a compound of Formula (I), or a pharmaceutically acceptable salt, solvate, hydrate, polymorph, co-crystal, tautomer, stereoisomer, isotopically labeled derivative, or prodrug thereof; or a composition as described herein; and instructions for using the compound, pharmaceutically acceptable salt, solvate, hydrate, polymorph, co-crystal, tautomer, stereoisomer, isotopically labeled derivative, prodrug, or pharmaceutical composition.

The details of certain embodiments of the invention are set forth in the Detailed Description of Certain Embodiments, as described below. Other features, objects, and advantages of the invention will be apparent from the Definitions, Figures, Examples, and Claims.

DEFINITIONS

Figure 1:
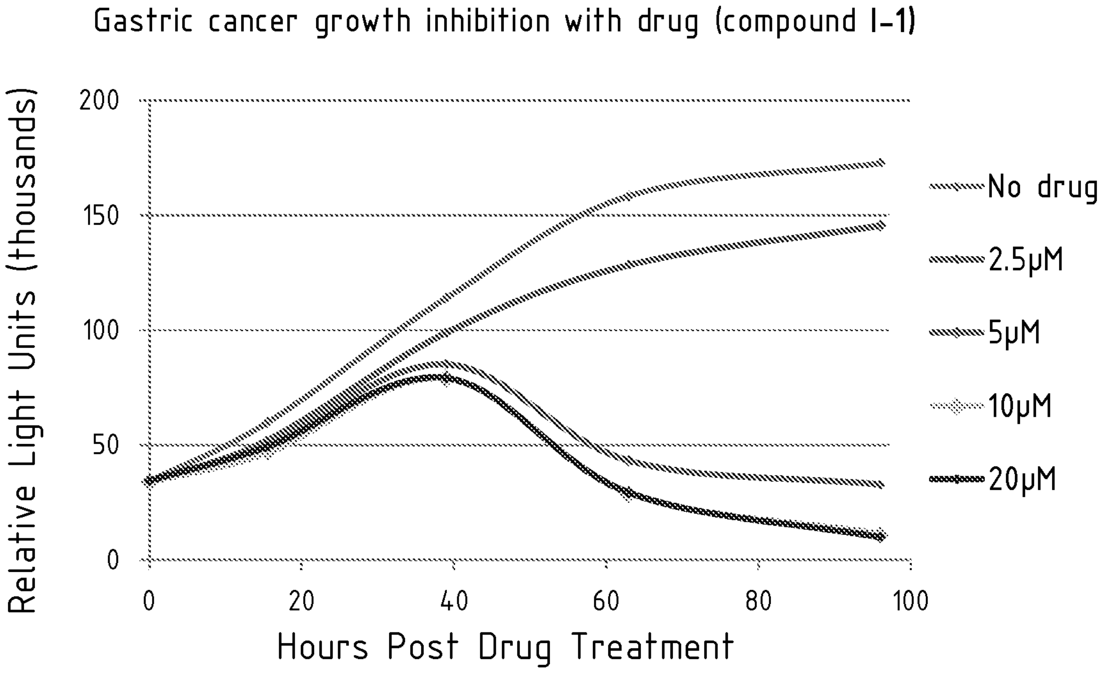
FIG. 1 shows that compound I-1 depleted populations of embryonic-like gastric cell populations in gastric cancer.

For convenience, certain terms employed herein, in the specification, examples and appended claims are collected herein.

Unless otherwise required by context, singular terms shall include pluralities, and plural terms shall include the singular.

The language "in some embodiments" and the language "in certain embodiments" are used interchangeably.

The following definitions are more general terms used throughout the present application:

The singular terms "a," "an," and "the" include plural references unless the context clearly indicates otherwise. Similarly, the word "or" is intended to include "and" unless the context clearly indicates otherwise.

Other than in the examples, or where otherwise indicated, all numbers expressing quantities of ingredients or reaction conditions used herein should be understood as modified in all instances by the term "about." "About" and "approximately" shall generally mean an acceptable degree of error for the quantity measured given the nature or precision of the measurements. Exemplary degrees of error are within 20 percent (%), typically, within 10%, or more typically, within 5%, 4%, 3%, 2% or 1% of a given value or range of values.

Definitions of specific functional groups and chemical terms are described in more detail below. The chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, Some Modern Methods of Organic Synthesis, $3^{rd}$ Edition, Cambridge University Press, Cambridge, 1987.

Compounds described herein can include one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, IN 1972). The disclosure additionally encompasses compounds as individual isomers substantially free of other isomers, and alternatively, as mixtures of various isomers.

In a formula, 〰 is a single bond where the stereochemistry of the moieties immediately attached thereto is not specified, - - - is absent or a single bond, and ⚌ or ⚌ is a single or double bond.

Unless otherwise provided, a formula depicted herein includes compounds that do not include isotopically enriched atoms and also compounds that include isotopically enriched atoms. Compounds that include isotopically enriched atoms may be useful as, for example, analytical tools, and/or probes in biological assays.

The term "aliphatic" includes both saturated and unsaturated, nonaromatic, straight chain (i.e., unbranched), branched, acyclic, and cyclic (i.e., carbocyclic) hydrocarbons. In some embodiments, an aliphatic group is optionally substituted with one or more functional groups (e.g., halo, such as fluorine). As will be appreciated by one of ordinary skill in the art, "aliphatic" is intended herein to include alkyl, alkenyl, alkynyl, cycloalkyl, cycloalkenyl, and cycloalkynyl moieties.

When a range of values ("range") is listed, it is intended to encompass each value and sub-range within the range. A range is inclusive of the values at the two ends of the range unless otherwise provided. For example, "an integer between 1 and 4" refers to 1, 2, 3, and 4. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_5$) and the like. Unless otherwise specified, each instance of an alkyl group is independently optionally substituted, e.g., unsubstituted (an "unsubstituted alkyl") or substituted (a "substituted alkyl") with one or more substituents. In certain embodiments, the alkyl group is unsubstituted $C_{1-12}$ alkyl (e.g., $—CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted N-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is substituted $C_{1-12}$ alkyl (such as substituted $C_{1-6}$ alkyl, e.g., $—CH_2F$, $—CHF_2$, $—CF_3$, $—CH_2CH_2F$, $—CH_2CHF_2$, $—CH_2CF_3$, or benzyl (Bn)). The attachment point of alkyl may be a single bond (e.g., as in $—CH_3$), double bond (e.g., as in $=CH_2$), or triple bond (e.g., as in $\equiv CH$). The moieties $=CH_2$ and $\equiv CH$ are also alkyl.

In some embodiments, an alkyl group is substituted with one or more halogens. "Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include $—CF_3$, $—CF_2CF_3$, $—CF_2CF_2CF_3$, $—CFCl_3$, $—CFCl_2$, $—CF_2Cl$, and the like.

"Alkenyl" refers to a radical of a straight-chain or branched hydrocarbon group having from 2 to 20 carbon atoms, one or more (e.g., two, three, or four, as valency permits) carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_5$), octatrienyl ($C_5$), and the like. Unless otherwise specified, each instance of an alkenyl group is independently optionally substituted, e.g., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a $C=C$ double bond for which the stereochemistry is not specified (e.g., —CH=CHCH$_3$, 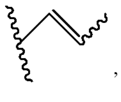, or 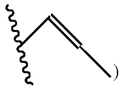)

may be in the (E)- or (Z)-configuration.

"Alkynyl" refers to a radical of a straight-chain or branched hydrocarbon group having from 2 to 20 carbon atoms, one or more (e.g., two, three, or four, as valency permits) carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, e.g., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 13 ring carbon atoms ("$C_{3-13}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl"). Carbocyclyl can be saturated, and saturated carbocyclyl is referred to as "cycloalkyl." In some embodiments, carbocyclyl is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl. Carbocyclyl can be partially unsaturated. Carbocyclyl may include zero, one, or more (e.g., two, three, or four, as valency permits) C=C double bonds in all the rings of the carbocyclic ring system that are not aromatic or heteroaromatic. Carbocyclyl including one or more (e.g., two or three, as valency permits) C=C double bonds in the carbocyclic ring is referred to as "cycloalkenyl." Carbocyclyl including one or more (e.g., two or three, as valency permits) C≡C triple bonds in the carbocyclic ring is referred to as "cycloalkynyl." Carbocyclyl includes aryl. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, e.g., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl. In certain embodiments, the carbocyclyl is substituted or unsubstituted, 3- to 7-membered, and monocyclic. In certain embodiments, the carbocyclyl is substituted or unsubstituted, 5- to 13-membered, and bicyclic.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 13-membered non-aromatic ring system having ring carbon atoms and 1 to 4 ring heteroatoms, wherein each heteroatom is independently selected from nitrogen, oxygen, and sulfur ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system such as a bicyclic system ("bicyclic heterocyclyl"). A heterocyclyl group can be saturated or can be partially unsaturated. Heterocyclyl may include zero, one, or more (e.g., two, three, or four, as valency permits) double bonds in all the rings of the heterocyclic ring system that are not aromatic or heteroaromatic. Partially unsaturated heterocyclyl groups includes heteroaryl. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, e.g., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl. In certain embodiments, the heterocyclyl is substituted or unsubstituted, 3- to 7-membered, and monocyclic. In certain embodiments, the heterocyclyl is substituted or unsubstituted, 5- to 13-membered, and bicyclic.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include aziridinyl, oxiranyl, or thiiranyl. Exemplary 4-membered heterocyclyl groups containing one heteroatom include azetidinyl, oxetanyl and thietanyl. Exemplary 5-membered heterocyclyl groups containing one heteroatom include tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include dioxolanyl, oxasulfuranyl, disulfuranyl, and oxazolidin-2-one. Exemplary 5-membered heterocyclyl groups containing three heteroatoms include triazolinyl, oxadiazolinyl, and thiadiazolinyl. Exemplary 6-membered heterocyclyl groups containing one heteroatom include piperidinyl, tetrahydropyranyl, dihydropyridinyl, and thianyl. Exemplary 6-membered heterocyclyl groups containing two heteroatoms include piperazinyl, morpholinyl, dithianyl, and dioxanyl. Exemplary 6-membered heterocyclyl groups containing two heteroatoms include triazinanyl. Exemplary 7-membered heterocyclyl groups containing one heteroatom include azepanyl, oxepanyl and thiepanyl. Exemplary 8-membered heterocyclyl groups containing one heteroatom include azocanyl, oxecanyl, and thiocanyl. Exemplary 5-membered heterocyclyl groups fused to a $C_6$ aryl ring (also referred to herein as a 5,6-bicyclic heterocyclic ring) include indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, e.g., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10 n electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, e.g., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include pyrrolyl, furanyl and thiophenyl. Exemplary 5-membered heteroaryl groups containing two heteroatoms include imidazolyl, pyrazolyl, oxazolyl, isoxazolyl, thiazolyl, and isothiazolyl. Exemplary 5-membered heteroaryl groups containing three heteroatoms include triazolyl, oxadiazolyl, and thiadiazolyl. Exemplary 5-membered heteroaryl groups containing four heteroatoms include tetrazolyl. Exemplary 6-membered heteroaryl groups containing one heteroatom include pyridinyl. Exemplary 6-membered heteroaryl groups containing two heteroatoms include pyridazinyl, pyrimidinyl, and pyrazinyl. Exemplary 6-membered heteroaryl groups containing three or four heteroatoms include triazinyl and tetrazinyl, respectively. Exemplary 7-membered heteroaryl groups containing one heteroatom include azepinyl, oxepinyl, and thiepinyl. Exemplary 5,6-bicyclic heteroaryl groups include indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include naphthyridinyl, pteridinyl, quinolinyl, isoquinolinyl, cinnolinyl, quinoxalinyl, phthalazinyl, and quinazolinyl.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

In some embodiments, aliphatic, alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. Unless otherwise provided, a substituent on a polycyclic ring may be on any substitutable position of any one of the monocyclic rings of the polycyclic ring. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include halogen, $-CN$, $-NO_2$, $-N_3$, $-SO_2H$, $-SO_3H$, $-OH$, $-OR^{aa}$, $-ON(R^{bb})_2$, $-N(R^{bb})_2$, $-N(R^{bb})_3^+X^-$, $-N(OR^{cc})R^{bb}$, $-SH$, $-SR^{aa}$, $-SSR^{cc}$, $-C(=O)R^{aa}$, $-CO_2H$, $-CHO$, $-C(OR^{cc})_2$, $-CO_2R^{aa}$, $-OC(=O)R^{aa}$, $-OCO_2R^{aa}$, $-C(=O)N(R^{bb})_2$, $-OC(=O)N(R^{bb})_2$, $-NR^{bb}C(=O)R^{aa}$, $-NR^{bb}CO_2R^{aa}$, $-NR^{bb}C(=O)N(R^{bb})_2$, $-C(=NR^{bb})R^{aa}$, $-C(=NR^{bb})OR^{aa}$, $-OC(=NR^{bb})R^{aa}$, $-OC(=NR^{bb})OR^{aa}$, $-C(=NR^{bb})N(R^{bb})_2$, $-OC(=NR^{bb})N(R^{bb})_2$, $-NR^{bb}C(=NR^{bb})N(R^{bb})_2$, $-C(=O)NR^{bb}SO_2R^{aa}$, $-NR^{bb}SO_2R^{aa}$, $-SO_2N(R^{bb})_2$, $-SO_2R^{aa}$, $-SO_2OR^{aa}$, $-OSO_2R^{aa}$, $-S(=O)R^{aa}$, $-OS(=O)R^{aa}$, $-Si(R^{aa})_3$, $-OSi(R^{aa})_3-C(=S)N(R^{bb})_2$, $-C(=O)SR^{aa}$, $-C(=S)SR^{aa}$, $-SC(=S)SR^{aa}$, $-SC(=O)SR^{aa}$, $-OC(=O)SR^{aa}$, $-SC(=O)OR^{aa}$, $-SC(=O)R^{aa}$, $-P(=O)(R^{aa})_2$, $-P(=O)(OR^{cc})_2$, $-OP(=O)(R^{aa})_2$, $-OP(=O)(OR^{cc})_2$, $-P(=O)(N(R^{bb})_2)_2$, $-OP(=O)(N(R^{bb})_2)_2$, $-NR^{bb}P(=O)(R^{aa})_2$, $-NR^{bb}P(=O)(OR^{cc})_2$, $-NR^{bb}P(=O)(N(R^{bb})_2)_2$, $-P(R^{cc})_2$, $-P(OR^{cc})_2$, $-P(R^{cc})_3^+X^-$, $-P(OR^{cc})_3^+X^-$, $-P(R^{cc})_4$, $-P(OR^{cc})_4$, $-OP(R^{cc})_2$, $-OP(R^{cc})_3^+X^-$, $-OP(OR^{cc})_2$, $-OP(OR^{cc})_3^+X^-$, $-OP(R^{cc})_4$, $-OP(OR^{cc})_4$, $-B(R^{aa})_2$, $-B(OR^{cc})_2$, $-BR^{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group $=O$, $=S$, $=NN(R^{bb})_2$, $=NNR^{bb}C(=O)R^{aa}$, $=NNR^{bb}C(=O)OR^{aa}$, $=NNR^{bb}S(=O)_2R^{aa}$, $=NR^{bb}$, or $=NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —C(═O)$R^{aa}$, —C(═O)$N(R^{cc})_2$, —$CO_2R^{aa}$, —$SO_2R^{aa}$, —C(═$NR^{cc}$)$OR^{aa}$, —C(═$NR^{cc}$)$N(R^{cc})_2$, —$SO_2N(R^{cc})_2$, —$SO_2R^{aa}$, —$SO_2OR^{cc}$, —$SOR^{aa}$, —C(═S)$N(R^{cc})_2$, —C(═O)$SR^{cc}$, —C(═S)$SR^{cc}$, —P(═O)$(R^{aa})_2$, —P(═O)$(OR^{cc})_2$, —P(═O)$(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of R is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two RC groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3{}^+X^-$, —$N(OR^{ee})R^{ff}$, —SH, —$SR^{ee}$, —$SSR^{ee}$, —C(═O)$R^{ee}$, —$CO_2H$, —$CO_2R^{ee}$, —OC(═O)$R^{ee}$, —$OCO_2R^{ee}$, —C(═O)$N(R^{ff})_2$, —OC(═O)$N(R^{ff})_2$, —$NR^{ff}$C(═O)$R^{ee}$, —$NR^{ff}CO_2R^{ee}$, —$NR^{ff}$C(═O)$N(R^{ff})_2$, —C(═$NR^{ff}$)$OR^{ee}$, —OC(═$NR^{ff}$)$R^{ee}$, —OC(═$NR^{ff}$)$OR^{ee}$, —C(═$NR^{ee}$)$N(R^{ff}(R^{ff})_2$, —OC(═$NR^{ff}$)$N(R^{ff})_2$, —$NR^{ff}$C(═$NR^{ff}$)$N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —S(═O)$R^{ee}$, —$Si(R^{ee})_3$, —$OSi(R^{ee})_3$, —C(═S)$N(R^{ff})_2$, —C(═O)$SR^{ee}$, —C(═S)$SR^{ee}$, —SC(═S)$SR^{ee}$, —P(═O)$(OR^{ee})_2$, —P(═O)$(R^{ee})_2$, —OP(═O)$(R^{ee})_2$, —OP(═O)$(OR^{ee})_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form ═O or ═S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^f$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3{}^+X^-$, —$NH(C_{1-6}$ alkyl$)_2{}^+X^-$, —$NH_2(C_{1-6}$ alkyl$)^+X^-$, —$NH_3{}^+X^-$, —$N(OC_{1-6}$ alkyl$)(C_{1-6}$ alkyl), —N(OH)$(C_{1-6}$ alkyl), —NH(OH), —SH, —$SC_{1-6}$ alkyl, —$SS(C_{1-6}$ alkyl), —C(═O)$(C_{1-6}$ alkyl), —$CO_2H$, —$CO_2(C_{1-6}$ alkyl), —OC(═O)$(C_{1-6}$ alkyl), —$OCO_2(C_{1-6}$ alkyl), —C(═O)$NH_2$, —C(═O)$N(C_{1-6}$ alkyl$)_2$, —OC(═O)$NH(C_{1-6}$ alkyl), —NHC(═O)$(C_{1-6}$ alkyl), —$N(C_{1-6}$ alkyl)C(═O)$(C_{1-6}$ alkyl), —$NHCO_2(C_{1-6}$ alkyl), —NHC(═O)$N(C_{1-6}$ alkyl$)_2$, —NHC(═O)$NH(C_{1-6}$ alkyl), —NHC(═O)$NH_2$, —C(═NH)$O(C_{1-6}$ alkyl), —OC(═NH)$(C_{1-6}$ alkyl), —OC(═NH)$OC_{1-6}$ alkyl, —C(═NH)$N(C_{1-6}$ alkyl$)_2$, —C(═NH)$NH(C_{1-6}$ alkyl), —C(═NH)$NH_2$, —OC(═NH)$N(C_{1-6}$ alkyl$)_2$, —OC(NH)$NH(C_{1-6}$ alkyl), —OC(NH)$NH_2$, —NHC(NH)$N(C_{1-6}$ alkyl$)_2$, —NHC(═NH)$NH_2$, —$NHSO_2(C_{1-6}$ alkyl), —$SO_2N(C_{1-6}$ alkyl$)_2$, —$SO_2NH(C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —$Si(C_{1-6}$ alkyl$)_3$, —$OSi(C_{1-6}$ alkyl$)_3$-C(═S)$N(C_{1-6}$ alkyl$)_2$, C(═S)$NH(C_{1-6}$ alkyl), C(═S)$NH_2$, —C(═O)$S(C_{1-6}$ alkyl), —C(═S)$SC_{1-6}$ alkyl, —SC(═S)$SC_{1-6}$ alkyl, —P(═O)$(OC_{1-6}$ alkyl$)_2$, —P(═O)$(C_{1-6}$ alkyl$)_2$, —OP(═O)$(C_{1-6}$ alkyl$)_2$, —OP(═O)$(OC_{1-6}$ alkyl$)_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{99}$ substituents can be joined to form ═O or ═S; wherein $X^-$ is a counterion.

In certain embodiments, the carbon atom substituents are independently halogen, substituted (e.g., substituted with one or more halogen) or unsubstituted $C_{1-6}$ alkyl, —$OR^{aa}$, —$SR^{aa}$, —$N(R^{bb})_2$, —CN, —SCN, —$NO_2$, —C(═O)$R^{aa}$, —$CO_2R^{aa}$, —C(═O)$N(R^{bb})_2$, —OC(═O)$R^{aa}$, —$OCO_2R^{aa}$, —OC(═O)$N(R^{bb})_2$, —$NR^{bb}$C(═O)$R^{aa}$, —$NR^{bb}CO_2R^{aa}$, or —$NR^{bb}$C(═O)$N(R^{bb})_2$. In certain embodiments, the carbon atom substituents are independently halogen, substituted (e.g., substituted with one or more halogen) or unsubstituted $C_{1-6}$ alkyl, —$OR^{aa}$, —$SR^{aa}$, —$N(R^{bb})_2$, —CN, —SCN, —$NO_2$, —C(═O)$R^{aa}$, —$CO_2R^{aa}$, —C(═O)$N(R^{bb})_2$, —OC(═O)$R^{aa}$, —$OCO_2R^{aa}$, —OC(═O)$N(R^{bb})_2$, —$NR^{bb}$C(═O)$R^{aa}$, —$NR^{bb}CO_2R^{aa}$, or —$NR^{bb}$C(═O)$N(R^{bb})_2$, wherein $R^{aa}$ is hydrogen, substituted (e.g., substituted with one or more halogen) or unsubstituted $C_{1-6}$ alkyl, an oxygen protecting group when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each $R^{bb}$ is independently hydrogen, substituted (e.g., substituted with one or more halogen) or unsubstituted $C_{1-6}$ alkyl, or a nitrogen protecting group. In certain embodiments, the carbon atom substituents are independently halogen, substituted (e.g., substituted with one or more halogen) or unsubstituted $C_{1-6}$ alkyl, —OR$^{aa}$, —SR$^{aa}$, —N(R$^{bb}$)$_2$, —CN, —SCN, or —NO$_2$. In certain embodiments, the carbon atom substituents are independently halogen, substituted (e.g., substituted with one or more halogen moieties) or unsubstituted $C_{1-6}$ alkyl, —OR$^{aa}$, —SR$^{aa}$, —N(R$^{bb}$)$_2$, —CN, —SCN, or —NO$_2$, wherein $R^{aa}$ is hydrogen, substituted (e.g., substituted with one or more halogen) or unsubstituted $C_{1-6}$ alkyl, an oxygen protecting group when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each $R^{bb}$ is independently hydrogen, substituted (e.g., substituted with one or more halogen) or unsubstituted $C_{1-6}$ alkyl, or a nitrogen protecting group.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5\text{-}(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —$C_1$), bromine (bromo, —Br), or iodine (iodo, —I).

Nitrogen atoms can be substituted or unsubstituted as valency permits, and include primary, secondary, tertiary, and quaternary nitrogen atoms. Exemplary nitrogen atom substituents include hydrogen, —OH, —OR$^{aa}$, —N(R$^{cc}$)$_2$, —CN, —C(═O)R$^{aa}$, —C(═O)N(R$^{cc}$)$_2$, —CO$_2$R$^{aa}$, —SO$_2$R$^{aa}$, —C(═NR$^{bb}$)R$^{aa}$, —C(═NR$^{cc}$)OR$^{aa}$, —C(═NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(═S)N(R$^{cc}$)$_2$, —C(═O)SR$^{cc}$, —C(═S)SR$^{cc}$, —P(═O)(OR$^{cc}$)$_2$, —P(═O)(R$^{cc}$)$_2$, —P(═O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two R groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the nitrogen atom substituents are independently substituted (e.g., substituted with one or more halogen) or unsubstituted $C_{1-6}$ alkyl, —C(═O)R$^{aa}$, —CO$_2$R$^{aa}$, —C(═O)N(R$^{bb}$)$_2$, or a nitrogen protecting group. In certain embodiments, the nitrogen atom substituents are independently substituted (e.g., substituted with one or more halogen) or unsubstituted $C_{1-6}$ alkyl, —C(═O)R$^{aa}$, —CO$_2$R$^{aa}$, —C(═O)N(R$^{bb}$)$_2$, or a nitrogen protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the nitrogen atom substituents are independently substituted (e.g., substituted with one or more halogen) or unsubstituted $C_{1-6}$ alkyl or a nitrogen protecting group.

In certain embodiments, the substituent present on a nitrogen atom is a nitrogen protecting group (also referred to as an amino protecting group). Nitrogen protecting groups include —OH, —OR$^{aa}$, —N(R$^{aa}$)$_2$, —C(═O)R$^{aa}$, —C(═O)N(R$^{cc}$)$_2$, —CO$_2$R$^{aa}$, —SO$_2$R$^{aa}$, —C(═NR$^{cc}$)R$^{aa}$, —C(═NR$^{cc}$)OR$^{aa}$, —C(═NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(═S)N(R$^{cc}$)$_2$, —C(═O)SR$^{cc}$, —C(═S)SR$^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Amide nitrogen protecting groups (e.g., —C(═O)R$^{aa}$) include formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —C(═O)OR$^{aa}$) include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Sulfonamide nitrogen protecting groups (e.g., $—S(=O)_2R^{aa}$) include p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, a nitrogen protecting group is Bn, Boc, Cbz, Fmoc, trifluoroacetyl, triphenylmethyl, acetyl, or Ts.

In certain embodiments, the oxygen atom substituents are independently substituted (e.g., substituted with one or more halogen) or unsubstituted $C_{1-6}$ alkyl, $—C(=O)R^{aa}$, $—CO_2R^{aa}$, $—C(=O)N(R^{bb})_2$, or an oxygen protecting group. In certain embodiments, the oxygen atom substituents are independently substituted (e.g., substituted with one or more halogen) or unsubstituted $C_{1-6}$ alkyl, $—C(=O)R^{aa}$, $—CO_2R^{aa}$, $—C(=O)N(R^{bb})_2$, or an oxygen protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the oxygen atom substituents are independently substituted (e.g., substituted with one or more halogen) or unsubstituted $C_{1-6}$ alkyl or an oxygen protecting group.

In certain embodiments, the substituent present on an oxygen atom is an oxygen protecting group (also referred to herein as an "hydroxyl protecting group"). Oxygen protecting groups include $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2$, $—P(R^{cc})_3^+X^-$, $—P(OR^{cc})_2$, $—P(OR^{cc})_3^+X^-$, $—P(=O)(R^{aa})_2$, $—P(=O)(OR^{cc})_2$, and $—P(=O)(N(R^{bb})_2)_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, an oxygen protecting group is silyl, TBDPS, TBDMS, TIPS, TES, TMS, MOM, THP, t-Bu, Bn, allyl, acetyl, pivaloyl, or benzoyl.

In certain embodiments, the sulfur atom substituents are independently substituted (e.g., substituted with one or more halogen) or unsubstituted $C_{1-6}$ alkyl, $—C(=O)R^{aa}$, $—CO_2R^{aa}$, $—C(=O)N(R^{bb})_2$, or a sulfur protecting group. In certain embodiments, the sulfur atom substituents are independently substituted (e.g., substituted with one or more halogen) or unsubstituted $C_{1-6}$ alkyl, $—C(=O)R^{aa}$, $—CO_2R^{aa}$, $—C(=O)N(R^{bb})_2$, or a sulfur protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the sulfur atom substituents are independently substituted (e.g., substituted with one or more halogen) or unsubstituted $C_{1-6}$ alkyl or a sulfur protecting group.

In certain embodiments, the substituent present on a sulfur atom is a sulfur protecting group (also referred to as a "thiol protecting group"). Sulfur protecting groups include $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2$, $—P(R^{cc})_3^+X^-$, $—P(OR^{cc})_2$, $—P(OR^{cc})_3^+X^-$, $—P(=O)(R^{aa})_2$, $—P(=O)(OR^{cc})_2$, and $—P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3rd edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

The "molecular weight" of —R, wherein —R is any monovalent moiety, is calculated by substracting the atomic weight of a hydrogen atom from the molecular weight of the molecule R—H. The "molecular weight" of -L-, wherein -L- is any divalent moiety, is calculated by substracting the combined atomic weight of two hydrogen atoms from the molecular weight of the molecule H-L-H.

In certain embodiments, the molecular weight of a substituent is lower than 200, lower than 150, lower than 100, lower than 50, or lower than 25 g/mol. In certain embodiments, a substituent consists of carbon, hydrogen, fluorine, chlorine, bromine, iodine, oxygen, sulfur, nitrogen, and/or silicon atoms. In certain embodiments, a substituent consists of carbon, hydrogen, fluorine, chlorine, bromine, and/or iodine atoms. In certain embodiments, a substituent consists of carbon, hydrogen, and/or fluorine atoms. In certain embodiments, a substituent does not comprise one or more, two or more, or three or more hydrogen bond donors. In certain embodiments, a substituent does not comprise one or more, two or more, or three or more hydrogen bond acceptors.

Affixing the suffix "ene" to a group indicates the group is a polyvalent (e.g., bivalent, trivalent, tetravalent, or pentavalent) moiety. In certain embodiments, affixing the suffix "ene" to a group indicates the group is a bivalent moiety.

The term "hydroxyl" or "hydroxy" refers to the group —OH.

The term "thiol" or "thio" refers to the group —SH.

The term "amine" or "amino" refers to the group —NH— or $—NH_2$.

The term "acyl" refers to a group having the general formula —C(═O)Rx, —C(═O)OR$^{X1}$, —C(═O)—O—C(═O)R$^{X1}$, —C(═O)SR$^{X1}$, —C(═O)N(R$^{X1}$)$_2$, —C(═S)R$^{X1}$, —C(═S)N(R$^{X1}$)$_2$, and —C(═S)S(R$^{X1}$), —C(═NR$^{X1}$)R$^{X1}$, —C(═NR$^{X1}$)OR$^{X1}$, —C(═NR$^{X1}$)SR$^{X1}$, and —C(═NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—$CO_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this disclosure include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences,* 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvent" refers to a substance that dissolves one or more solutes, resulting in a solution. A solvent may serve as a medium for any reaction or transformation described herein. The solvent may dissolve one or more reactants or reagents in a reaction mixture. The solvent may facilitate the mixing of one or more reagents or reactants in a reaction mixture. The solvent may also serve to increase or decrease the rate of a reaction relative to the reaction in a different solvent. Solvents can be polar or non-polar, protic or aprotic. Common solvents useful in the methods described herein include, but are not limited to, acetone, acetonitrile, benzene, benzonitrile, 1-butanol, 2-butanone, butyl acetate, tert-butyl methyl ether, carbon disulfide carbon tetrachloride, chlorobenzene, 1-chlorobutane, chloroform, cyclohexane, cyclopentane, 1,2-dichlorobenzene, 1,2-dichloroethane, dichloromethane (DCM), N,N-dimethylacetamide N,N-dimethylformamide (DMF), 1,3-dimethyl-3,4,5,6-tetrahydro-2-pyrimidinone (DMPU), 1,4-dioxane, 1,3-dioxane, diethylether, 2-ethoxyethyl ether, ethyl acetate, ethyl alcohol, ethylene glycol, dimethyl ether, heptane, n-hexane, hexanes, hexamethylphosphoramide (HMPA), 2-methoxyethanol, 2-methoxyethyl acetate, methyl alcohol, 2-methylbutane, 4-methyl-2-pentanone, 2-methyl-1-propanol, 2-methyl-2-propanol, 1-methyl-2-pyrrolidinone, dimethylsulfoxide (DMSO), nitromethane, 1-octanol, pentane, 3-pentanone, 1-propanol, 2-propanol, pyridine, tetrachloroethylene, tetrahyrdofuran (THF), 2-methyltetrahydrofuran, toluene, trichlorobenzene, 1,1,2-trichlorotrifluoroethane, 2,2,4-trimethylpentane, trimethylamine, triethylamine, N,N-diisopropylethylamine, diisopropylamine, water, o-xylene, and p-xylene.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R \cdot 0.5\ H_2O$)), and polyhydrates (x is a number greater than 1, e.g., dihydrates ($R \cdot 2\ H_2O$) and hexahydrates ($R \cdot 6\ H_2O$)).

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "co-crystal" refers to a crystalline structure comprising at least two different components (e.g., compound of Formula (I) and an acid), wherein each of the components is independently an atom, ion, or molecule. In certain embodiments, none of the components is a solvent. In certain embodiments, at least one of the components is a solvent. A co-crystal of compound of Formula (I) and an acid is different from a salt formed from a compound of Formula (I) and the acid. Co-crystals may be useful to improve the properties (e.g., solubility, stability, and ease of formulation) of a compound of Formula (I).

Further, the term "co-crystal" refers to a crystalline structure comprising at least two different components (e.g., compound of Formula (0) and an acid), wherein each of the components is independently an atom, ion, or molecule. In certain embodiments, none of the components is a solvent. In certain embodiments, at least one of the components is a solvent. A co-crystal of compound of Formula (0) or (0') and an acid is different from a salt formed from a compound of Formula (0) or (0') and the acid. Co-crystals may be useful to improve the properties (e.g., solubility, stability, and ease of formulation) of a compound of Formula (0) or (0').

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers". In certain embodiments, if a phenyl group contains two substituents that are each bonded to adjacent carbons then the compound may be designated the ortho isomer. In certain embodiments, if a phenyl group contains two substituents that are each bonded to carbons separated by one ring carbon then the compound may be designated the meta isomer. In certain embodiments, if a phenyl group contains two substituents that are each bonded to carbons separated by two ring carbon then the compound may be designated the para isomer.

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

As used herein, the term "agent" means a molecule, group of molecules, complex or substance administered to an organism for diagnostic, therapeutic, preventative medical, or veterinary purposes. In certain embodiments, the agent is a pharmaceutical agent (e.g., a therapeutic agent, a diagnostic agent, or a prophylactic agent). In certain embodiments, the compositions disclosed herein comprise an agent(s), e.g., a first therapeutic agent (e.g., at least one (including, e.g., at least two, at least three). In some embodiments, the compositions can further comprise a second therapeutic agent, a targeting moiety, a diagnostic moiety as described herein.

As used herein, the term "therapeutic agent" includes an agent that is capable of providing a local or systemic biological, physiological, or therapeutic effect in the biological system to which it is applied. For example, a therapeutic agent can act to control tumor growth, control infection or inflammation, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism.

An agent (e.g., a therapeutic agent) can include a wide variety of different compounds, including chemical compounds and mixtures of chemical compounds (e.g., small organic or inorganic molecules) such as drug compounds (e.g., compounds approved for human or veterinary use by the U.S. Food and Drug Administration as provided in the Code of Federal Regulations (CFR)); targeting agents; isotopically labeled chemical compounds; agents useful in bioprocessing; carbohydrates; saccharines; monosaccharides; oligosaccharides; polysaccharides; biological macromolecules (e.g., peptides, proteins, and peptide analogs and derivatives); peptidomimetics; antibodies and antigen binding fragments thereof; nucleic acids (e.g., DNA or RNA); nucleotides; nucleosides; oligonucleotides; antisense oligonucleotides; polynucleotides; nucleic acid analogs and derivatives; nucleoproteins; mucoproteins; lipoproteins; synthetic polypeptides or proteins; small molecules linked to proteins; glycoproteins; steroids; lipids; hormones; vitamins; vaccines; immunological agents; an extract made from biological materials such as bacteria, plants, fungi, or animal cells; animal tissues; naturally occurring or synthetic compositions; and any combinations thereof.

In some embodiments, the agent is in the form of a prodrug. The term "prodrug" refers to a compound that becomes active, e.g., by solvolysis, reduction, oxidation, or under physiological conditions, to provide a pharmaceutically active compound, e.g., in vivo. A prodrug can include a derivative of a pharmaceutically active compound, such as, for example, to form an ester by reaction of the acid, or acid anhydride, or mixed anhydrides moieties of the prodrug moiety with the hydroxyl moiety of the pharmaceutical active compound, or to form an amide prepared by the acid, or acid anhydride, or mixed anhydrides moieties of the prodrug moiety with a substituted or unsubstituted amine of the pharmaceutically active compound. Simple aliphatic or aromatic esters, amides, and anhydrides derived from acidic groups may comprise prodrugs. In some embodiments, the composition described herein incorporates one therapeutic agent or prodrug thereof. In some embodiments, the compositions described herein incorporates more than one therapeutic agents or prodrugs.

In some embodiments, the agent (e.g., a therapeutic agent) is a small molecule. As used herein, the term "small molecule" can refer to compounds that are "natural product-like." However, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

Exemplary agents (e.g., a therapeutic agents) in the compositions include, but are not limited to, those found in *Harrison's Principles of Internal Medicine,* 13th Edition, Eds. T. R. Harrison et al. McGraw-Hill N.Y., NY; Physicians' Desk Reference, 50th Edition, 1997, Oradell New Jersey, Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

In some embodiments, exemplary therapeutic agents in the compositions include, but are not limited to, one or more of the agents listed in Paragraph [0148] of U.S. Pat. No. 9,381,253, incorporated by reference herein.

In other embodiments, exemplary therapeutic agents in the compositions include, but are not limited to, one or more of the therapeutic agents listed in WO 2013/169739, including the anti-hypertensive and/or a collagen modifying agents ("AHCM") disclosed, e.g., in Paragraphs 40-49, 283, 286-295; the microenvironment modulators disclosed, e.g., in Paragraphs 113-121, of WO 2013/169739, incorporated herein by reference. In some embodiments, the composition comprising the AHCM and/or the microenvironment modulator causes one or more of: reduces solid stress (e.g., growth-induced solid stress in tumors); decreases tumor fibrosis; reduces interstitial hypertension or interstitial fluid pressure (IFP); increases interstitial tumor transport; increases tumor or vessel perfusion; increases vascular diameters and/or enlarges compressed or collapsed blood vessels; reduces or depletes one or more of: cancer cells, or stromal cells (e.g., tumor associated fibroblasts or immune cells); decreases the level or production of extracellular matrix components, such as fibers (e.g., collagen, procollagen), and/or polysaccharides (e.g., glycosaminoglycans such as hyaluronan or hyaluronic acid); decreases the level or production of collagen or procollagen; decreases the level or production of hyaluronic acid; increases tumor oxygenation; decreases tumor hypoxia; decreases tumor acidosis; enables immune cell infiltration; decreases immunosuppression; increases antitumor immunity; decreases the production of cancer stem cells (also referred to herein as tumor-initiating cells); or enhances the efficacy (e.g., penetration or diffusion), of the therapy, e.g., the cancer therapy (e.g., radiation, photodynamic therapy, chemotherapeutics and immunotherapies) in a tumor or tumor vasculature, in the subject.

Agents, e.g., therapeutic agents, include the herein disclosed categories and specific examples. It is not intended that the category be limited by the specific examples. Those of ordinary skill in the art will recognize also numerous other compounds that fall within the categories and that are useful according to the present disclosure.

Examples of therapeutic agents include, but are not limited to, antimicrobial agents, analgesics, antinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anti-cancer properties, or a combination thereof. Other suitable therapeutic agents include contraceptives and vitamins as well as micro- and macronutrients. Still other examples include antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; anti-hypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird. The non-human animal may be a male or female at any stage of development. The non-human animal may be a transgenic animal or genetically engineered animal.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a medical history of symptoms). Treatment may also be continued after symptoms have resolved, for example, to delay and/or prevent recurrence of the disease or disorder.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population of subjects.

The terms "condition," "disease," and "disorder" are used interchangeably.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, diseases associated with angiogenesis, inflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary,* 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstram's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

Cancer cells exhibit properties that are similar to the properties of embryonic stem cells. As used herein, cancer stem eclls (CSCs) are embryonic-like cancer cells that have one or more embryonic features. CSCs are generally considered to be problematic cancer cells due to the ability to metastasize and form tumors at other sites in the body. As used herein, "embryonic features" refers to gene and/or miRNA expression and/or similar biological properties as an embryonic cell. Non-differentiated, cancer cells with embryonic properties have the ability to metastasize, are resistant to chemotherapies and radiation therapy, and have the ability to re-grow a tumor after most of the tumor has been removed or diminished after surgery and/or additional cancer therapeutic treatment.

In some embodiments, the cancer stem cells are characterized by expression of genes and/or miRNAs associated with the embryonic state. In some embodiments, the cancer stem cells express one or more (e.g., 1, 2, 3, 4, 5, 6, or more) genes or miRNAs associated with the embryonic state.

In some embodiments, the cancer stem cells are characterized by one or more embryonic features. Examples of embryonic features include, without limitation, cellular self-renewal properties, hyperproliferative activity, multipotency, pluripotency, expression of embryonic markers, lack of differentiation markers, resistance to chemotherapy, motility, and the ability to give rise to different lineages of cells.

As used herein, the term "regenerative medicine" or "regenerative therapy" refers to promoting the regenerative capacity of a cell, tissue, and/or organ. Regenerative medicine encompasses cellular and/or tissue engineering to replace, engineer, or regenerate cells, tissues, and/or organs and/or restoring or improving one or more biological function of a cell, tissue, and/or organ that is dysfunctional or impaired; as well as tissue engineering and organ regeneration. As used herein, "regenerative capacity" refers to conversion of a cell, such as a stem cell, into dividing progenitor cell and differentiated tissue-specific cell. Regenerative capacity may additionally or alternatively refer to the ability of a cell, tissue, and/or organ to replicate, proliferate, regain function, and/or regenerate.

An "effective amount" of a composition described herein refers to an amount sufficient to elicit the desired biological response. An effective amount of a composition described herein may vary depending on such factors as the desired biological endpoint, the pharmacokinetics of the composition, the condition being treated, the mode of administration, and the age and health of the subject. In certain embodiments, an effective amount is a therapeutically effective amount. In certain embodiments, an effective amount is a prophylactically effective amount. In certain embodiments, an effective amount is the amount of a composition or pharmaceutical composition described herein in a single dose. In certain embodiments, an effective amount is the combined amounts of a composition or pharmaceutical composition described herein in multiple doses.

A "therapeutically effective amount" of a composition described herein is an amount sufficient to provide a therapeutic benefit in the treatment of a condition or to delay or minimize one or more symptoms associated with the condition. A therapeutically effective amount of a composition means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "gene" refers to a nucleic acid fragment that provides a template that can be used for producing a gene product. In certain embodiments, the nucleic acid fragment includes regulatory sequences preceding and following the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

The terms "nucleic acid" or "nucleic acid sequence", "nucleic acid molecule", "nucleic acid fragment" or "polynucleotide" are used interchangeably. A polynucleotide molecule is a biopolymer composed of nucleotide monomers covalently bonded in a chain. DNA (deoxyribonucleic acid) and RNA (ribonucleic acid) are examples of polynucleotides with distinct biological function. DNA consists of two chains of polynucleotides, with each chain in the form of a helical spiral. RNA is more often found in nature as a single-strand folded onto itself. Exemplary types of RNA include double-stranded RNA (dsRNA), small interfering RNA (siRNA), short hairpin (shRNA), microRNA (miRNA), messenger RNA (mRNA), antisense RNA, transfer RNA (tRNA), small nuclear RNA (snRNA), and ribosomal RNA (rRNA).

The disclosure is not intended to be limited in any manner by the above exemplary listing of substituents. Additional terms may be defined in other sections of this disclosure.

DETAILED DESCRIPTION OF CERTAIN EMBODIMENTS

Before the disclosed systems, compounds, compositions, methods, uses, and kits are described in more detail, it should be understood that the aspects described herein are not limited to specific embodiments, methods, apparati, or configurations, and as such can, of course, vary. It is also to be understood that the terminology used herein is for the purpose of describing particular aspects only and, unless specifically defined herein, is not intended to be limiting.

The compounds of the disclosure, and compositions and kits thereof, are useful for cancer treatment and the treatment of proliferative diseases. The compounds may differentiate embryonic-like cancer stem cells, disrupt their proliferation, and/or inhibit their ability to form new tumors. Embryonic-like properties, including embryonic gene expression patterns, are re-activated across a variety of different types of cancers. In certain embodiments, the cancer is colorectal cancer, gastric cancer, gastrointestinal stromal tumor, ovarian cancer, lung cancer, breast cancer, pancreatic cancer, prostate cancer, testicular cancer, or lymphoma. For example, embryonic-like properties have been found in cancer stem cells from solid tumors, such as colorectal cancer, gastric cancer, ovarian cancer, lung cancer, breast cancer, pancreatic cancer, and prostate cancer.[10] Embryonic-like properties have been also found in cancer stem cells from hematopoietic cancers, such as leukemias and lymphoma.[14]

Compounds

In certain aspects, the present disclosure provides compounds of Formula (0) and (0').

The present disclosure describes compounds of Formula (I) as described herein.

In certain embodiments, the compound is a compound of Formula (0):

(0)

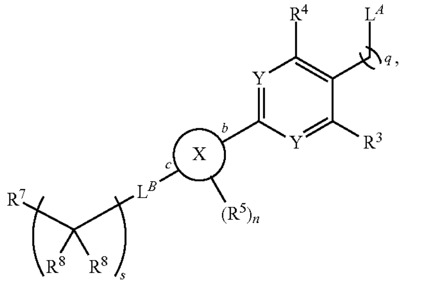

or a pharmaceutically acceptable salt, solvate, hydrate, polymorph, co-crystal, tautomer, stereoisomer, isotopically labeled derivative, or prodrug thereof, wherein:

$L^A$ is —N($R^2$)($L^1R^1$) or —C(═O)N$R^1R^2$;

$L^1$ is a single bond or —C(═O)—;

when $L^1$ is a single bond, $R^1$ is substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, or substituted or unsubstituted, 5- to 11-membered, monocyclic or bicyclic heteroaryl;

when $L^1$ is —C(═O)—, $R^1$ is substituted $C_{1-6}$ alkyl, wherein the substituent comprises at least one double bond, triple bond, or heteroatom; substituted or unsubstituted, $C_{2-6}$ alkenyl, substituted or unsubstituted, $C_{2-6}$ alkynyl; substituted or unsubstituted, 3- to 13-membered, monocyclic or bicyclic carbocyclyl; substituted or unsubstituted, 3- to 13-membered, monocyclic or bicyclic heterocyclyl; substituted or unsubstituted, 6- to 11-membered, monocyclic or bicyclic aryl; or substituted or unsubstituted, 5- to 11-membered, monocyclic or bicyclic heteroaryl;

$R^2$ is hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 5- to 11-membered, monocyclic or bicyclic heteroaryl, or a nitrogen protecting group;

$R^3$ is hydrogen, halogen, substituted or unsubstituted, $C_{1-6}$ alkyl, —$OR^a$, —$N(R^a)_2$, or —CN;

each instance of $R^a$ is independently hydrogen, substituted or unsubstituted, $C_{1-6}$ alkyl, an oxygen protecting group when attached to an oxygen atom, or a nitrogen protecting group when attached to a nitrogen atom;

or $R^2$ and $R^3$ are joined with their intervening atoms to form substituted or unsubstituted, 5-membered, monocyclic, heterocyclyl or heteroaryl;

q is 0 or 1;

each instance of Y is independently N or $CR^4$;

each instance of $R^4$ is independently hydrogen, halogen, substituted or unsubstituted, $C_{1-6}$ alkyl, —$OR^a$, —$N(R^a)_2$, or —CN;

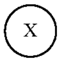

is phenyl, pyridinyl, pyridazinyl, pyrimidinyl, pyrazinyl, imidazolyl, oxazolyl, thiazolyl, piperidinyl, piperazinyl, morpholinyl, thiomorpholinyl, azetidinyl, —C≡C—, or

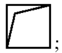;

bond b and bond c are meta or para to each other when

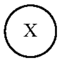

is phenyl, pyridinyl, pyridazinyl, pyrimidinyl, or pyrazinyl;

each instance of $R^5$ is independently hydrogen, halogen, substituted or unsubstituted, $C_{1-6}$ alkyl, —$OR^a$, —$N(R^a)_2$, or —CN;

n is 0, 1, 2, 3, or 4, as valency permits, wherein when n is 1, 2, 3, or 4, no instance of $R^5$ is attached to a nitrogen atom;

$L^B$ is —$N(R^6)L^2$-, or -$L^2N(R^6)$—;

$L^2$ is —C(═O)—,

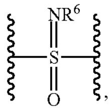, or —$S(═O)_2$—;

each $R^6$ is independently hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, substituted or unsubstituted, 5- to 11-membered, monocyclic or bicyclic heteroaryl, or a nitrogen protecting group;

s is 0 or 1;

$R^7$ is substituted or unsubstituted, 3- to 7-membered, monocyclic carbocyclyl, substituted or unsubstituted, 3- to 7-membered, monocyclic heterocyclyl, substituted or unsubstituted phenyl, or substituted or unsubstituted, 5- or 6-membered, monocyclic heteroaryl; and each instance of $R^8$ is independently hydrogen, halogen, substituted or unsubstituted, $C_{1-6}$ alkyl, —$OR^a$, —$N(R^a)_2$, or —CN.

In certain embodiments, a compound of Formula (0') is of the formula:

(0')

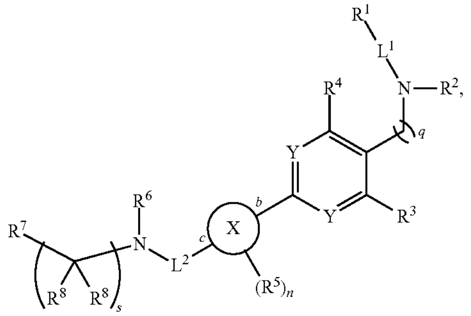

or a pharmaceutically acceptable salt, solvate, hydrate, polymorph, co-crystal, tautomer, stereoisomer, isotopically labeled derivative, or prodrug thereof, wherein:

$L^1$ is a single bond or —C(═O)—;

when $L^1$ is a single bond, $R^1$ is substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, or substituted or unsubstituted, 5- to 11-membered, monocyclic or bicyclic heteroaryl;

when $L^1$ is —C(═O)—, $R^1$ is substituted $C_{1-6}$ alkyl, wherein the substituent comprises at least one double bond, triple bond, or heteroatom; substituted or unsubstituted, $C_{2-6}$ alkenyl, substituted or unsubstituted, $C_{2-6}$ alkynyl; substituted or unsubstituted, 3- to 13-membered, monocyclic or bicyclic carbocyclyl; substituted or unsubstituted, 3- to 13-membered, monocyclic or bicyclic heterocyclyl; substituted or unsubstituted, 6- to 11-membered, monocyclic or bicyclic aryl; or substituted or unsubstituted, 5- to 11-membered, monocyclic or bicyclic heteroaryl;

$R^2$ is hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 5- to 11-membered, monocyclic or bicyclic heteroaryl, or a nitrogen protecting group;

$R^3$ is hydrogen, halogen, substituted or unsubstituted, $C_{1-6}$ alkyl, —$OR^a$, —$N(R^a)_2$, or —CN;

each instance of $R^a$ is independently hydrogen, substituted or unsubstituted, $C_{1-6}$ alkyl, an oxygen protecting group when attached to an oxygen atom, or a nitrogen protecting group when attached to a nitrogen atom;

or $R^2$ and $R^3$ are joined with their intervening atoms to form substituted or unsubstituted, 5-membered, monocyclic, heterocyclyl or heteroaryl;

q is 0 or 1;

each instance of Y is independently N or $CR^4$;

each instance of $R^4$ is independently hydrogen, halogen, substituted or unsubstituted, $C_{1-6}$ alkyl, —$OR^a$, —$N(R^a)_2$, or —CN;

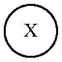

is phenyl, pyridinyl, pyridazinyl, pyrimidinyl, pyrazinyl, imidazolyl, oxazolyl, thiazolyl, piperidinyl, piperazinyl, morpholinyl, thiomorpholinyl, azetidinyl, —C≡C—, or

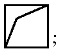;

bond b and bond c are meta or para to each other when

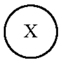

is phenyl, pyridinyl, pyridazinyl, pyrimidinyl, or pyrazinyl;

each instance of $R^5$ is independently hydrogen, halogen, substituted or unsubstituted, $C_{1-6}$ alkyl, —$OR^a$, —$N(R^a)_2$, or —CN;

n is 0, 1, 2, 3, or 4, as valency permits, wherein when n is 1, 2, 3, or 4, no instance of $R^5$ is attached to a nitrogen atom;

$L^2$ is —C(═O)—,

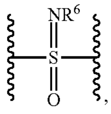, or —$S(═O)_2$—;

each $R^6$ is independently hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, substituted or unsubstituted, 5- to 11-membered, monocyclic or bicyclic heteroaryl, or a nitrogen protecting group;

s is 0 or 1;

$R^7$ is substituted or unsubstituted, 3- to 7-membered, monocyclic carbocyclyl, substituted or unsubstituted, 3- to 7-membered, monocyclic heterocyclyl, substituted or unsubstituted phenyl, or substituted or unsubstituted, 5- or 6-membered, monocyclic heteroaryl; and each instance of $R^8$ is independently hydrogen, halogen, substituted or unsubstituted, $C_{1-6}$ alkyl, —$OR^a$, —$N(R^a)_2$, or —CN.

In certain embodiments, the compound is a compound of Formula (I):

(I)

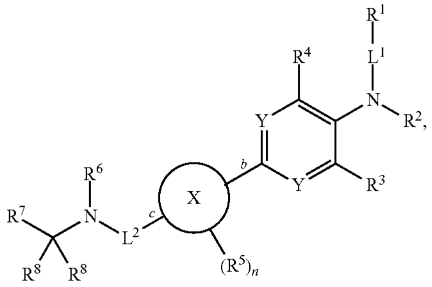

or a pharmaceutically acceptable salt, solvate, hydrate, polymorph, co-crystal, tautomer, stereoisomer, isotopically labeled derivative, or prodrug thereof, wherein:

$L^1$ is a single bond or —C(═O)—;

when $L^1$ is a single bond, $R^1$ is substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, or substituted or unsubstituted, 5- to 11-membered, monocyclic or bicyclic heteroaryl;

when $L^1$ is —C(═O)—, $R^1$ is substituted $C_{1-6}$ alkyl that comprises at least one double bond, triple bond, or heteroatom; substituted or unsubstituted, $C_{2-6}$ alkenyl, substituted or unsubstituted, $C_{2-6}$ alkynyl; substituted or unsubstituted, 3- to 13-membered, monocyclic or bicyclic carbocyclyl; substituted or unsubstituted, 3- to 13-membered, monocyclic or bicyclic heterocyclyl; substituted or unsubstituted, 6- to 11-membered, monocyclic or bicyclic aryl; or substituted or unsubstituted, 5- to 11-membered, monocyclic or bicyclic heteroaryl;

$R^2$ is hydrogen, substituted or unsubstituted, $C_{1-6}$ alkyl, or a nitrogen protecting group;

$R^3$ is halogen, substituted or unsubstituted, $C_{1-6}$ alkyl, —$OR^a$, —$N(R^a)_2$, or —CN;

each instance of $R^a$ is independently hydrogen, substituted or unsubstituted, $C_{1-6}$ alkyl, an oxygen protecting group when attached to an oxygen atom, or a nitrogen protecting group when attached to a nitrogen atom;

or $R^2$ and $R^3$ are joined with their intervening atoms to form substituted or unsubstituted, 5-membered, monocyclic, heterocyclyl or heteroaryl;

each instance of Y is independently N or $CR^4$;

each instance of $R^4$ is independently hydrogen, halogen, substituted or unsubstituted, $C_{1-6}$ alkyl, —$OR^a$, —$N(R^a)_2$, or —CN;

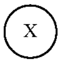

is phenyl, pyridinyl, pyridazinyl, pyrimidinyl, pyrazinyl, imidazolyl, oxazolyl, azetidinyl, —C≡C—, or

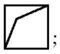;

bond b and bond c are meta or para to each other;

each instance of $R^5$ is independently hydrogen, halogen, substituted or unsubstituted, $C_{1-6}$ alkyl, —$OR^a$, —$N(R^a)_2$, or —CN;

n is 0, 1, 2, 3, or 4, as valency permits, wherein when n is 1, 2, 3, or 4, no instance of $R^5$ is attached to a nitrogen atom;

$L^2$ is —C(═O)— or —$S(═O)_2$—;

$R^6$ is hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, substituted or unsubstituted, 5- to 11-membered, monocyclic or bicyclic heteroaryl, or a nitrogen protecting group;

$R^7$ is substituted or unsubstituted, 3- to 7-membered, monocyclic carbocyclyl, substituted or unsubstituted, 3- to 7-membered, monocyclic heterocyclyl, substituted or unsubstituted phenyl, or substituted or unsubstituted, 5- or 6-membered, monocyclic heteroaryl; and each instance of $R^8$ is independently hydrogen, halogen, substituted or unsubstituted, $C_{1-6}$ alkyl, —$OR^a$, —$N(R^a)_2$, or —CN.

In certain embodiments:

$L^1$ is a single bond or —C(═O)—;

when $L^1$ is a single bond, $R^1$ is substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, or substituted or unsubstituted, 5- to 11-membered, monocyclic or bicyclic heteroaryl;

when $L^1$ is —C(═O)—, $R^1$ is substituted $C_{1-6}$ alkyl that comprises at least one double bond, triple bond, or heteroatom; substituted or unsubstituted, $C_{2-6}$ alkenyl, substituted or unsubstituted, $C_{2-6}$ alkynyl; substituted or unsubstituted, 3- to 13-membered, monocyclic or bicyclic carbocyclyl; substituted or unsubstituted, 3- to 13-membered, monocyclic or bicyclic heterocyclyl; substituted or unsubstituted, 6- to 11-membered, monocyclic or bicyclic aryl; or substituted or unsubstituted, 5- to 11-membered, monocyclic or bicyclic heteroaryl;

$R^2$ is hydrogen, substituted or unsubstituted, $C_{1-6}$ alkyl, or a nitrogen protecting group;

$R^3$ is halogen, substituted or unsubstituted, $C_{1-6}$ alkyl, —$OR^a$, —$N(R^a)_2$, or —CN;

each instance of $R^a$ is independently hydrogen, substituted or unsubstituted, $C_{1-6}$ alkyl, an oxygen protecting group when attached to an oxygen atom, or a nitrogen protecting group when attached to a nitrogen atom;

or $R^2$ and $R^3$ are joined with their intervening atoms to form substituted or unsubstituted, 5-membered, monocyclic, heterocyclyl or heteroaryl;

each instance of Y is independently N or $CR^4$;

each instance of $R^4$ is independently hydrogen, halogen, substituted or unsubstituted, $C_{1-6}$ alkyl, —$OR^a$, —$N(R^a)_2$, or —CN;

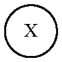

is phenyl, pyridinyl, pyridazinyl, pyrimidinyl, or pyrazinyl;

bond b and bond c are meta or para to each other;

each instance of $R^5$ is independently hydrogen, halogen, substituted or unsubstituted, $C_{1-6}$ alkyl, —$OR^a$, —$N(R^a)_2$, or —CN;

n is 0, 1, 2, 3, or 4, as valency permits, wherein when n is 1, 2, 3, or 4, no instance of $R^5$ is attached to a nitrogen atom;

$L^2$ is —C(═O)— or —$S(═O)_2$—;

$R^6$ is hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, substituted or unsubstituted, 5- to 11-membered, monocyclic or bicyclic heteroaryl, or a nitrogen protecting group;

$R^7$ is substituted or unsubstituted, 3- to 7-membered, monocyclic carbocyclyl, substituted or unsubstituted, 3- to 7-membered, monocyclic heterocyclyl, substituted or unsubstituted phenyl, or substituted or unsubstituted, 5- or 6-membered, monocyclic heteroaryl; and each instance of $R^8$ is independently hydrogen, halogen, substituted or unsubstituted, $C_{1-6}$ alkyl, —$OR^a$, —$N(R^a)_2$, or —CN.

In certain embodiments, the compound is a compound of Formula (I):

(I)

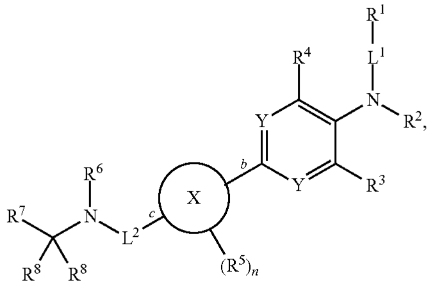

or a pharmaceutically acceptable salt, solvate, hydrate, polymorph, co-crystal, tautomer, stereoisomer, isotopically labeled derivative, or prodrug thereof, wherein:

$L^1$ is a single bond or —C(═O)—;

when $L^1$ is a single bond, $R^1$ is substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, or substituted or unsubstituted, 5- to 11-membered, monocyclic or bicyclic heteroaryl;

when $L^1$ is —C(═O)—, $R^1$ is substituted $C_{1-6}$ alkyl that comprises at least one double bond, triple bond, or heteroatom; substituted or unsubstituted, $C_{2-6}$ alkenyl, substituted or unsubstituted, $C_{2-6}$ alkynyl; substituted or unsubstituted, 3- to 13-membered, monocyclic or bicyclic carbocyclyl; substituted or unsubstituted, 3- to 13-membered, monocyclic or bicyclic heterocyclyl; substituted or unsubstituted, 6- to 11-membered, monocyclic or bicyclic aryl; or substituted or unsubstituted, 5- to 11-membered, monocyclic or bicyclic heteroaryl;

$R^2$ is hydrogen, substituted or unsubstituted, $C_{1-6}$ alkyl, or a nitrogen protecting group;

$R^3$ is halogen, substituted or unsubstituted, $C_{1-6}$ alkyl, —$OR^a$, —$N(R^a)_2$, or —CN;

each instance of $R^a$ is independently hydrogen, substituted or unsubstituted, $C_{1-6}$ alkyl, an oxygen protecting group when attached to an oxygen atom, or a nitrogen protecting group when attached to a nitrogen atom;

or $R^2$ and $R^3$ are joined with their intervening atoms to form substituted or unsubstituted, 5-membered, monocyclic, heterocyclyl or heteroaryl;

each instance of Y is independently N or $CR^4$;

each instance of $R^4$ is independently hydrogen, halogen, substituted or unsubstituted, $C_{1-6}$ alkyl, —$OR^a$, —$N(R^a)_2$, or —CN;

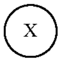

is phenyl, pyridinyl, pyridazinyl, pyrimidinyl, or pyrazinyl; bond b and bond c are meta or para to each other;

each instance of $R^5$ is independently hydrogen, halogen, substituted or unsubstituted, $C_{1-6}$ alkyl, —$OR^a$, —$N(R^a)_2$, or —CN;

n is 0, 1, 2, 3, or 4, as valency permits, wherein when n is 1, 2, 3, or 4, no instance of $R^5$ is attached to a nitrogen atom;

$L^2$ is —C(═O)— or —S(═O)$_2$—;

$R^6$ is hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, substituted or unsubstituted, 5- to 11-membered, monocyclic or bicyclic heteroaryl, or a nitrogen protecting group;

$R^7$ is substituted or unsubstituted, 3- to 7-membered, monocyclic carbocyclyl, substituted or unsubstituted, 3- to 7-membered, monocyclic heterocyclyl, substituted or unsubstituted phenyl, or substituted or unsubstituted, 5- or 6-membered, monocyclic heteroaryl; and each instance of $R^8$ is independently hydrogen, halogen, substituted or unsubstituted, $C_{1-6}$ alkyl, —$OR^a$, —$N(R^a)_2$, or —CN.

In certain embodiments, Formula (I) is Formula (I-A):

(I-A)

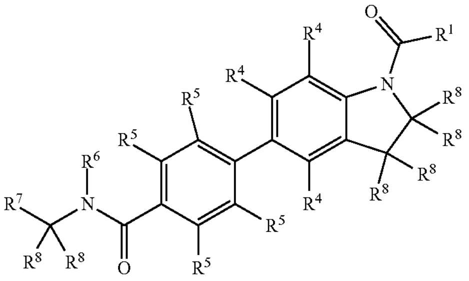

(e.g.,

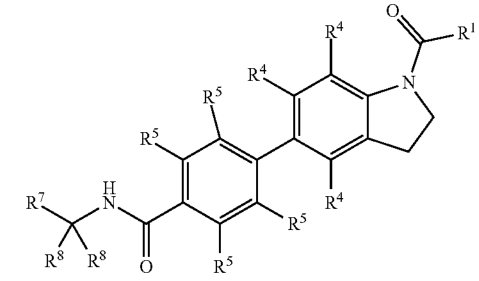

,

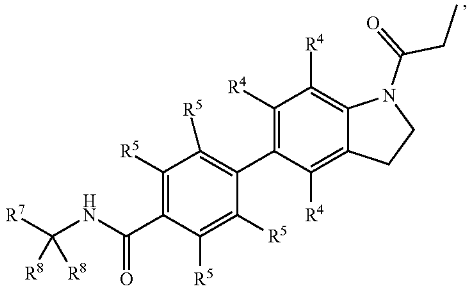

,

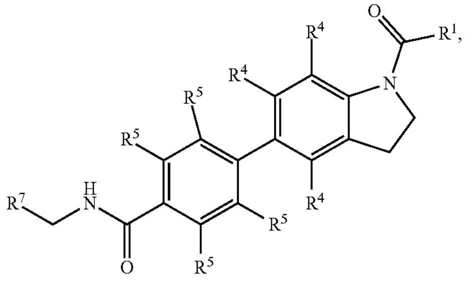

,

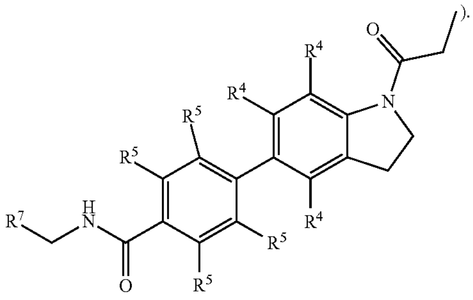

).

In certain embodiments, Formula (I) is the formula:

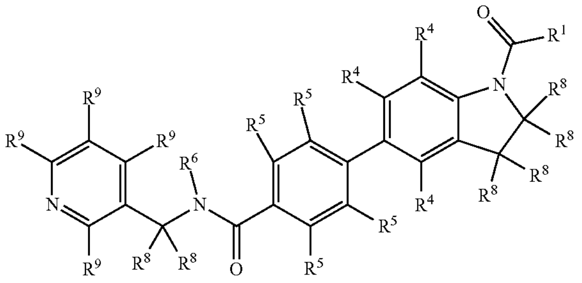

(e.g.,

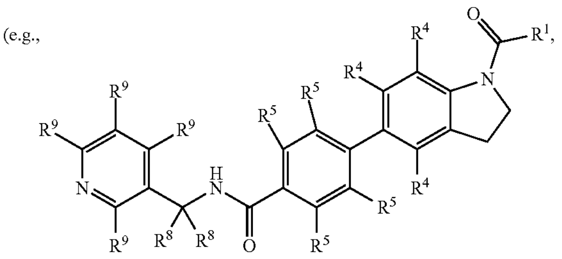

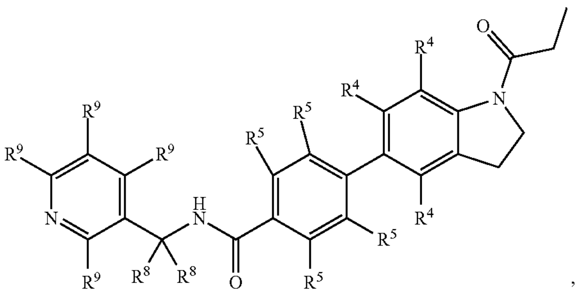

,

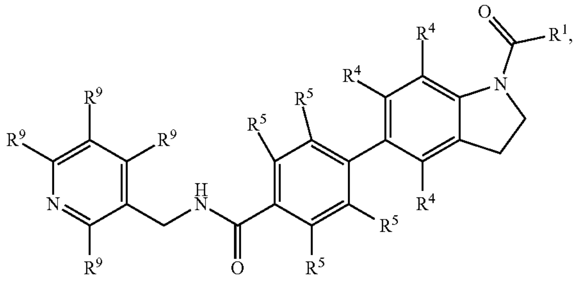

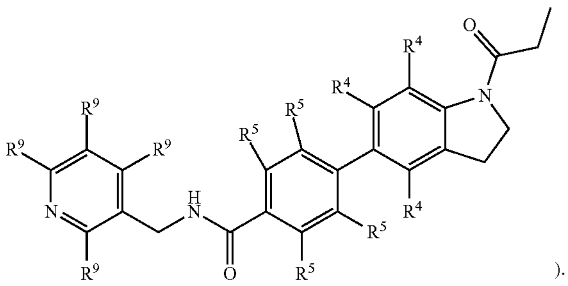

).

In certain embodiments, Formula (I) is Formula (I-B):

(I-B)

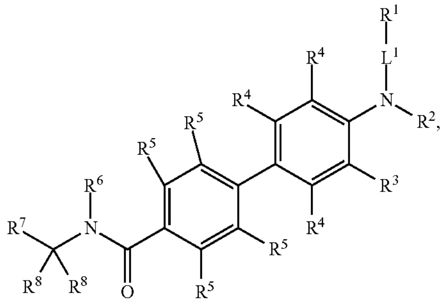

wherein $R^7$ is substituted or unsubstituted, 3-pyridinyl.

In certain embodiments, Formula (I) is Formula (I-C):

(I-C)

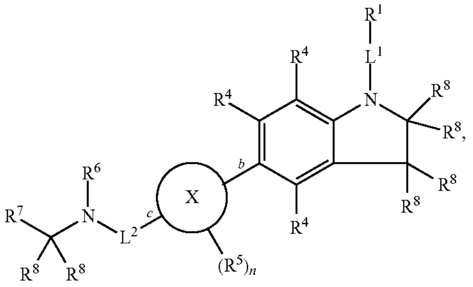

wherein

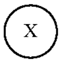

is pyridinyl, pyridazinyl, pyrimidinyl, or pyrazinyl. In certain embodiments, Formula (I) is Formula (I-C), wherein

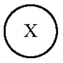

is imidazolyl or oxazolyl. In certain embodiments, Formula (I) is Formula (I-C), wherein

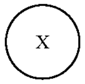

is azetidinyl. In certain embodiments, Formula (I) is Formula (I-C), wherein

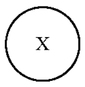

is —C≡C—. In certain embodiments, Formula (I) is Formula (I-C), wherein

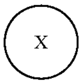

is

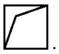.

In certain embodiments, a compound of Formula (I) is of the Formula (I-C):

(I-C)

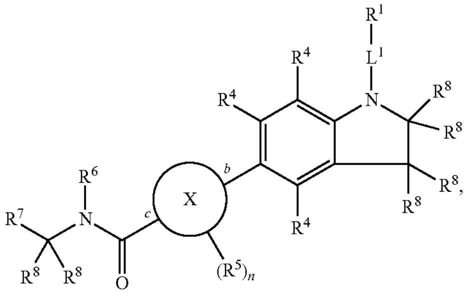

wherein

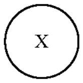

is thiazolyl, piperidinyl, piperazinyl, morpholinyl or thiomorpholinyl. In certain embodiments, Formula (I) is Formula (I-C), wherein

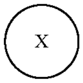

is thiazolyl. In certain embodiments, Formula (I) is Formula (I-C), wherein

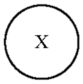

is piperidinyl, piperazinyl, morpholinyl or thiomorpholinyl. In certain embodiments, Formula (I) is Formula (I-C), wherein

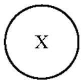

is piperazinyl.

In certain embodiments, Formula (I) is Formula (I-D):

(I-D)

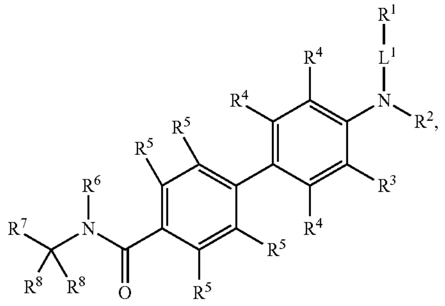

wherein $R^7$ is substituted or unsubstituted, 3- to 7-membered, monocyclic heterocyclyl or substituted or unsubstituted, 5- or 6-membered, monocyclic heteroaryl.

In certain embodiments, Formula (I) is the formula:

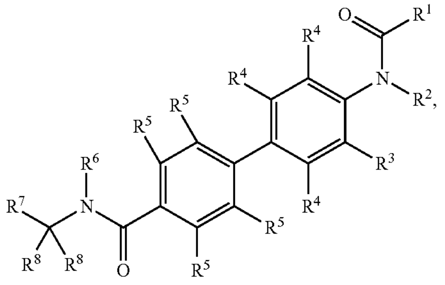

wherein $R^7$ is substituted or unsubstituted, 5- or 6-membered, monocyclic heteroaryl (e.g., substituted or unsubstituted, 3-pyridinyl).

In certain embodiments, Formula (I) is the formula:

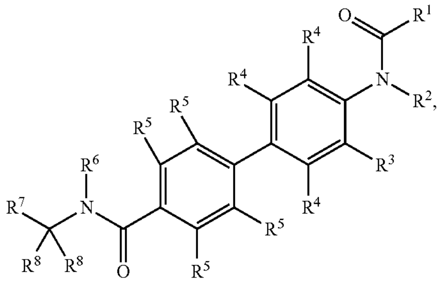

wherein:

$R^1$ is substituted or unsubstituted, $C_{1-6}$ alkyl (e.g., unsubstituted $C_{1-6}$ alkyl);

$R^2$ is substituted or unsubstituted, $C_{1-6}$ alkyl (e.g., unsubstituted $C_{1-3}$ alkyl); and $R^7$ is substituted or unsubstituted pyridinyl (e.g., substituted or unsubstituted, 3-pyridinyl).

In certain embodiments, Formula (I) is the formula:

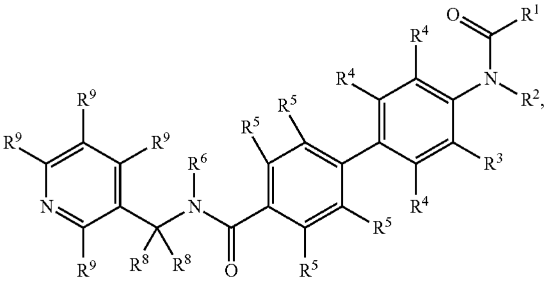

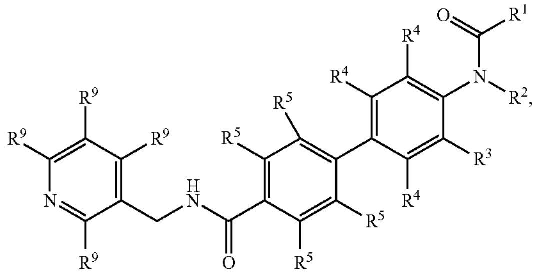

(e.g.,

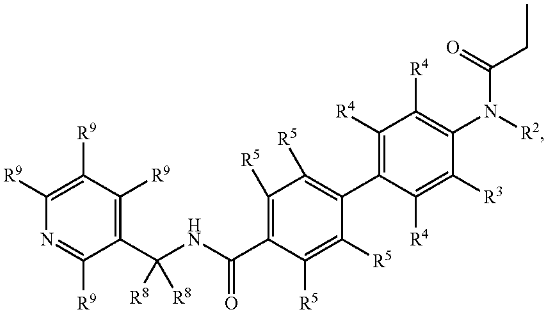

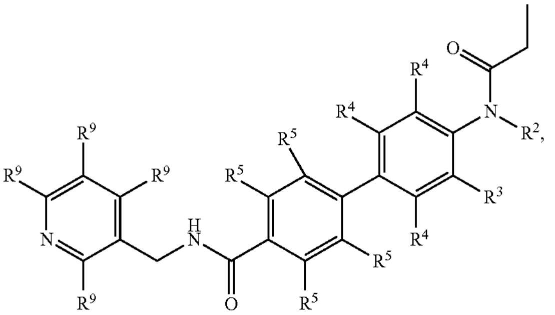

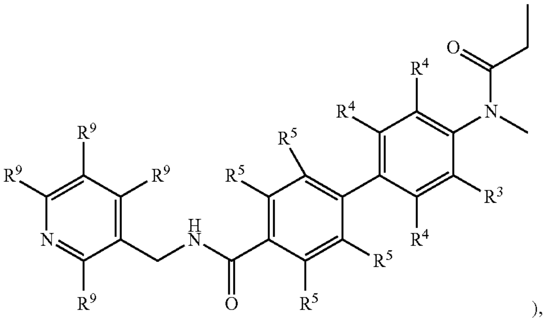

), wherein $R^2$ is substituted or unsubstituted, $C_{1-6}$ alkyl (e.g., Me).

In certain embodiments, Formula (I) is Formula (I-1A):

(I-1A)

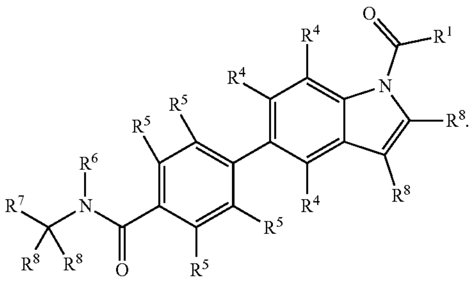

In certain embodiments, Formula (I) is Formula (I-1B):

(I-1B)

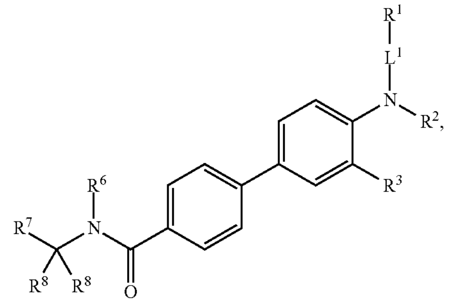

wherein $R^7$ is substituted or unsubstituted, 3-pyridinyl.

In certain embodiments, Formula (I) is Formula (I-1C):

(I-1C)

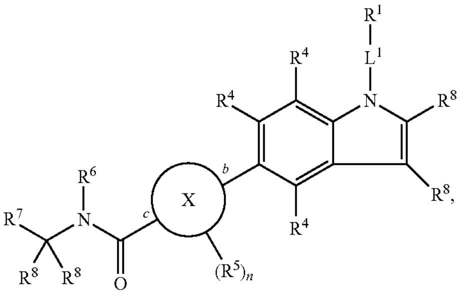

wherein

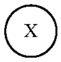

is pyridinyl, pyridazinyl, pyrimidinyl, or pyrazinyl. In certain embodiments, Formula (I) is Formula (I-1C), wherein

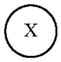

is imidazolyl, oxazolyl, azetidinyl, —C≡C—, or

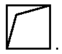.

In certain embodiments, Formula (I) is Formula (I-1C):

(I-1C)

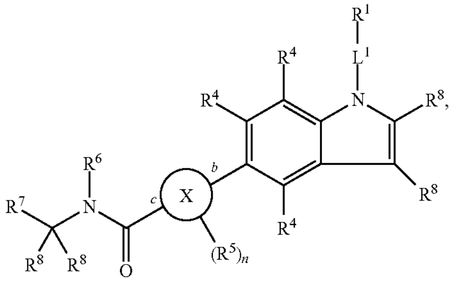

wherein

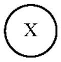

is thiazolyl, piperidinyl, piperazinyl, morpholinyl, or thiomorpholinyl.

In certain embodiments, Formula (I) is Formula (I-1D):

(I-1D)

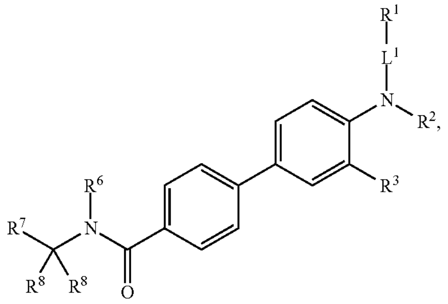

wherein $R^7$ is substituted or unsubstituted, 3- to 7-membered, monocyclic heterocyclyl or substituted or unsubstituted, 5- or 6-membered, monocyclic heteroaryl.

In certain embodiments, Formula (I) is the formula:

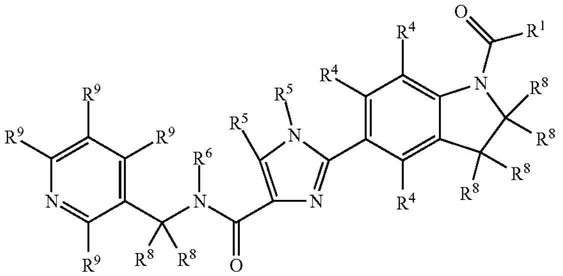

-continued (e.g.,

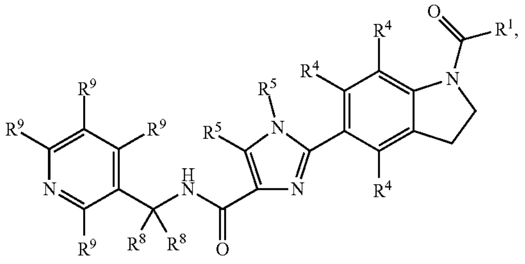

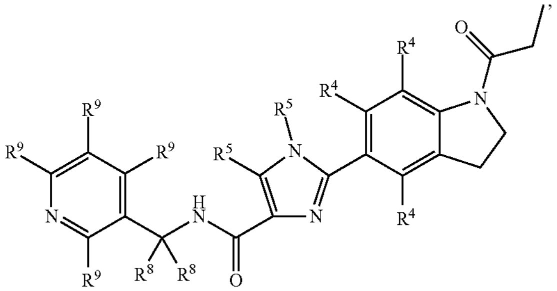

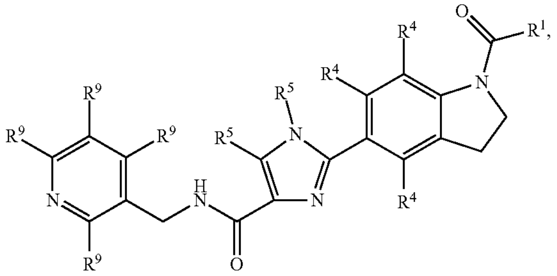

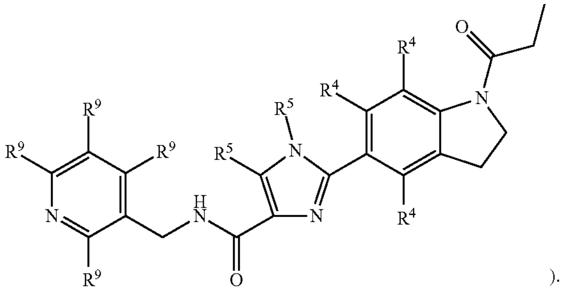

).

In certain embodiments, Formula (I) is the formula:

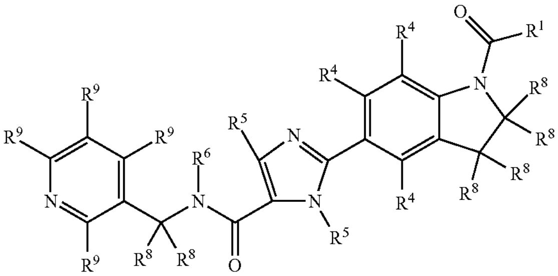

(e.g.,
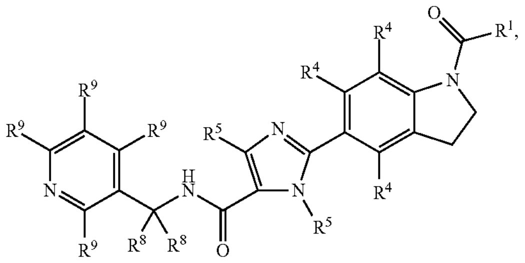
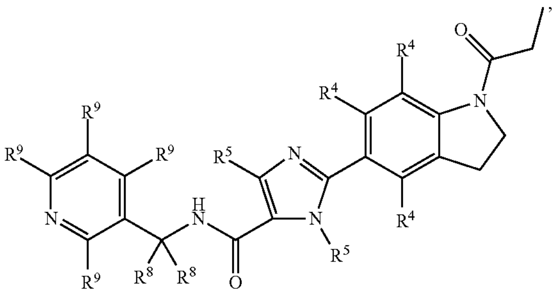
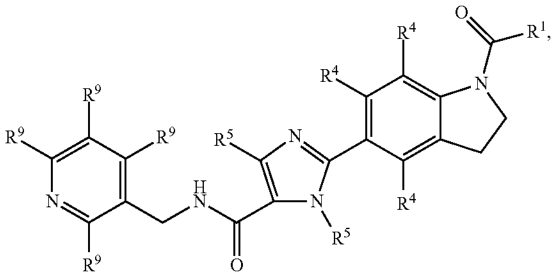
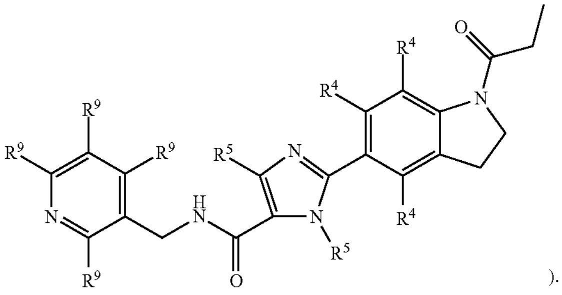
).
In certain embodiments, Formula (I) is the formula:
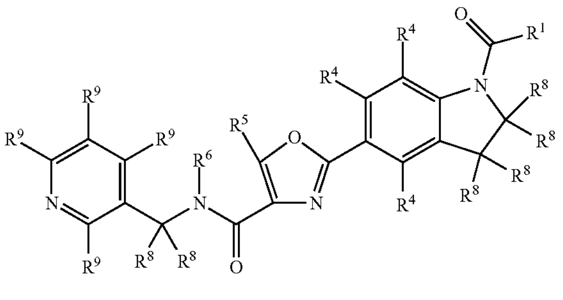
(e.g.,
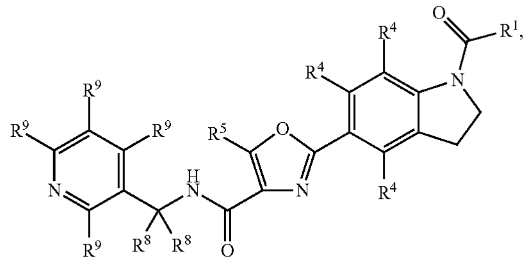
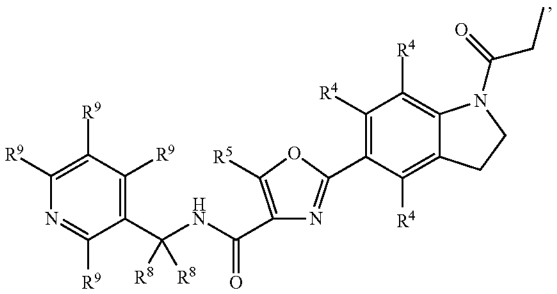
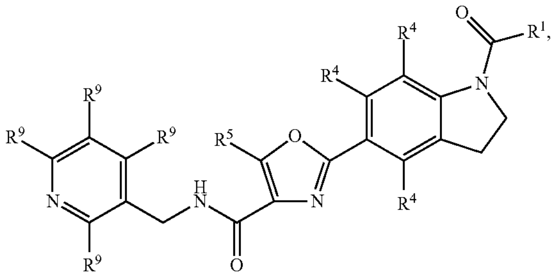
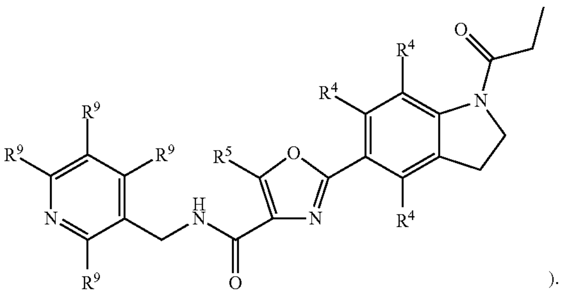
).
In certain embodiments, Formula (I) is the formula:
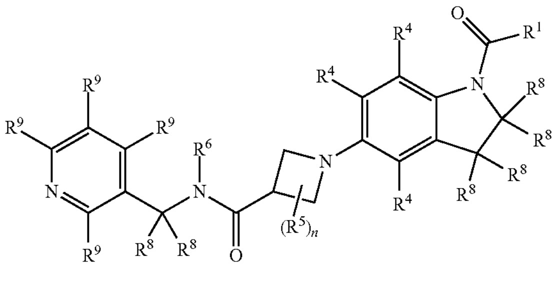

-continued
(e.g.,
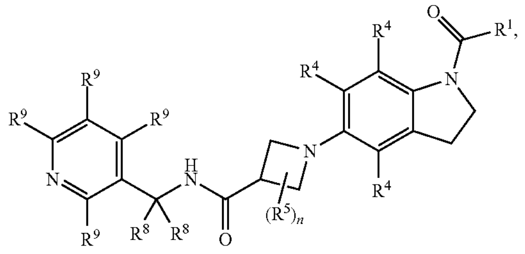
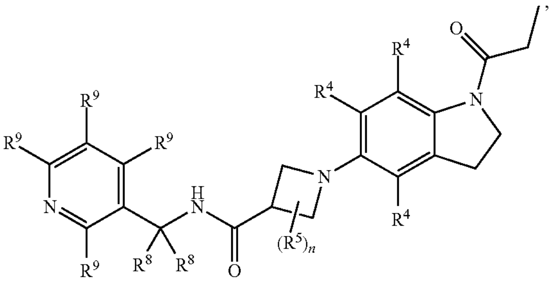
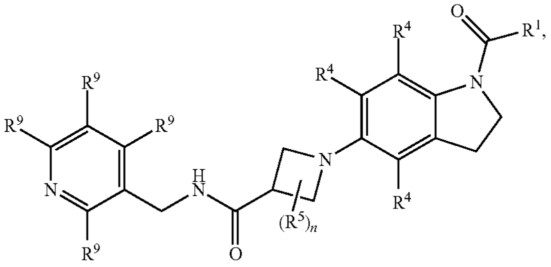
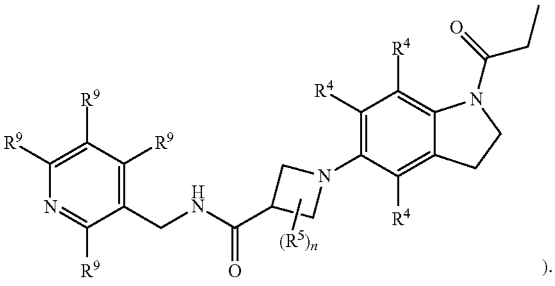
).
In certain embodiments, Formula (I) is the formula:
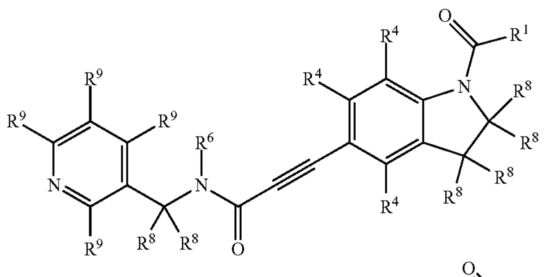
(e.g.,
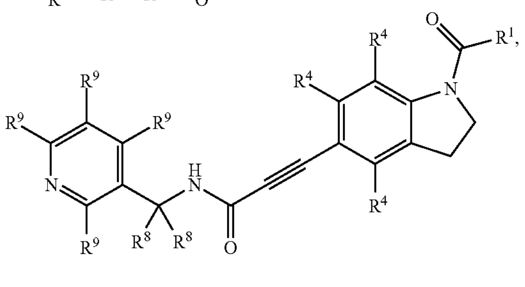
-continued
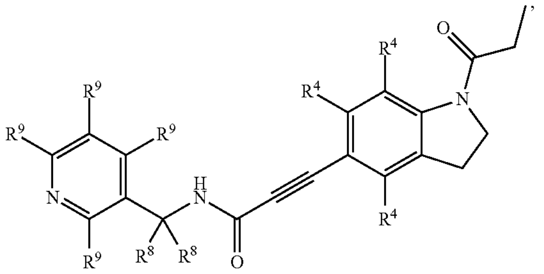
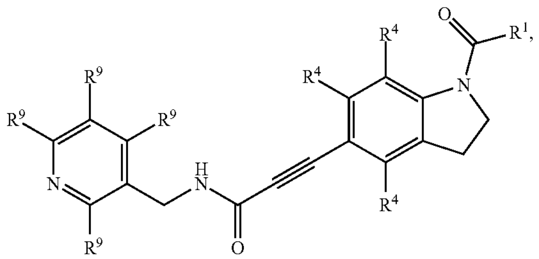
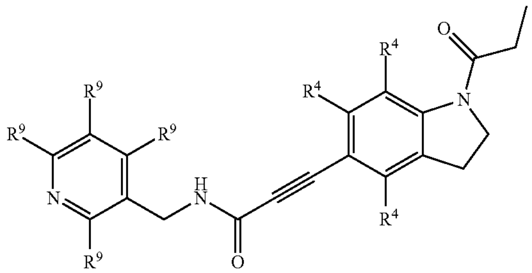
).
In certain embodiments, Formula (I) is the formula:
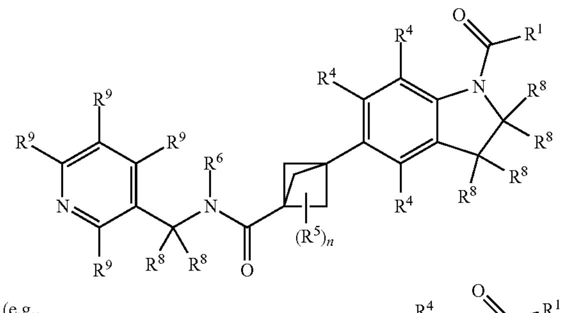
(e.g.,
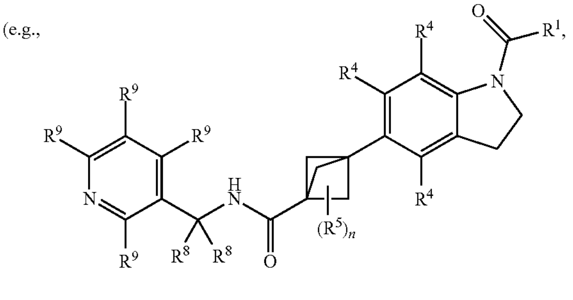

-continued

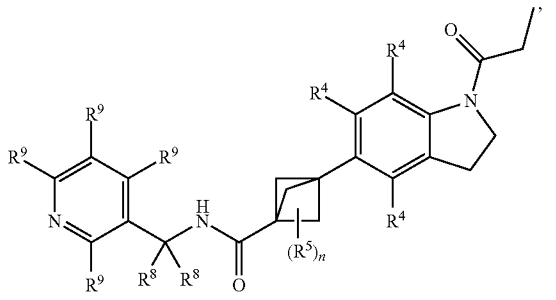

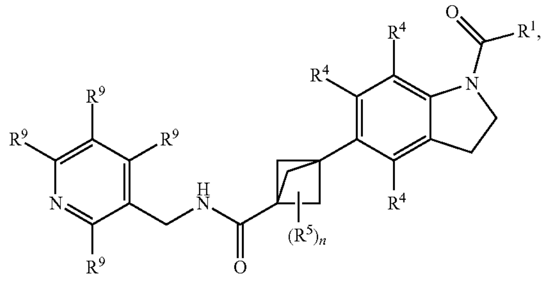

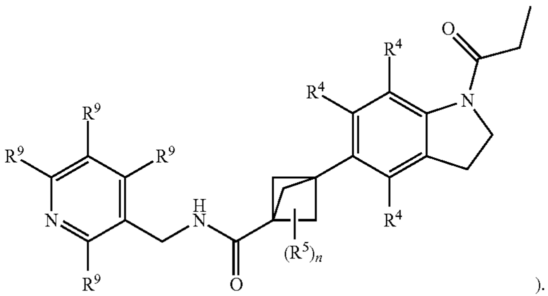

).

In certain embodiments, q is 0 or 1. In some embodiments, q is 1. In certain embodiments, q is 0.

In certain embodiments, $L^A$ is —C(=O)NR$^1$R$^2$. In certain embodiments, a compound of Formula (0) is of formula:

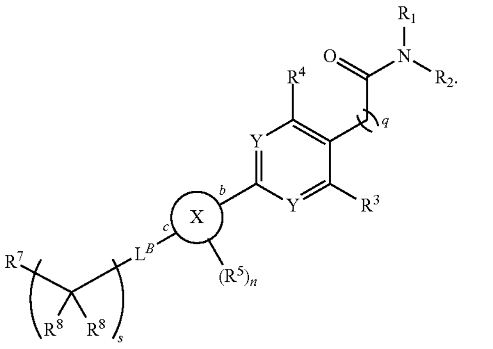

In certain embodiments, q is 0 or 1. In some embodiments, q is 1. In certain embodiments, q is 0.

In some embodiments, $L^A$ is —N(R$^2$)(L$^1$R$^1$). In certain embodiments, a compound of Formula (0) is of formula:

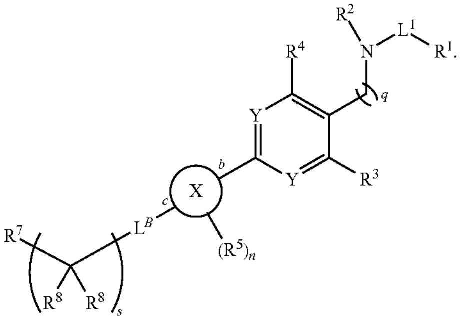

In certain embodiments, q is 0 or 1. In some embodiments, q is 1. In certain embodiments, q is 0. In certain embodiments, L is a single bond. In some embodiments, a compound of Formula (0) is of formula:

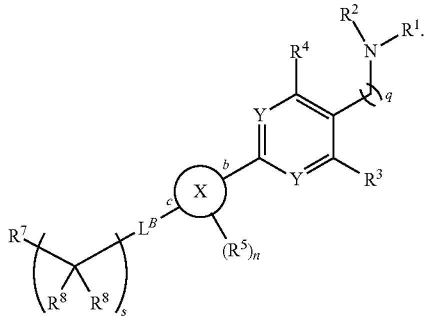

In certain embodiments, $L^1$ is —C(=O)—. In certain embodiments, a compound of Formula (0) is of formula:

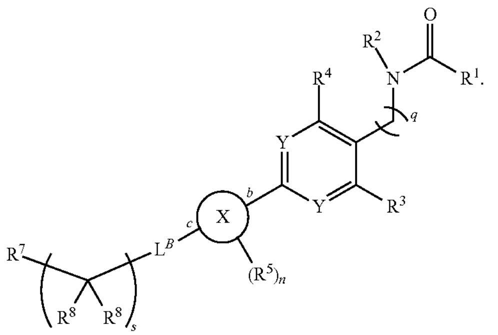

In certain embodiments, L is a single bond. In certain embodiments, $L^1$ is —C(=O)—.

In certain embodiments, L is a single bond and $R^1$ is substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, or substituted or unsubstituted, 5- to 11-membered, monocyclic or bicyclic heteroaryl. In certain embodiments, $R^1$ is substituted or unsubstituted, $C_{1-6}$ alkyl. In certain embodiments, $R^1$ is unsubstituted $C_{1-6}$ alkyl. In certain embodiments, $R^1$ is unsubstituted $C_1$ alkyl. In certain embodiments, $R^1$ is unsubstituted $C_2$ alkyl. In certain embodiments, $R^1$ is unsubstituted $C_3$ alkyl. In certain embodiments, $R^1$ is unsubstituted $C_4$ alkyl. In certain embodiments, $R^1$ is unsubstituted $C_5$ alkyl. In certain embodiments, $R^1$ is unsubstituted $C_6$ alkyl. In certain embodiments, $R^1$ is substituted $C_{1-6}$ alkyl. In certain embodiments, $R^1$ is substituted $C_1$ alkyl. In certain embodiments, $R^1$ is substituted $C_2$ alkyl. In certain embodiments, $R^1$ is substituted $C_3$ alkyl. In certain embodiments, $R^1$ is substituted $C_4$ alkyl. In certain embodiments, $R^1$ is substituted $C_5$ alkyl. In certain embodiments, $R^1$ is substituted $C_6$ alkyl. In certain embodiments, $R^1$ is fluorinated $C_{1-6}$ alkyl (e.g., —$CF_3$). In certain embodiments, $R^1$ is substituted or unsubstituted, $C_{2-6}$ alkenyl. In certain embodiments, $R^1$ is substituted or unsubstituted, $C_{2-6}$ alkenyl. In certain embodiments, $R^1$ is substituted or unsubstituted, $C_{2-6}$ alkynyl. In certain embodiments, $R^1$ is substituted or unsubstituted, 3- to 13-membered, monocyclic or bicyclic carbocyclyl. In certain embodiments, $R^1$ is substituted or unsubstituted, 3- to 13-membered, monocyclic or bicyclic heterocyclyl. In certain embodiments, $R^1$ substituted or unsubstituted, 5- to 11-membered, monocyclic or bicyclic heteroaryl.

In certain embodiments, $L^1$ is —C(═O)—; and $R^1$ is substituted $C_{1-6}$ alkyl that comprises at least one double bond, triple bond, or heteroatom; substituted or unsubstituted, $C_{2-6}$ alkenyl, substituted or unsubstituted, $C_{2-6}$ alkynyl; substituted or unsubstituted, 3- to 13-membered, monocyclic or bicyclic carbocyclyl; substituted or unsubstituted, 3- to 13-membered, monocyclic or bicyclic heterocyclyl; substituted or unsubstituted, 6- to 11-membered, monocyclic or bicyclic aryl; or substituted or unsubstituted, 5- to 11-membered, monocyclic or bicyclic heteroaryl. In certain embodiments, $R^1$ is substituted $C_{1-6}$ alkyl that comprises at least one heteroatom. In certain embodiments, $R^1$ is substituted $C_{1-6}$ alkyl that comprises at least one double bond. In certain embodiments, $R^1$ is substituted $C_{1-6}$ alkyl that comprises at least one triple bond.

In certain embodiments, $R^2$ is hydrogen. In certain embodiments, $R^2$ is not hydrogen. In certain embodiments, $R^2$ is substituted or unsubstituted, $C_{1-6}$ alkyl. In certain embodiments, $R^2$ is unsubstituted $C_{1-6}$ alkyl. In certain embodiments, $R^2$ is Me. In certain embodiments, $R^2$ is Et, Pr, or Bu. In certain embodiments, $R^2$ is fluorinated $C_{1-6}$ alkyl (e.g., fluorinated methyl, such as —$CF_3$). In certain embodiments, $R^2$ is a nitrogen protecting group.

In certain embodiments, $R^2$ is substituted or unsubstituted, 3- to 7-membered, monocyclic carbocyclyl. In certain embodiments, $R^2$ is substituted or unsubstituted, 3- to 5-membered, monocyclic carbocyclyl. In certain embodiments, $R^2$ is substituted or unsubstituted, 3- to 7-membered, monocyclic heterocyclyl. In certain embodiments, $R^2$ is substituted or unsubstituted, 3- to 5-membered, monocyclic heterocyclyl. In certain embodiments, $R^2$ is substituted or unsubstituted phenyl. In certain embodiments, $R^2$ is substituted or unsubstituted, 5- to 6-membered, monocyclic heteroaryl.

In some embodiments, $R^3$ is hydrogen, halogen, substituted or unsubstituted, $C_{1-6}$ alkyl, —$OR^a$, —$N(R^a)_2$, or —CN. In some embodiments, $R^3$ is hydrogen.

In certain embodiments, $R^3$ is halogen, substituted or unsubstituted, $C_{1-6}$ alkyl, —$OR^a$, —$N(R^a)_2$, or —CN. In certain embodiments, $R^3$ is halogen, substituted or unsubstituted, $C_{1-6}$ alkyl, or —$OR^a$. In certain embodiments, $R^3$ is —$N(R^a)_2$ or —CN. In certain embodiments, $R^3$ is halogen. In certain embodiments, $R^3$ is F. In certain embodiments, $R^3$ is Cl. In certain embodiments, $R^3$ is substituted or unsubstituted, $C_{1-6}$ alkyl (e.g., unsubstituted $C_{1-6}$ alkyl). In certain embodiments, $R^3$ is Me. In certain embodiments, $R^3$ is Et, Pr, or Bu. In certain embodiments, $R^3$ is fluorinated $C_{1-6}$ alkyl (e.g., fluorinated methyl, e.g., —$CF_3$). In certain embodiments, $R^3$ is —$OR^a$. In certain embodiments, $R^3$ is —OH. In certain embodiments, $R^3$ is —O(substituted or unsubstituted, $C_{1-6}$ alkyl) (e.g., —OMe). In certain embodiments, $R^3$ is —$N(R^a)_2$. In certain embodiments, $R^3$ is —$NH_2$. In certain embodiments, $R^3$ is —$NHR^a$(e.g., —NH(substituted or unsubstituted, $C_{1-6}$ alkyl), e.g., —NHMe). In certain embodiments, $R^3$ is —N(substituted or unsubstituted, $C_{1-6}$ alkyl)$_2$, e.g., —$N(Me)_2$). In certain embodiments, $R^3$ is —CN.

In certain embodiments, each instance of $R^a$ is independently hydrogen, substituted or unsubstituted, $C_{1-6}$ alkyl, an oxygen protecting group when attached to an oxygen atom, or a nitrogen protecting group when attached to a nitrogen atom. In certain embodiments, each instance of $R^a$ is hydrogen. In certain embodiments, no instance of $R^a$ is hydrogen. In certain embodiments, at least one instance of $R^a$ is substituted or unsubstituted, $C_{1-6}$ alkyl (e.g., unsubstituted $C_{1-6}$ alkyl). In certain embodiments, at least one instance of $R^a$ is Me. In certain embodiments, at least one instance of $R^a$ is Et, Pr, or Bu. In certain embodiments, at least one instance of $R^a$ is fluorinated $C_{1-6}$ alkyl (e.g., fluorinated methyl, e.g., —$CF_3$).

In certain embodiments, $R^2$ and $R^3$ are joined with their intervening atoms to form substituted or unsubstituted, 5-membered, monocyclic, heterocyclyl or heteroaryl. In certain embodiments, $R^2$ and $R^3$ are joined with their intervening atoms to form unsubstituted, 5-membered, monocyclic, heterocyclyl. In certain embodiments, $R^2$ and $R^3$ are joined with their intervening atoms to form substituted, 5-membered, monocyclic, heteroaryl. In certain embodiments,

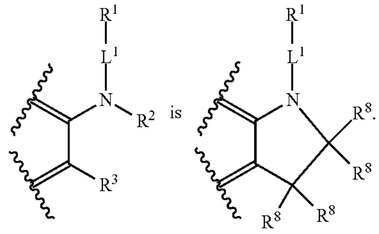

In certain embodiments,

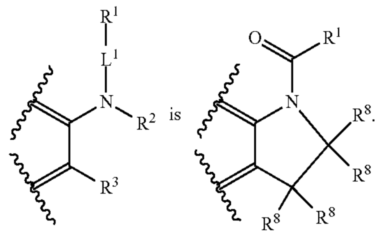

In certain embodiments,

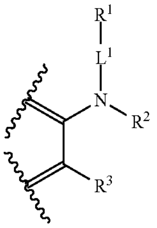
is
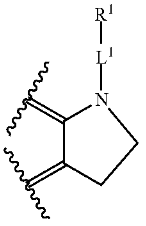
(e.g.,
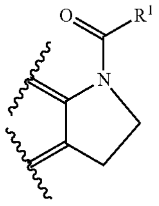
, e.g.,
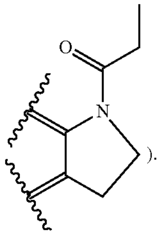
).

In certain embodiments,

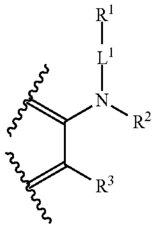
is
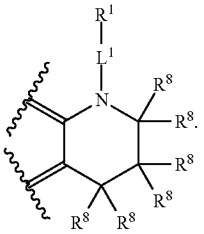

In certain embodiments,

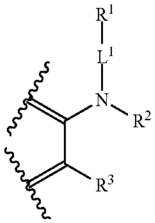
is
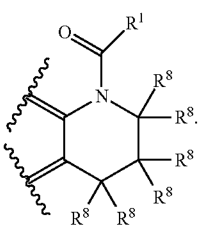

In certain embodiments,

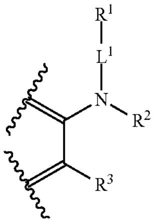
is
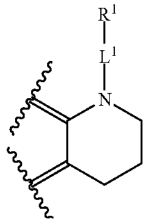
(e.g.,

-continued

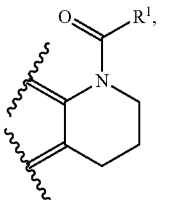
e.g.,
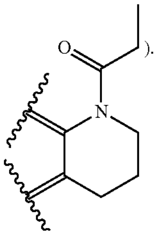
).

In certain embodiments, $R^2$ and $R^3$ are joined with their intervening atoms to form substituted, 5-membered, monocyclic, heteroaryl. In certain embodiments,

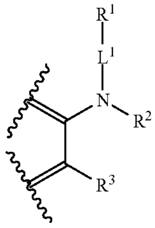
is
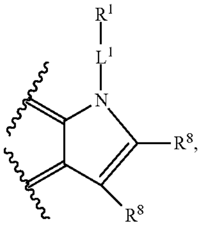

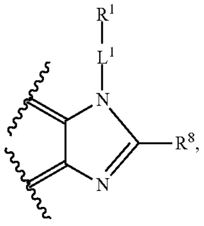
or
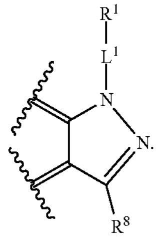

In certain embodiments, at least one instance of Y is $CR^4$. In certain embodiments, each instance of Y is $CR^4$. In certain embodiments, at least one instance of Y is N. In certain embodiments, each instance of Y is N.

In certain embodiments,

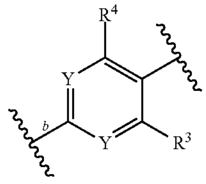
is
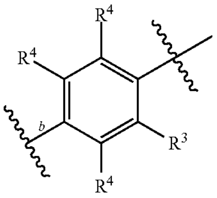
.

In certain embodiments,

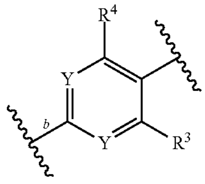
(e.g.,
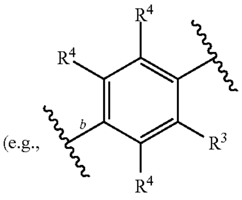
) is

-continued

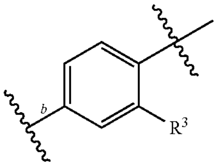

.

In certain embodiments,

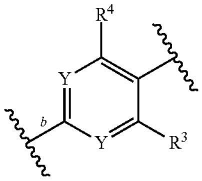

(e.g.,

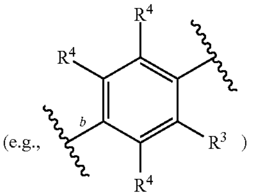

) is

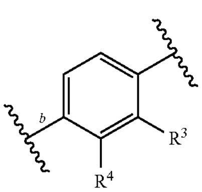

,

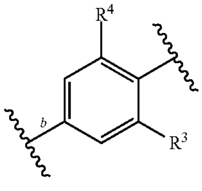

, or

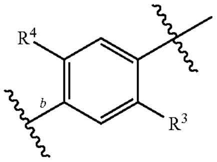

.

In certain embodiments,

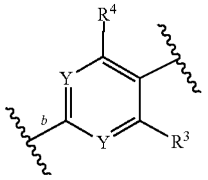

(e.g.,

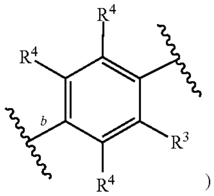

) is

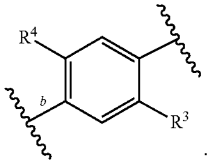

.

In certain embodiments,

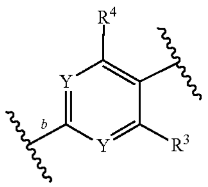

(e.g.,

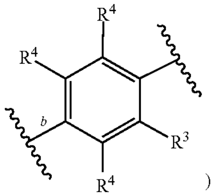

) is

-continued

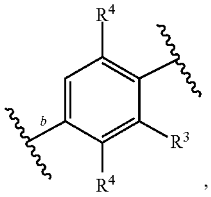

,

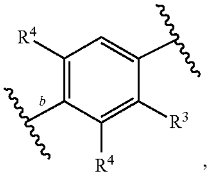

, or

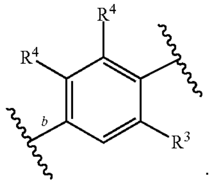

.

In certain embodiments, each instance of $R^4$ is independently hydrogen, halogen, substituted or unsubstituted, $C_{1-6}$ alkyl, —$OR^a$, —$N(R^a)_2$, or —CN. In certain embodiments, at least one instance of $R^4$ is hydrogen. In certain embodiments, each instance of $R^4$ is hydrogen. In certain embodiments, at least one instance of $R^4$ is not hydrogen. In certain embodiments, no instance of $R^4$ is hydrogen. In certain embodiments, at least one instance of $R^4$ is halogen or substituted or unsubstituted, $C_{1-6}$ alkyl. In certain embodiments, at least one instance of $R^4$ is halogen. In certain embodiments, at least one instance of $R^4$ is F. In certain embodiments, at least one instance of $R^4$ is Cl. In certain embodiments, at least one instance of $R^4$ is substituted or unsubstituted, $C_{1-6}$ alkyl (e.g., unsubstituted $C_{1-6}$ alkyl). In certain embodiments, at least one instance of $R^4$ is Me. In certain embodiments, at least one instance of $R^4$ is Et, Pr, or Bu. In certain embodiments, at least one instance of $R^4$ is fluorinated $C_{1-6}$ alkyl (e.g., fluorinated methyl, e.g., —$CF_3$). In certain embodiments, at least one instance of $R^4$ is —$OR^a$. In certain embodiments, at least one instance of $R^4$ is —OH. In certain embodiments, at least one instance of $R^4$ is —O(substituted or unsubstituted, $C_{1-6}$ alkyl) (e.g., —OMe). In certain embodiments, at least one instance of $R^4$ is —$N(R^a)_2$. In certain embodiments, at least one instance of $R^4$ is —$NH_2$. In certain embodiments, at least one instance of $R^4$ is —$NHR^a$(e.g., —NH(substituted or unsubstituted, $C_{1-6}$ alkyl), e.g., —NHMe). In certain embodiments, at least one instance of $R^4$ is —N(substituted or unsubstituted, $C_{1-6}$ alkyl)$_2$, e.g., —$N(Me)_2$). In certain embodiments, at least one instance of $R^4$ is —CN.

In certain embodiments,

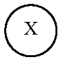

is a 6-membered, monocyclic aryl or heteroaryl. In certain embodiments,

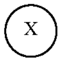

is phenyl. In certain embodiments,
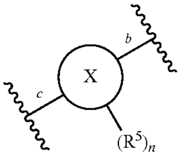
is
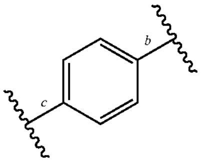
.
In certain embodiments,
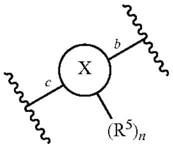
is
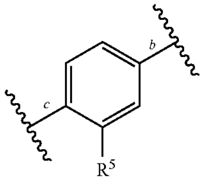
.
In certain embodiments,
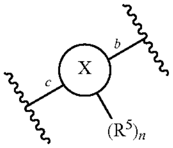
is
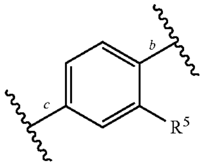
.
In certain embodiments,
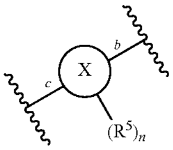
is
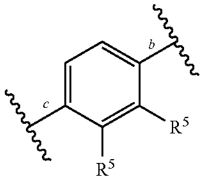
,
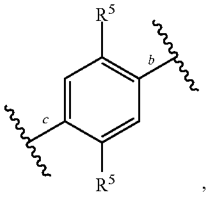
,
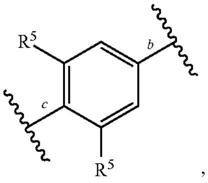
, or
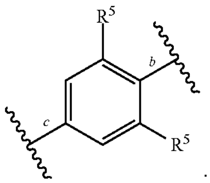
.
In certain embodiments,
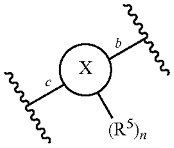
is
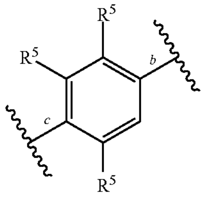
or
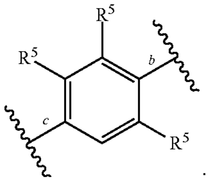
.
In certain embodiments,
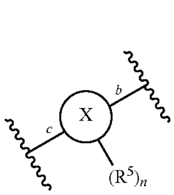
is
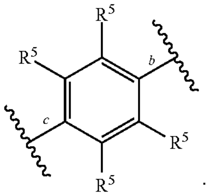
.
In certain embodiments,
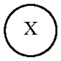
is pyridinyl, pyridazinyl, pyrimidinyl, or pyrazinyl. In certain embodiments,
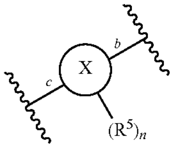
is
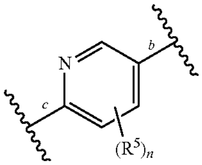
(e.g.,
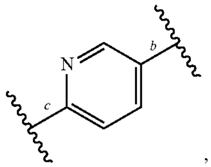
,
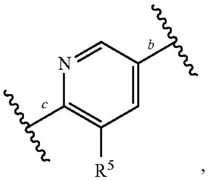
,
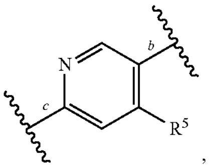
,
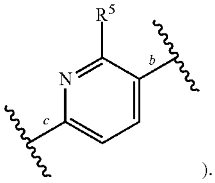
).

In certain embodiments,
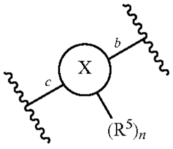
is
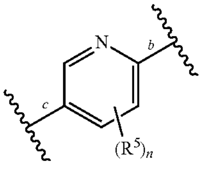
(e.g.,
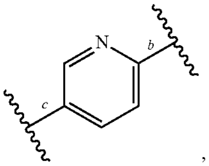
,
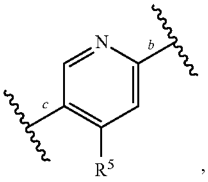
,
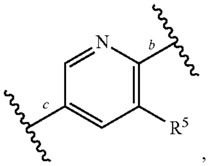
,
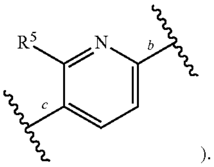
).
In certain embodiments,
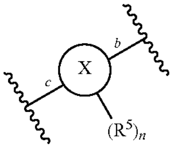
is
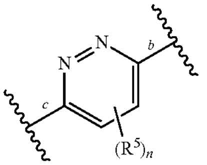
(e.g.,
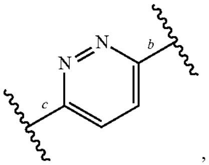
,
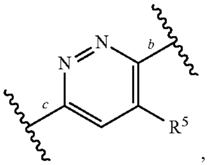
,
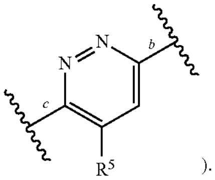
).
In certain embodiments,
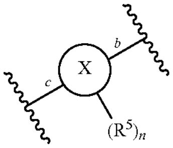
is
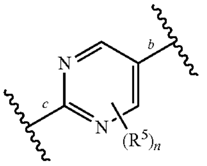
(e.g.,
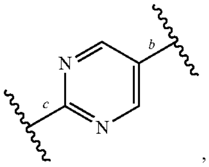
,
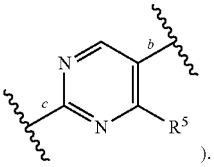
).
In certain embodiments,
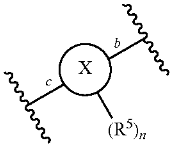
is
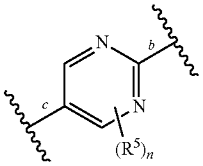
(e.g.,
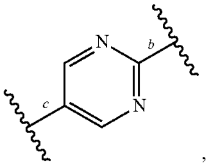
,
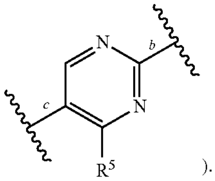
).
In certain embodiments,
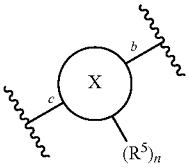
is
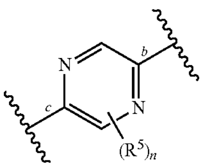
(e.g.,
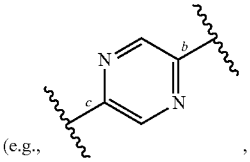
,
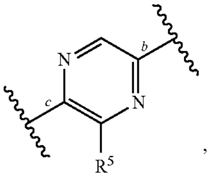
,
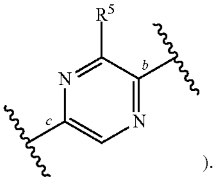
).
In certain embodiments,
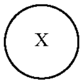
is imidazolyl. In certain embodiments,
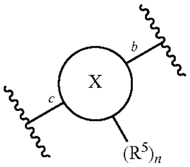
is
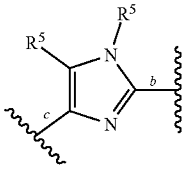
(e.g.,
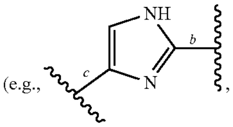
,
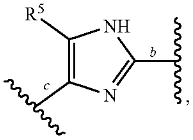
, -continued
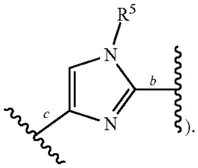
).
In certain embodiments,
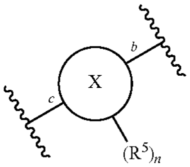
is
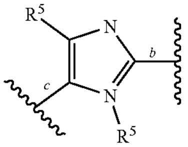
(e.g.,
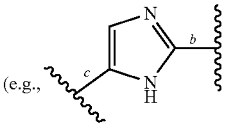
,
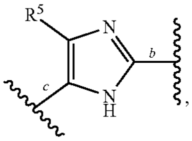
,
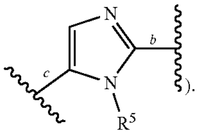
).
In certain embodiments,
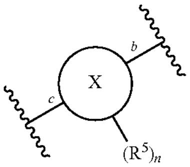
is
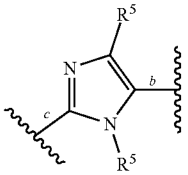
(e.g.,
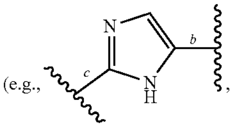
,
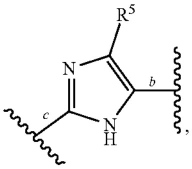
,
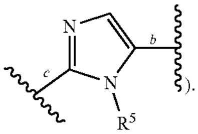
).
In certain embodiments,
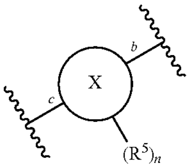
is
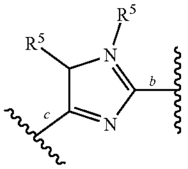
-continued
(e.g.,
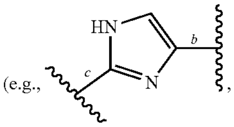
,
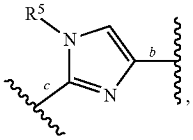
,
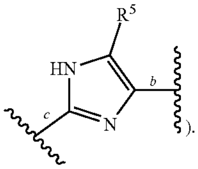
).
In certain embodiments,
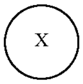
is oxazolyl. In certain embodiments,
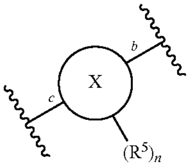
is
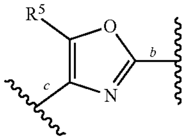
(e.g.,
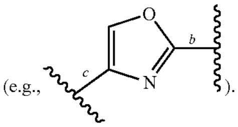
).
In certain embodiments,
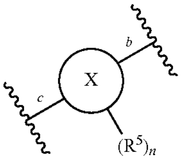
is
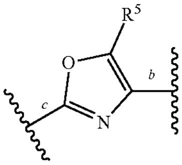
(e.g.,
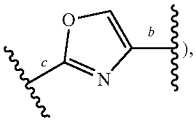
),
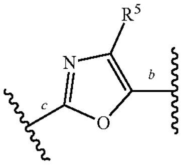
(e.g.,
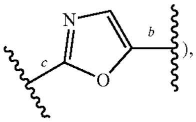
), or
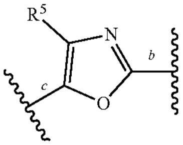
(e.g.,
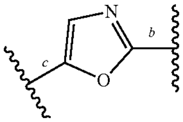
).

In certain embodiments,

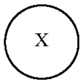

is azetidinyl. In certain embodiments,

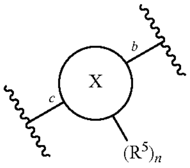

is

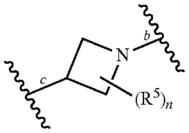

(e.g.,

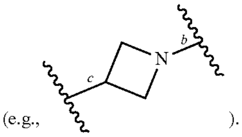

).

In certain embodiments,

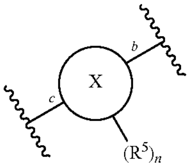

is

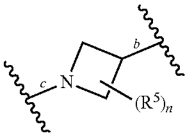

(e.g.,

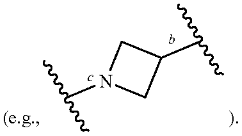

).

In certain embodiments,

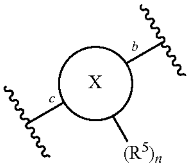

is —C≡C—. In certain embodiments,

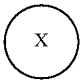

is

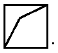

.

In certain embodiments,

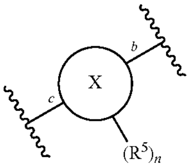

is

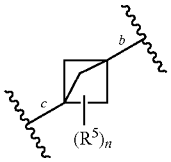

-continued (e.g.,

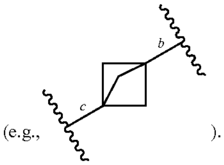

).

In certain embodiments, bond b and bond c are para to each other. In certain embodiments, bond b and bond c are meta to each other.

In certain embodiments, bond b and bond c are para to each other when

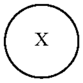

is phenyl, pyridinyl, pyridazinyl, pyrimidinyl, or pyrazinyl. In certain embodiments, bond b and bond c are meta to each other when

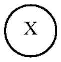

is phenyl, pyridinyl, pyridazinyl, pyrimidinyl, or pyrazinyl.

In certain embodiments,

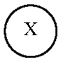

is thiazolyl. In certain embodiments,

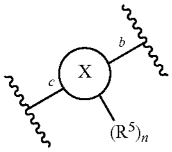

is

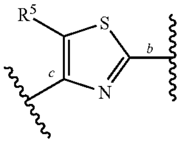

(e.g.,

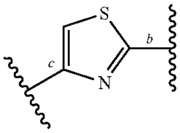

).

In certain embodiments,

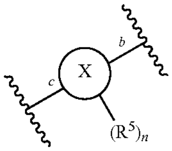

is

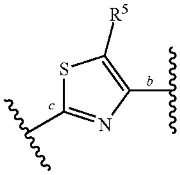

-continued
(e.g., 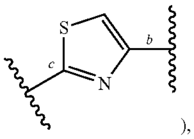 ), 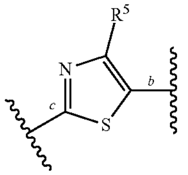
(e.g., 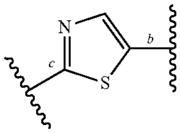 ), or 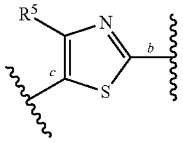
(e.g., 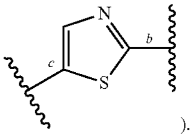 ).
In certain embodiments,
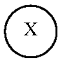
is a 6-membered, monocyclic carbocyclyl or heterocyclyl. In certain embodiments,
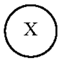
is piperazinyl. In certain embodiments,
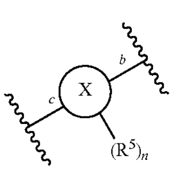 is 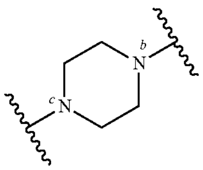 .
In certain embodiments,
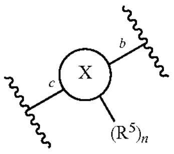 is 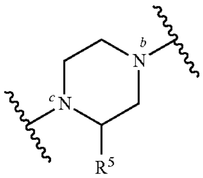 .
In certain embodiments,
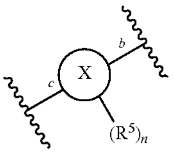 is 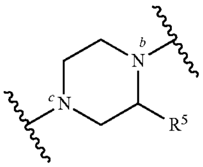 .
In certain embodiments,
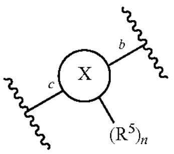 is 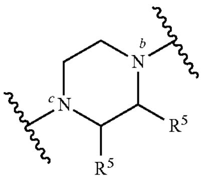 ,
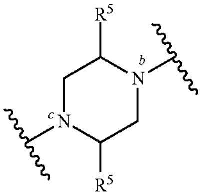 , 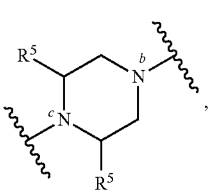 , or
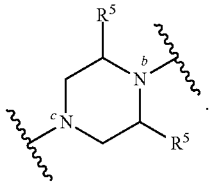 .
In certain embodiments,
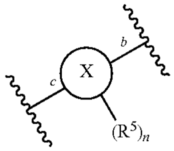 is 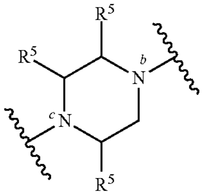 or
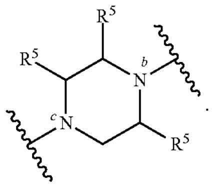 .
In certain embodiments,
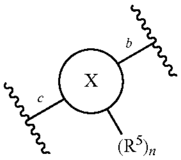 is 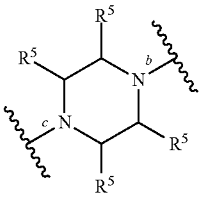 .

In certain embodiments,
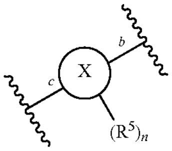 is 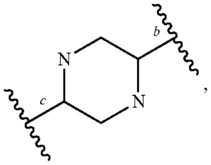, 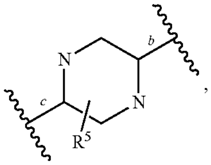, or 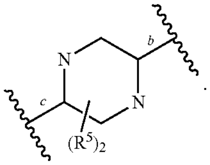.
In certain embodiments,
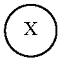
is piperidinyl. In certain embodiments,
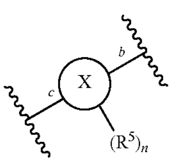 is 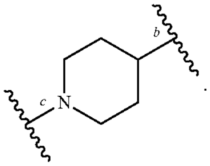.
In certain embodiments,
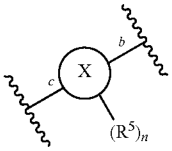 is 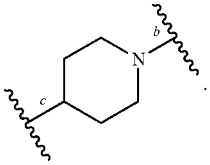.
In certain embodiments,
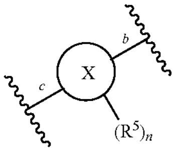 is 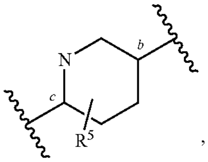, 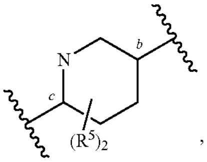, 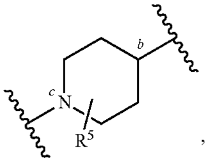, or 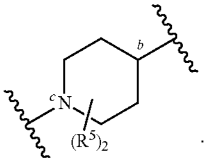.
In certain embodiments,
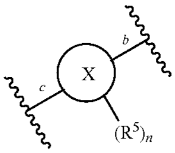 is 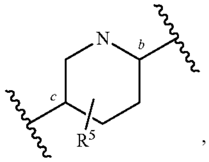, 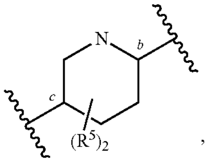, 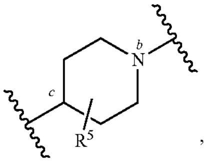, or 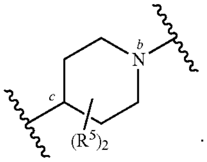.
In certain embodiments,
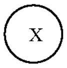
is morpholinyl. In certain embodiments,
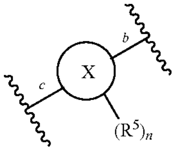 is 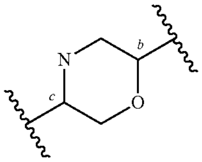 or 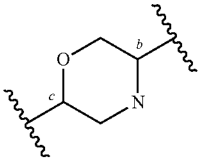.
In certain embodiments,
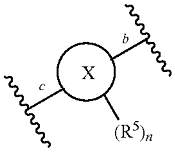 is 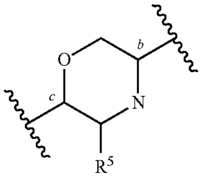 or 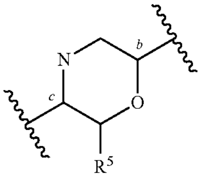.

In certain embodiments,

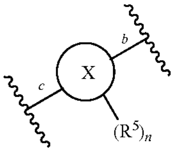

is

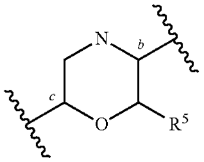

or

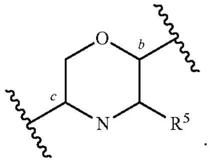

.

In certain embodiments,

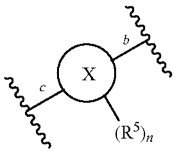

is

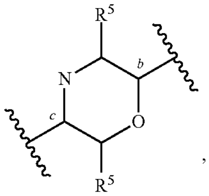

,

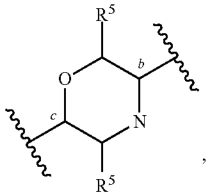

,

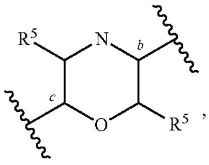

, or

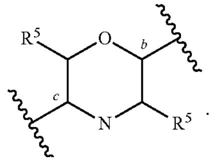

.

In certain embodiments,

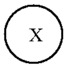

is thiomorpholinyl. In certain embodiments,

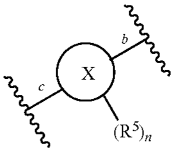

is

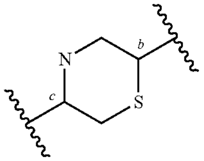

or

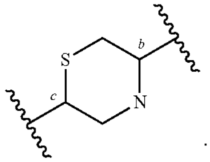

.

In certain embodiments,

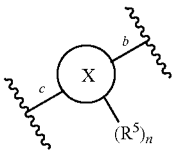

is

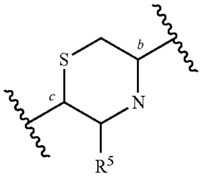

or

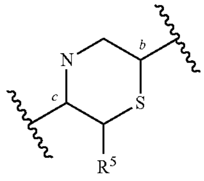

.

In certain embodiments,

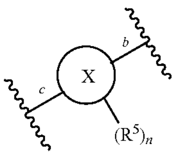

is

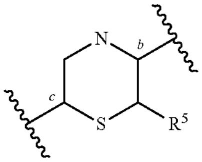

or

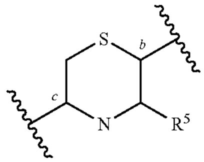

.

In certain embodiments,

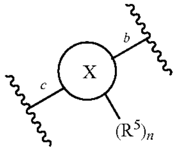

is

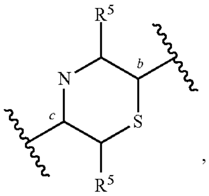

,

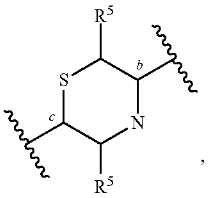

,

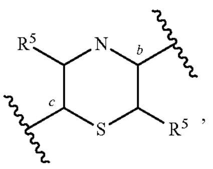

, or

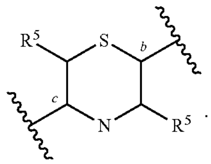

.

In certain embodiments, each instance of $R^5$ is independently hydrogen, halogen, substituted or unsubstituted, $C_{1-6}$ alkyl, —$OR^a$, —$N(R^a)_2$, or —CN. In certain embodiments, at least one instance of $R^5$ is hydrogen. In certain embodiments, each instance of $R^5$ is hydrogen. In certain embodiments, at least one instance of $R^5$ is not hydrogen. In certain embodiments, no instance of $R^5$ is hydrogen. In certain embodiments, at least one instance of $R^5$ is halogen. In certain embodiments, at least one instance of $R^5$ is F. In certain embodiments, at least one instance of $R^5$ is Cl. In certain embodiments, at least one instance of $R^5$ is substituted or unsubstituted, $C_{1-6}$ alkyl (e.g., unsubstituted $C_{1-6}$ alkyl). In certain embodiments, at least one instance of $R^5$ is Me. In certain embodiments, at least one instance of $R^5$ is Et, Pr, or Bu. In certain embodiments, at least one instance of $R^5$ is fluorinated $C_{1-6}$ alkyl (e.g., fluorinated methyl, e.g., —$CF_3$). In certain embodiments, at least one instance of $R^5$ is —$OR^a$. In certain embodiments, at least one instance of $R^5$ is —OH. In certain embodiments, at least one instance of $R^5$ is —O(substituted or unsubstituted, $C_{1-6}$ alkyl) (e.g., —OMe). In certain embodiments, at least one instance of $R^5$ is —$N(R^a)_2$. In certain embodiments, at least one instance of $R^5$ is —$NH_2$. In certain embodiments, at least one instance of $R^5$ is —$NHR^a$ (e.g., —NH(substituted or unsubstituted, $C_{1-6}$ alkyl), e.g., —NHMe). In certain embodiments, at least one instance of $R^5$ is —N(substituted or unsubstituted, $C_1$_s alkyl)$_2$, e.g., —$N(Me)_2$. In certain embodiments, at least one instance of $R^5$ is —CN. In certain embodiments, at least one instance of $R^5$ is halogen, substituted or unsubstituted, $C_{1-6}$ alkyl, or —$OR^a$.

In some embodiments, $L^B$ is —$N(R^6)L^2$-. In some embodiments, a compound of Formula (0) is of the formula:

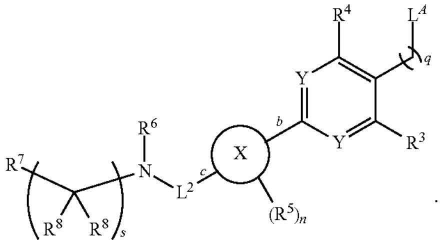

In some embodiments, $L^2$ is C═O. In certain embodiments, a compound of Formula (0) is of the formula:

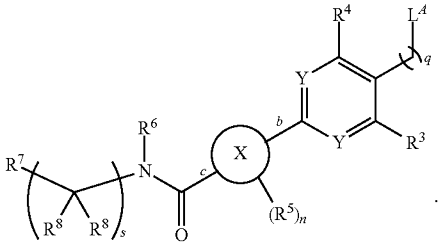

In some embodiments, $L^2$ is $S(═O)_2$. In certain embodiments, a compound of formula (0) is of the formula:

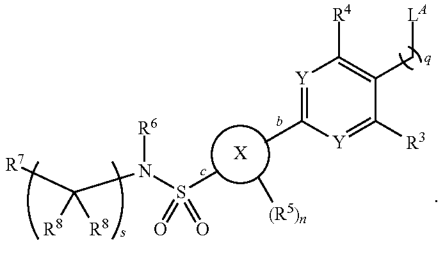

In certain aspects, a $L^2$ is

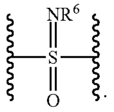

In some embodiments a compound of Formula (0) is of the formula:

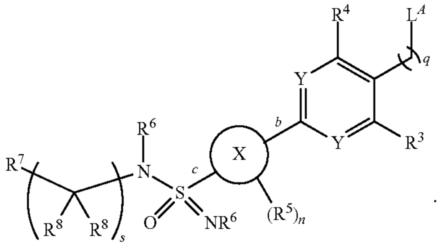

In certain embodiments, each $R^6$ is independently hydrogen. In some embodiments, one $R^6$ is methyl, and one $R^6$ is hydrogen.

In certain embodiments, $L^B$ is -$L^2N(R^6)$—. In some embodiments a compound of Formula (0) is of the formula:

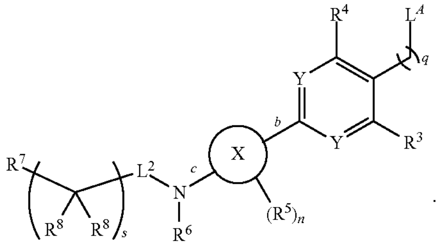

In some embodiments, $L^2$ is C═O. In certain embodiments, a compound of Formula (0) is of the formula:

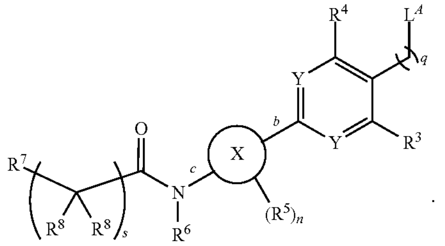

In some embodiments, $L^2$ is $S(=O)_2$. In certain embodiments, a compound of Formula (0) is of the formula:

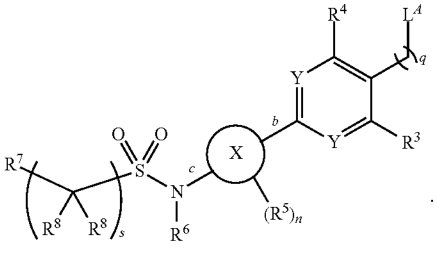

In certain aspects, a $L^2$ is

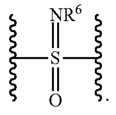

In some embodiments a compound of Formula (0) is of the formula:

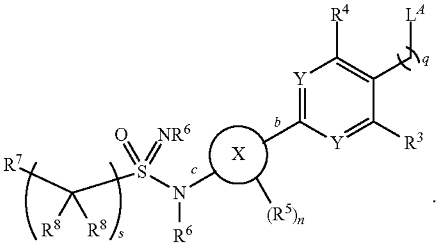

In certain embodiments, each $R^6$ is hydrogen. In some embodiments, one $R^6$ is methyl and one $R^6$ is hydrogen. In some embodiments, a compound of Formula (0) is of the formula:

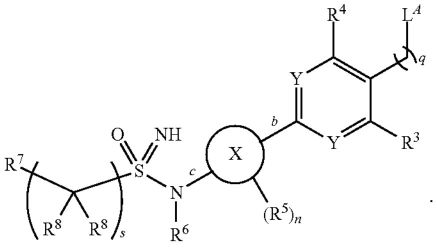

In certain embodiments, a compound for Formula (0) is of Formula (0'):

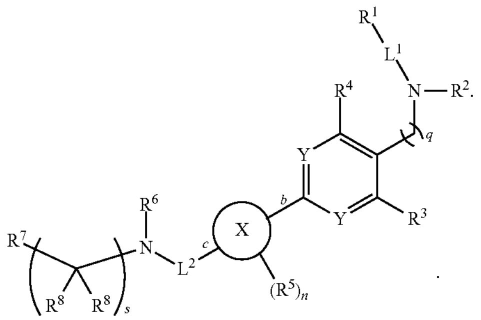

In certain embodiments, a compound of Formula (0') is of the formula:

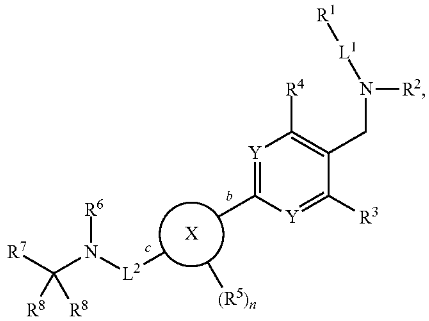

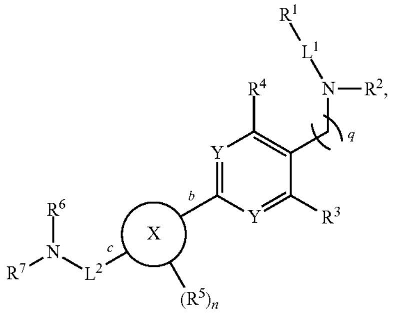

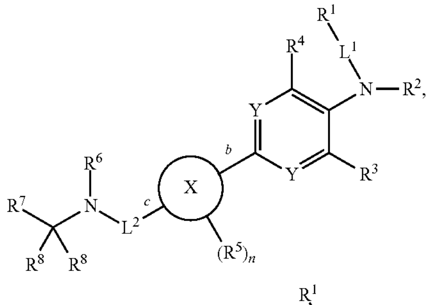

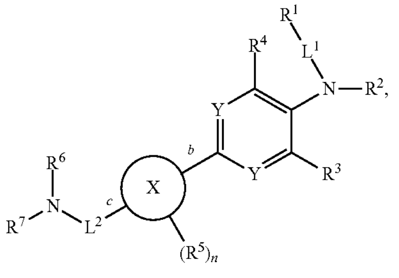

-continued

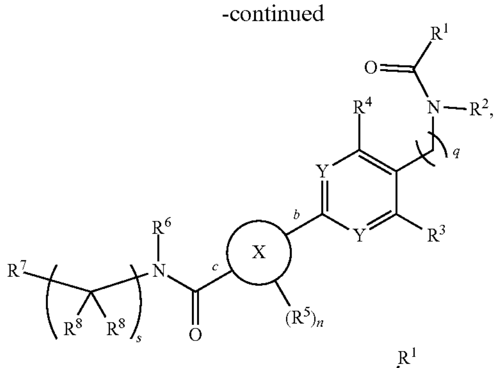

or

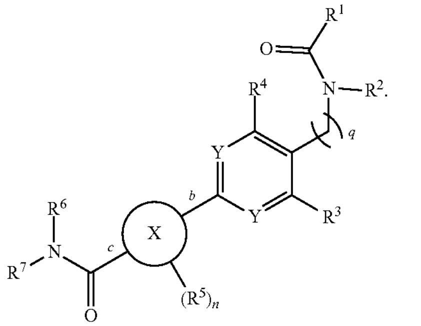

In certain embodiments, $L^2$ is —C(═O)—. In certain embodiments, $L^2$ is —$S(═O)_2$—.

In certain embodiments, $L^2$ is

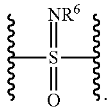

In some embodiments, $L^2$ is

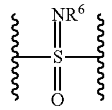

and $R^6$ is hydrogen. In some embodiments, $L^2$ is

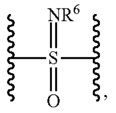

and $R^6$ is methyl.

In certain embodiments, each $R^6$ is independently hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, substituted or unsubstituted, 5- to 11-membered, monocyclic or bicyclic heteroaryl, or a nitrogen protecting group. In certain embodiments, each $R^6$ is independently substituted or unsubstituted, $C_{1-6}$ alkyl, substituted or unsubstituted, 6- to 11-membered, monocyclic or bicyclic aryl, or substituted or unsubstituted, 5- to 11-membered, monocyclic or bicyclic heteroaryl. In certain embodiments, each $R^6$ is independently hydrogen. In certain embodiments, each $R^6$ is independently substituted or unsubstituted, $C_{1-6}$ alkyl (e.g., Me). In certain embodiments, each instance of $R^6$ is the same. In some embodiments, each instance of $R^6$ is different.

In certain embodiments, $R^6$ is hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, substituted or unsubstituted, 5- to 11-membered, monocyclic or bicyclic heteroaryl, or a nitrogen protecting group. In certain embodiments, $R^6$ is substituted or unsubstituted, $C_{1-6}$ alkyl, substituted or unsubstituted, 6- to 11-membered, monocyclic or bicyclic aryl, or substituted or unsubstituted, 5- to 11-membered, monocyclic or bicyclic heteroaryl. In certain embodiments, $R^6$ is hydrogen. In certain embodiments, $R^6$ is substituted or unsubstituted, $C_{1-6}$ alkyl (e.g., Me).

In certain embodiments, $R^7$ is substituted or unsubstituted, 3- to 7-membered, monocyclic carbocyclyl. In certain embodiments, $R^7$ is substituted or unsubstituted, 3- to 7-membered, monocyclic heterocyclyl. In certain embodiments, $R^7$ is substituted or unsubstituted, phenyl. In certain embodiments, $R^7$ is substituted or unsubstituted, 5- to 6-membered, monocyclic heteroaryl. In certain embodiments, $R^7$ is substituted or unsubstituted pyridinyl, substituted or unsubstituted pyrimidinyl, or substituted or unsubstituted pyridazinyl. In certain embodiments, $R^7$ is substituted or unsubstituted, 3-pyridinyl. In certain embodiments, $R^7$ is unsubstituted 3-pyridinyl. In certain embodiments, $R^7$ is

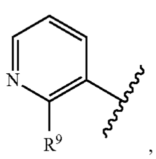

,

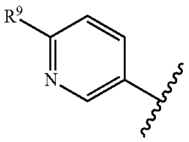

,

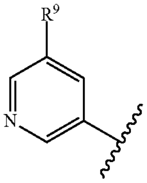

, or

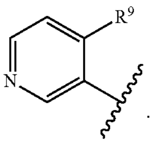

.

In certain embodiments, $R^7$ is

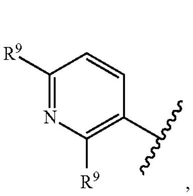

,

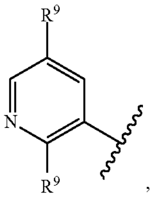

,

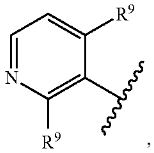

,

-continued

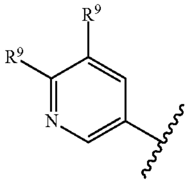,
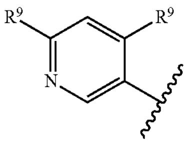, or
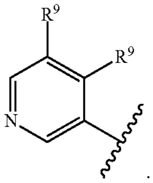.

In certain embodiments, $R^7$ is

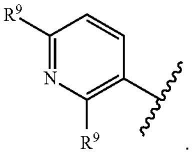.

In certain embodiments, $R^7$ is

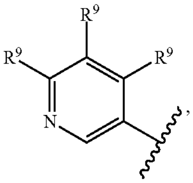,
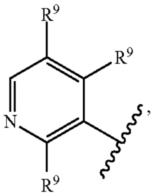,
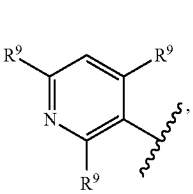, or
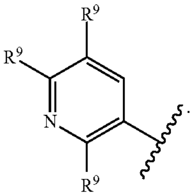.

In certain embodiments, $R^7$ is

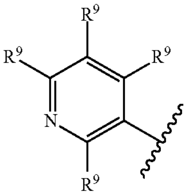.

In certain embodiments, $R^7$ is substituted or unsubstituted, 2-pyridinyl or 4-pyridinyl. In certain embodiments, $R^7$ is substituted or unsubstituted, 2-pyridinyl. In certain embodiments, $R^7$ is unsubstituted 2-pyridinyl. In certain embodiments, $R^7$ is

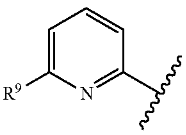,
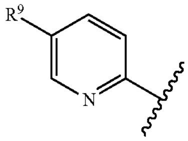,
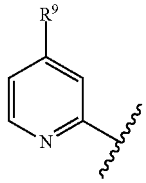, or
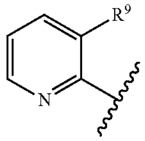.

In certain embodiments, $R^7$ is

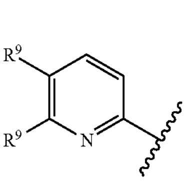,
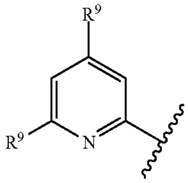,
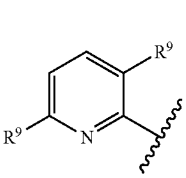,
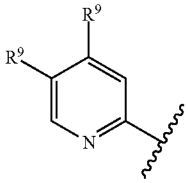,
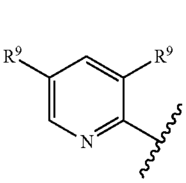, or
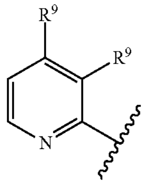.

In certain embodiments, $R^7$ is

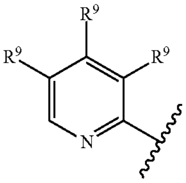,
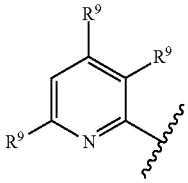,
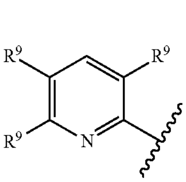, or
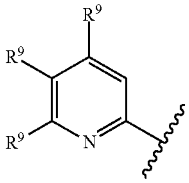.

In certain embodiments, $R^7$ is

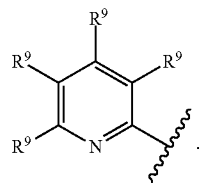

In certain embodiments, each instance of $R^8$ is independently —$OR^a$, —$N(R^a)_2$, or —CN. In certain embodiments, each instance of $R^8$ is hydrogen. In certain embodiments, at least one instance of $R^8$ is halogen or substituted or unsubstituted, $C_{1-6}$ alkyl. In certain embodiments, at least one instance of $R^8$ is unsubstituted $C_{1-6}$ alkyl (e.g., Me). In certain embodiments, at least one instance of $R^8$ is $C_{1-6}$ alkyl substituted with at least one instance of halogen (e.g., F).

Each instance of $R^9$ is independently hydrogen, halogen, substituted or unsubstituted, $C_{1-6}$ alkyl, —$OR^a$, —$N(R^a)_2$, or —CN. In certain embodiments, at least one instance of $R^9$ is hydrogen. In certain embodiments, each instance of $R^9$ is hydrogen. In certain embodiments, at least one instance of $R^9$ is not hydrogen. In certain embodiments, no instance of $R^9$ is hydrogen. In certain embodiments, at least one instance of $R^9$ is halogen. In certain embodiments, at least one instance of $R^9$ is F. In certain embodiments, at least one instance of $R^9$ is Cl. In certain embodiments, at least one instance of $R^9$ is substituted or unsubstituted, $C_{1-6}$ alkyl (e.g., unsubstituted $C_{1-6}$ alkyl). In certain embodiments, at least one instance of $R^9$ is Me. In certain embodiments, at least one instance of $R^9$ is Et, Pr, or Bu. In certain embodiments, at least one instance of $R^9$ is fluorinated $C_{1-6}$ alkyl (e.g., fluorinated methyl, e.g., —$CF_3$). In certain embodiments, at least one instance of $R^9$ is —$OR^a$. In certain embodiments, at least one instance of $R^9$ is —OH. In certain embodiments, at least one instance of $R^9$ is —O(substituted or unsubstituted, $C_{1-6}$ alkyl) (e.g., —OMe). In certain embodiments, at least one instance of $R^9$ is —$N(R^a)_2$. In certain embodiments, at least one instance of $R^9$ is —$NH_2$. In certain embodiments, at least one instance of $R^9$ is —$NHR^a$(e.g., —NH(substituted or unsubstituted, $C_{1-6}$ alkyl), e.g., —NHMe). In certain embodiments, at least one instance of $R^9$ is —N(substituted or unsubstituted, $C_{1-6}$ alkyl)$_2$, e.g., —$N(Me)_2$). In certain embodiments, at least one instance of $R^9$ is —CN. In certain embodiments, at least one instance of $R^9$ is halogen, substituted or unsubstituted, $C_{1-6}$ alkyl, or —$OR^a$.

In some embodiments, s is 1. In certain embodiments, s is 0.

In certain embodiments s is 1. In some embodiments a compound of Formula (0) is of the formula:

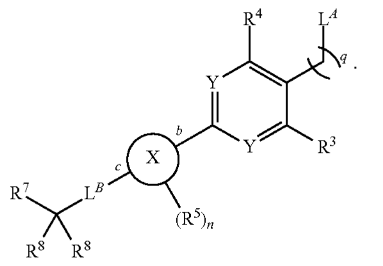

In some embodiments, s is 0. In certain embodiments, a compound of Formula (0) is of the formula:

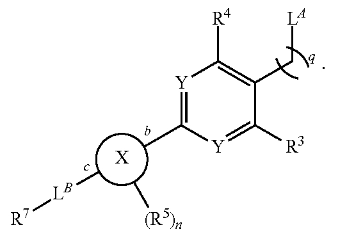

In some embodiments, s is 0, and a compound of Formula (0) is selected from the group of formula consisting of:

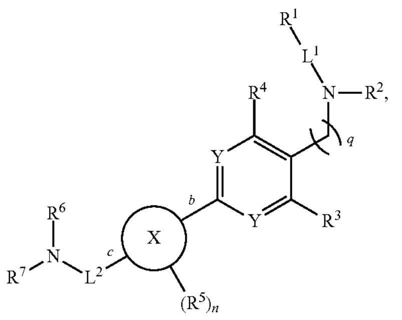

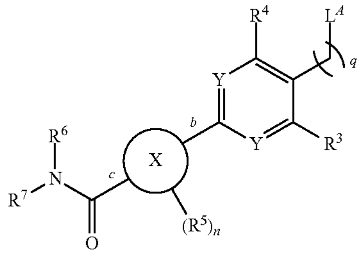

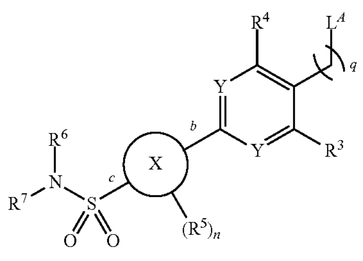

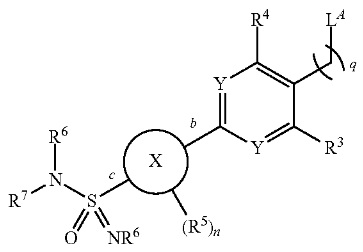

-continued
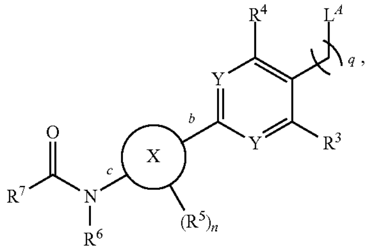
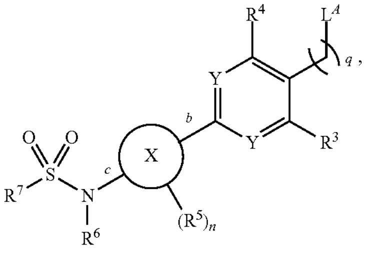
and
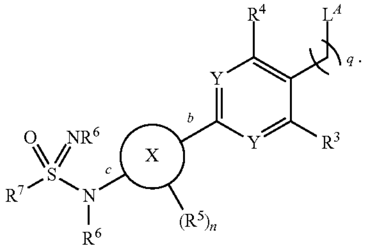
In certain embodiments s is 1. In some embodiments a compound of Formula (0') is of the formula:
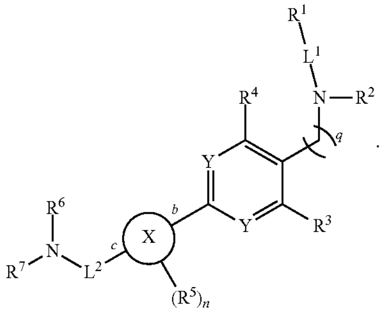
In some embodiments, s is 0. In certain embodiments, a compound of Formula (0') is of the formula:
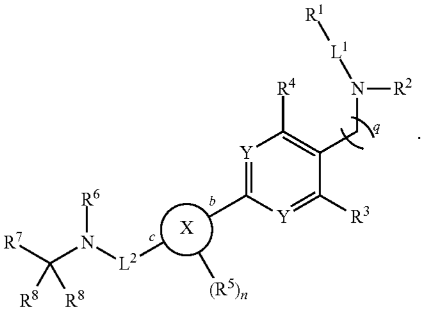
In some embodiments, s is 0, and a compound of Formula (0') is selected from the group of formula consisting of:
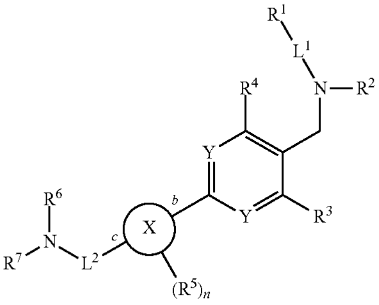
,
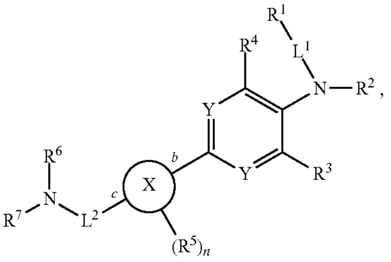
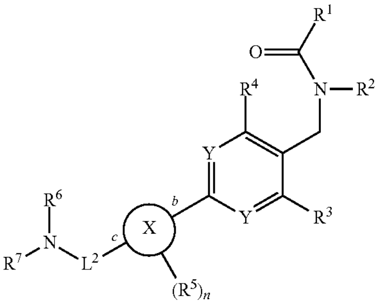
,
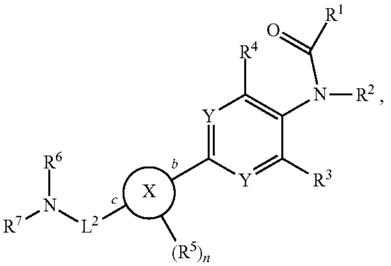
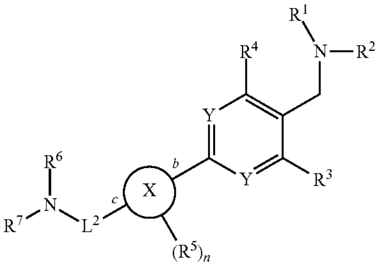
, and
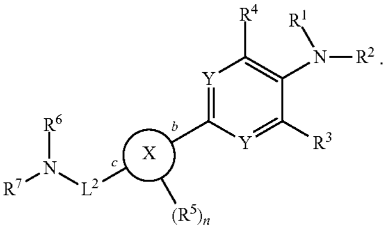

In certain embodiments, the compound is of the formula:
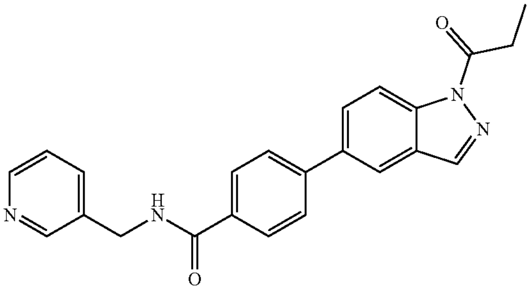
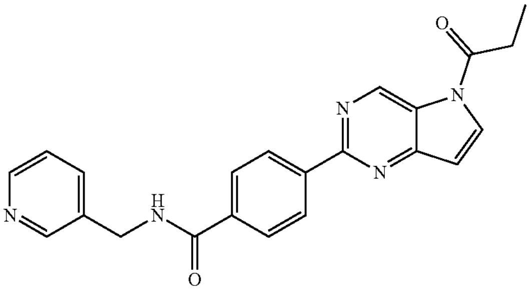
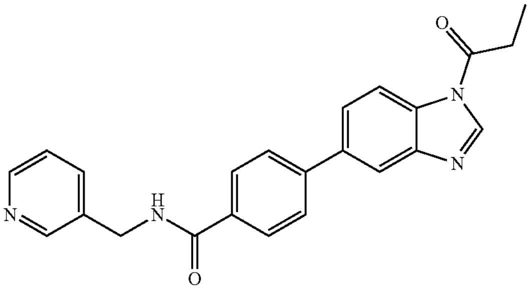
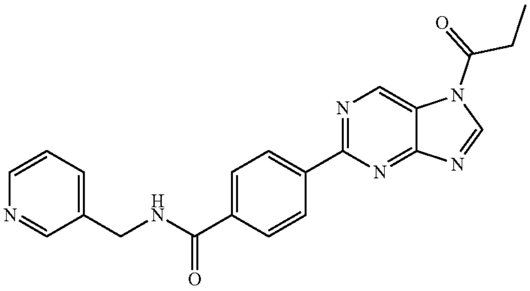
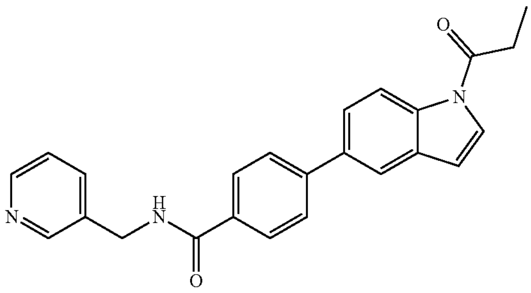
,
or a pharmaceutically acceptable salt, solvate, hydrate, polymorph, co-crystal, tautomer, stereoisomer, isotopically labeled derivative, or prodrug thereof.
In certain embodiments, the compound is of the formula:
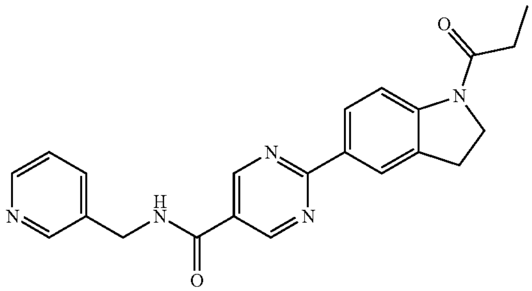
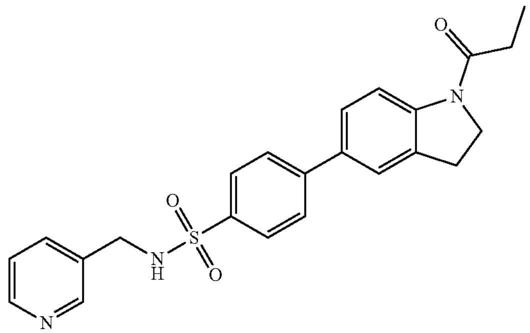
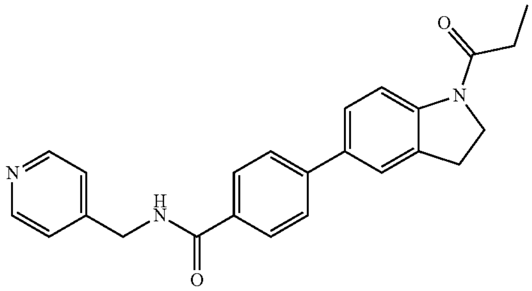
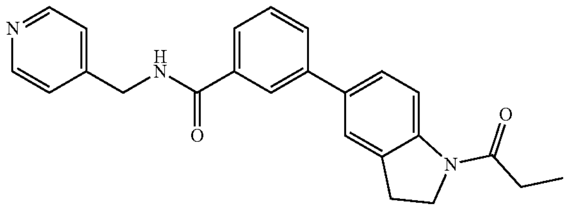
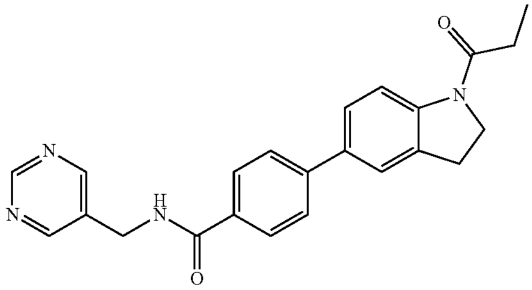
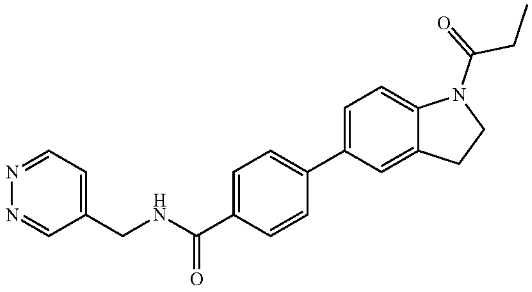

-continued

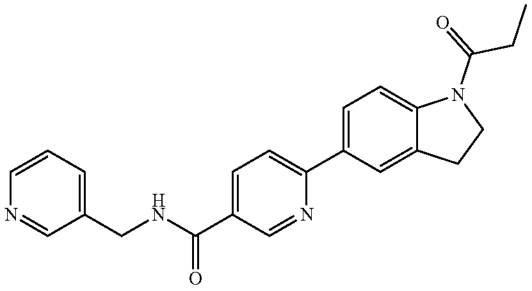

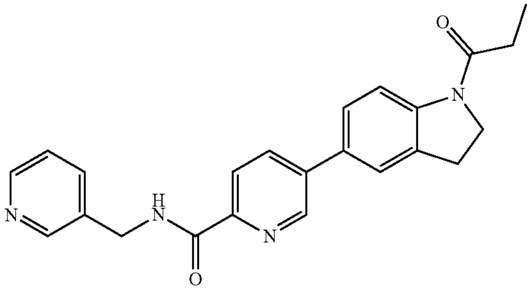

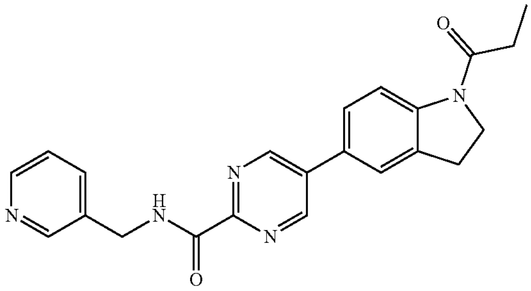

, or a pharmaceutically acceptable salt, solvate, hydrate, polymorph, co-crystal, tautomer, stereoisomer, isotopically labeled derivative, or prodrug thereof.

In certain embodiments, the compound is of the formula:

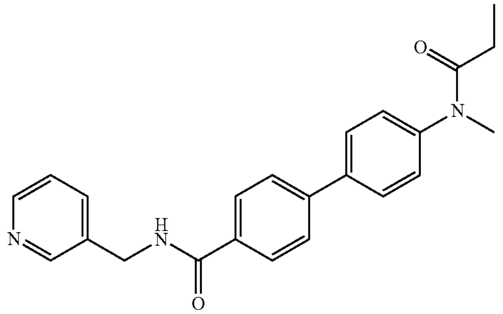

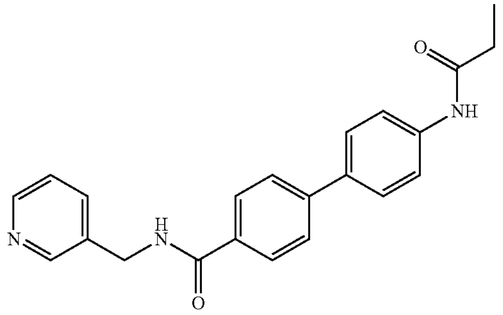

-continued

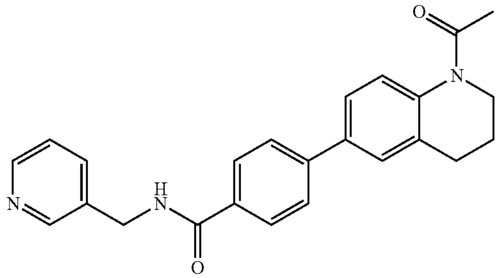

, or a pharmaceutically acceptable salt, solvate, hydrate, polymorph, co-crystal, tautomer, stereoisomer, isotopically labeled derivative, or prodrug thereof.

In certain embodiments, the compound is of the formula:

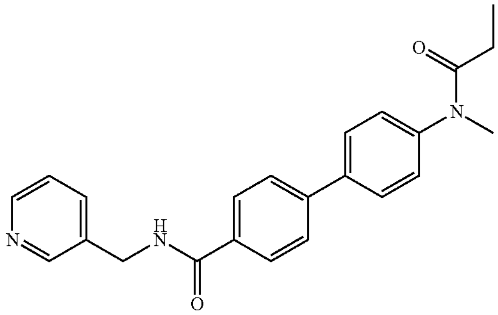

, or a pharmaceutically acceptable salt, solvate, hydrate, polymorph, co-crystal, tautomer, stereoisomer, isotopically labeled derivative, or prodrug thereof.

In certain embodiments, the compound is of the formula:

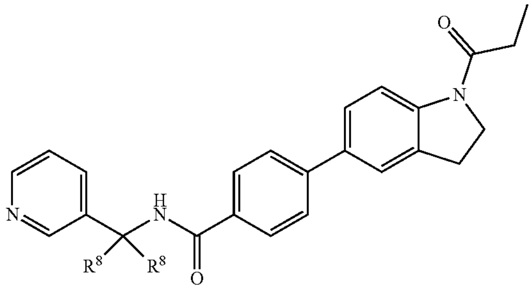

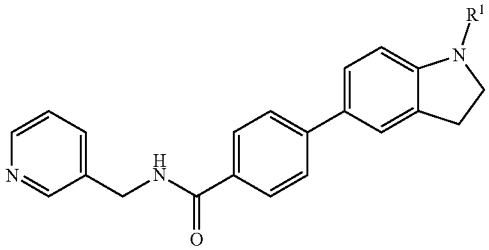

-continued

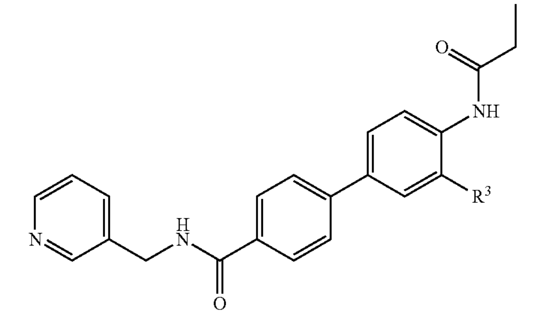

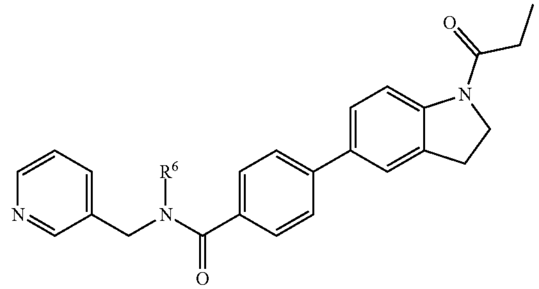

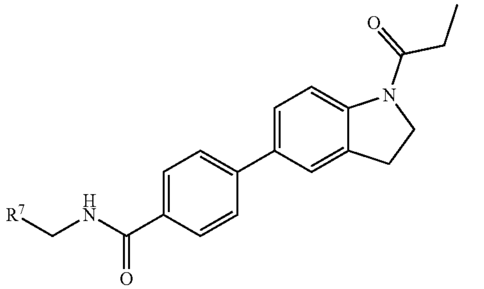

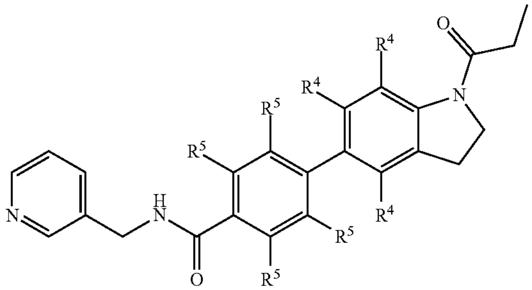

, or a pharmaceutically acceptable salt, solvate, hydrate, polymorph, co-crystal, tautomer, stereoisomer, isotopically labeled derivative, or prodrug thereof.

In certain embodiments, the compound is of the formula:

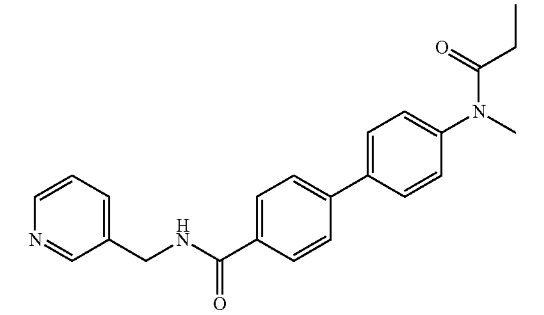

-continued

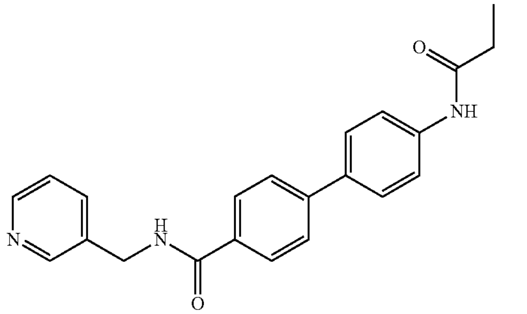

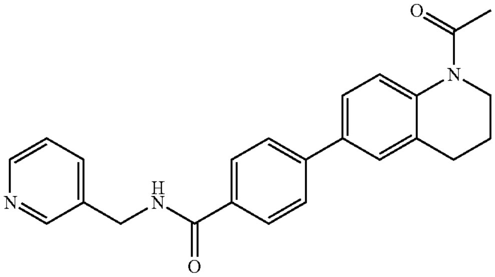

, or a pharmaceutically acceptable salt, solvate, hydrate, polymorph, co-crystal, tautomer, stereoisomer, isotopically labeled derivative, or prodrug thereof.

In certain embodiments, the compound is of the formula:

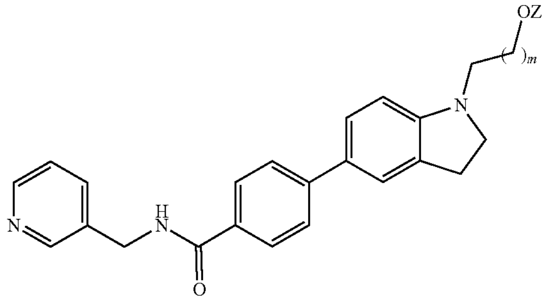

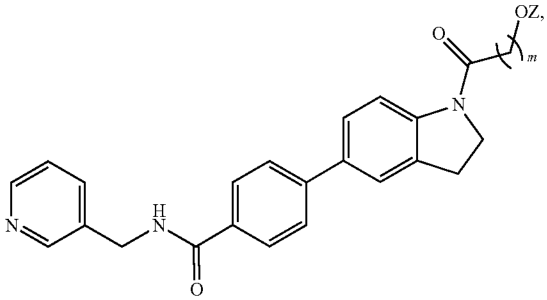

or a pharmaceutically acceptable salt, solvate, hydrate, polymorph, co-crystal, tautomer, stereoisomer, isotopically labeled derivative, or prodrug thereof, wherein Z is hydrogen or substituted or unsubstituted, $C_{1-6}$ alkyl; and m is 1, 2, 3, 4, 5, or 6.

In certain embodiments, the compound is of the formula:
I-17
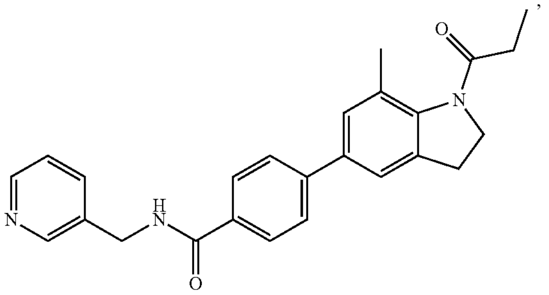
I-47
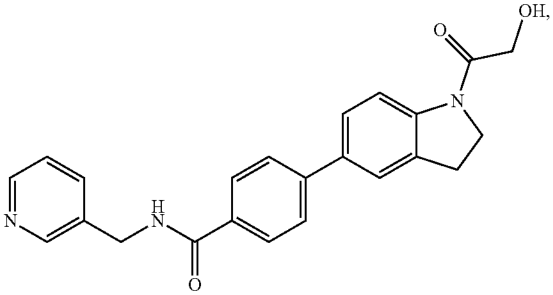
I-57
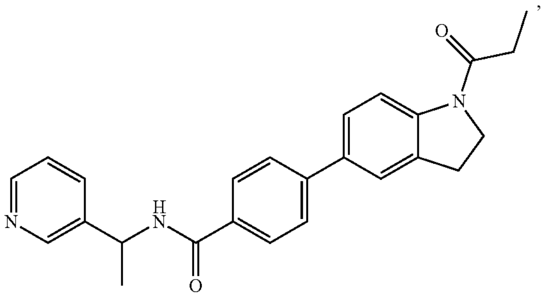
I-58
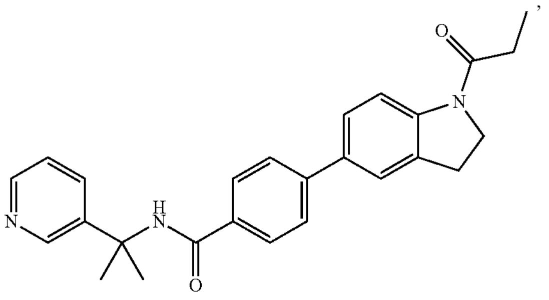
-continued
I-59
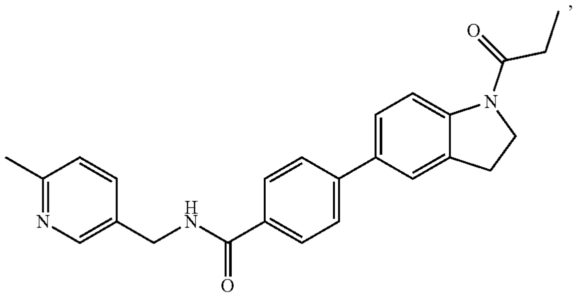
I-60
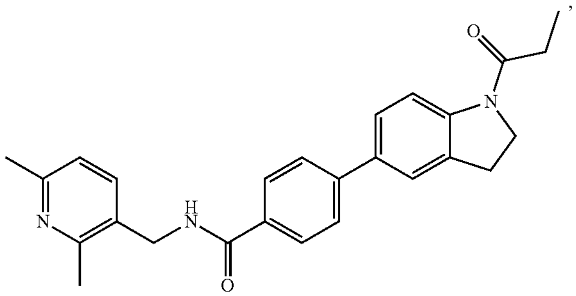
I-61
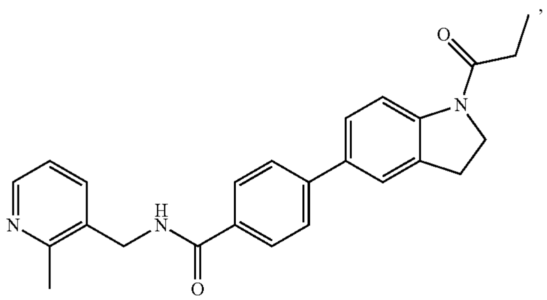
I-62
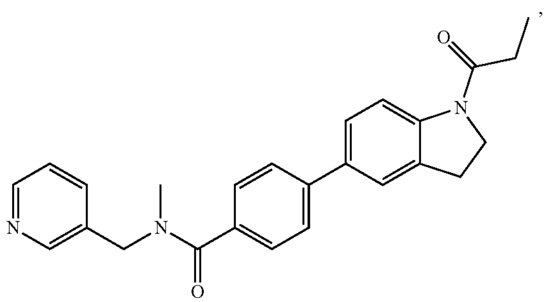

-continued
I-63
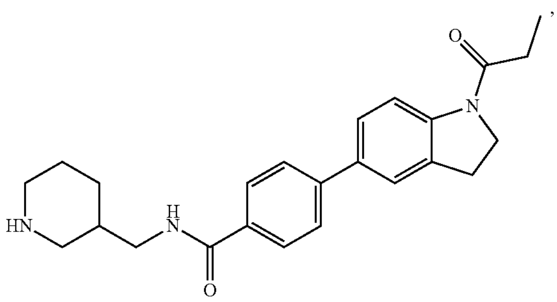
,
I-68
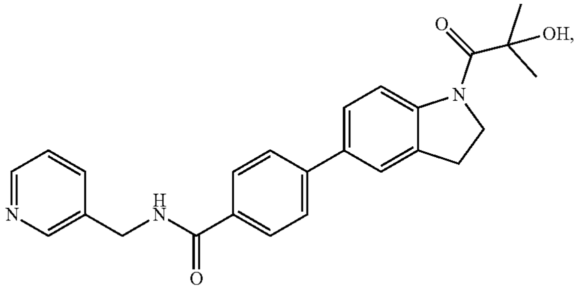
,
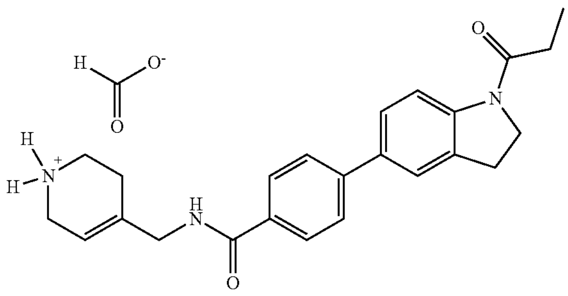
,
Monoformate salt of I-69
I-70
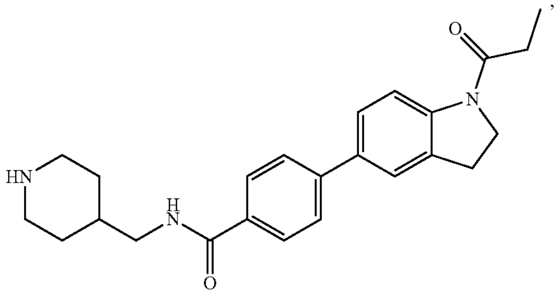
,
-continued
I-71
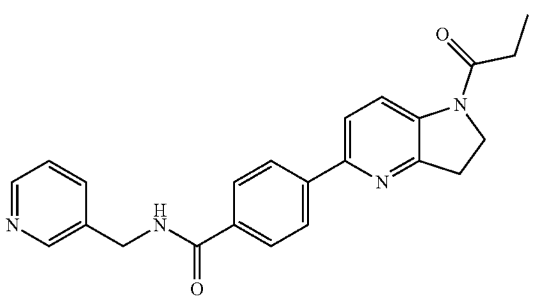
,
I-72
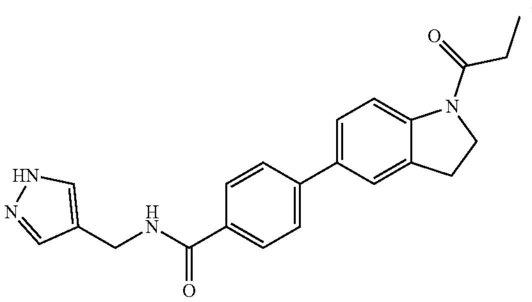
,
I-73
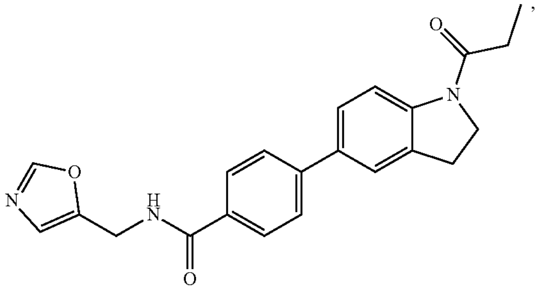
,
I-80
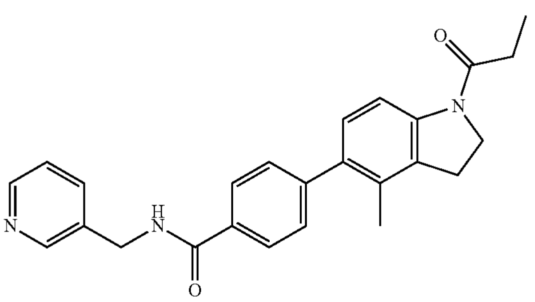
, -continued
I-91
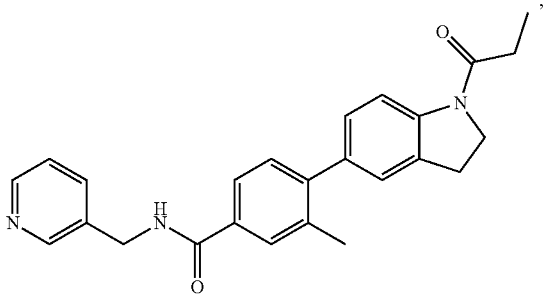
I-93
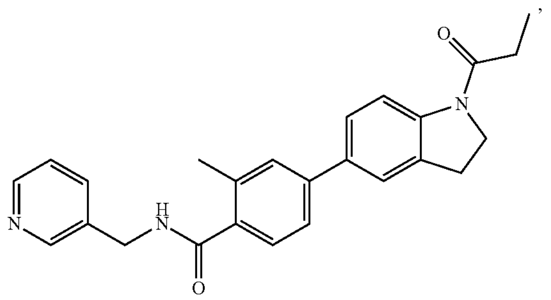
I-94
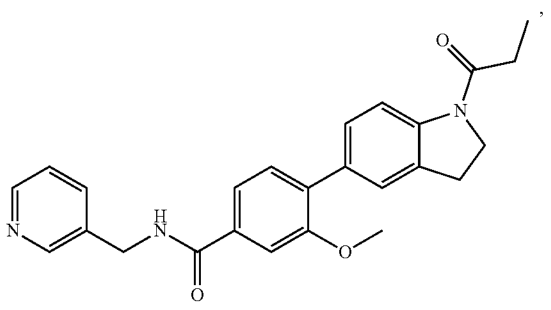
I-96
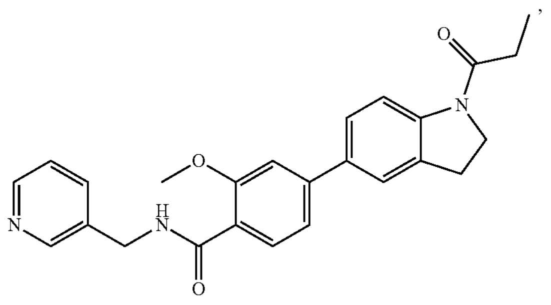
-continued
I-97
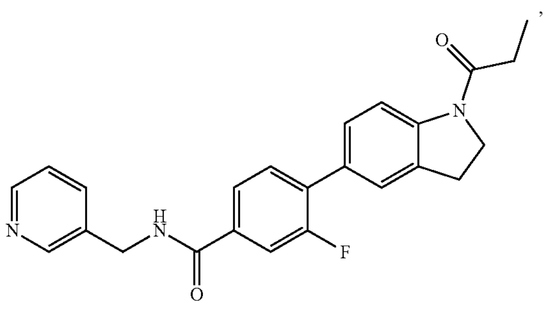
I-98
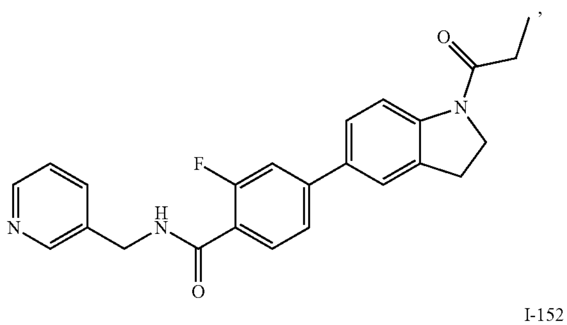
I-152
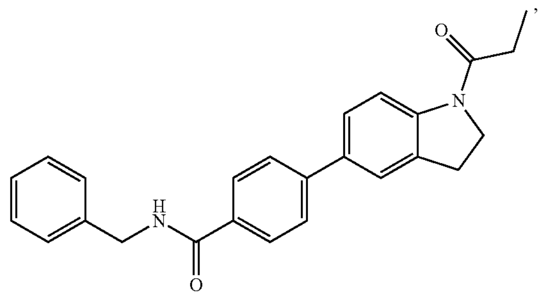
I-156
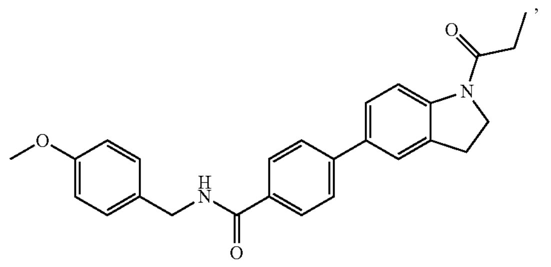
I-157
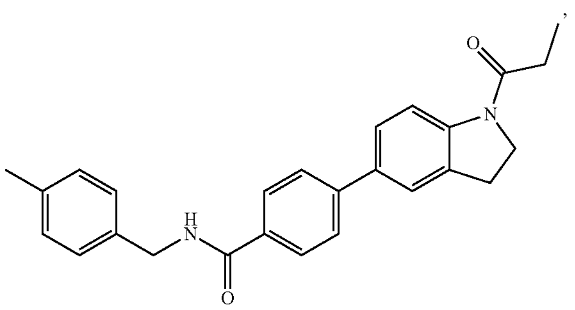

-continued
I-160
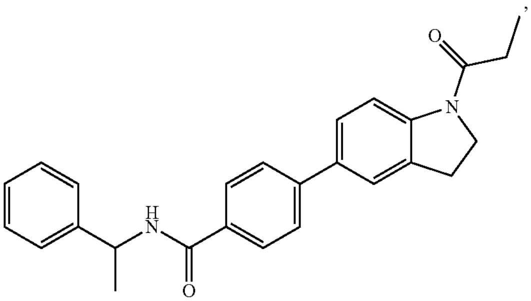
,
I-168
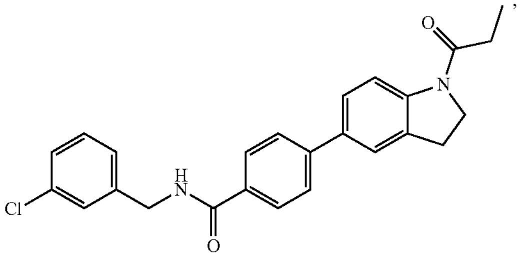
,
I-171
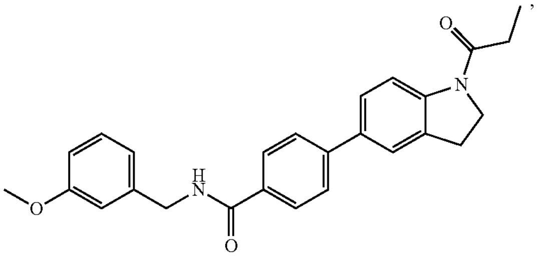
,
I-174
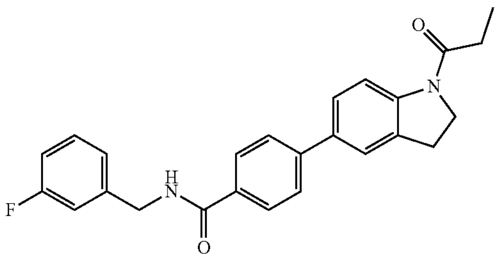
,
I-175
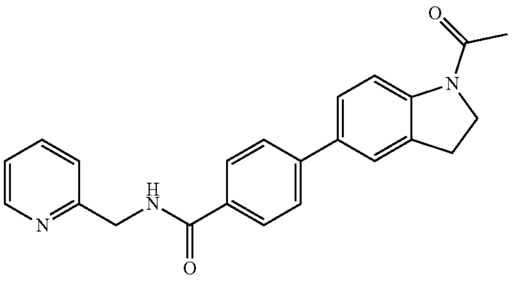
,
-continued
I-176
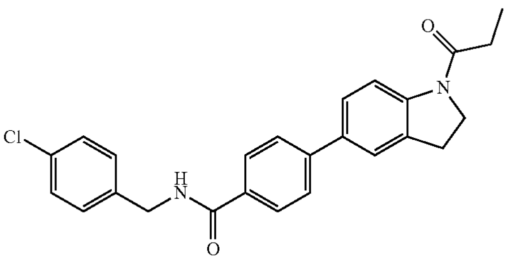
,
I-178
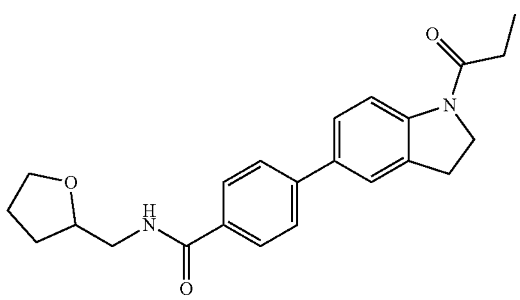
,
I-179
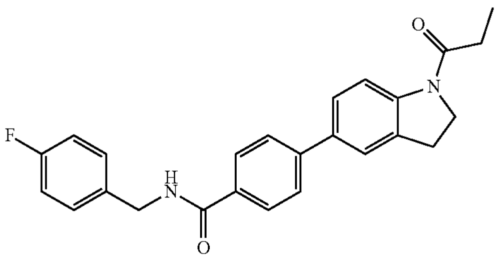
,
I-180
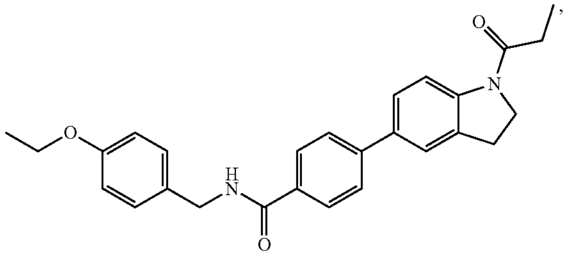
,
I-181
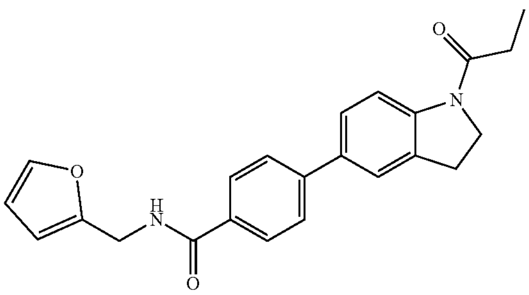
, -continued
I-185
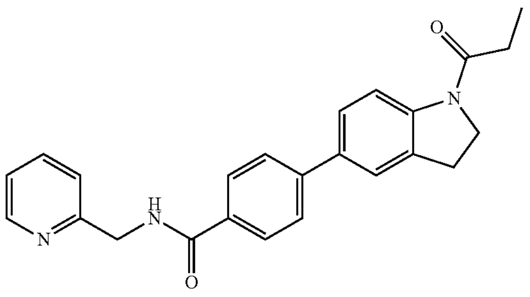,
I-186
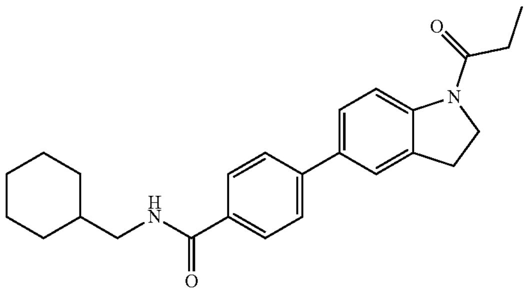,
I-188
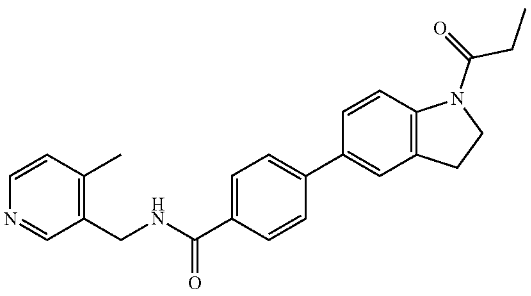,
I-191
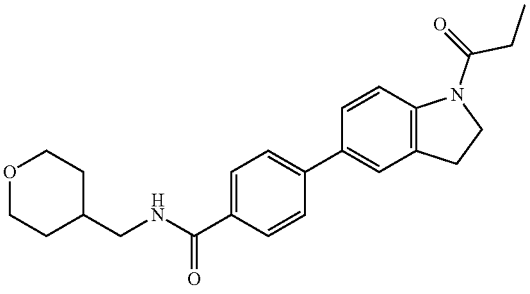,
-continued
I-197
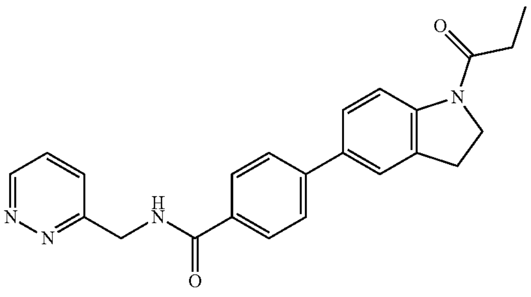,
I-198
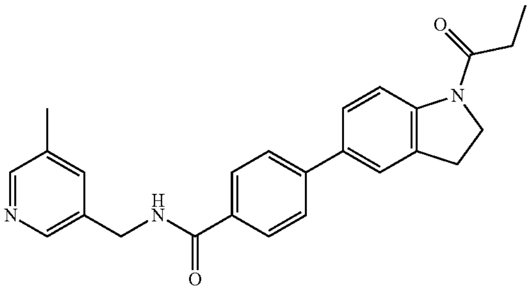,
I-199
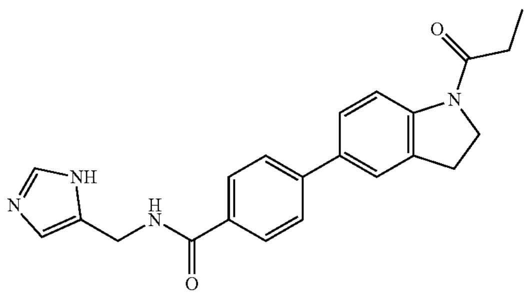,
I-200
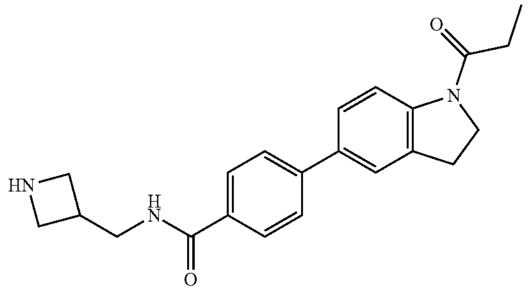, -continued

I-203

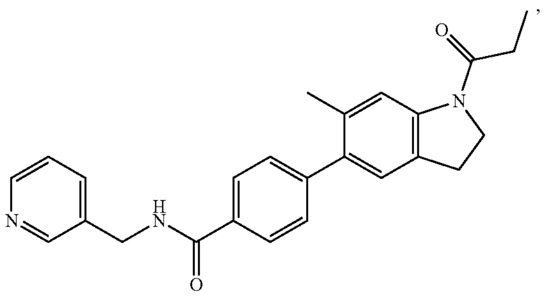

I-204

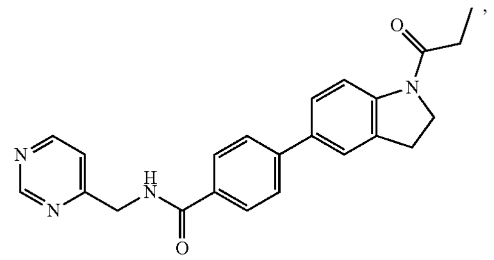

, or

I-69

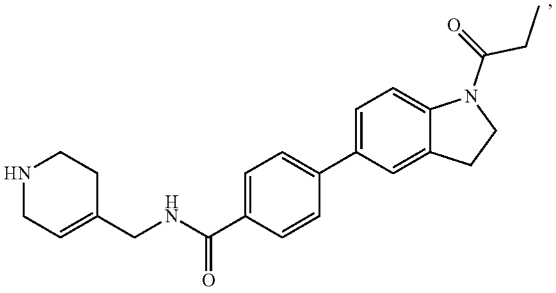

or a pharmaceutically acceptable salt, solvate, hydrate, polymorph, co-crystal, tautomer, stereoisomer, isotopically labeled derivative, or prodrug thereof.

In certain embodiments, the compound is of the formula:

I-53

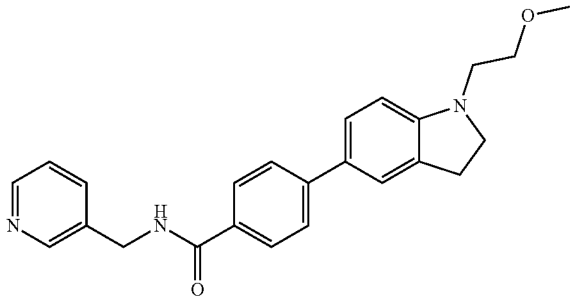

-continued

I-75 or

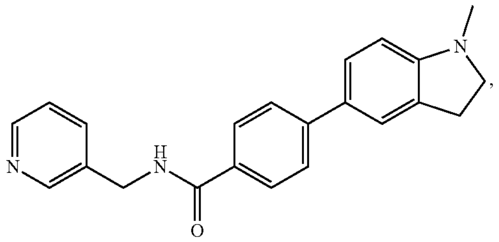

or a pharmaceutically acceptable salt, solvate, hydrate, polymorph, co-crystal, tautomer, stereoisomer, isotopically labeled derivative, or prodrug thereof.

In certain embodiments, the compound is of the formula:

I-202

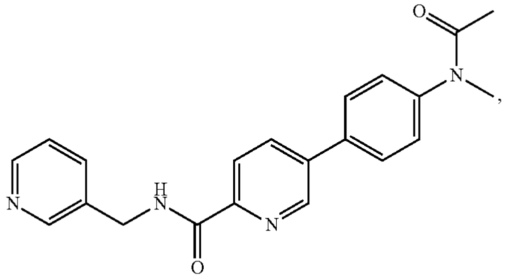

or a pharmaceutically acceptable salt, solvate, hydrate, polymorph, co-crystal, tautomer, stereoisomer, isotopically labeled derivative, or prodrug thereof.

In certain embodiments, the compound is of the formula:

I-208

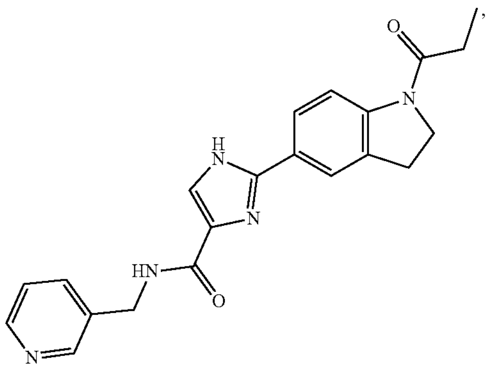

, or

-continued

I-187

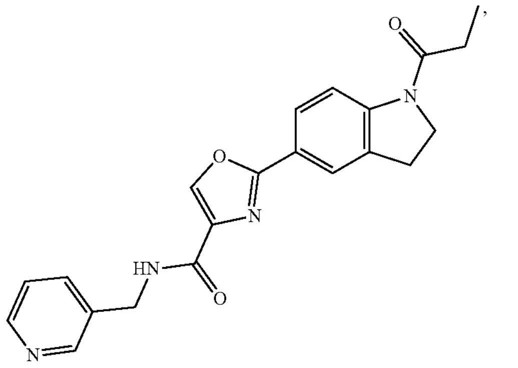

or a pharmaceutically acceptable salt, solvate, hydrate, polymorph, co-crystal, tautomer, stereoisomer, isotopically labeled derivative, or prodrug thereof.

In certain embodiments, the compound is of the formula:

I-209

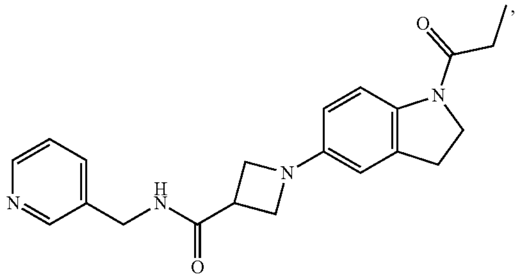

or a pharmaceutically acceptable salt, solvate, hydrate, polymorph, co-crystal, tautomer, stereoisomer, isotopically labeled derivative, or prodrug thereof.

In certain embodiments, the compound is of the formula:

I-201

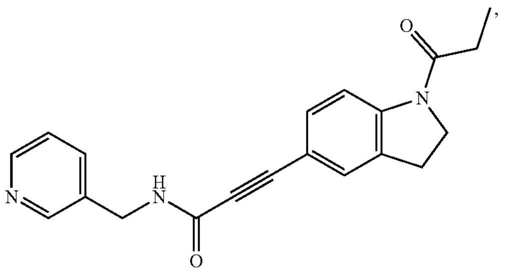

or a pharmaceutically acceptable salt, solvate, hydrate, polymorph, co-crystal, tautomer, stereoisomer, isotopically labeled derivative, or prodrug thereof.

In certain embodiments, a compound of the disclosure (a compound described herein) is a compound of Formula (0) or (0'), or a pharmaceutically acceptable salt, solvate, hydrate, polymorph, co-crystal, tautomer, stereoisomer, isotopically labeled derivative, or prodrug thereof. In certain embodiments, a compound of the disclosure is a compound of Formula (0) or (0'), or a pharmaceutically acceptable salt, tautomer, or stereoisomer thereof. In certain embodiments, a compound of the disclosure is a compound of Formula (0) or (0'), or a pharmaceutically acceptable salt thereof.

In certain embodiments, a compound of the disclosure (a compound described herein) is a compound of Formula (I), or a pharmaceutically acceptable salt, solvate, hydrate, polymorph, co-crystal, tautomer, stereoisomer, isotopically labeled derivative, or prodrug thereof. In certain embodiments, a compound of the disclosure is a compound of Formula (I), or a pharmaceutically acceptable salt, tautomer, or stereoisomer thereof. In certain embodiments, a compound of the disclosure is a compound of Formula (I), or a pharmaceutically acceptable salt thereof.

The compounds of the present disclosure may have a safe in vitro pharmacological profile. Compared to certain similar known compounds, the compounds of the present disclosure may have a safer (e.g., at least 10%, at least 20%, at least 50%, at least 100%, at least 200%, at least 500%, or at least 1,000% safer) in vitro pharmacological profile.

The compounds of the present disclosure may have a high aqueous solubility. Compared to certain similar known compounds, the compounds of the present disclosure may have a higher (e.g., at least 10%, at least 20%, at least 50%, at least 100%, at least 200%, at least 500%, or at least 1,000% higher) aqueous solubility.

The compounds of the present disclosure may have a high microsomal stability. Compared to certain similar known compounds, the compounds of the present disclosure may have a higher (e.g., at least 10%, at least 20%, at least 50%, at least 100%, at least 200%, at least 500%, or at least 1,000% higher) microsomal stability.

Exemplary compounds of the present disclosure include the compounds in Table A, Table 5, and following compounds:

I-T 460

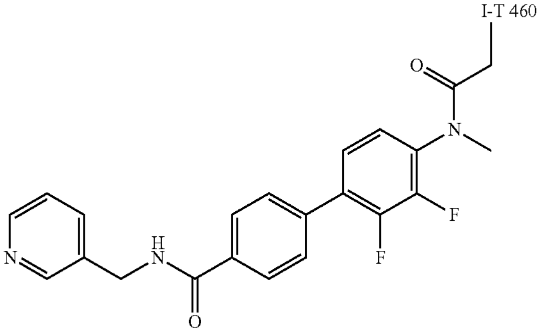

I-T 461

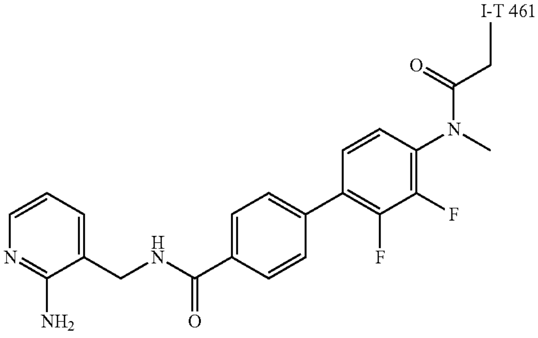

-continued
I-T 462
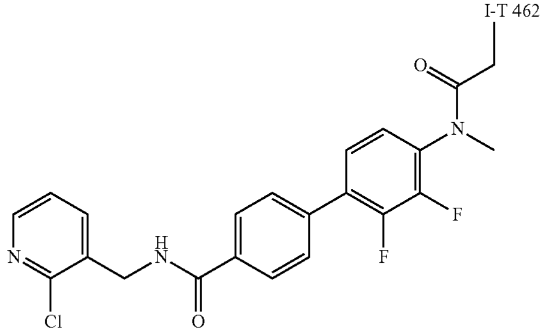
I-T 463
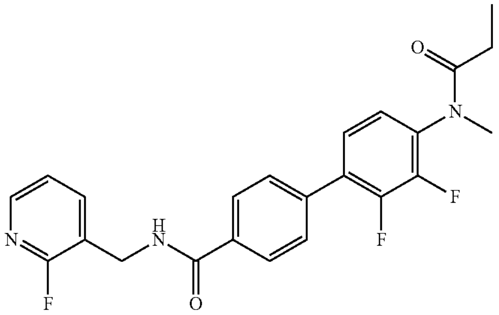
,
I-T 464
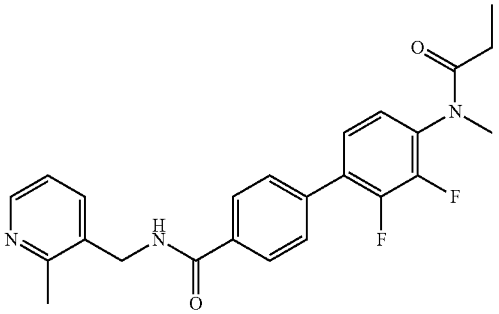
,
I-T 465
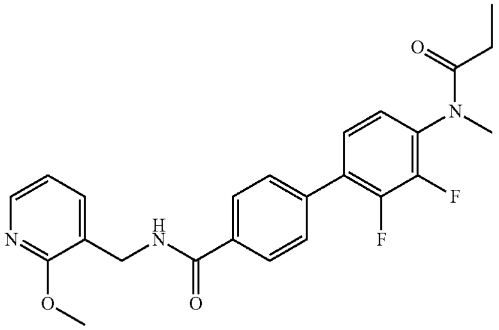
,
-continued
I-T 466
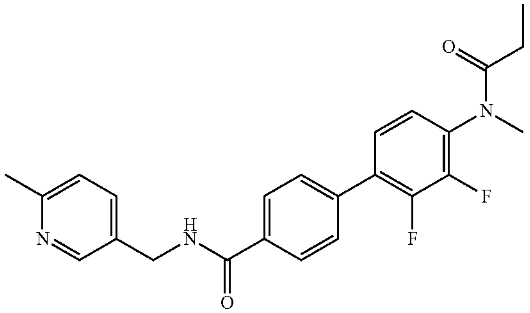
,
I-T 467
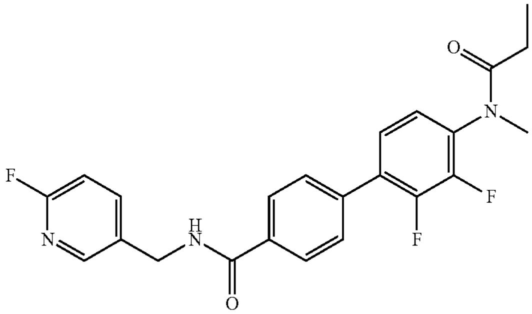
I-T 468
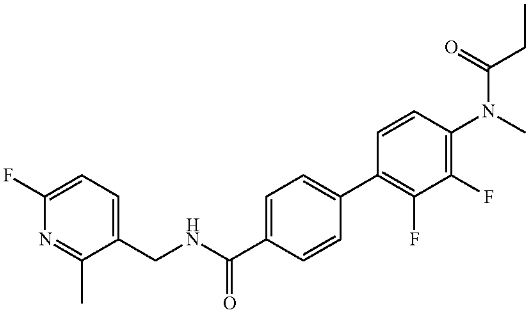
,
I-T 469
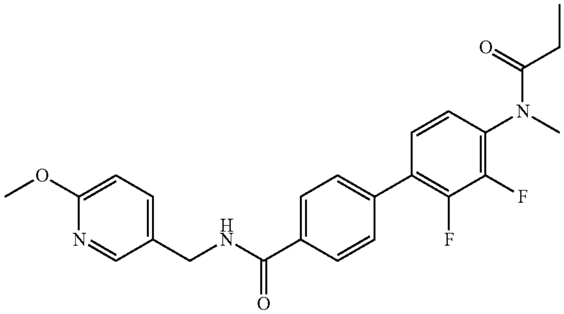

-continued
I-T 470
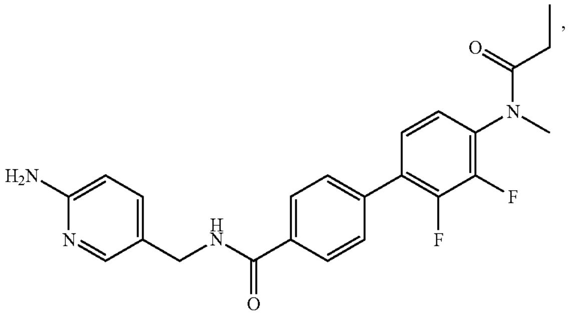
I-T 471
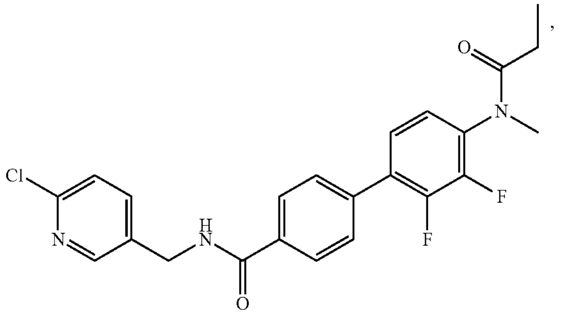
I-T 472
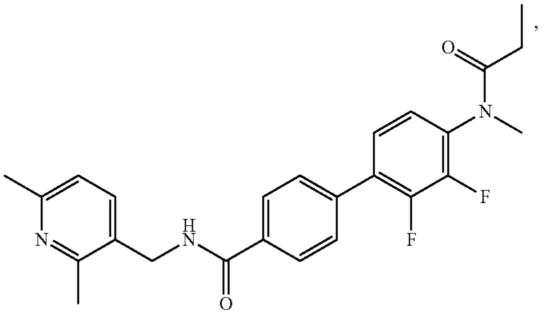
I-T 473
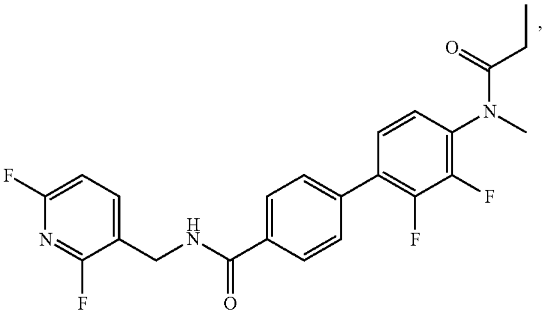
-continued
I-T 474
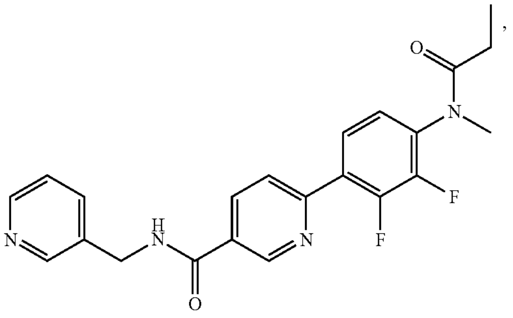
I-T 475
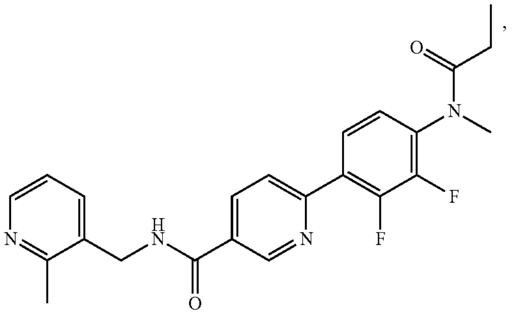
I-T 476
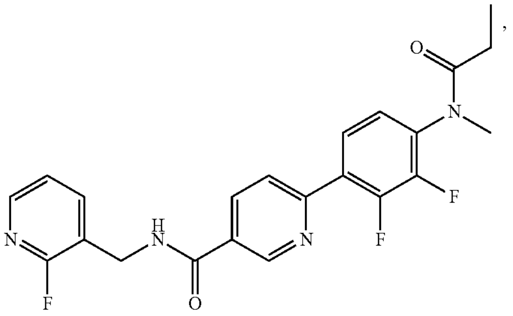
I-T 477
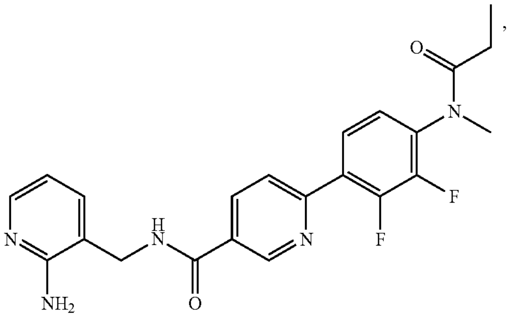

-continued
I-T 478
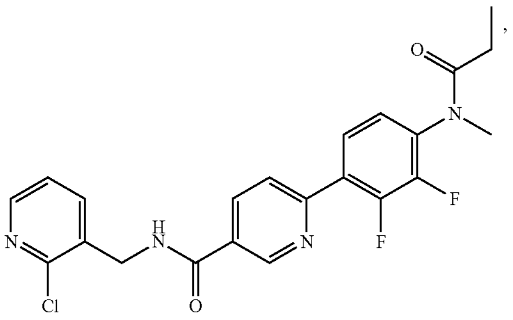
,
I-T 479
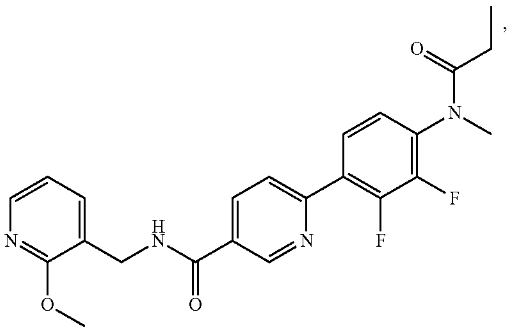
,
I-T 480
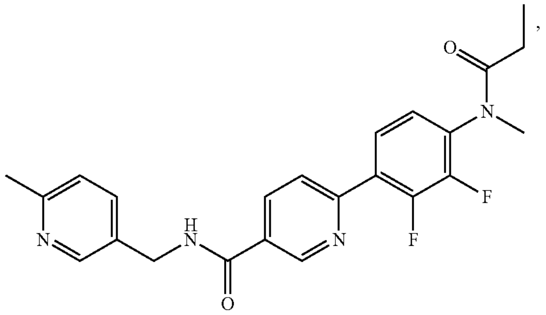
,
I-T 481
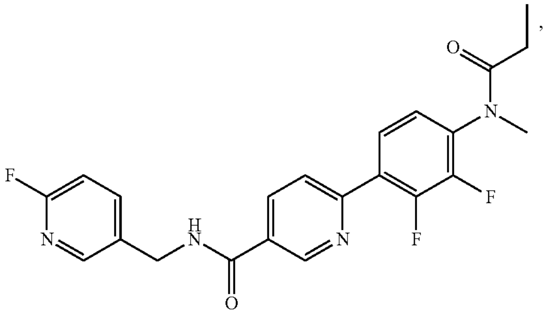
,
-continued
I-T 482
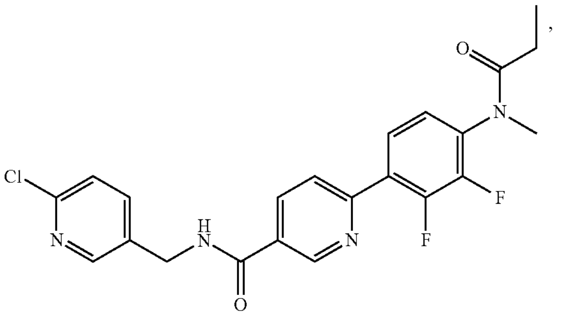
,
I-T 483
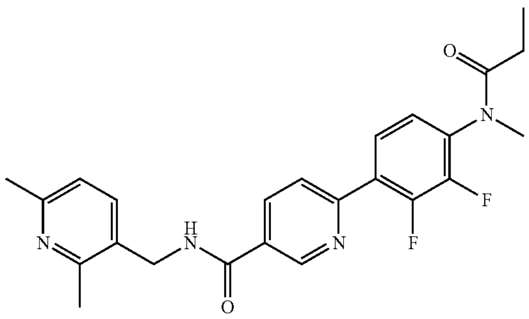
I-T 484
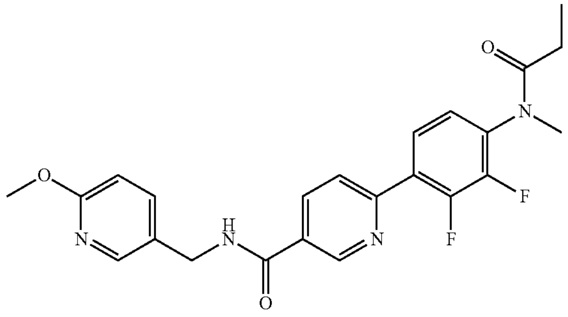
I-T 485
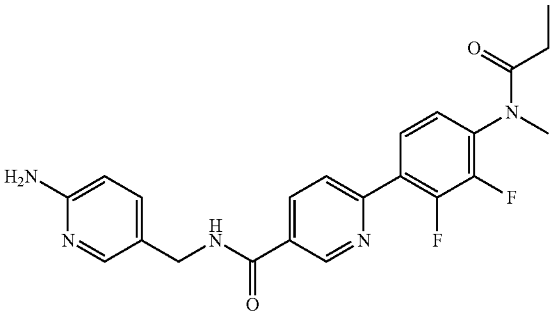

-continued
I-T 486
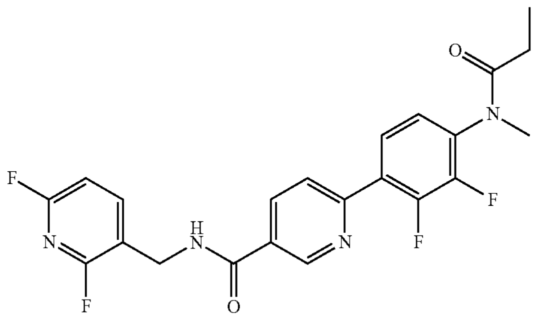
I-T 487
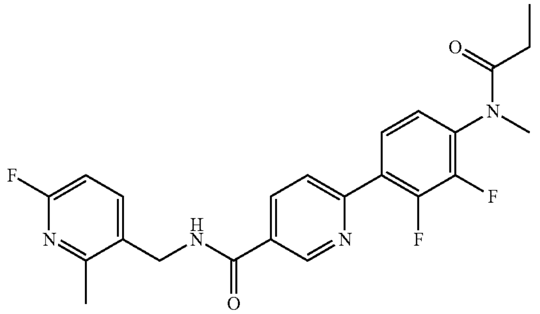
I-T 488
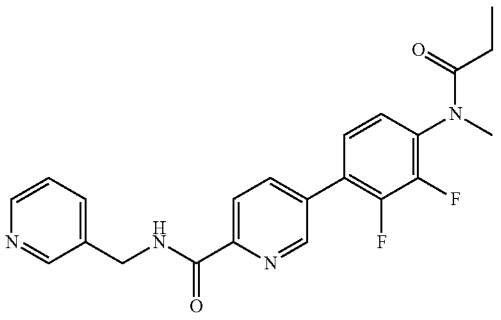
I-T 489
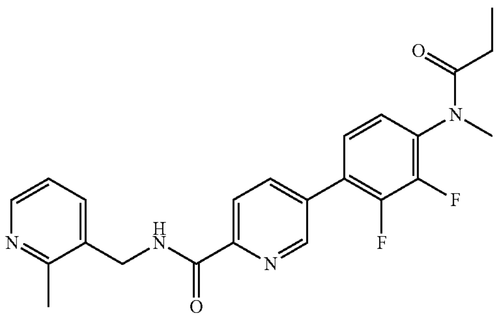
-continued
I-T 490
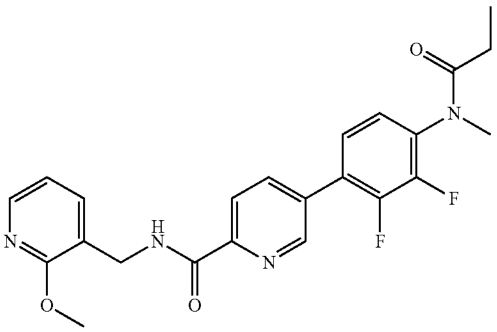
I-T 491
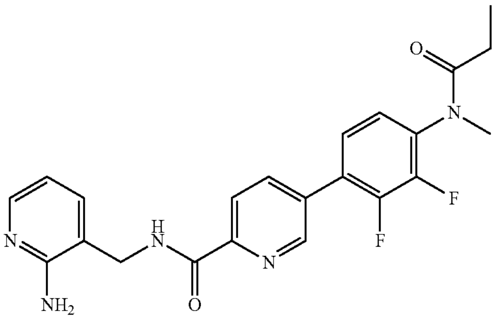
I-T 492
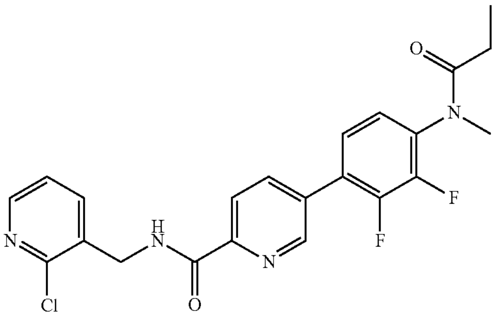
I-T 493
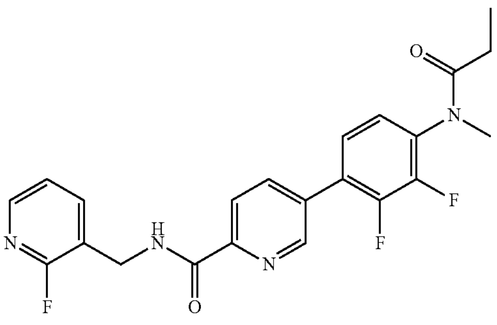

-continued
I-T 494
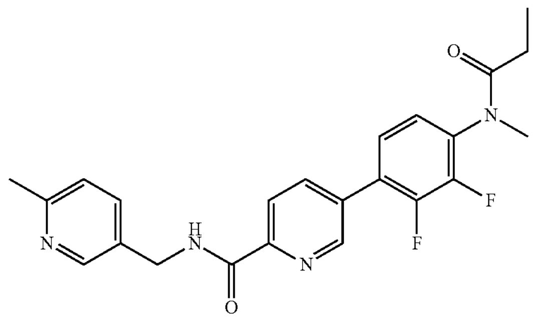
I-T 495
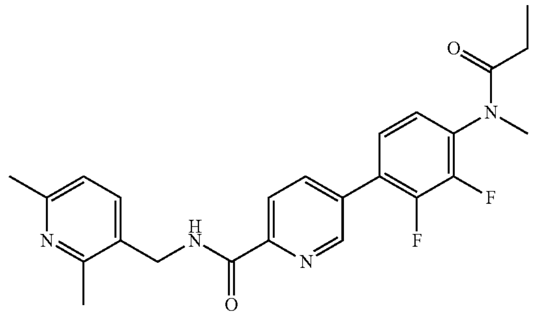
I-T 496
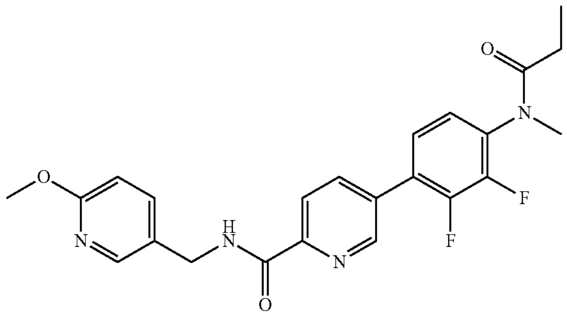
I-T 497
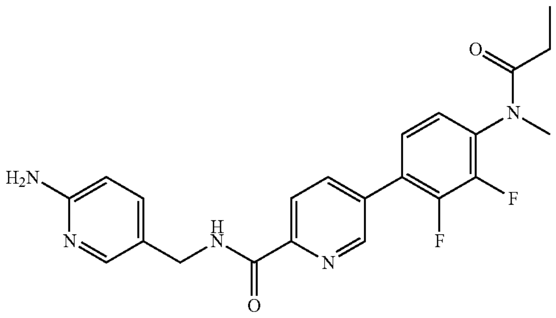
-continued
I-T 498
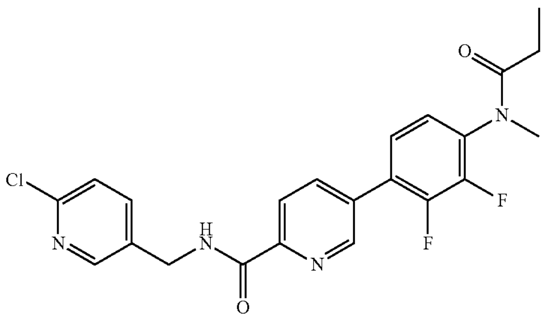
I-T 499
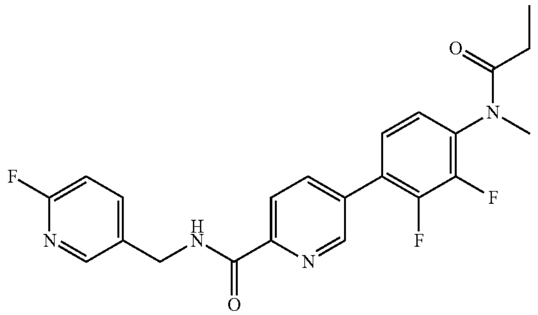
I-T 500
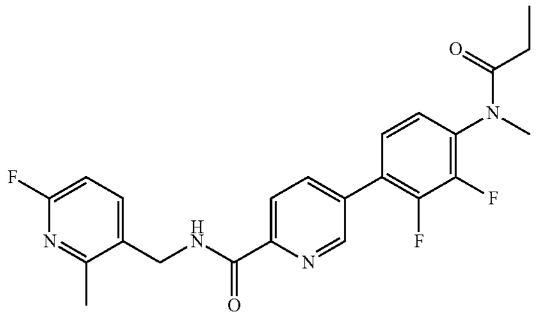
I-T 501
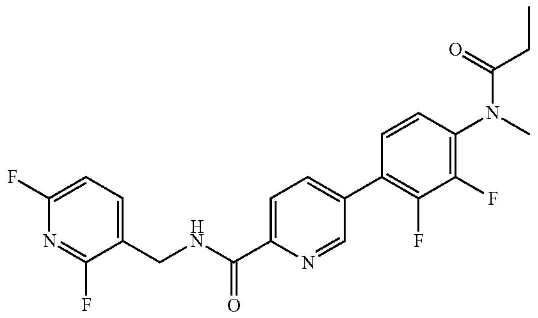

-continued
I-T 502
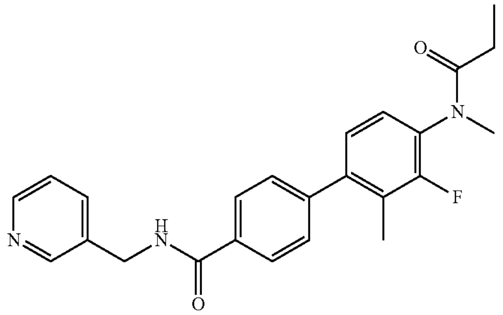
I-T 503
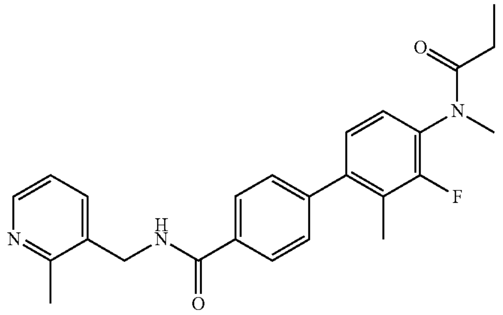
I-T 504
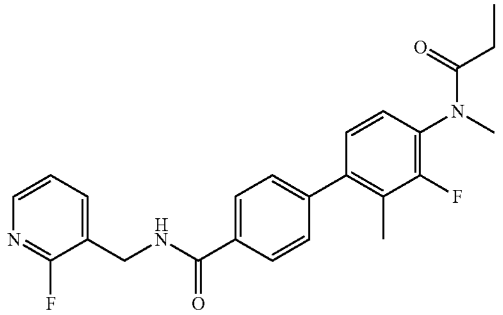
I-T 505
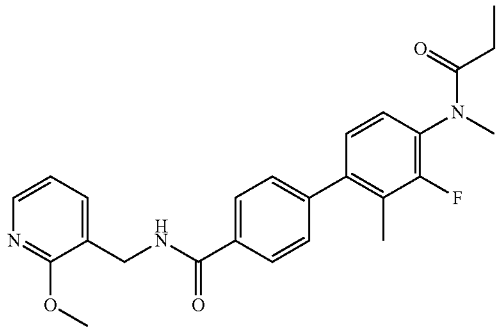
-continued
I-T 506
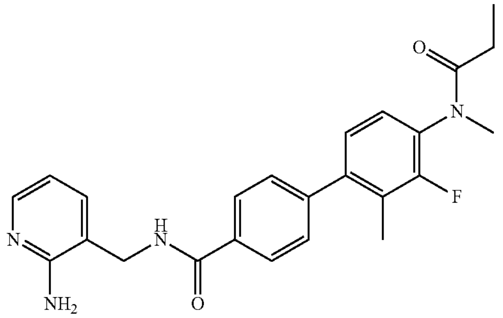
I-T 507
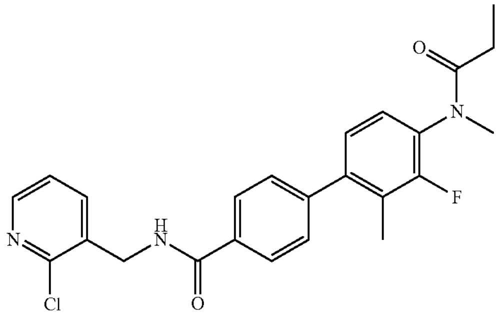
I-T 508
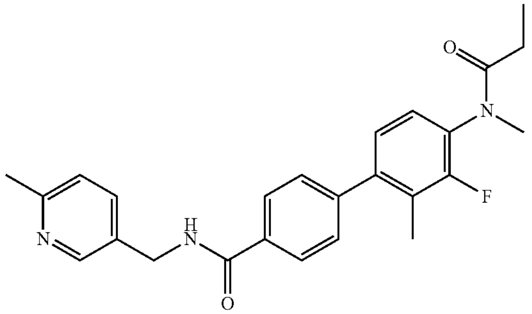
I-T 509
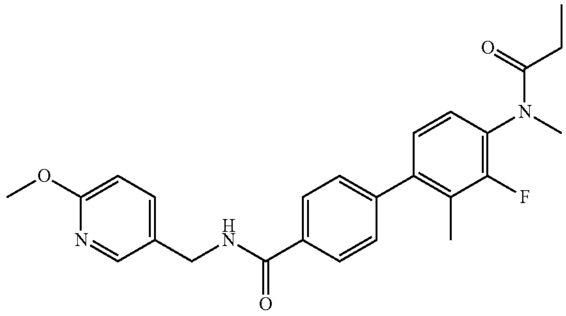

-continued
I-T 510
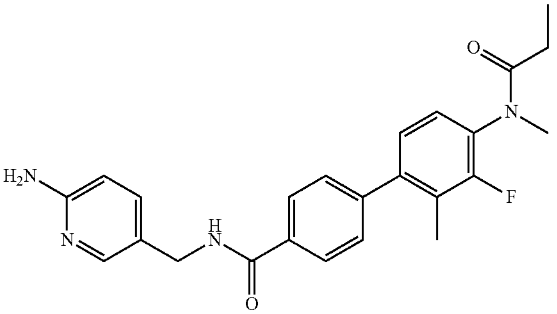
I-T 511
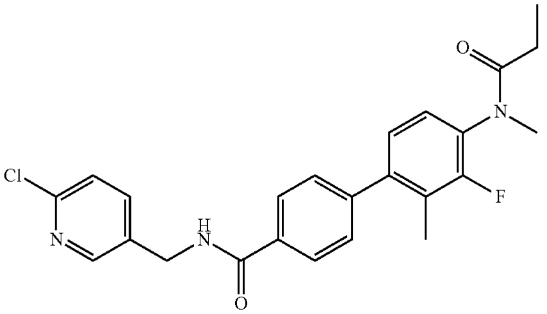
I-T 512
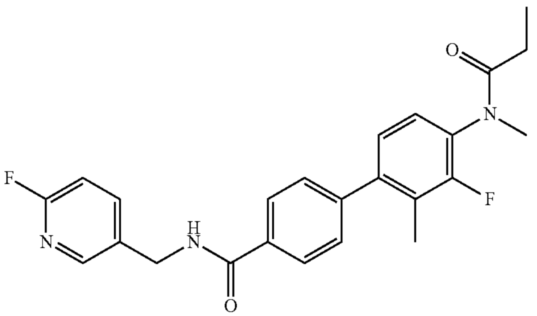
I-T 513
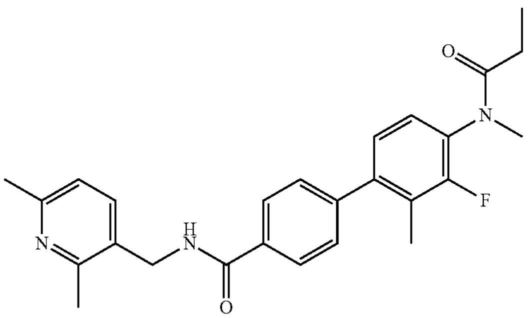
-continued
I-T 514
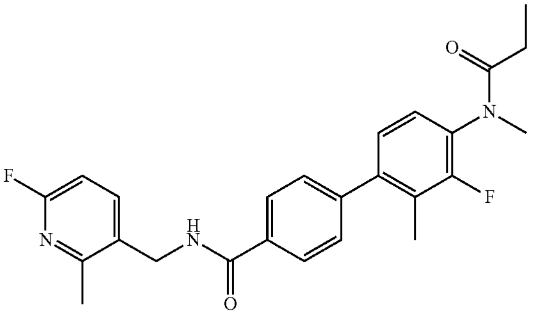
I-T 515
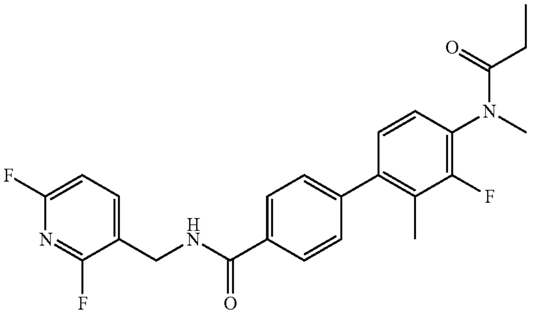
I-T 516
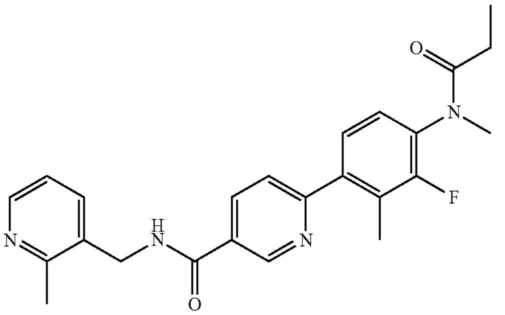
I-T 517
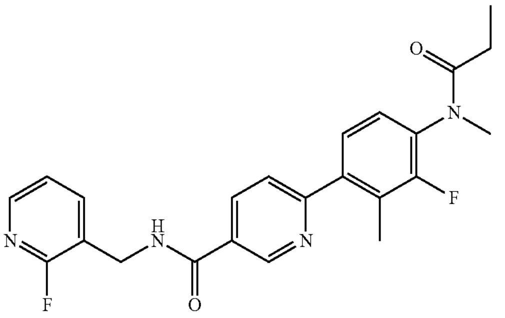

-continued
I-T 518
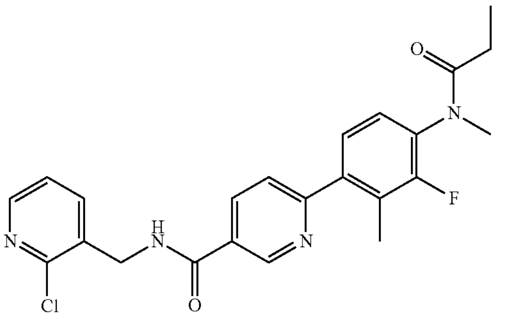
I-T 519
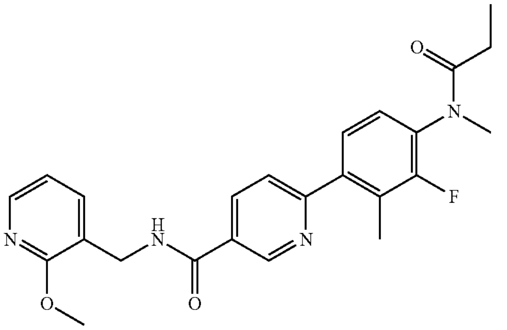
I-T 520
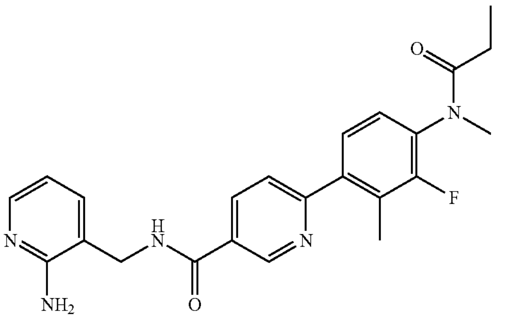
I-T 521
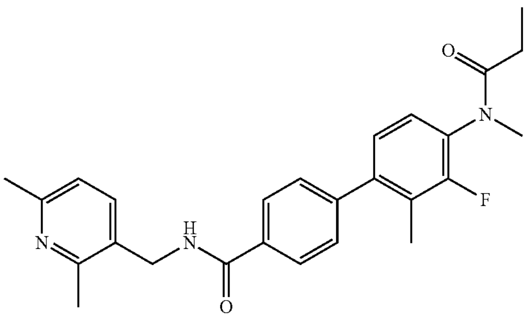
-continued
I-T 522
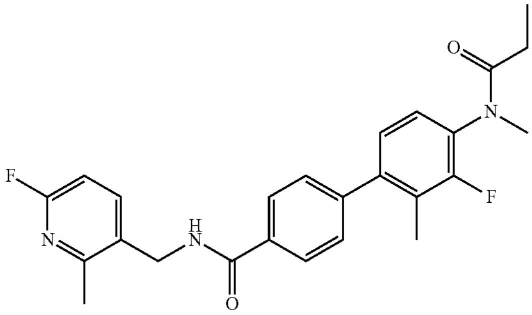
I-T 523
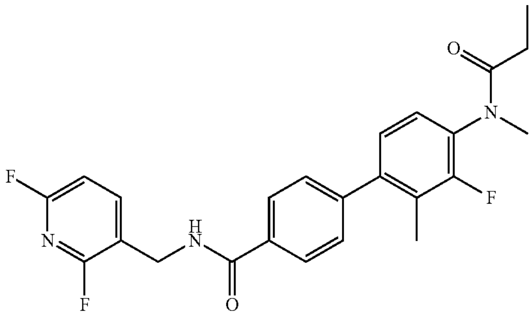
I-T 524
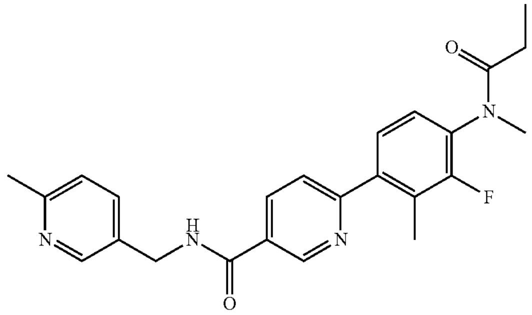
I-T 525
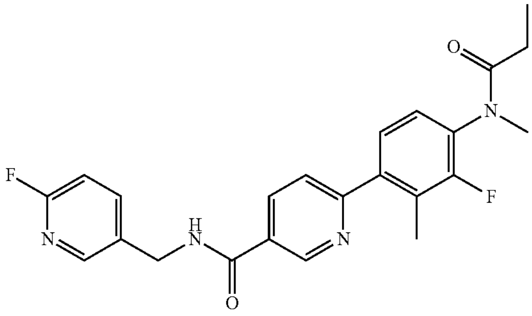

-continued
I-T 526
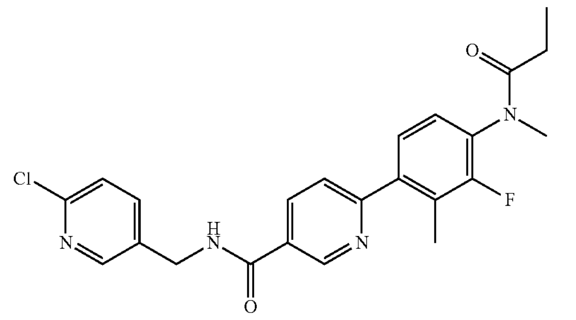
I-T 527
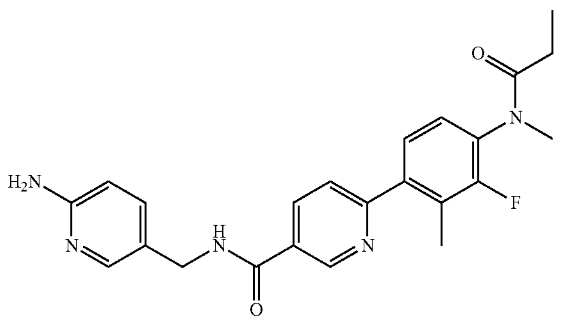
I-T 528
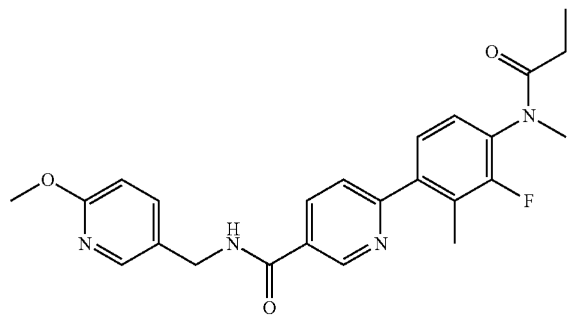
I-T 529
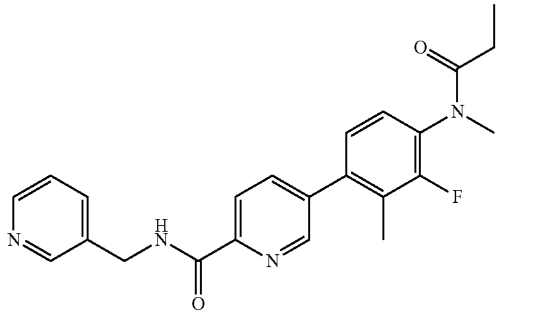
-continued
I-T 530
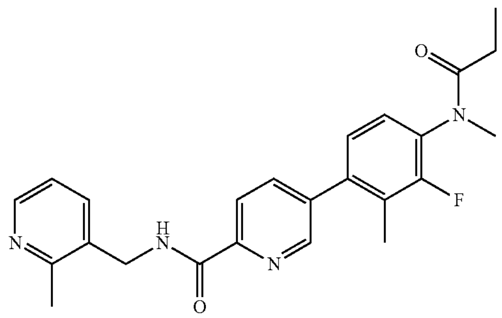
I-T 531
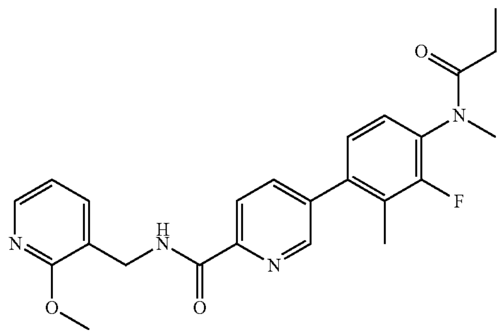
I-T 532
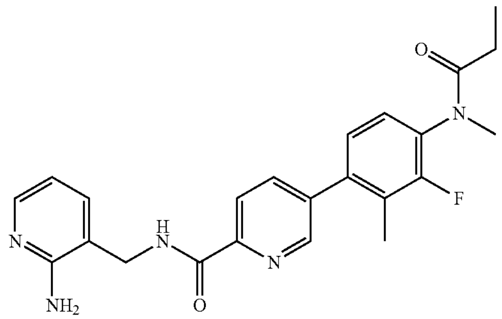
I-T 533
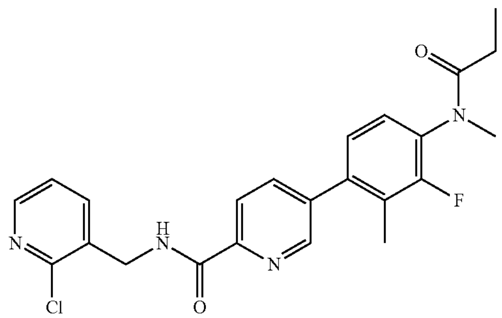

-continued
I-T 534
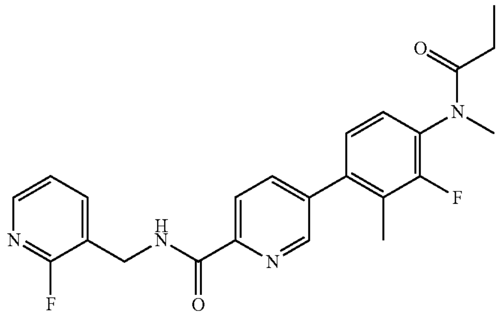
I-T 535
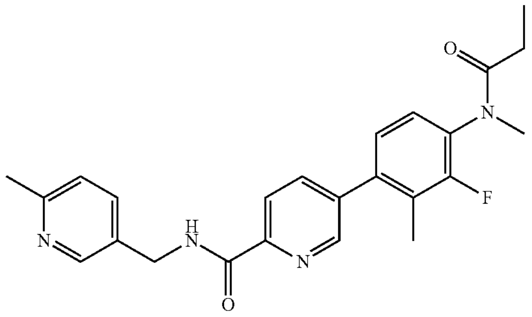
I-T 536
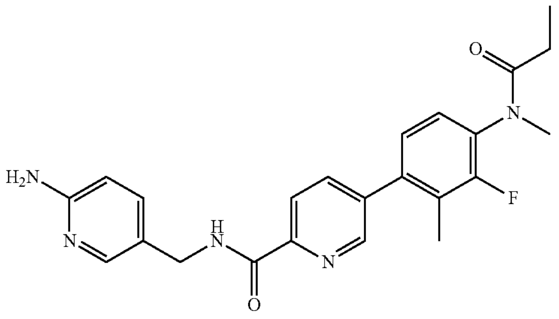
I-T 537
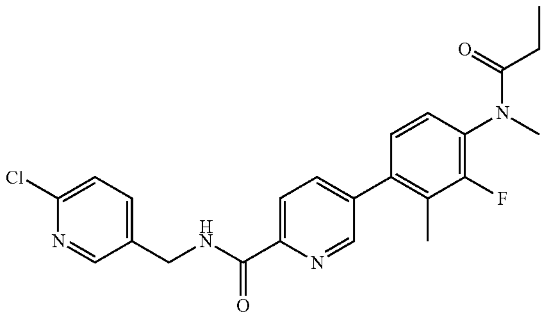
-continued
I-T 538
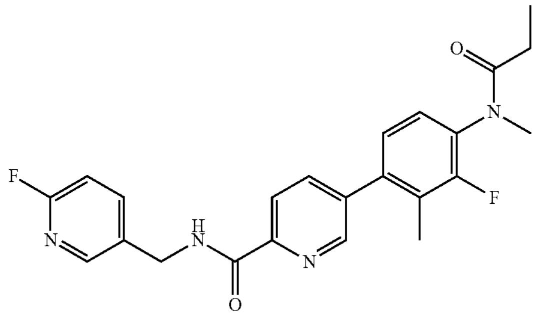
I-T 539
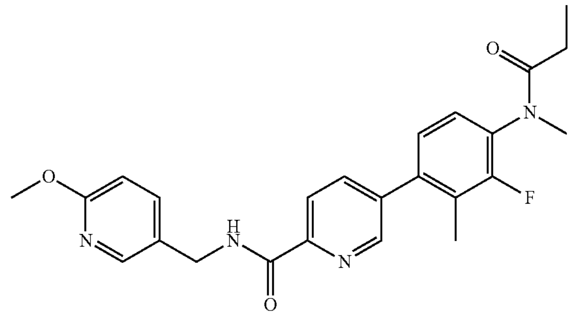
I-T 540
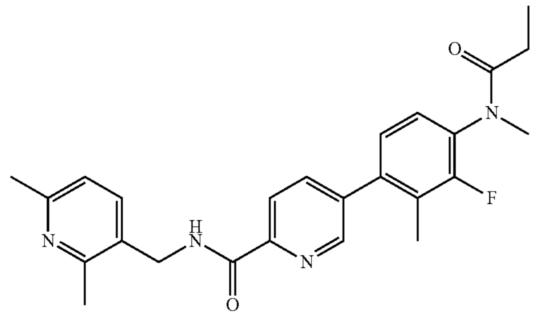
I-T 541
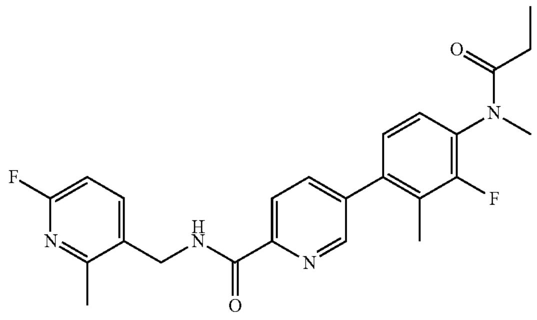

-continued
I-T 542
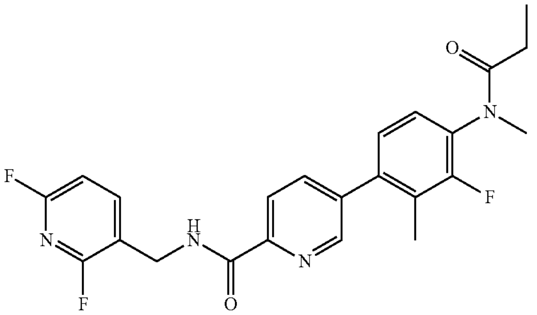
I-T 543
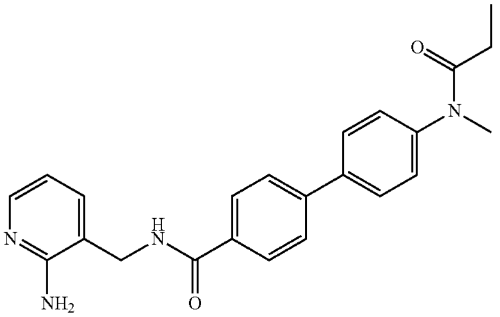
I-T 544
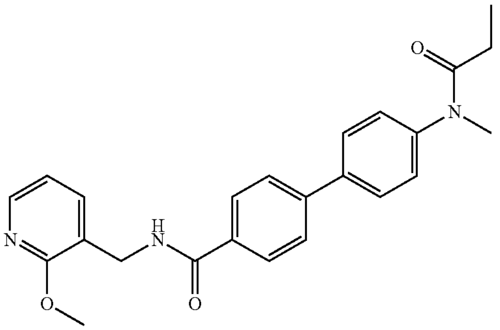
I-T 545
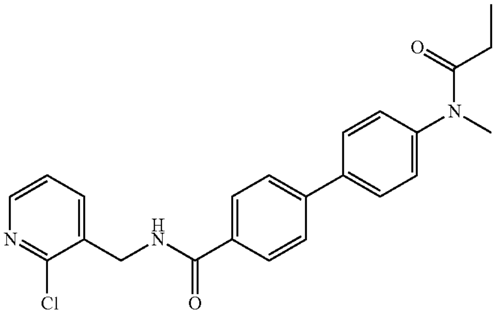
-continued
I-T 546
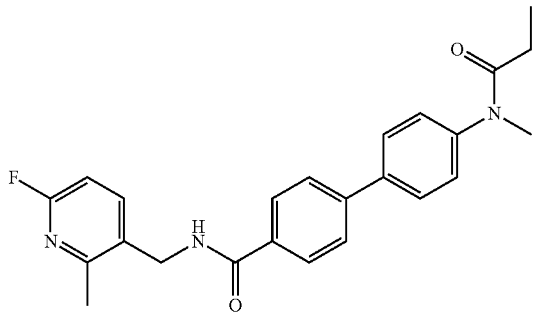
I-T 547
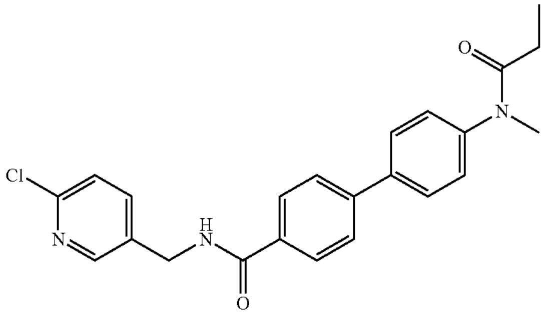
I-T 548
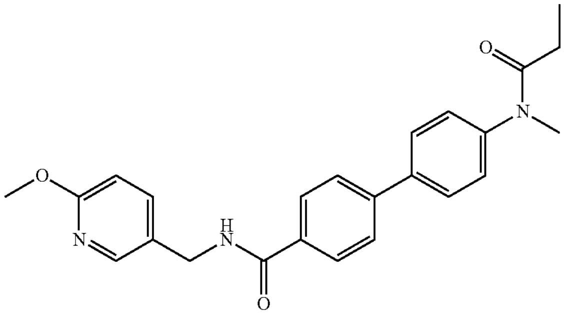
I-T 549
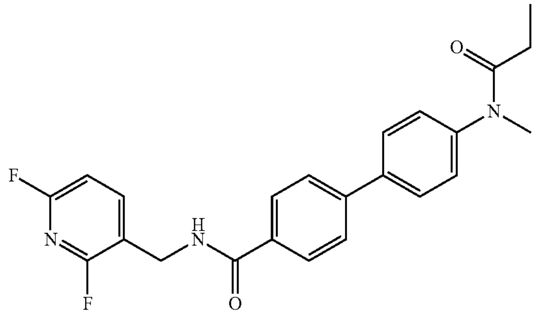

-continued
I-T 550
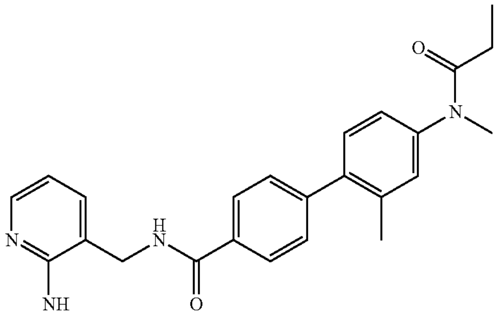
I-T 551
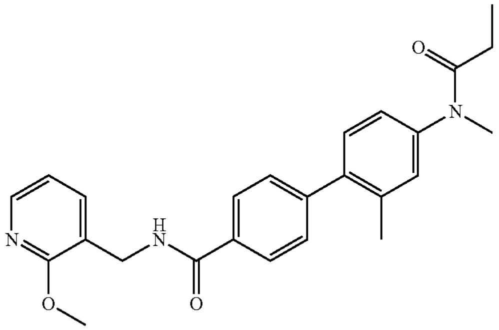
I-T 552
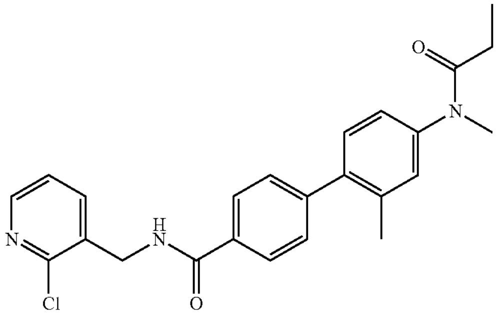
I-T 553
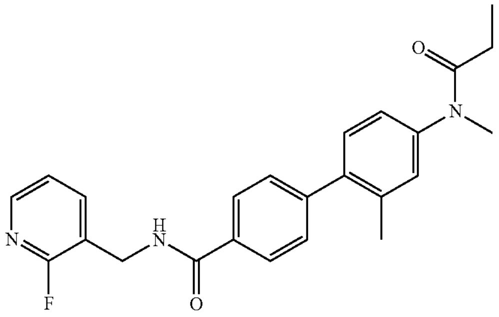
-continued
I-T 554
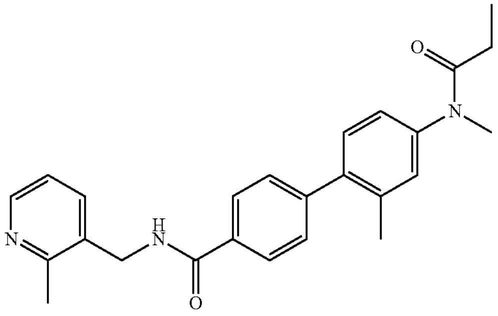
I-T 555
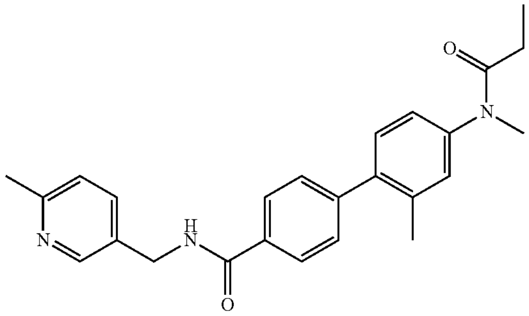
I-T 556
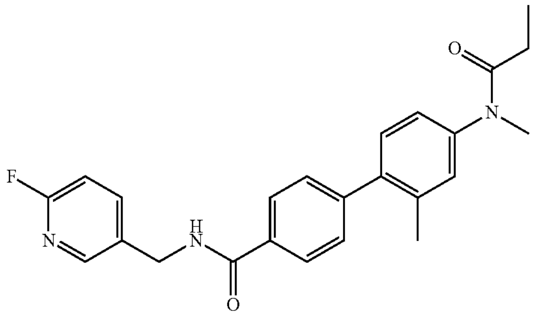
I-T 557
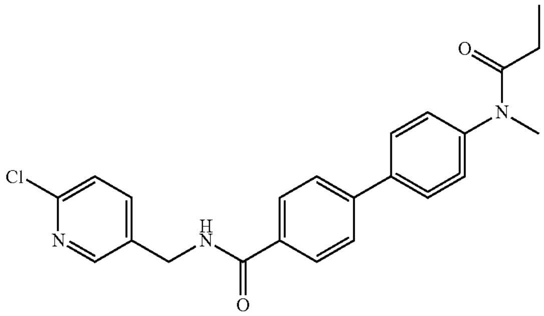

-continued
I-T 558
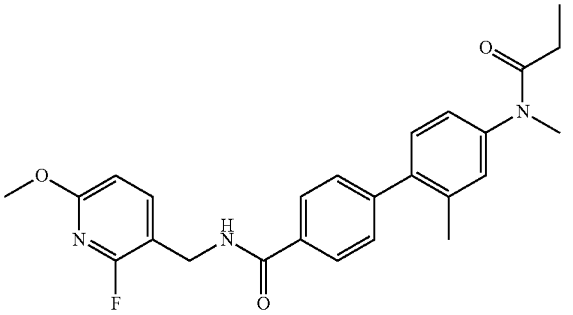
I-T 559
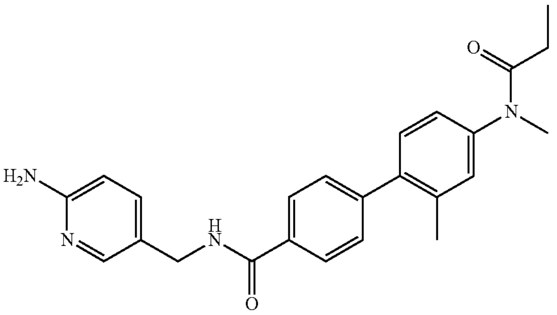
I-T 560
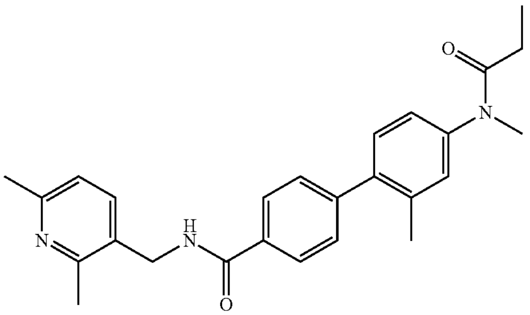
I-T 561
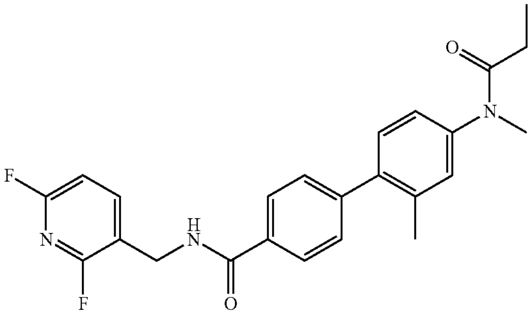
-continued
I-T 562
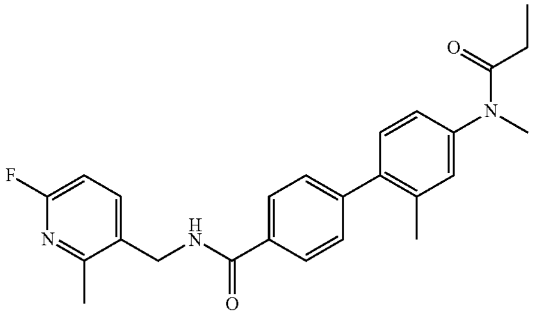
I-T 563
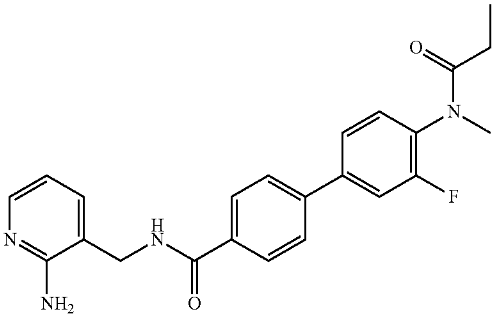
I-T 564
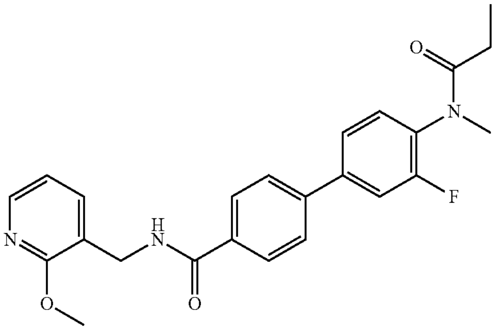
I-T 565
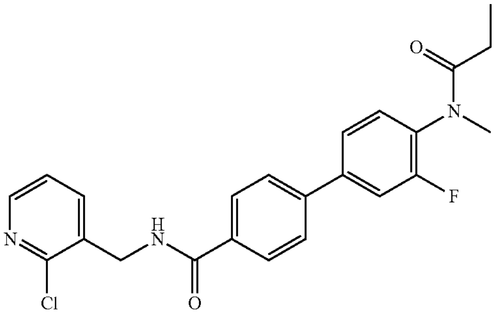

-continued
I-T 566
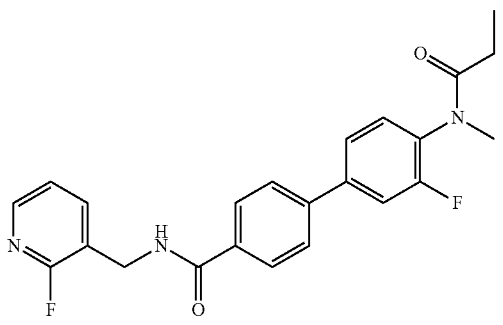
I-T 567
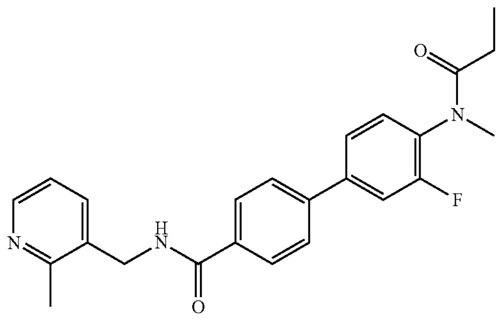
I-T 568
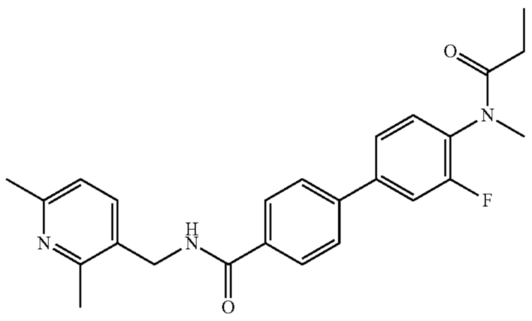
I-T 569
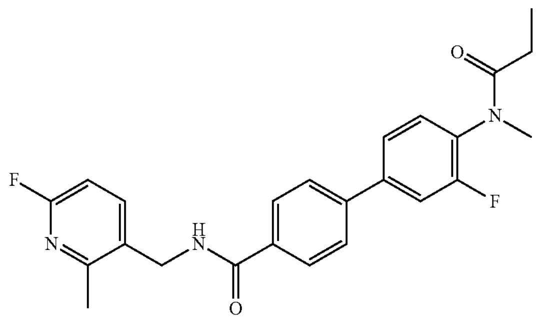
-continued
I-T 570
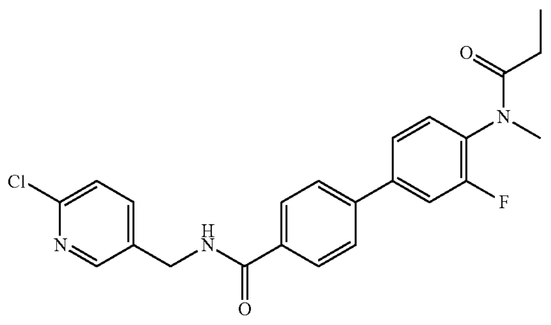
I-T 571
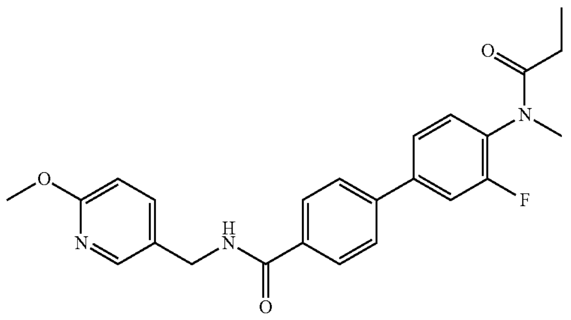
I-T 572
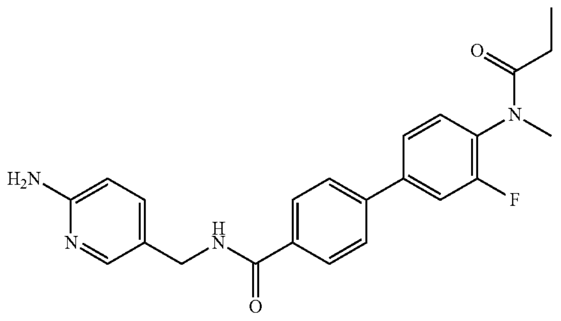
I-T 573
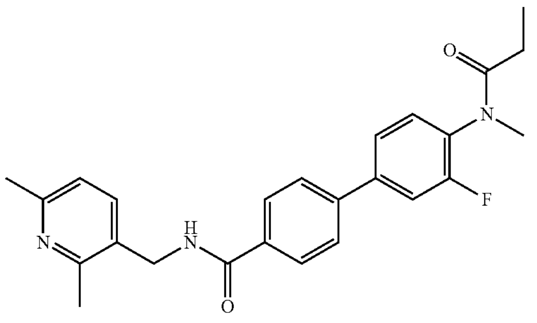

-continued
I-T 574
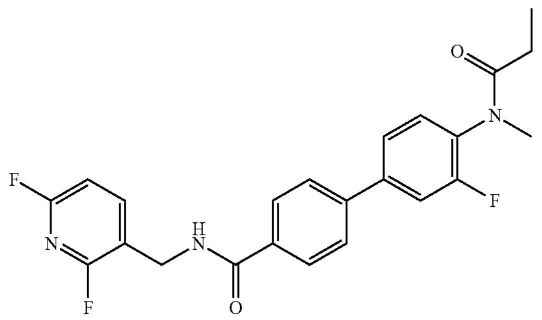
I-T 575
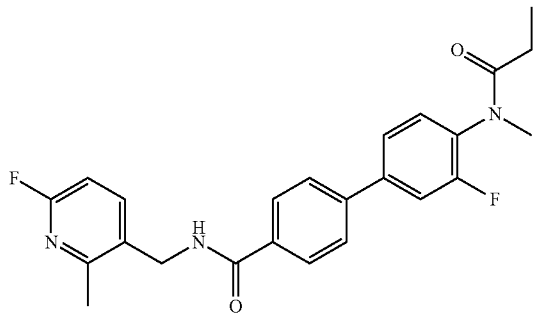
I-T 576
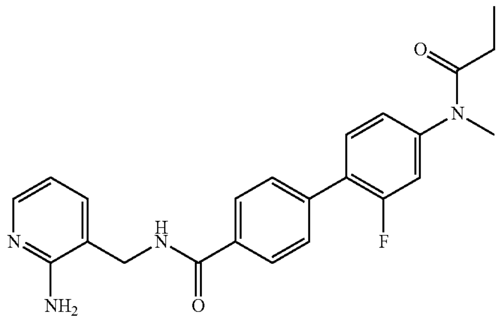
I-T 577
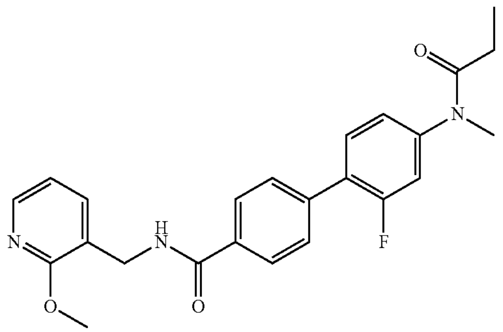
-continued
I-T 578
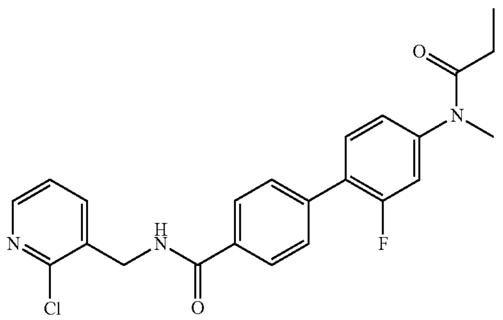
I-T 579
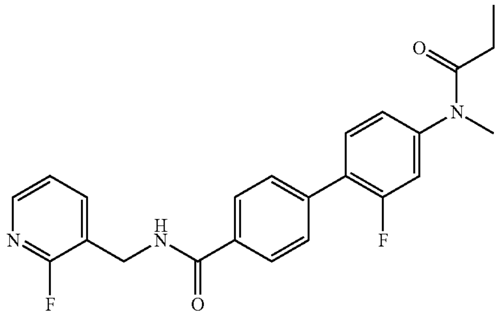
I-T 580
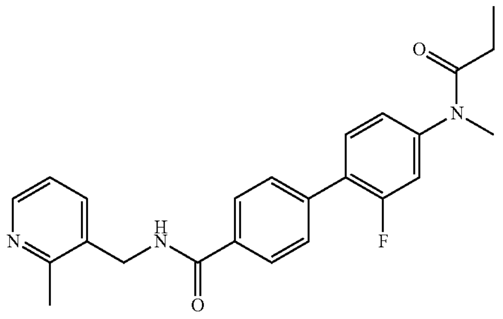
I-T 581
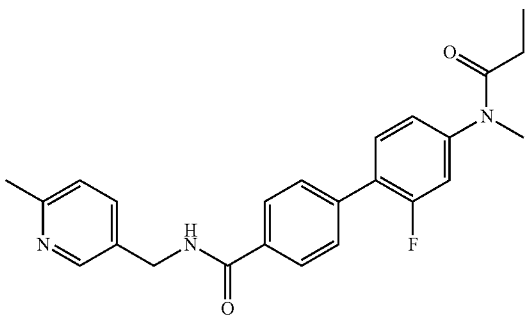

-continued
I-T 582
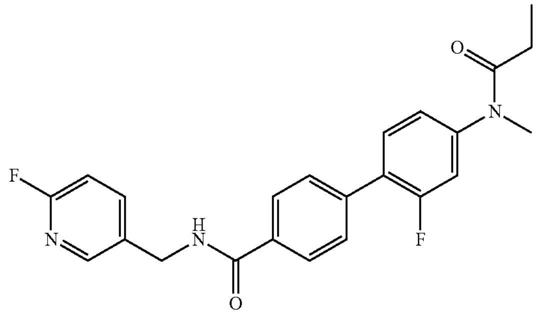
I-T 583
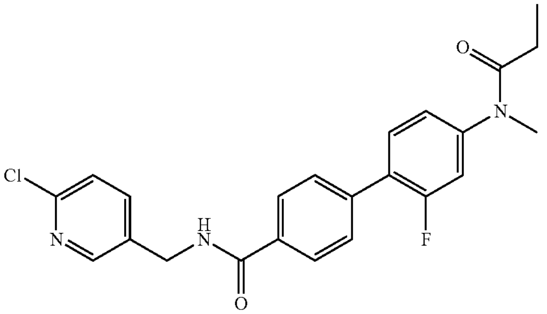
I-T 584
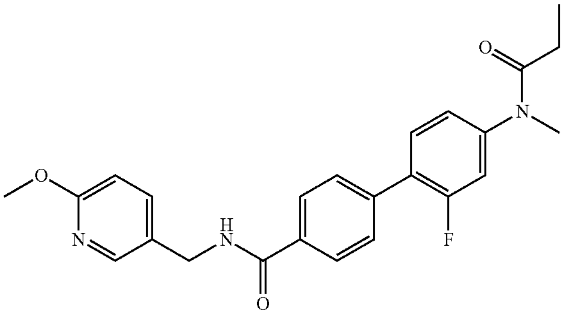
I-T 585
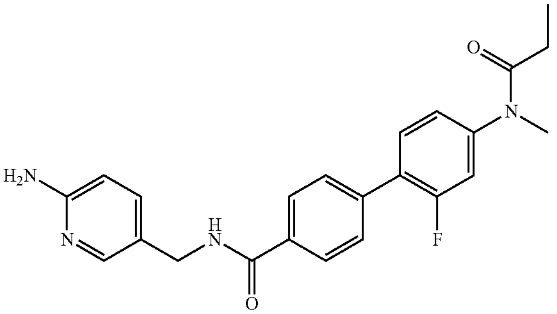
-continued
I-T 586
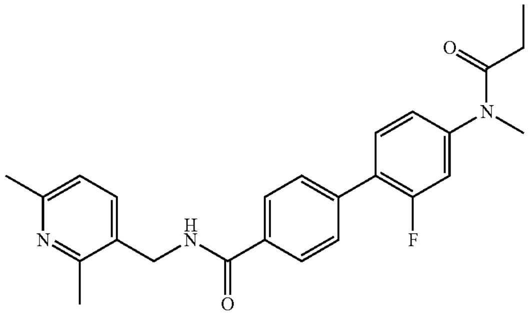
I-T 587
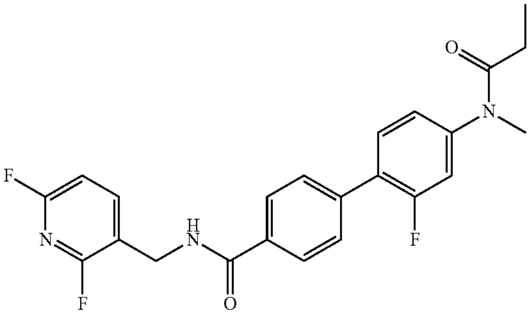
I-T 588
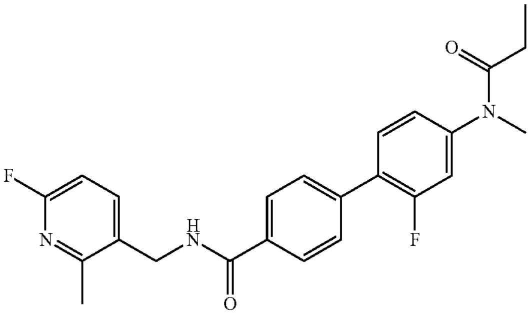
I-T 589
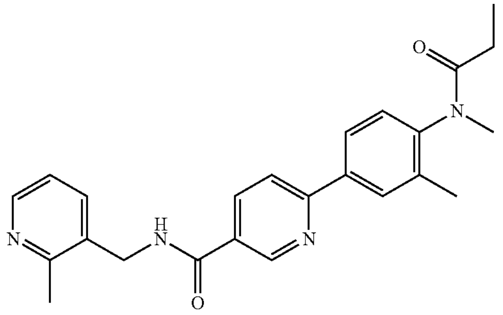

-continued
I-T 590
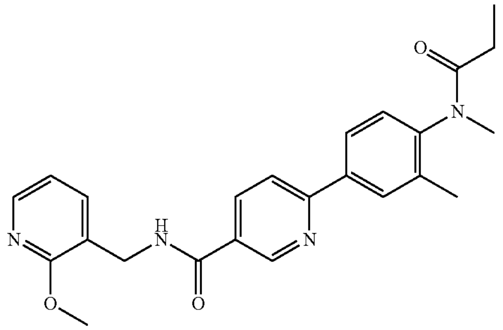
I-T 591
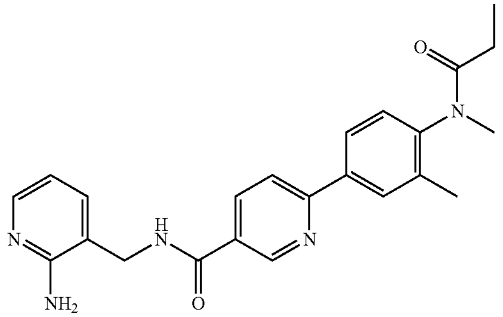
I-T 592
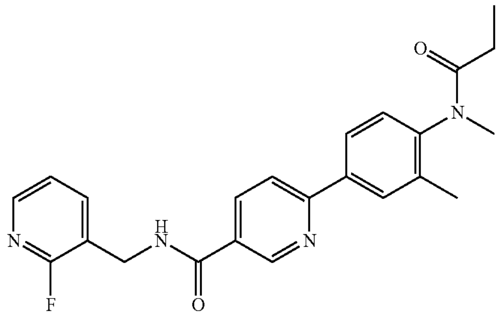
I-T 593
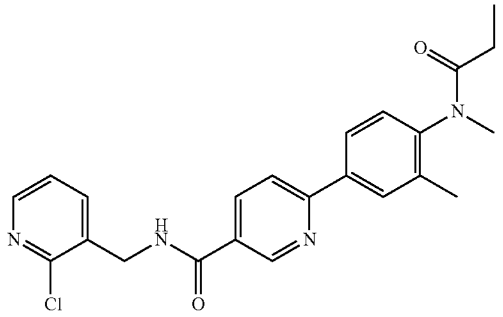
-continued
I-T 594
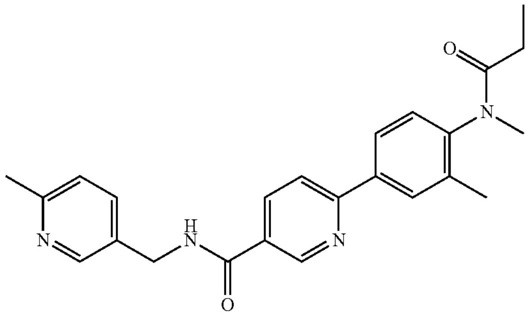
I-T 595
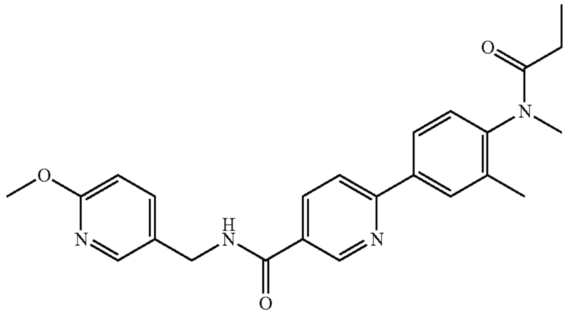
I-T 596
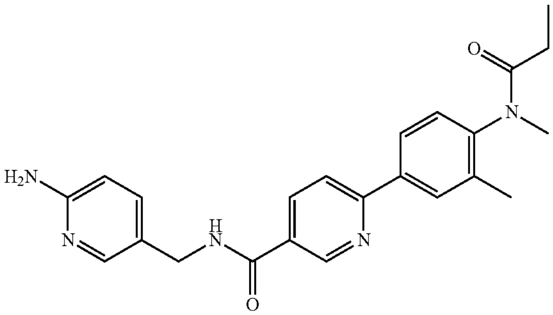
I-T 597
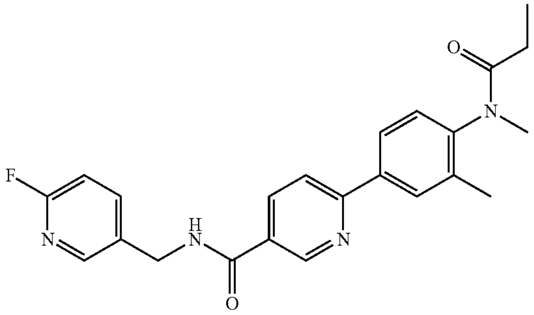

-continued
I-T 598
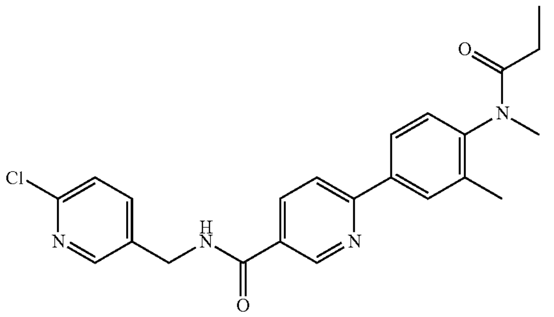
I-T 599
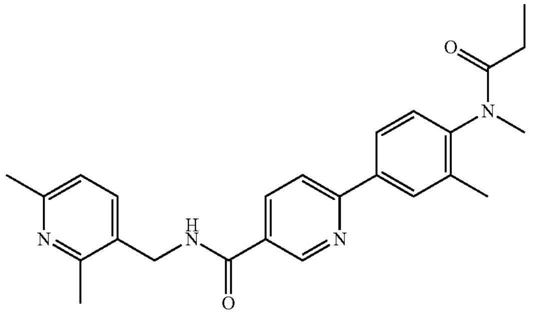
I-T 600
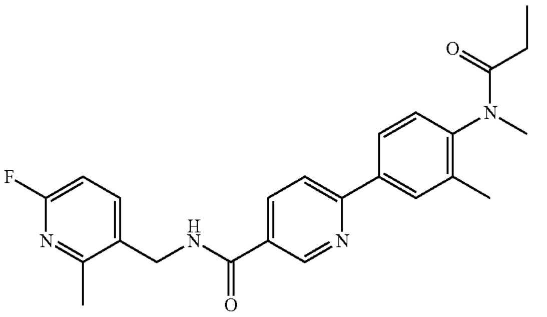
I-T 601
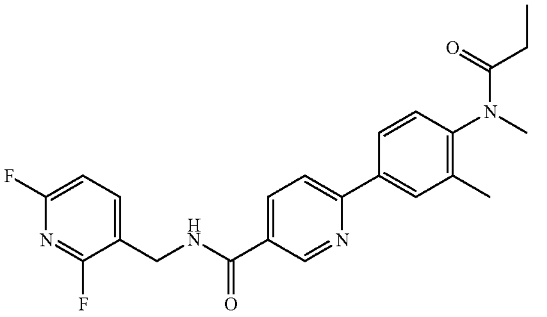
-continued
I-T 602
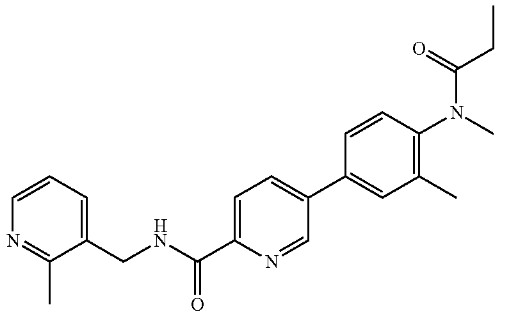
I-T 603
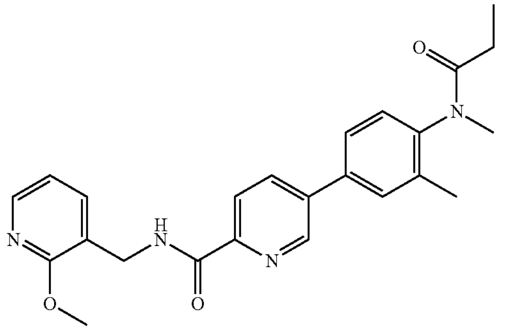
I-T 604
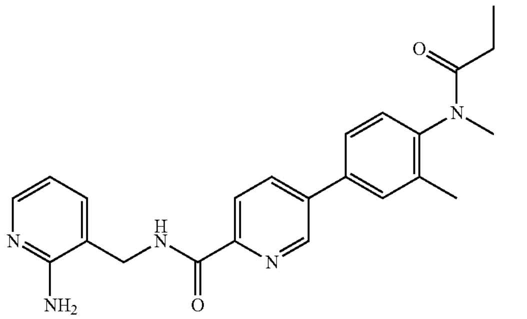
I-T 605
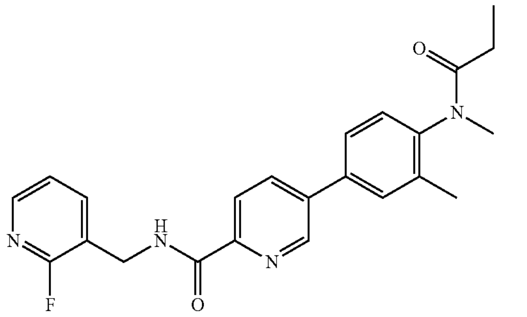

-continued
I-T 606
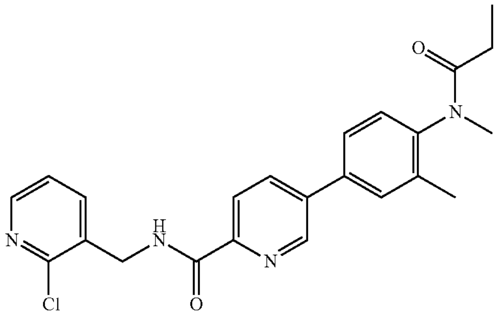
I-T 607
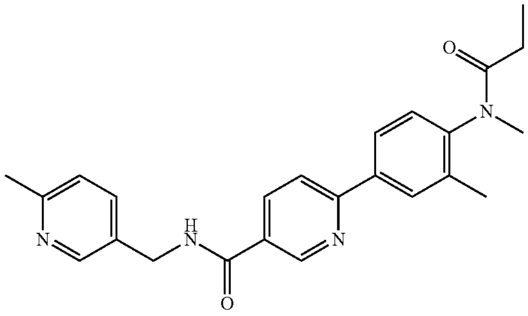
I-T 608
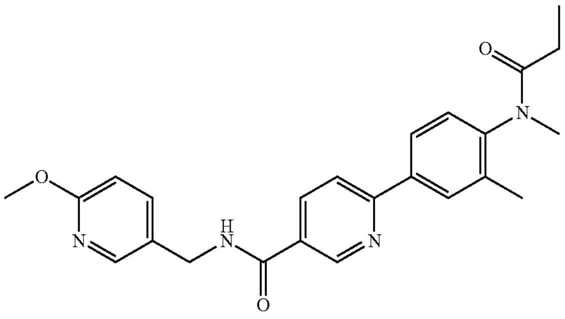
I-T 609
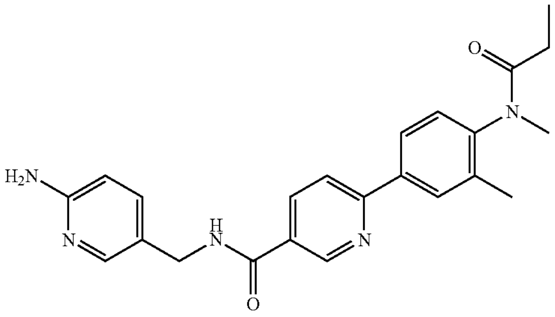
-continued
I-T 610
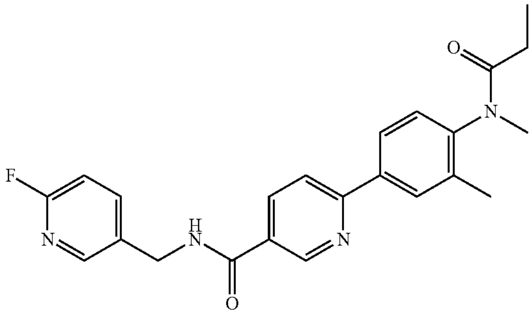
I-T 611
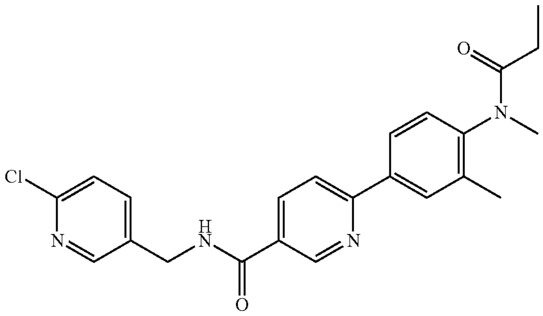
I-T 612
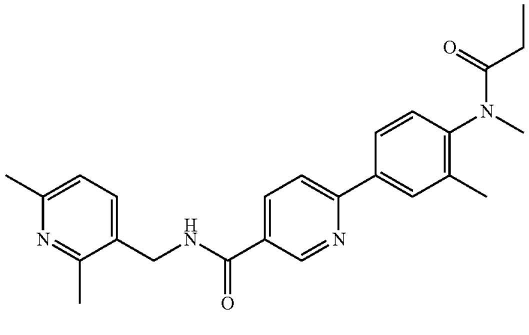
I-T 613
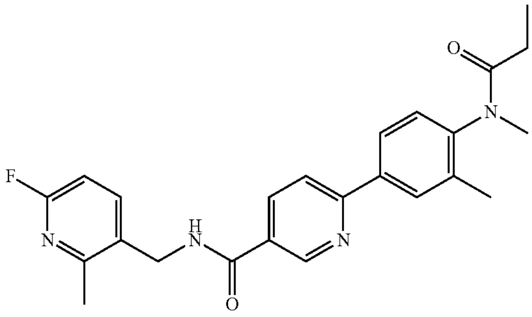

-continued
I-T 614
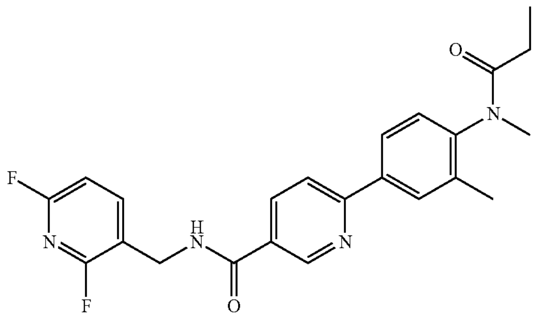
I-T 615
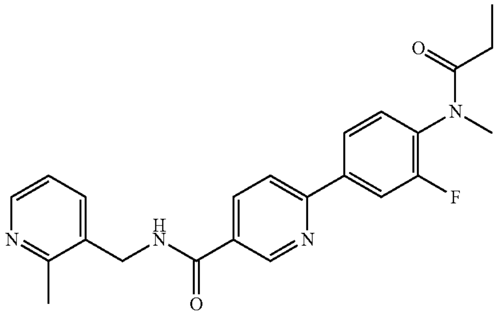
I-T 616
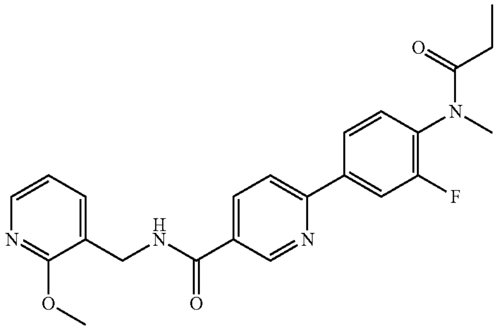
I-T 617
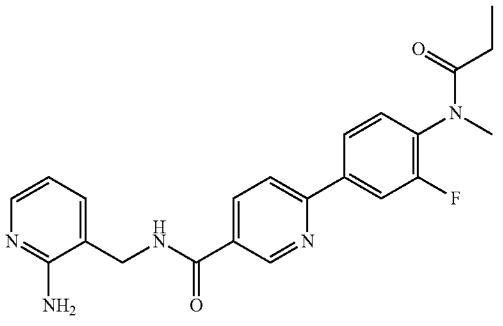
-continued
I-T 618
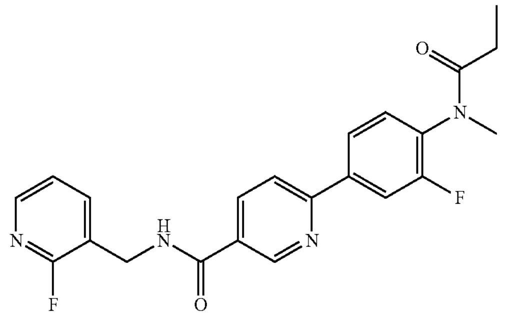
I-T 619
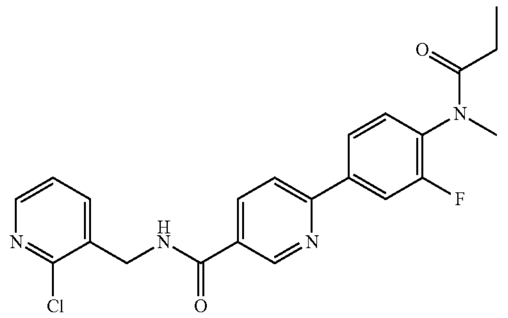
I-T 620
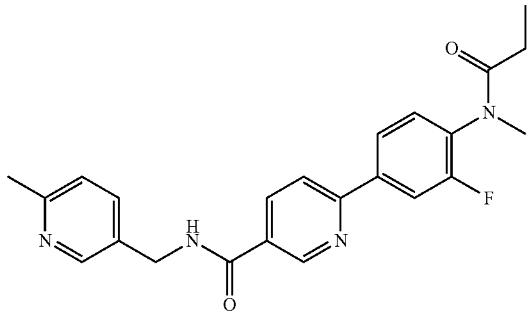
I-T 621
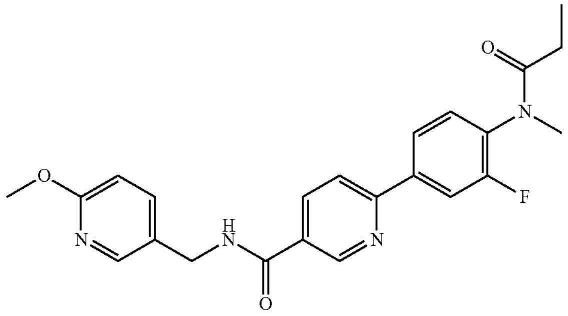

-continued
I-T 622
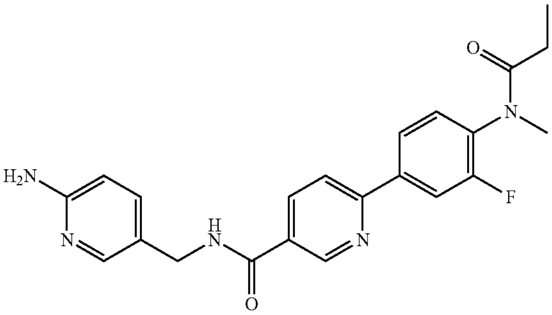
I-T 623
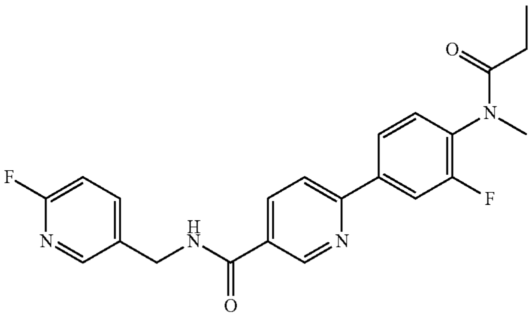
I-T 624
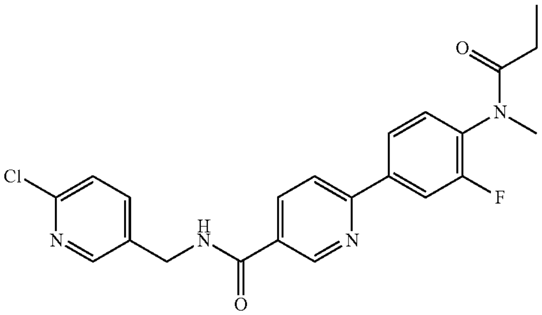
I-T 625
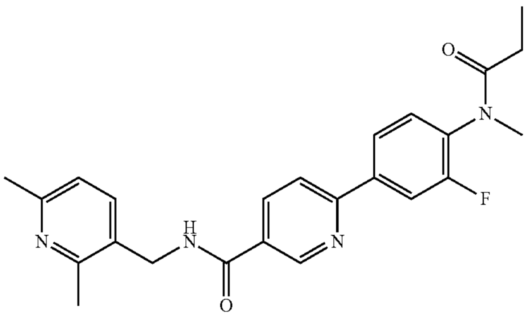
-continued
I-T 626
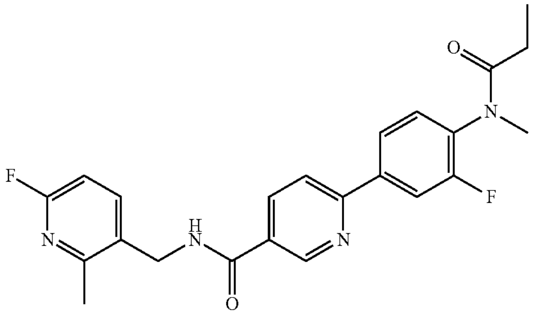
I-T 627
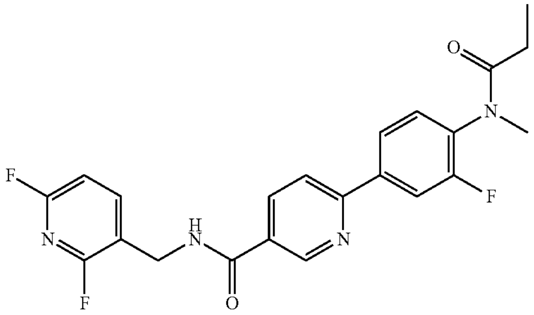
I-T 628
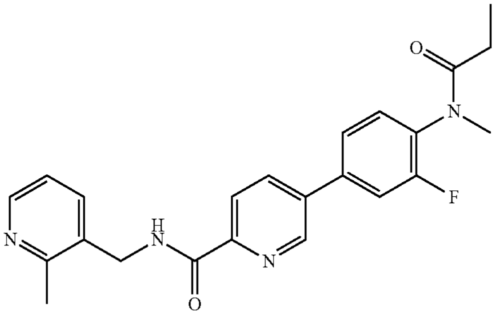
I-T 629
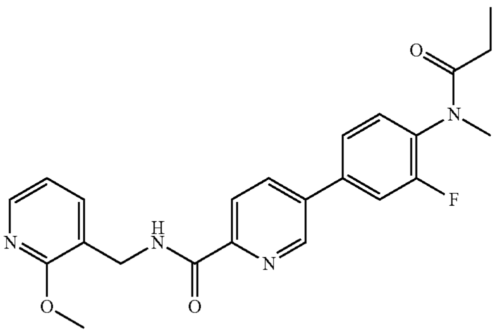

-continued
I-T 630
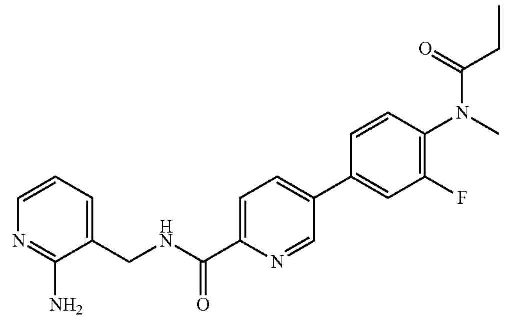
I-T 631
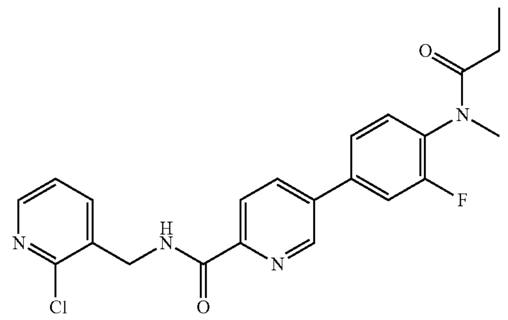
I-T 632
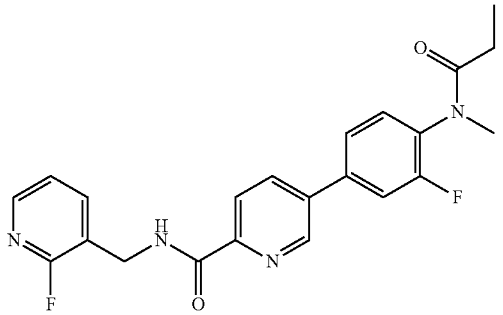
I-T 633
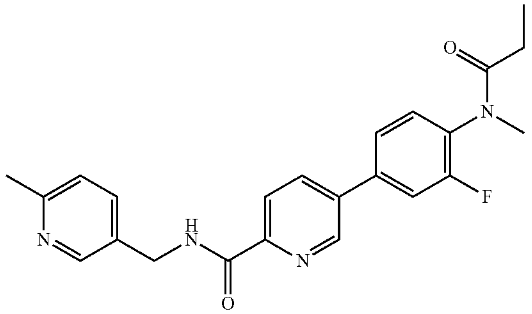
-continued
I-T 634
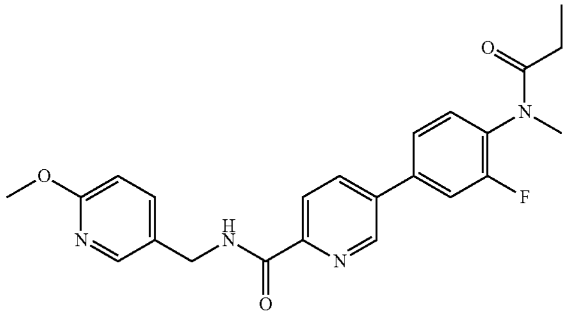
I-T 635
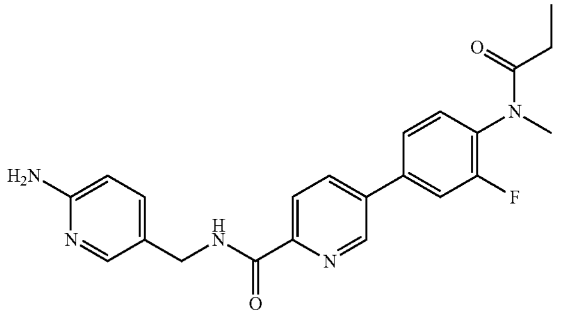
I-T 636
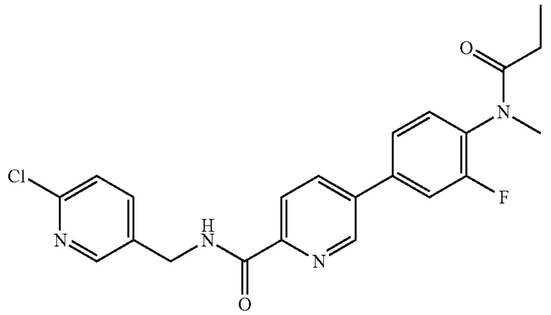
I-T 637
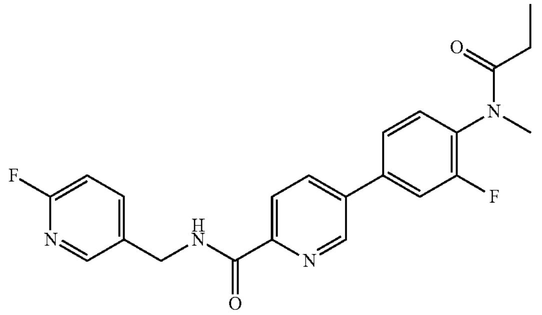

-continued
I-T 638
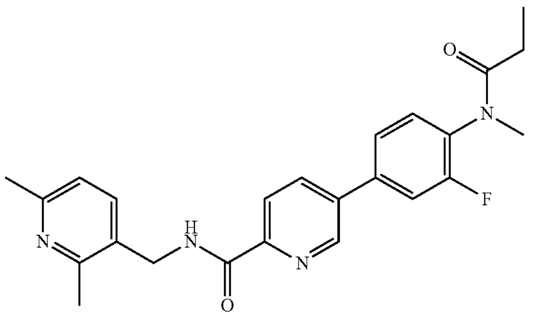
I-T 639
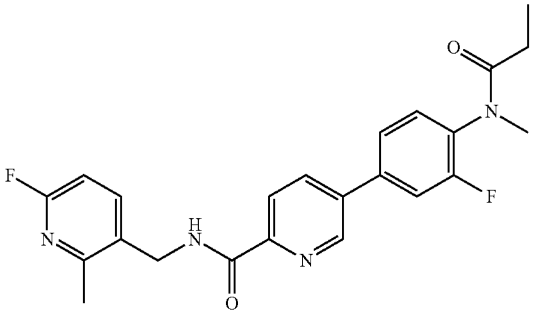
I-T 640
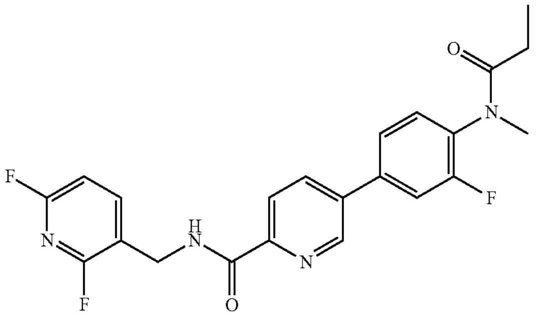
I-T 641
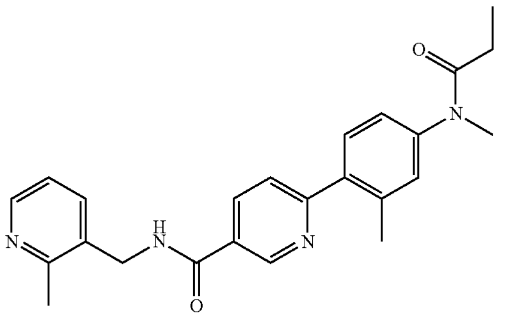
-continued
I-T 642
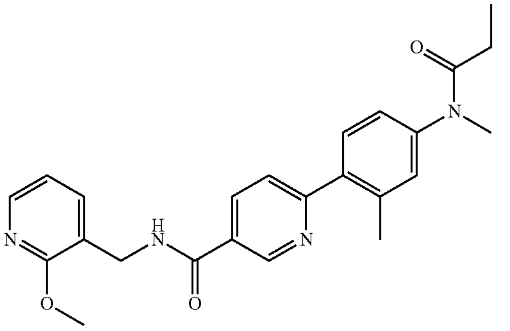
I-T 643
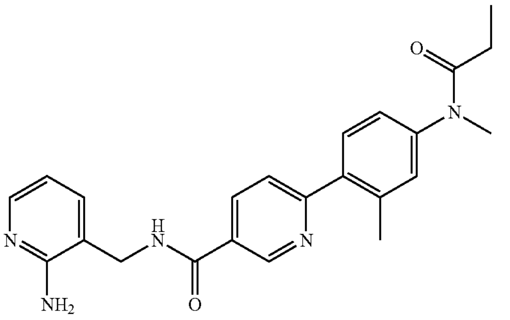
I-T 644
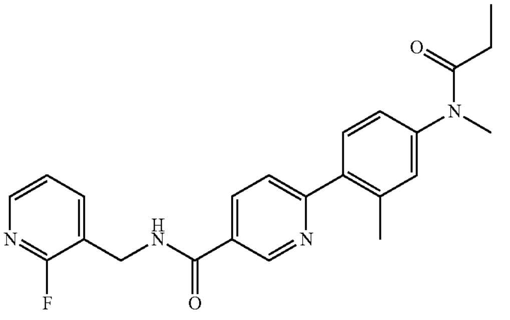
I-T 645
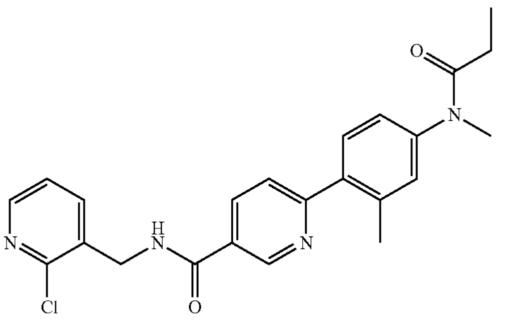

-continued
I-T 646
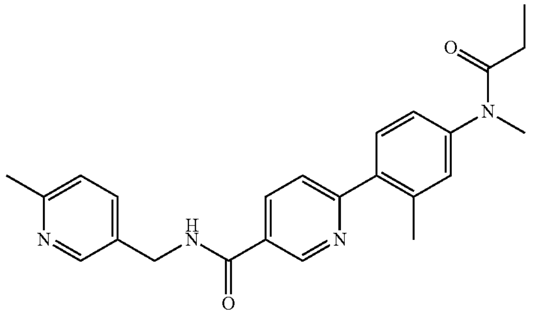
I-T 647
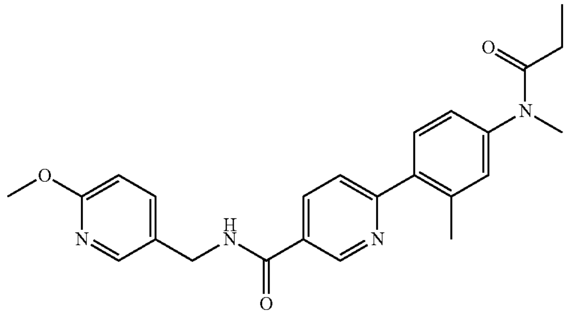
I-T 648
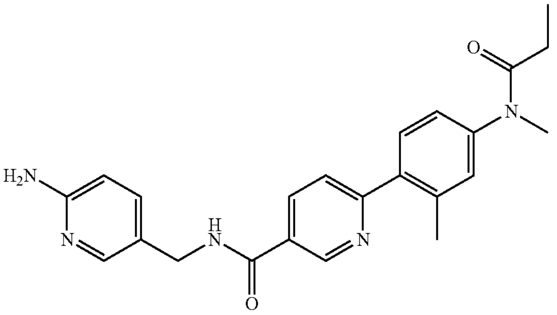
I-T 649
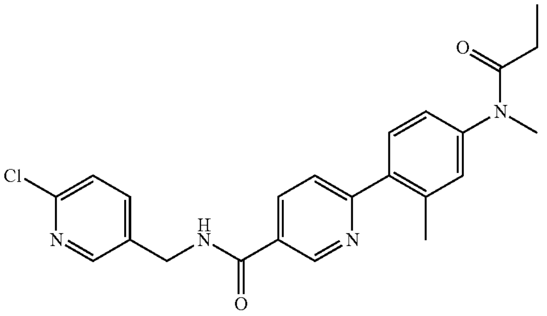
-continued
I-T 650
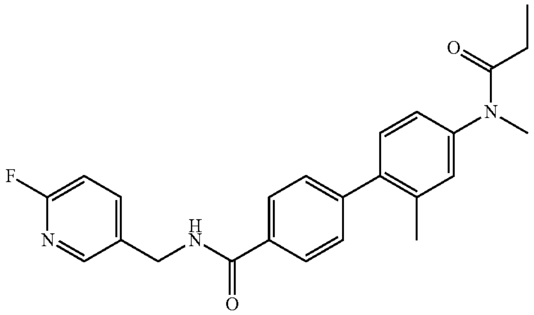
I-T 651
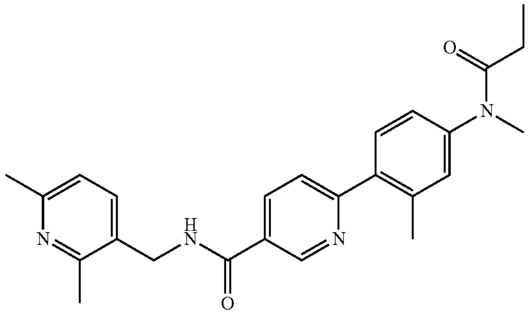
I-T 652
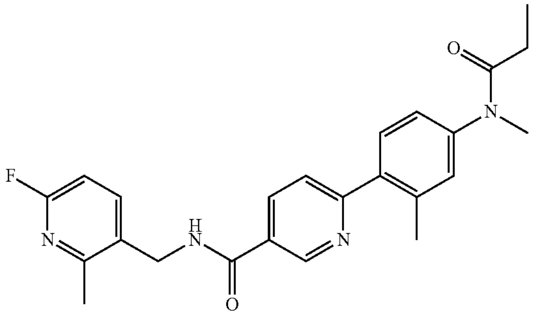
I-T 653
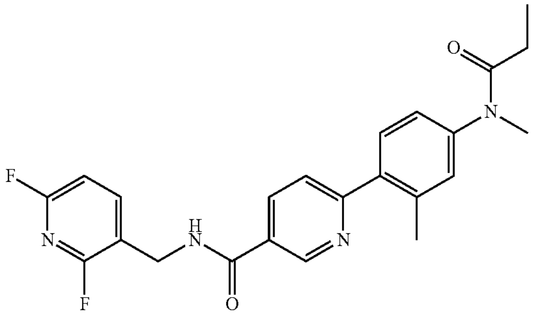

-continued
I-T 654
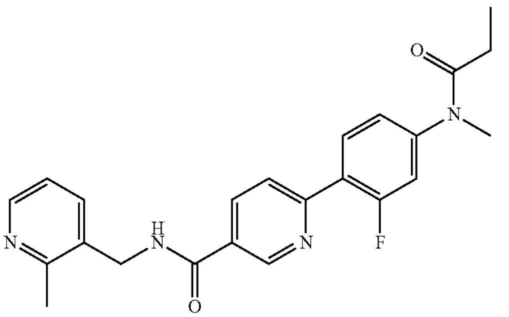
I-T 655
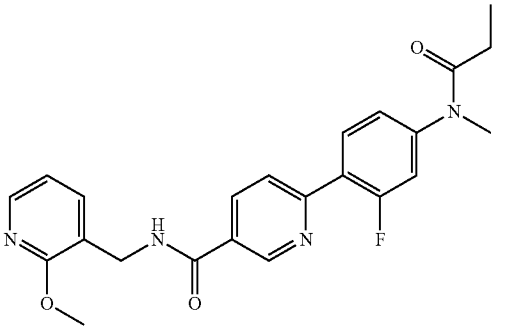
I-T 656
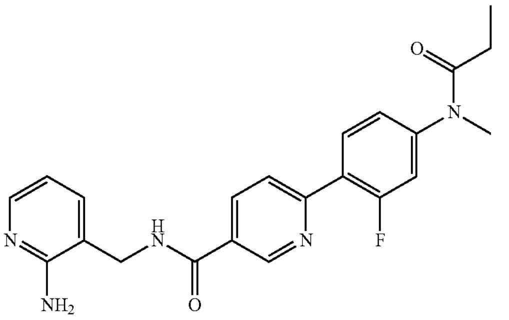
I-T 657
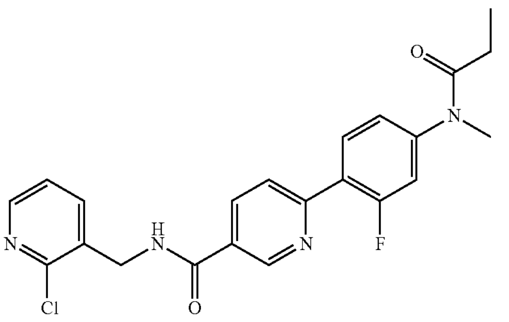
-continued
I-T 658
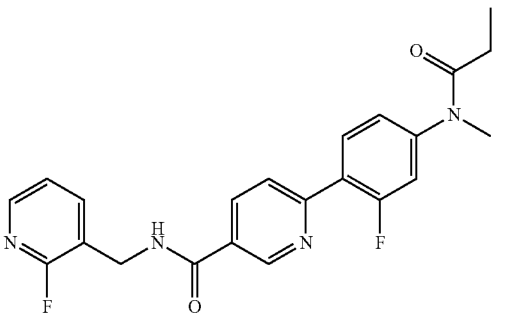
I-T 659
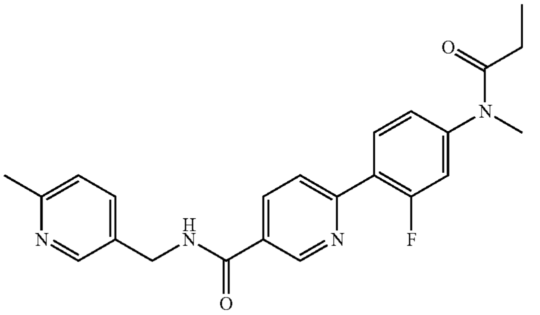
I-T 660
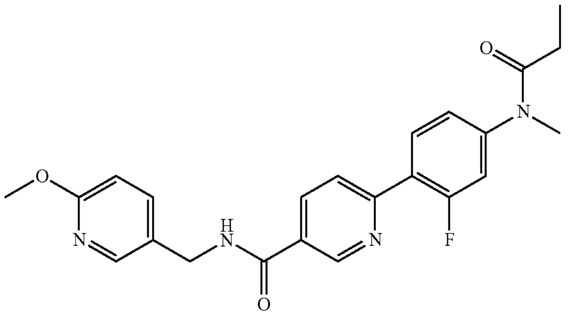
I-T 661
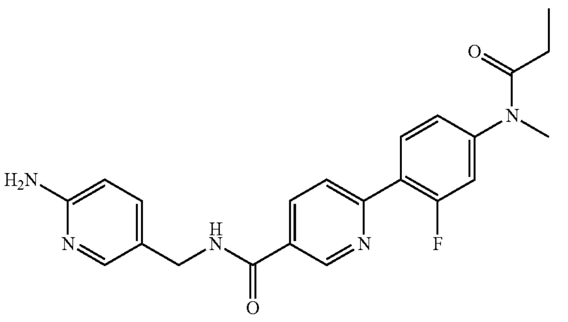

I-T 662
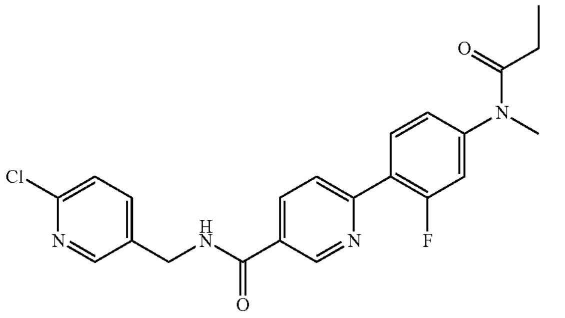
I-T 663
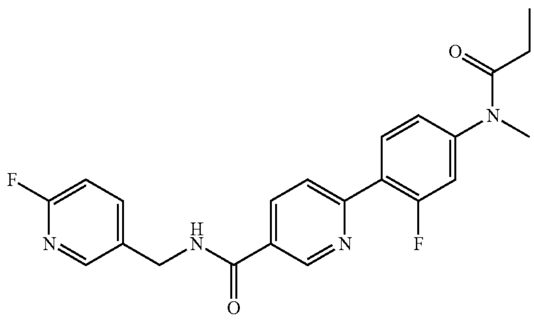
I-T 664
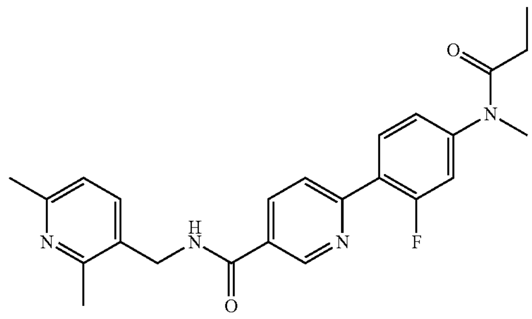
I-T 665
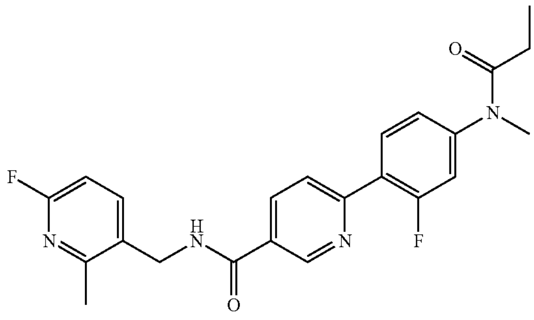
I-T 666
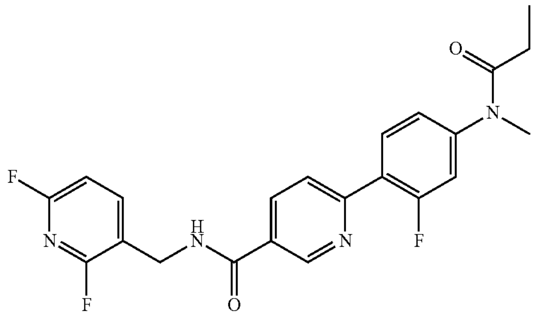
I-T 667
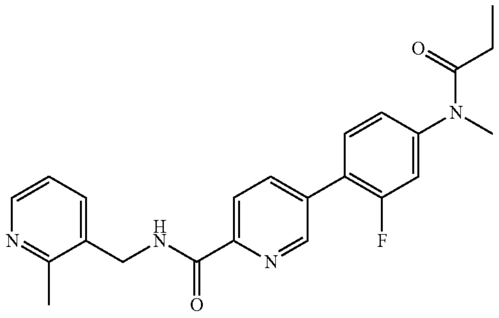
I-T 668
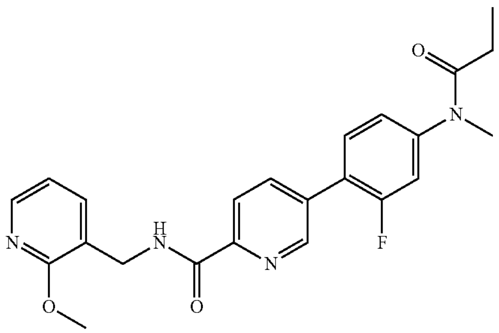
I-T 669
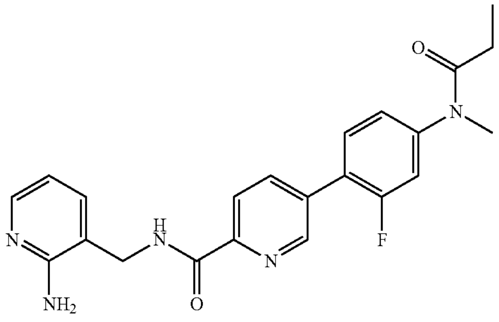

-continued
I-T 670
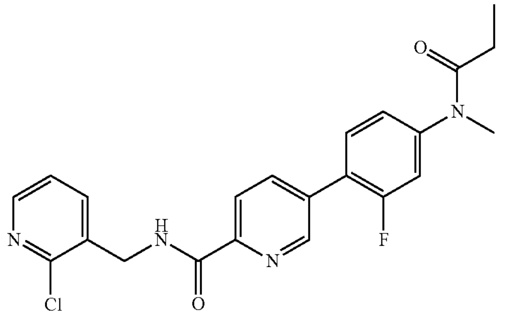
I-T 671
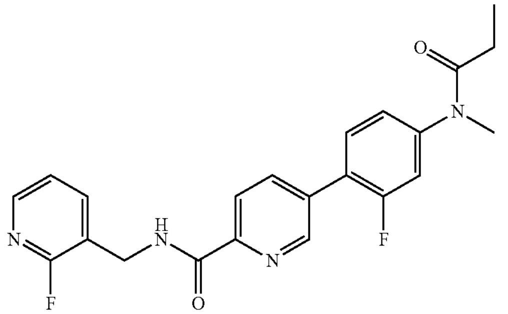
I-T 672
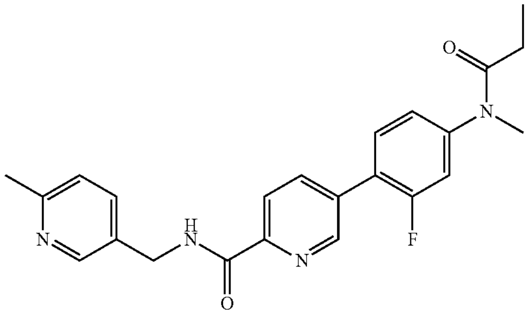
I-T 673
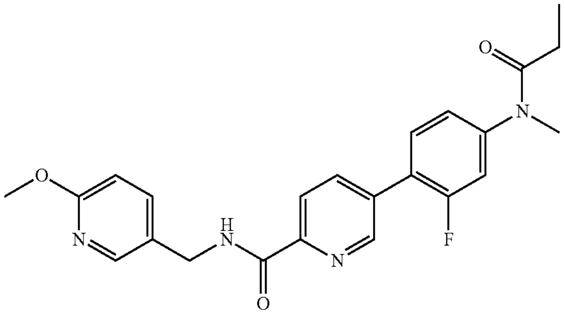
-continued
I-T 674
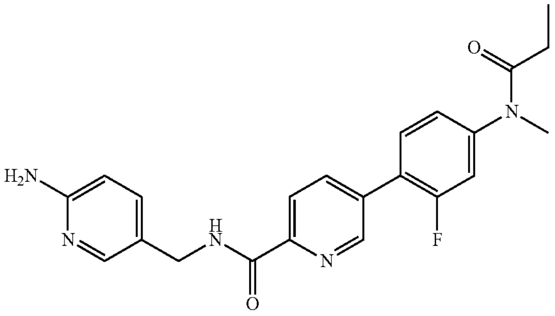
I-T 675
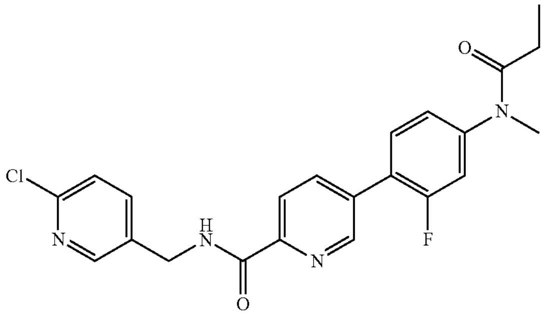
I-T 676
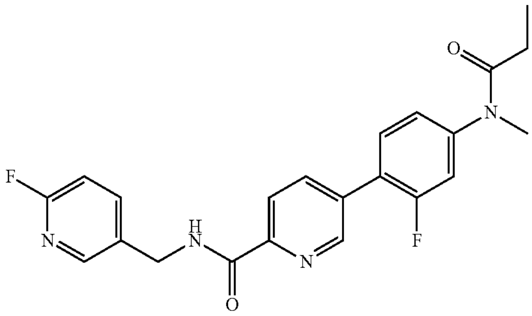
I-T 677
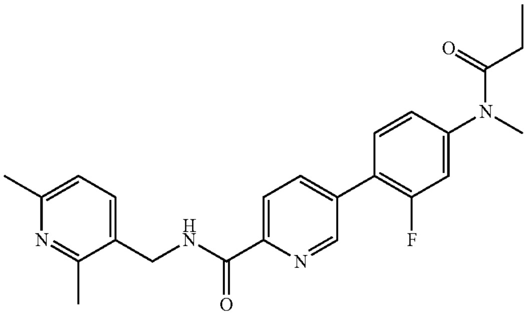

-continued
I-T 678
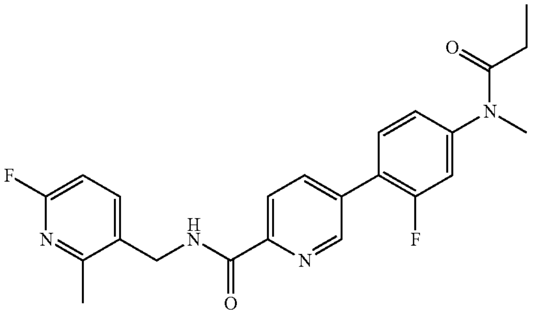
I-T 679
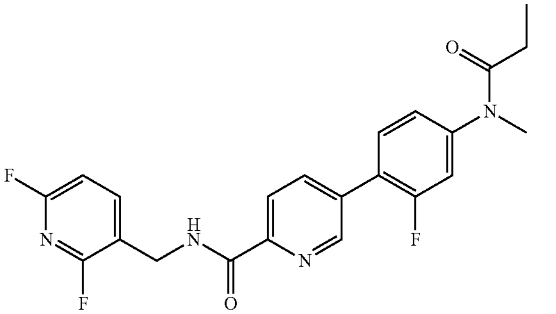
I-T 680
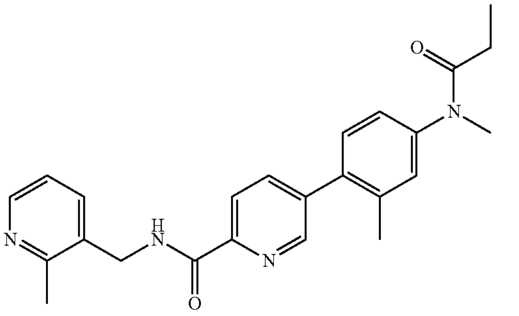
I-T 681
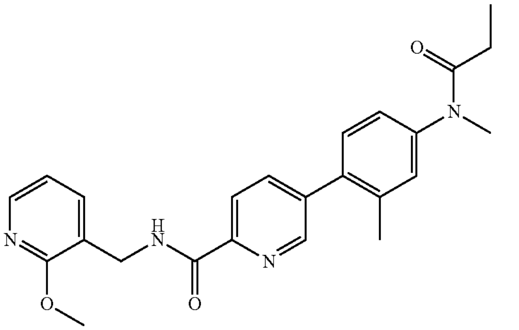
-continued
I-T 682
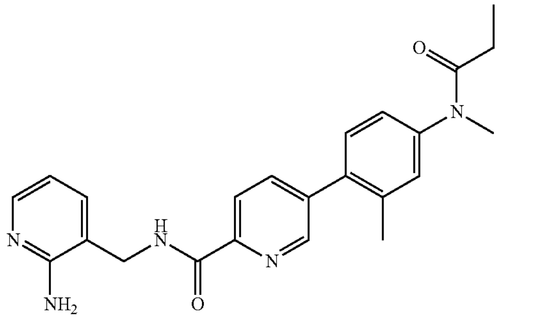
I-T 683
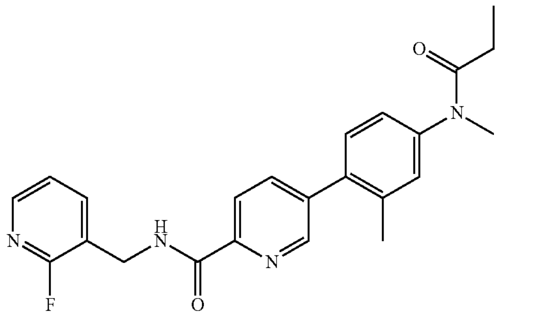
I-T 684
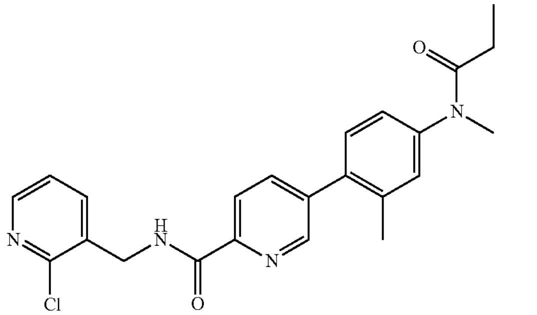
I-T 685
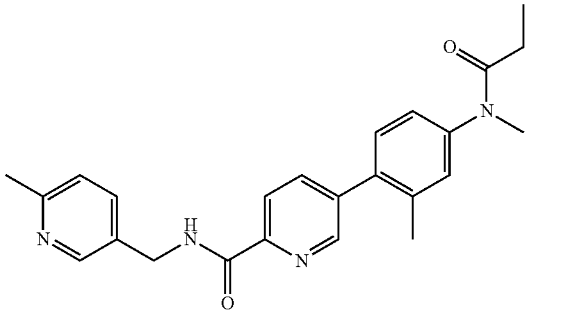

-continued
I-T 686
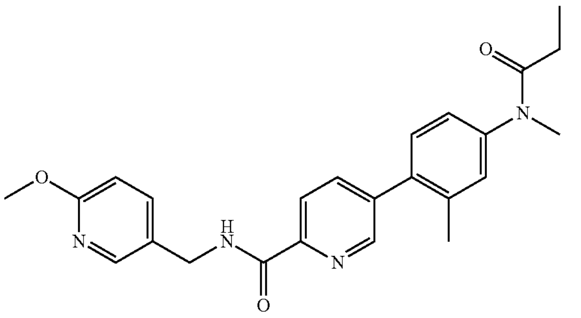
I-T 687
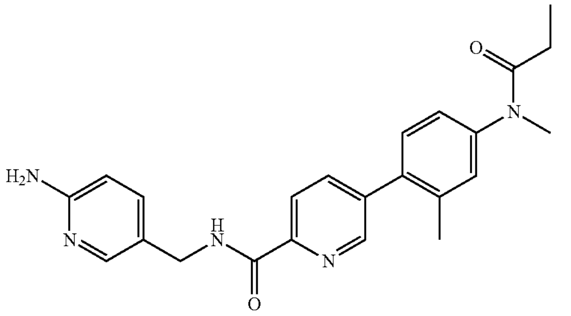
I-T 688
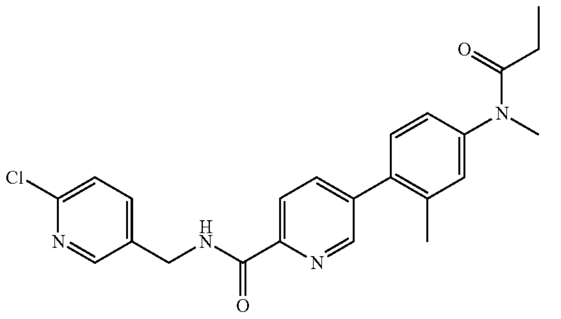
I-T 689
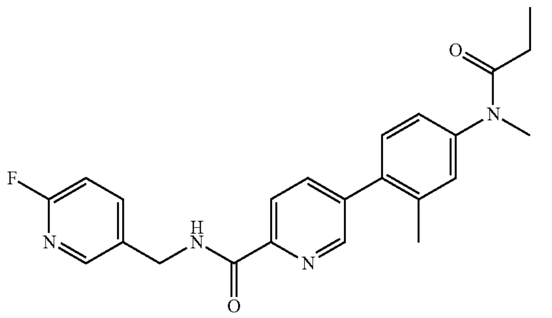
-continued
I-T 690
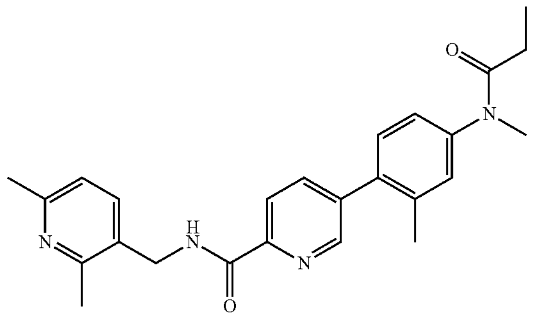
I-T 691
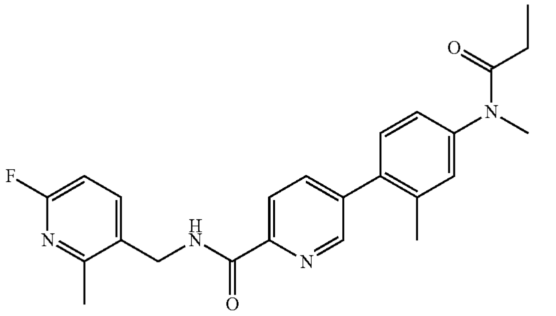
I-T 692
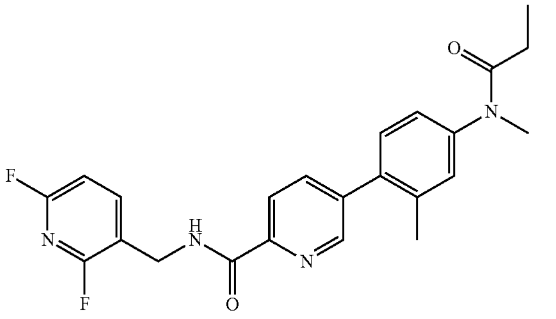
I-T 693
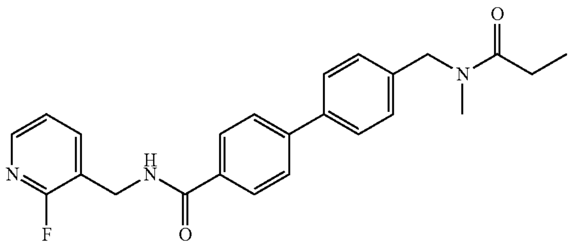
I-T 694
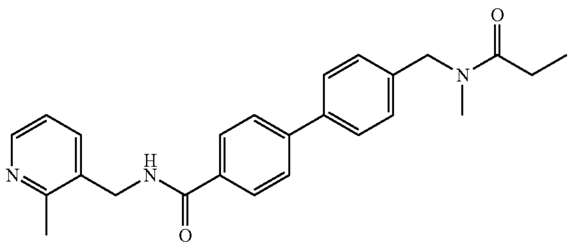

I-T 695
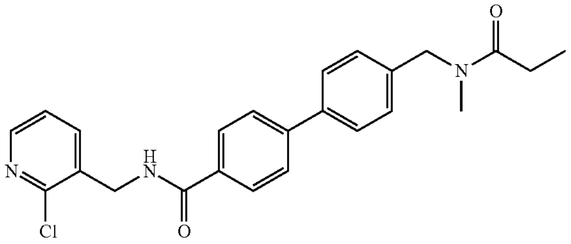
I-T 696
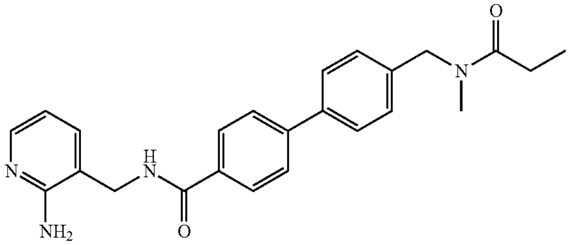
I-T 697
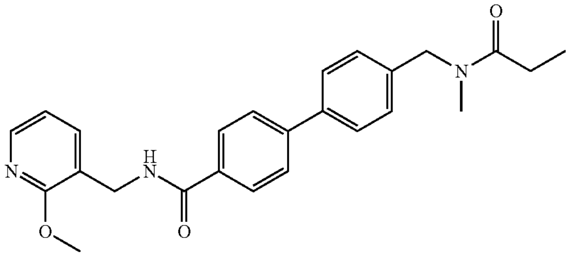
I-T 698
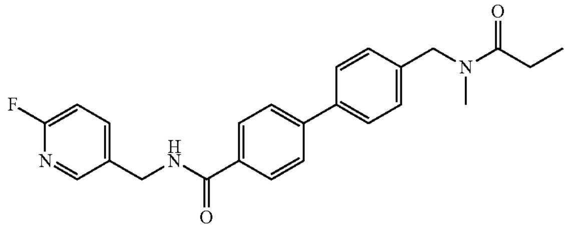
I-T 699
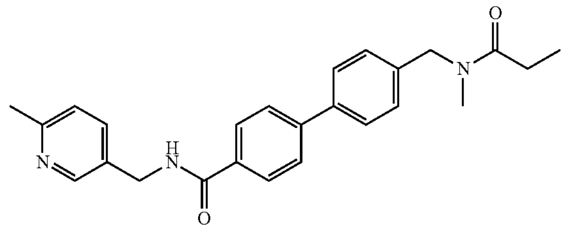
I-T 700
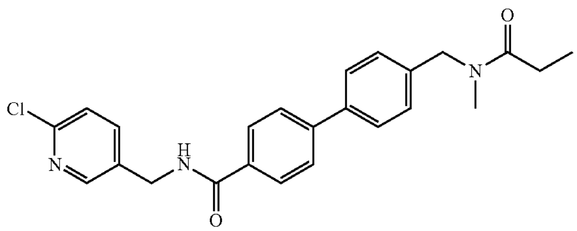
I-T 701
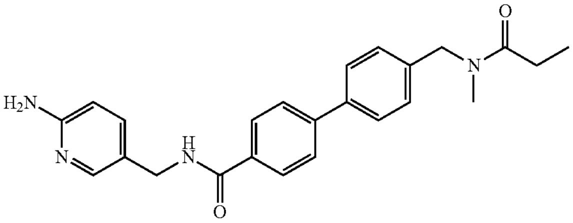
I-T 702
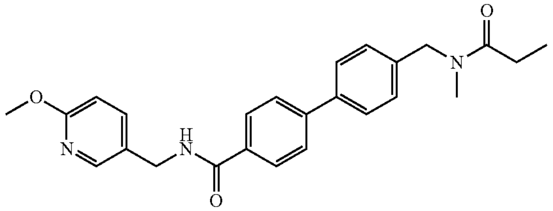
I-T 703
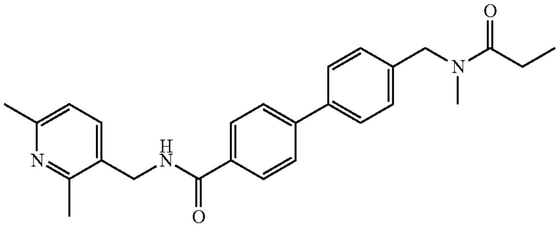
I-T 704
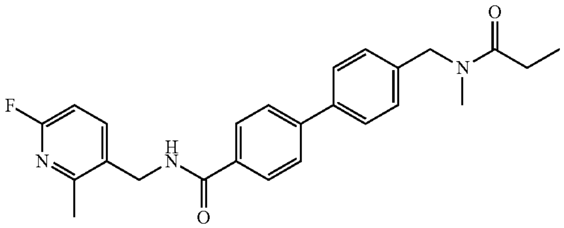
I-T 705
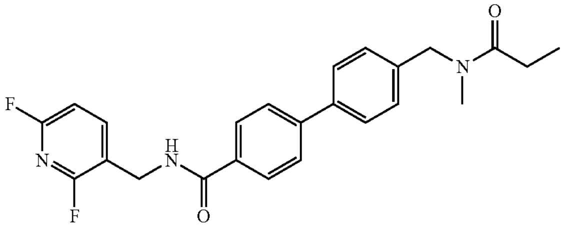
I-T 706
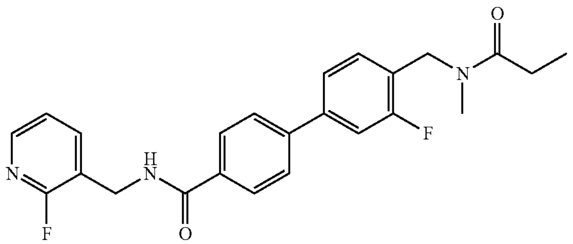

-continued
I-T 707
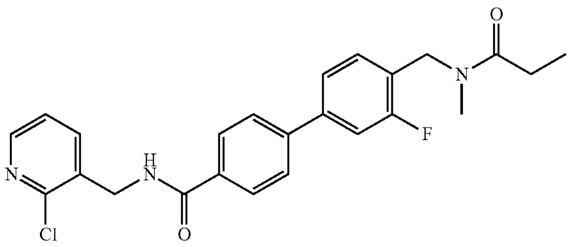
I-T 708
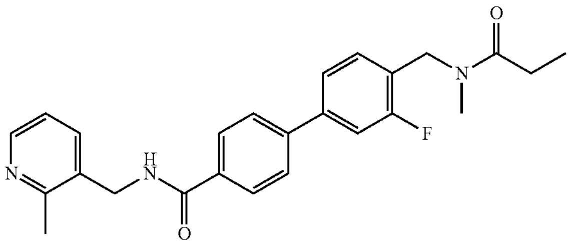
I-T 709
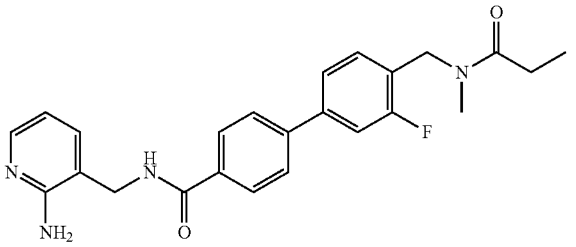
I-T 710
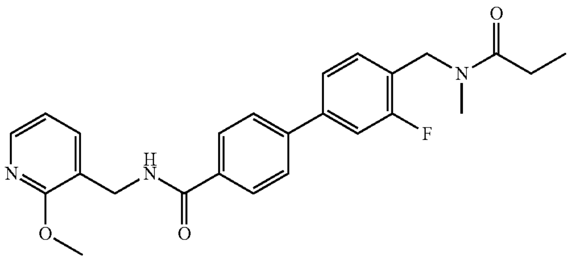
I-T 711
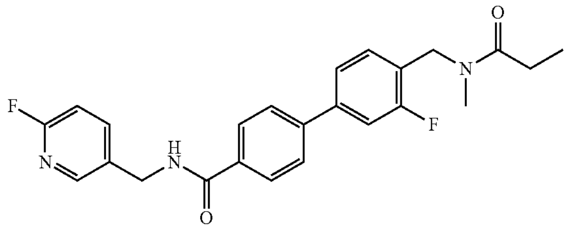
I-T 712
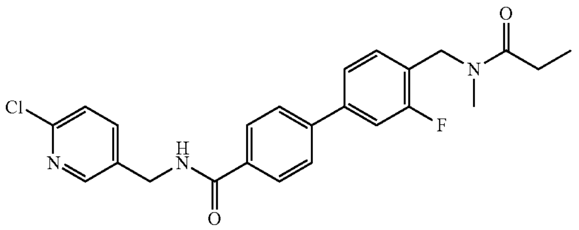
-continued
I-T 713
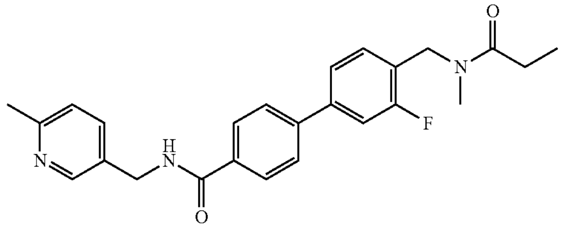
I-T 714
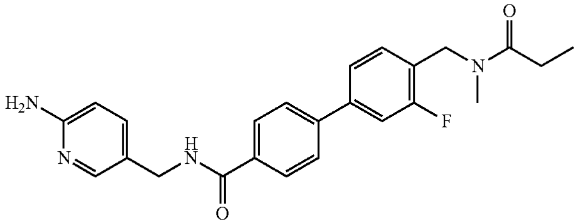
I-T 715
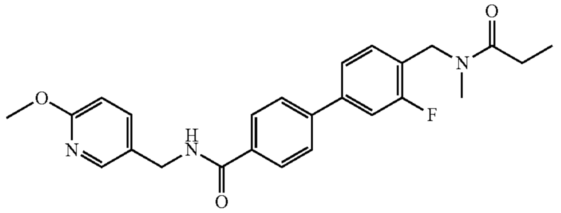
I-T 716
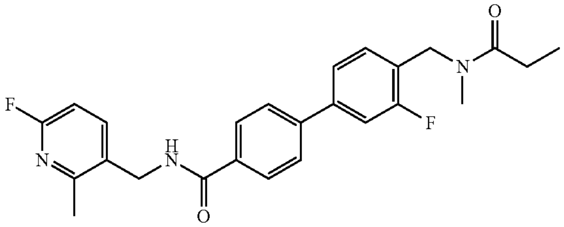
I-T 717
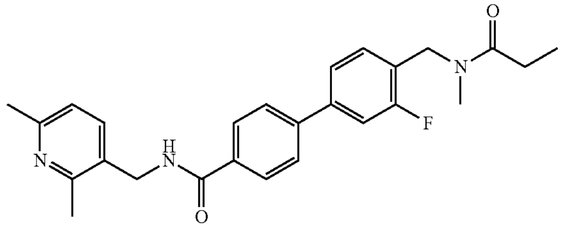
I-T 718
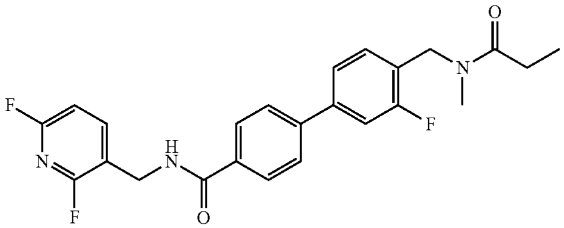

-continued
I-T 719
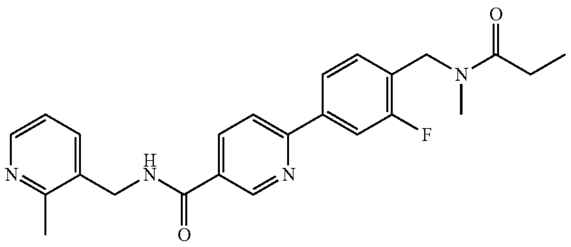
I-T 720
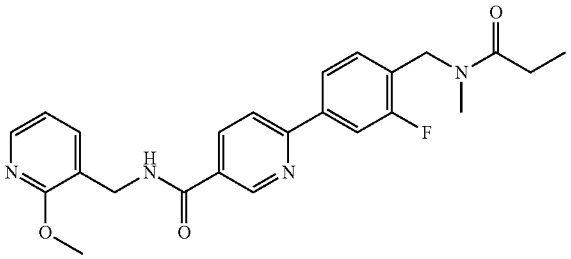
I-T 721
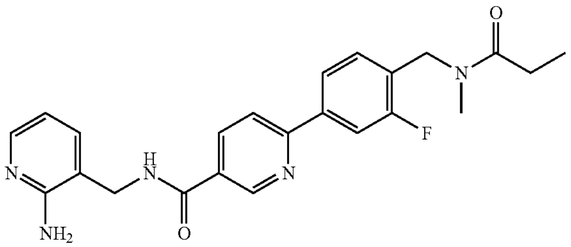
I-T 722
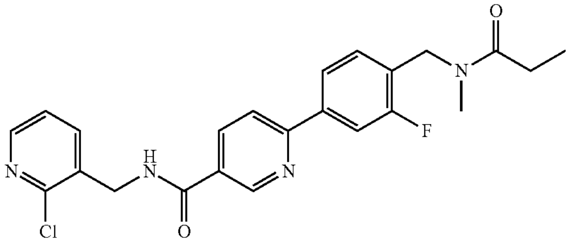
I-T 723
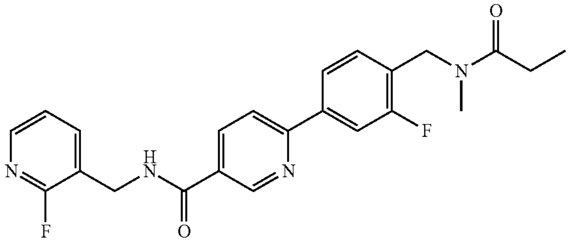
I-T 724
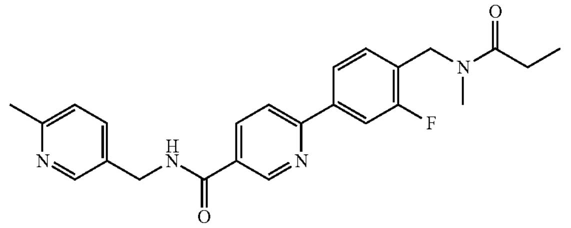
-continued
I-T 725
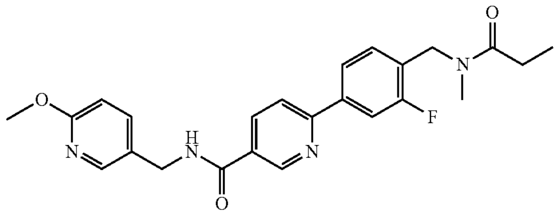
I-T 726
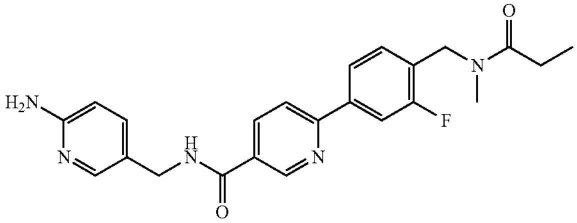
I-T 727
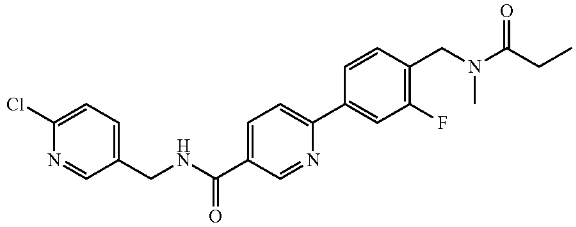
I-T 728
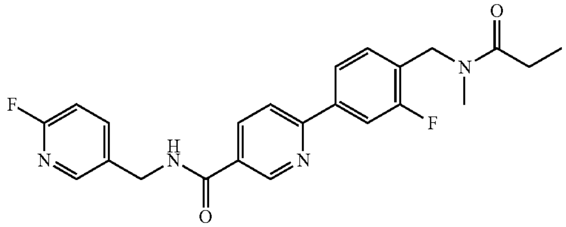
I-T 729
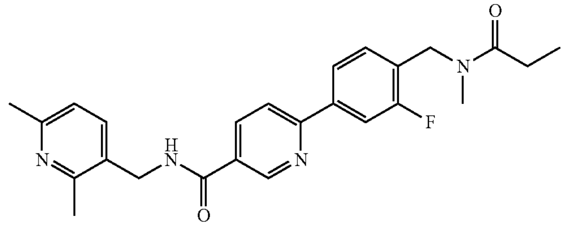
I-T 730
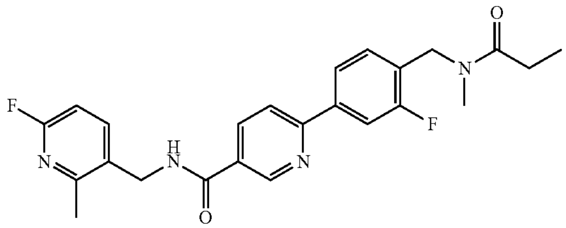

-continued
I-T 731
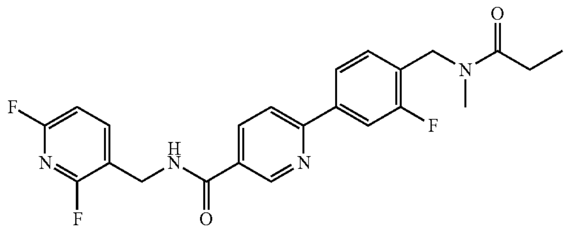
I-T 732
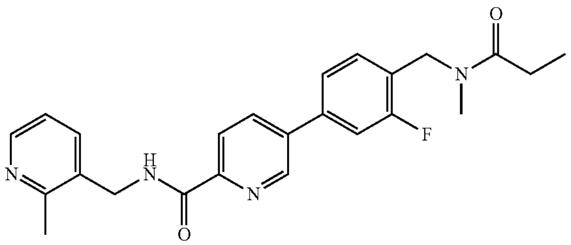
I-T 733
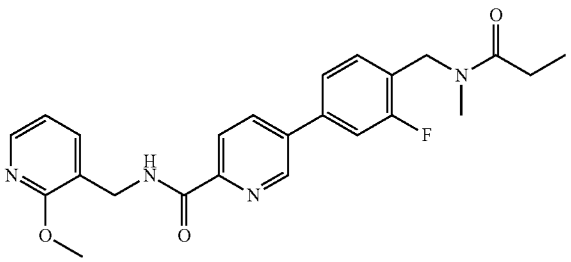
I-T 734
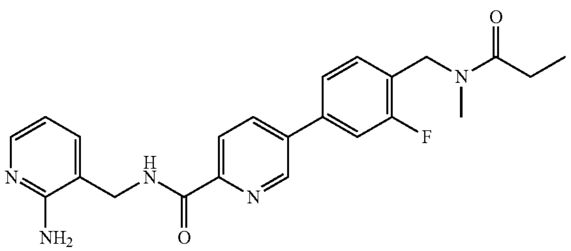
I-T 735
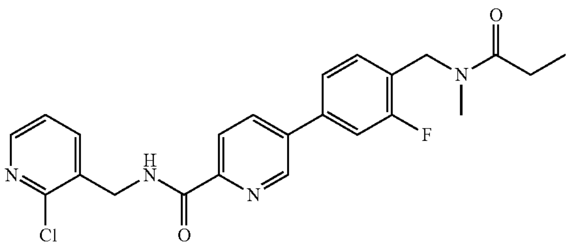
I-T 736
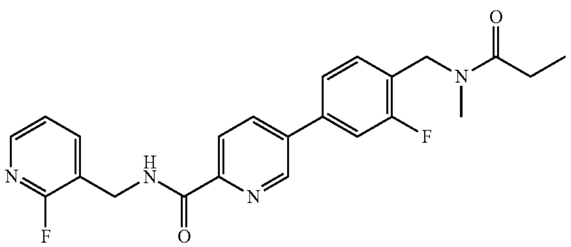
-continued
I-T 737
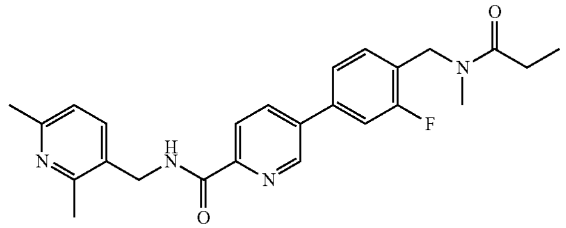
I-T 738
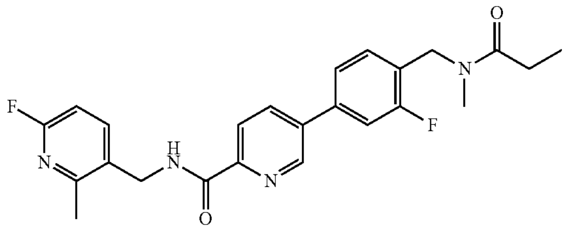
I-T 739
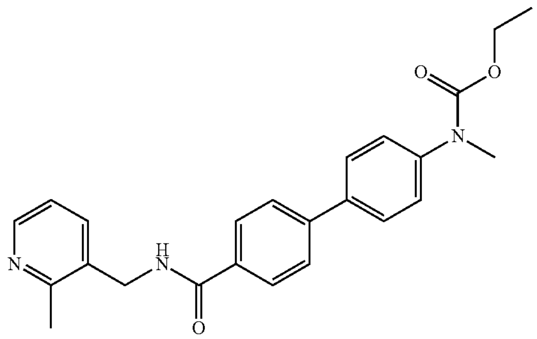
I-T 740
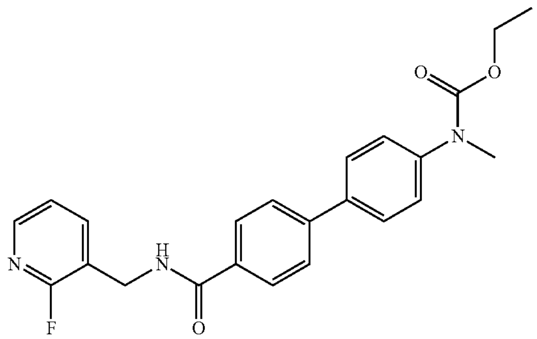
I-T 741
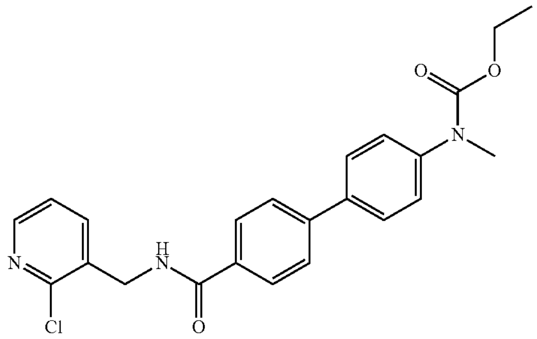

-continued
I-T 742
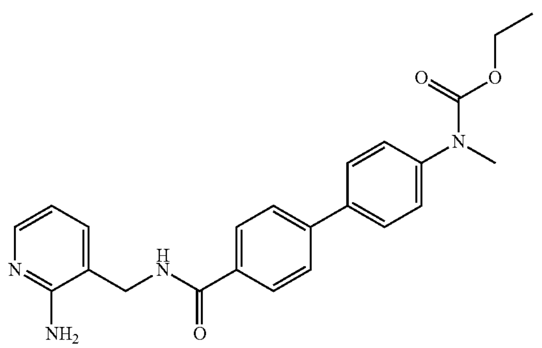
I-T 743
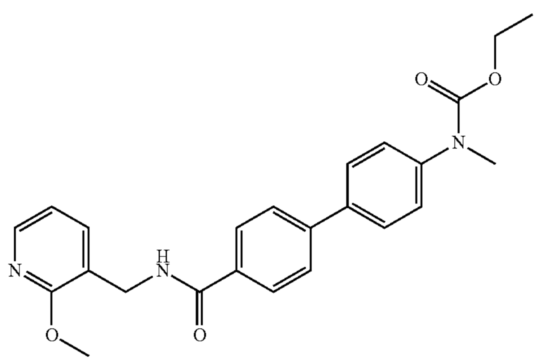
I-T 744
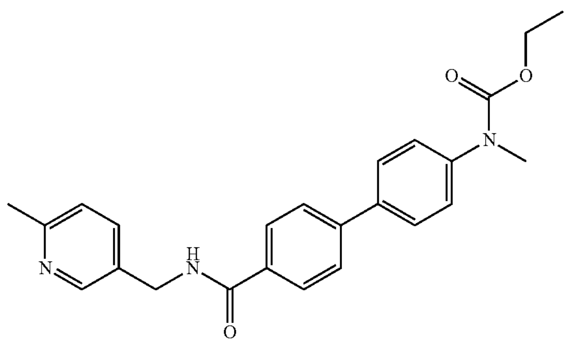
I-T 745
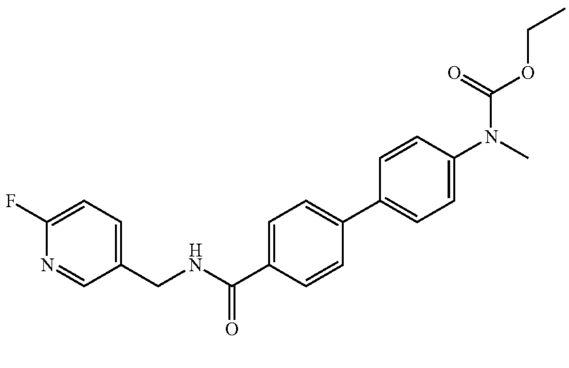
-continued
I-T 746
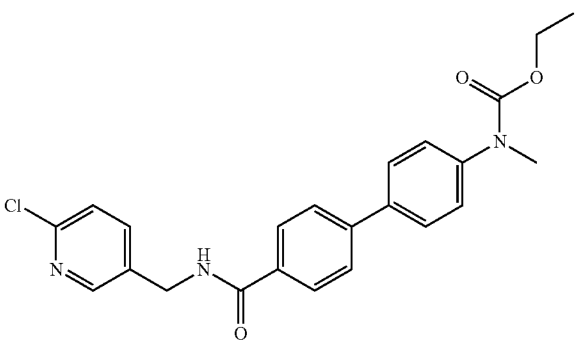
I-T 747
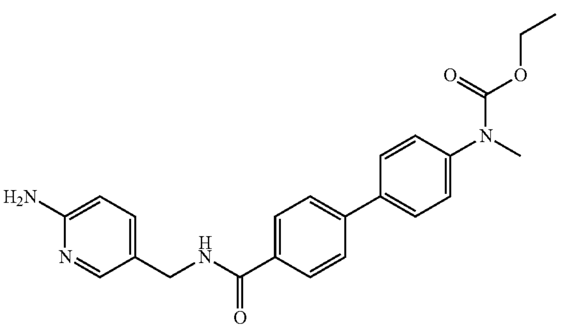
I-T 748
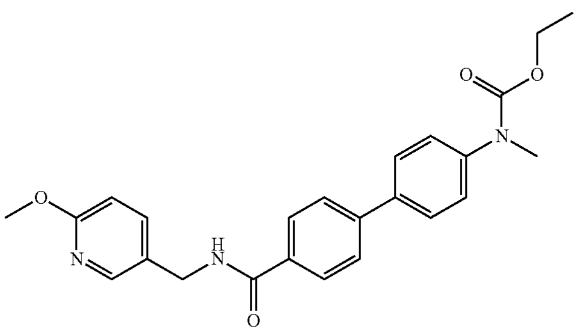
I-T 749
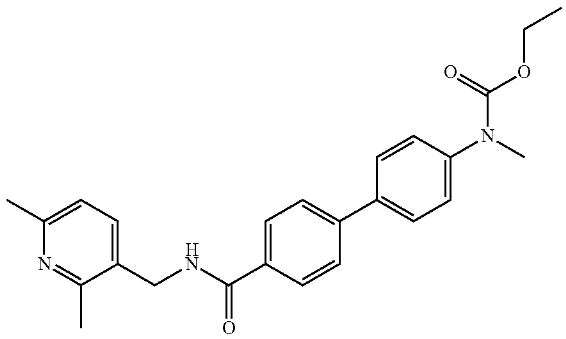

-continued
I-T 750
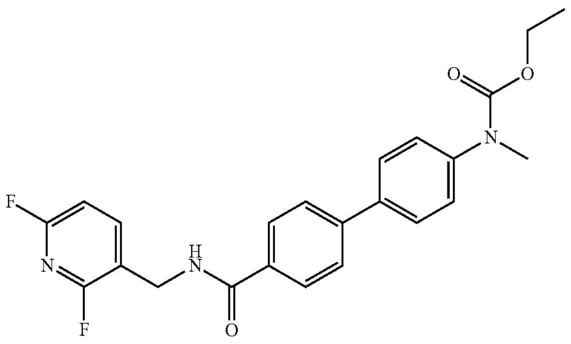
I-T 751
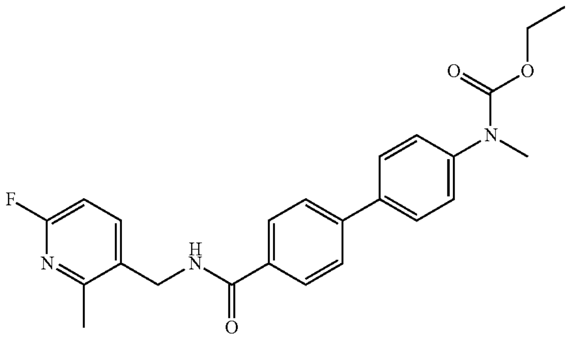
I-T 752
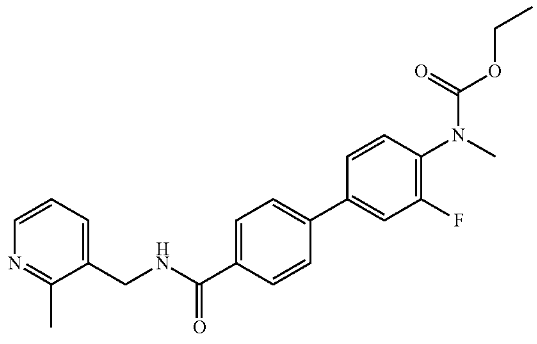
I-T 753
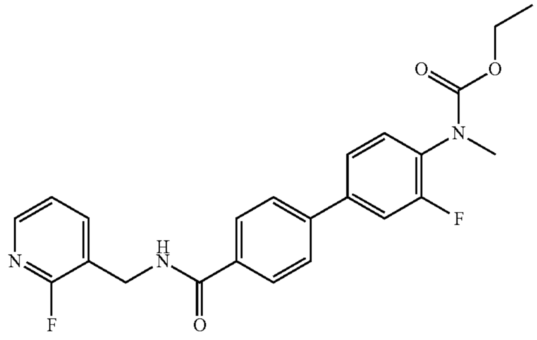
-continued
I-T 754
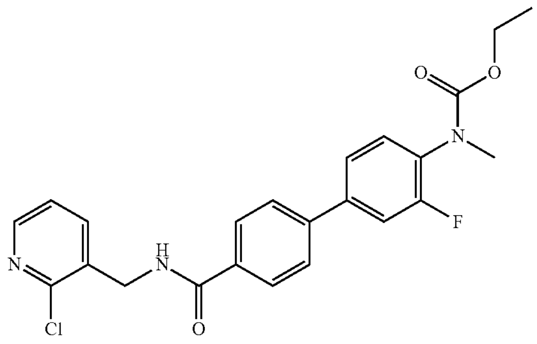
I-T 755
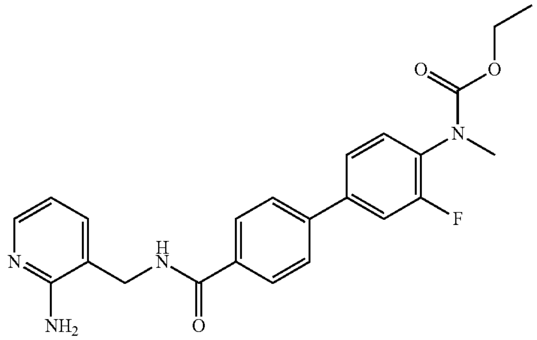
I-T 756
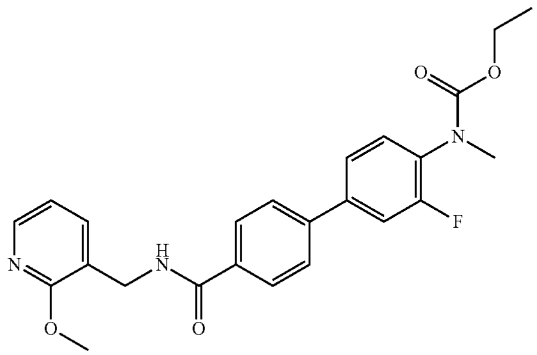
I-T 757
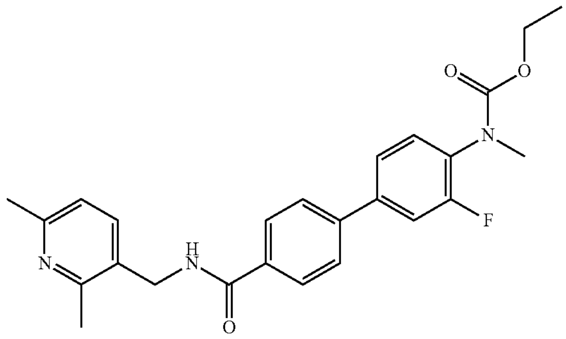

I-T 758
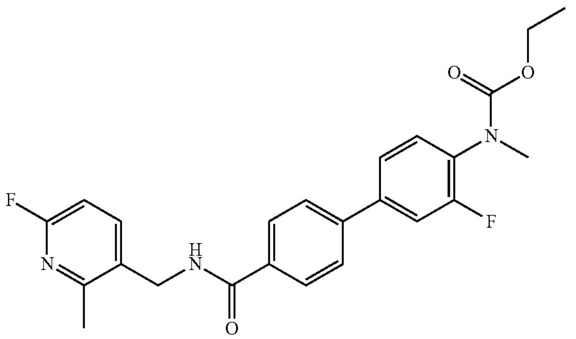
I-T 759
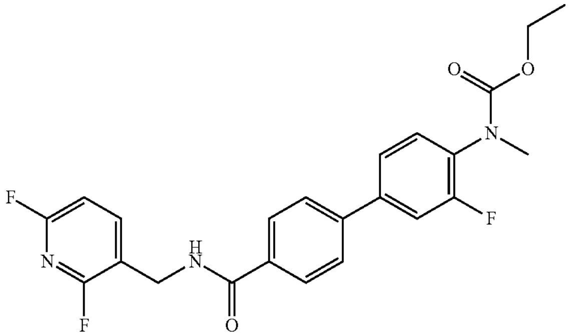
I-T760
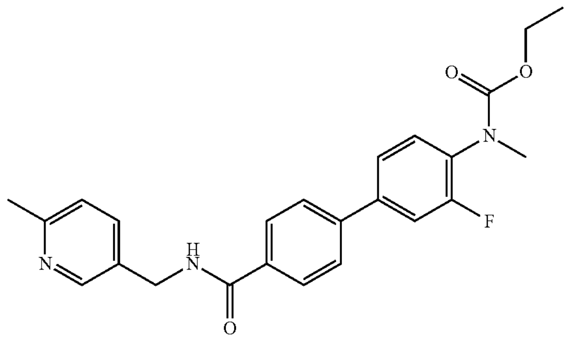
I-T761
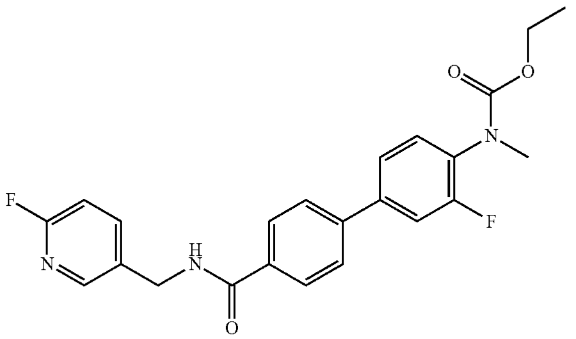
I-T762
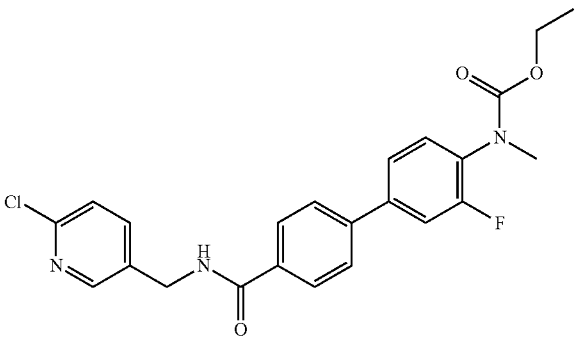
I-T763
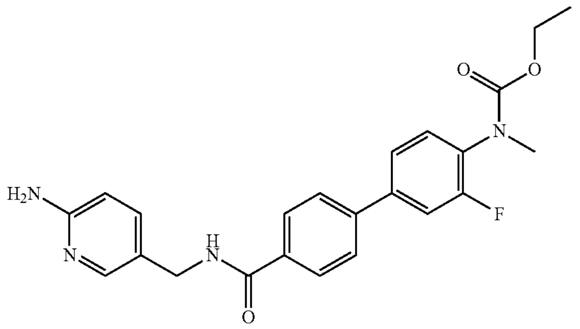
I-T764
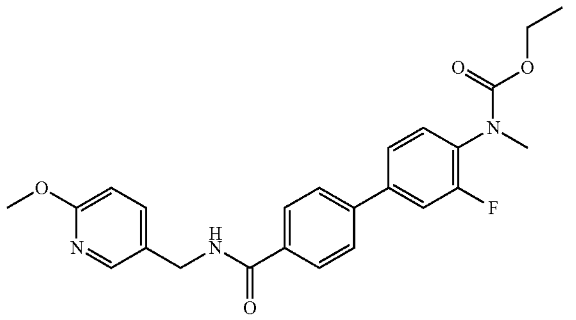
I-T765
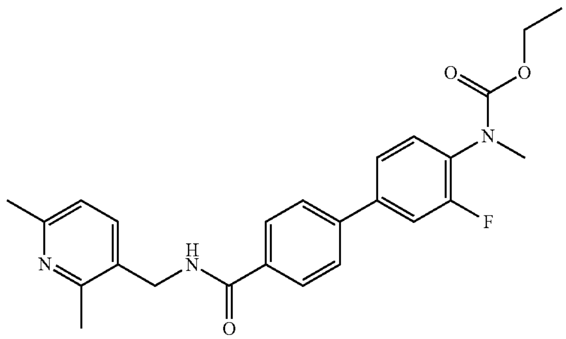

-continued
I-T766
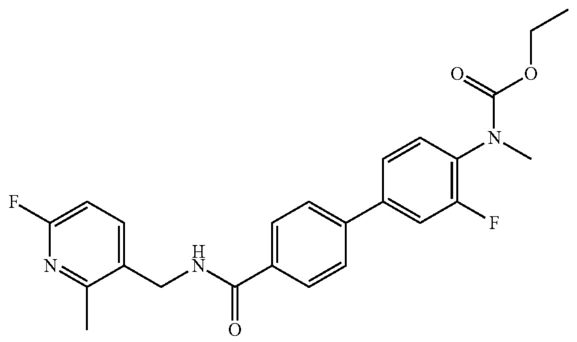
I-T767
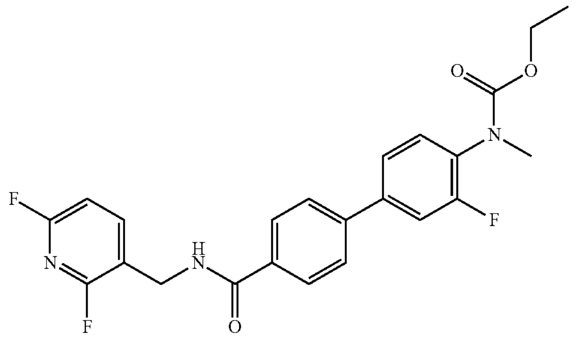
I-T768
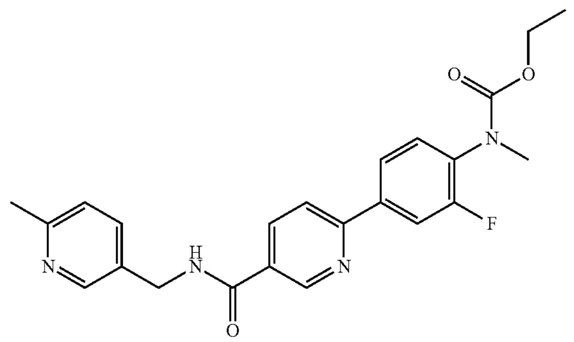
I-T769
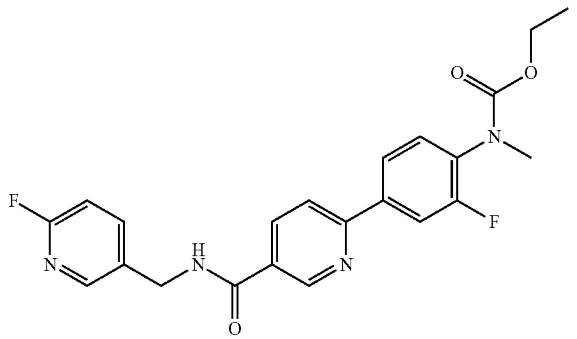
-continued
I-T770
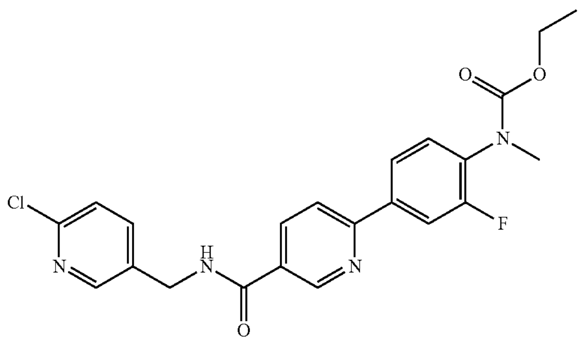
I-T771
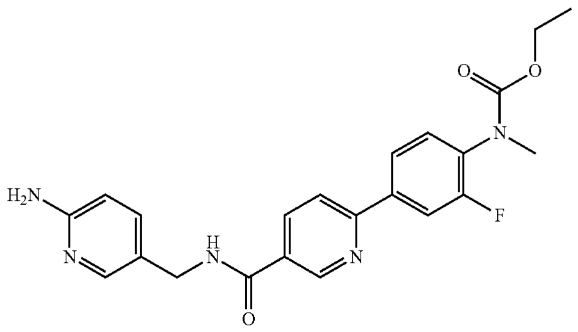
I-T772
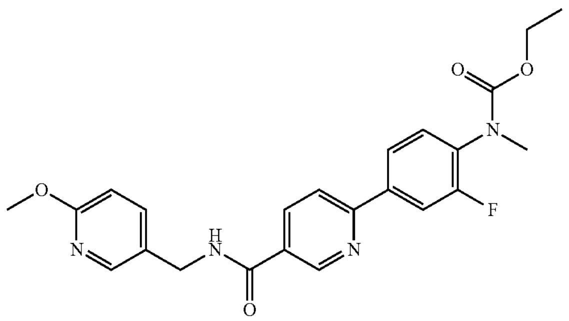
I-T773
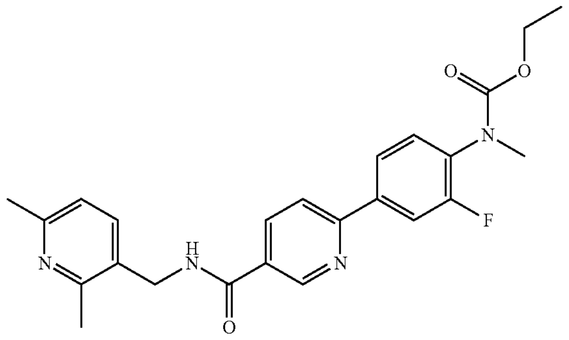

-continued
I-T774
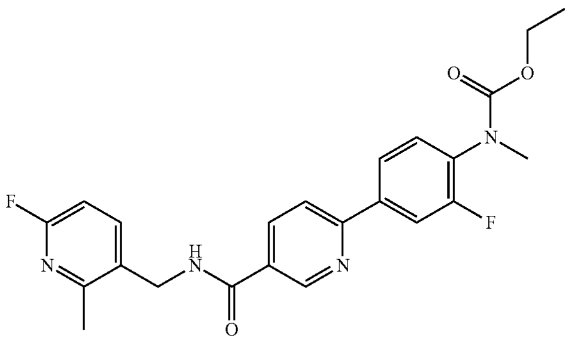
I-T775
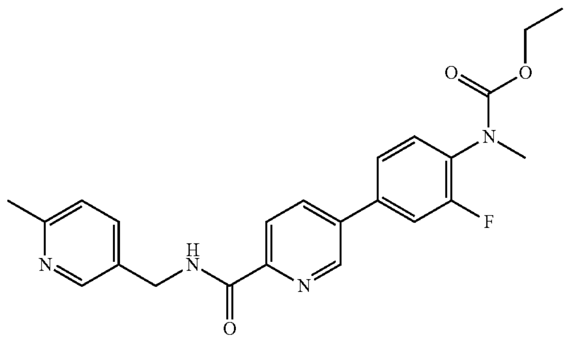
I-T776
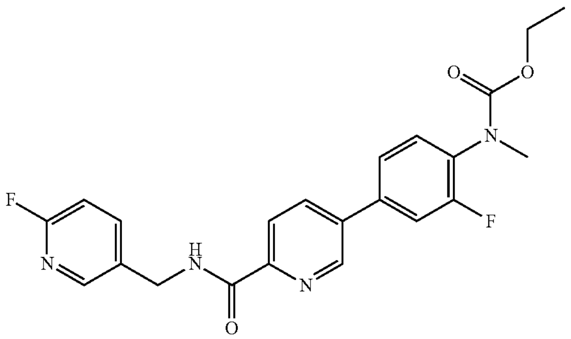
I-T777
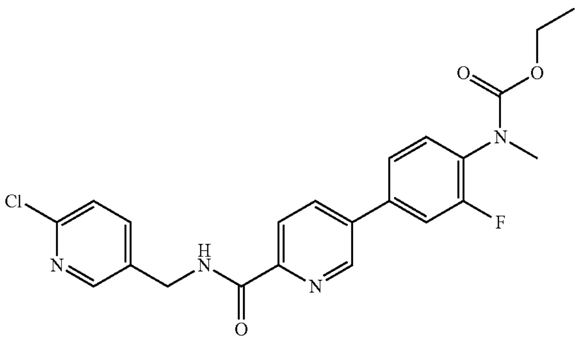
-continued
I-T778
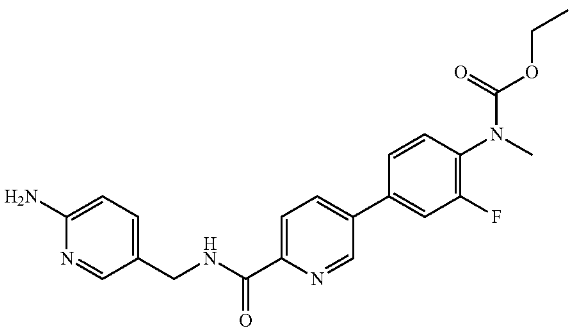
I-T779
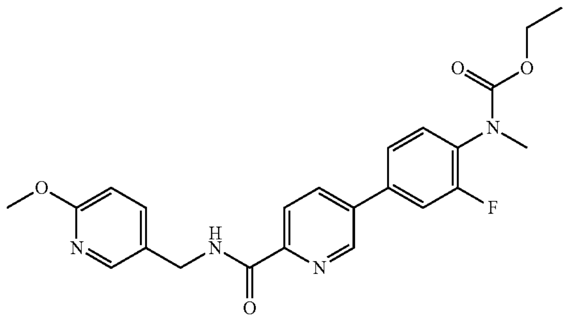
I-T780
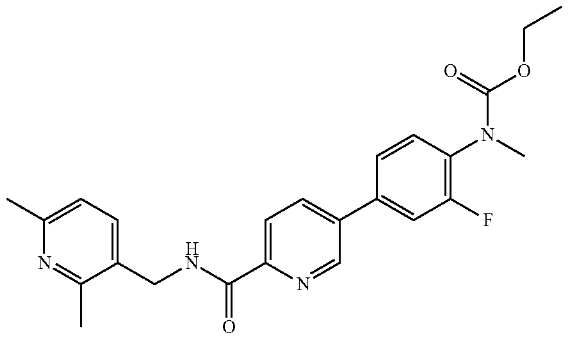
I-T781
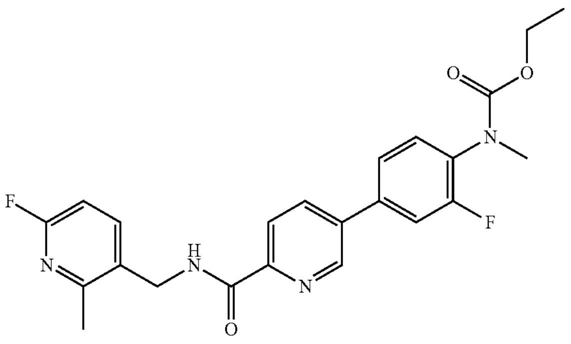

-continued
I-T782
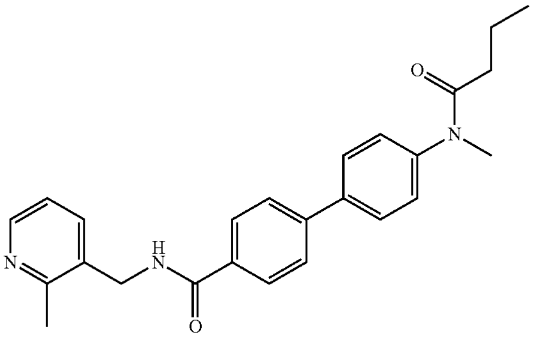
I-T783
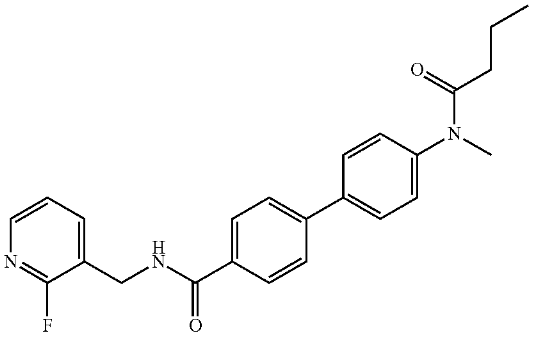
I-T784
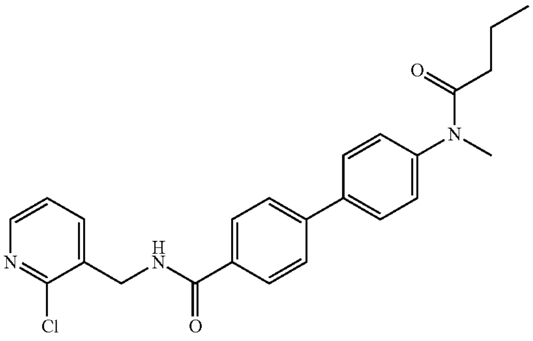
I-T785
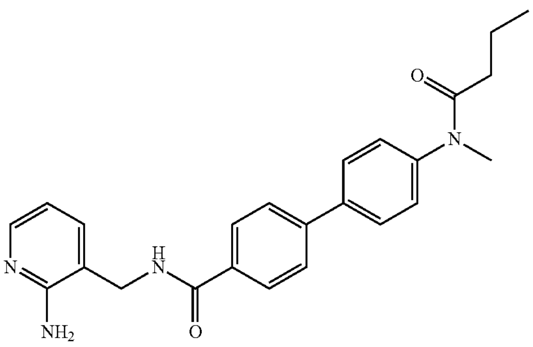
-continued
I-T786
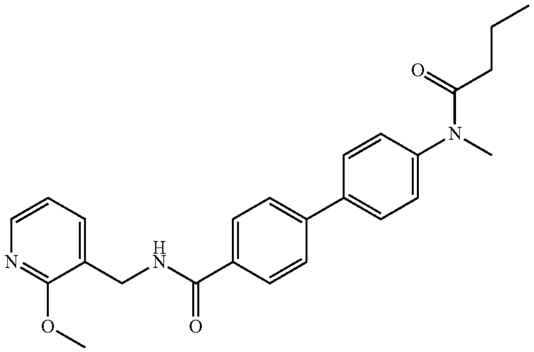
I-T787
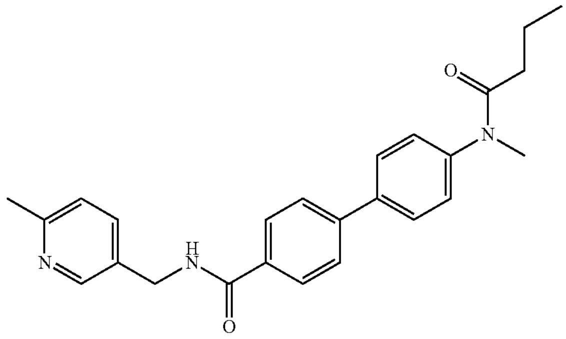
I-T788
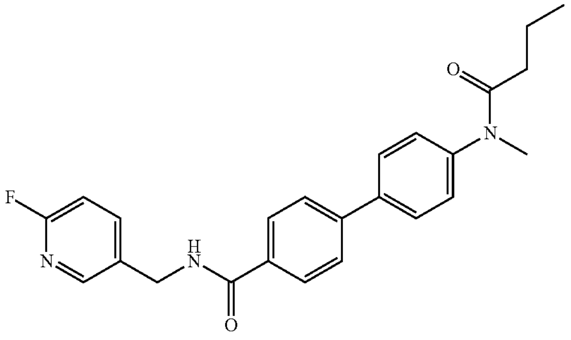
I-T789
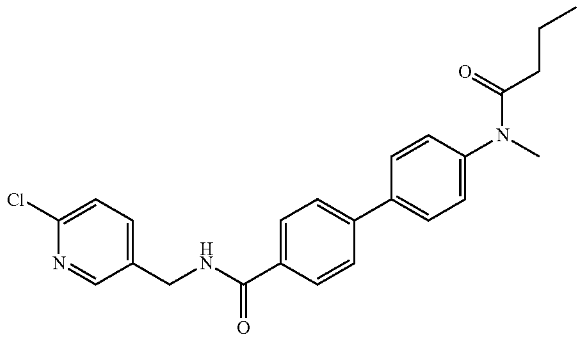

-continued
I-T790
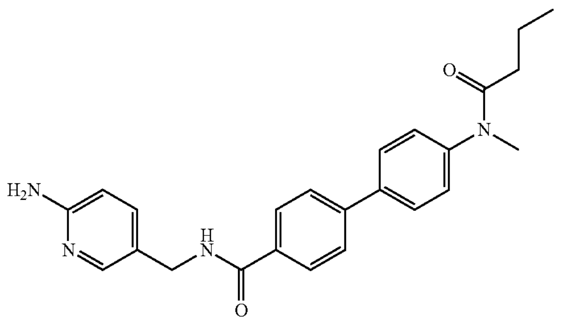
I-T791
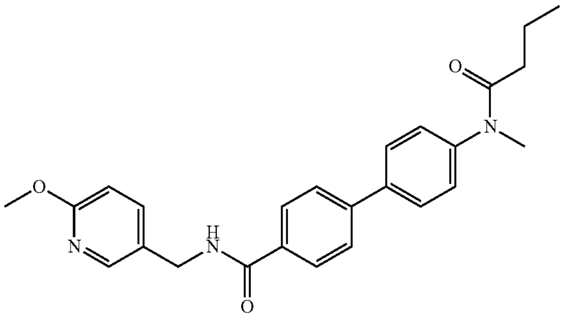
I-T792
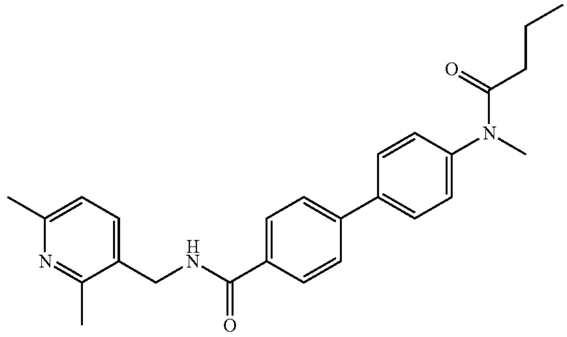
I-T793
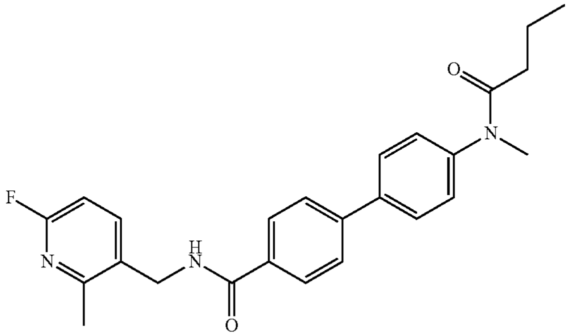
-continued
I-T794
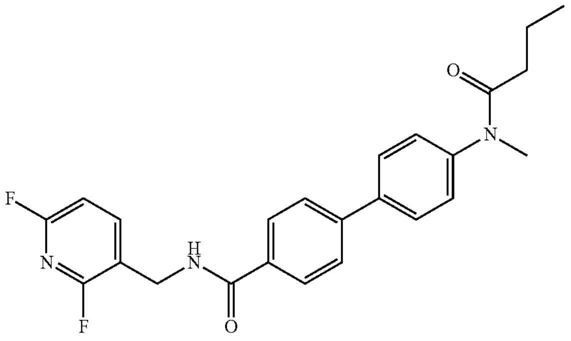
I-T795
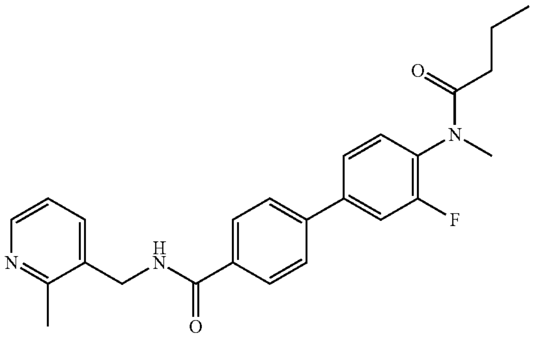
I-T796
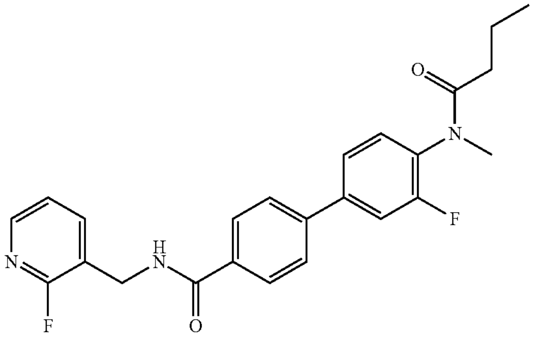
I-T797
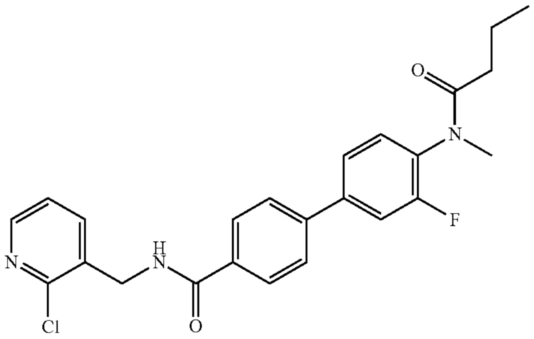

-continued
I-T798
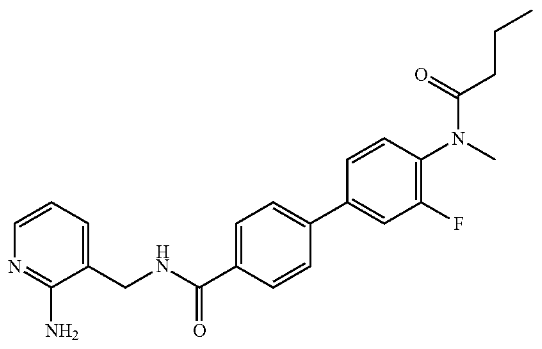
I-T799
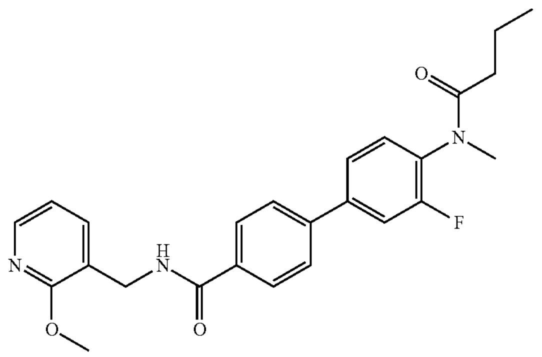
I-T800
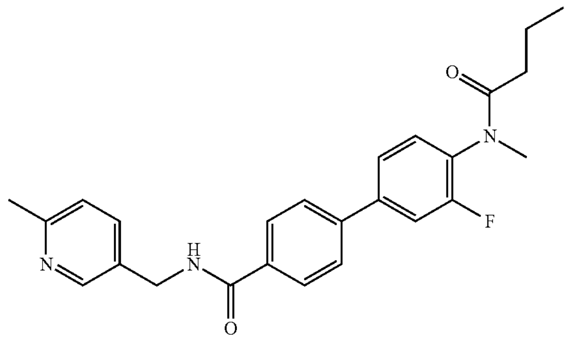
I-T801
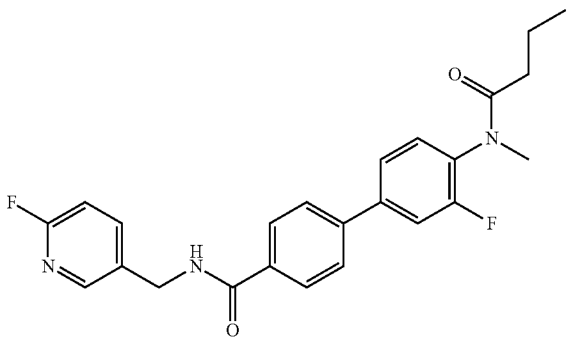
-continued
I-T802
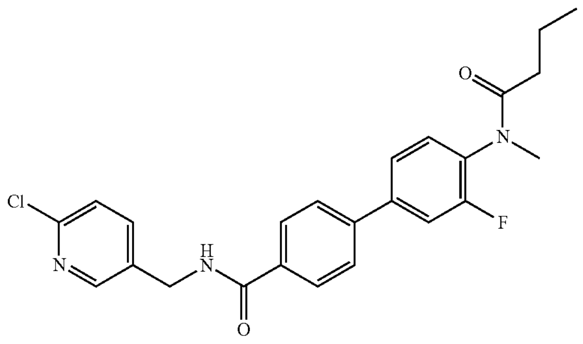
I-T803
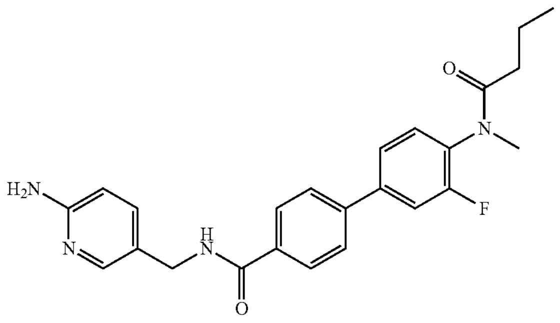
I-T804
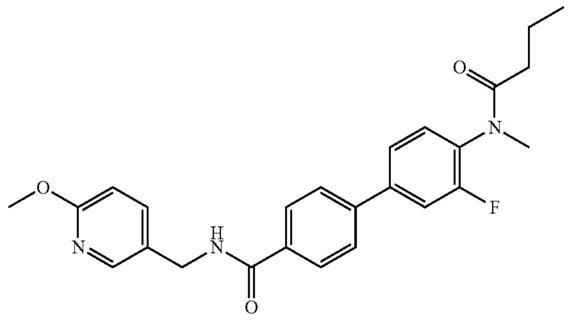
I-T805
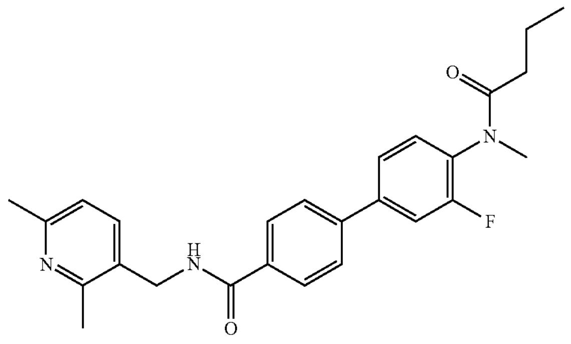

I-T806
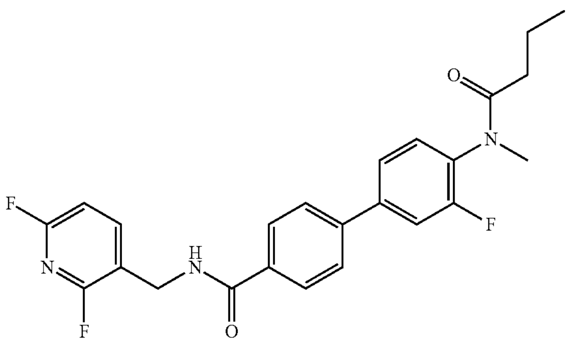
I-T807
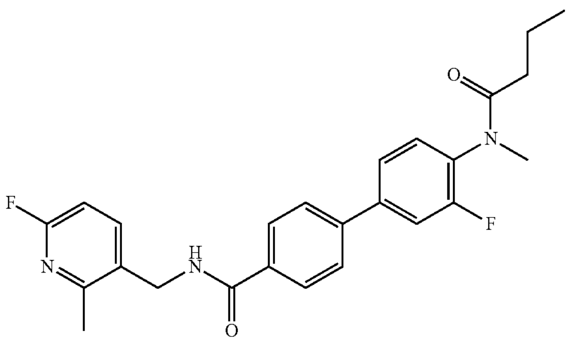
I-T808
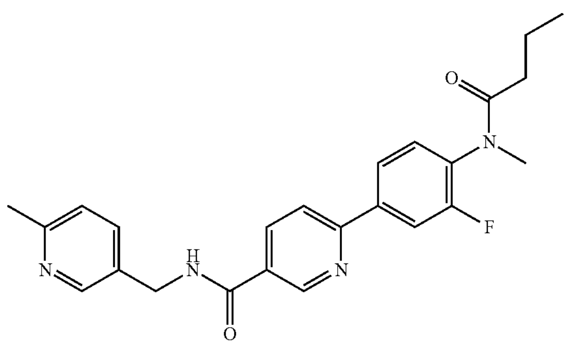
I-T809
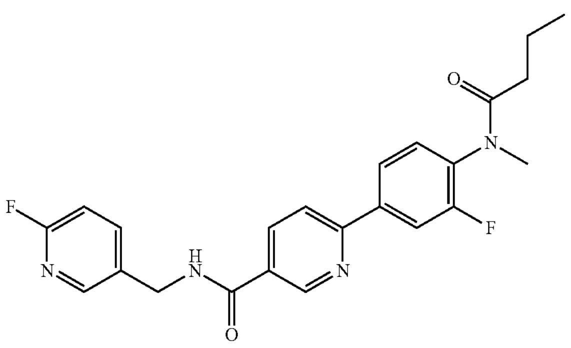
I-T810
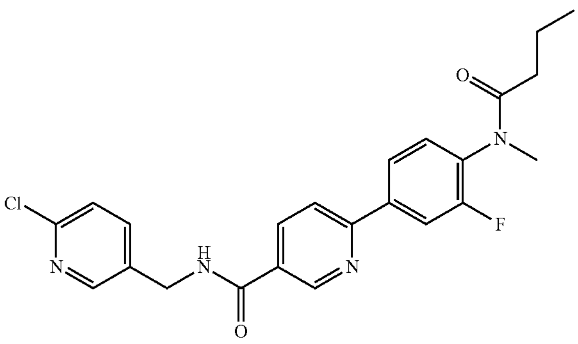
I-T811
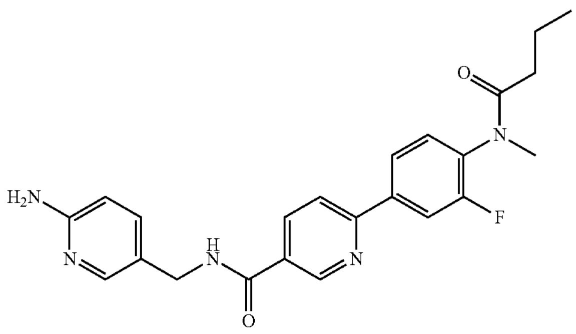
I-T812
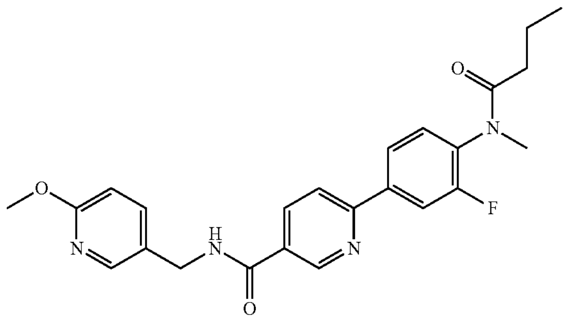
I-T813
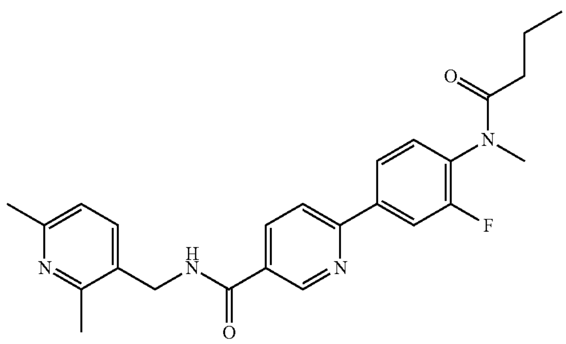

I-T814
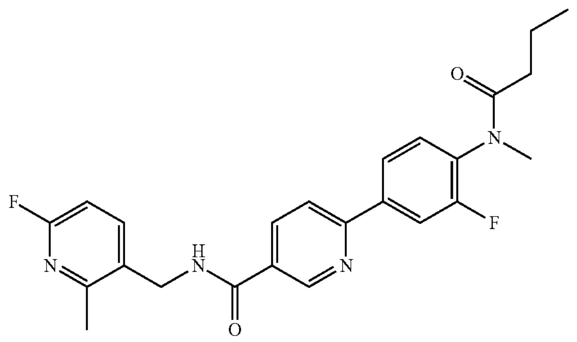
I-T815
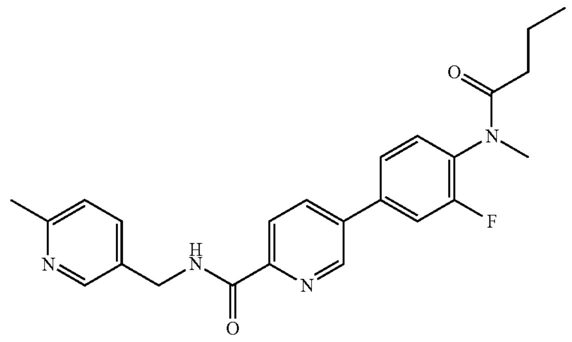
I-T816
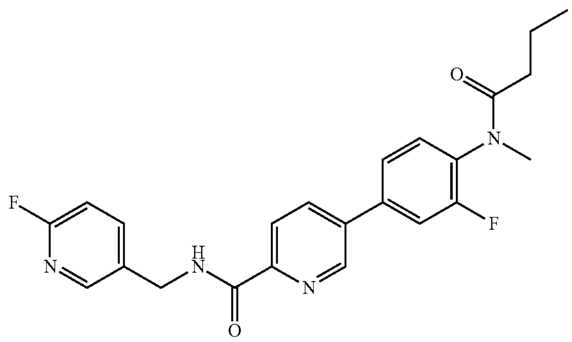
I-T817
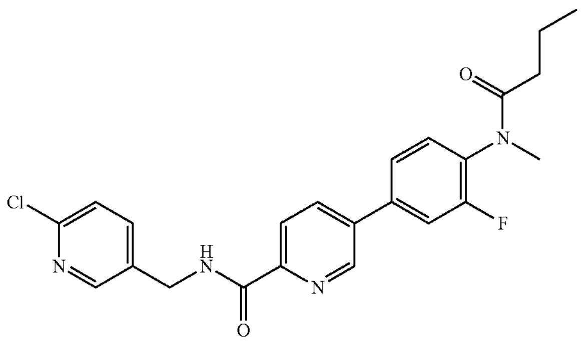
I-T818
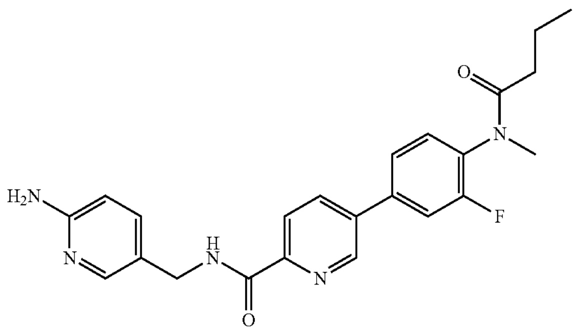
I-T819
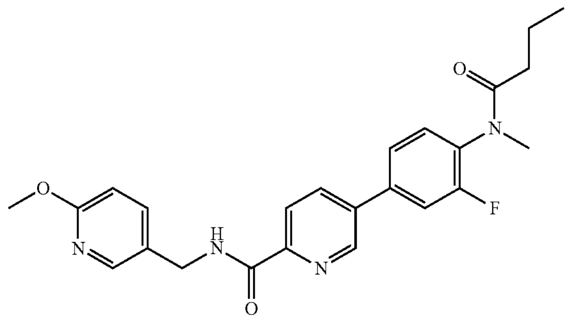
I-T820
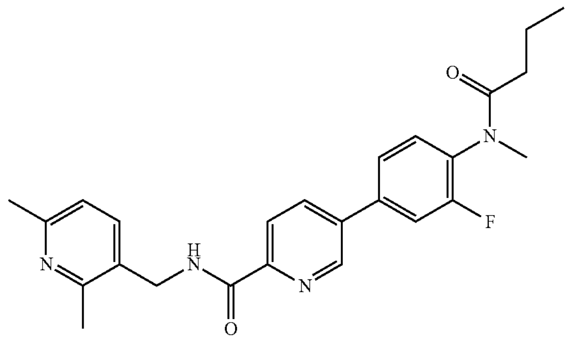
I-T821
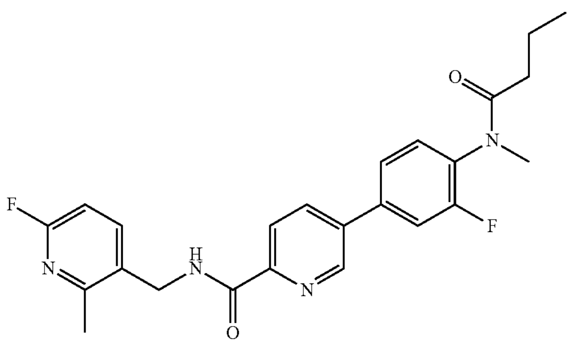

-continued
I-T822
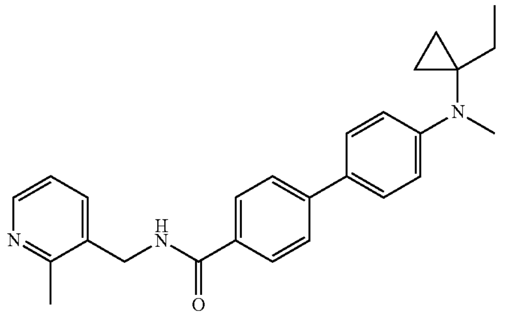
I-T823
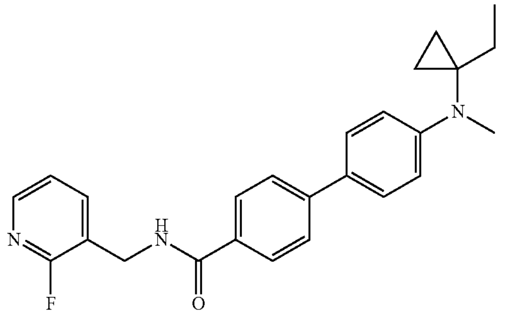
I-T824
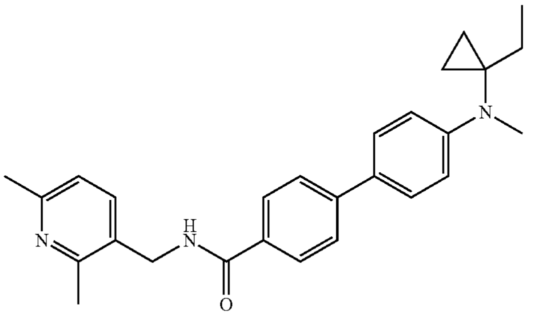
I-T825
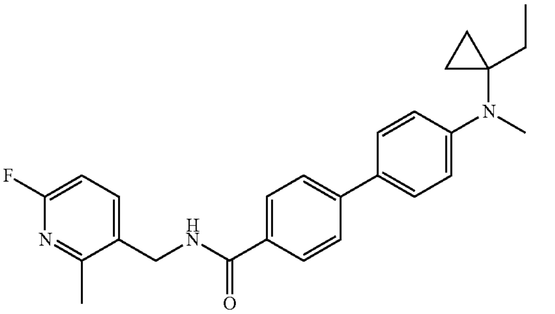
-continued
I-T826
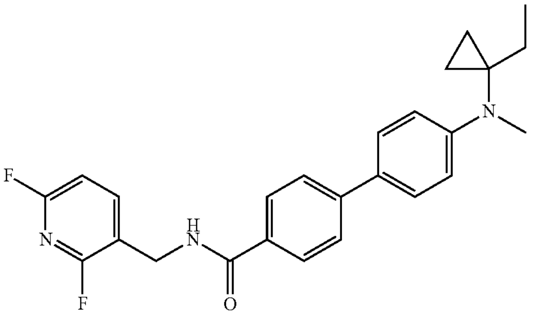
I-T827
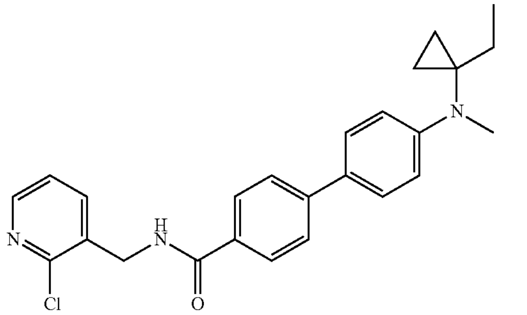
I-T828
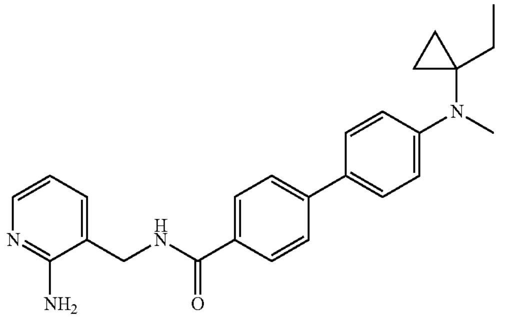
I-T829
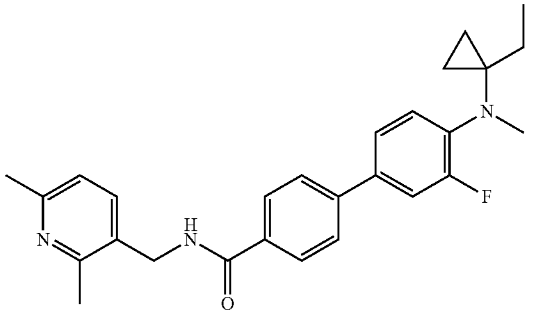

-continued
I-T830
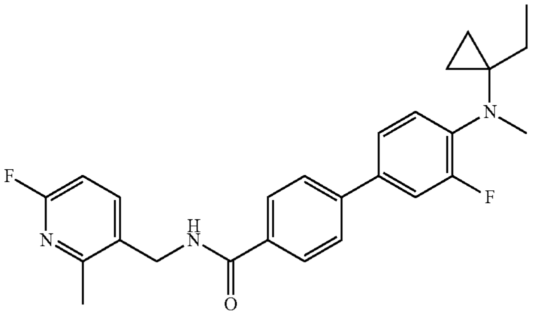
I-T831
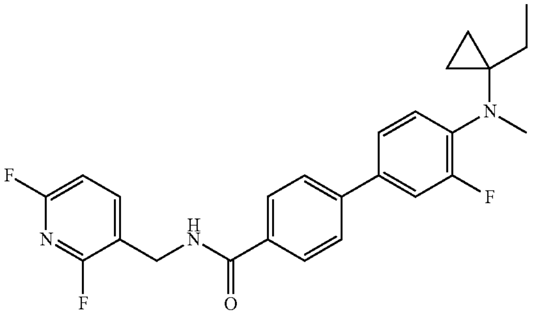
I-T832
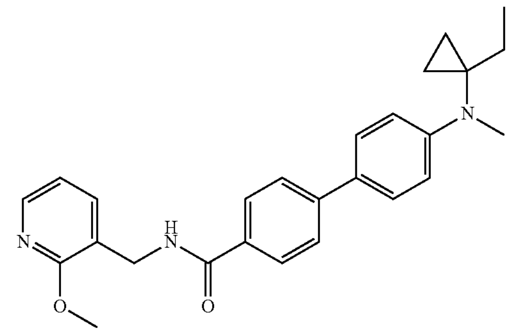
I-T833
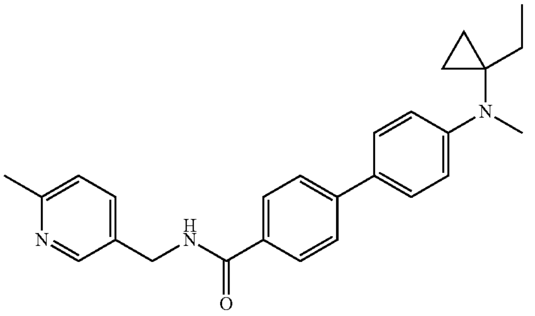
-continued
I-T834
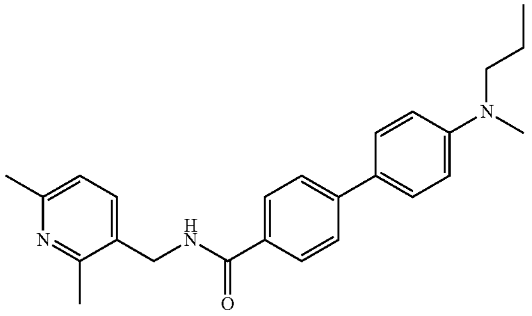
I-T835
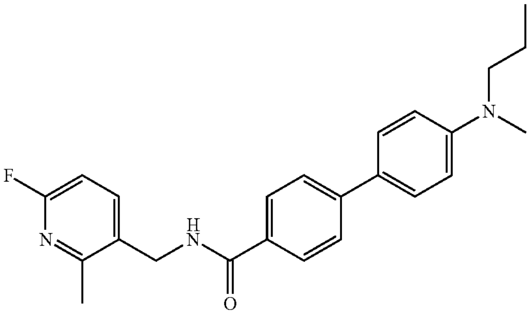
I-T836
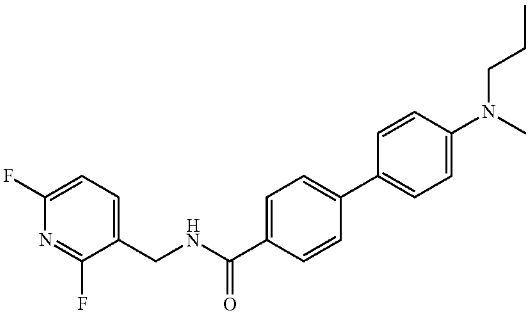
I-T837
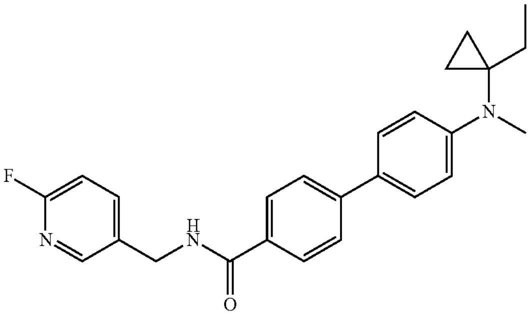

-continued
I-T838
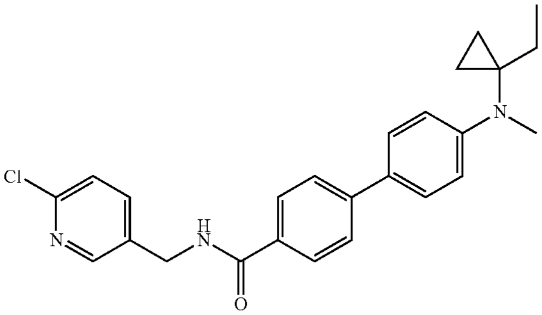
I-T839
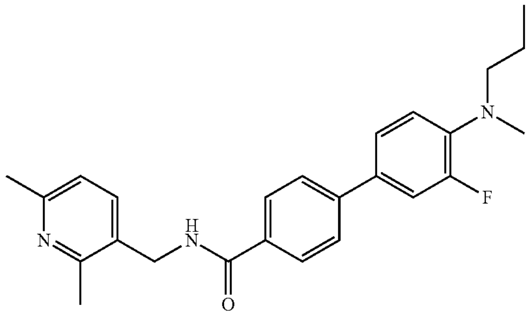
I-T840
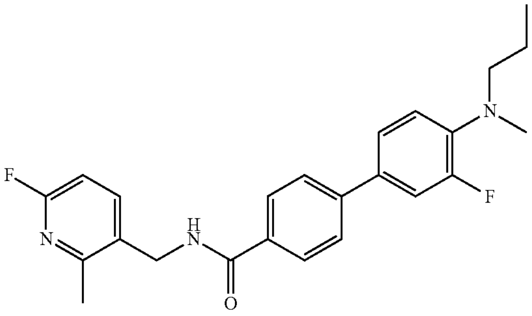
I-T841
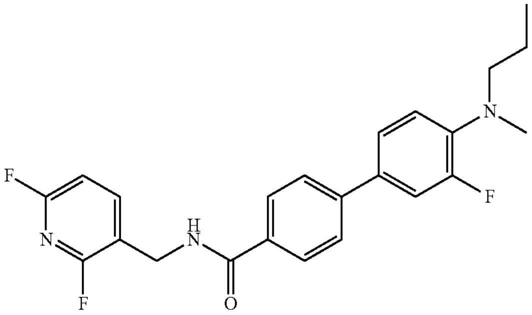
-continued
I-T842
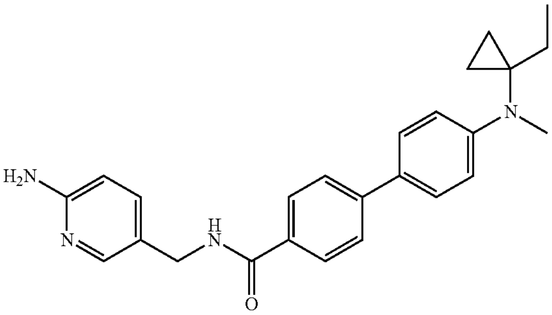
I-T843
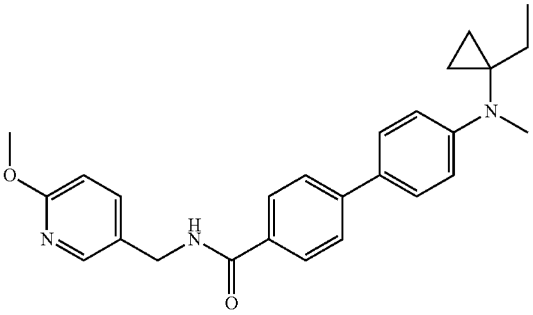
I-T844
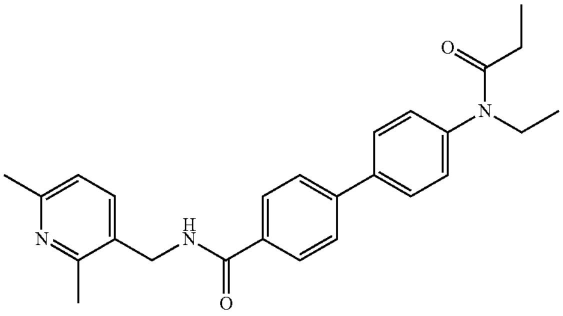
I-T845
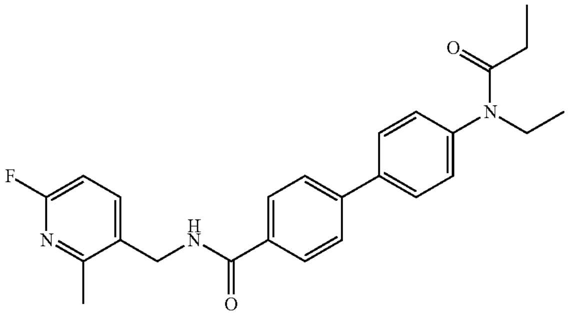

-continued
I-T846
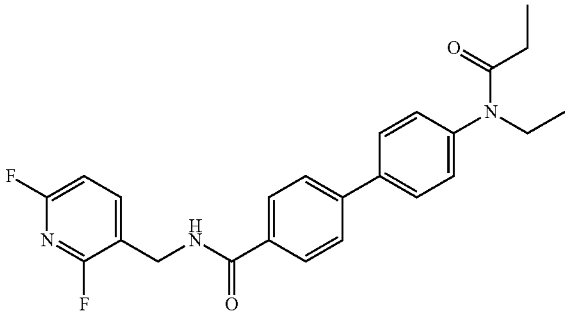
I-T847
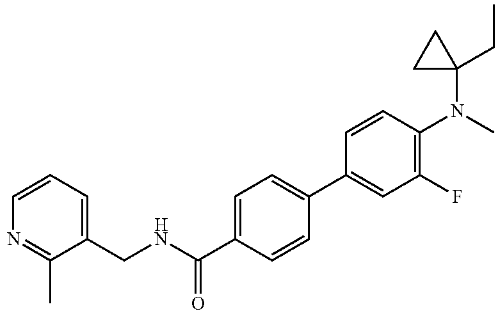
I-T848
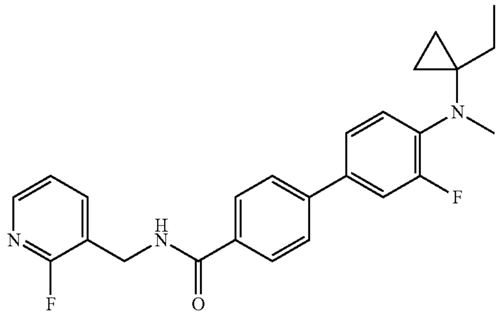
I-T849
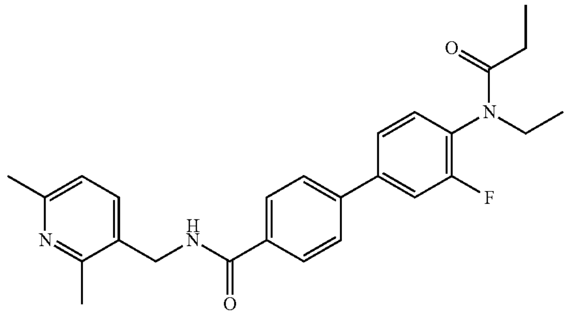
-continued
I-T850
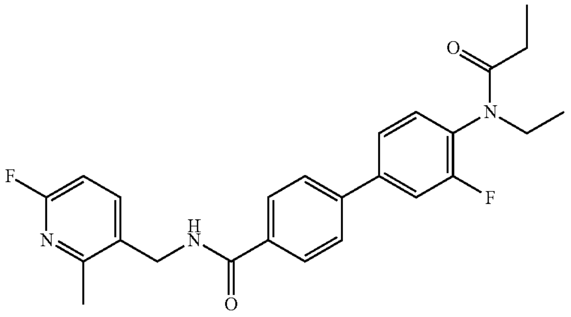
I-T851
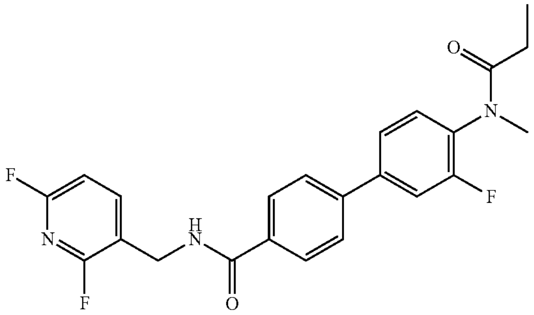
I-T852
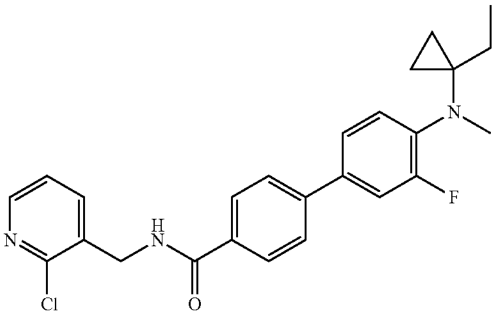
I-T853
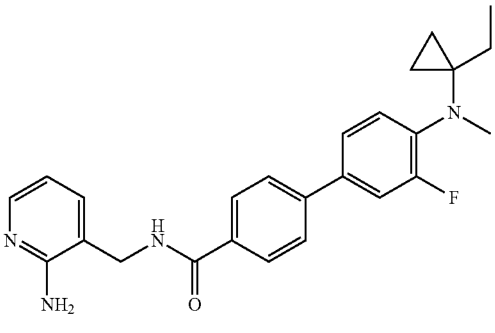

I-T854
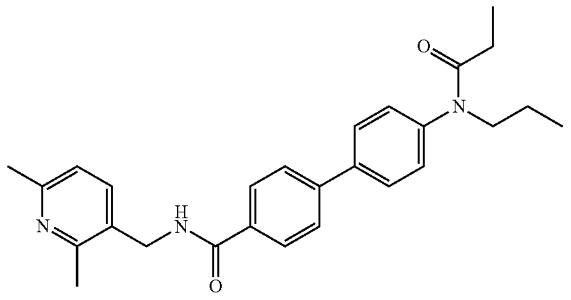
I-T855
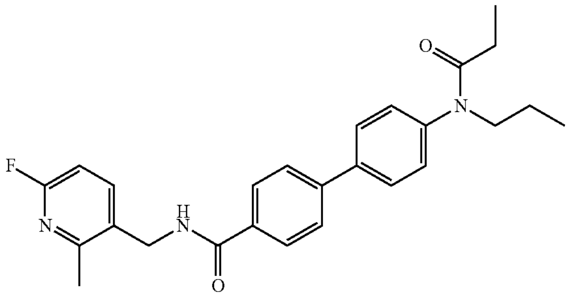
I-T856
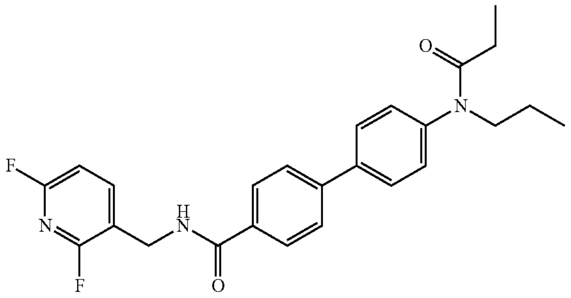
I-T857
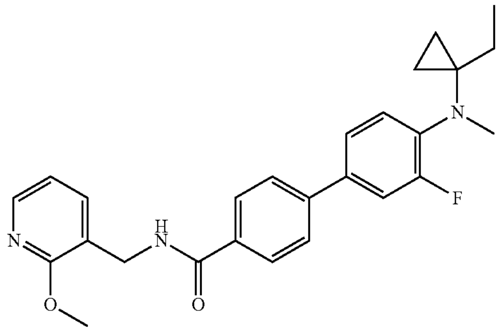
I-T858
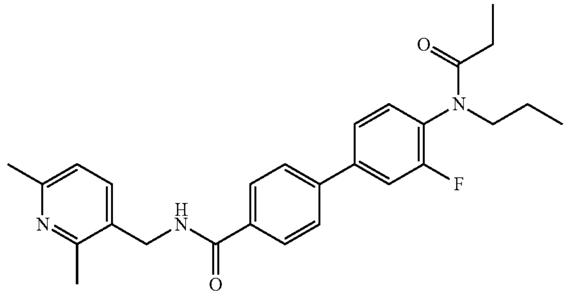
I-T859
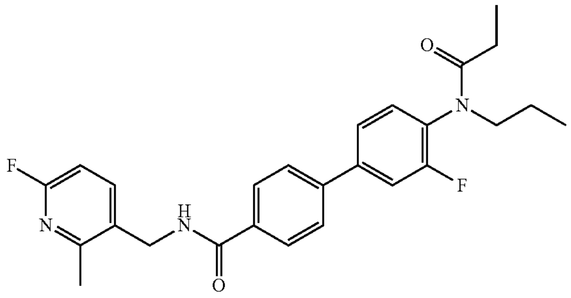
I-T860
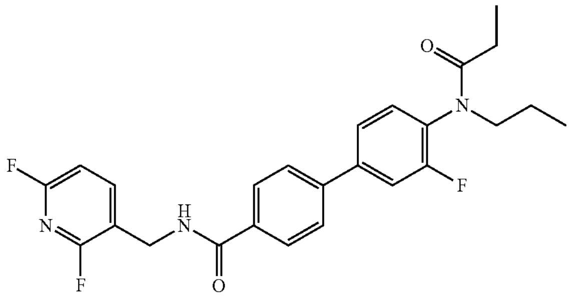
I-T861
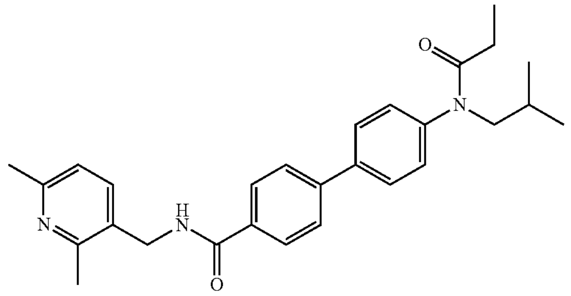
I-T862
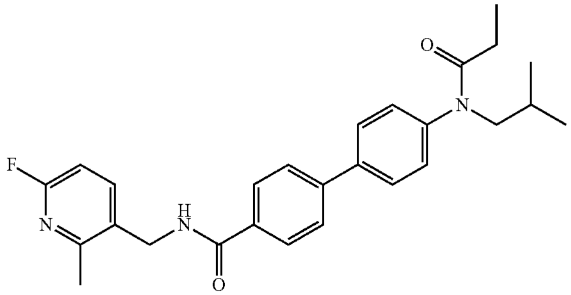
I-T863
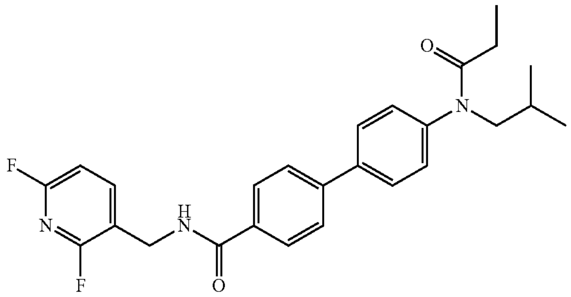

-continued
I-T864
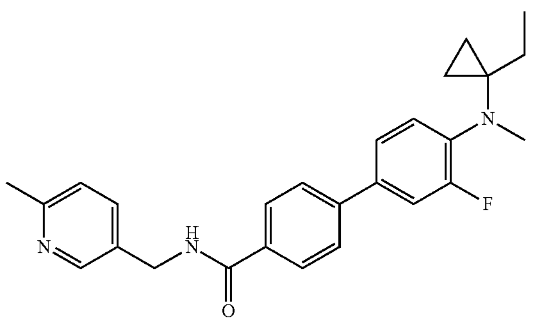
I-T865
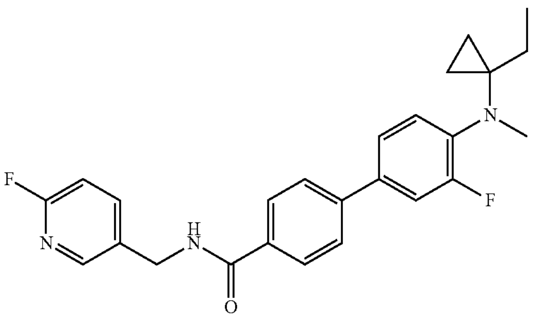
I-T866
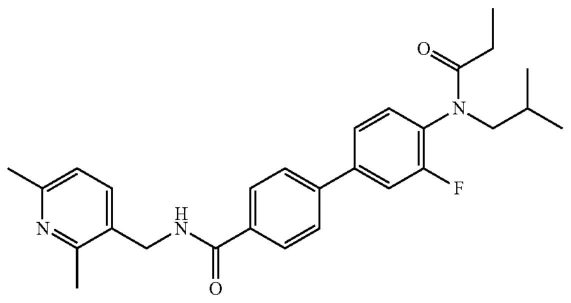
I-T867
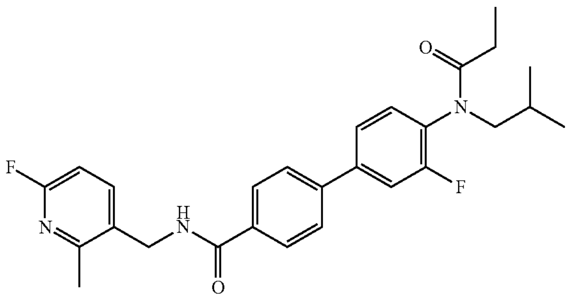
I-T868
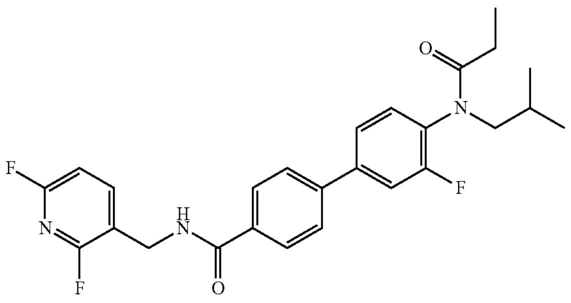
-continued
I-T869
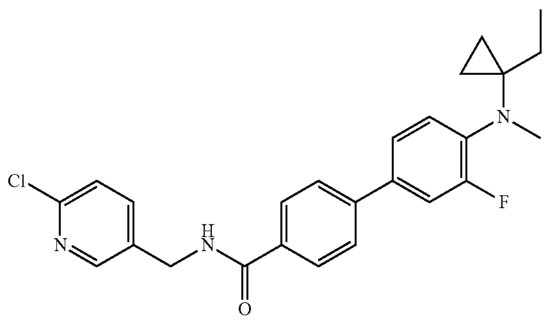
I-T870
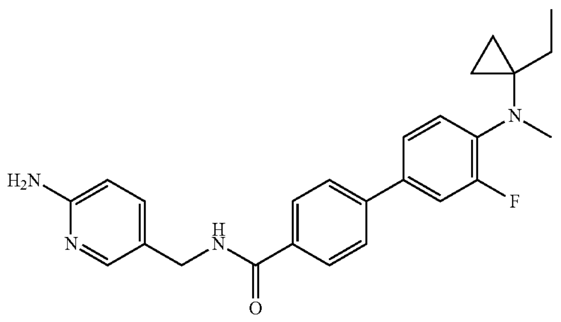
I-T871
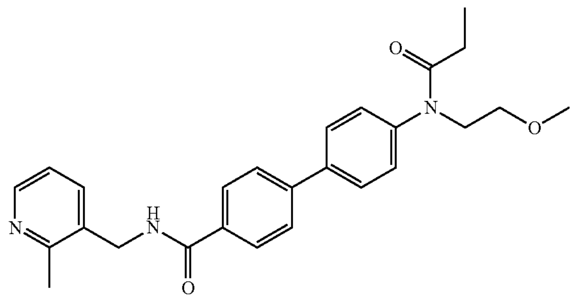
I-T872
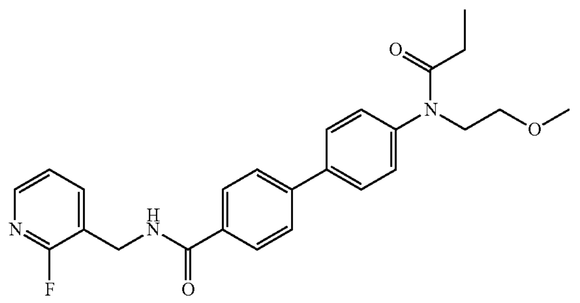
I-T873
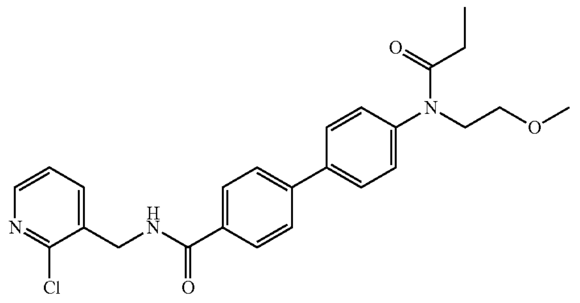

-continued
I-T874
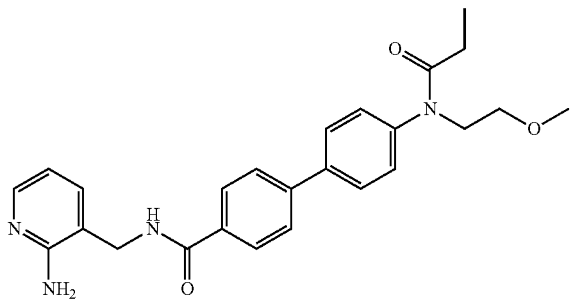
I-T875
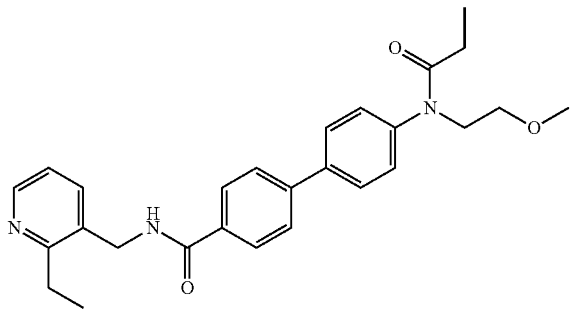
I-T876
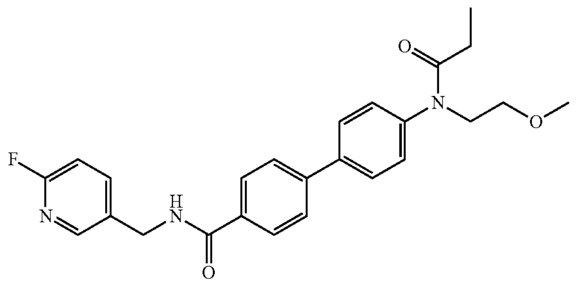
I-T877
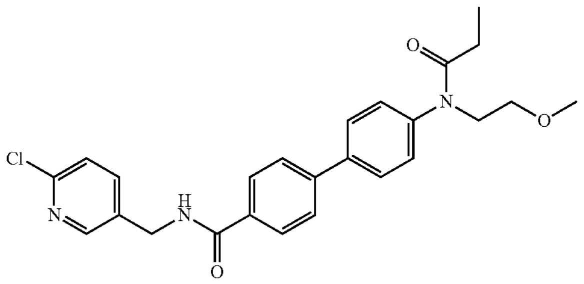
I-T878
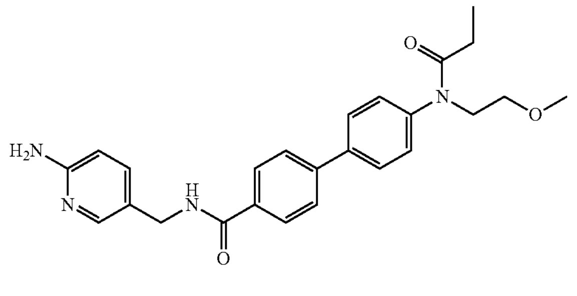
-continued
I-T879
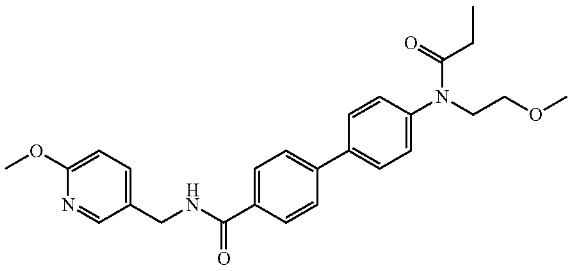
I-T880
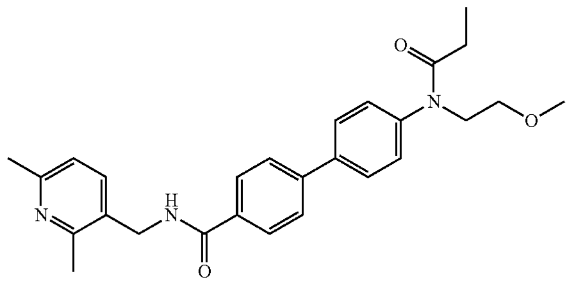
I-T881
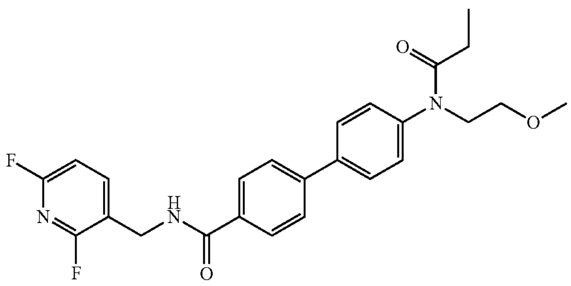
I-T 882
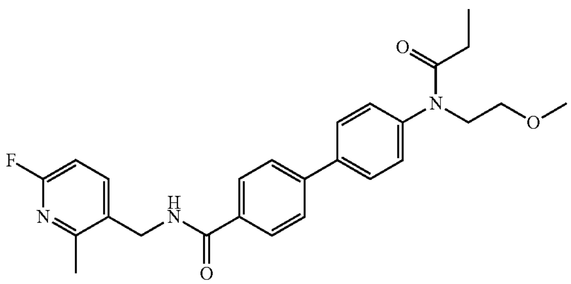
I-T883
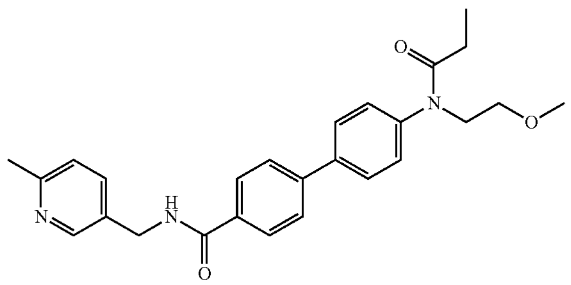

-continued
I-T884
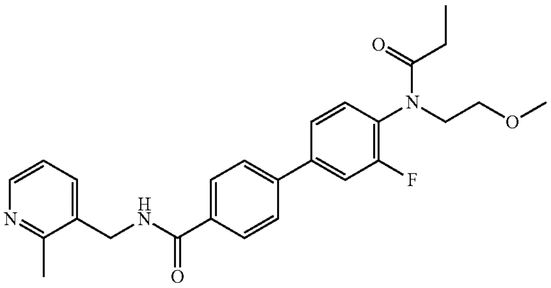
I-T885
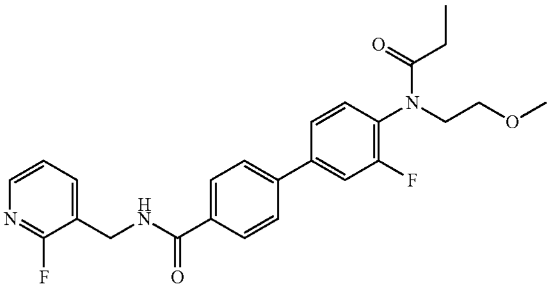
I-T886
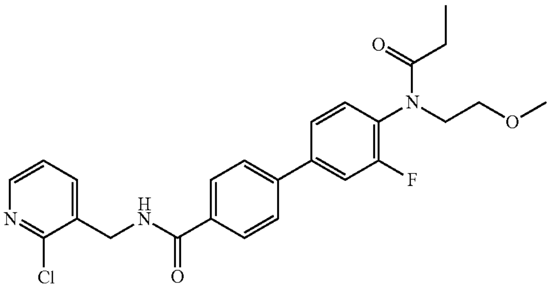
I-T887
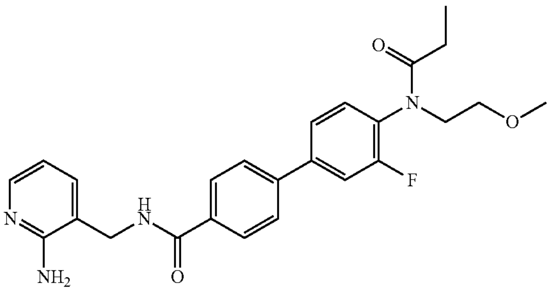
I-T888
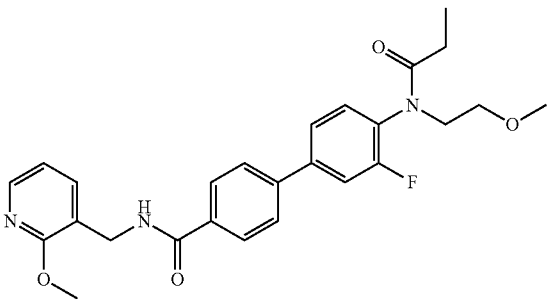
-continued
I-T889
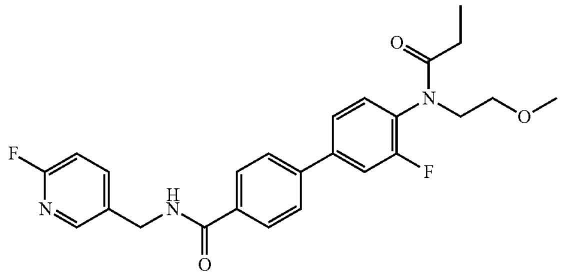
I-T890
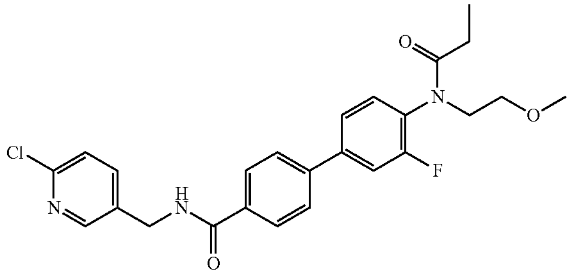
I-T891
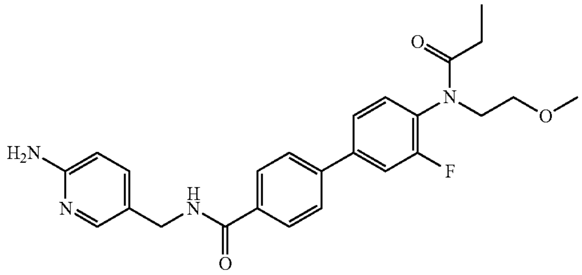
I-T892
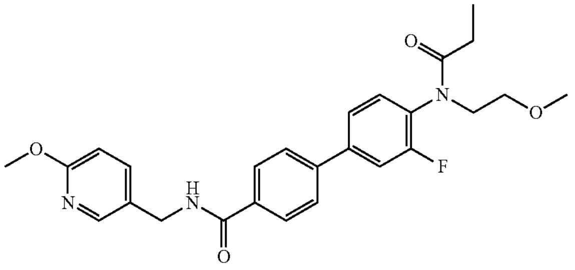
I-T893
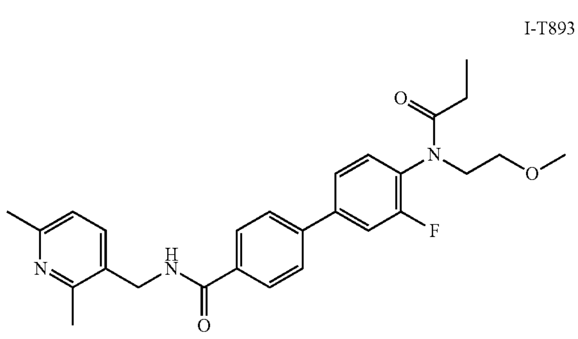

-continued
I-T894
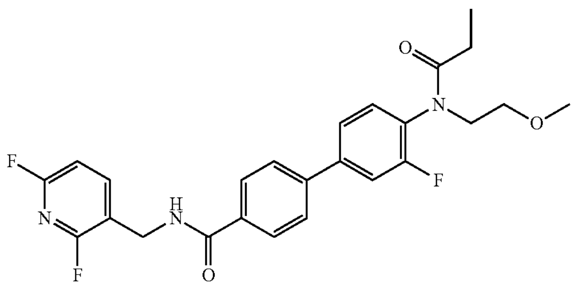
I-T895
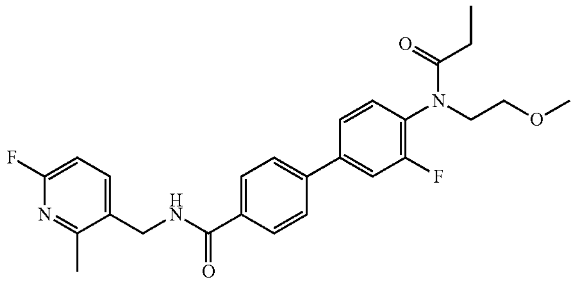
I-T896
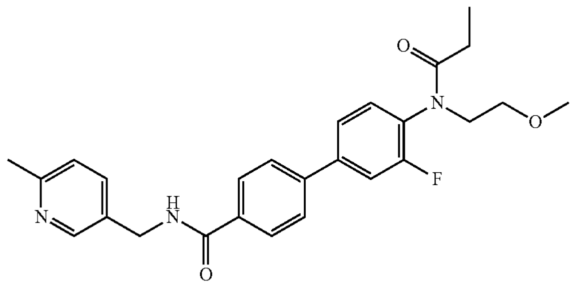
I-T897
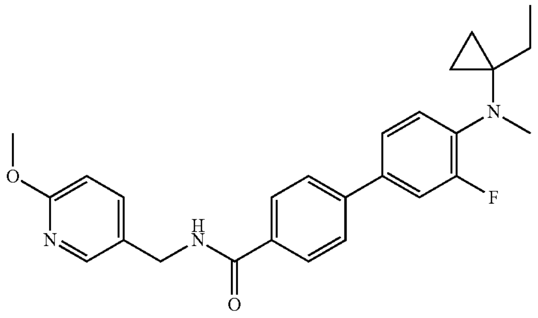
I-T898
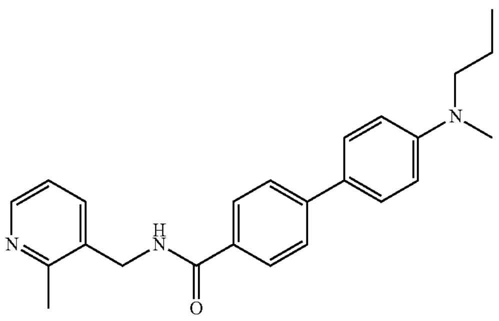
-continued
I-T899
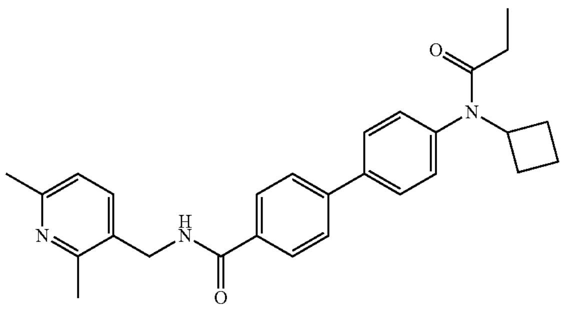
I-T900
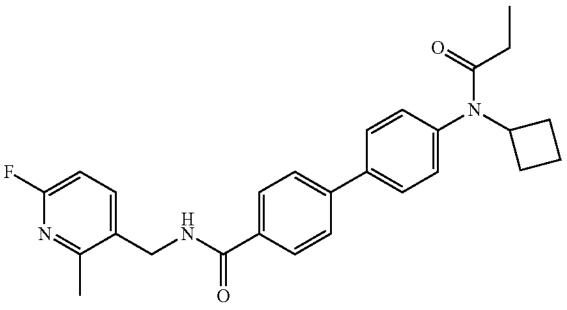
I-T901
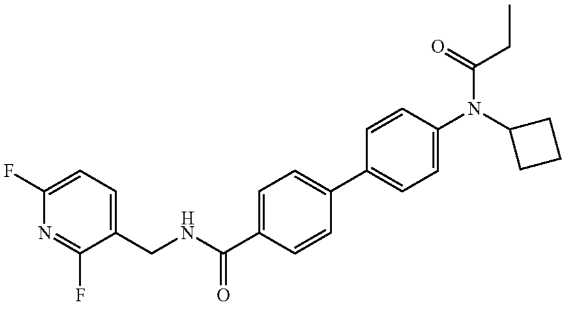
I-T902
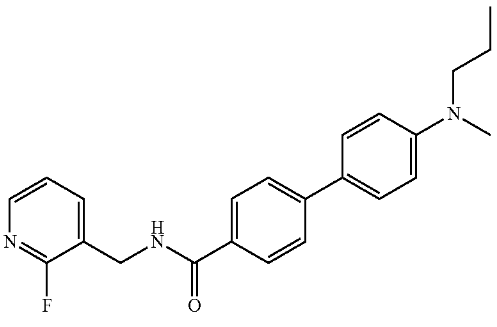

-continued
I-T903
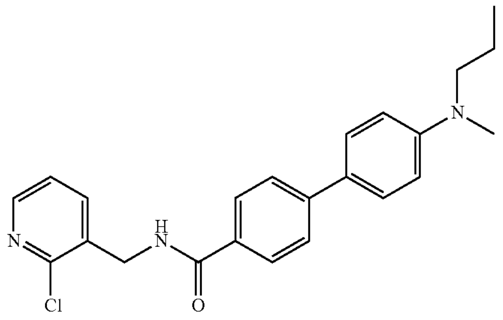
I-T904
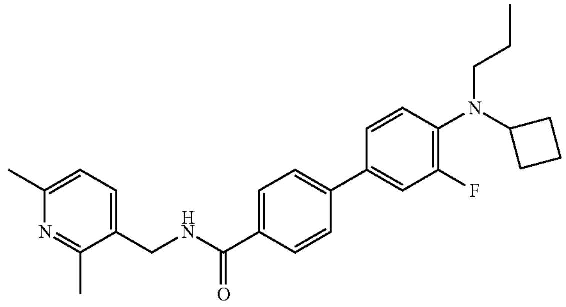
I-T905
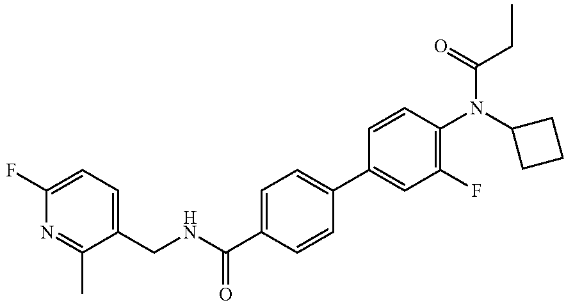
I-T906
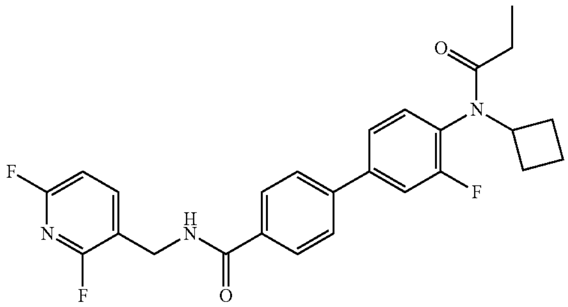
-continued
I-T907
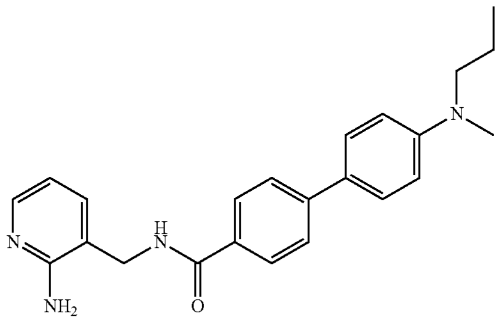
I-T908
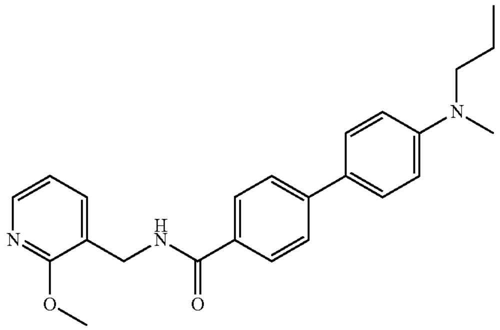
I-T909
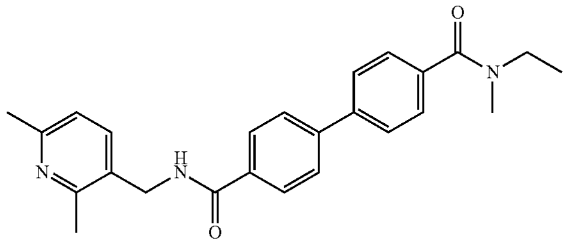
I-T910
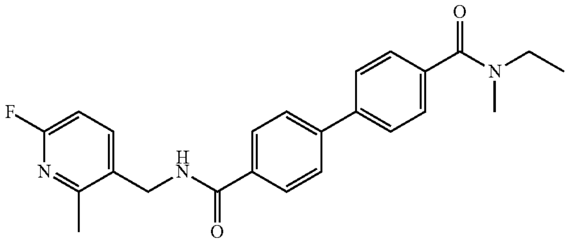
I-T911
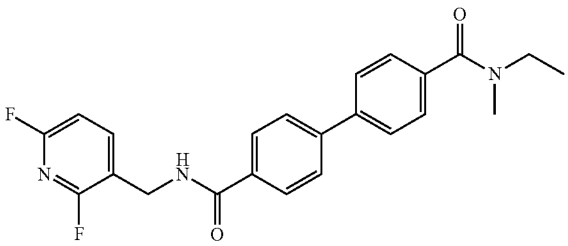

-continued
I-T912
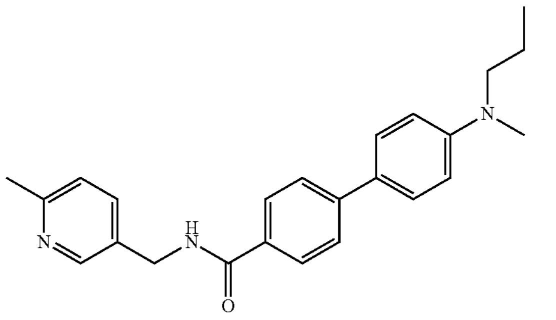
I-T913
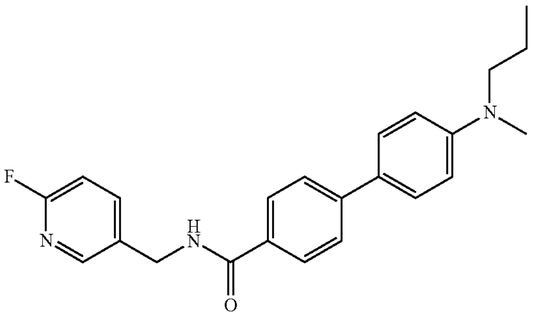
I-T914
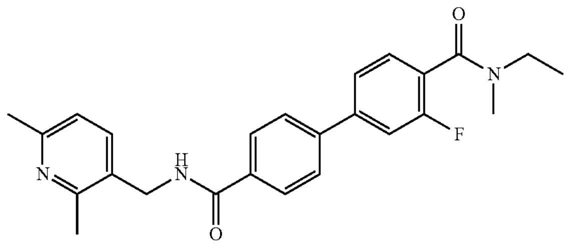
I-T915
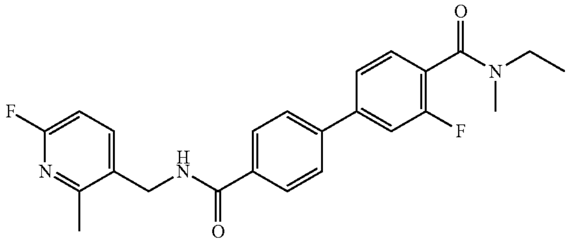
I-T916
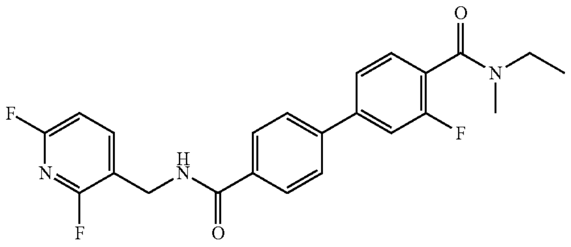
-continued
I-T917
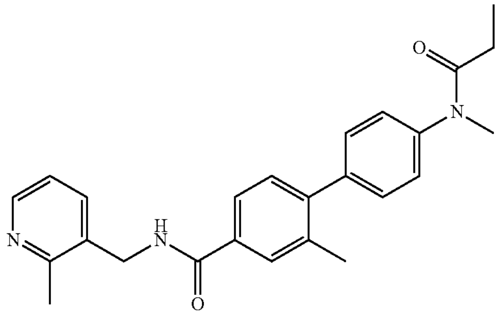
I-T918
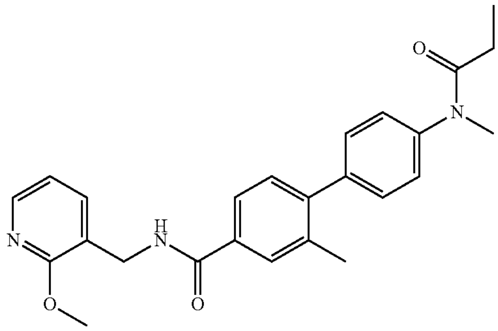
I-T919
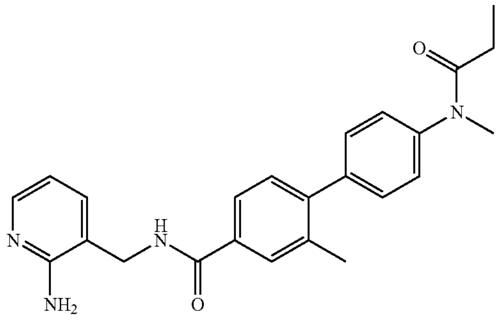
I-T920
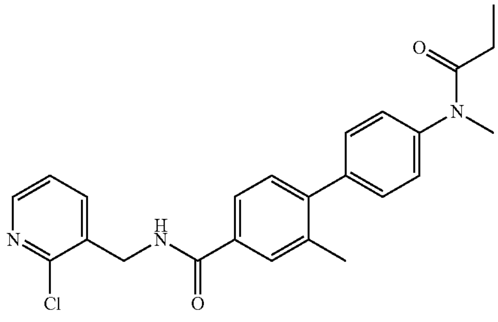

-continued
I-T921
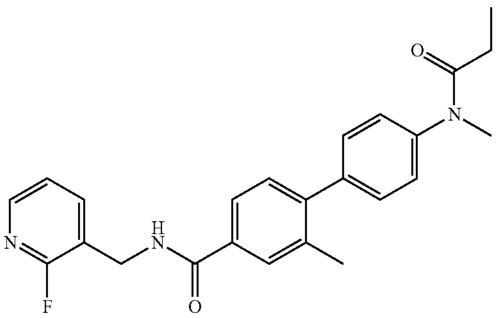
I-T922
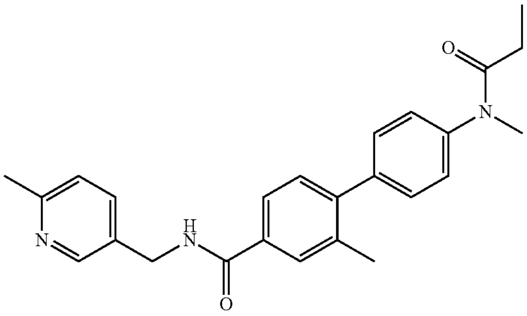
I-T923
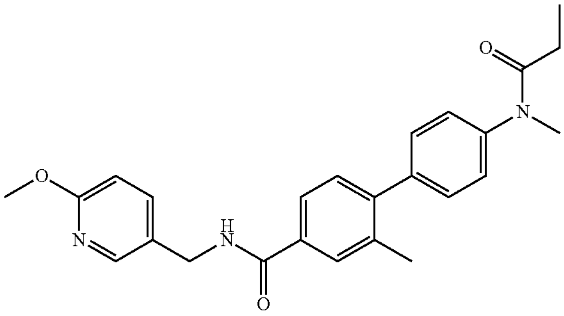
I-T924
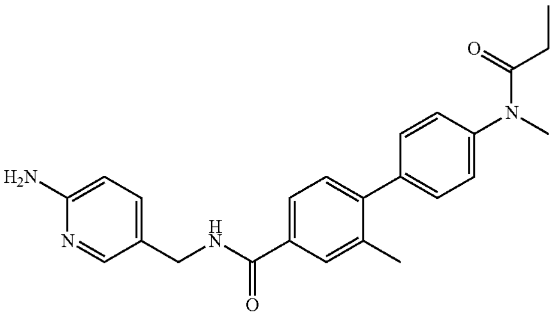
-continued
I-T925
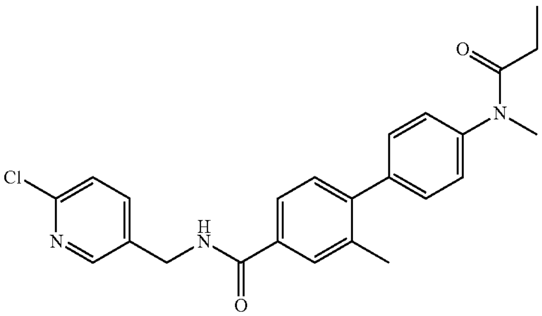
I-T926
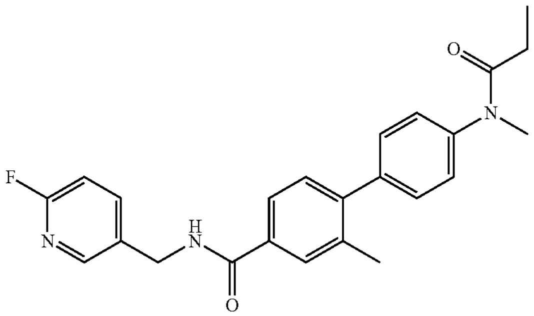
I-T927
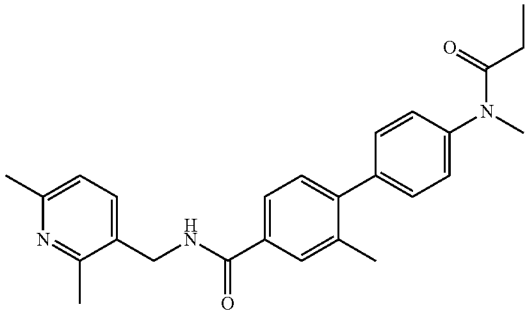
I-T928
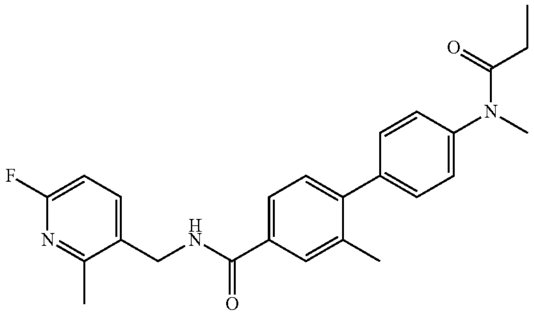

-continued
I-T929
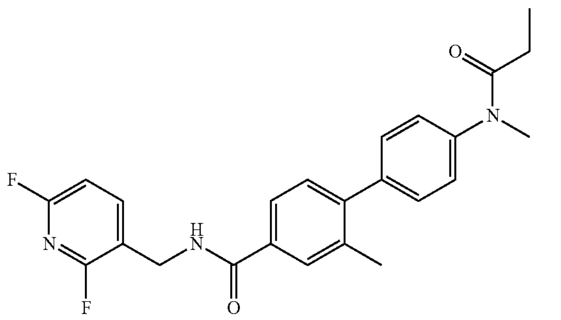
I-T930
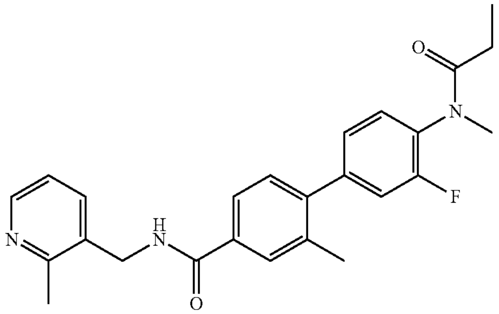
I-T931
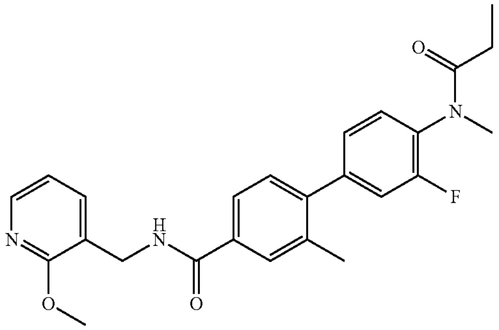
I-T932
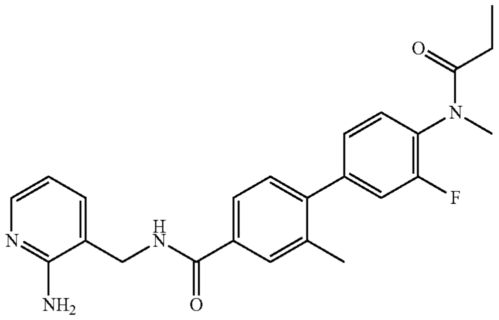
-continued
I-T933
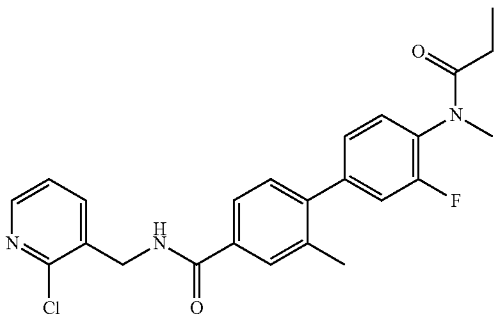
I-T934
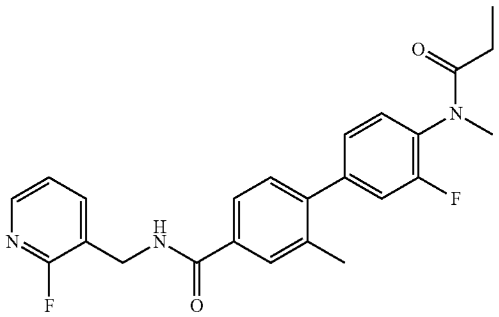
I-T935
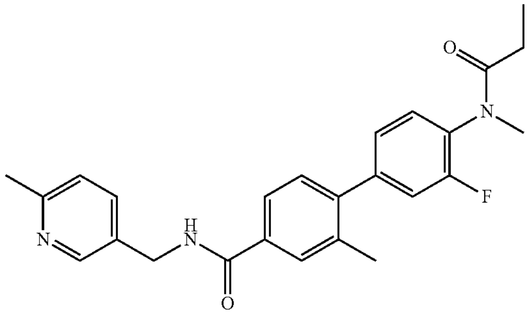
I-T936
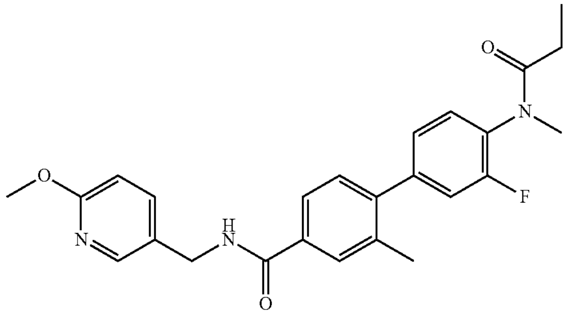

-continued
I-T937
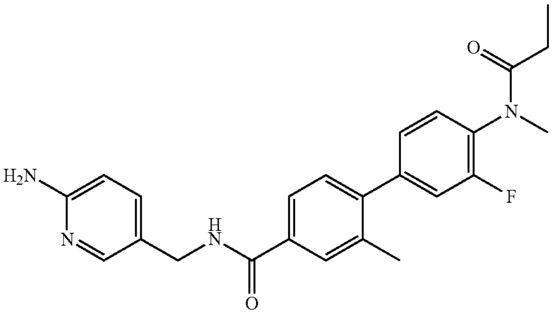
I-T938
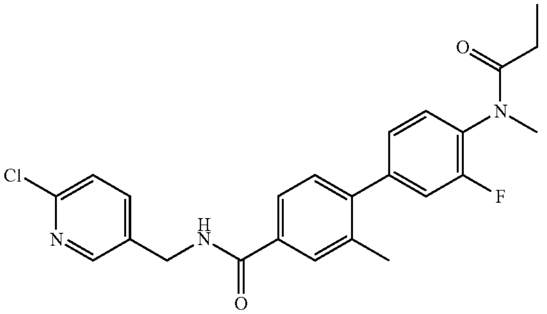
I-T939
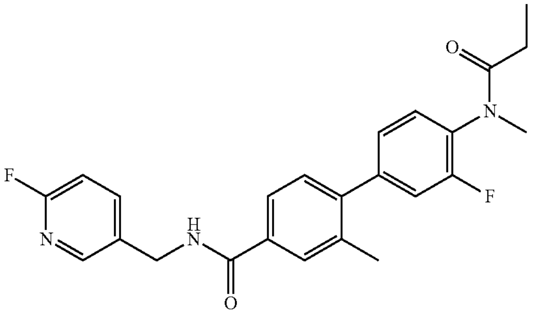
I-T940
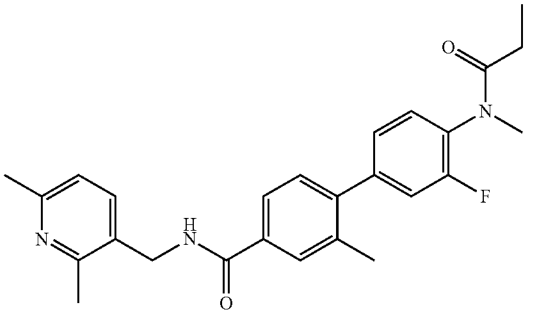
-continued
I-T941
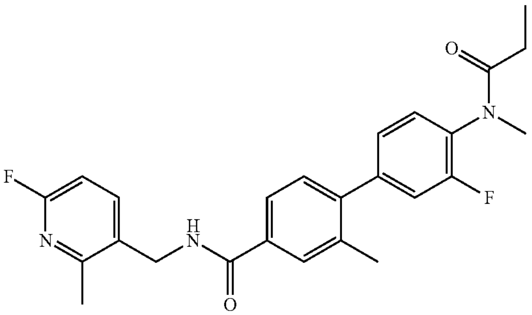
I-T941
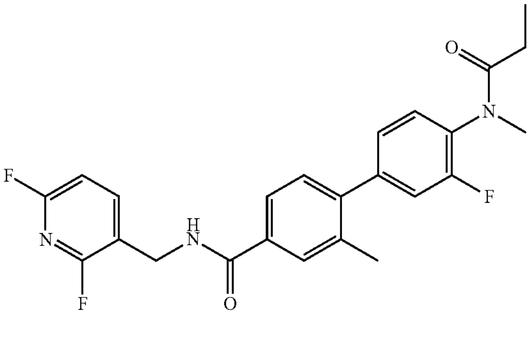
I-T943
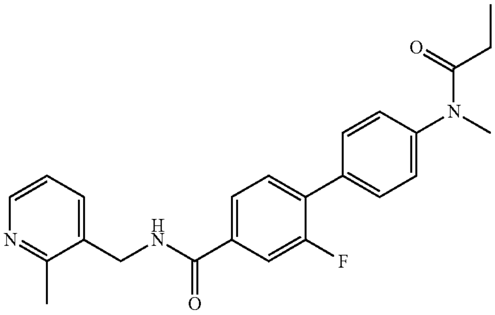
I-T944
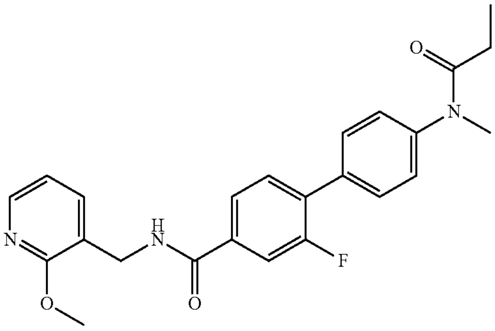

-continued
I-T945
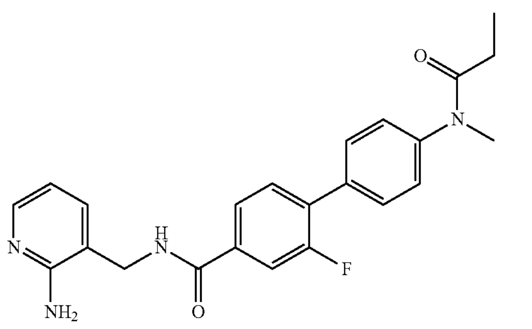
I-T946
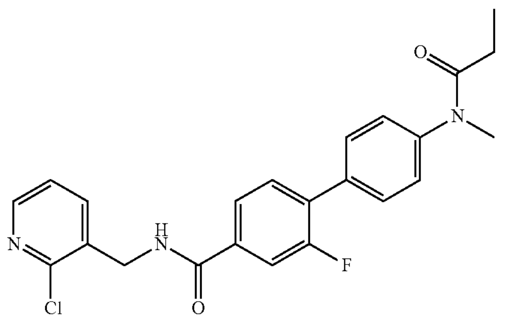
I-T947
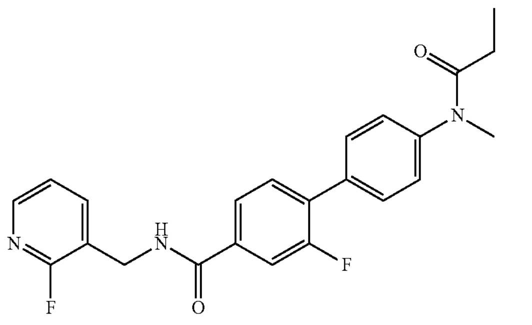
I-T948
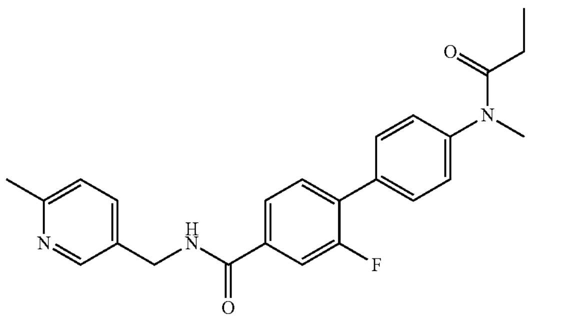
-continued
I-T949
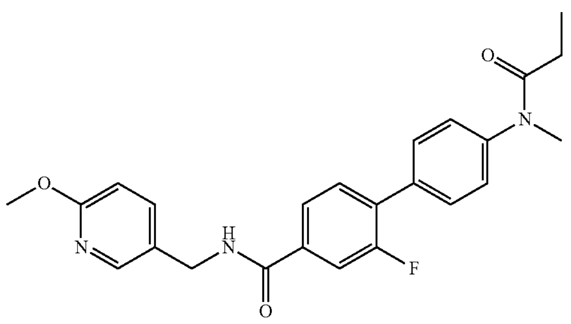
I-T950
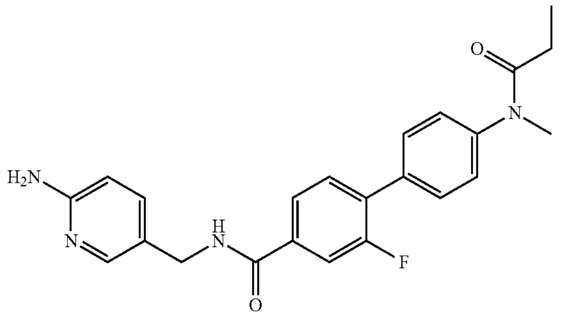
I-T951
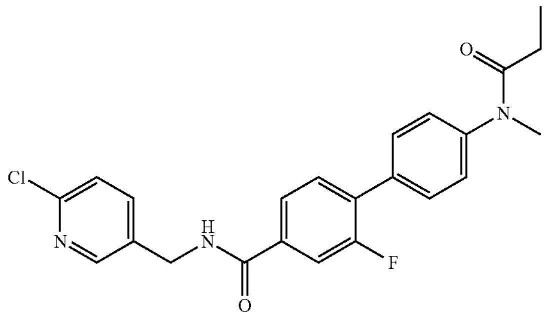
I-T952
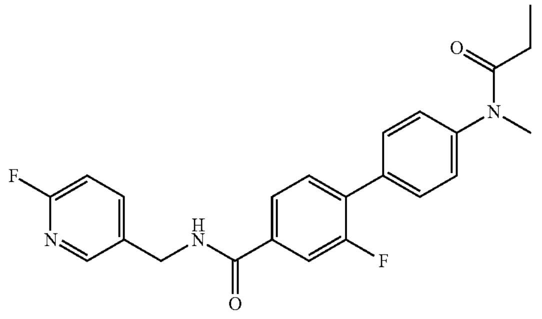

-continued
I-T953
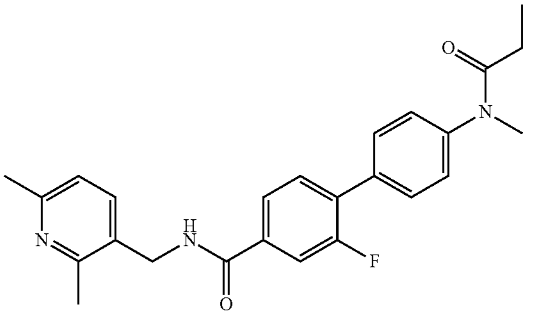
I-T954
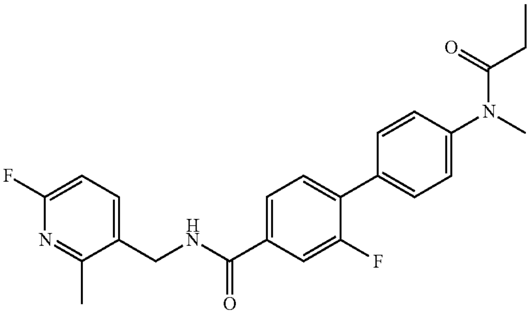
I-T955
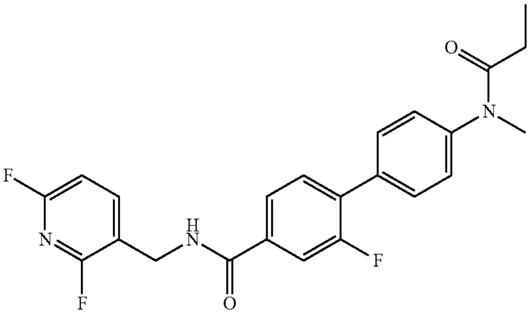
I-T956
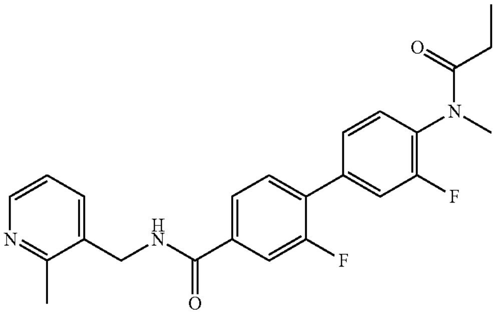
-continued
I-T957
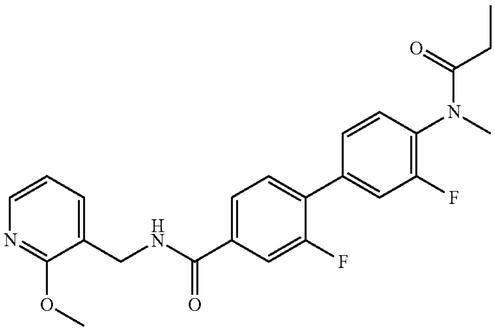
I-T958
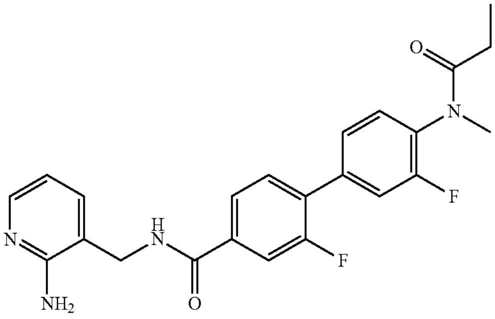
I-T959
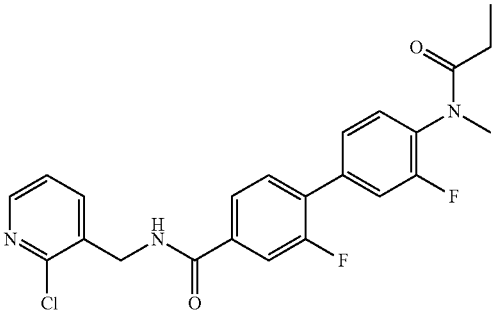
I-T960
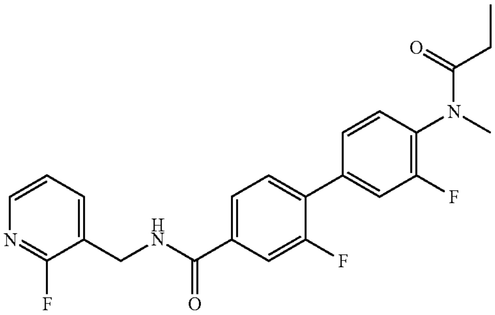

I-T961
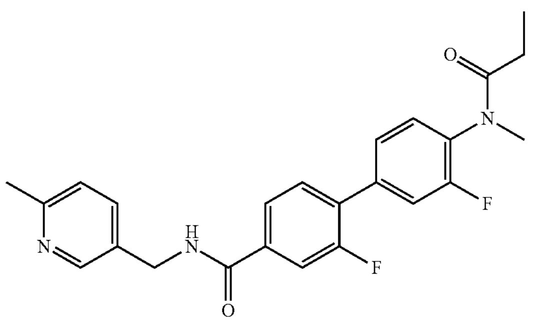
I-T962
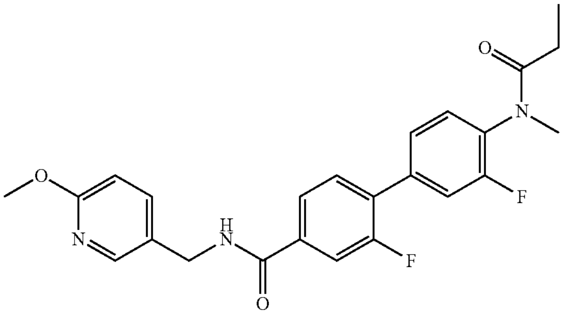
I-T963
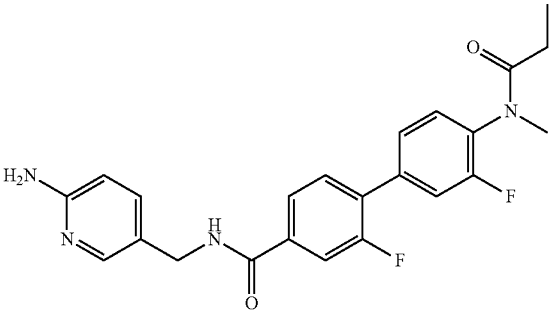
I-T964
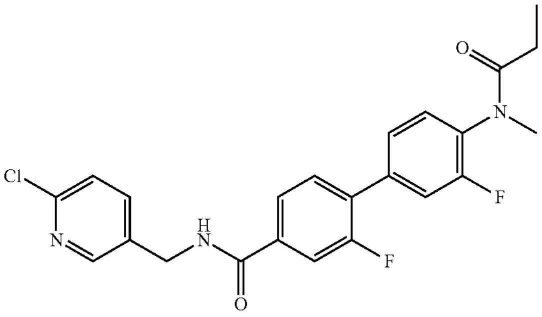
I-T965
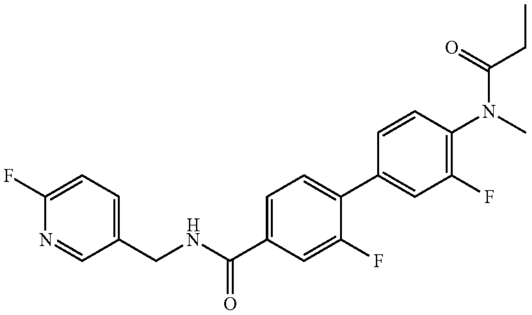
I-T966
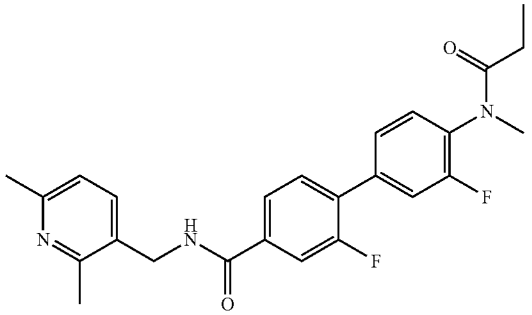
I-T967
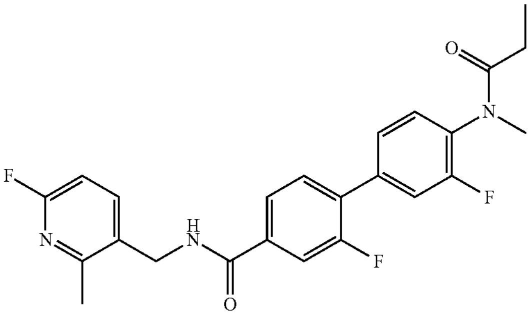
I-T968
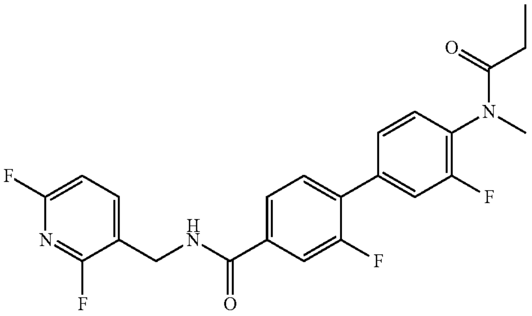

-continued
I-T969
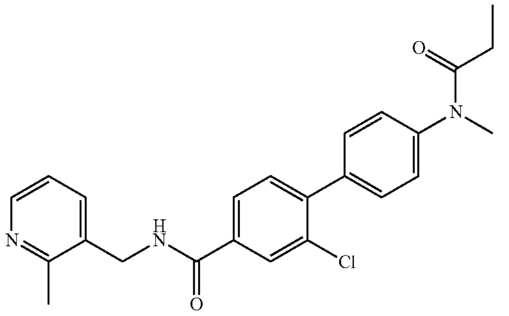
I-T970
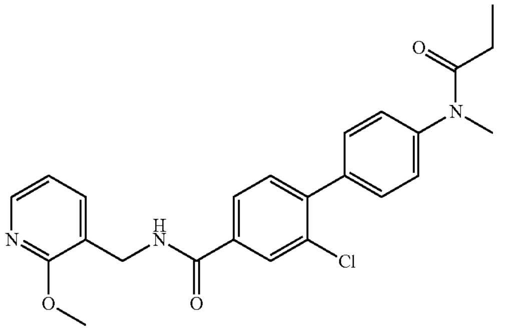
I-T971
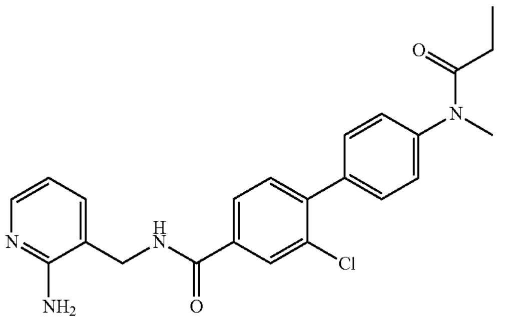
I-T972
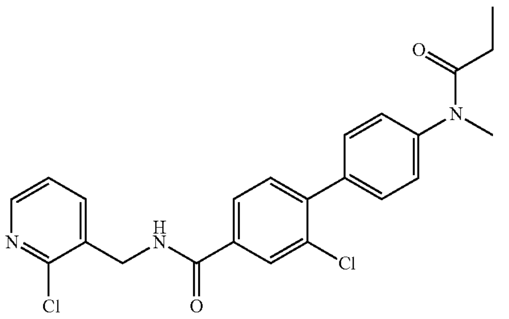
-continued
I-T973
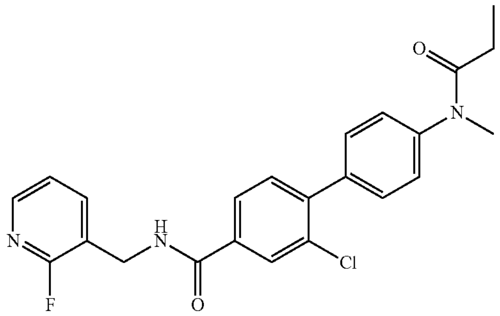
I-T974
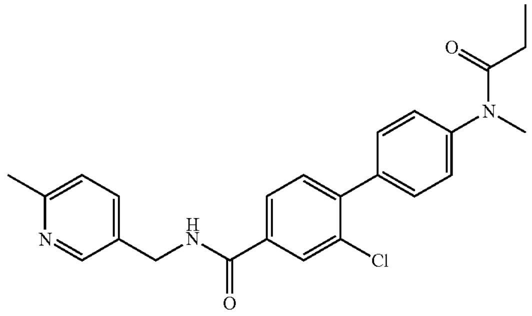
I-T975
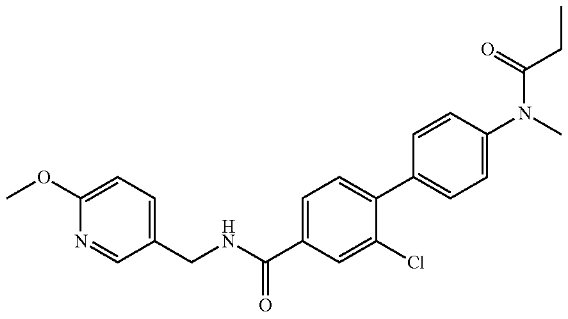
I-T976
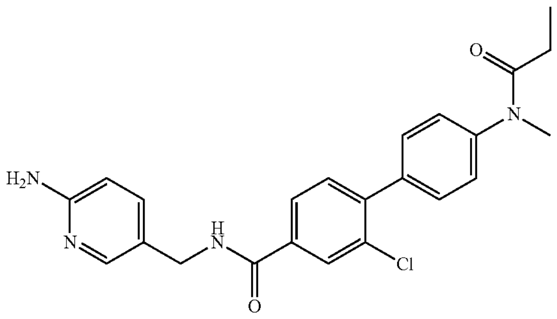

I-T977
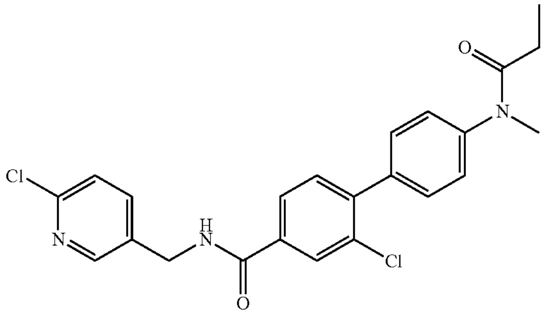
I-T978
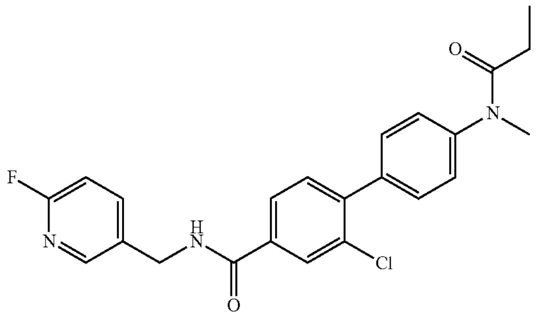
I-T979
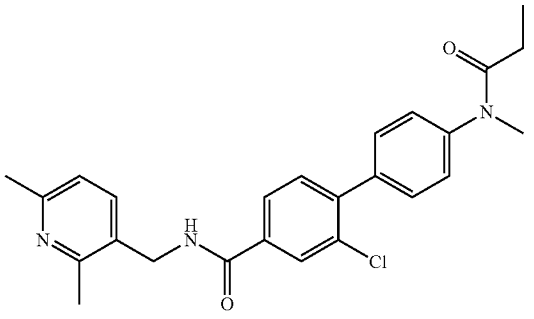
I-T980
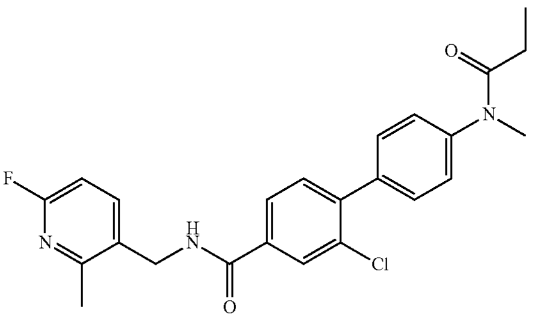
I-T981
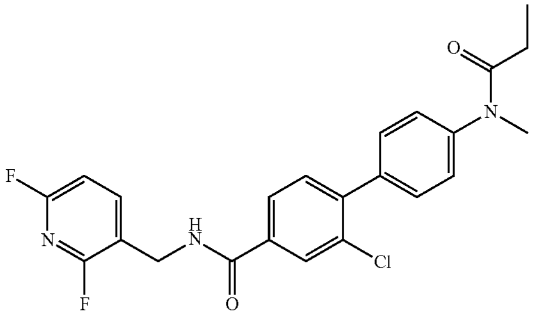
I-T982
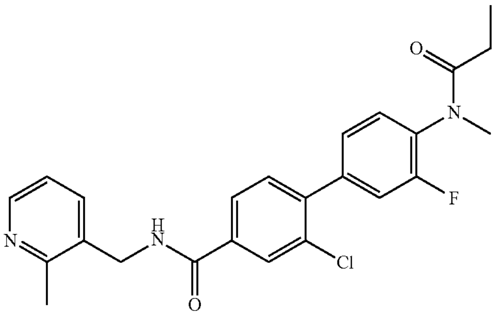
I-T983
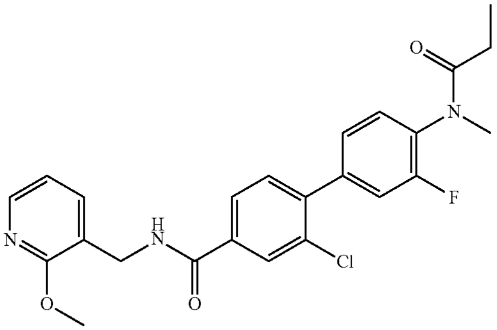
I-T984
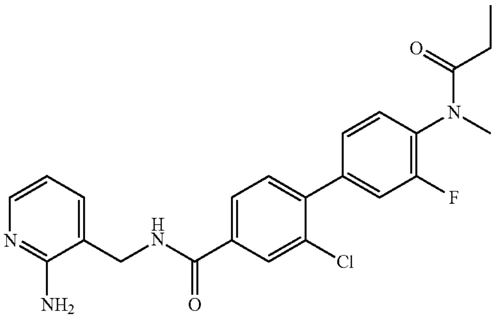

I-T985
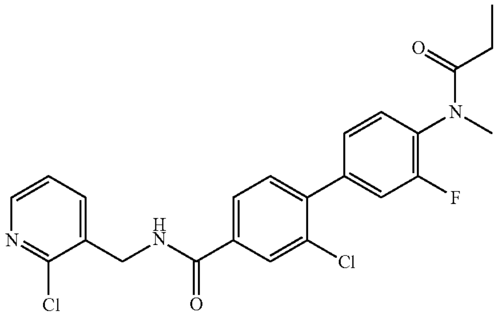
I-T986
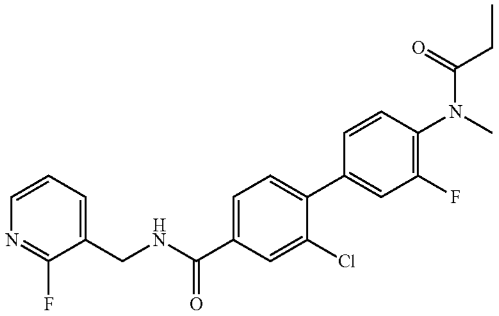
I-T987
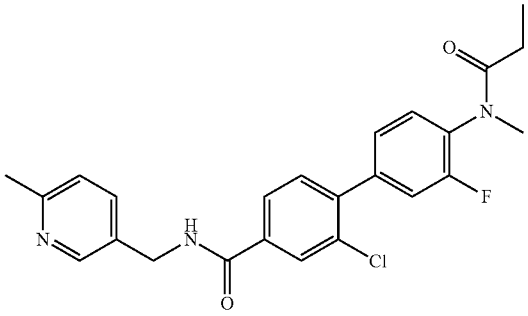
I-T988
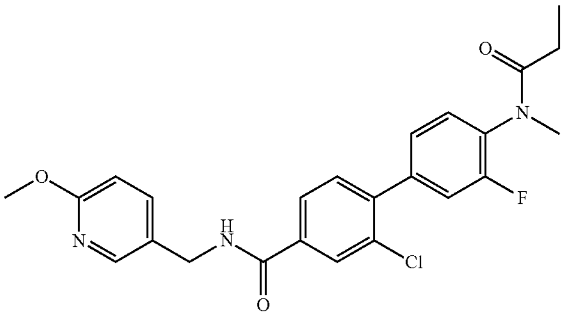
I-T988
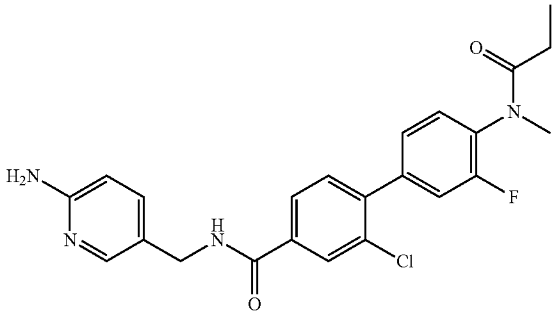
I-T989
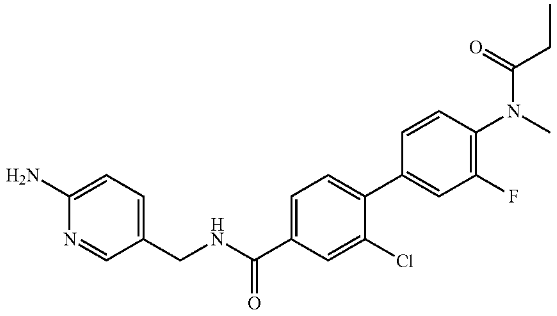
I-T990
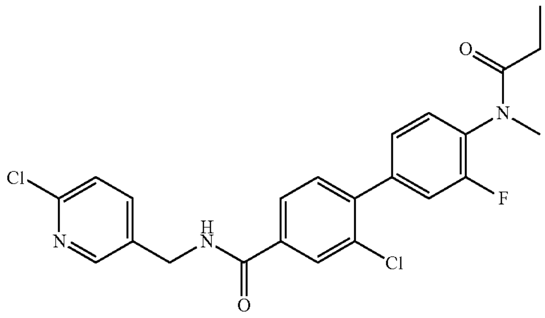
I-T991
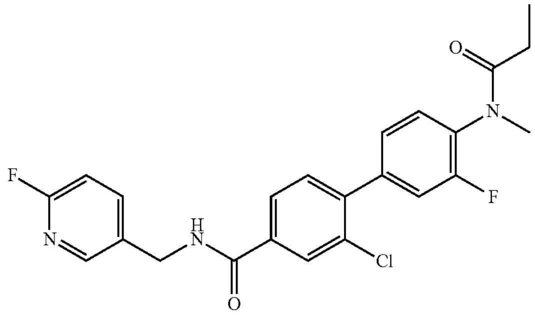

-continued
I-T992
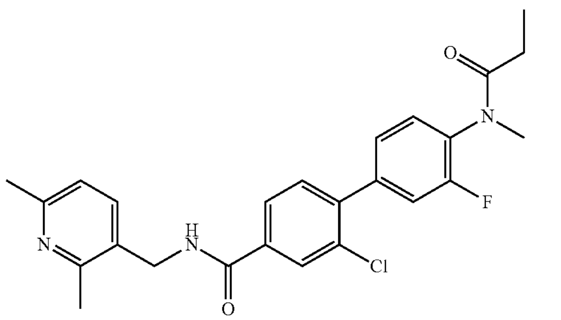
I-T993
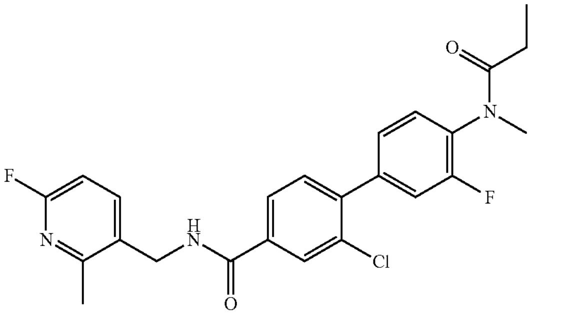
I-T994
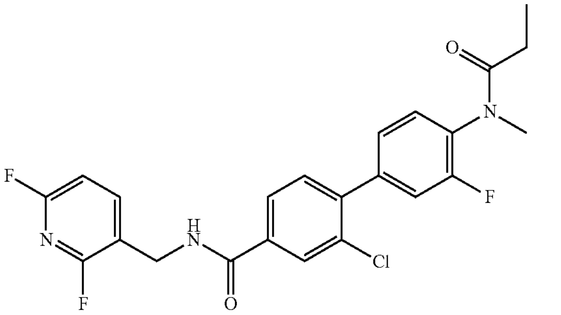
I-T995
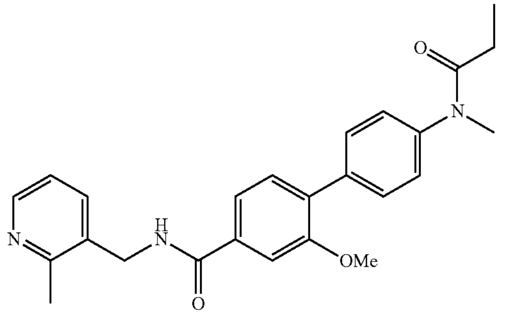
-continued
I-T996
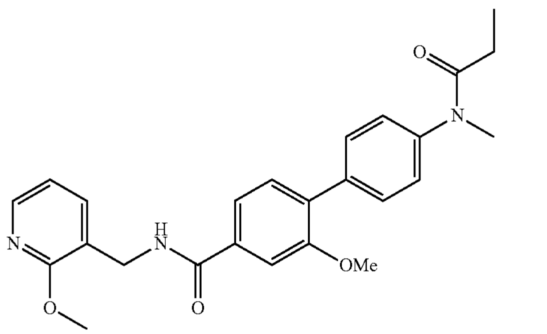
I-T997
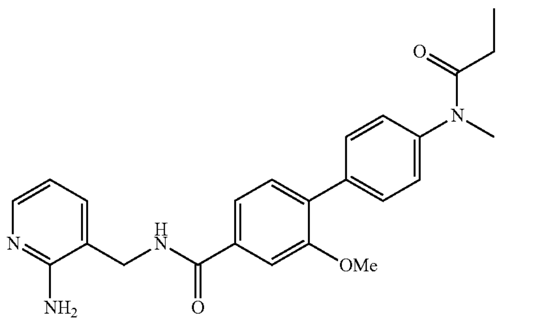
I-T998
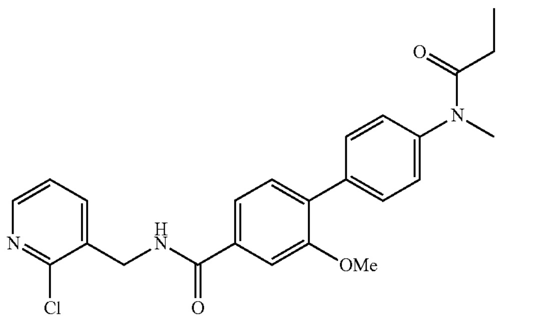
I-T999
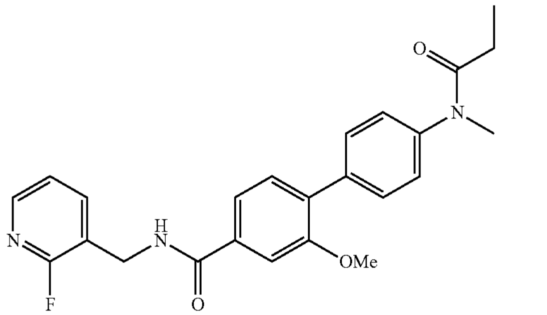

-continued
I-T1000
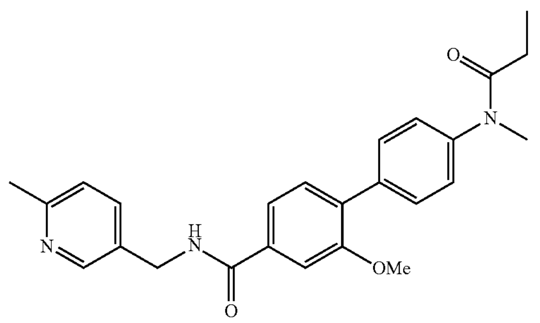
I-T1001
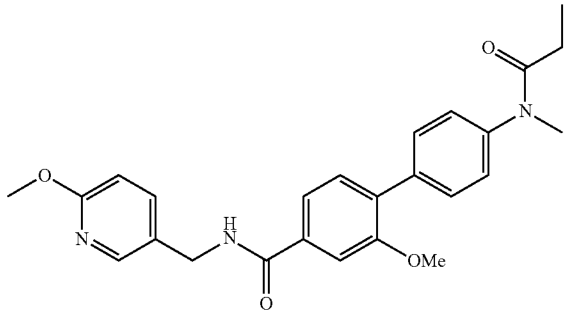
I-T1002
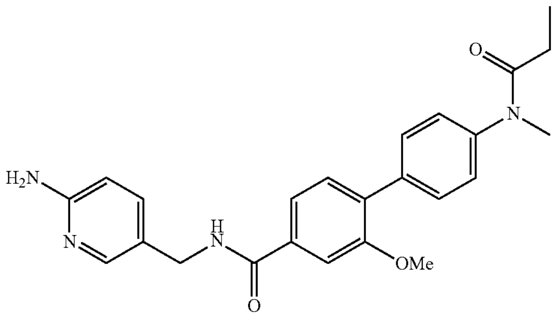
I-T1003
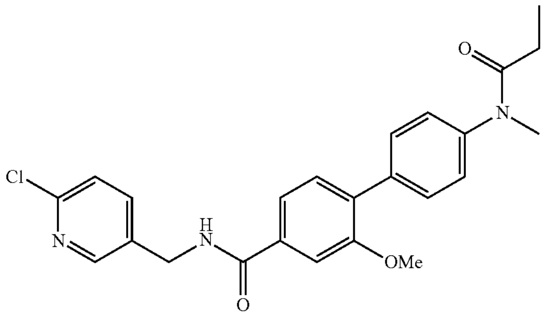
-continued
I-T1004
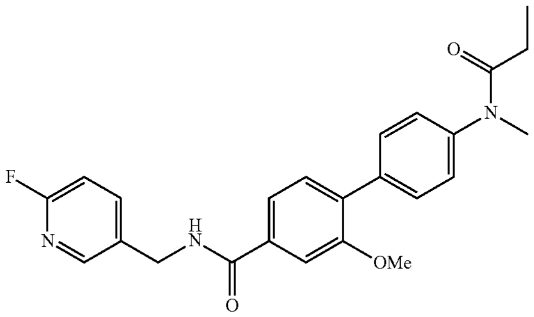
I-T1005
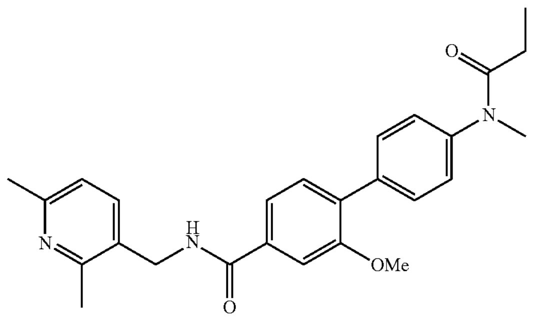
I-T1006
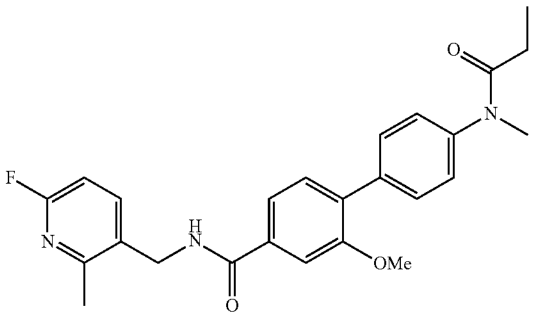
I-T1007
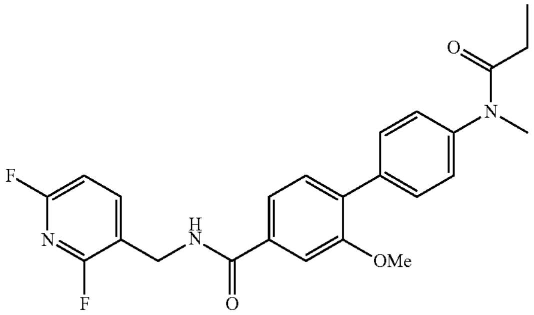

-continued
I-T1008
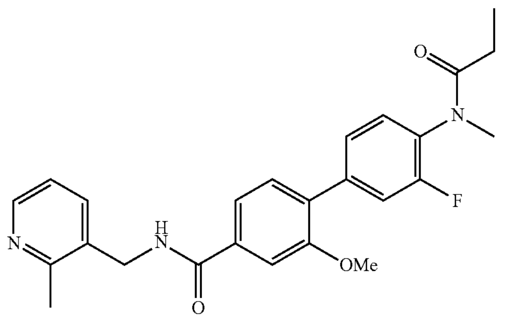
I-T1009
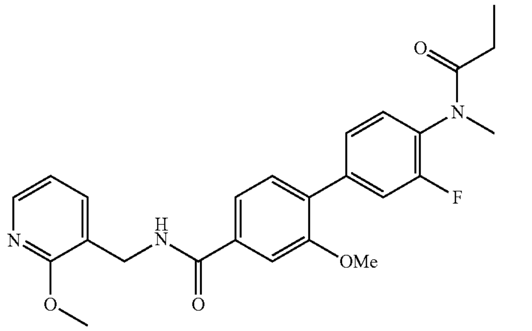
I-T1010
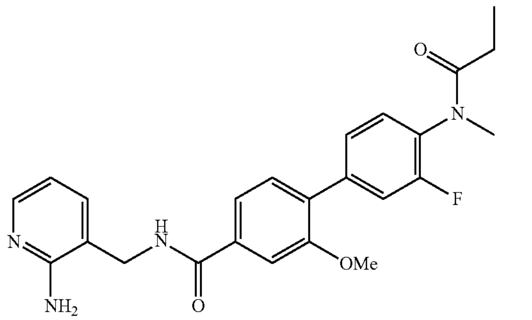
I-T1011
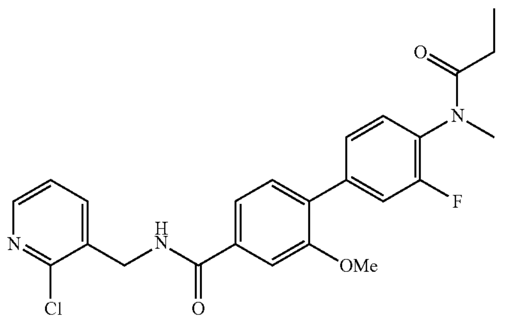
-continued
I-T1012
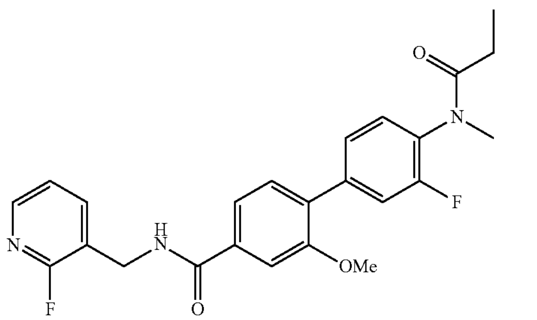
I-T1013
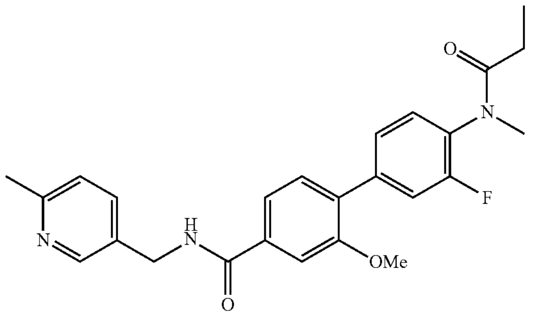
I-T1014
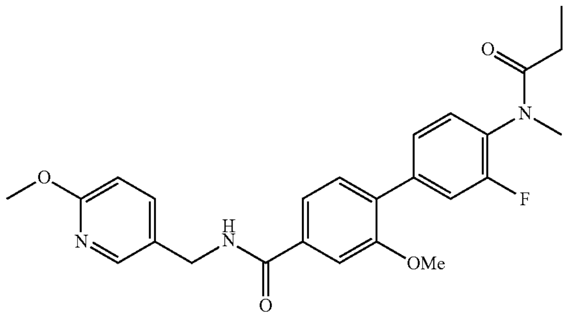
I-T1015
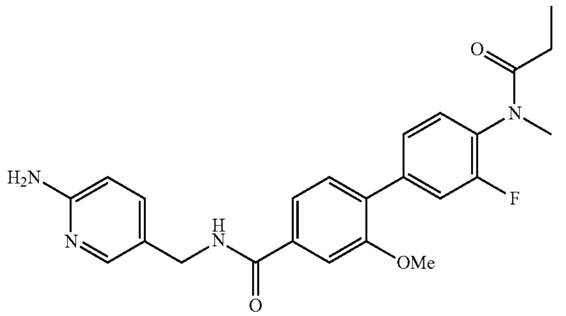

-continued
I-T1016
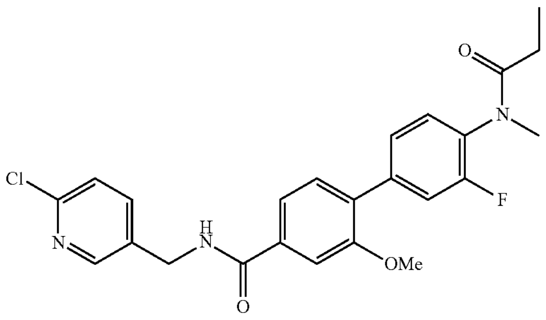
I-T1017
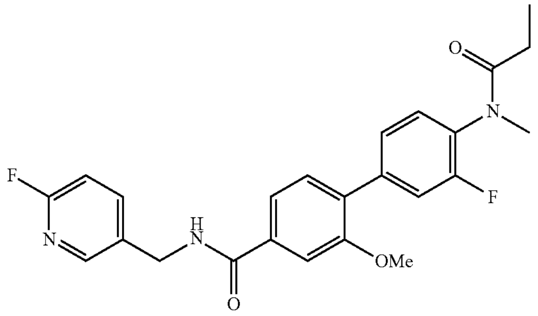
I-T1018
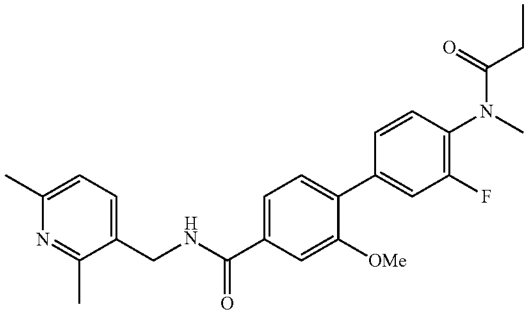
I-T1019
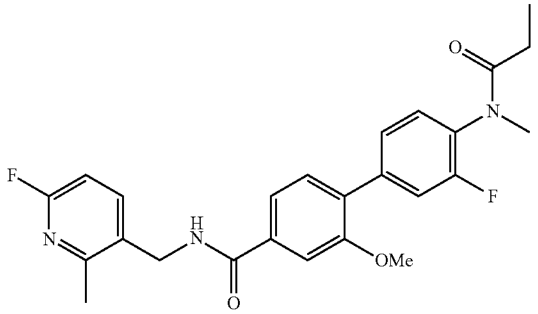
-continued
I-T1020
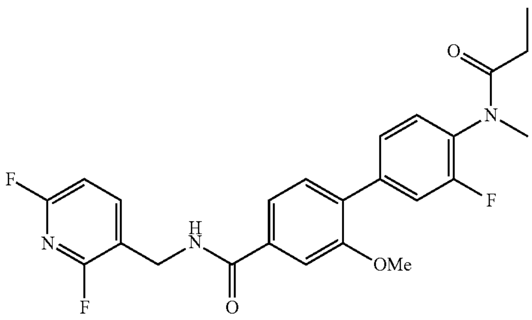
I-T1021
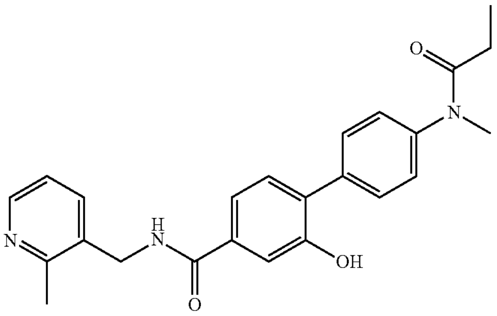
I-T1022
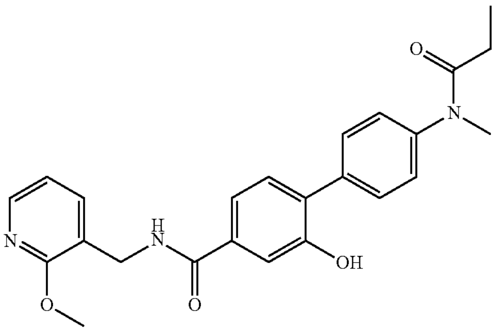
I-T1023
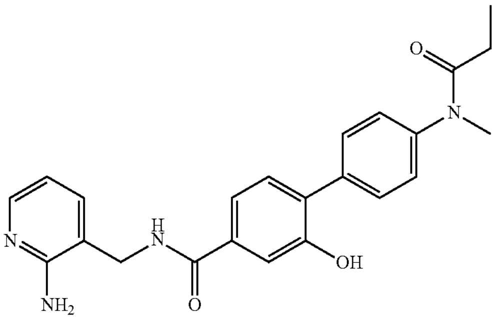

-continued
I-T1024
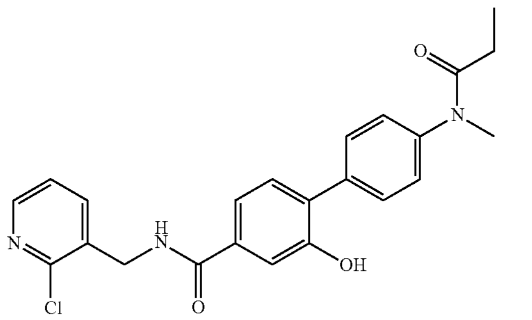
I-T1025
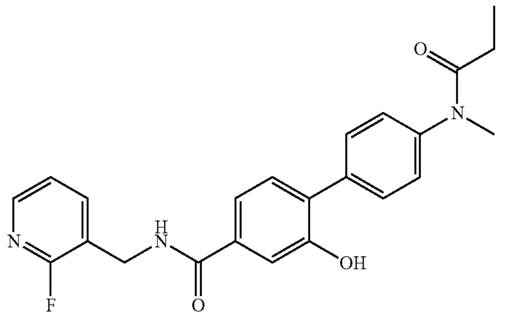
I-T1026
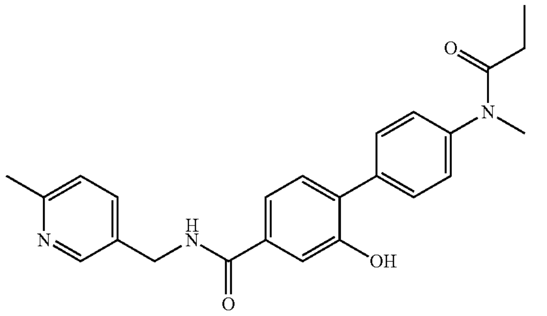
I-T1027
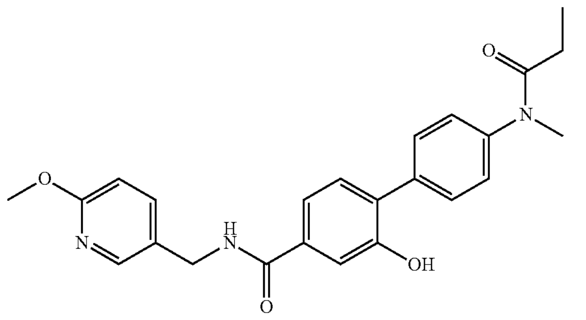
-continued
I-T1028
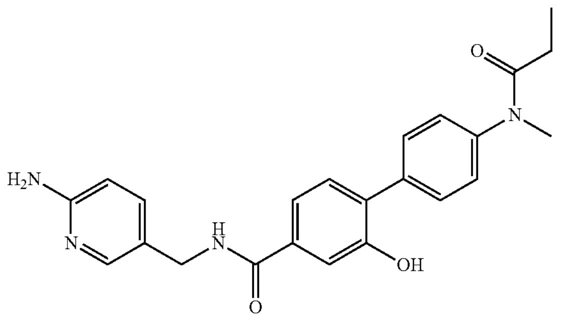
I-T1029
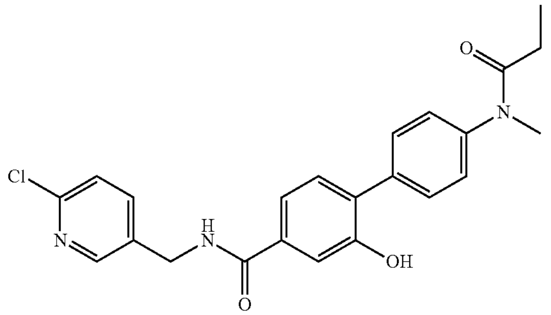
I-T1030
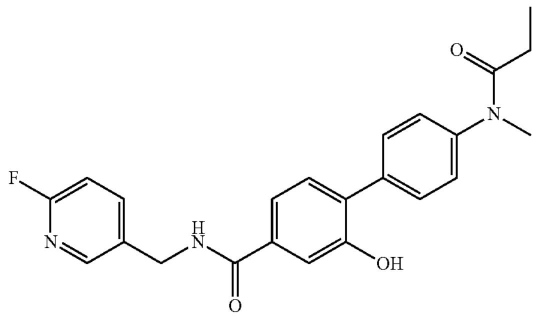
I-T1031
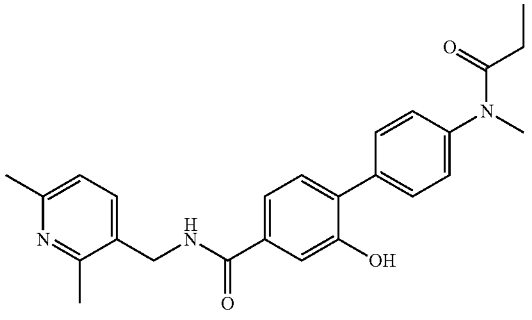

-continued
I-T1032
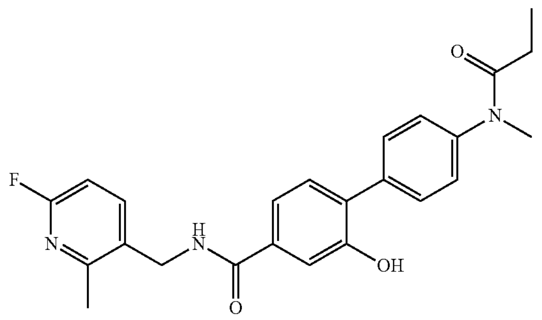
I-T1033
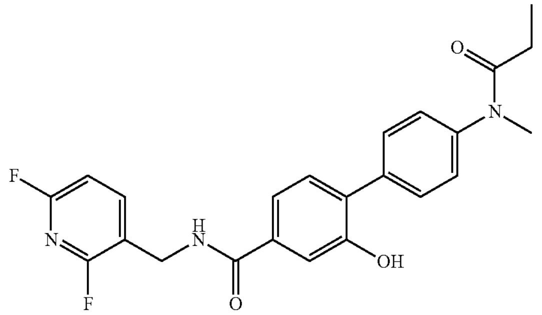
I-T1034
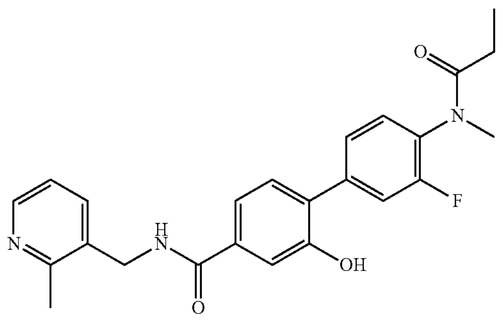
I-T1035
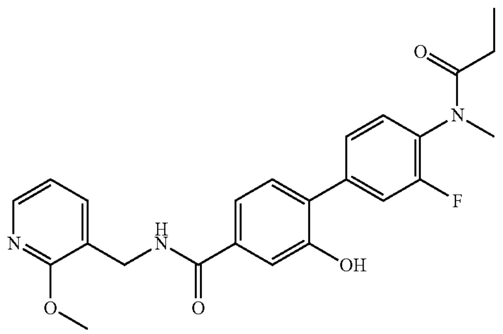
-continued
I-T1036
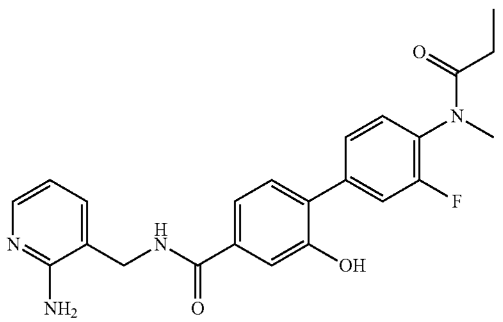
I-T1037
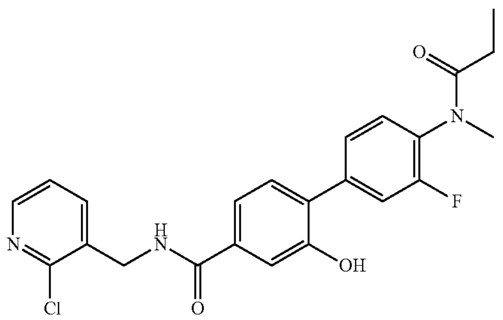
I-T1038
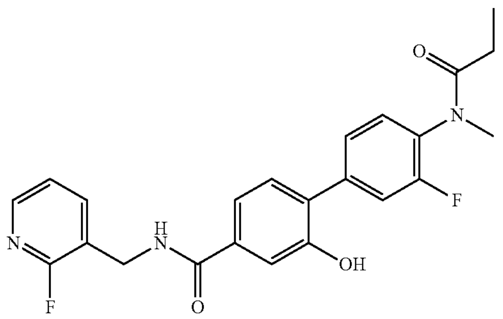
I-T1039
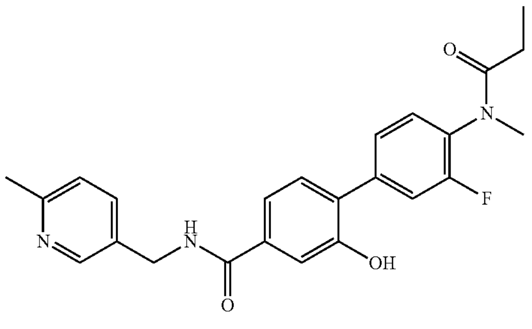

-continued
I-T1040
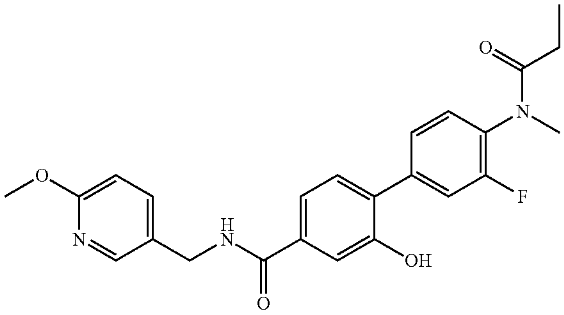
I-T1041
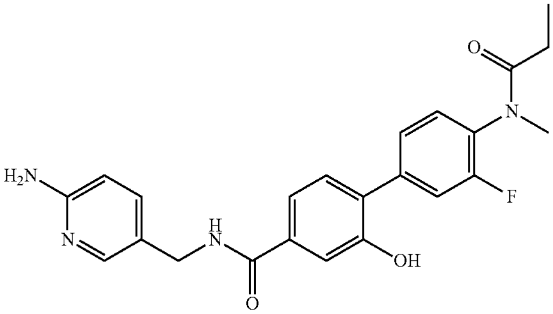
I-T1042
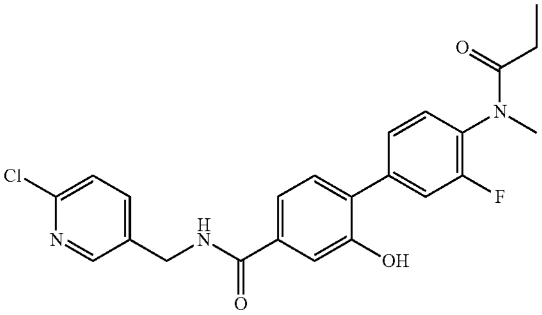
I-T1043
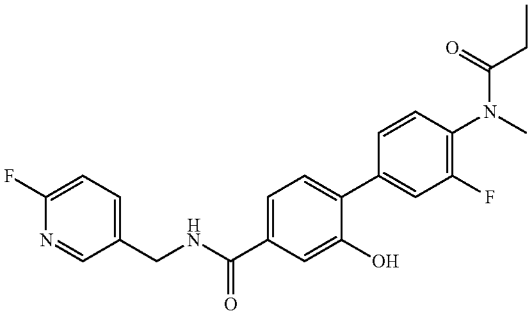
-continued
I-T1044
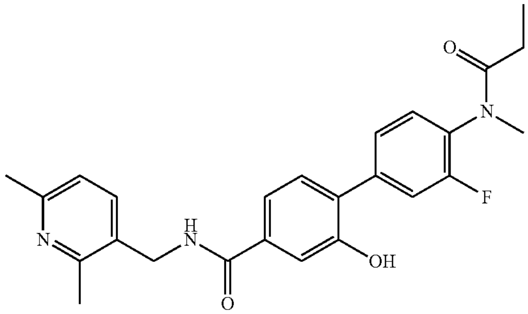
I-T1045
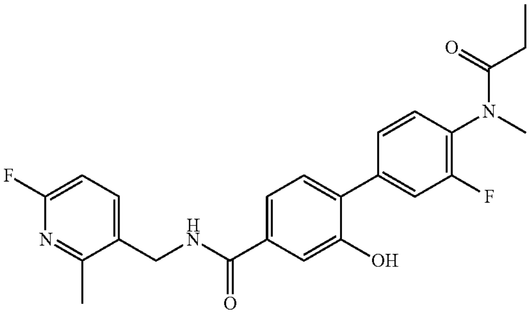
I-T1046
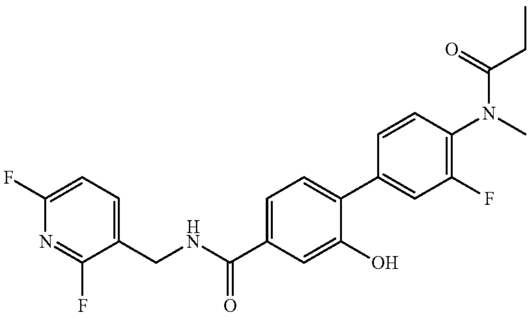
I-T1047
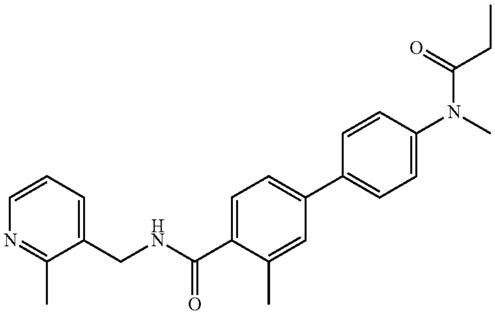

-continued
I-T1048
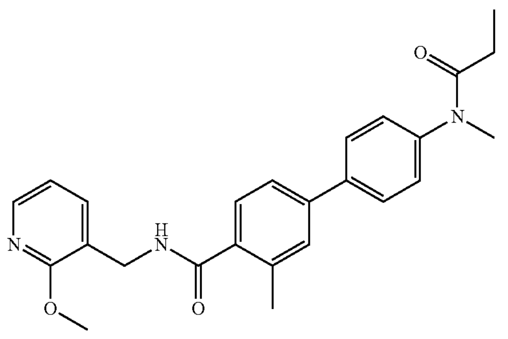
I-T1049
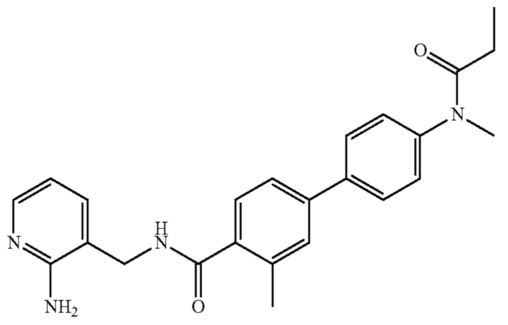
I-T1050
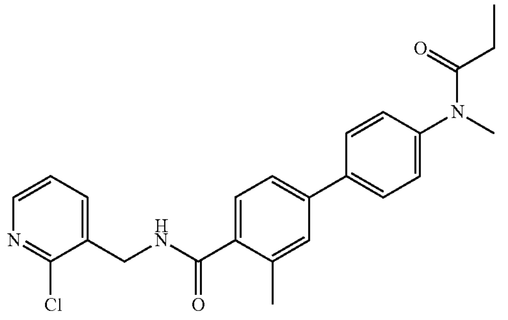
I-T1051
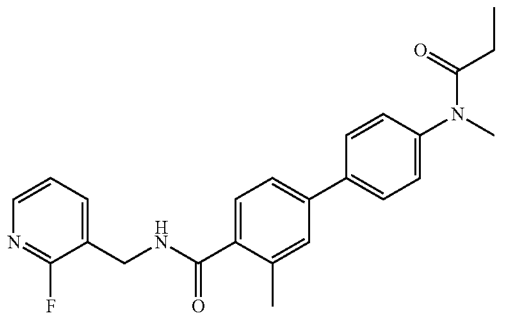
-continued
I-T1052
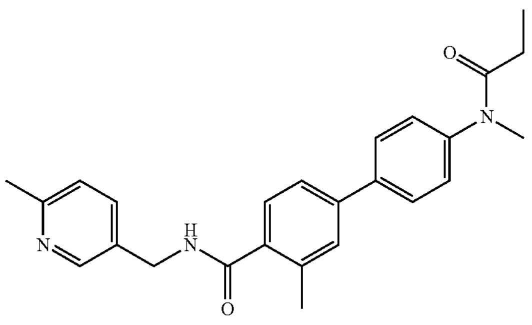
I-T1053
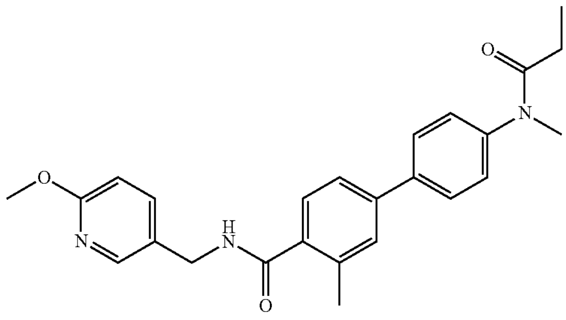
I-T1054
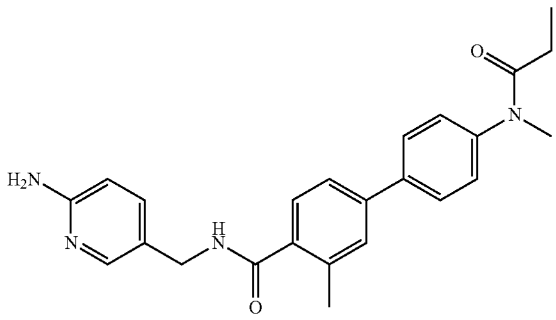
I-T1055
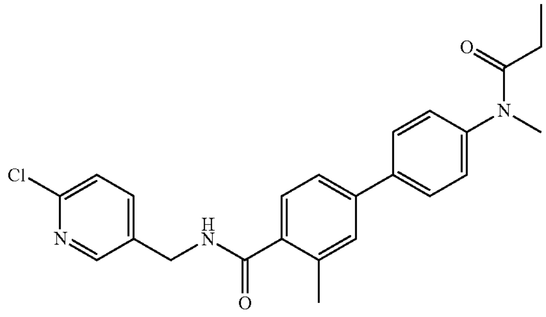

-continued
I-T1056
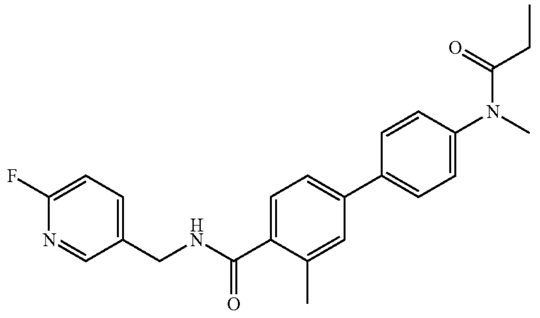
I-T1057
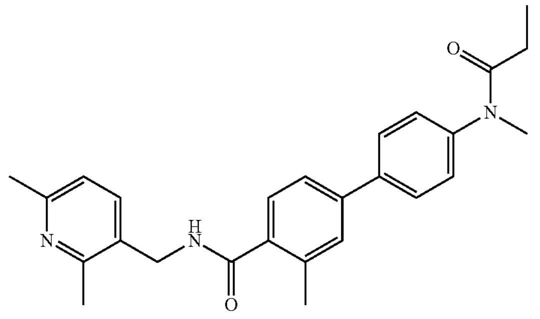
I-T 1058
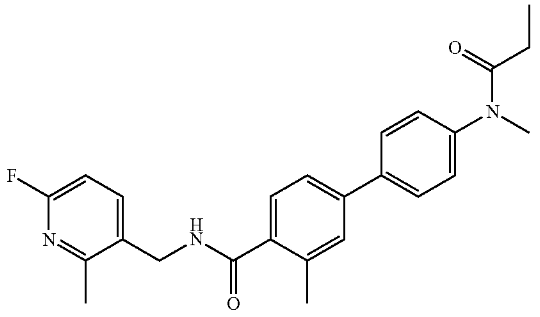
I-T 1059
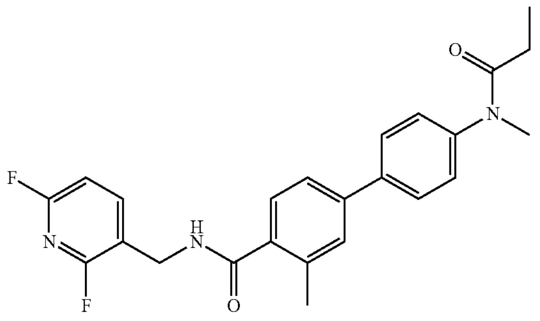
-continued
I-T 1060
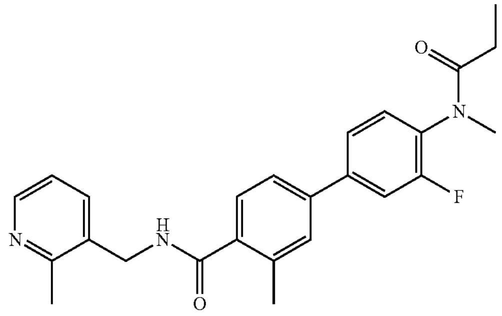
I-T 1061
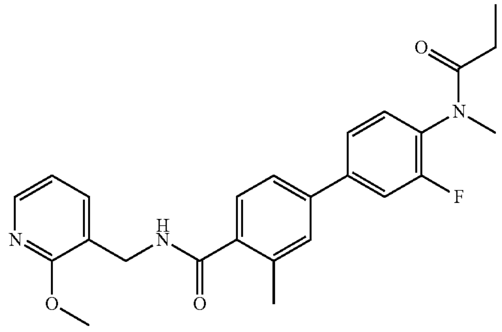
I-T 1062
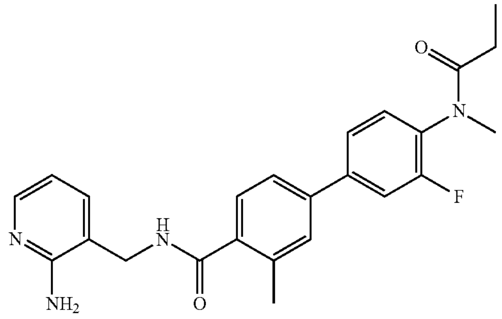
I-T 1063
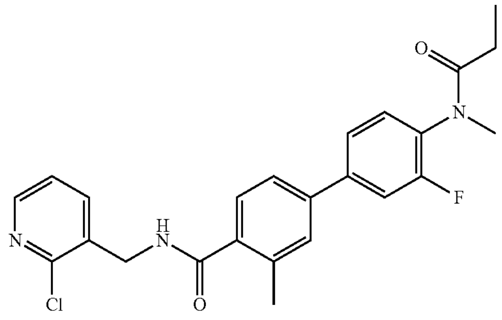

-continued
I-T 1064
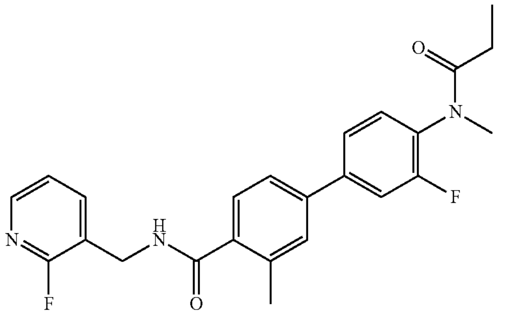
I-T 1065
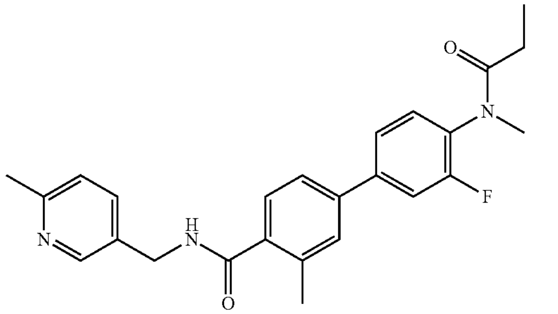
I-T 1066
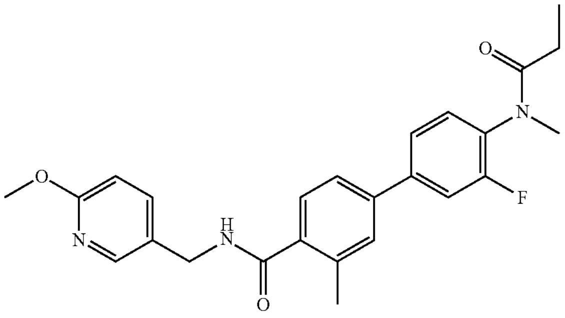
I-T 1067
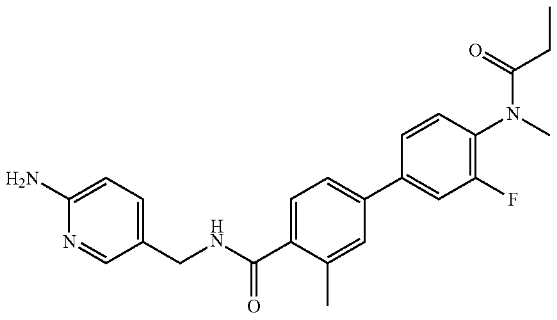
-continued
I-T 1068
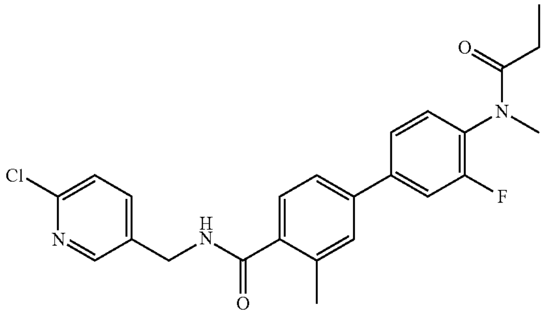
I-T 1069
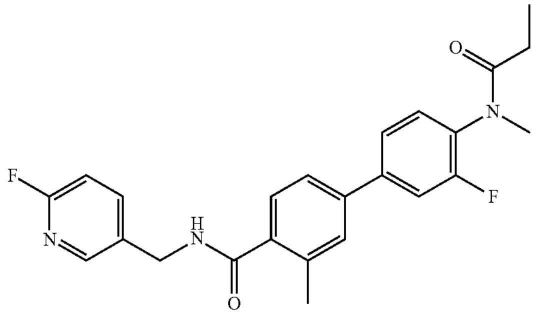
I-T 1070
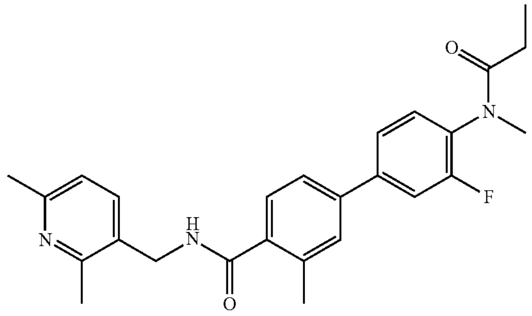
I-T 1071
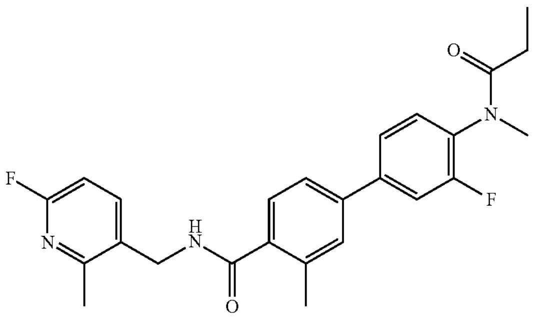

I-T 1072
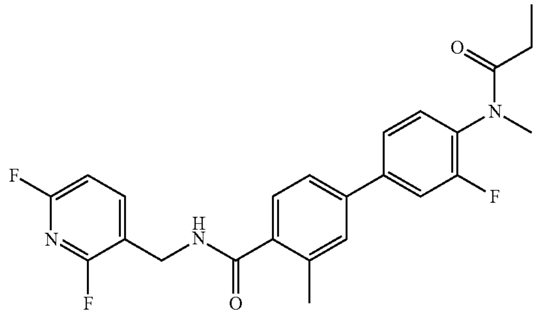
I-T 1073
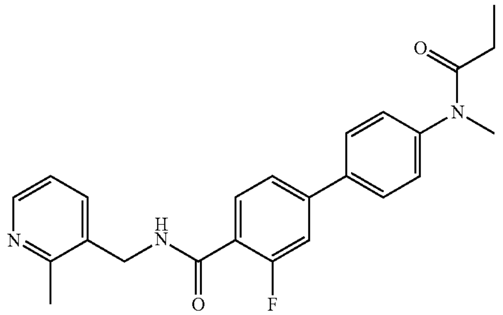
I-T 1074
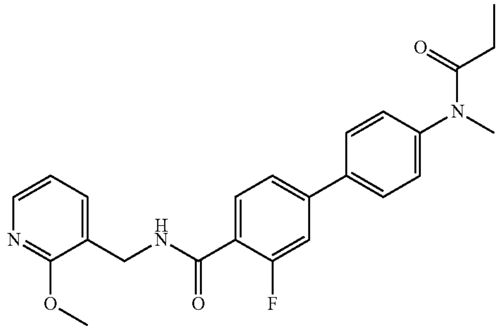
I-T 1075
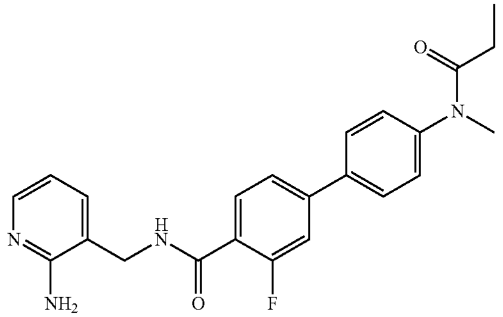
I-T 1076
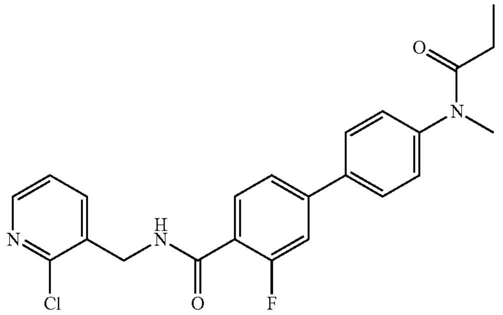
I-T 1077
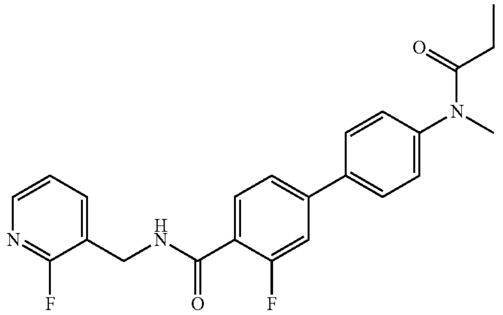
I-T 1078
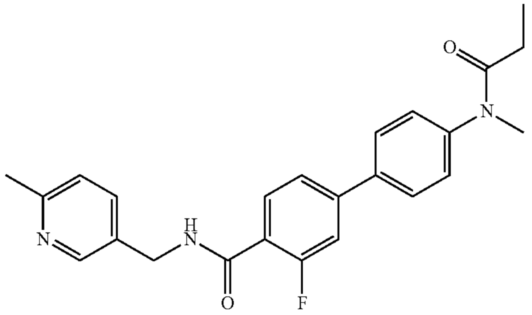
I-T 1079
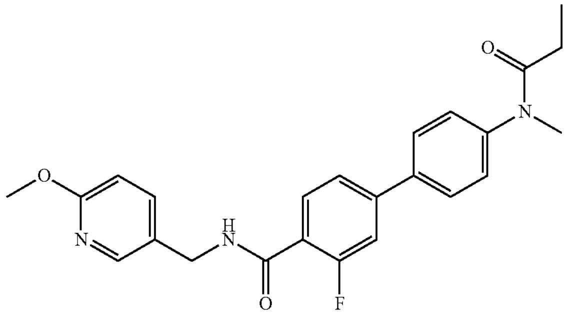

I-T 1080
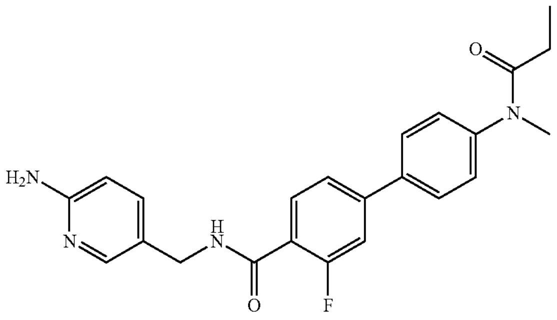
I-T 1081
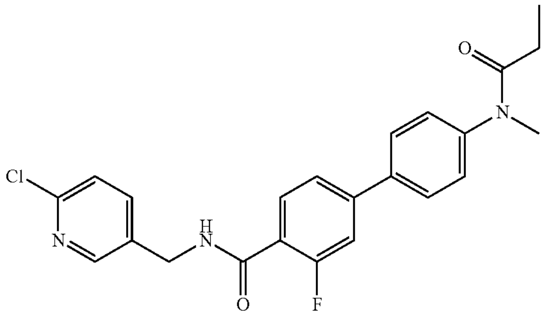
I-T 1082
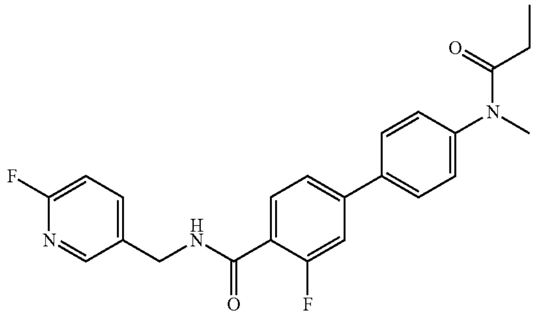
I-T 1083
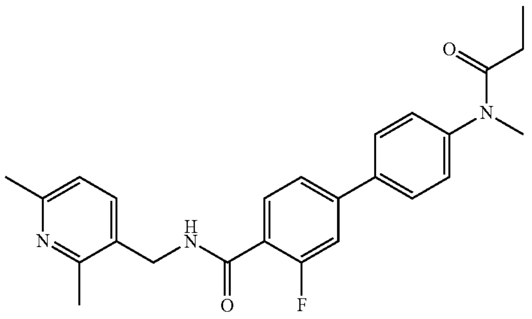
I-T 1084
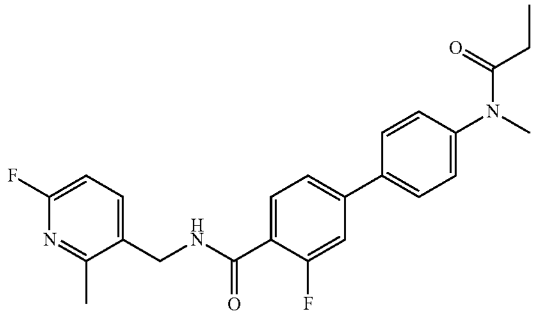
I-T 1085
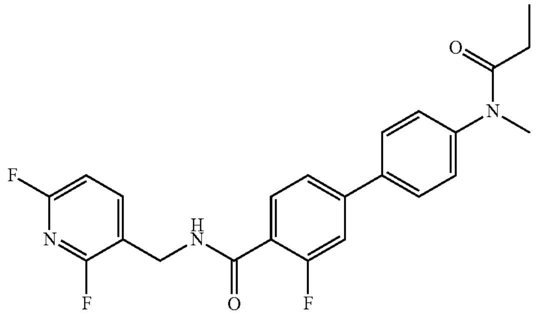
I-T 1086
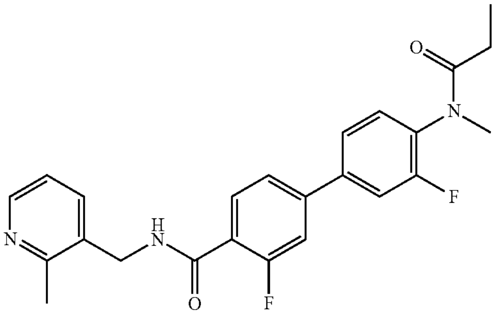
I-T 1087
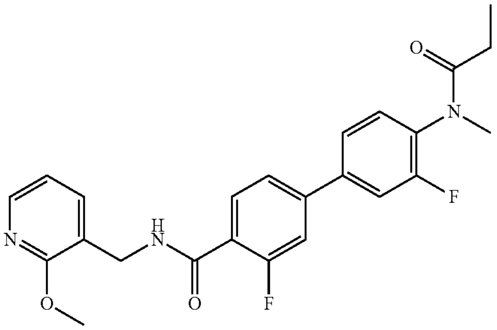

-continued
I-T 1088
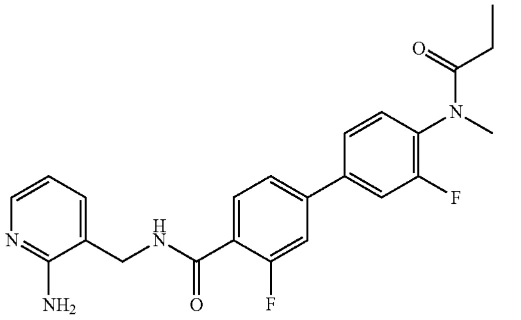
I-T 1089
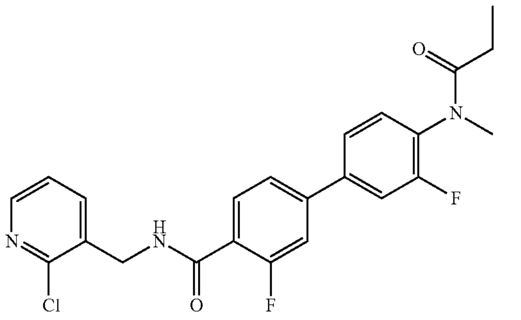
I-T 1090
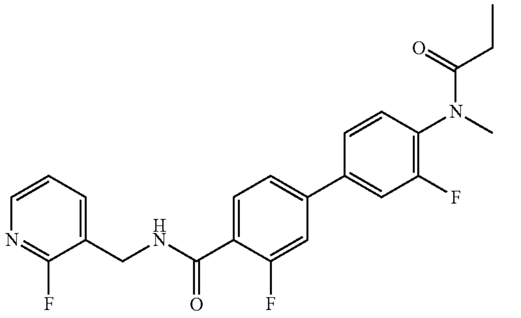
I-T 1091
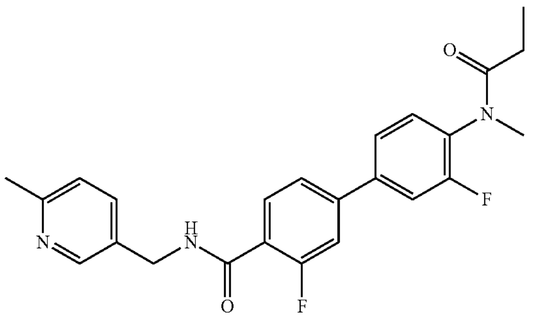
-continued
I-T 1092
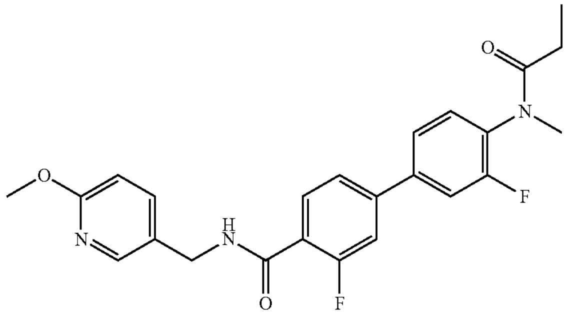
I-T 1093
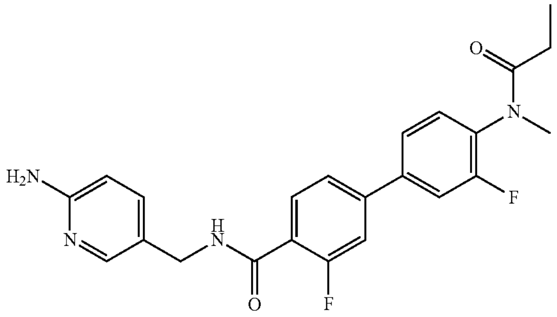
I-T 1094
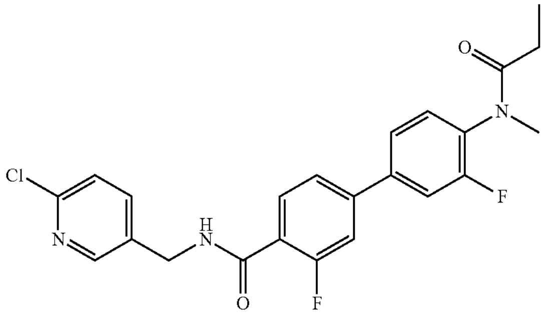
I-T 1095
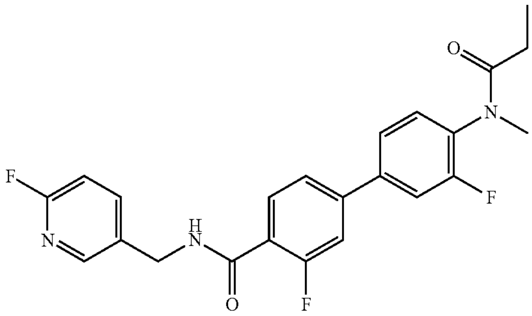

-continued
I-T 1096
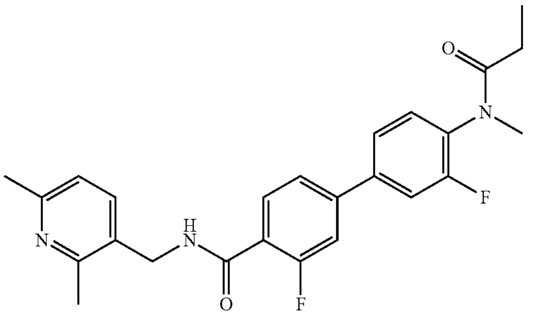
I-T 1097
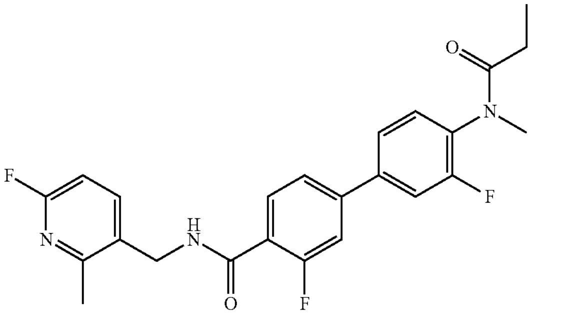
I-T 1098
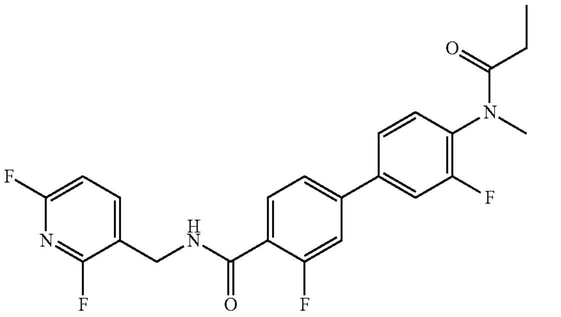
I-T 1099
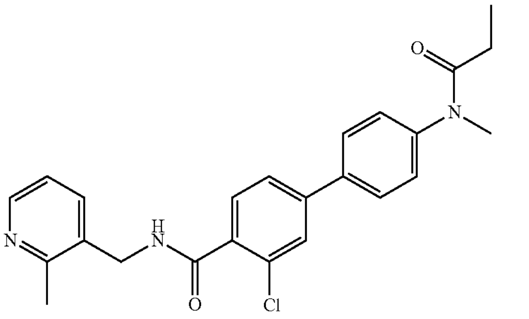
-continued
I-T 1100
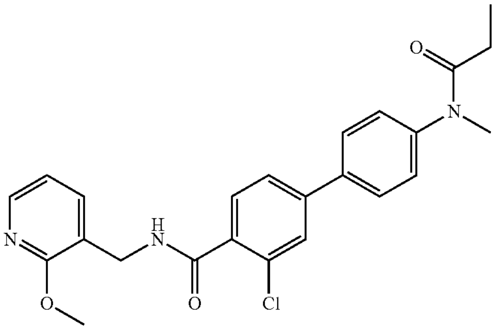
I-T 1101
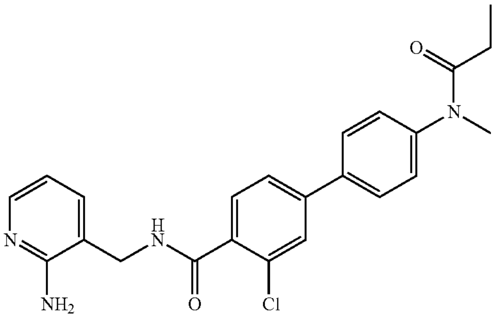
I-T 1102
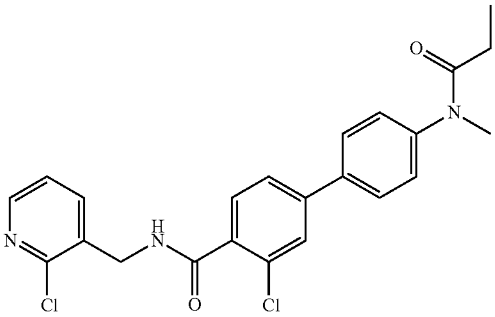
I-T 1103
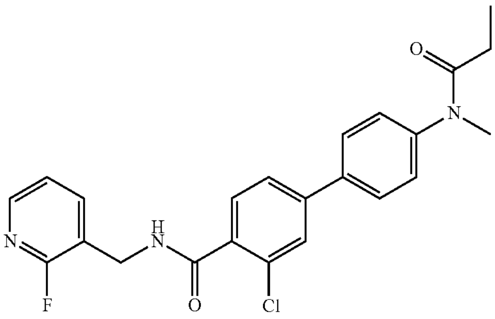

-continued
I-T 1104
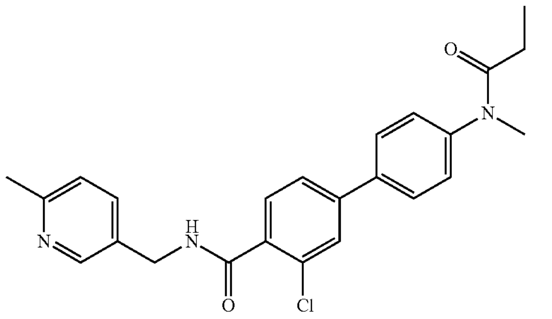
I-T 1105
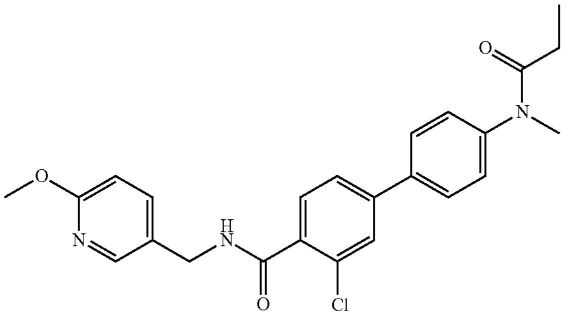
I-T 1106
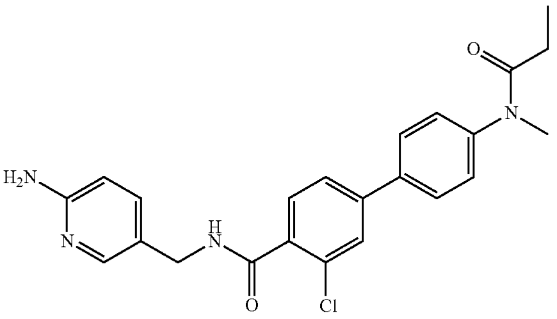
I-T 1107
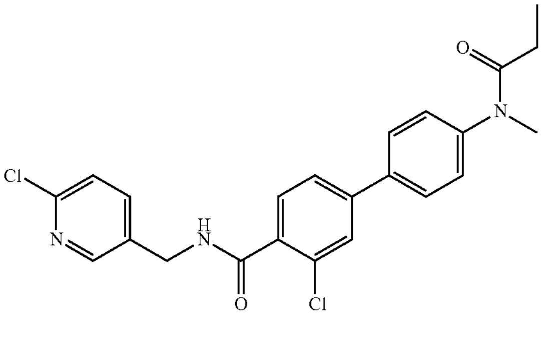
-continued
I-T 1108
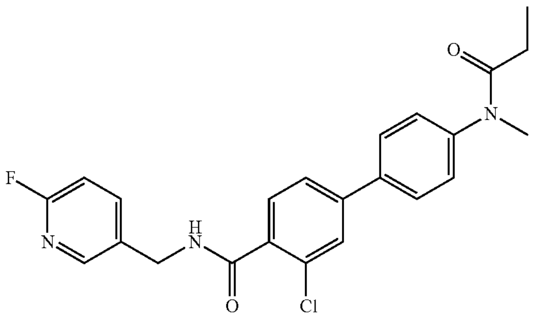
I-T 1109
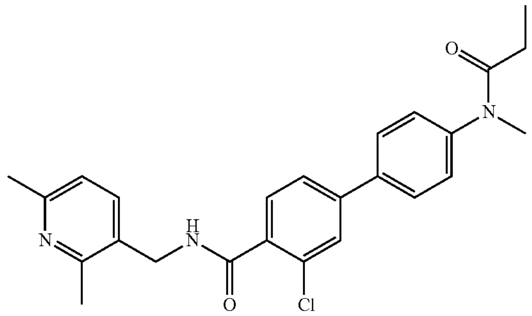
I-T 1110
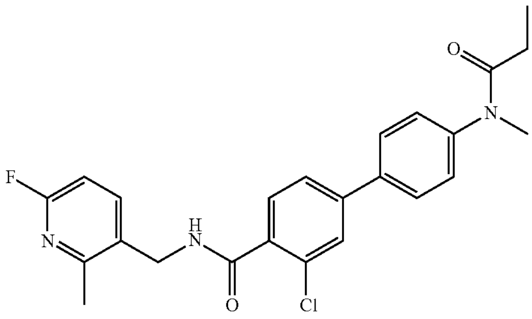
I-T 1111
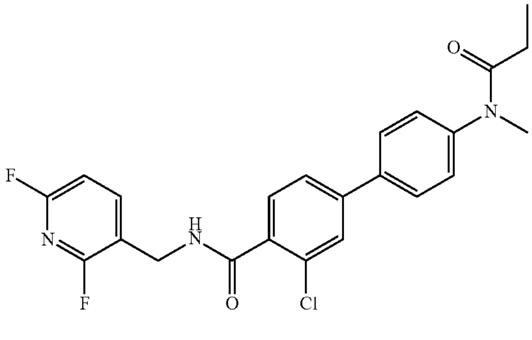

-continued
I-T 1112
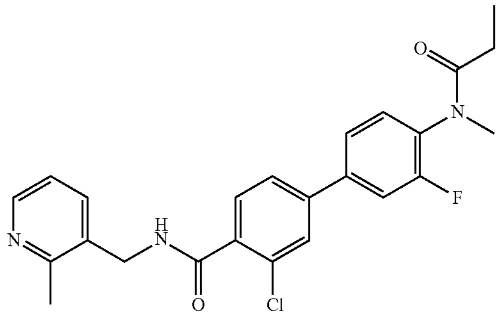
I-T 1113
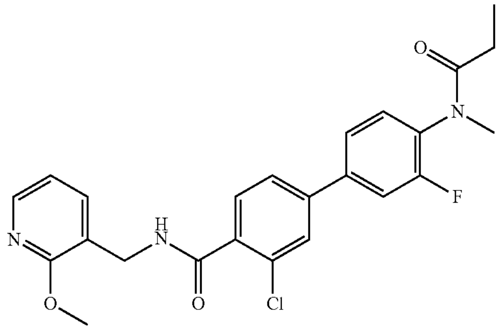
I-T 1114
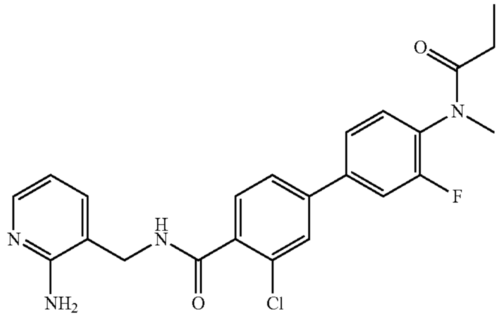
I-T 1115
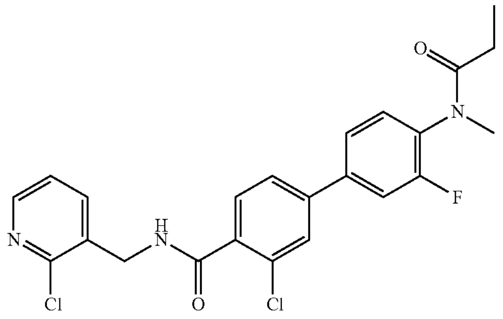
-continued
I-T 1116
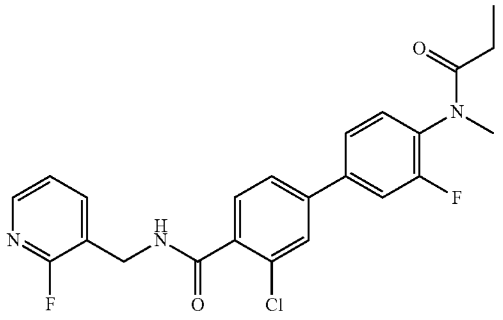
I-T 1117
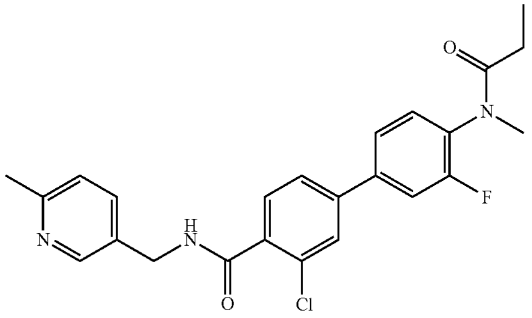
I-T 1118
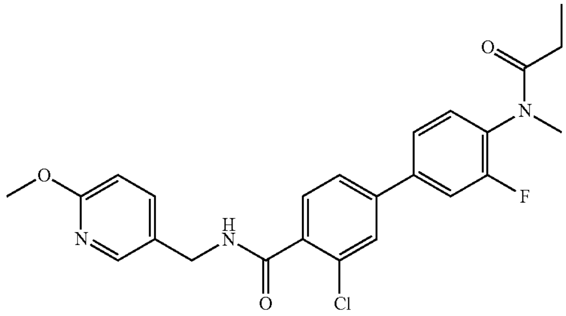
I-T 1119
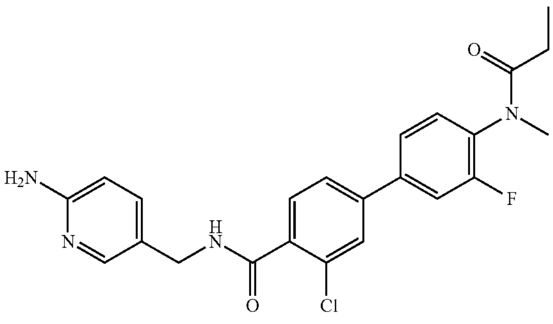

-continued
I-T 1120
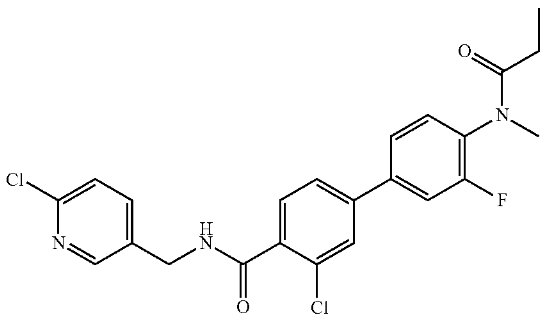
I-T 1121
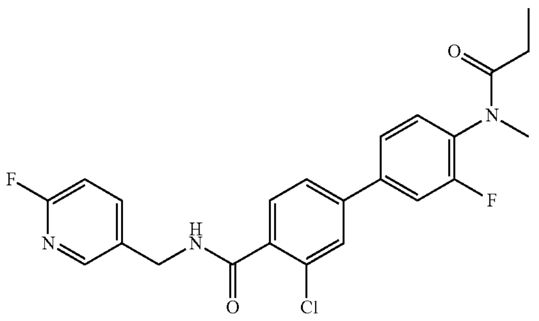
I-T 1122
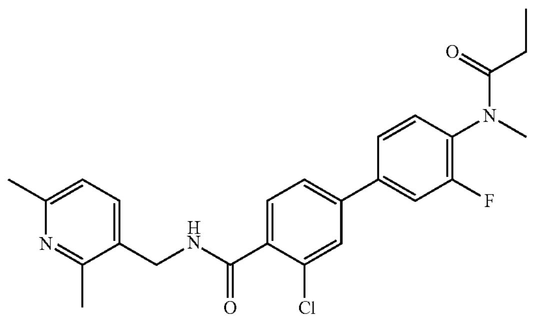
I-T 1123
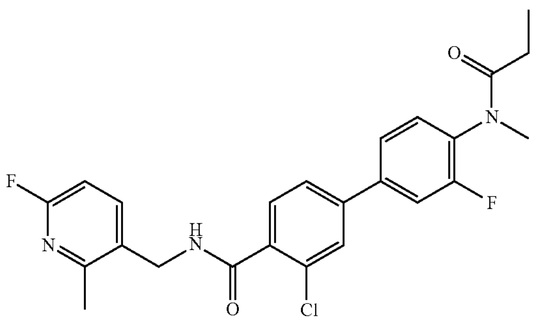
-continued
I-T 1124
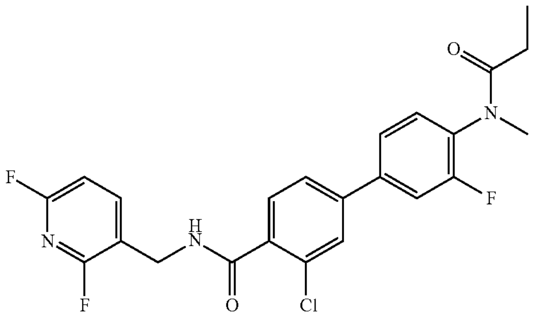
I-T 1125
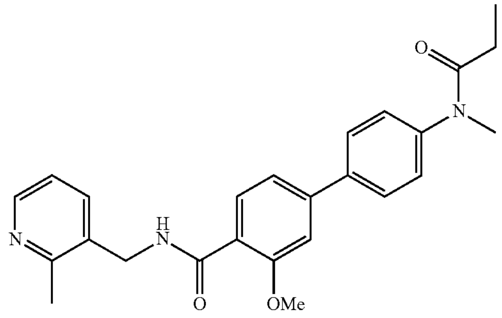
I-T 1126
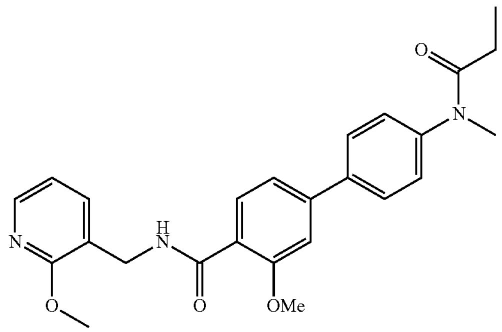
I-T 1127
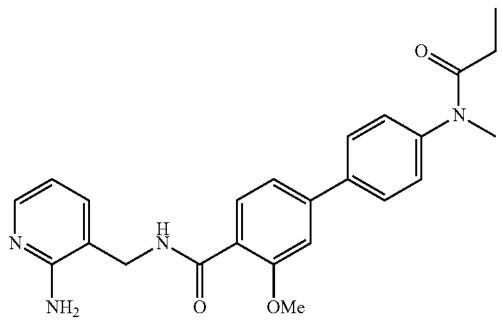

-continued
I-T 1128
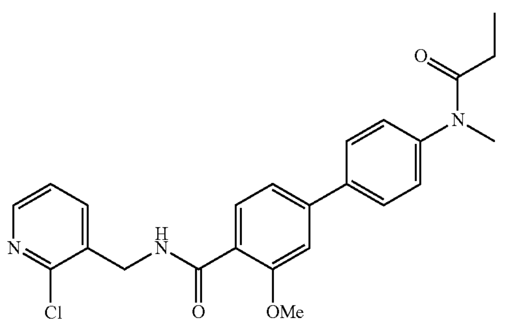
I-T 1129
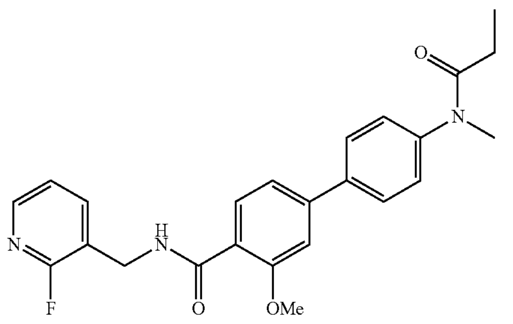
I-T 1130
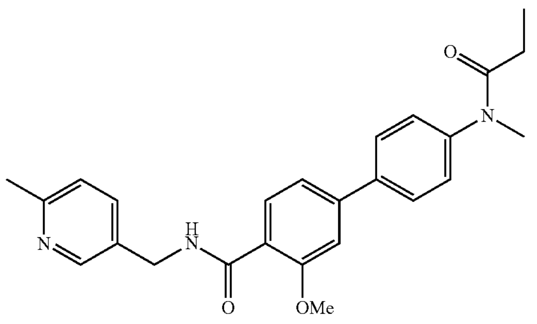
I-T 1131
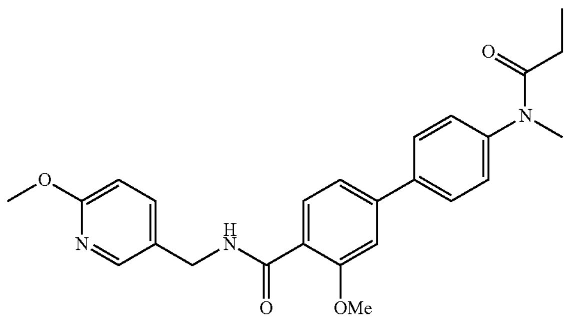
-continued
I-T 1132
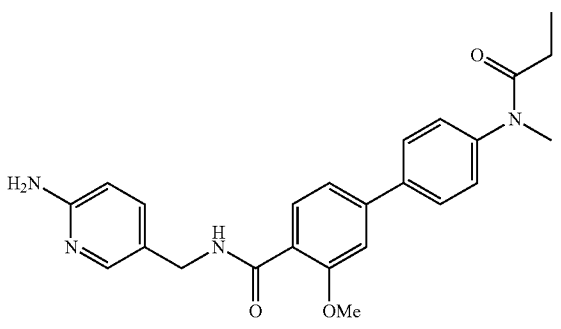
I-T 1133
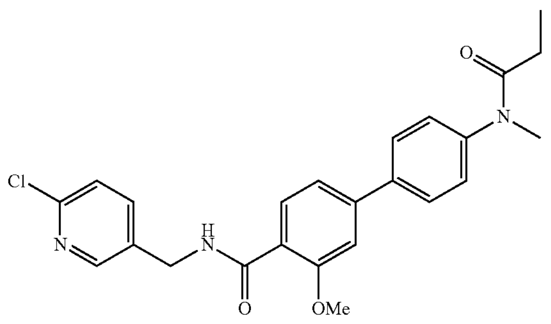
I-T 1134
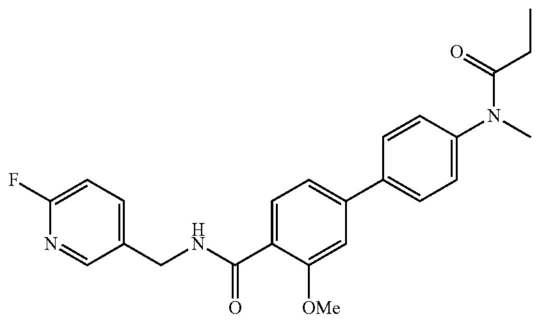
I-T 1135
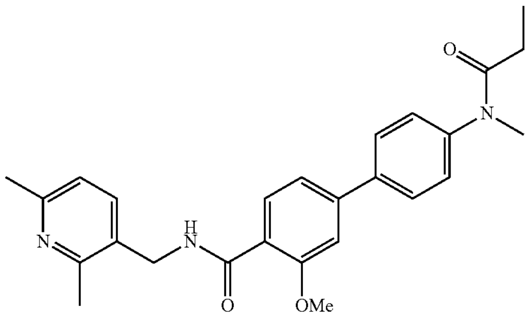

-continued
I-T 1136
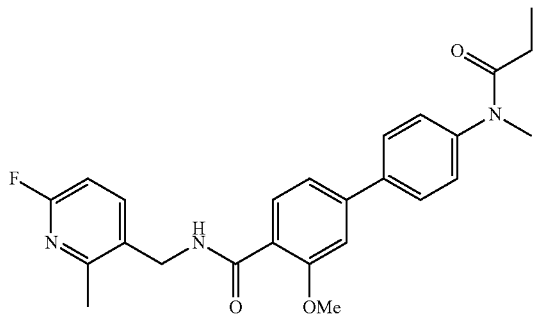
I-T 1137
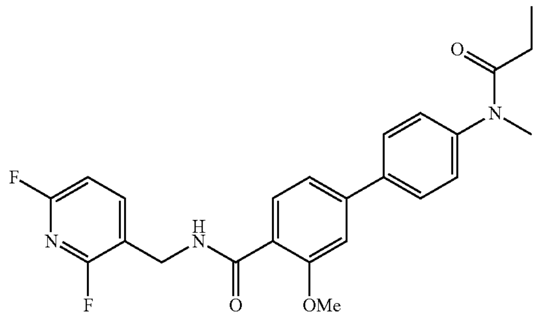
I-T 1138
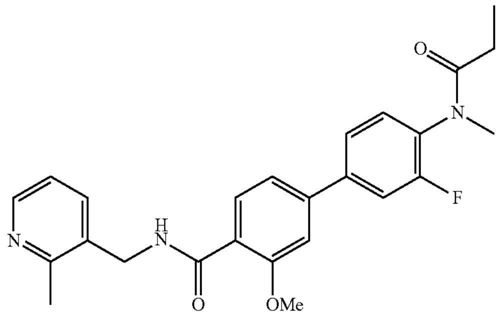
I-T 1139
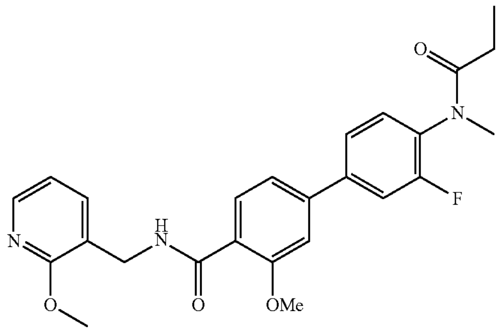
-continued
I-T 1140
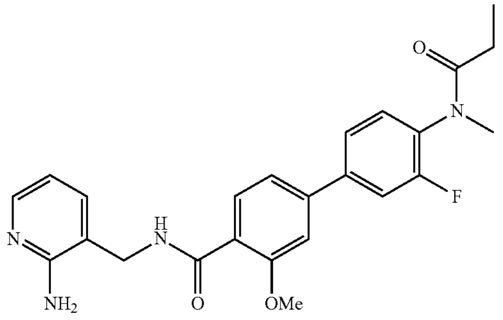
I-T 1141
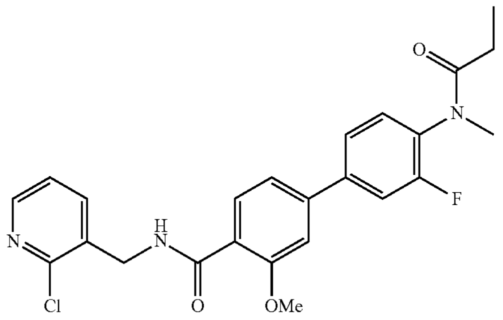
I-T 1142
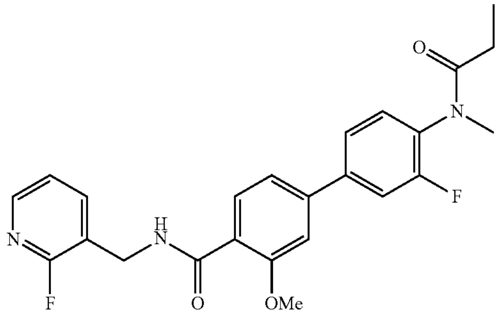
I-T 1143
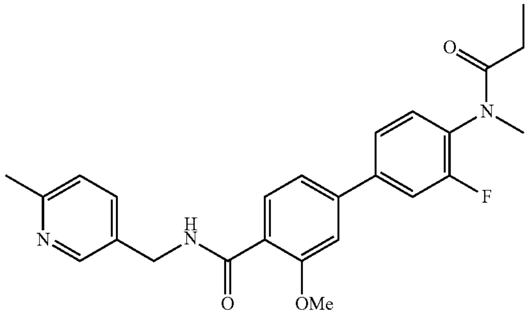

-continued
I-T 1144
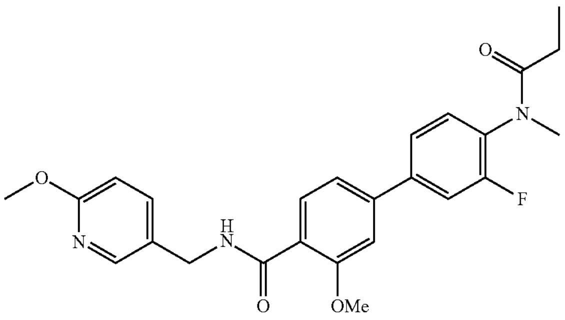
I-T 1145
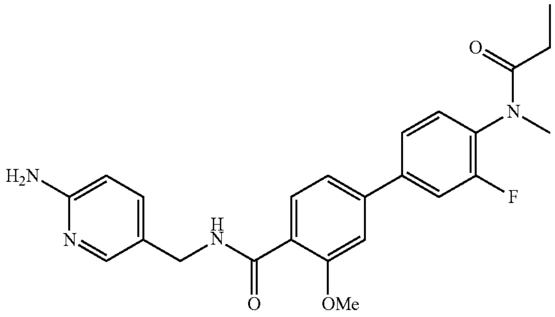
I-T 1146
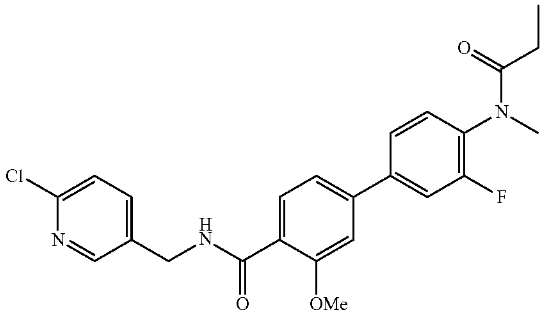
I-T 1147
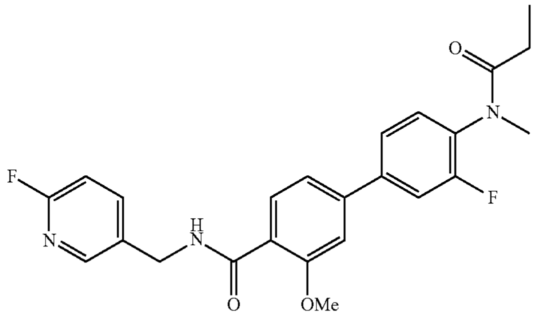
-continued
I-T 1148
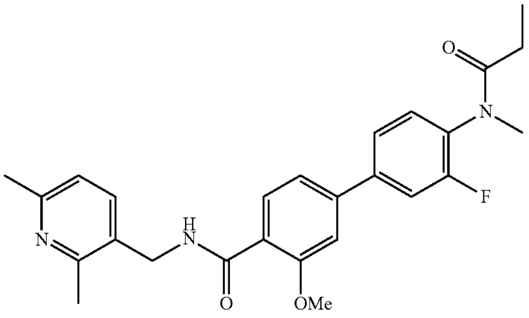
I-T 1149
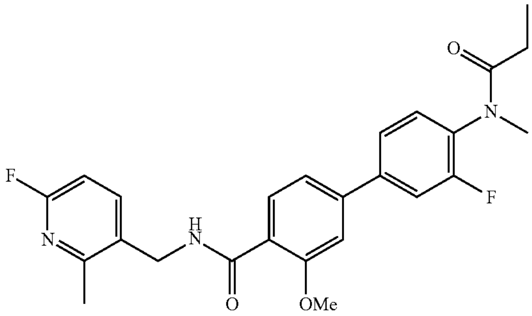
I-T 1150
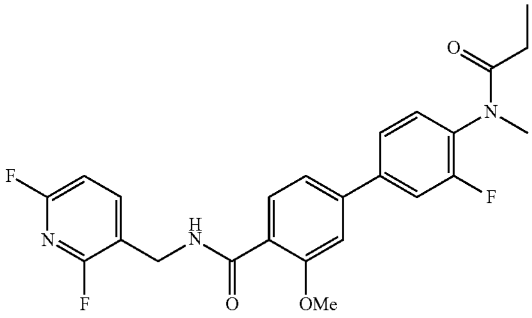
I-T 1151
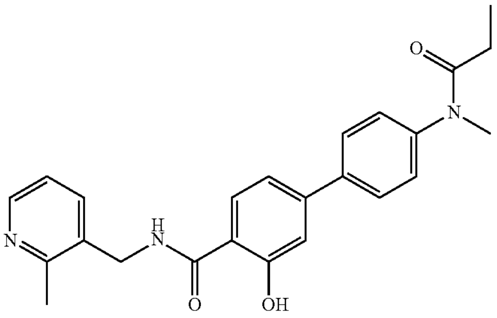

-continued
I-T 1152
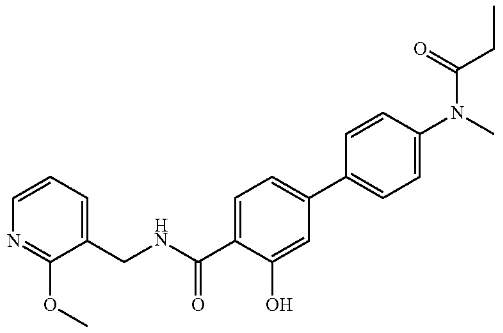
I-T 1153
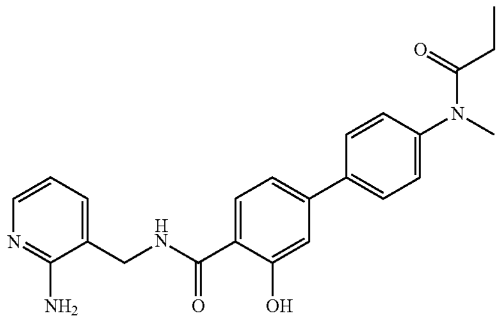
I-T 1154
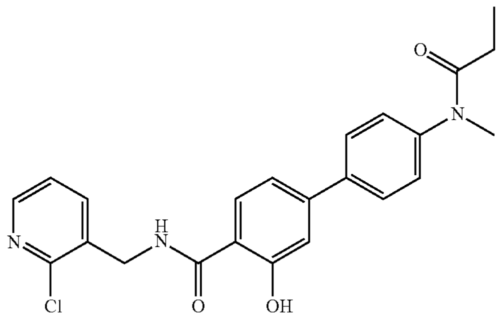
I-T 1155
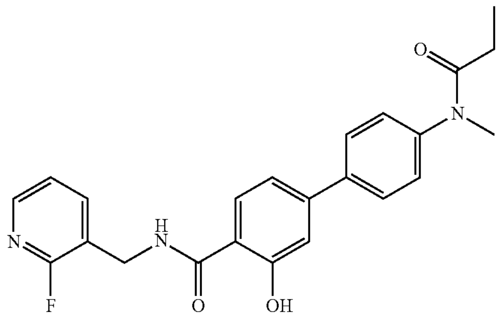
-continued
I-T 1156
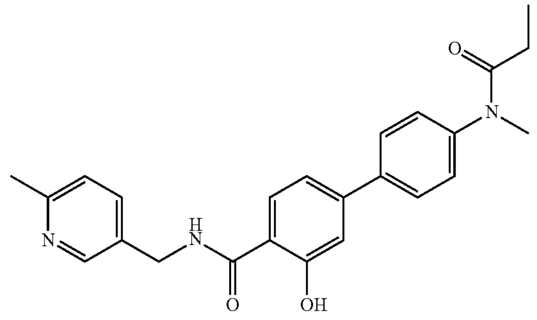
I-T 1157
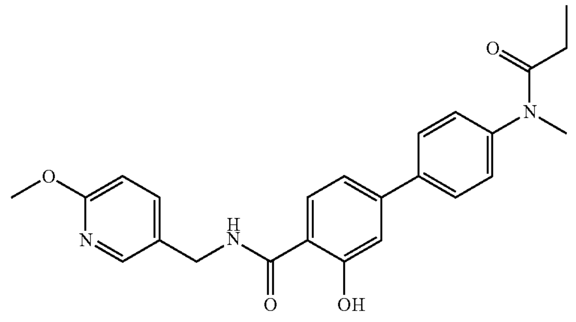
I-T 1158
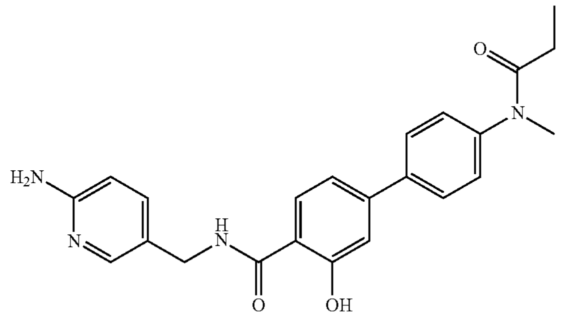
I-T 1159
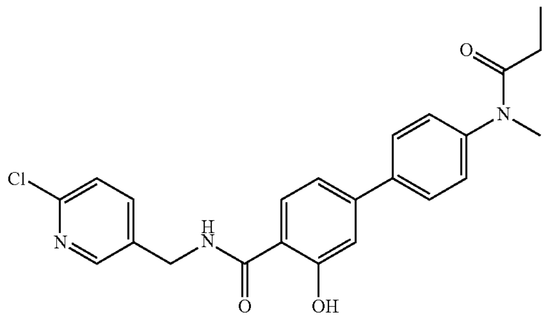

-continued
I-T 1160
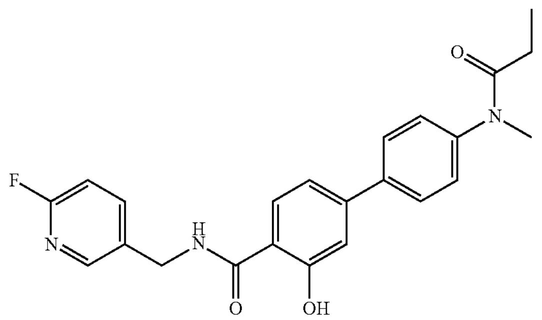
I-T 1161
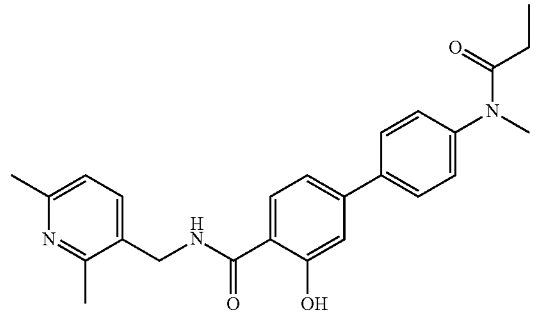
I-T 1162
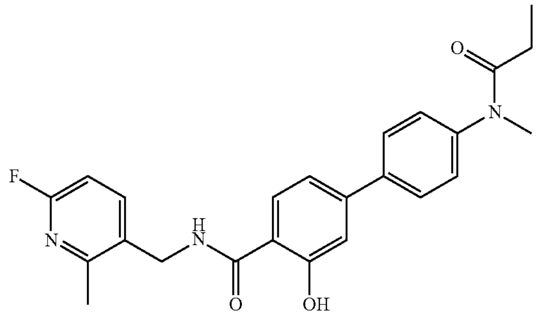
I-T 1163
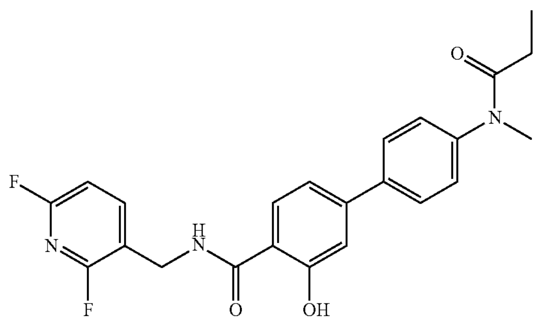
-continued
I-T 1164
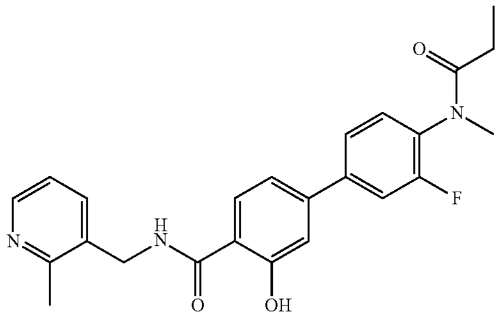
I-T 1165
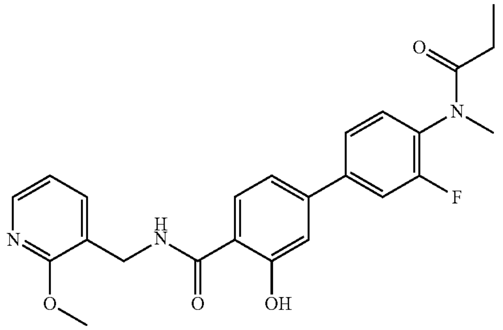
I-T 1166
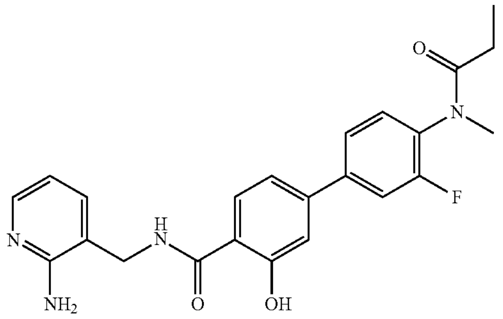
I-T 1167
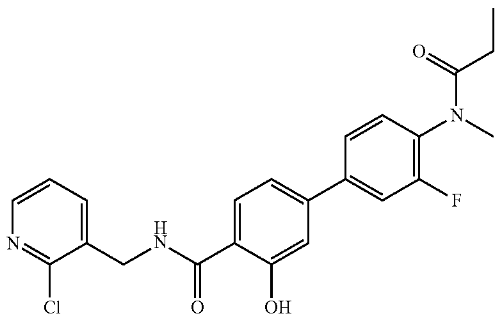

-continued
I-T 1168
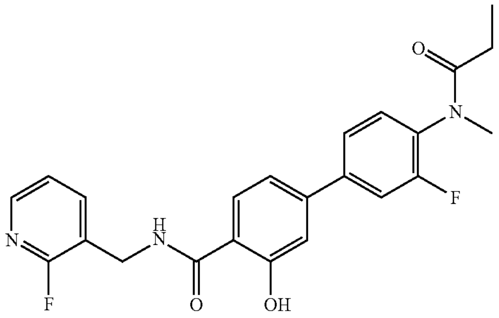
I-T 1169
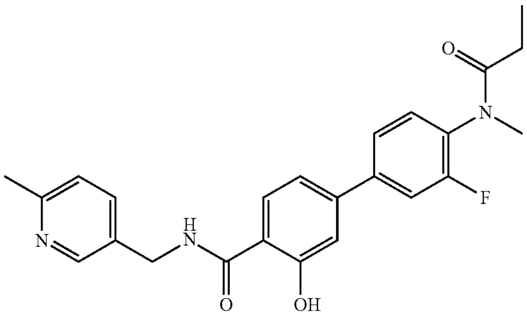
I-T 1170
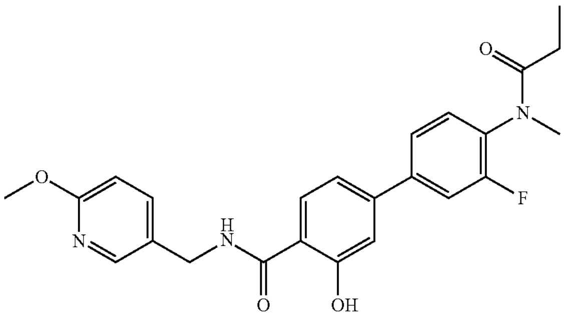
I-T 1171
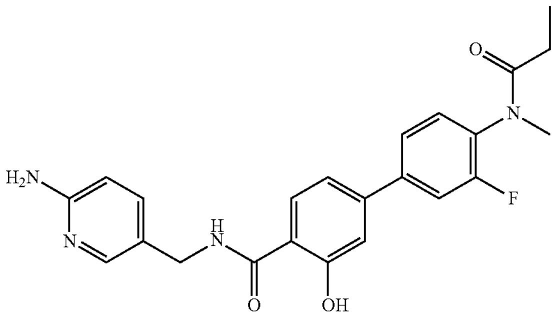
-continued
I-T 1172
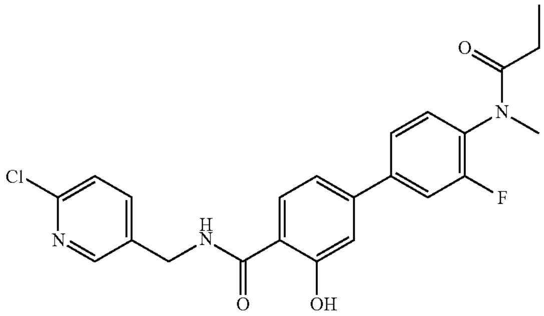
I-T 1173
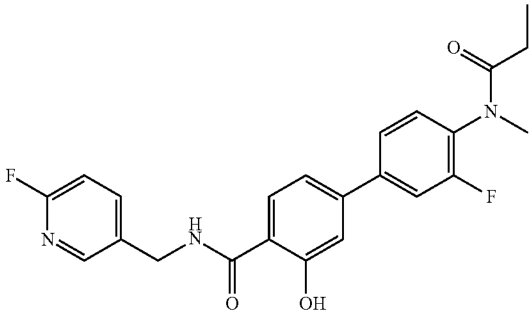
I-T 1174
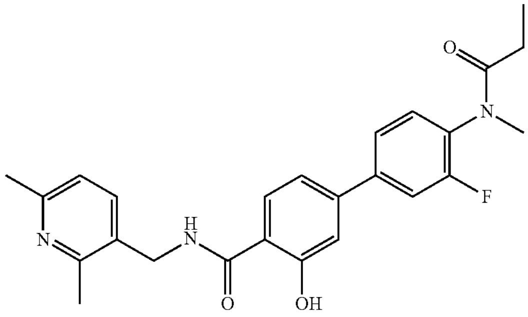
I-T 1175
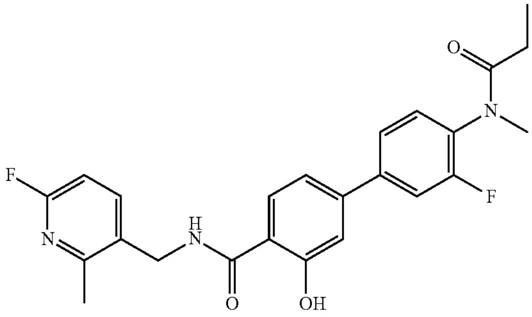

-continued
I-T 1176
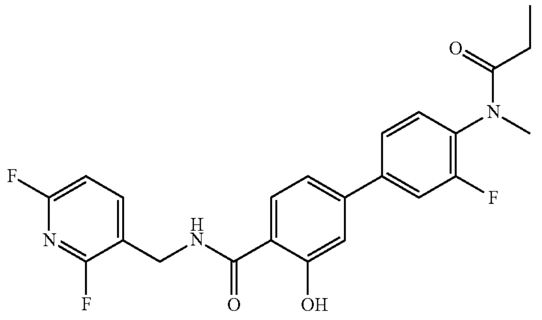
I-T 1177
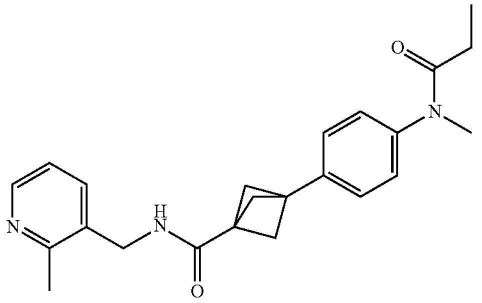
I-T 1178
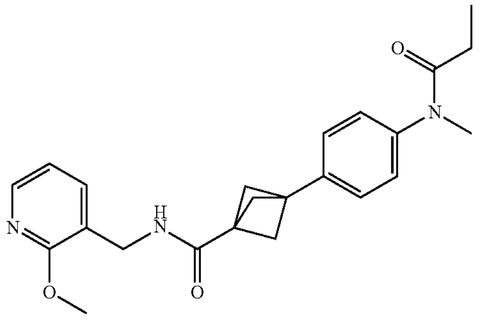
I-T 1179
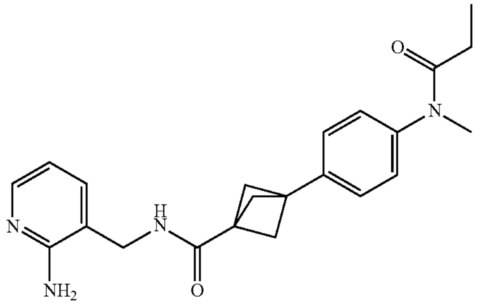
I-T 1180
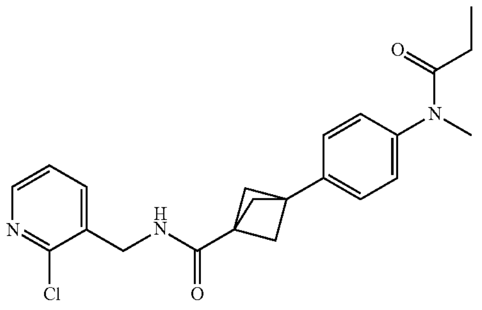
-continued
I-T 1181
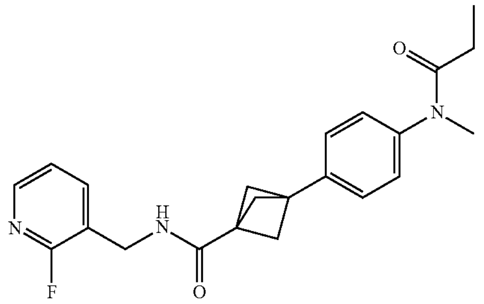
I-T 1182
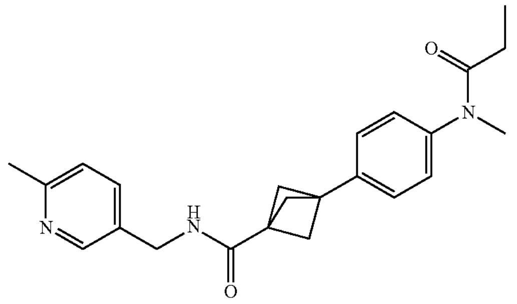
I-T 1183
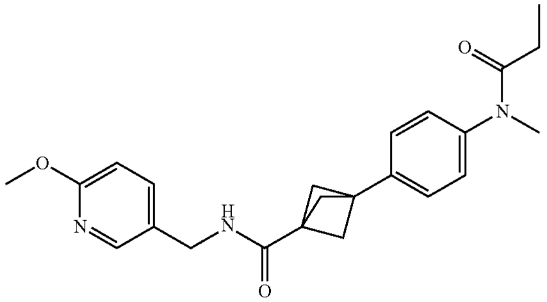
I-T 1184
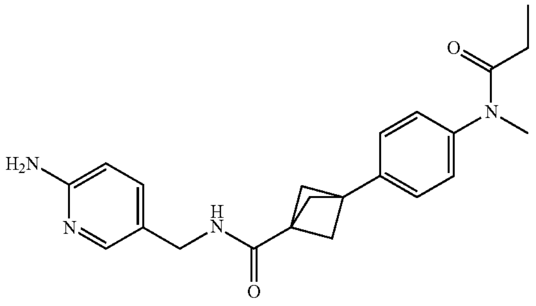
I-T 1185
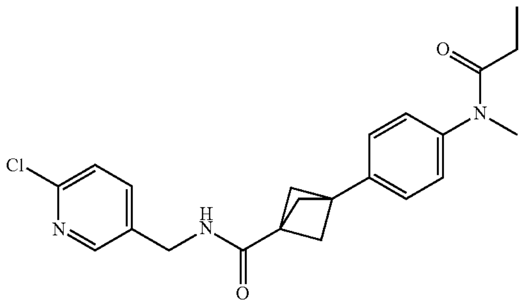

-continued
I-T 1186
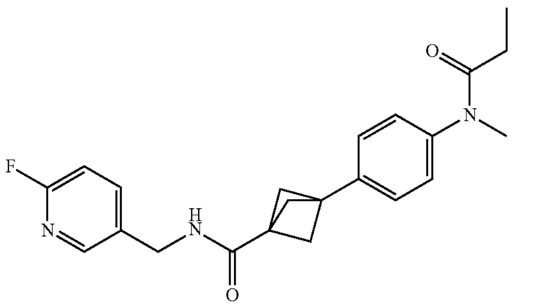
I-T 1187
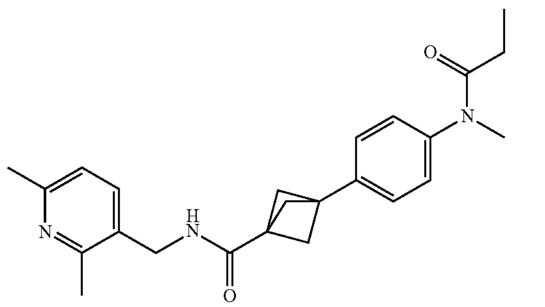
I-T 1188
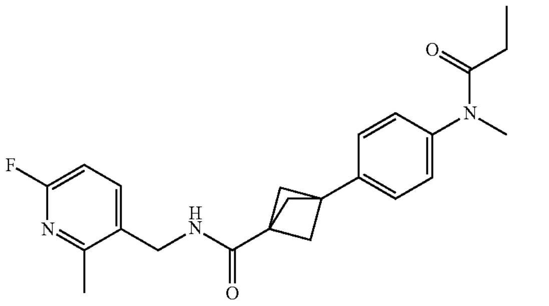
I-T 1189
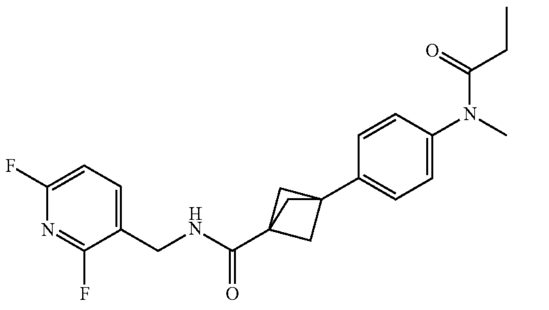
I-T 1190
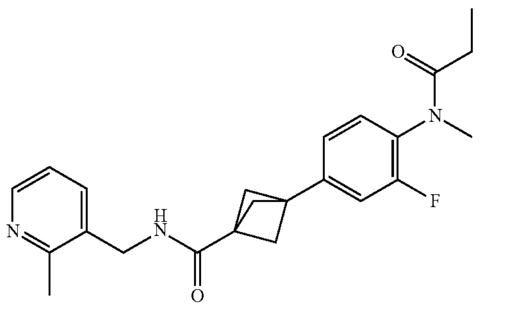
-continued
I-T 1191
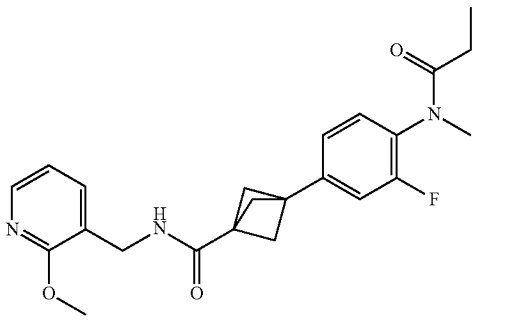
I-T 1192
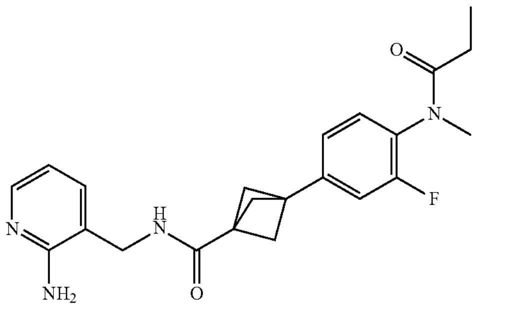
I-T 1193
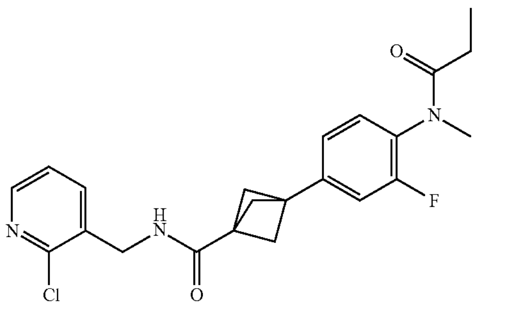
I-T 1194
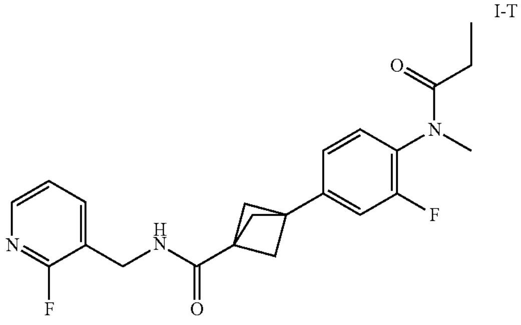
I-T 1195
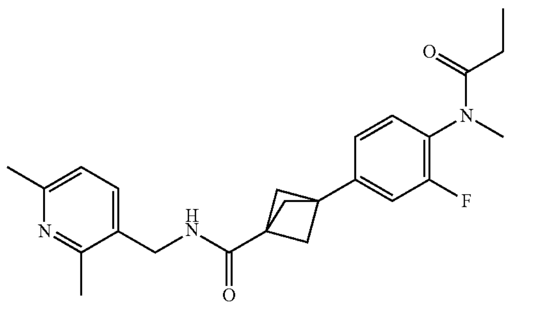

-continued
I-T 1196
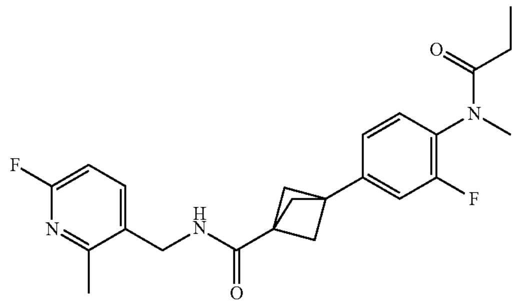
I-T 1197
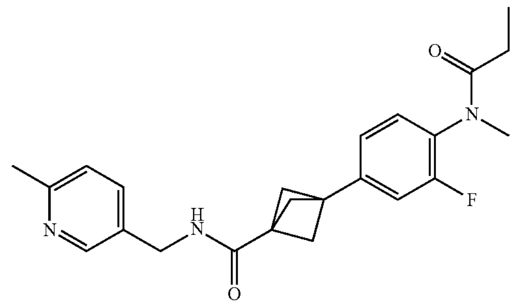
I-T 1198
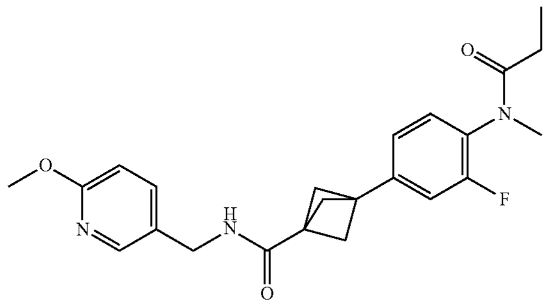
I-T 1199
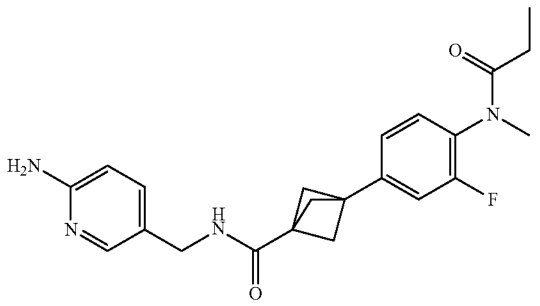
I-T 1200
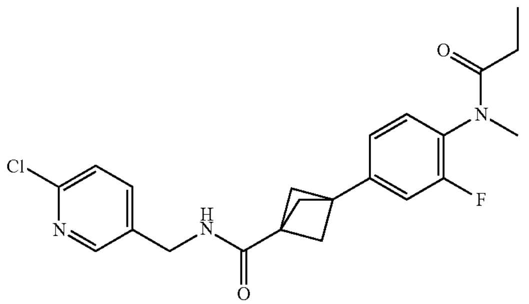
-continued
I-T 1201
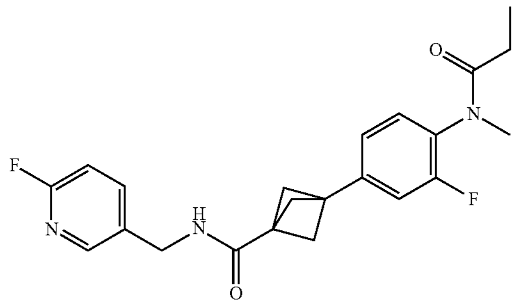
I-T 1202
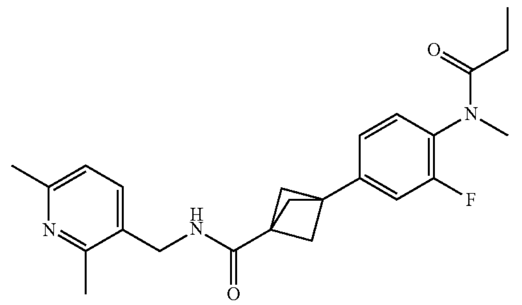
I-T 1203
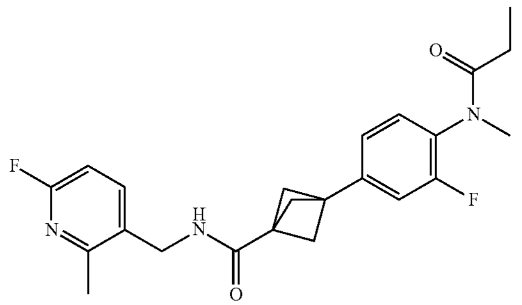
I-T 1204
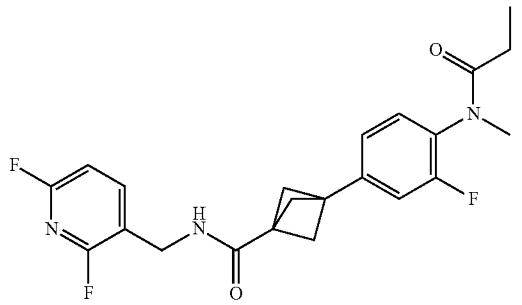
I-T 1205
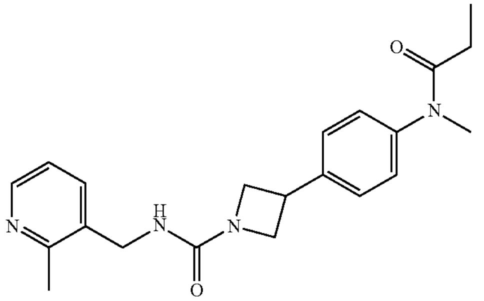

-continued
I-T 1206
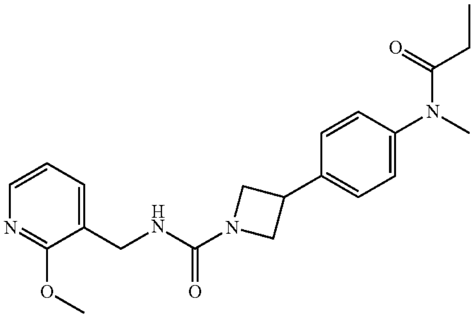
I-T 1207
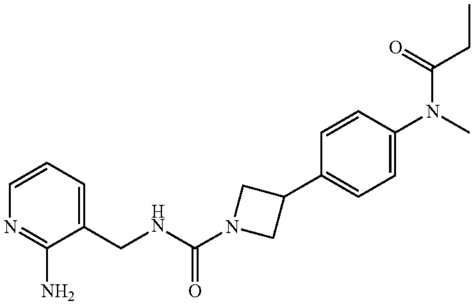
I-T 1208
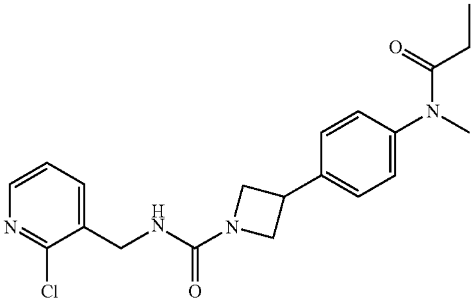
I-T 1209
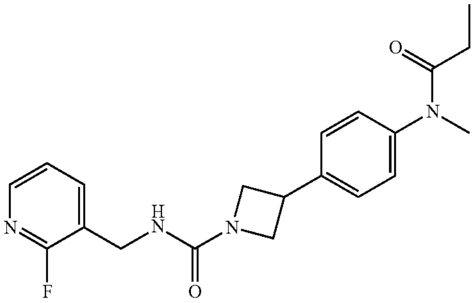
-continued
I-T 1210
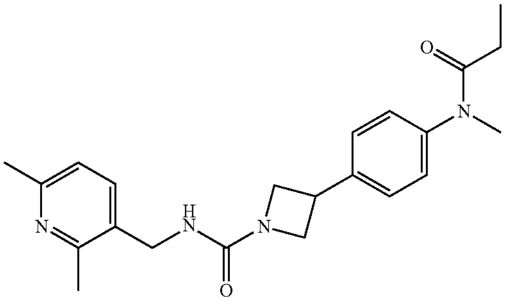
I-T 1211
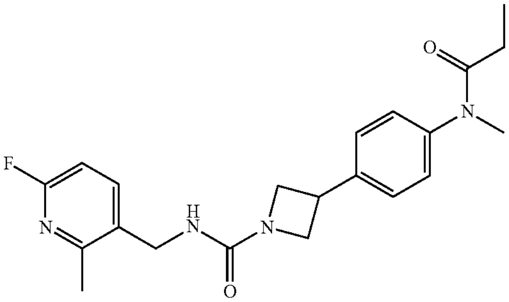
I-T 1212
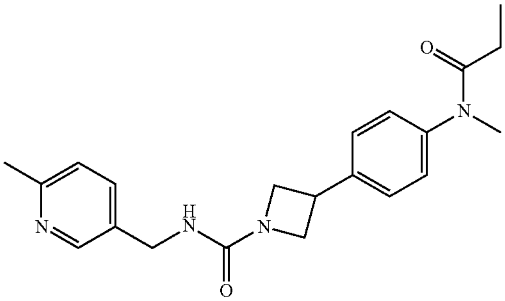
I-T 1213
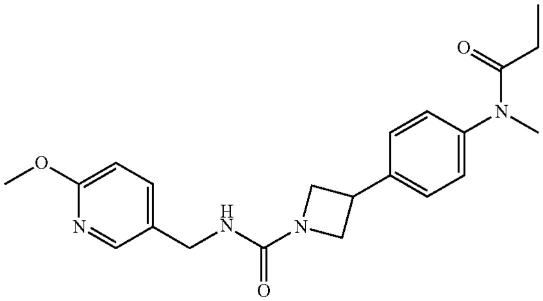
I-T 1214
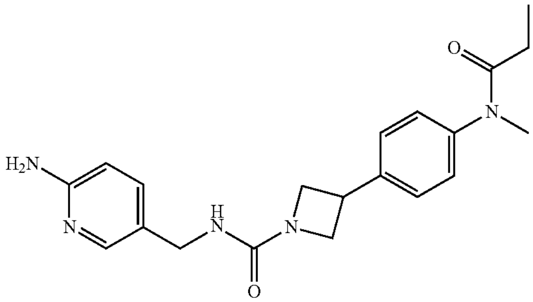

-continued
I-T 1215
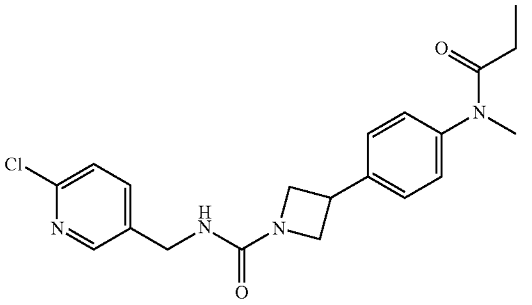
I-T 1216
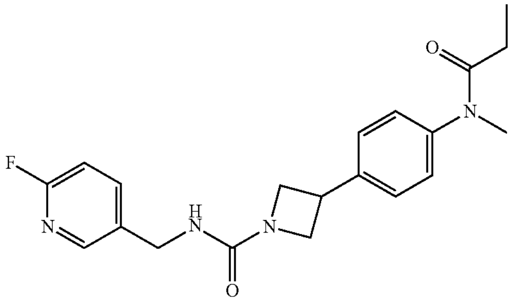
I-T 1217
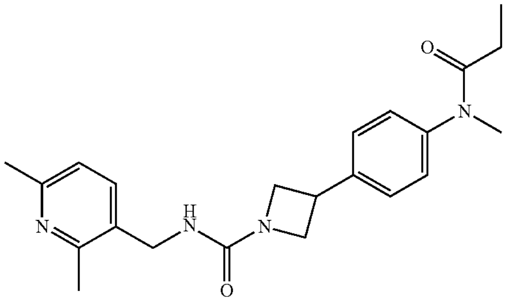
I-T 1218
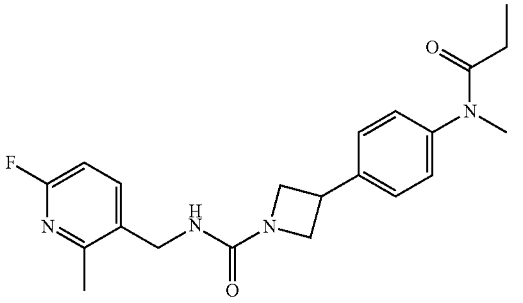
I-T 1219
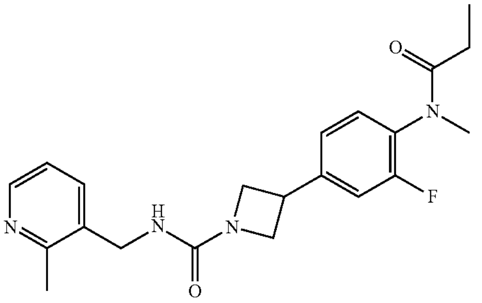
-continued
I-T 1220
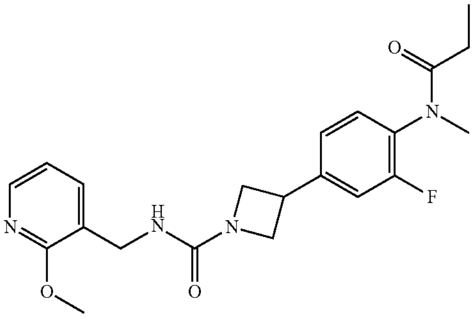
I-T 1221
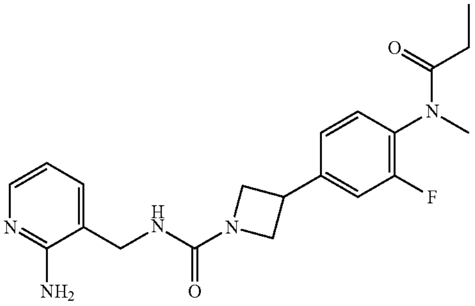
I-T 1222
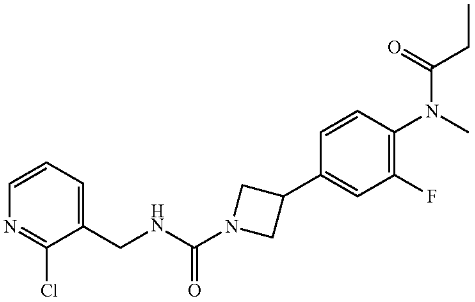
I-T 1223
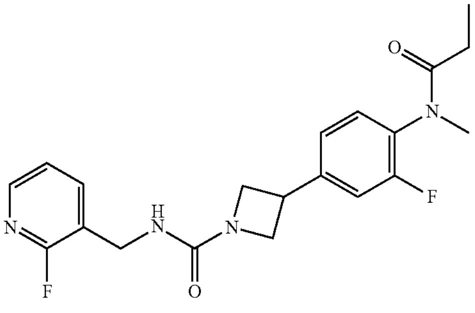
I-T 1224
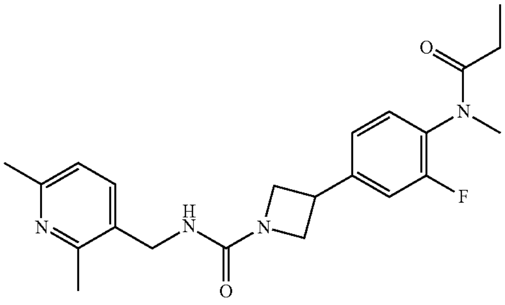

-continued
I-T 1225
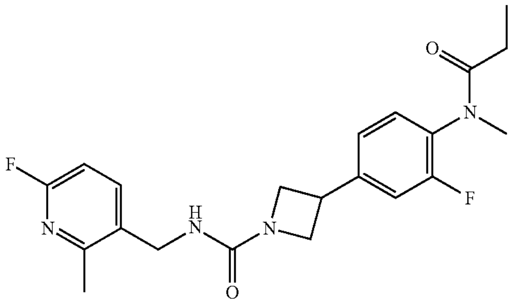
I-T 1226
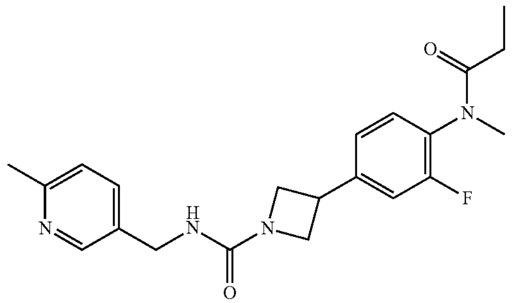
I-T 1227
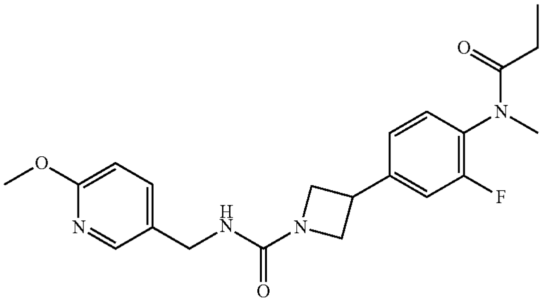
I-T 1228
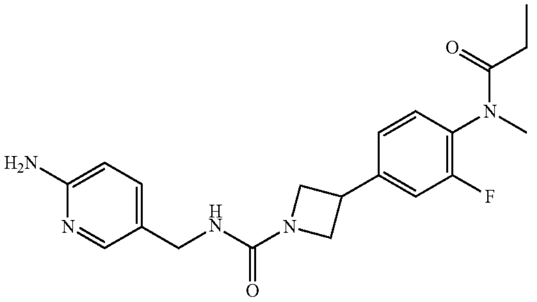
I-T 1229
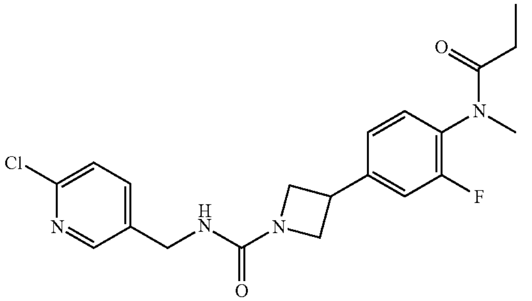
-continued
I-T 1230
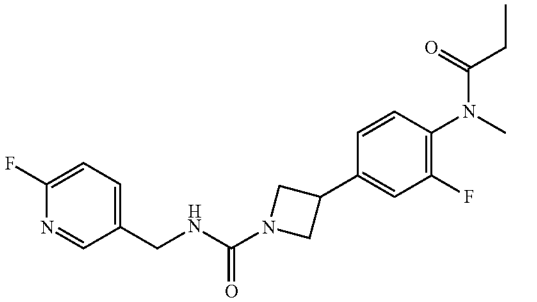
I-T 1231
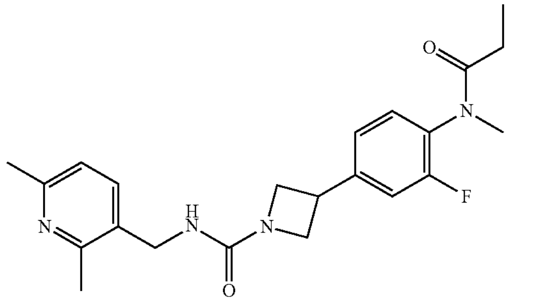
I-T 1232
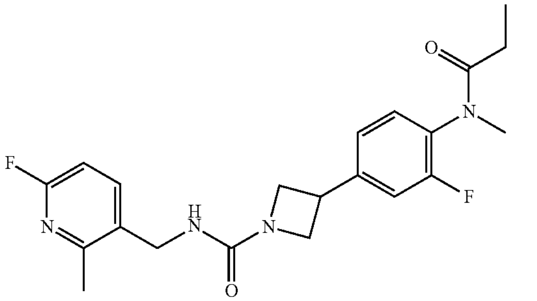
I-T 1233
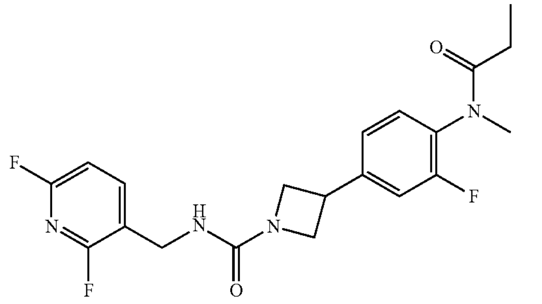
I-T 1234
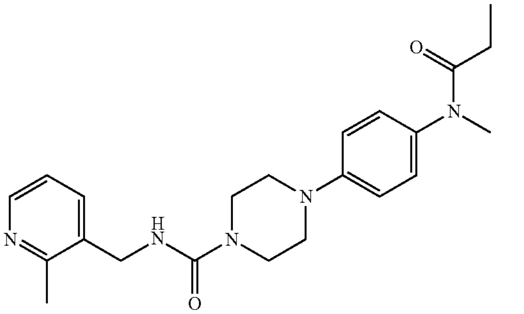

-continued
I-T 1235
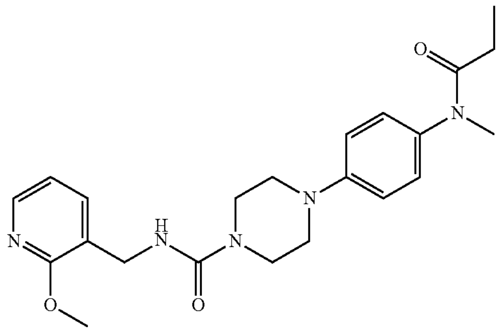
I-T 1236
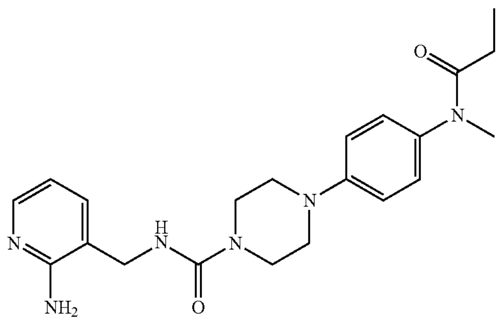
I-T 1237
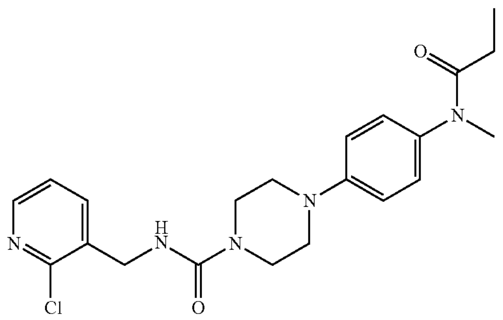
I-T 1238
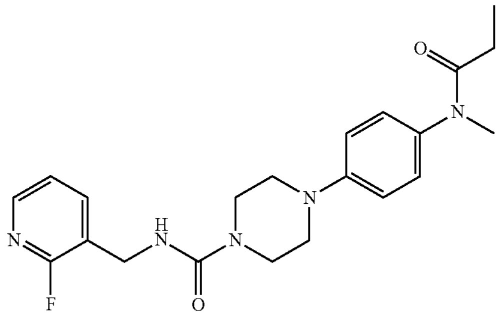
-continued
I-T 1239
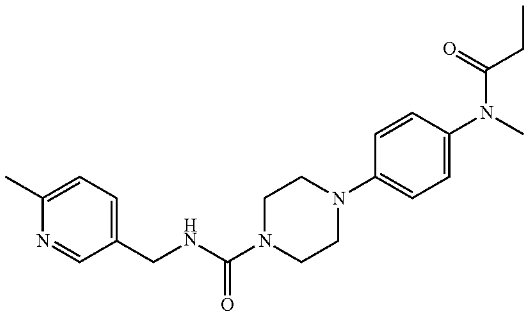
I-T 1240
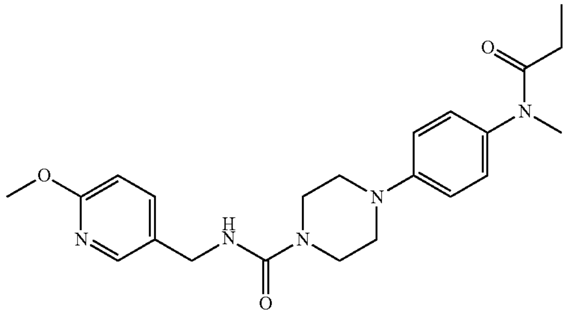
I-T 1241
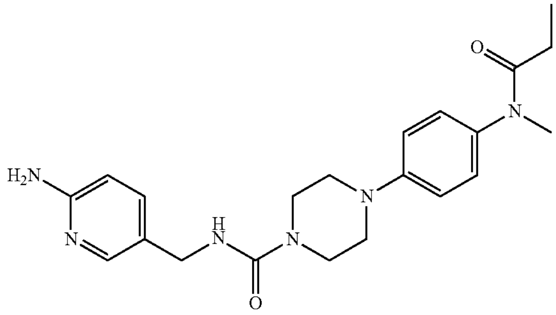
I-T 1242
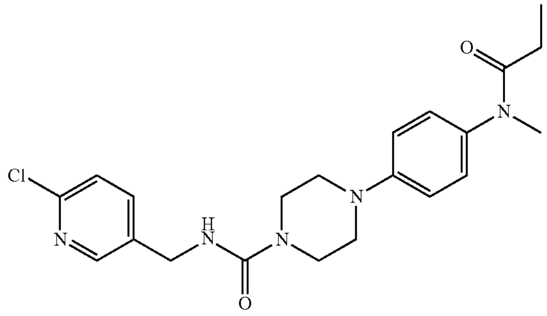

-continued
I-T 1243
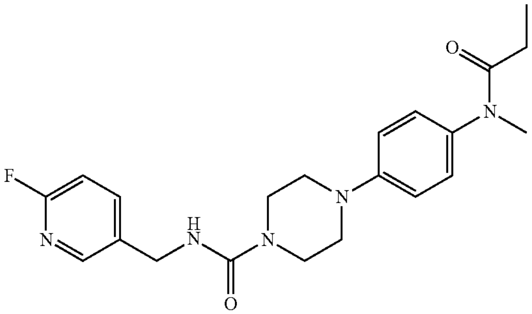
I-T 1244
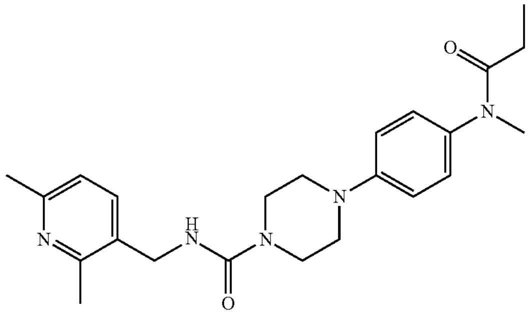
I-T 1245
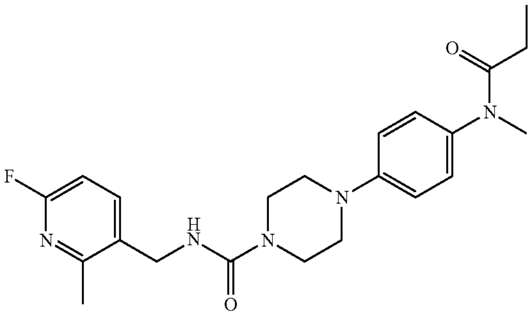
I-T 1246
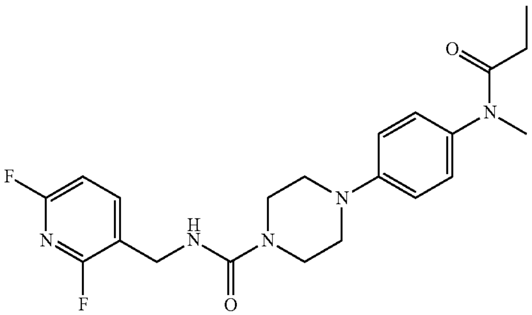
-continued
I-T 1247
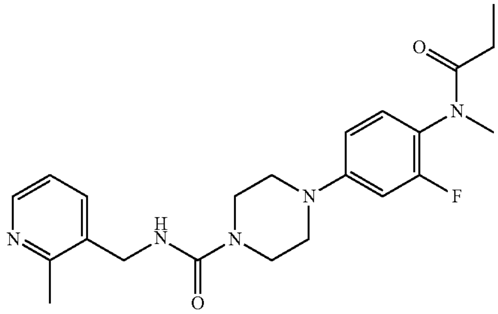
I-T 1248
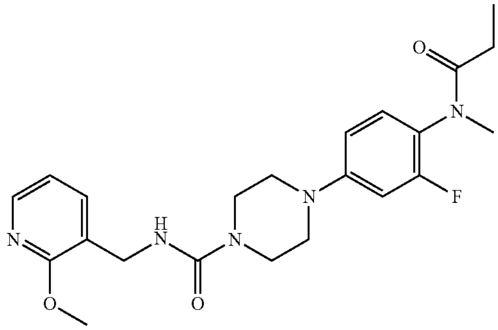
I-T 1249
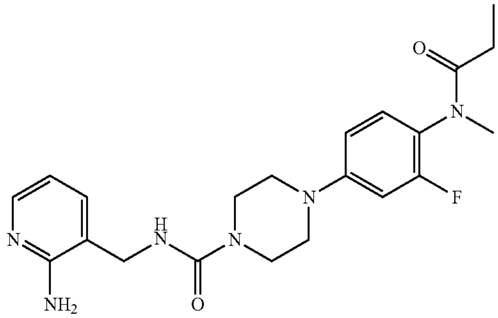
I-T 1250
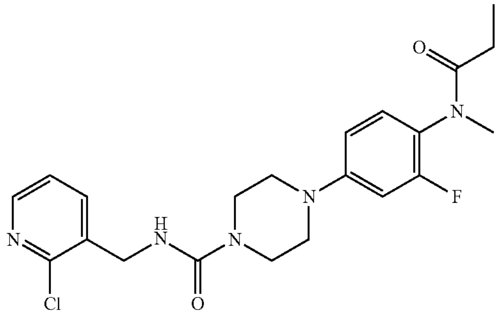

-continued
I-T 1251
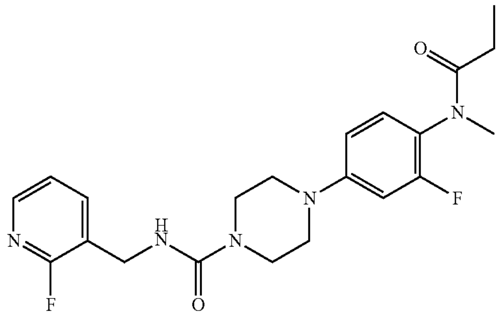
I-T 1252
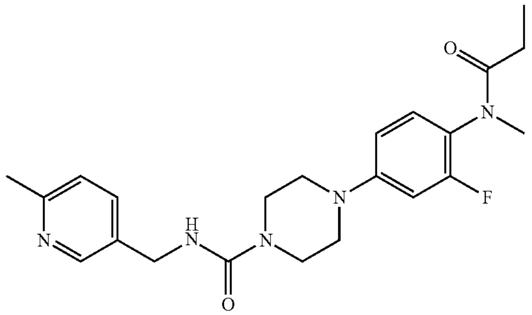
I-T 1253
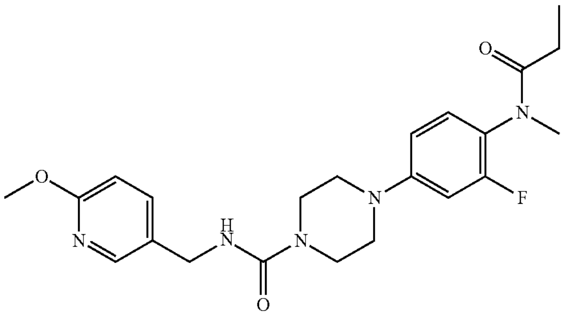
I-T 1254
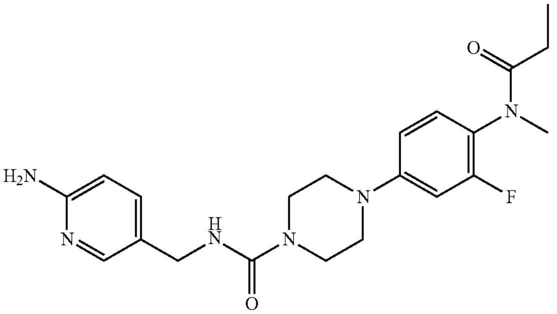
-continued
I-T 1255
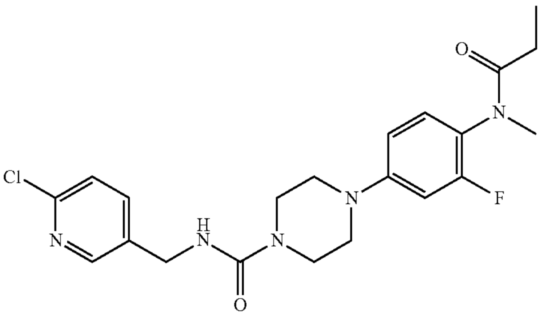
I-T 1256
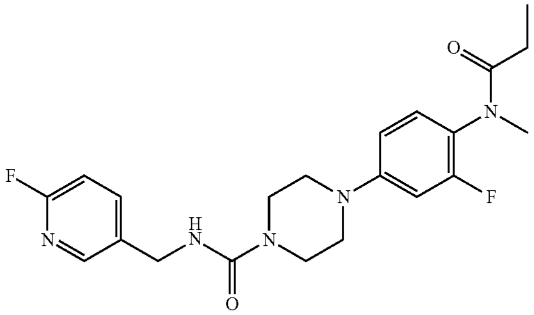
I-T 1257
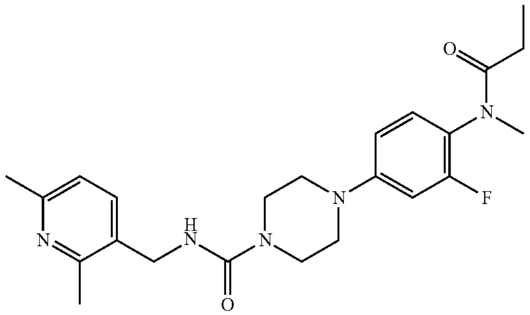
I-T 1258
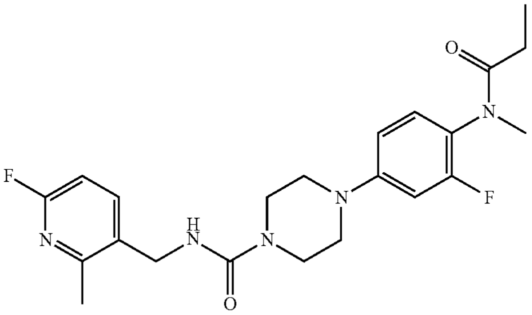

-continued
I-T 1259
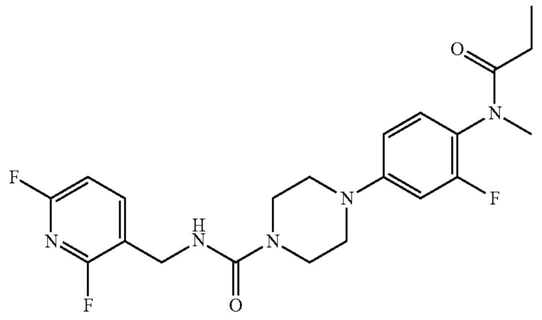
I-T 1260
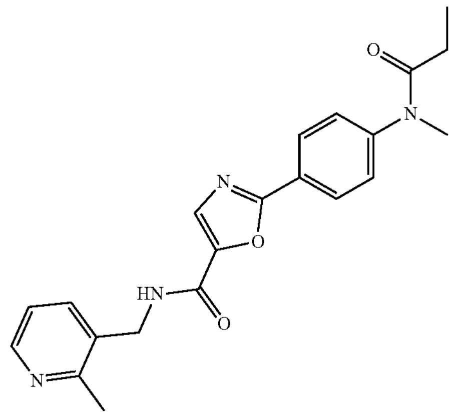
I-T 1261
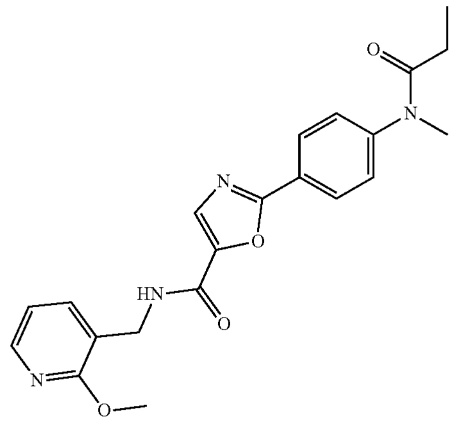
-continued
I-T 1262
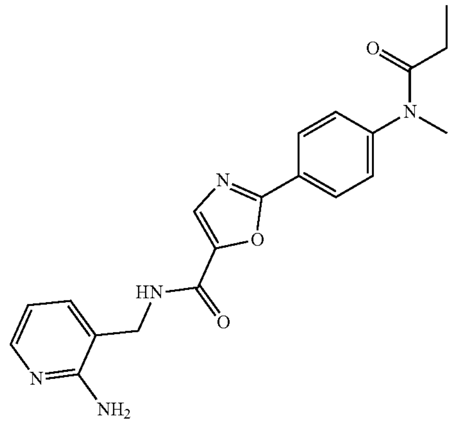
I-T 1263
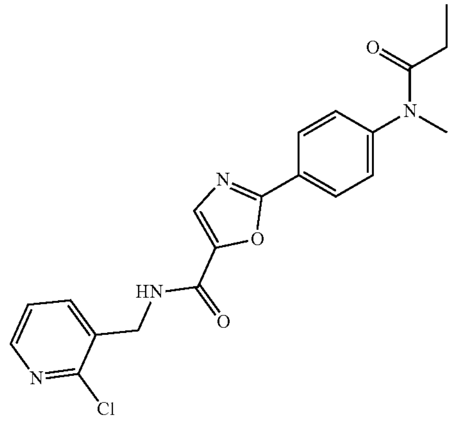
I-T 1264
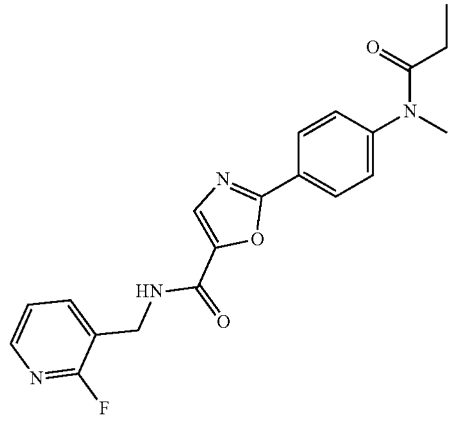

-continued
I-T 1265
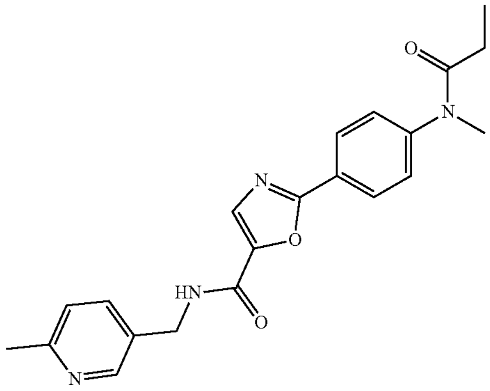
I-T 1266
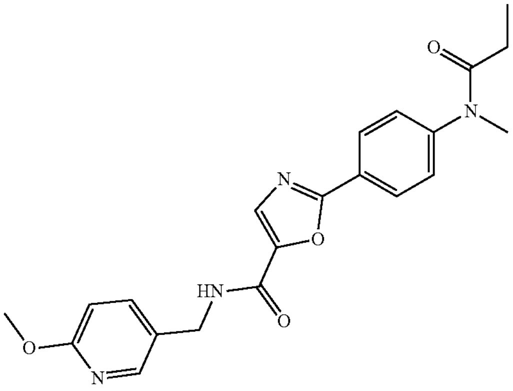
I-T 1267
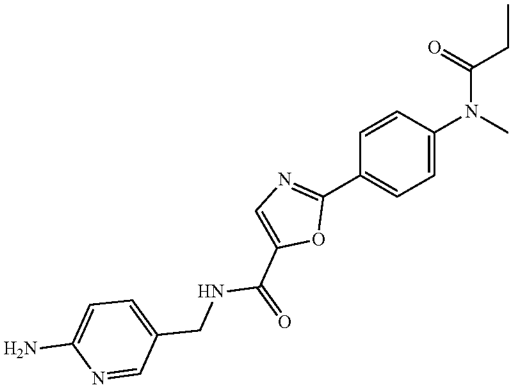
I-T 1268
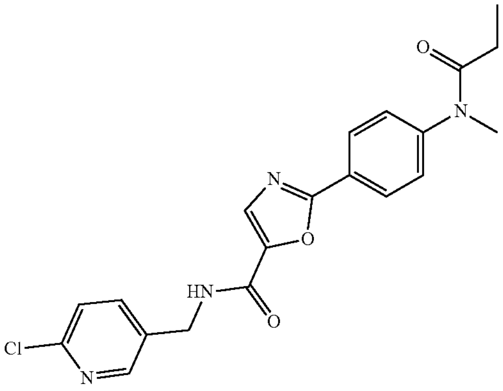
-continued
I-T 1269
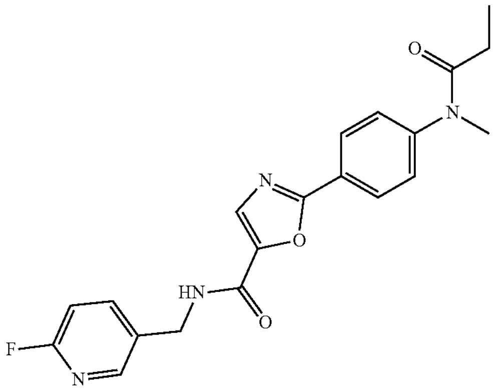
I-T 1270
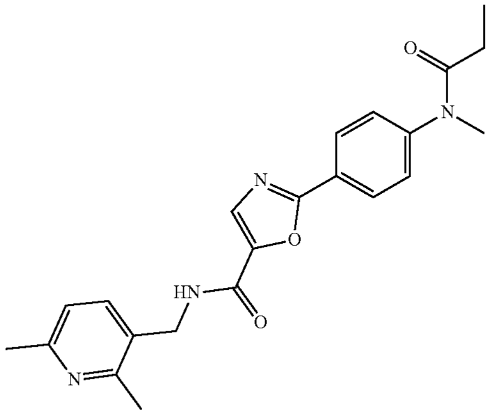
I-T 1271
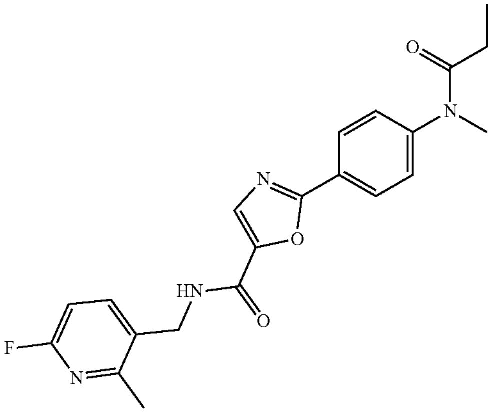

-continued
I-T 1272
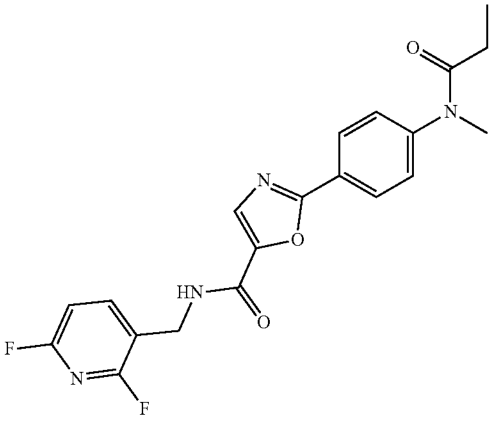
I-T 1273
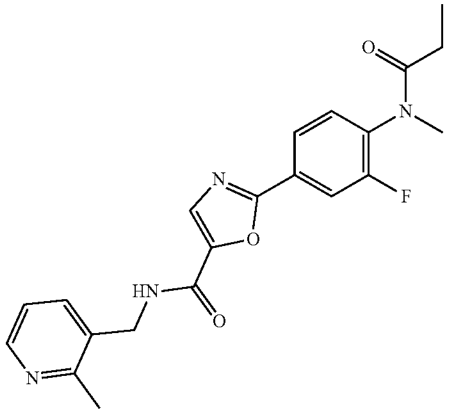
I-T 1274
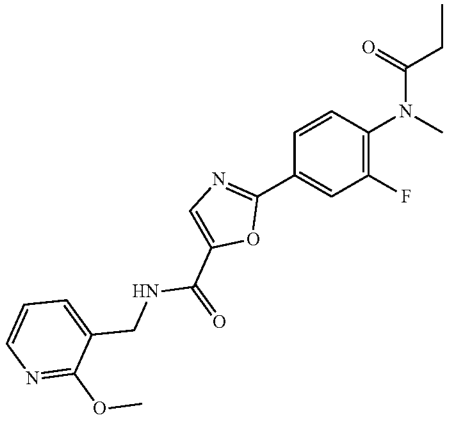
-continued
I-T 1275
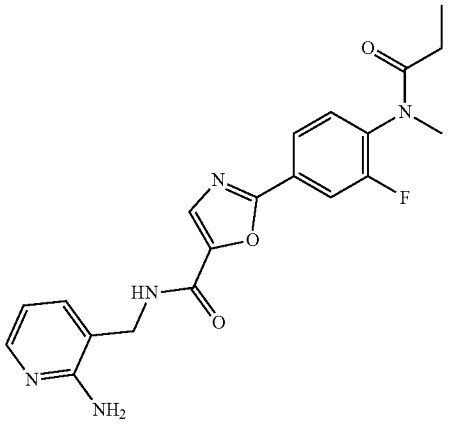
I-T 1276
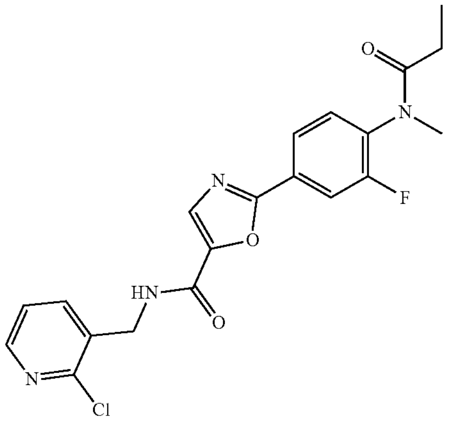
I-T 1277
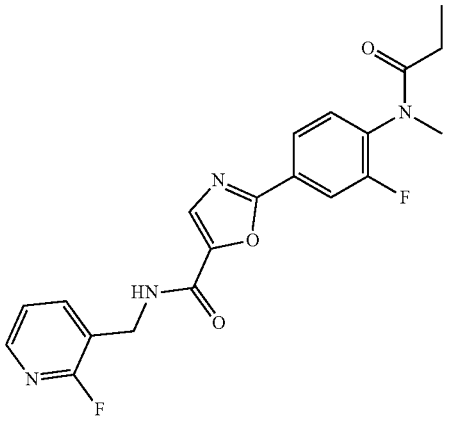

-continued
I-T 1278
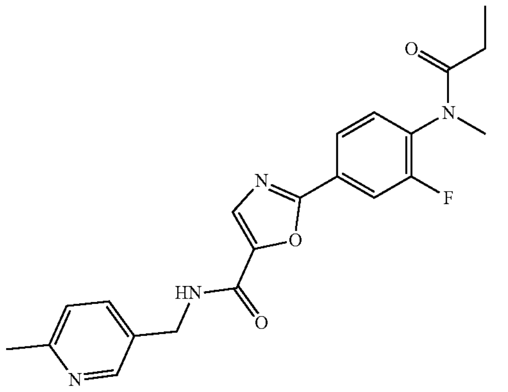
I-T 1279
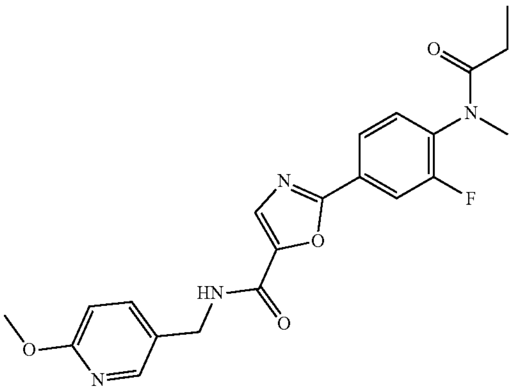
I-T 1280
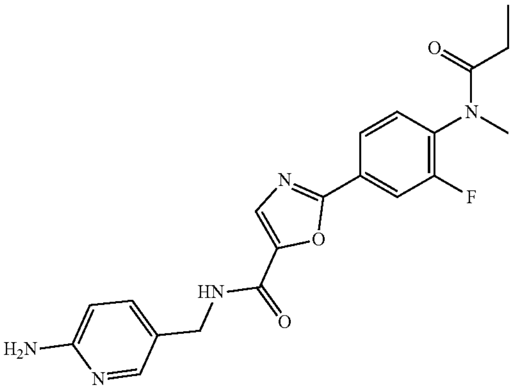
I-T 1281
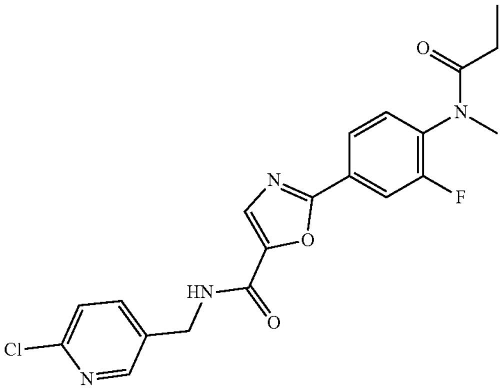
-continued
I-T 1282
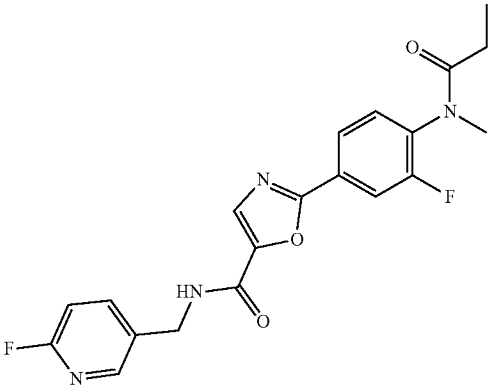
I-T 1283
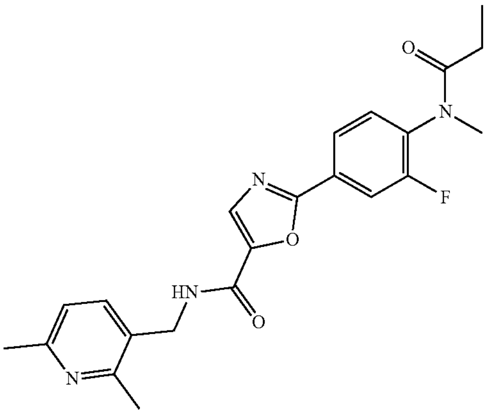
I-T 1284
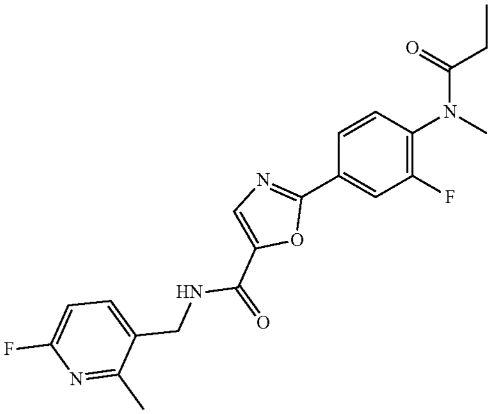

-continued
I-T 1285
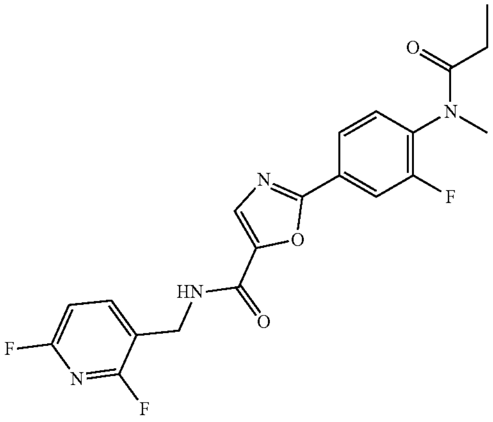
I-T 1286
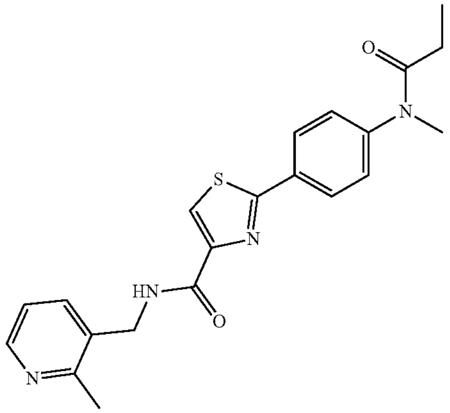
I-T 1287
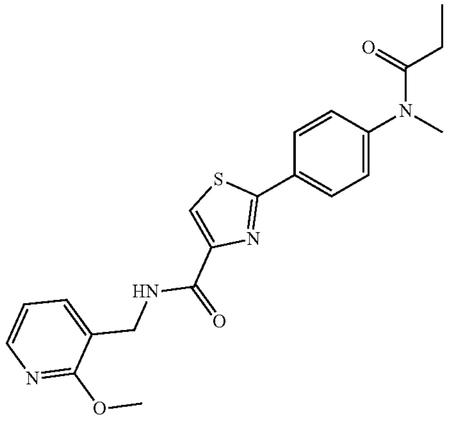
-continued
I-T 1288
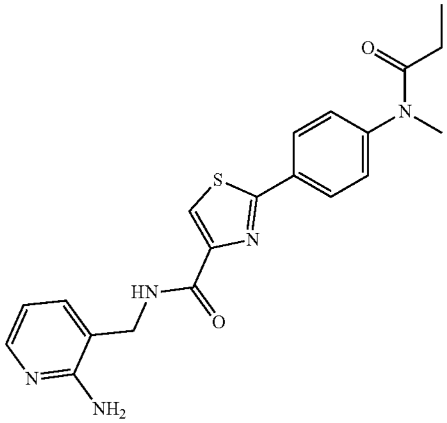
I-T 1289
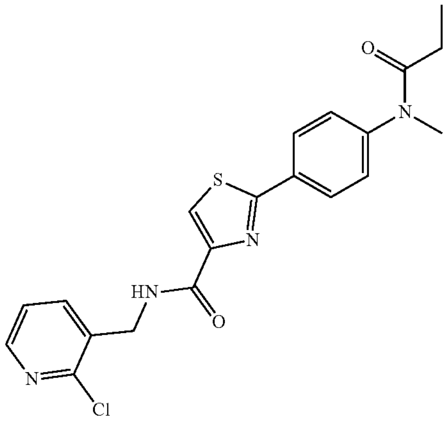
I-T 1290
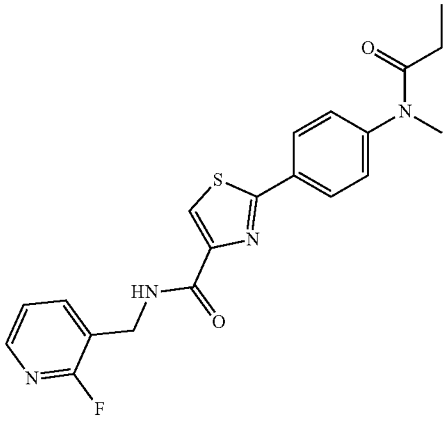

-continued
I-T 1291
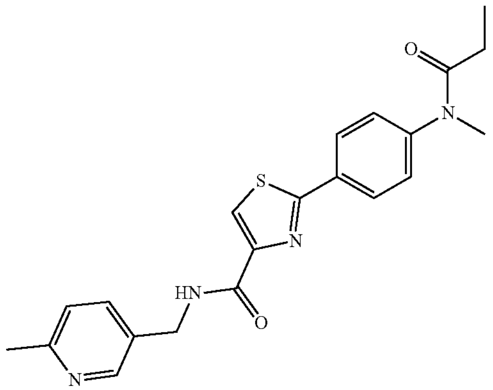
I-T 1292
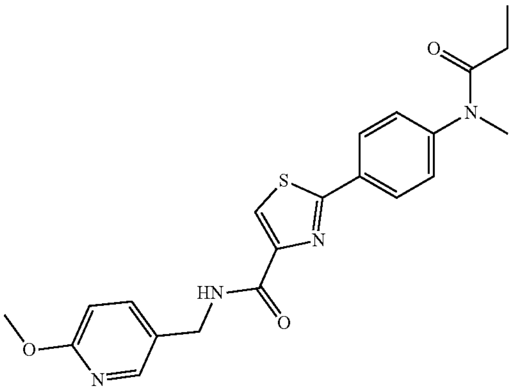
I-T 1293
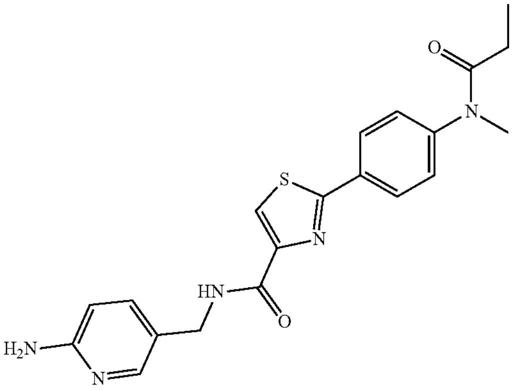
I-T 1294
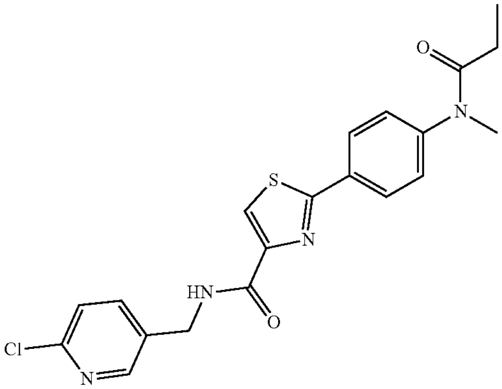
-continued
I-T 1295
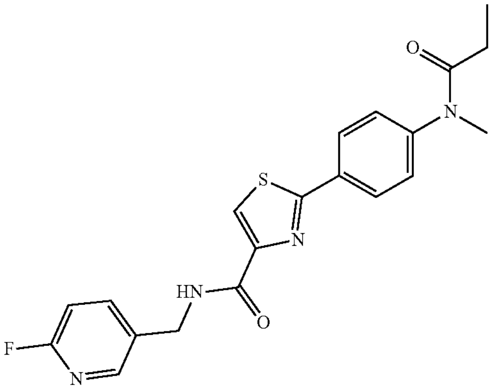
I-T 1296
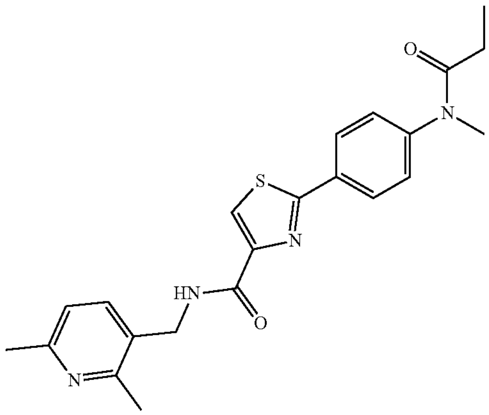
I-T 1297
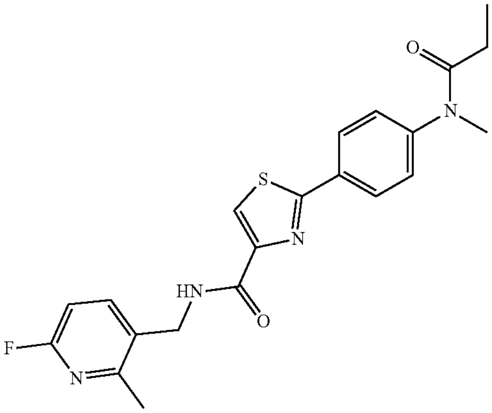

-continued
I-T 1298
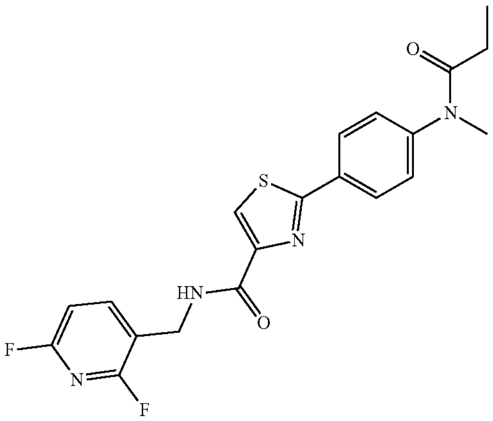
I-T 1299
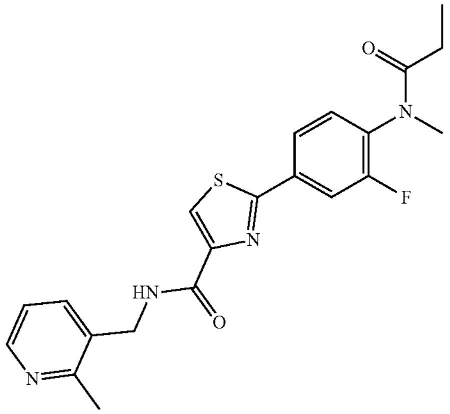
I-T 1300
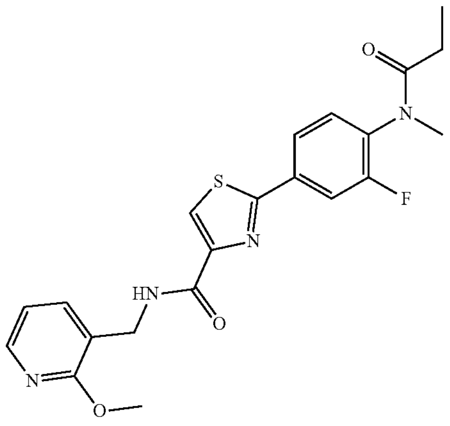
-continued
I-T 1301
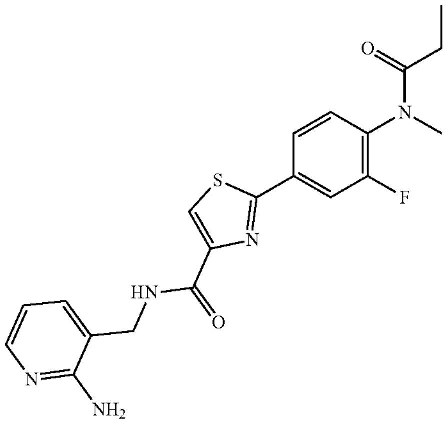
I-T 1302
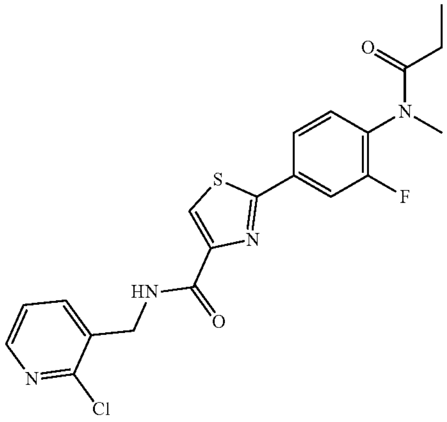
I-T 1303
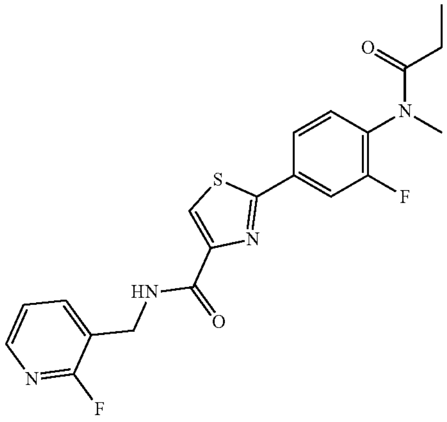

-continued
I-T 1304
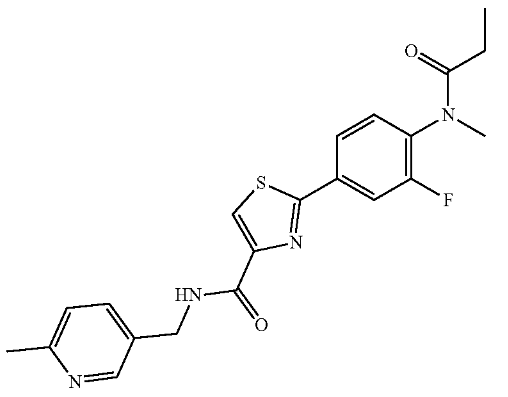
I-T 1305
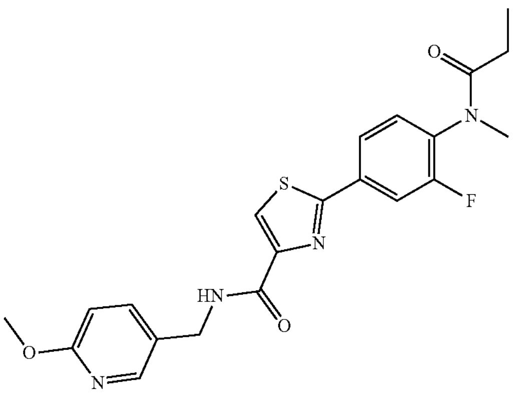
I-T 1306
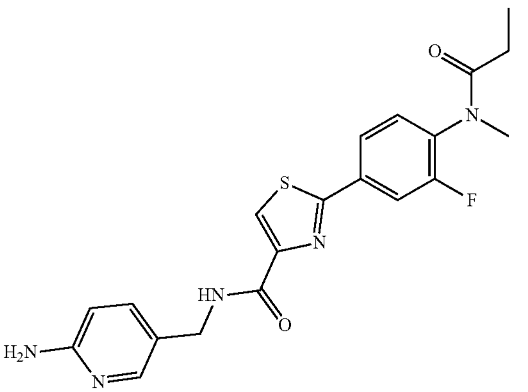
I-T 1307
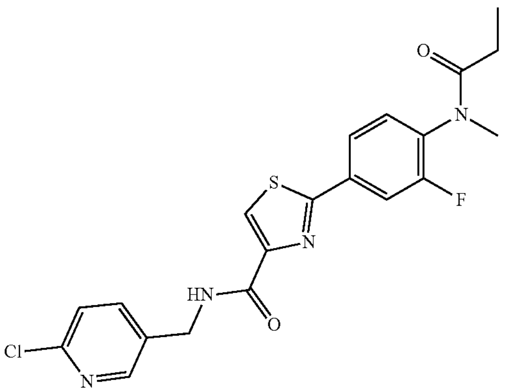
-continued
I-T 1308
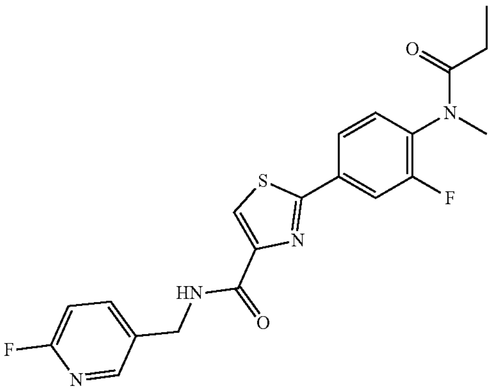
I-T 1309
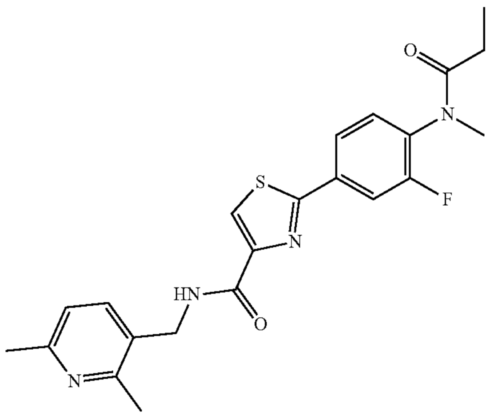
I-T 1310
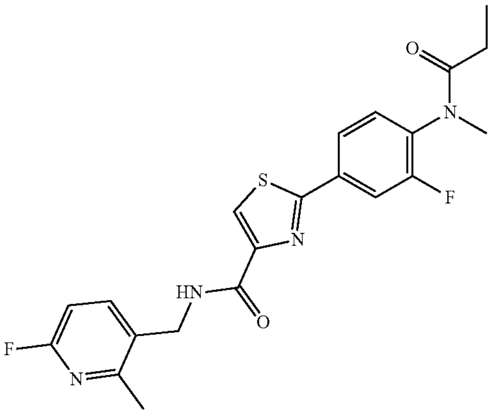

-continued
I-T 1311
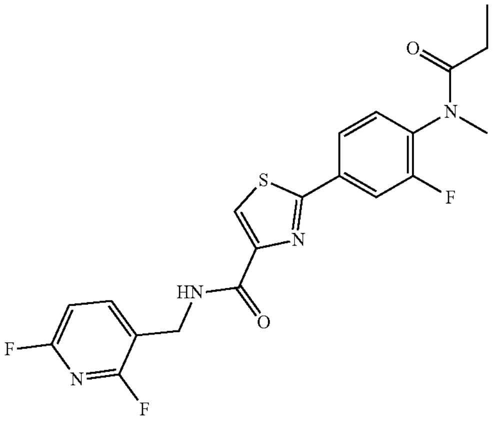
I-T 1312
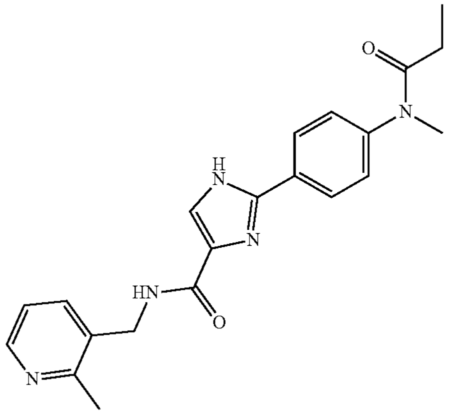
I-T 1313
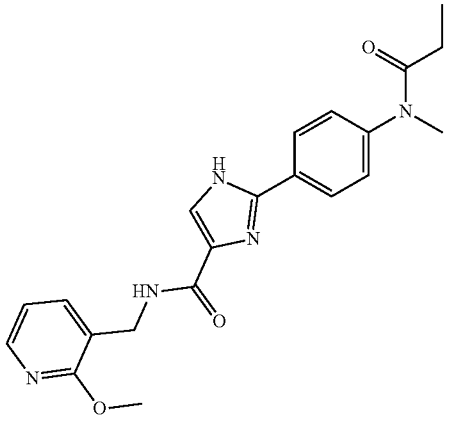
-continued
I-T 1314
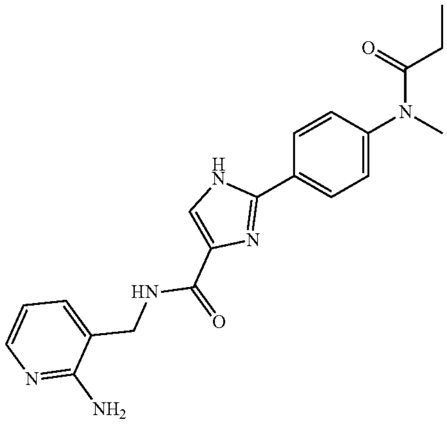
I-T 1315
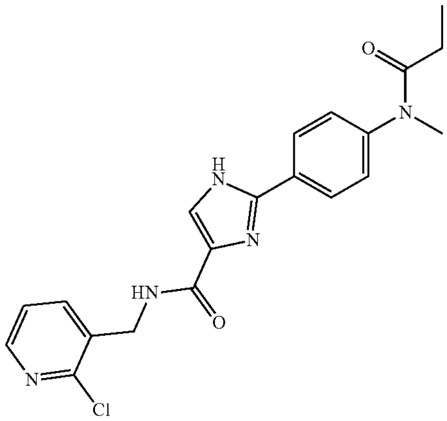
I-T 1316
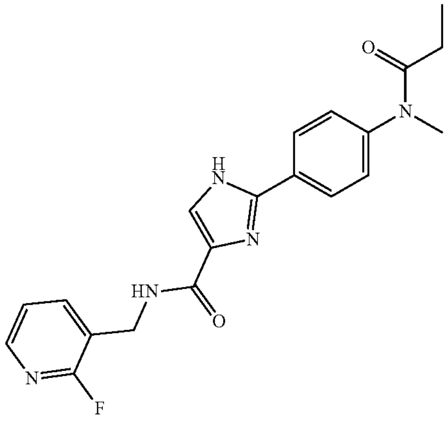

I-T 1317
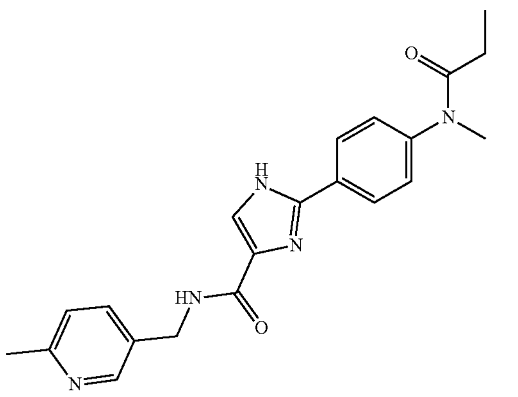
I-T 1318
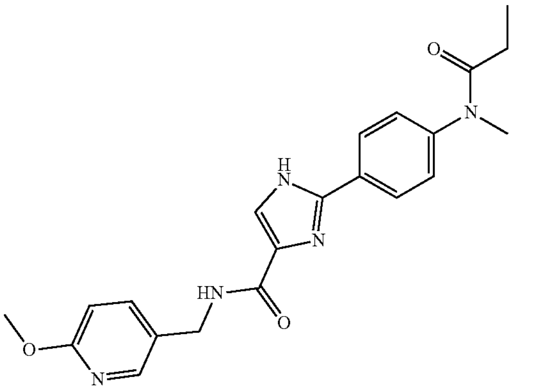
I-T 1319
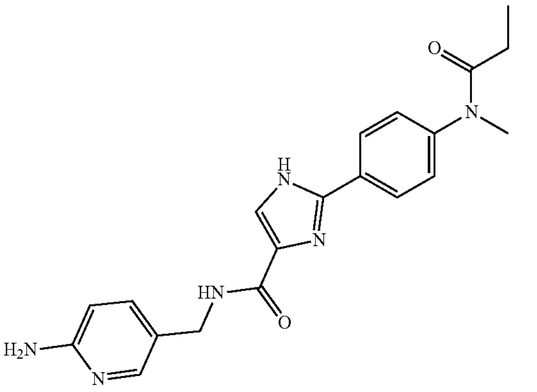
I-T 1320
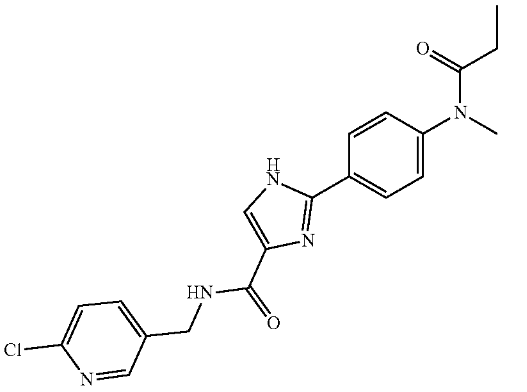
I-T 1321
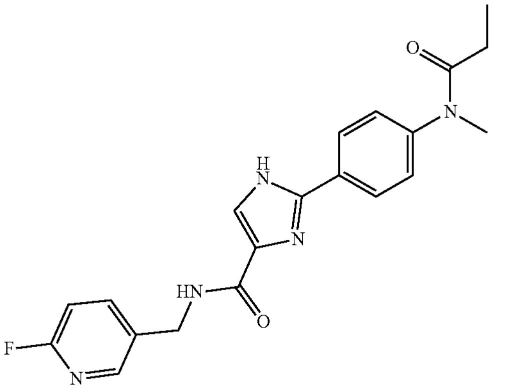
I-T 1322
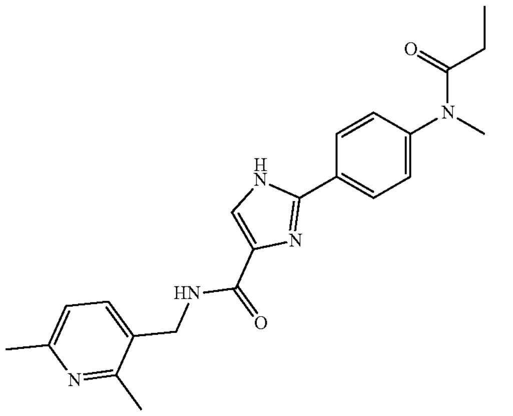
I-T 1323
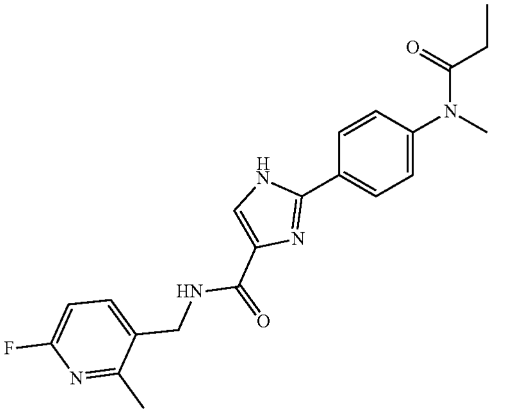

-continued
I-T 1324
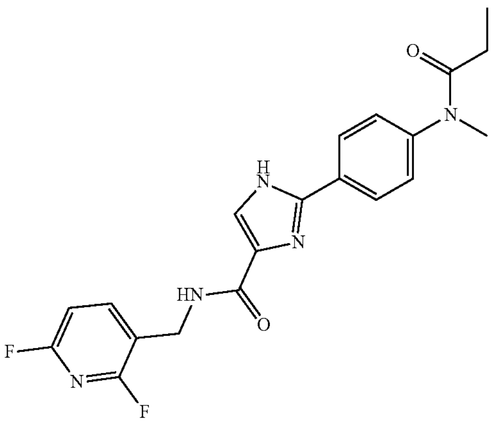
I-T 1325
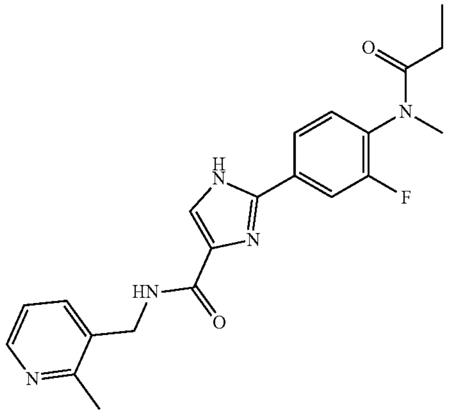
I-T 1326
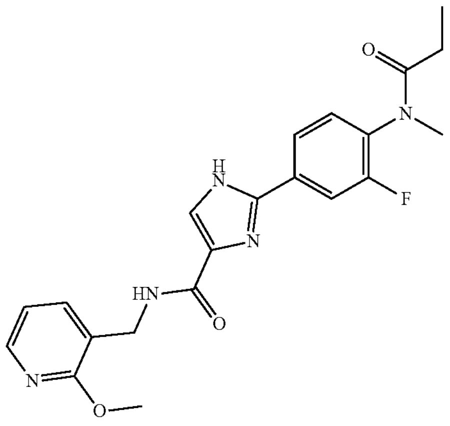
-continued
I-T 1327
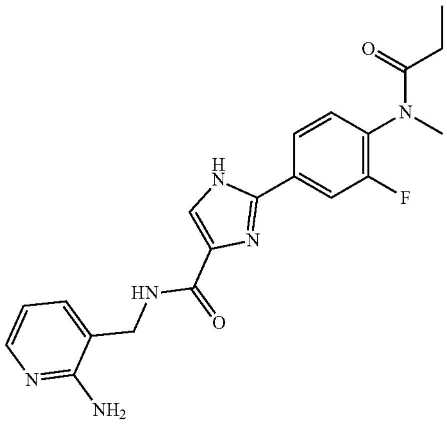
I-T 1328
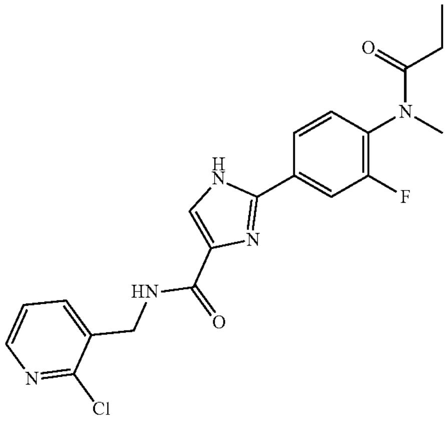
I-T 1329
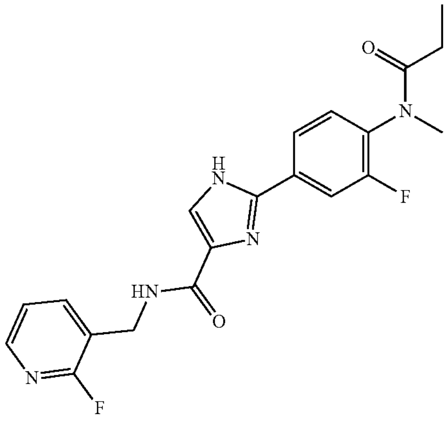

-continued
I-T 1330
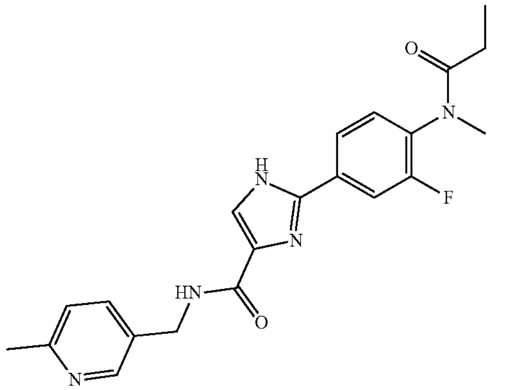
I-T 1331
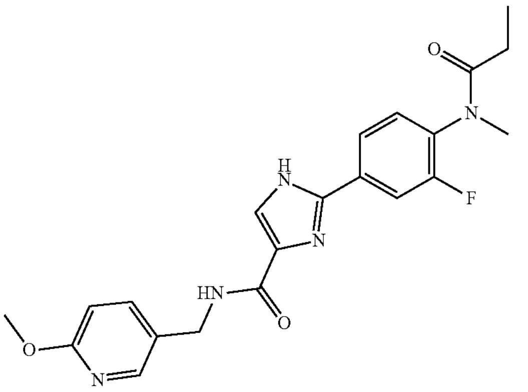
I-T 1332
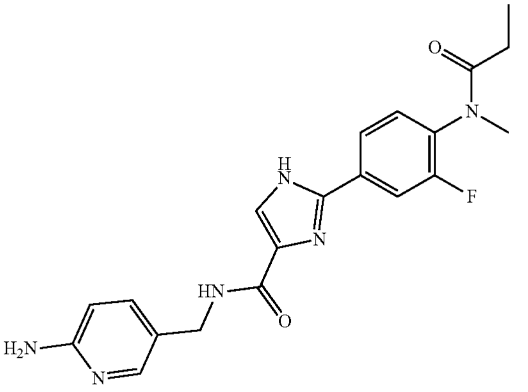
I-T 1333
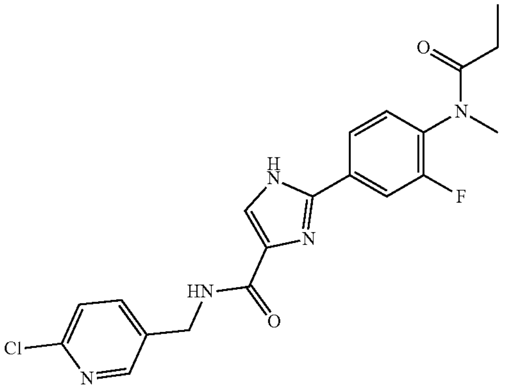
-continued
I-T 1334
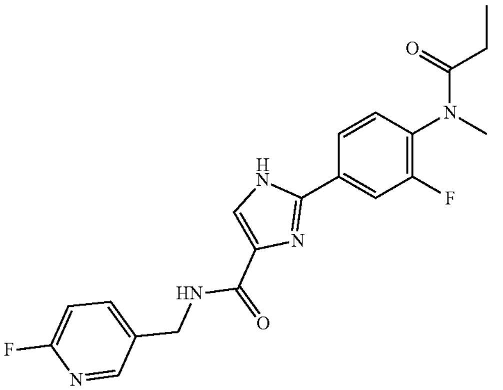
I-T 1335
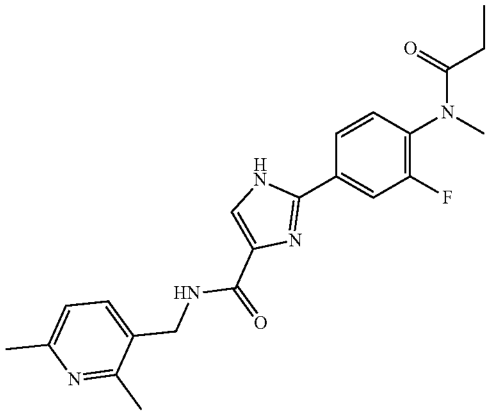
I-T 1336
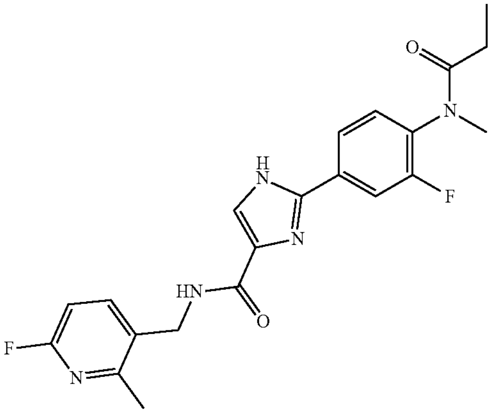

-continued
I-T 1337
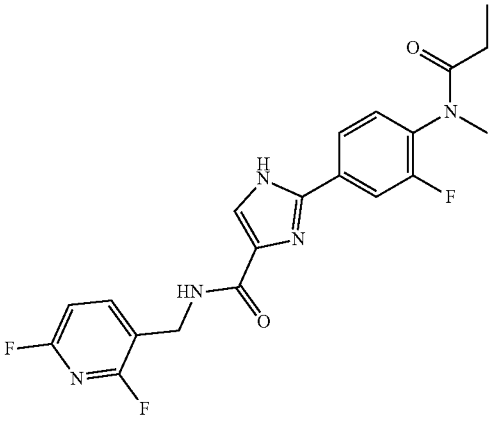
I-T 1338
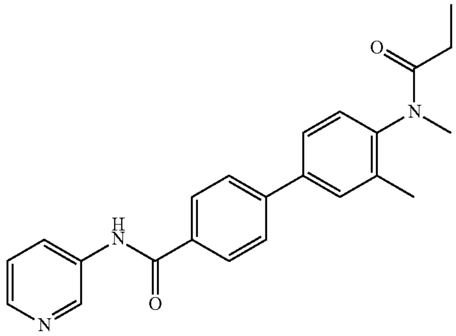
I-T 1339
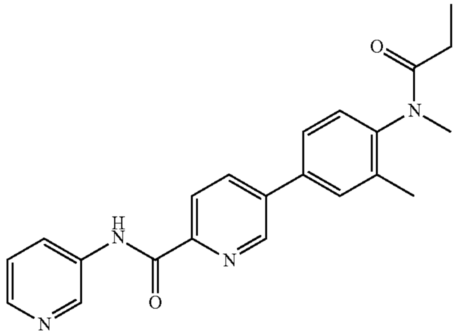
I-T 1340
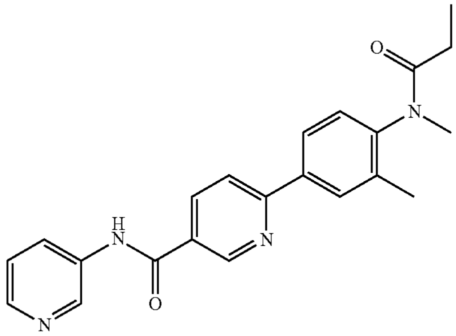
-continued
I-T 1341
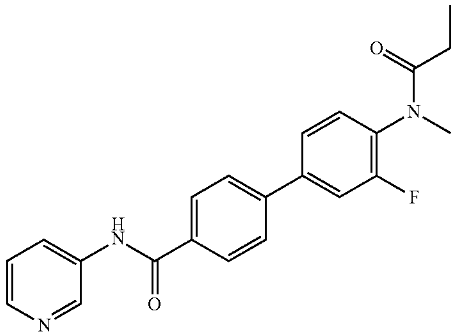
I-T 1342
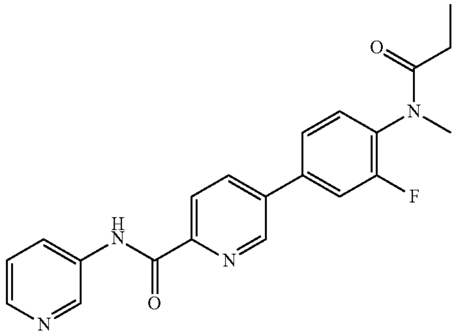
I-T 1343
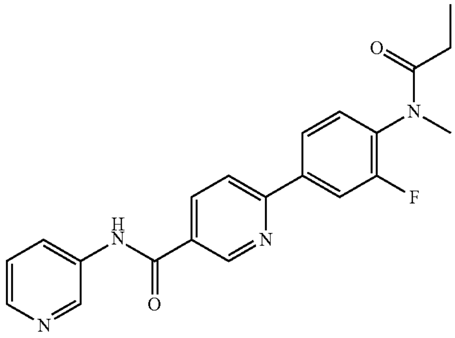
I-T 1344
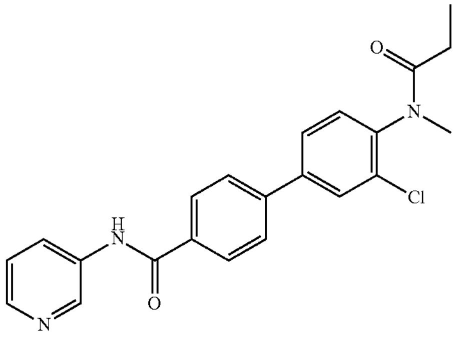

-continued
I-T 1345
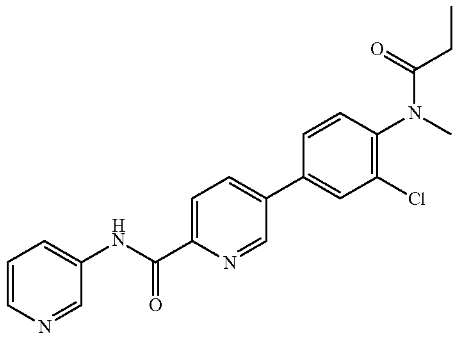
I-T 1346
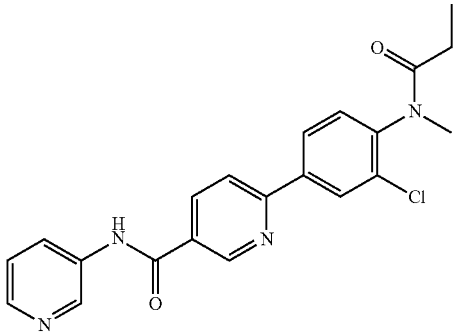
I-T 1347
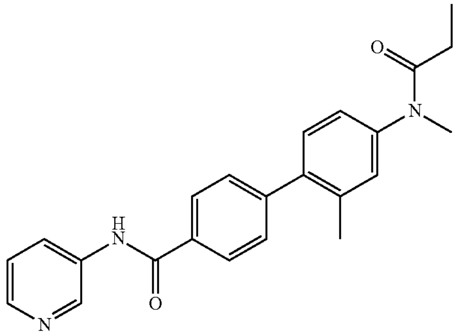
I-T 1348
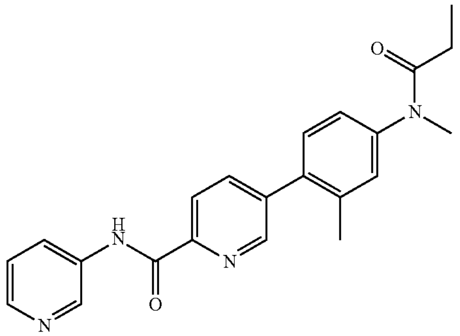
-continued
I-T 1349
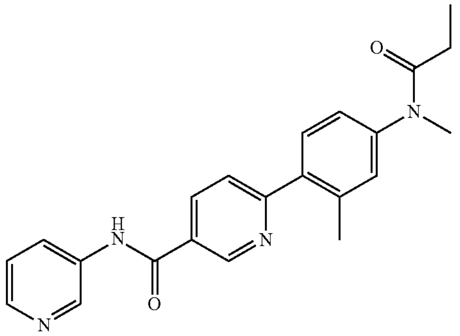
I-T 1350
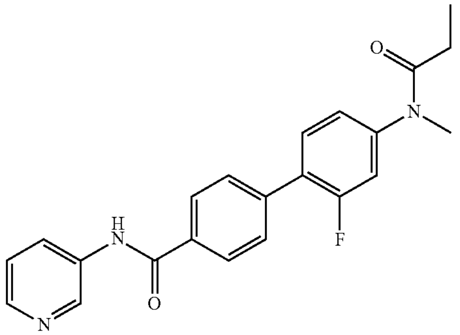
I-T 1351
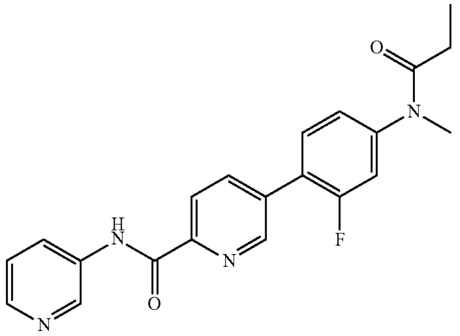
I-T 1352
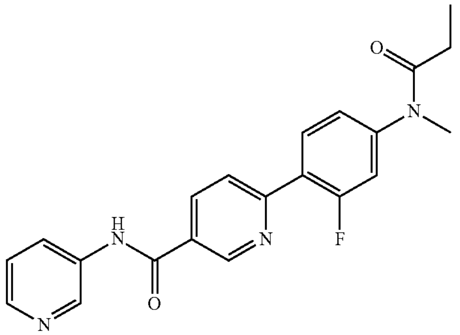

-continued
I-T 1353
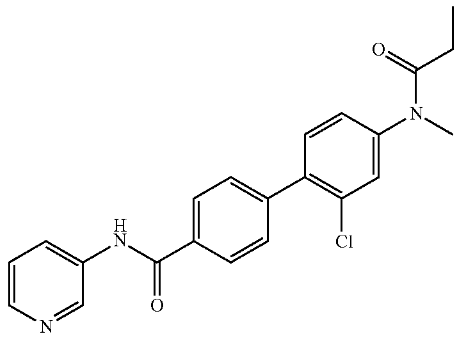
I-T 1354
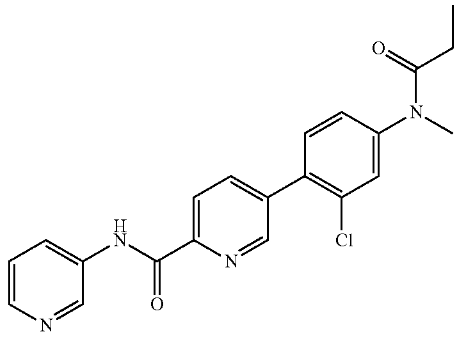
I-T 1355
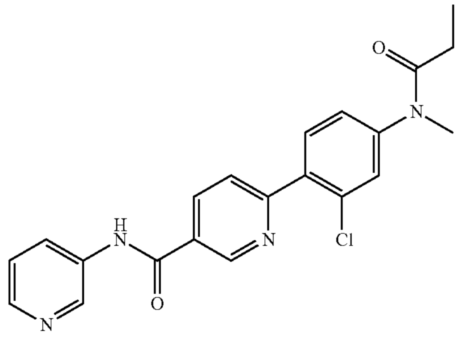
I-T 1356
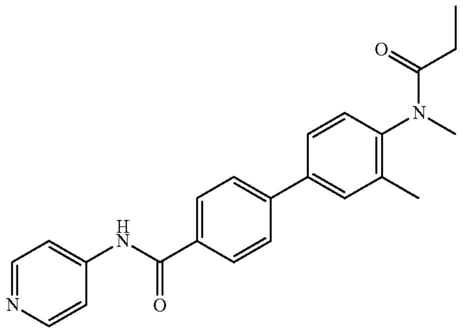
-continued
I-T 1357
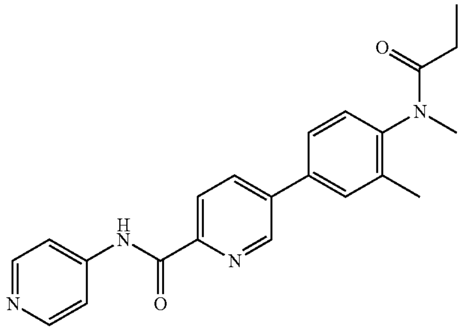
I-T 1358
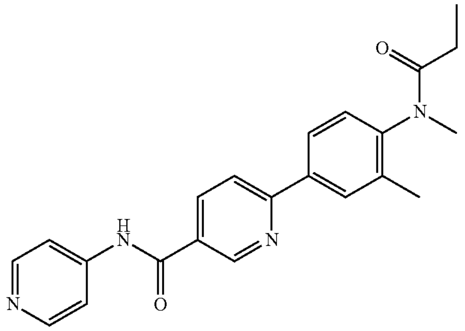
I-T 1359
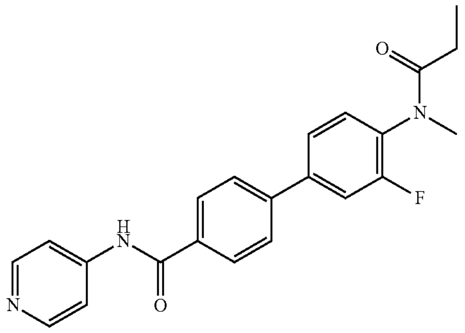
I-T 1360
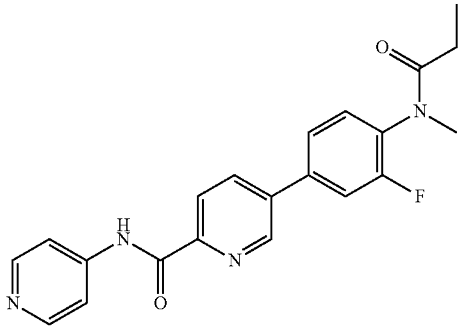

-continued
I-T 1361
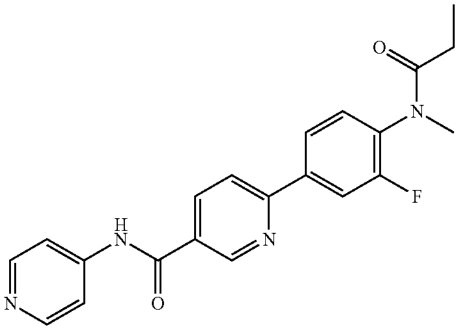
I-T 1362
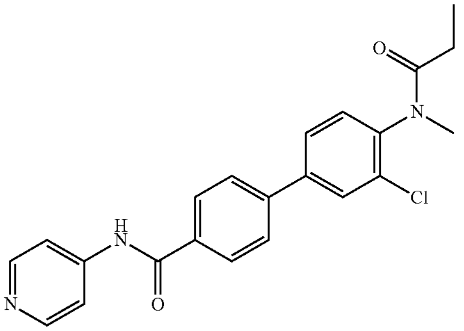
I-T 1363
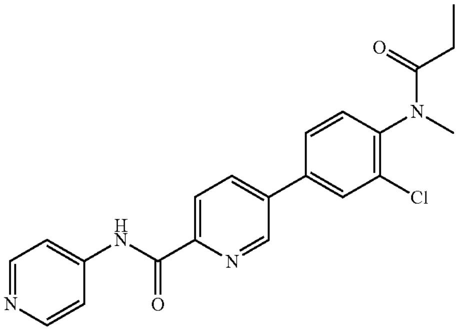
I-T 1364
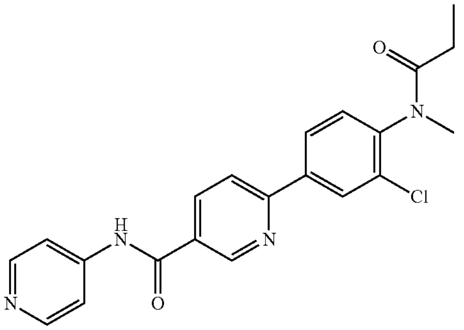
-continued
I-T 1365
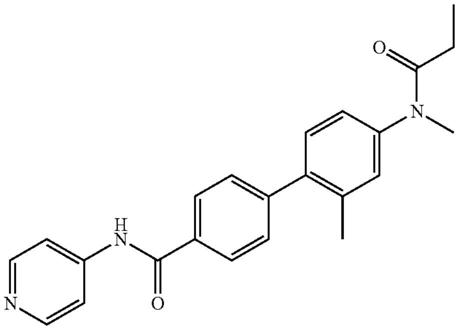
I-T 1366
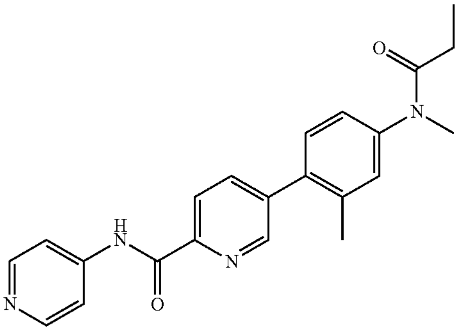
I-T 1367
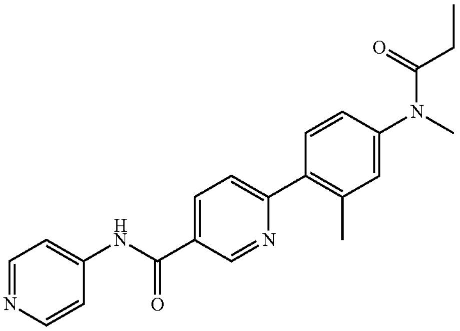
I-T 1368
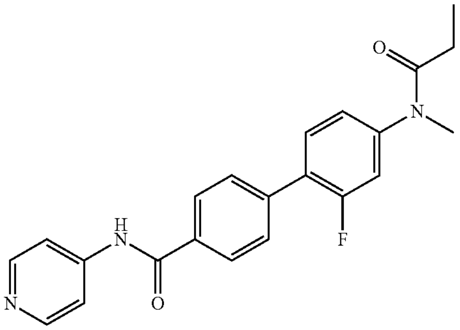

-continued
I-T 1369
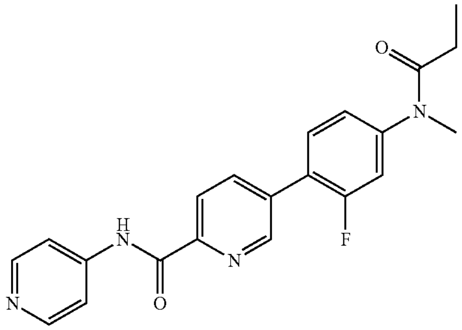
I-T 1370
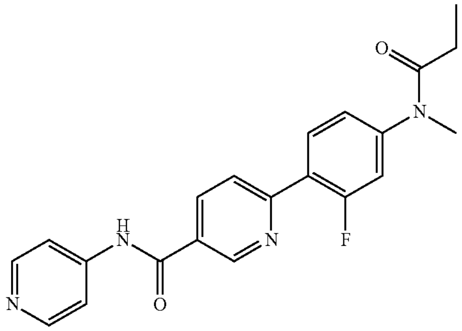
I-T 1371
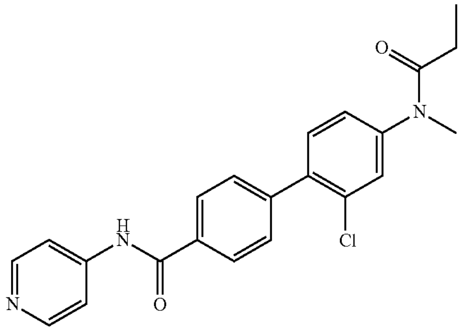
I-T 1372
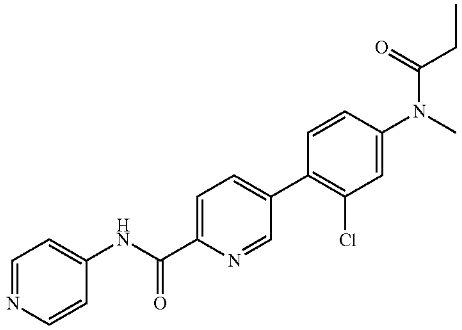
-continued
I-T 1373
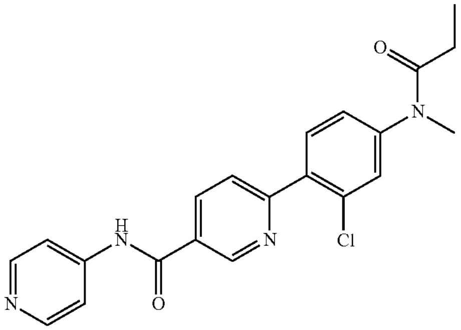
I-T 1374
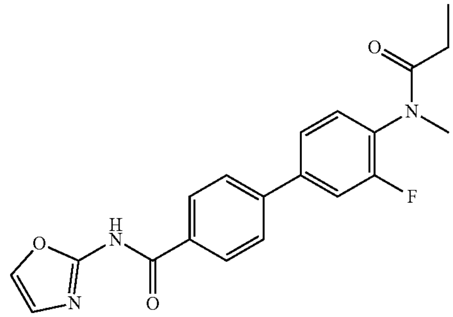
I-T 1375
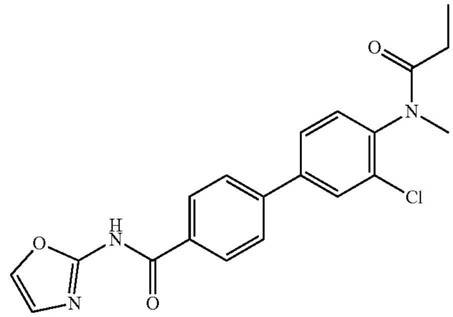
I-T 1376
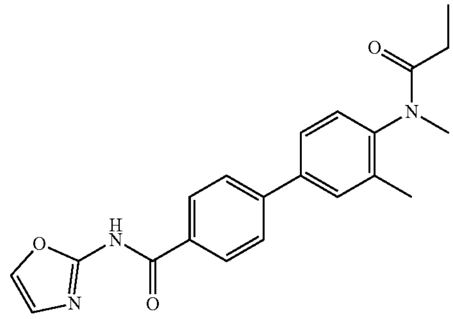
I-T 1377
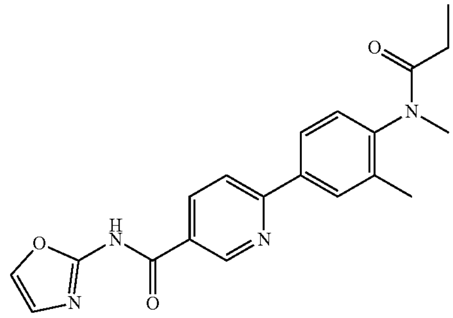

-continued
I-T 1378
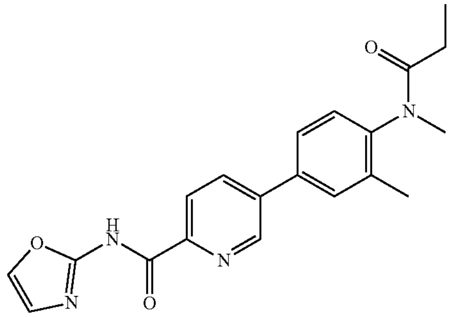
I-T 1379
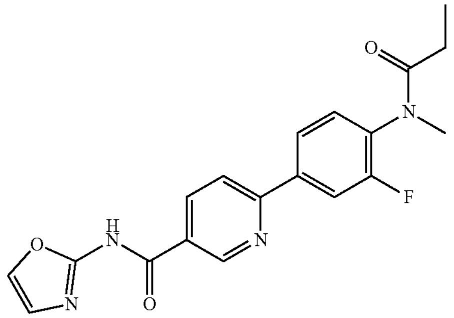
I-T 1380
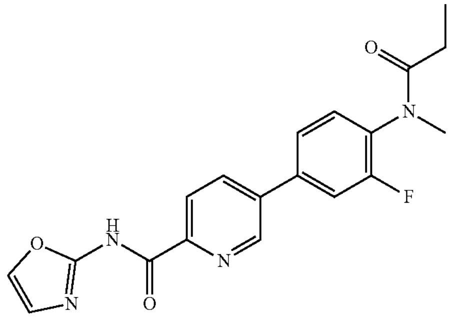
I-T 1381
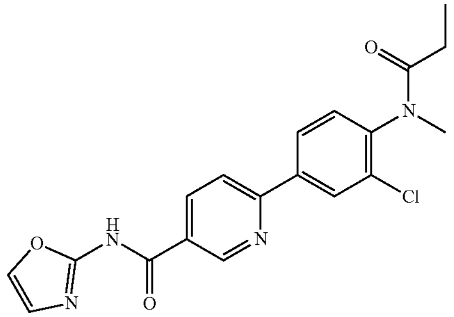
I-T 1382
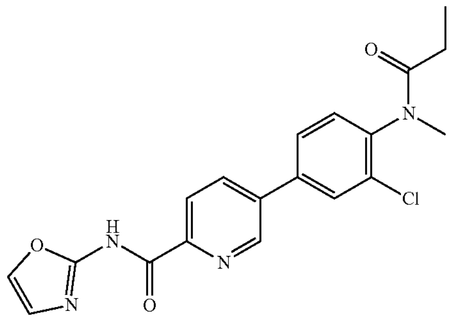
-continued
I-T 1383
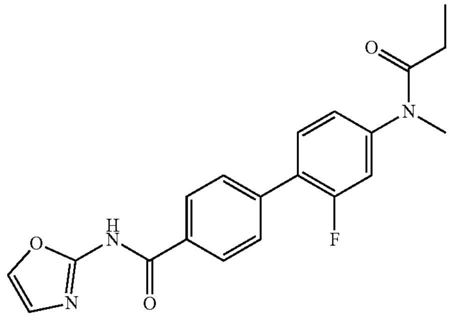
I-T 1384
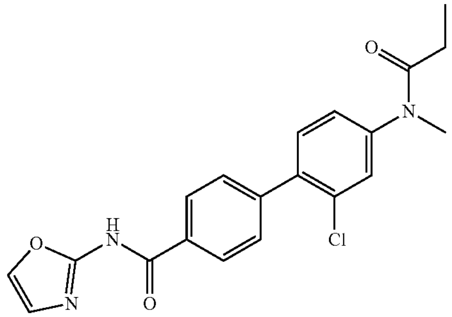
I-T 1385
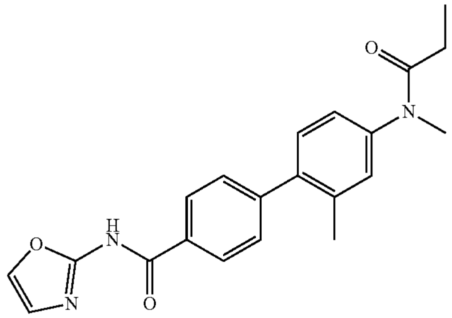
I-T 1386
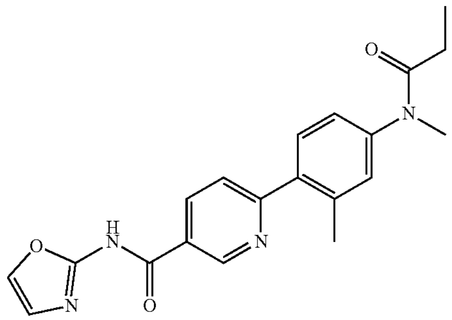
I-T 1387
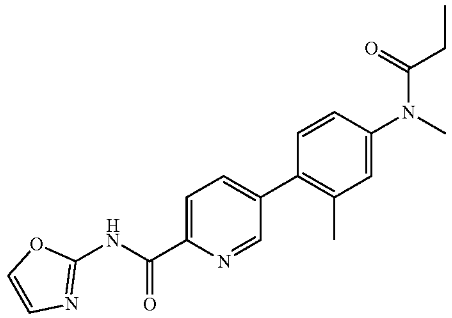

-continued
I-T 1388
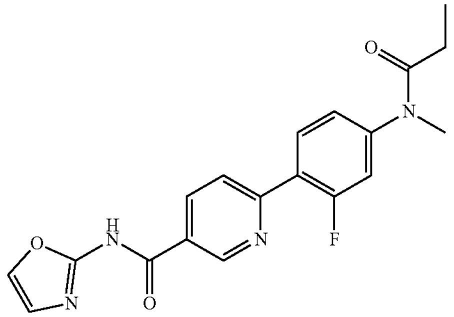
I-T 1389
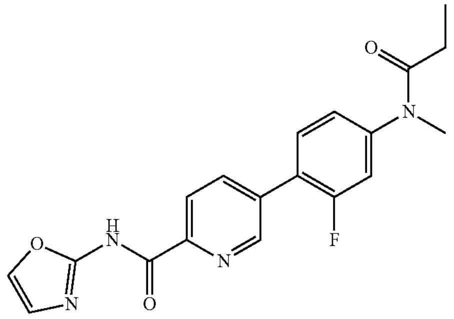
I-T 1390
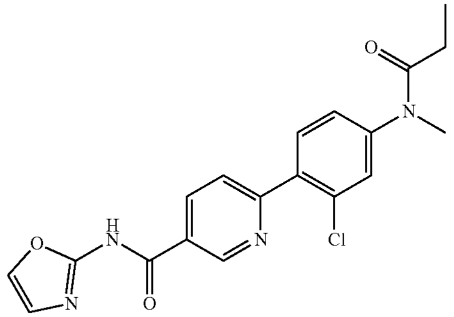
I-T 1391
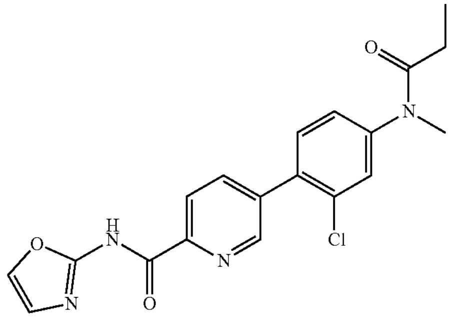
I-T 1392
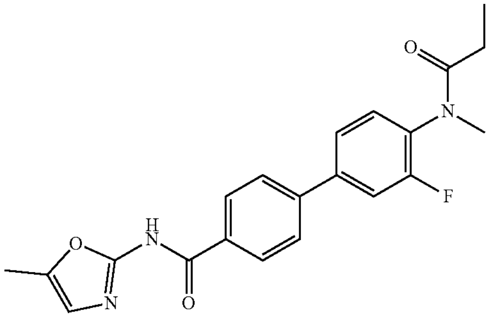
-continued
I-T 1393
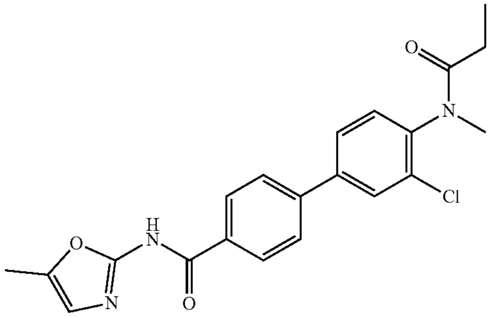
I-T 1394
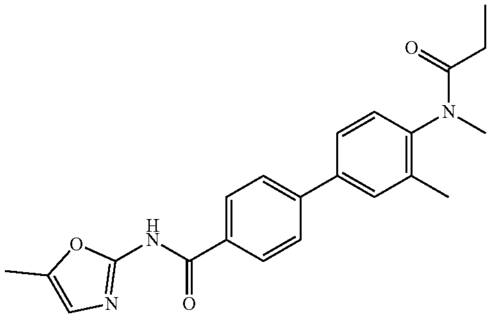
I-T 1395
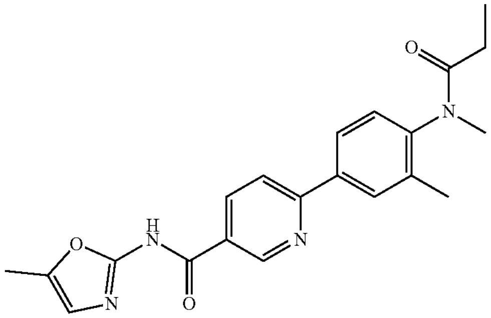
I-T 1396
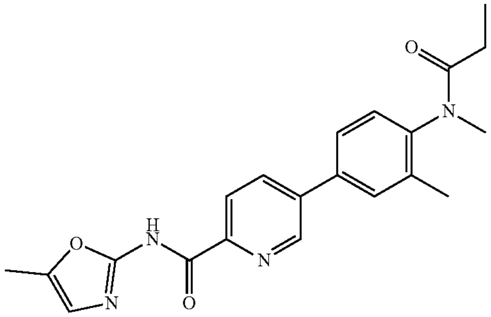

-continued
I-T 1397
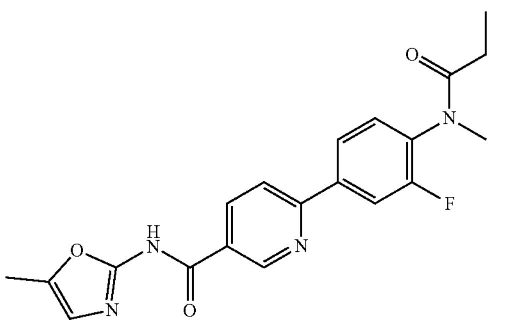
I-T 1398
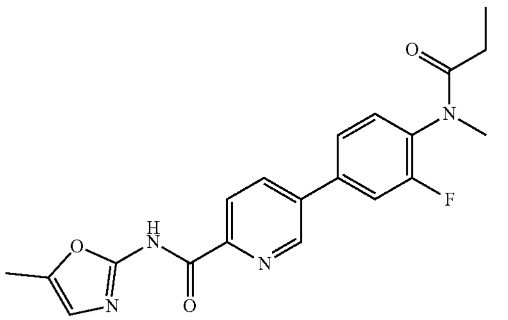
I-T 1399
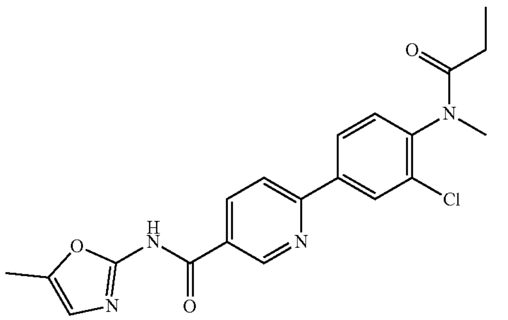
I-T 1400
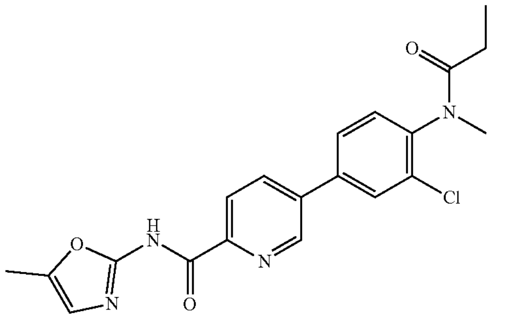
-continued
I-T 1401
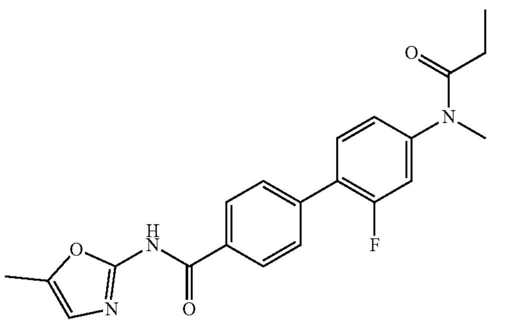
I-T 1402
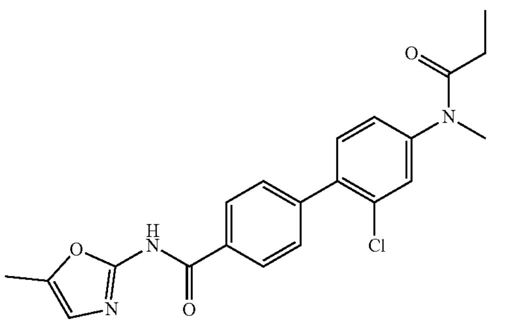
I-T 1403
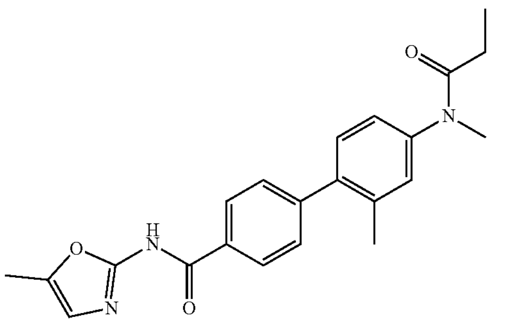
I-T 1404
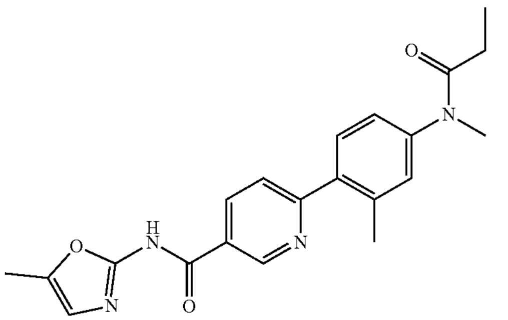

-continued
I-T 1405
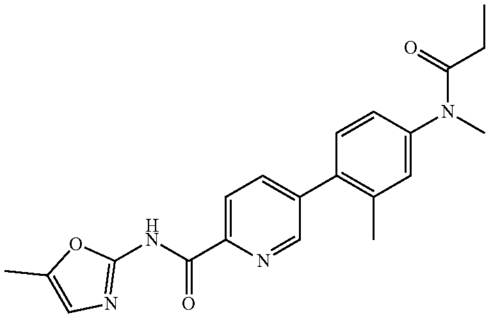
I-T 1406
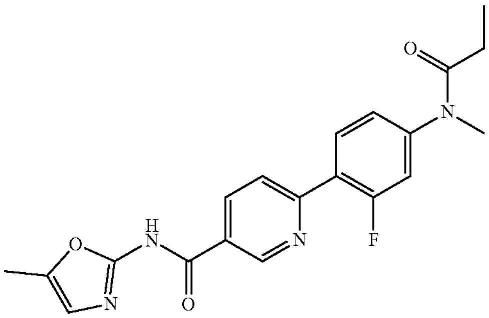
I-T 1407
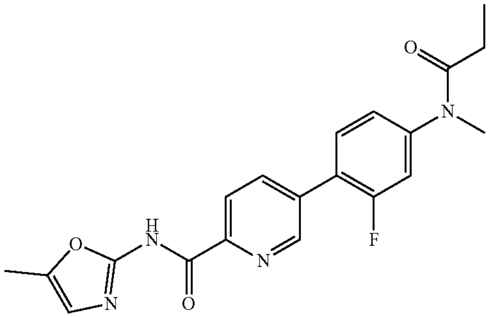
I-T 1408
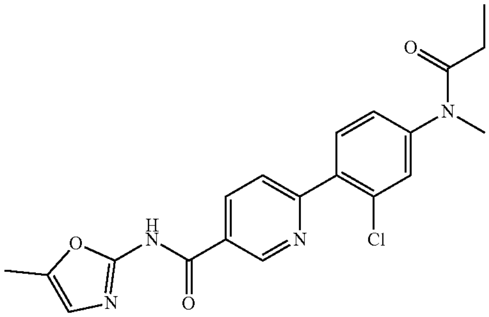
-continued
I-T 1409
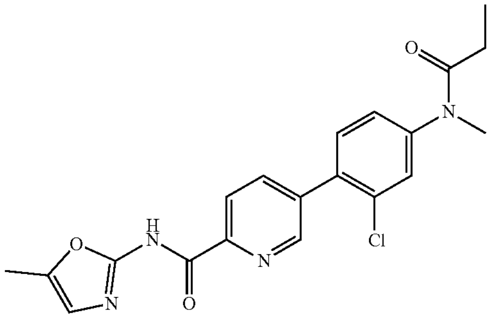
I-T 1410
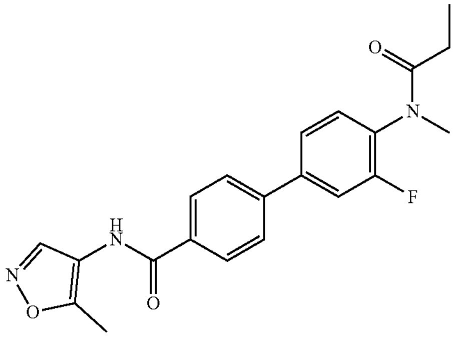
I-T 1411
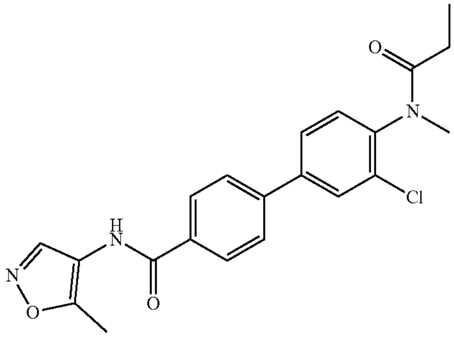
I-T 1412
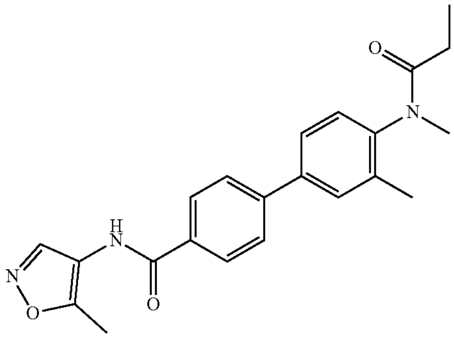

-continued
I-T 1413
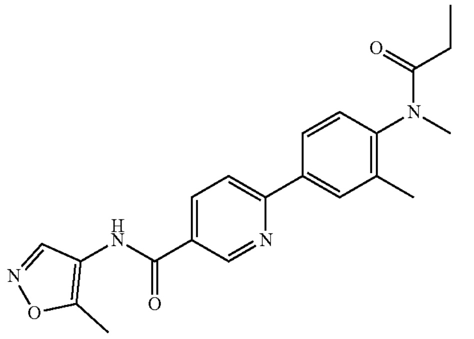
I-T 1414
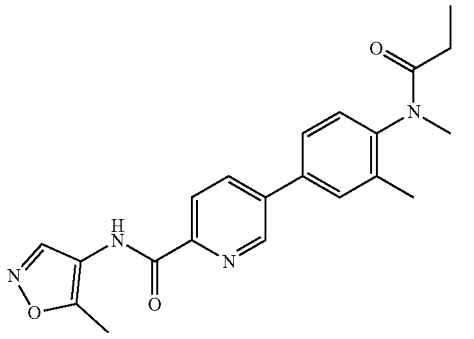
I-T 1415
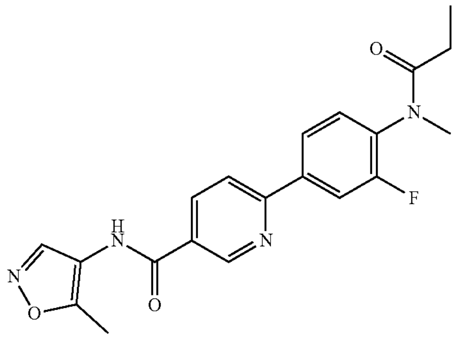
I-T 1416
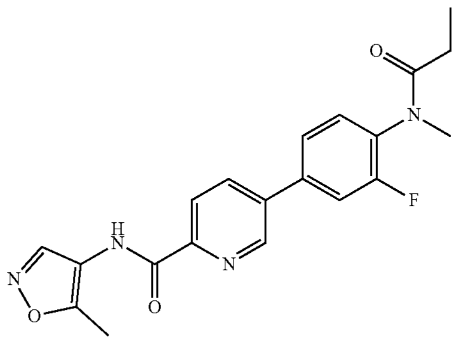
-continued
I-T 1417
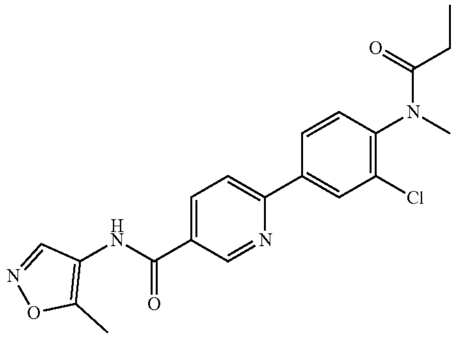
I-T 1418
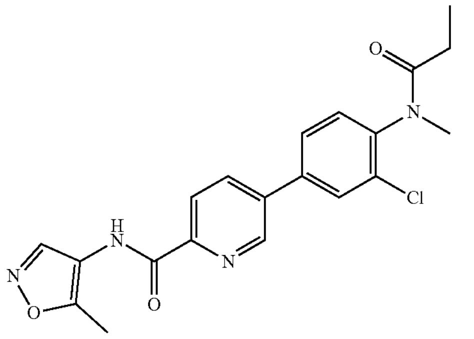
I-T 1419
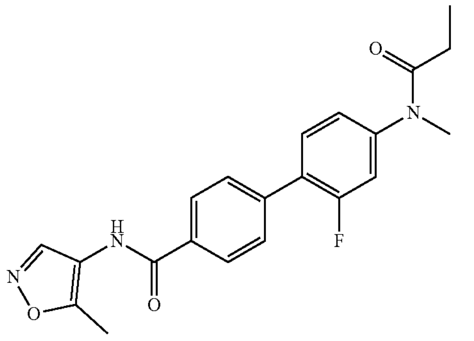
I-T 1420
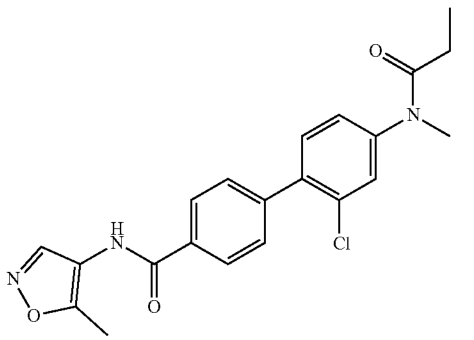

-continued
I-T 1421
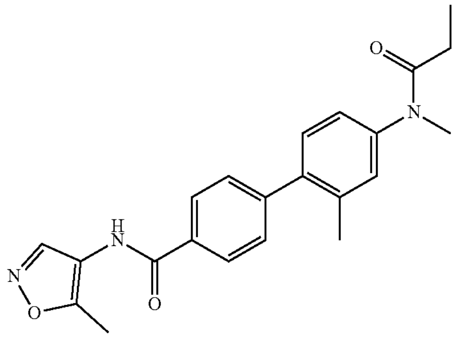
I-T 1422
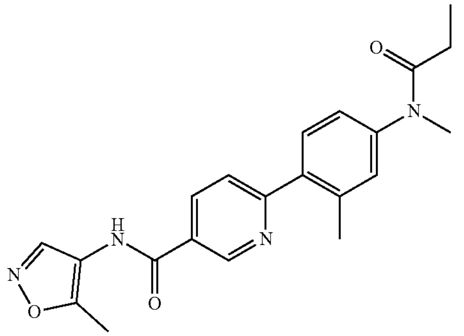
I-T 1423
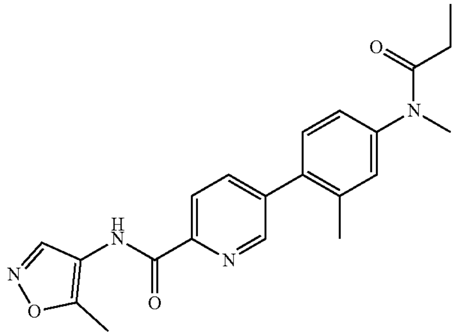
I-T 1424
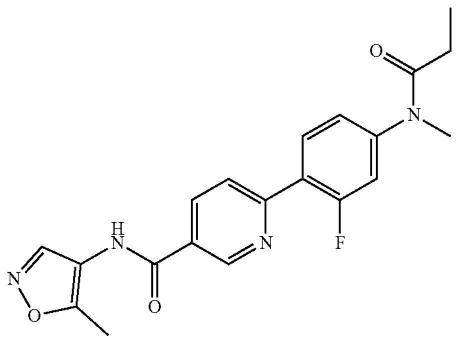
-continued
I-T 1425
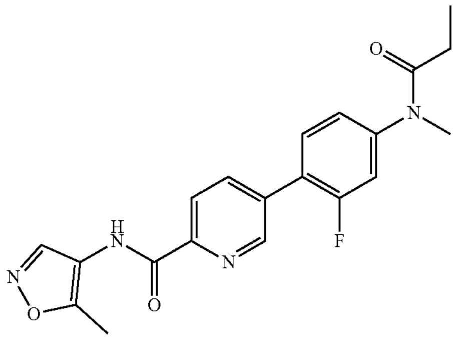
I-T 1426
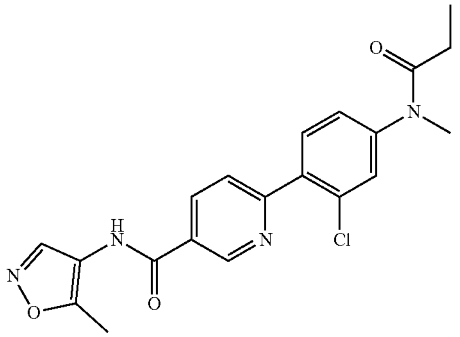
I-T 1427
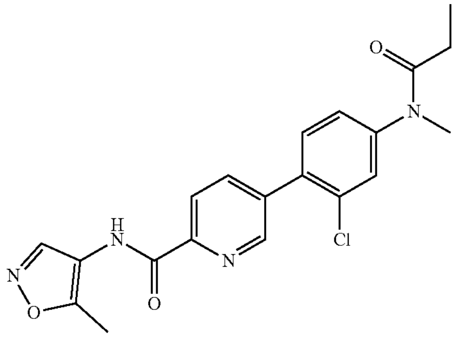
I-T 1428
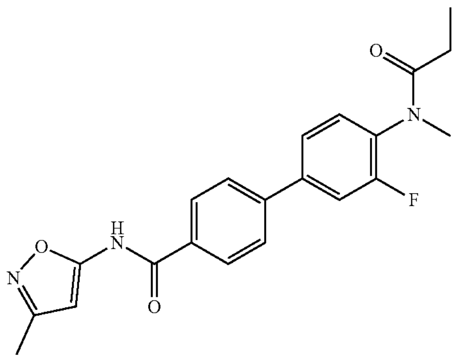

I-T 1429
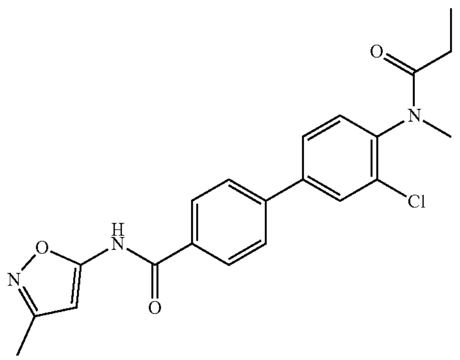
I-T 1430
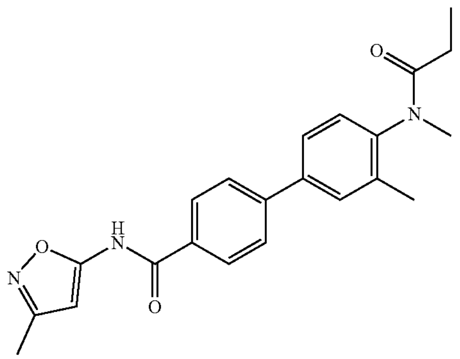
I-T 1431
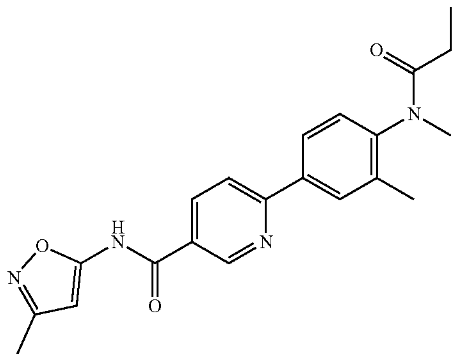
I-T 1432
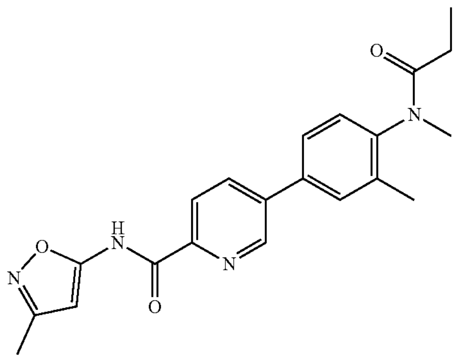
I-T 1433
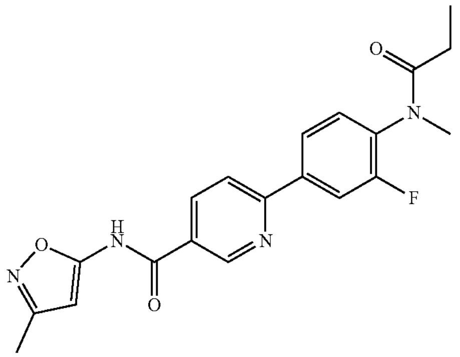
I-T 1434
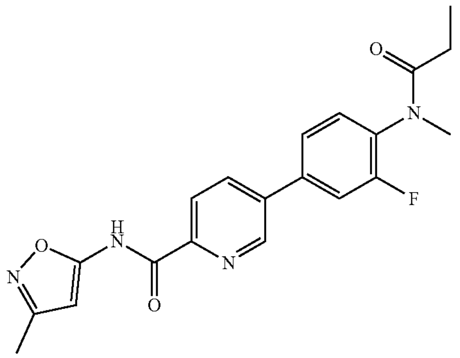
I-T 1435
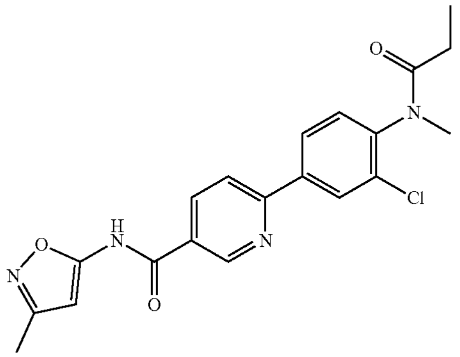
I-T 1436
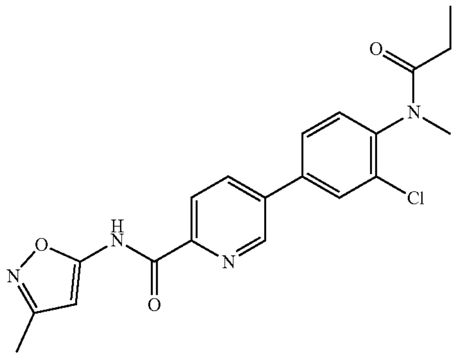

I-T 1437
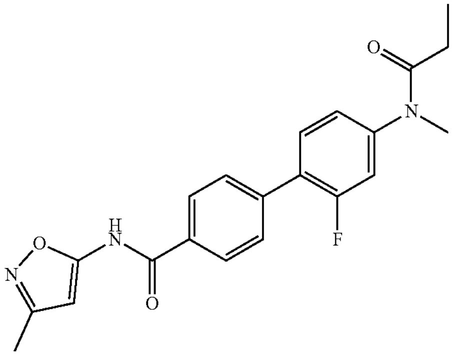
I-T 1438
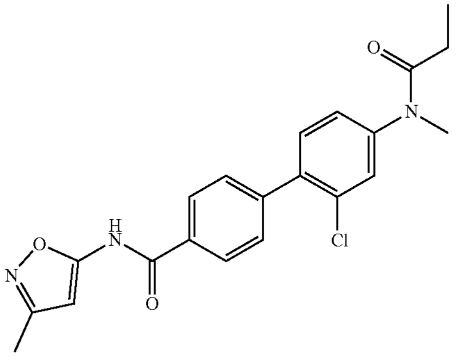
I-T 1439
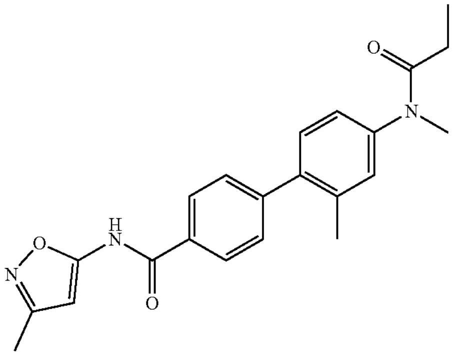
I-T 1440
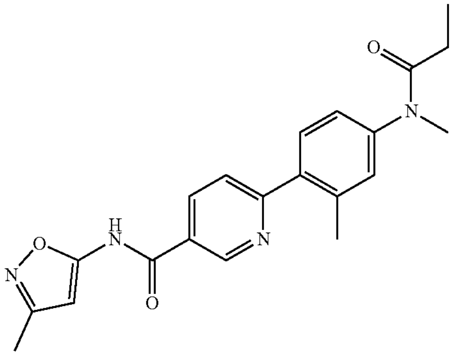
I-T 1441
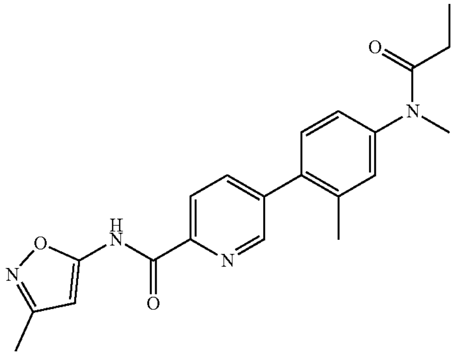
I-T 1442
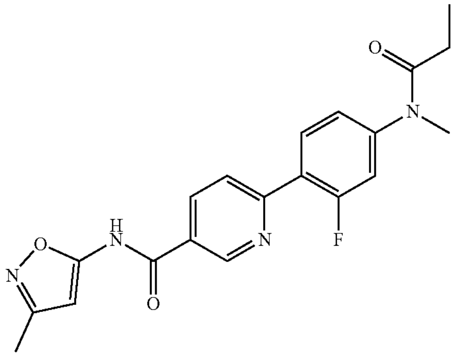
I-T 1443
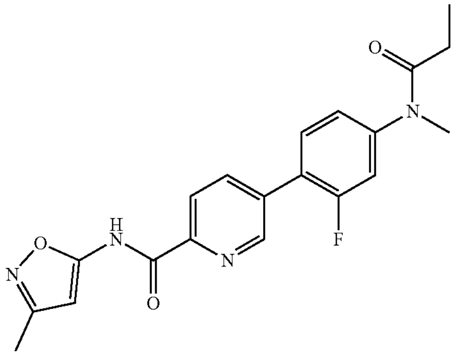
I-T 1444
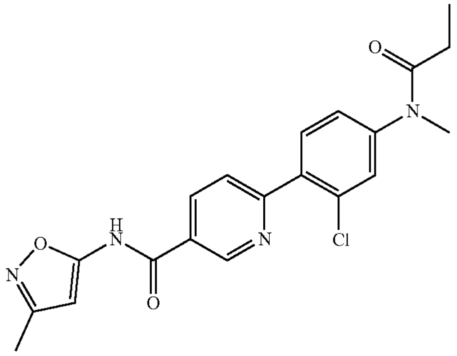

-continued
I-T 1445
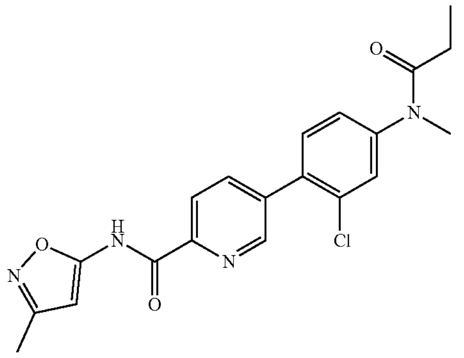
I-T 1446
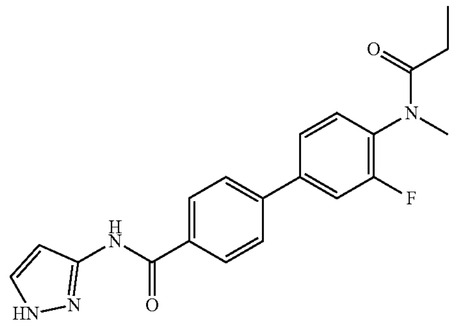
I-T 1447
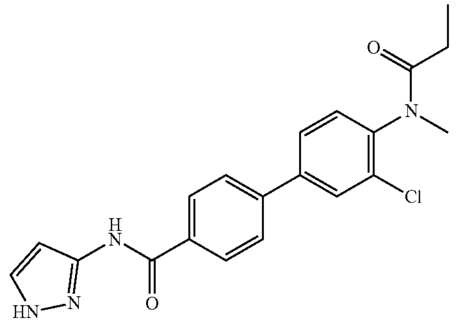
I-T 1448
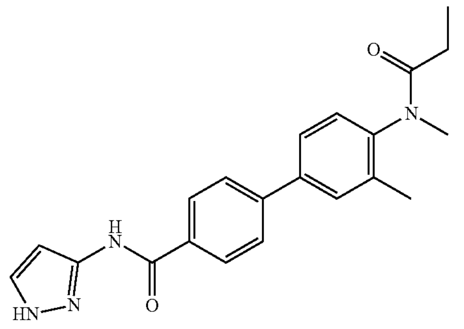
-continued
I-T 1449
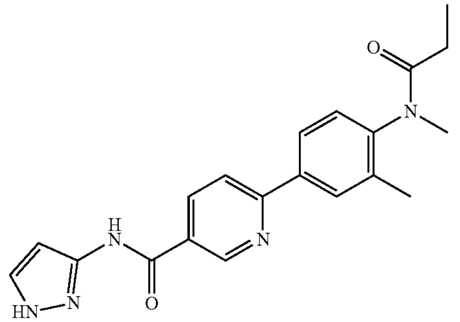
I-T 1450
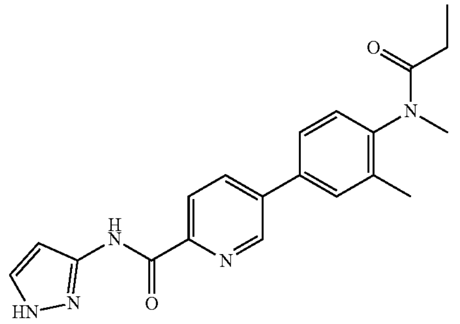
I-T 1451
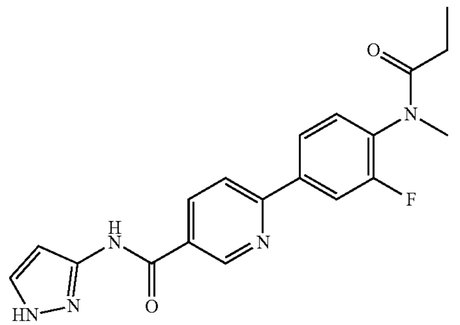
I-T 1452
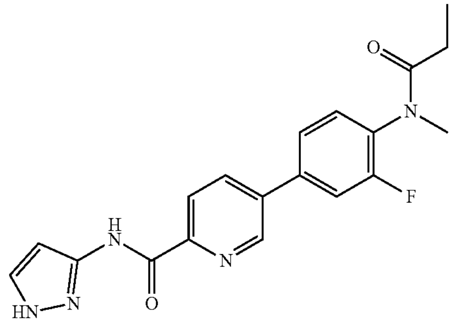

-continued
I-T 1453
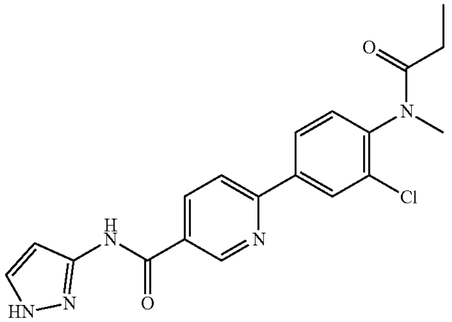
I-T 1454
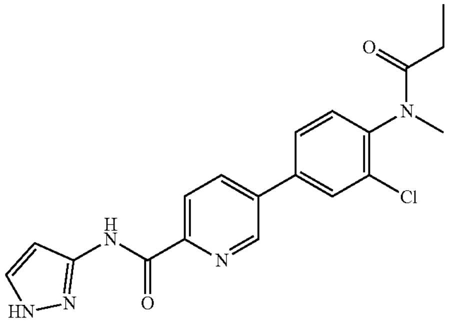
I-T 1455
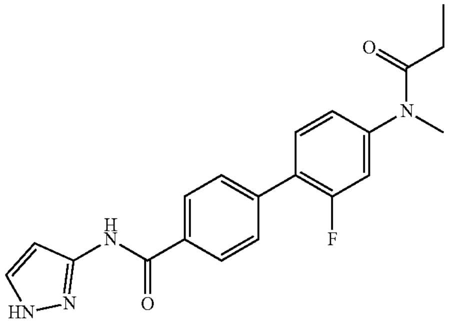
I-T 1456
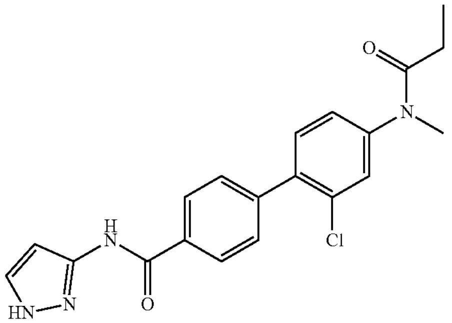
I-T 1457
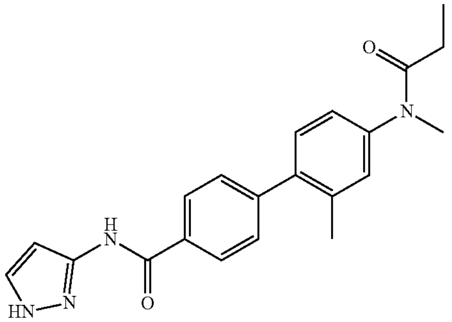
-continued
I-T 1458
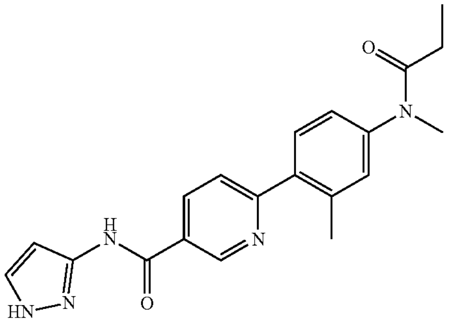
I-T 1459
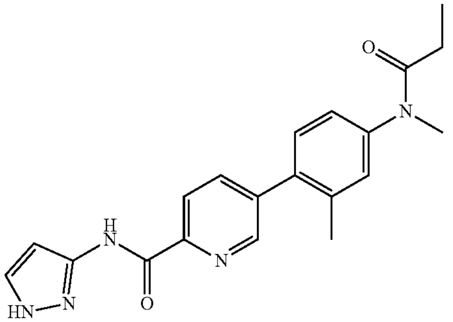
I-T 1460
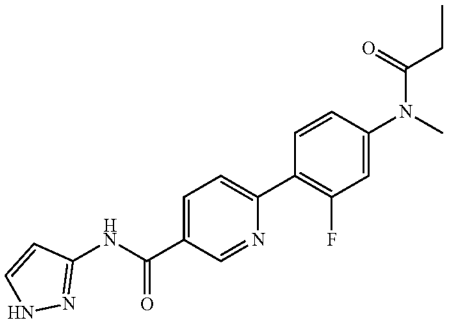
I-T 1461
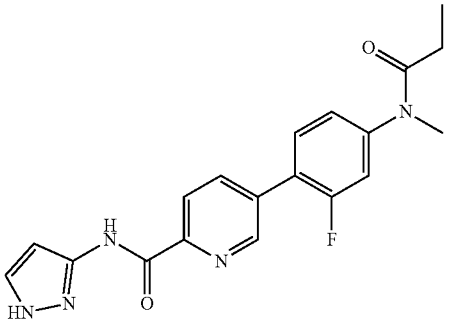
I-T 1462
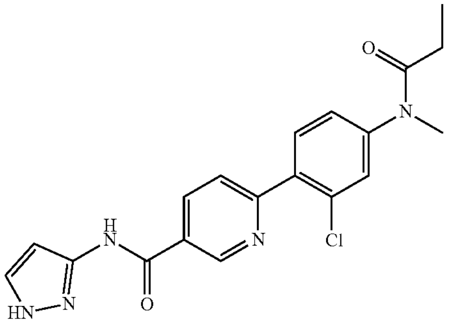

-continued
I-T 1463
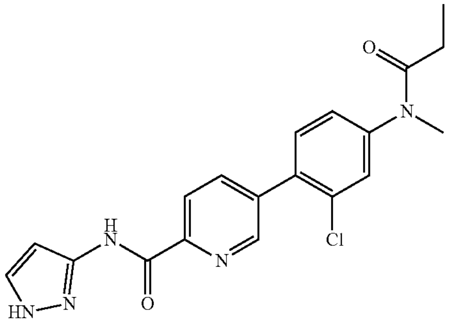
I-T 1464
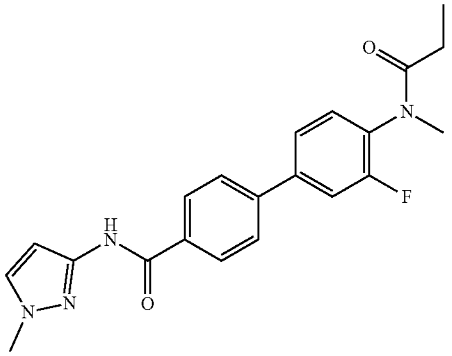
I-T 1465
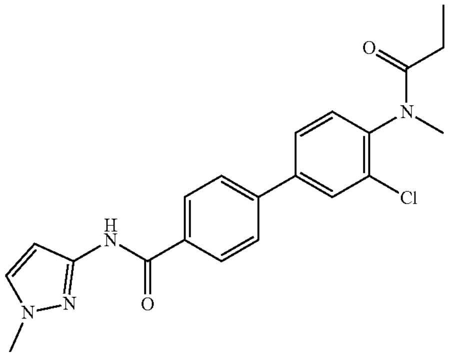
I-T 1466
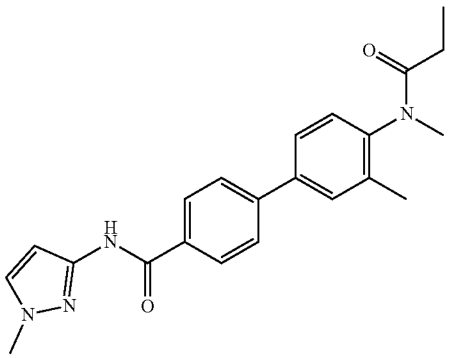
-continued
I-T 1467
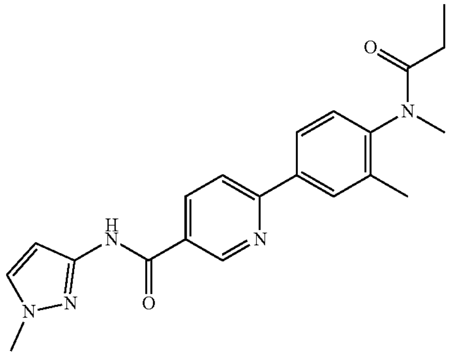
I-T 1468
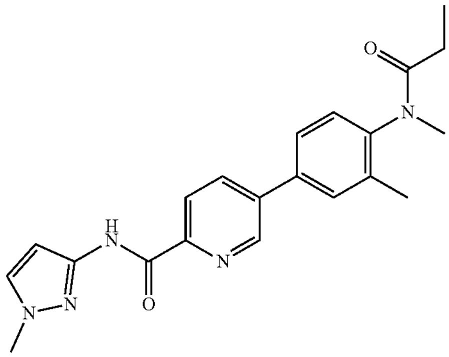
I-T 1469
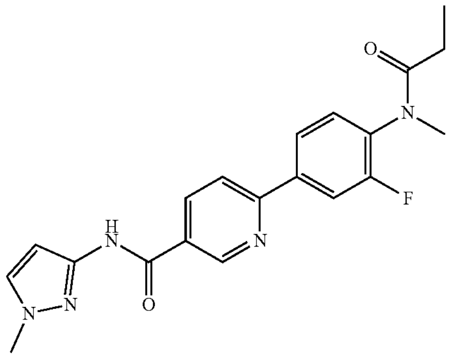
I-T 1470
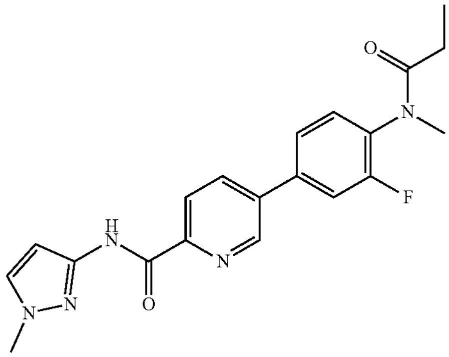

-continued
I-T 1471
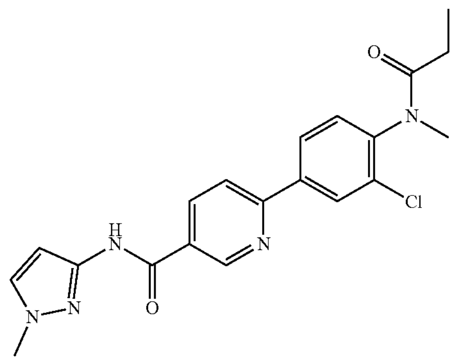
I-T 1472
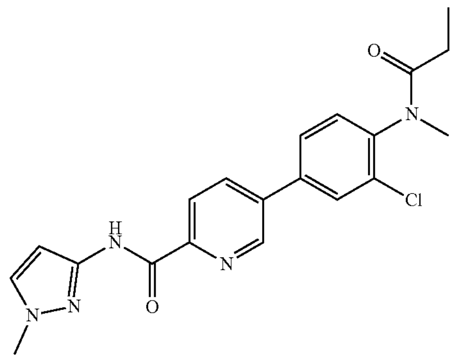
I-T 1473
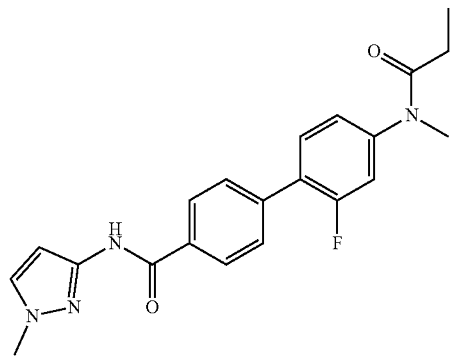
I-T 1474
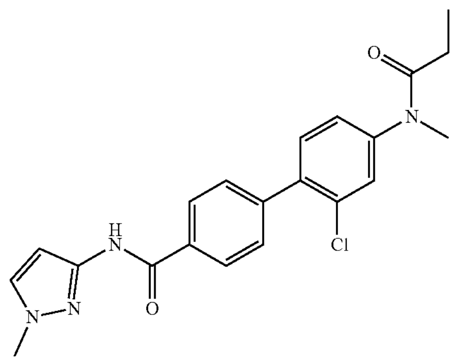
-continued
I-T 1475
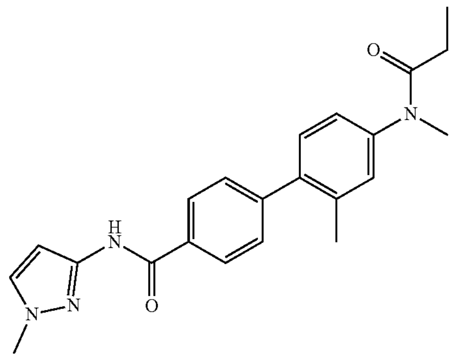
I-T 1476
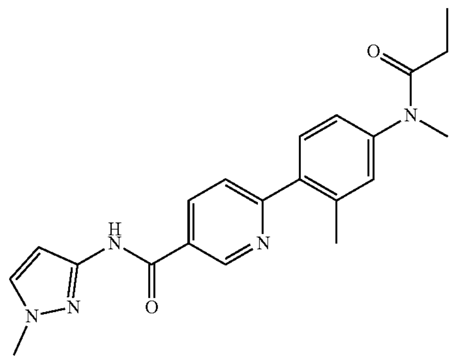
I-T 1477
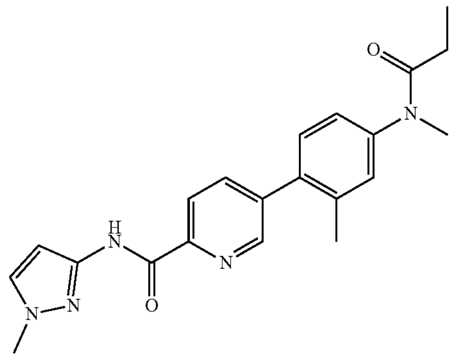
I-T 1478
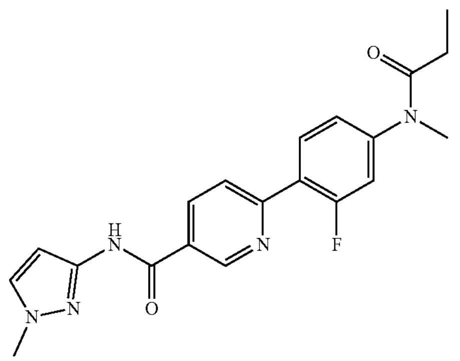

-continued
I-T 1479
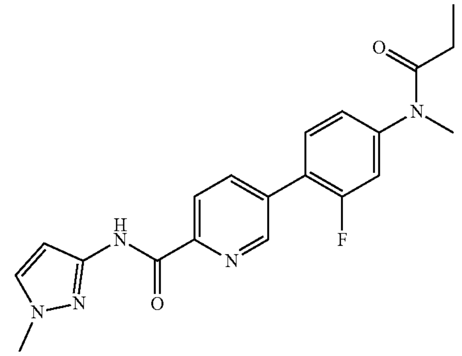
I-T 1480
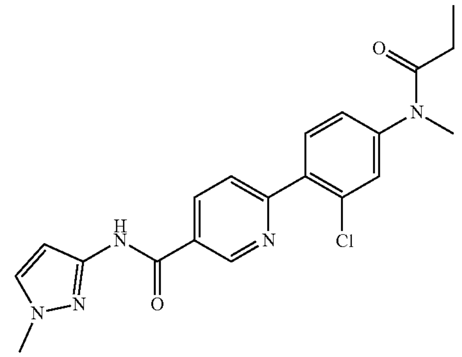
I-T 1481
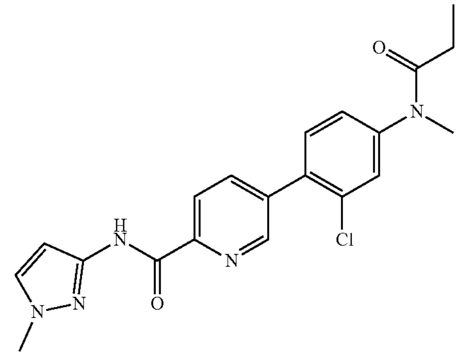
I-T 1482
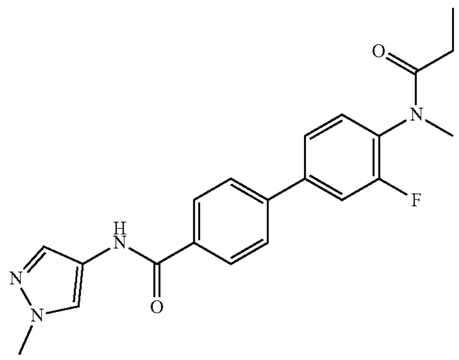
-continued
I-T 1483
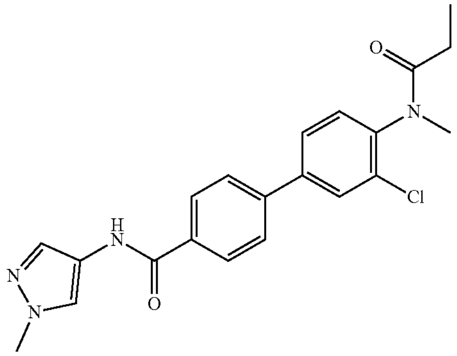
I-T 1484
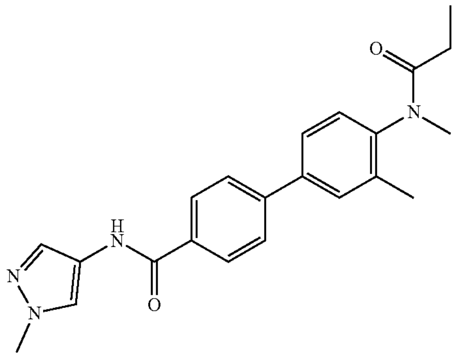
I-T 1485
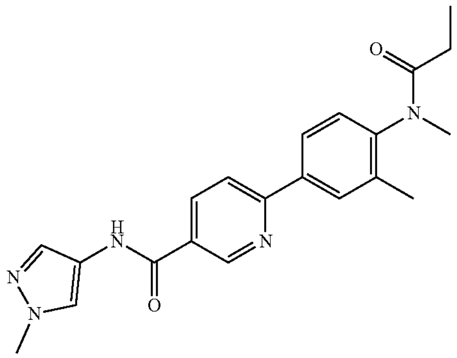
I-T 1486
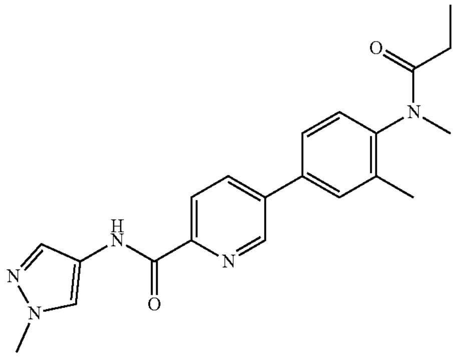

-continued
I-T 1487
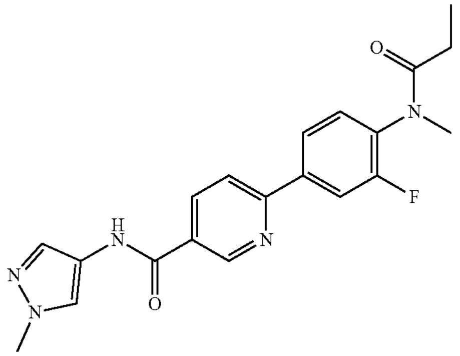
I-T 1488
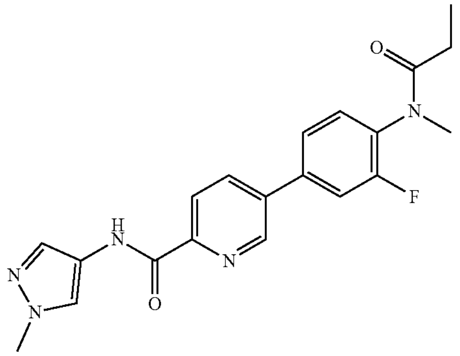
I-T 1489
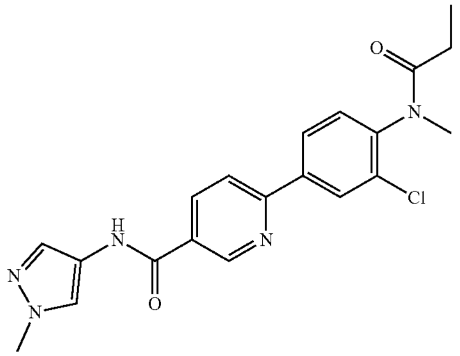
I-T 1490
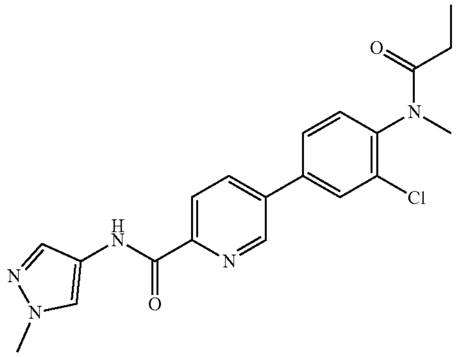
-continued
I-T 1491
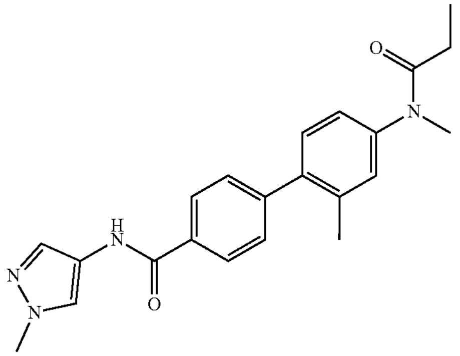
I-T 1492
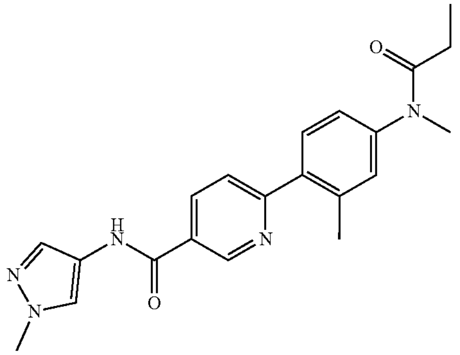
I-T 1493
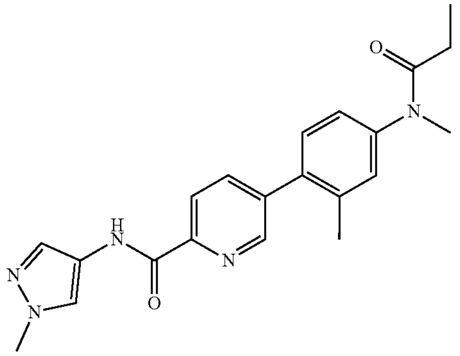
I-T 1494
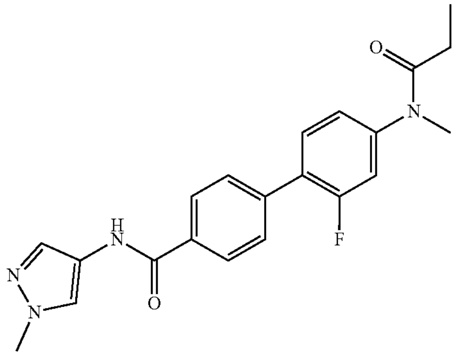

I-T 1495
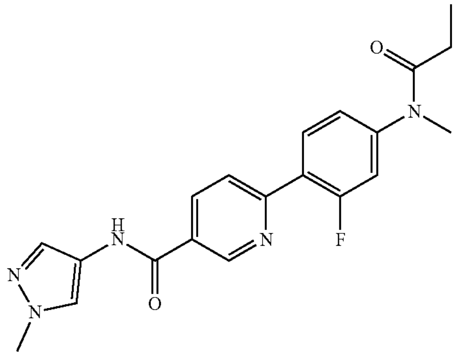
I-T 1496
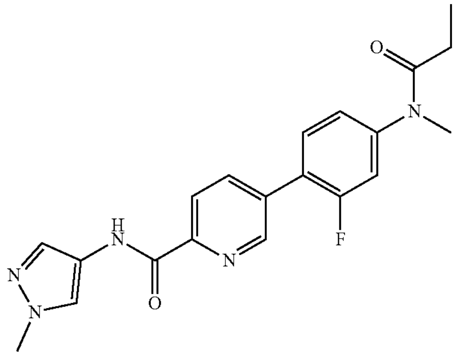
I-T 1497
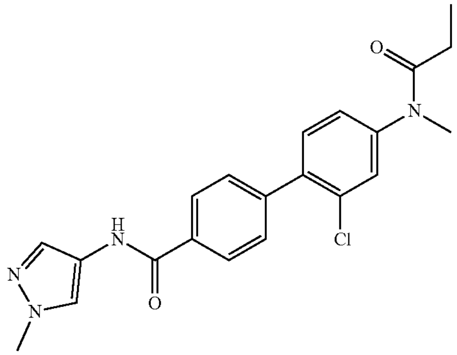
I-T 1498
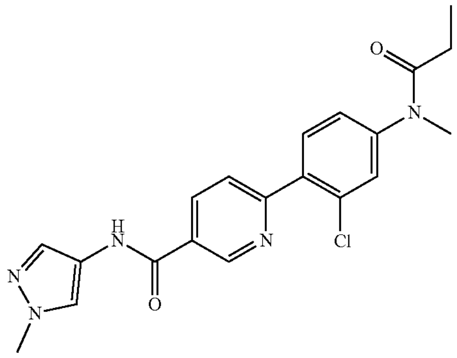
I-T 1499
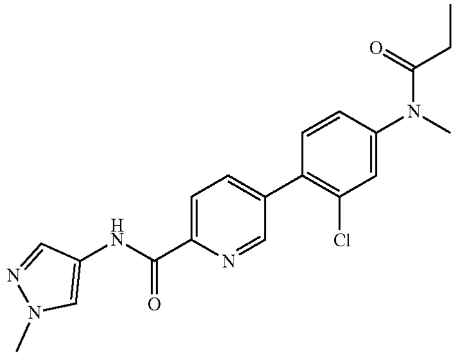
I-T 1500
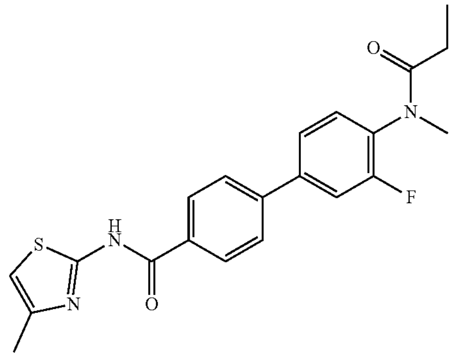
I-T 1501
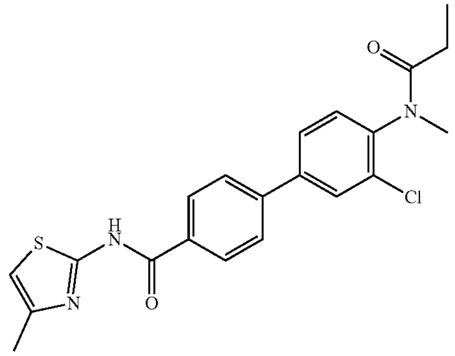
I-T 1502
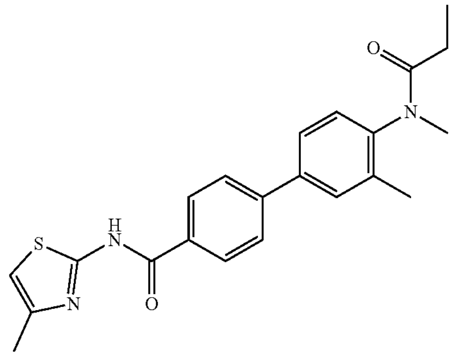

I-T 1503
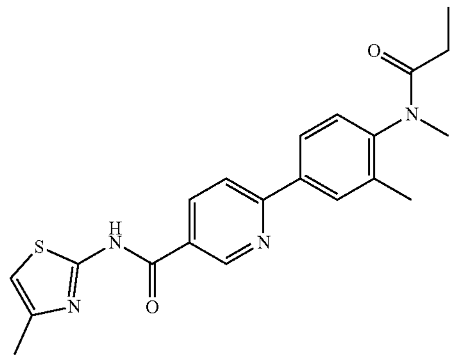
I-T 1504
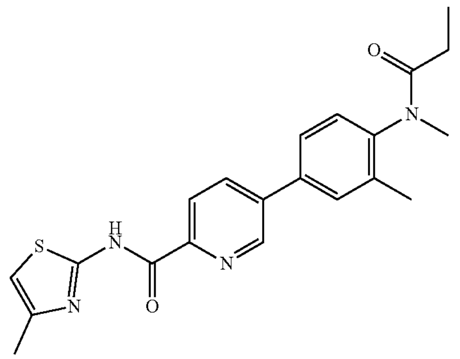
I-T 1505
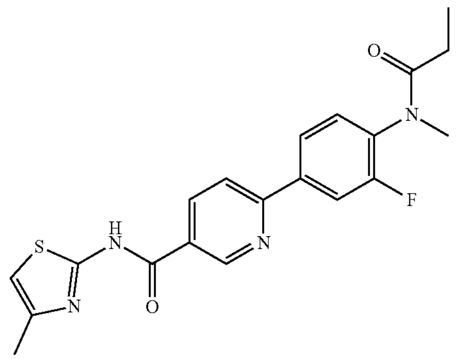
I-T 1506
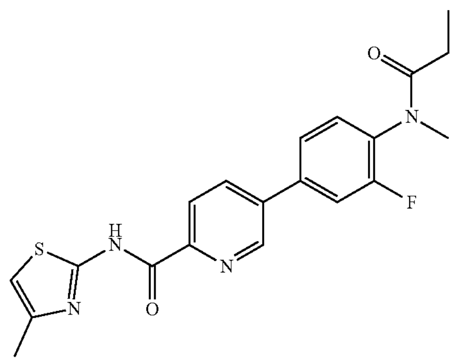
I-T 1507
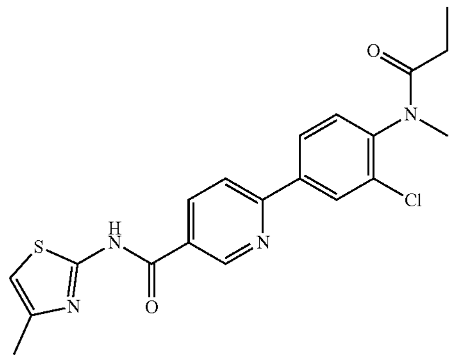
I-T 1508
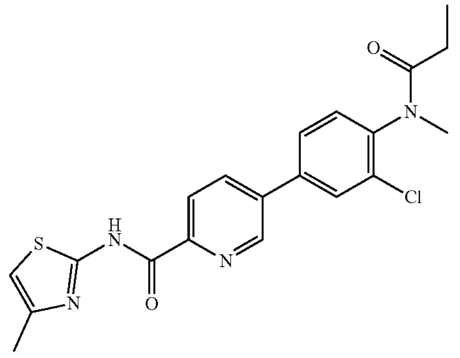
I-T 1509
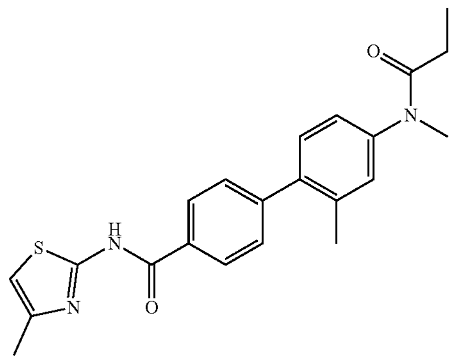
I-T 1510
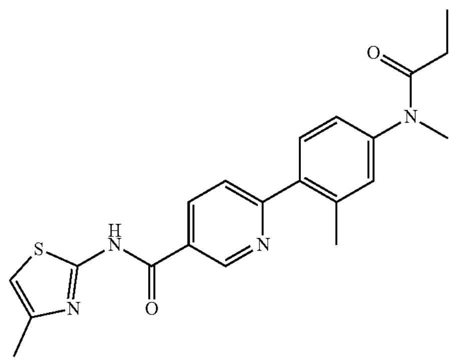

-continued
I-T 1511
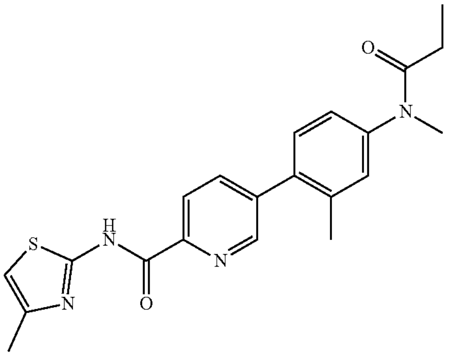
I-T 1512
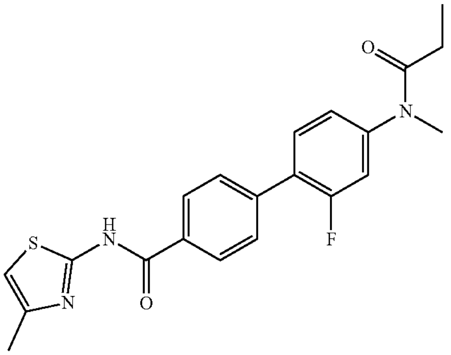
I-T 1513
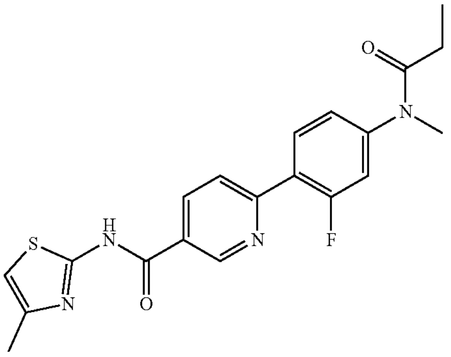
I-T 1514
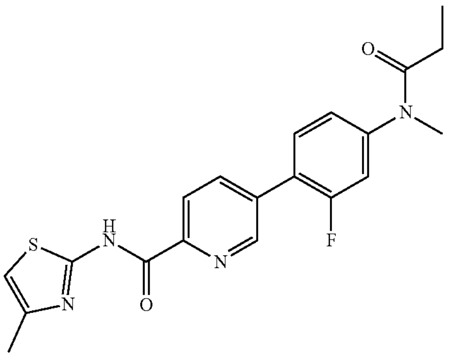
-continued
I-T 1515
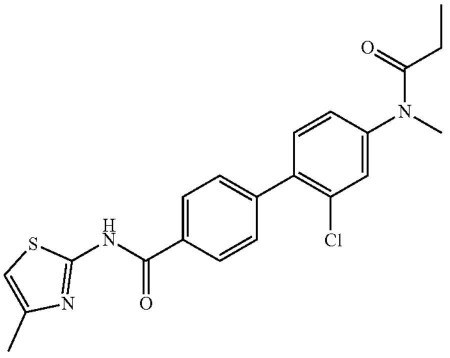
I-T 1516
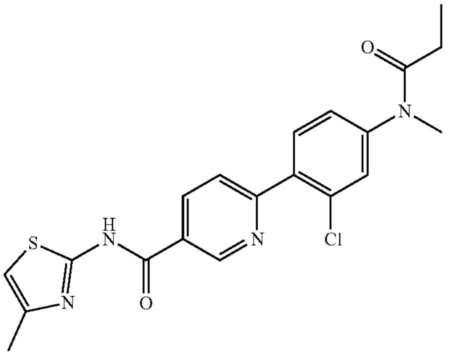
I-T 1517
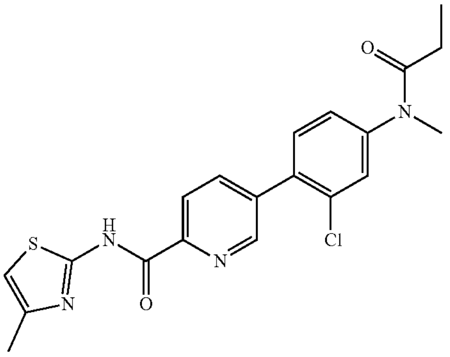
I-T 1518
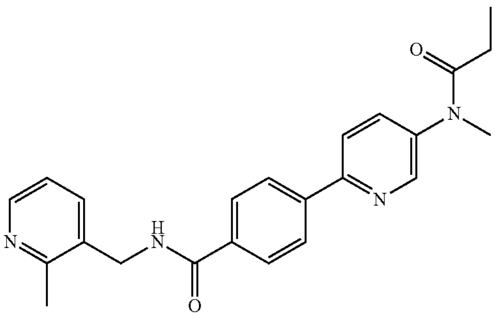

-continued
I-T 1519
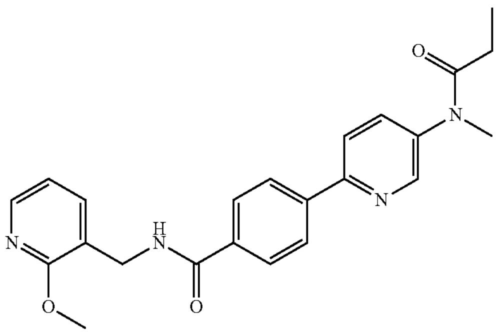
I-T 1520
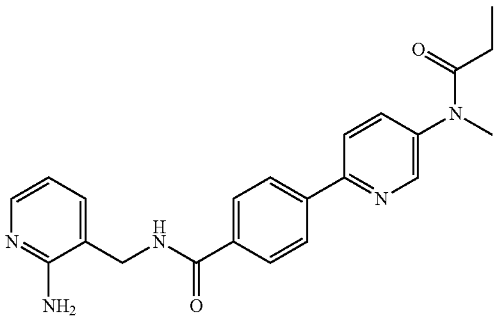
I-T 1521
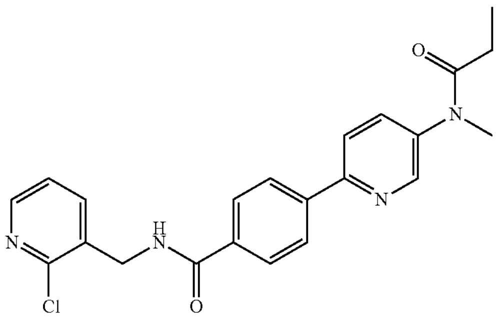
I-T 1522
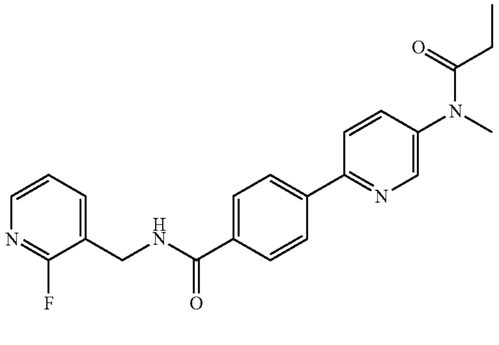
-continued
I-T 1523
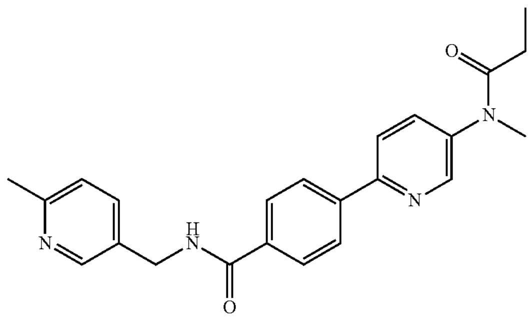
I-T 1524
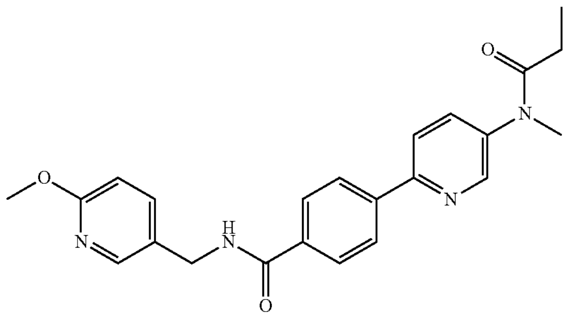
I-T 1525
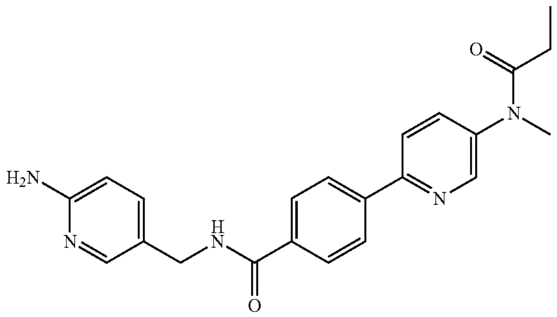
I-T 1526
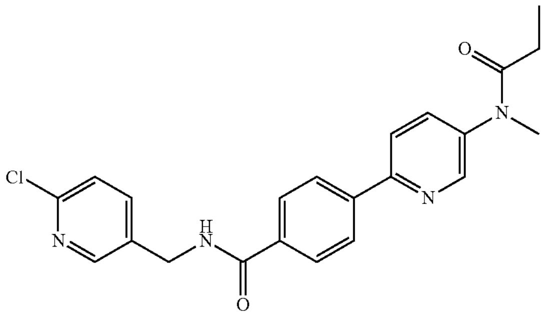

-continued
I-T 1527
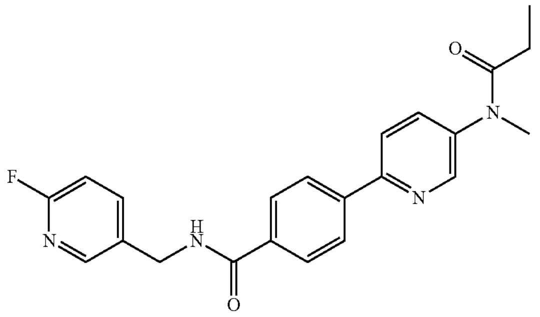
I-T 1528
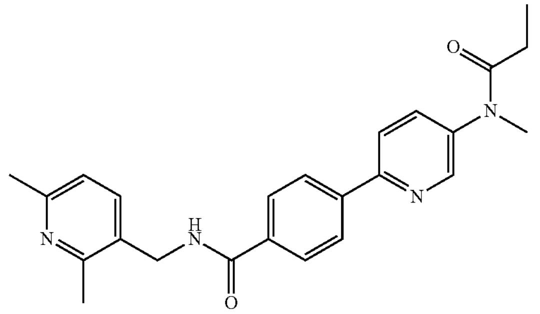
I-T 1529
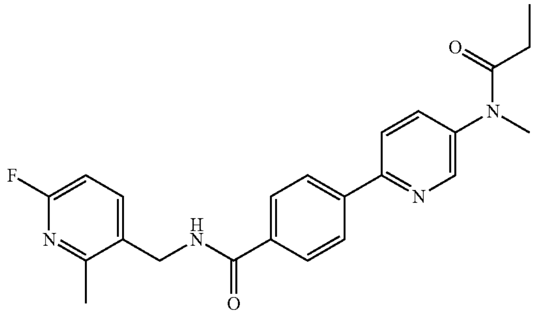
I-T 1530
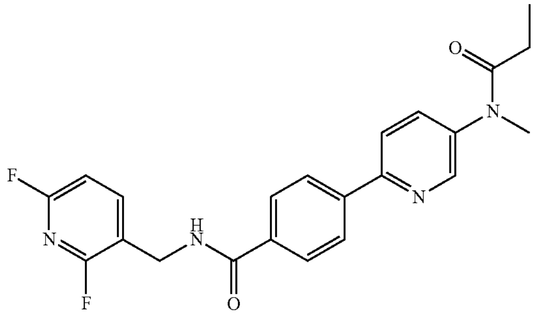
-continued
I-T 1531
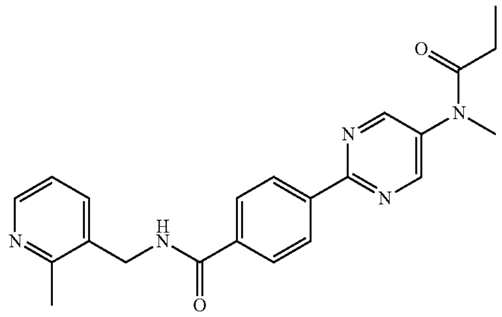
I-T 1532
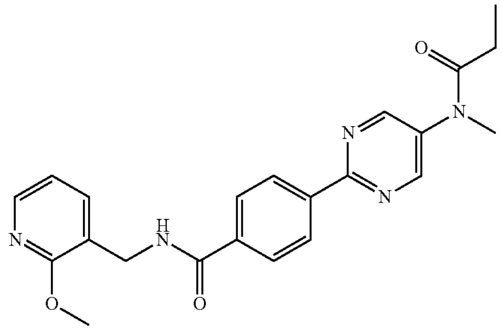
I-T 1533
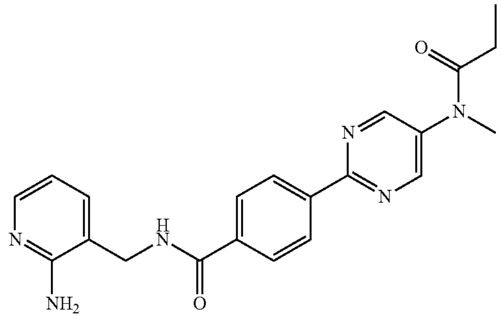
I-T 1534
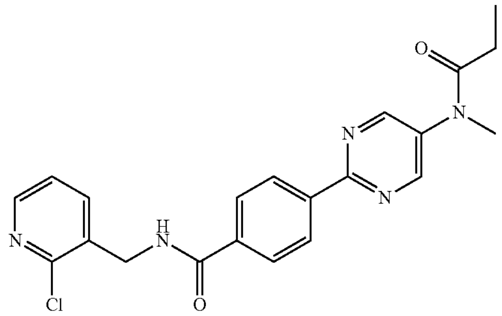

-continued
I-T 1535
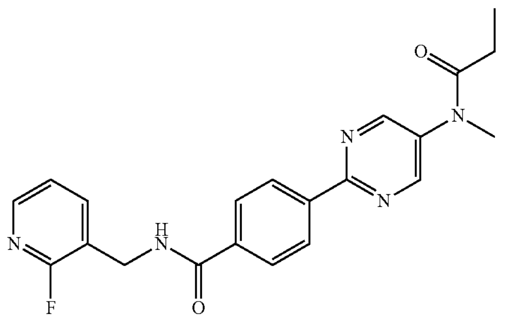
I-T 1536
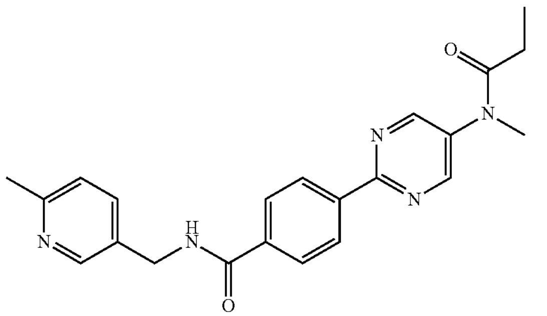
I-T 1537
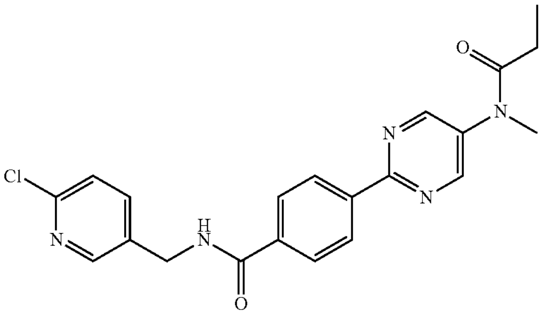
I-T 1538
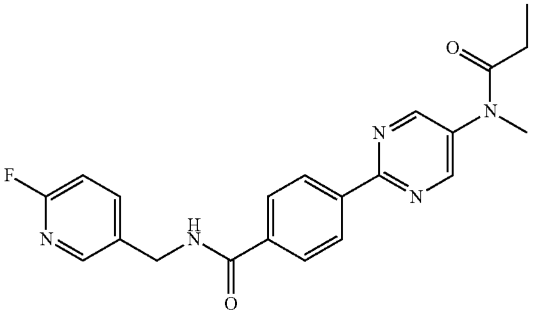
-continued
I-T 1539
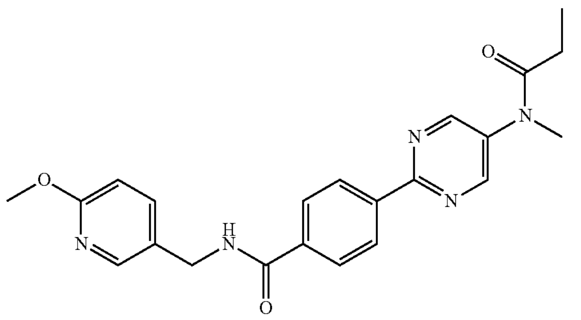
I-T 1540
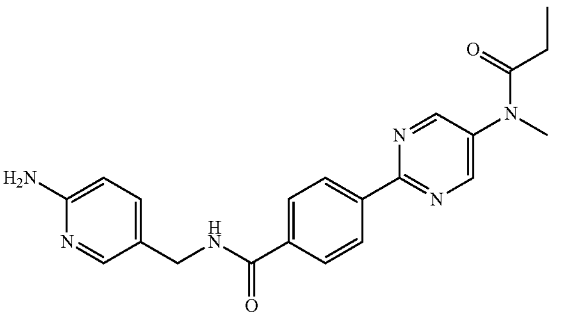
I-T 1541
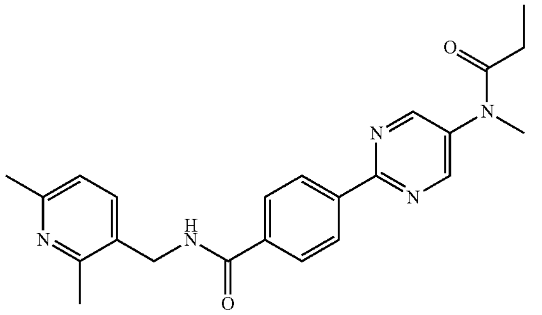
I-T 1542
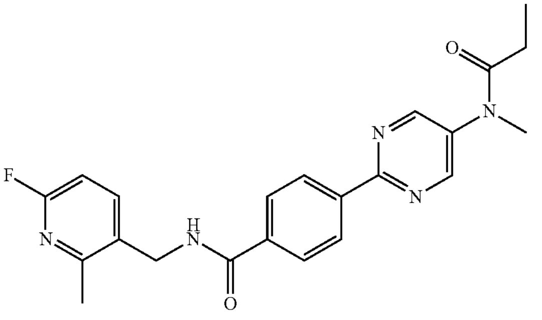

-continued
I-T 1543
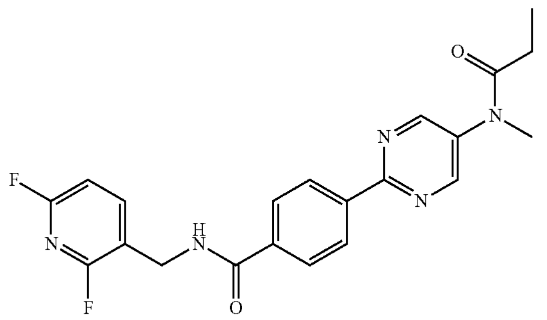
I-T1544
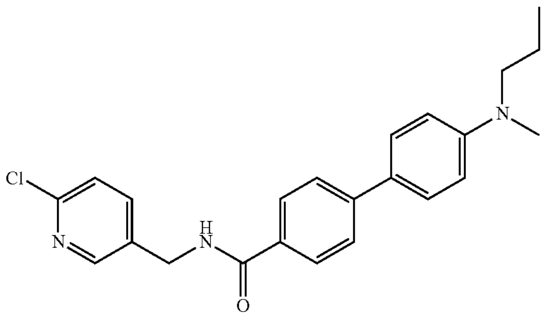
I-T 1545
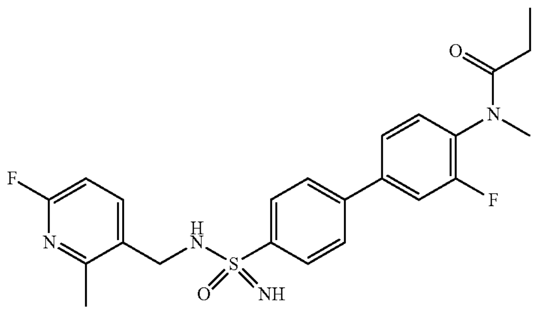
I-T 1546
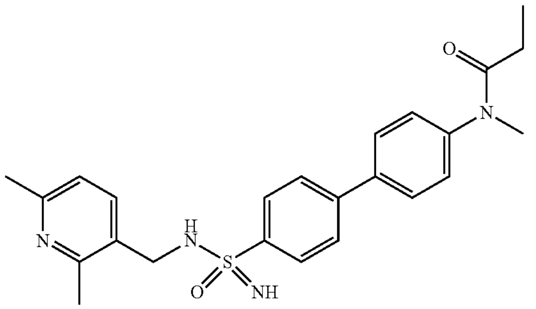
-continued
I-T 1547
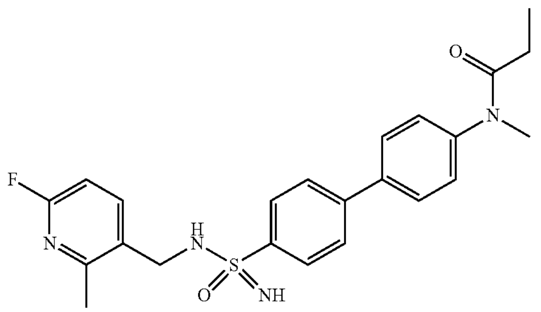
I-T 1548
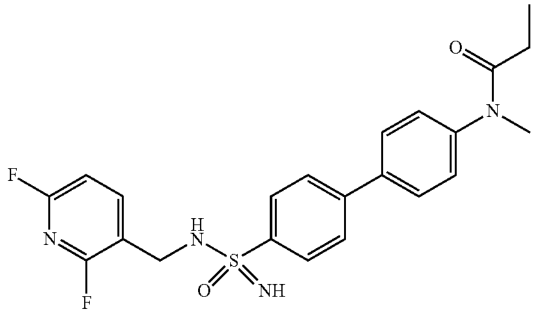
I-T 1549
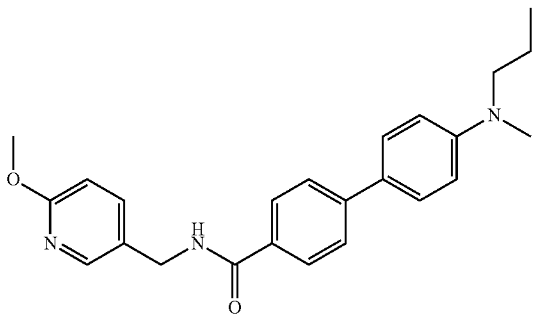
I-T 1550
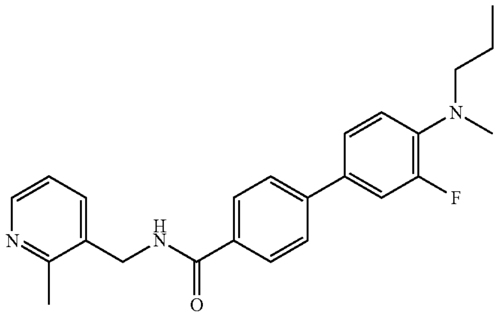

-continued
I-T 1551
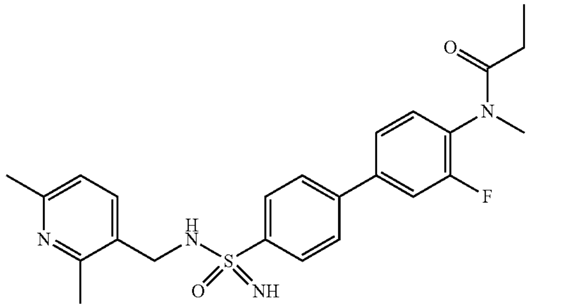
I-T 1552
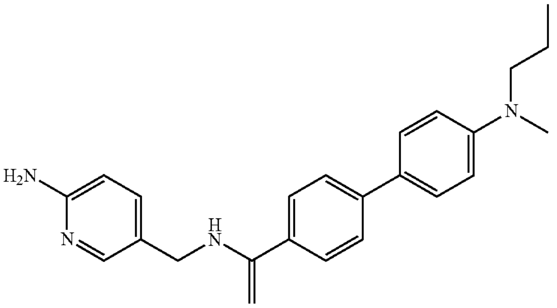
I-T 1553
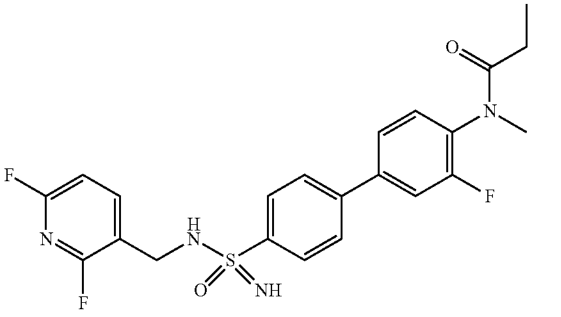
I-T 1554
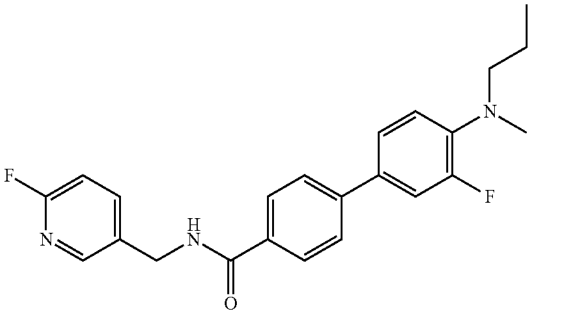
-continued
I-T 1555
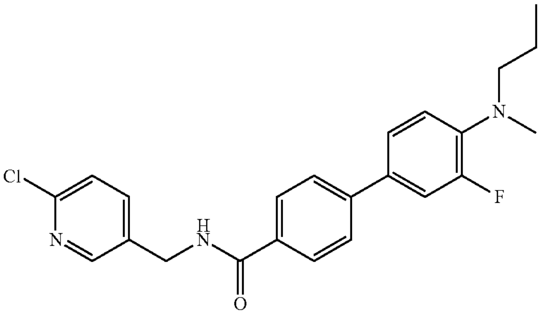
I-T 1556
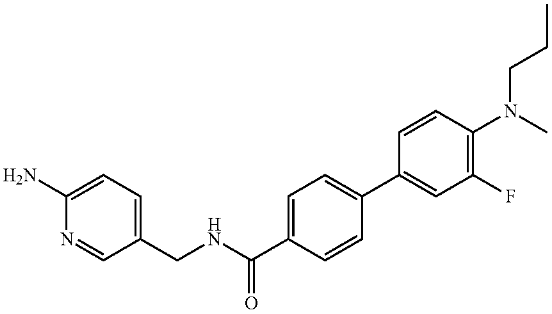
I-T 1557
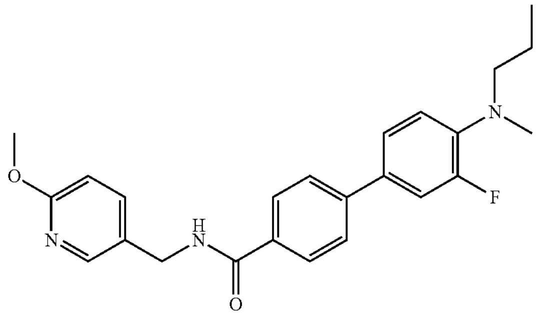
I-T 1558
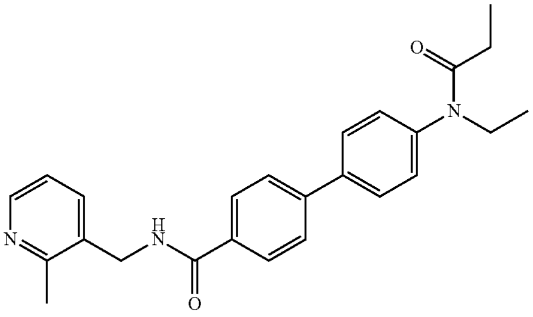

-continued
I-T 1559
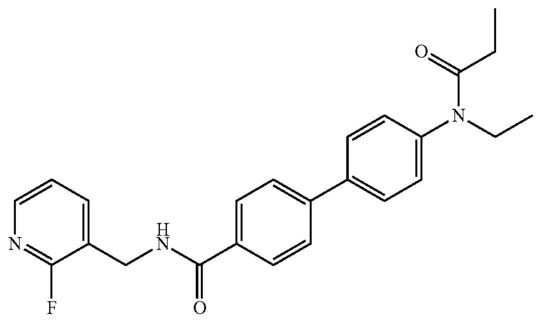
I-T 1560
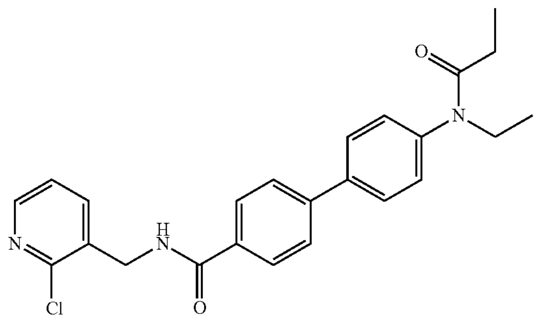
I-T 1561
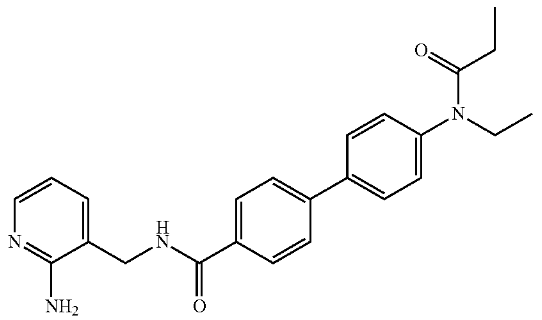
I-T 1562
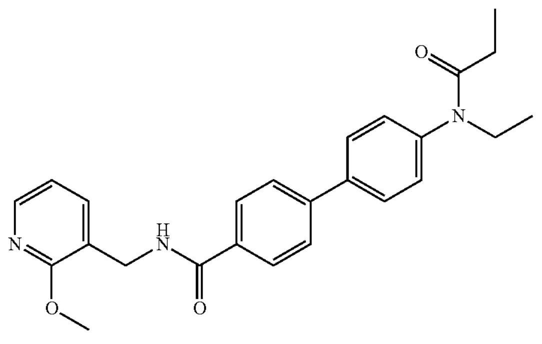
-continued
I-T 1563
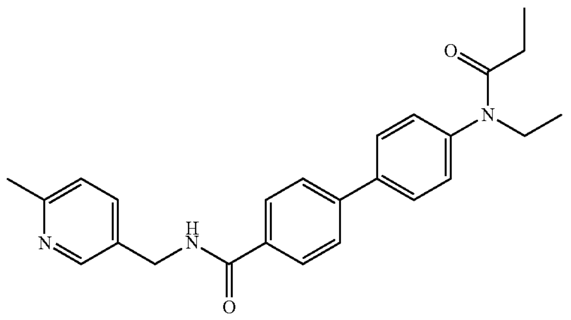
I-T 1564
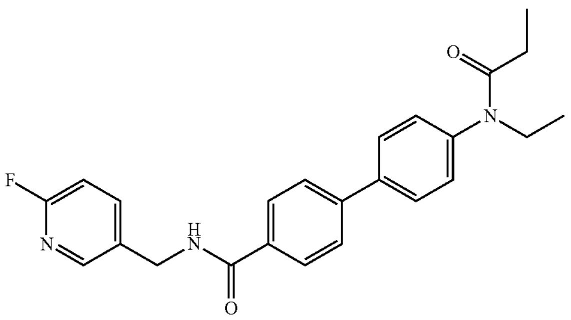
I-T 1565
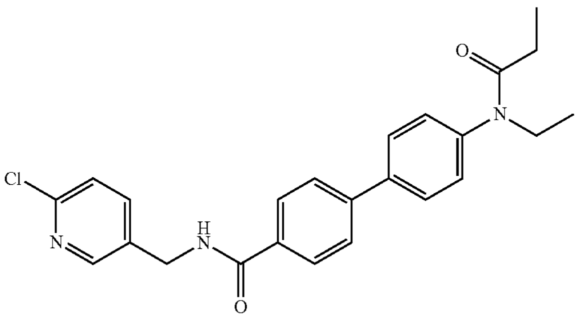
I-T 1566
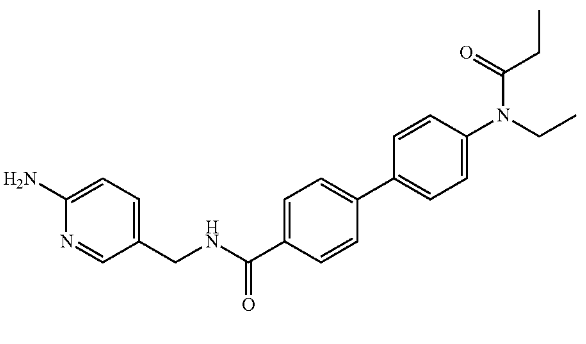

-continued
I-T 1567
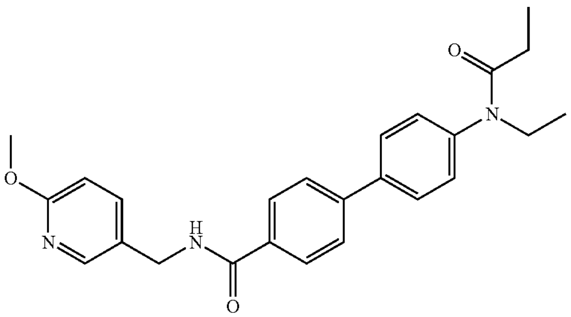
I-T 1568
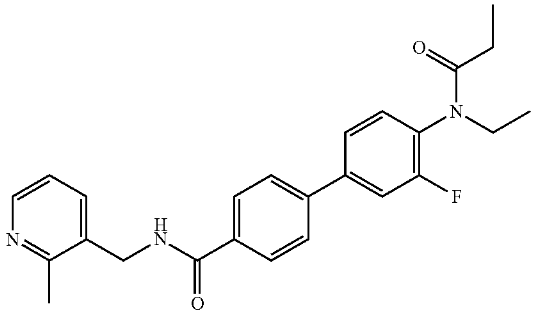
I-T 1569
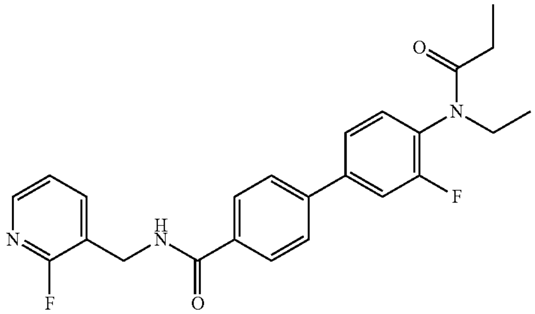
I-T 1570
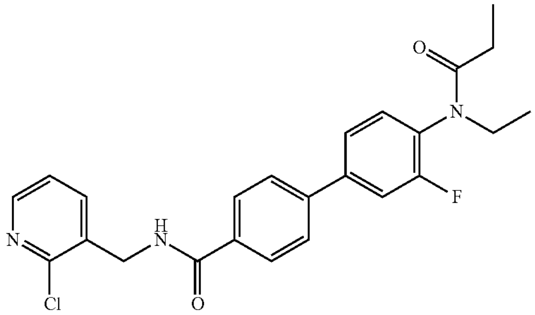
-continued
I-T 1571
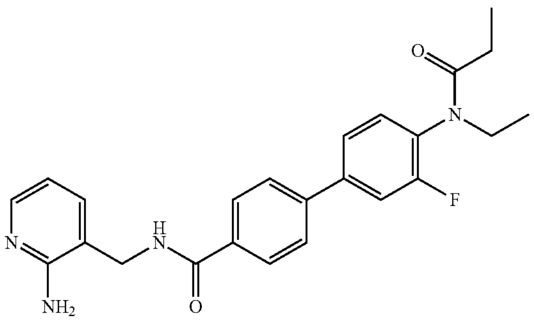
I-T 1572
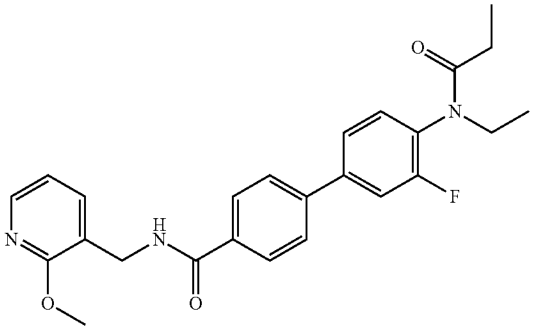
I-T 1573
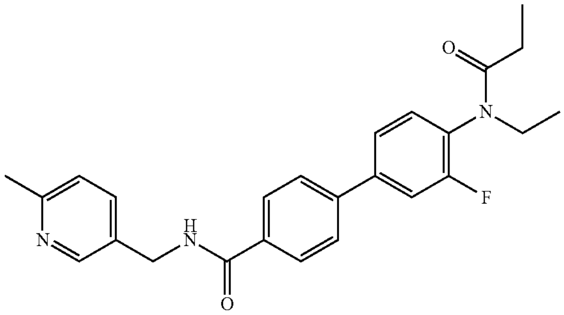
I-T 1574
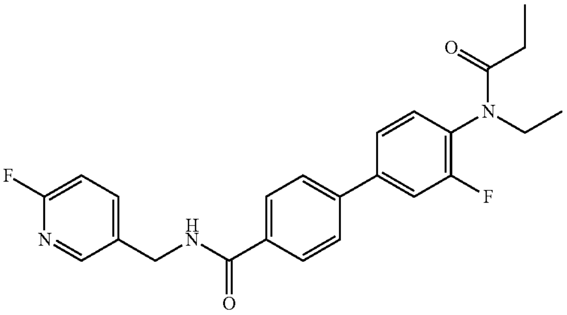

-continued
I-T 1575
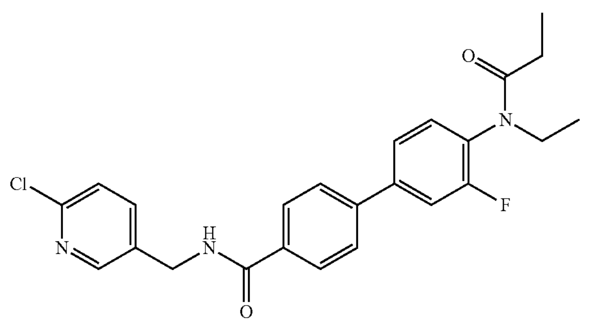
I-T 1576
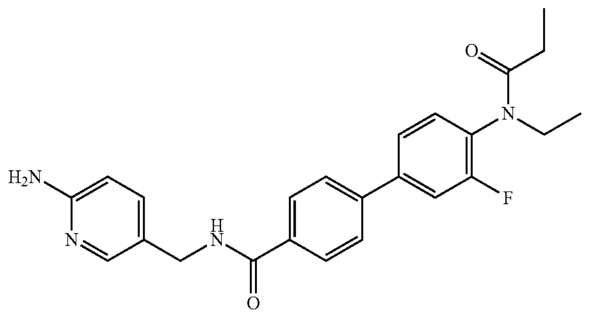
I-T 1577
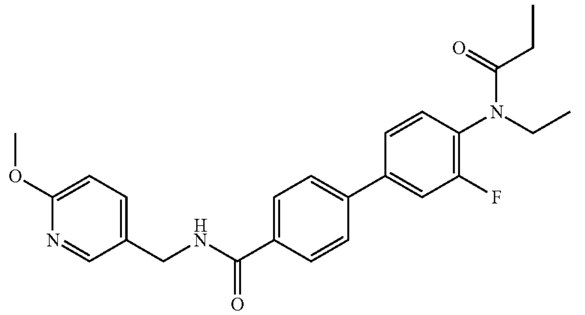
I-T 1578
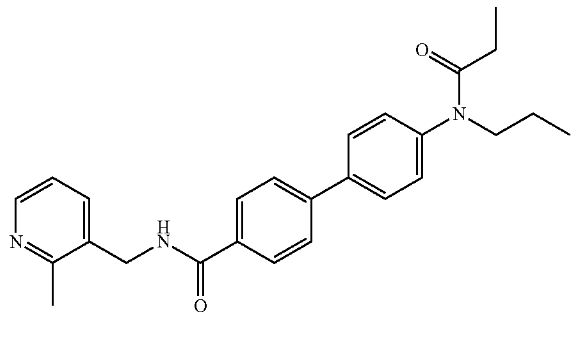
-continued
I-T 1579
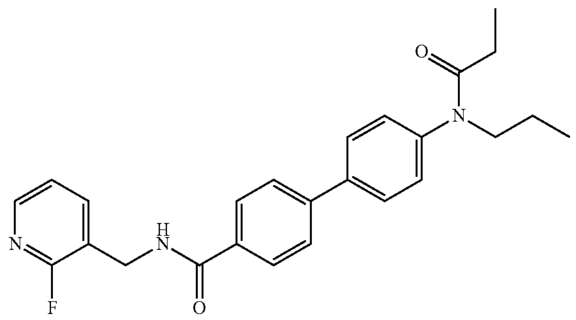
I-T 1580
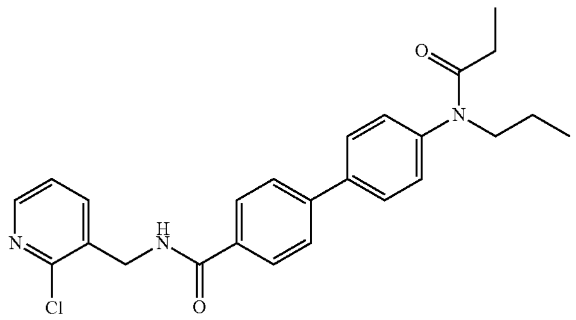
I-T 1581
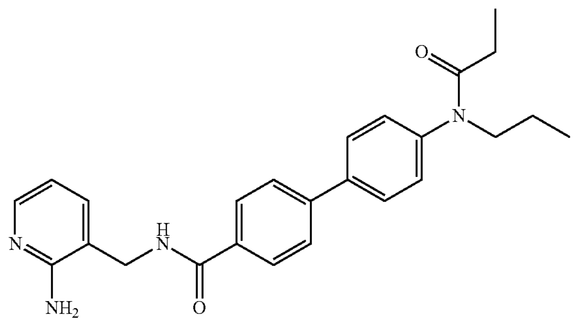
I-T 1582
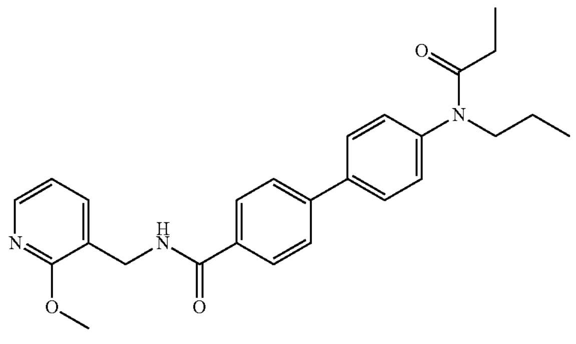

-continued
I-T 1583
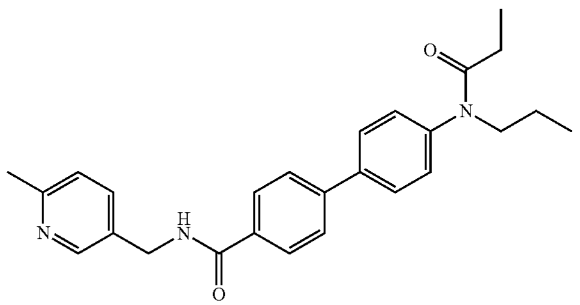
I-T 1584
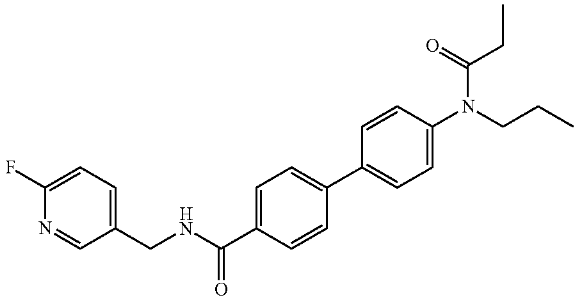
I-T 1585
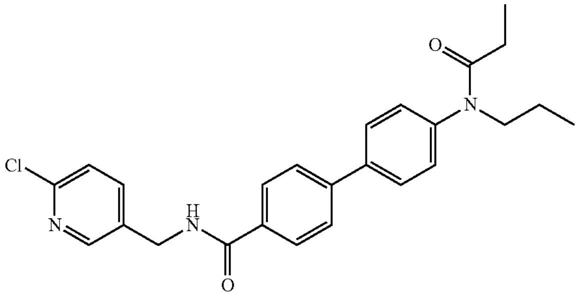
I-T 1586
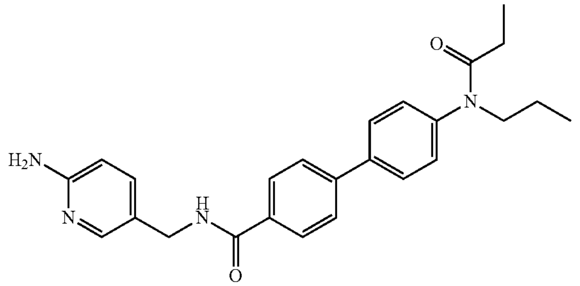
I-T 1587
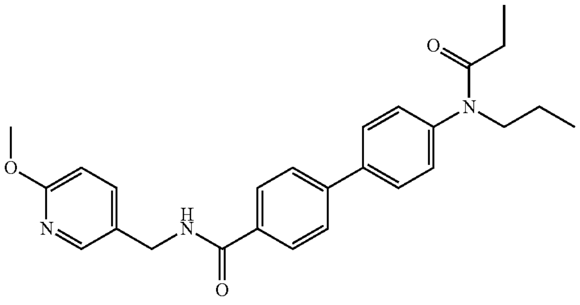
-continued
I-T 1588
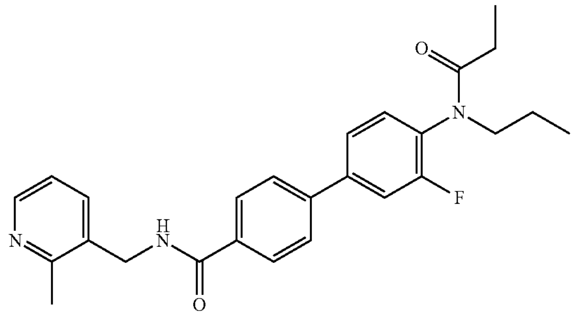
I-T 1589
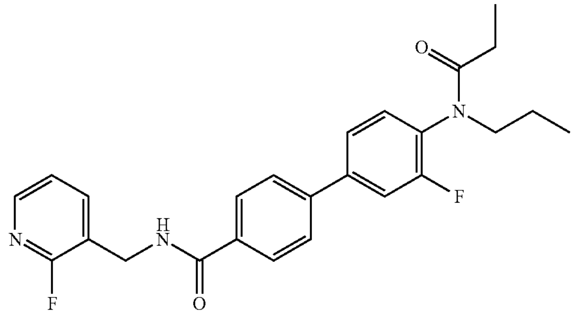
I-T 1590
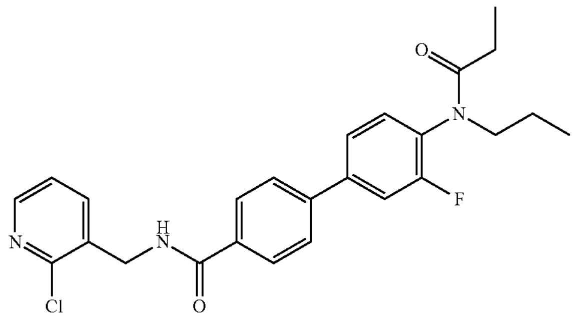
I-T 1591
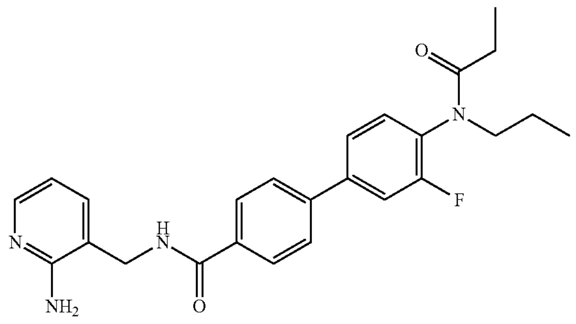

-continued
I-T 1592
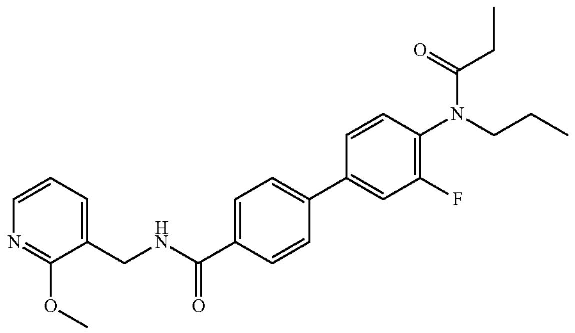
I-T 1593
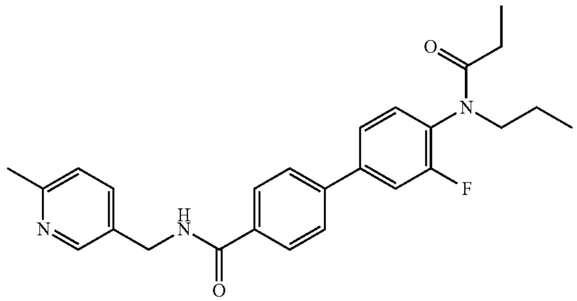
I-T 1594
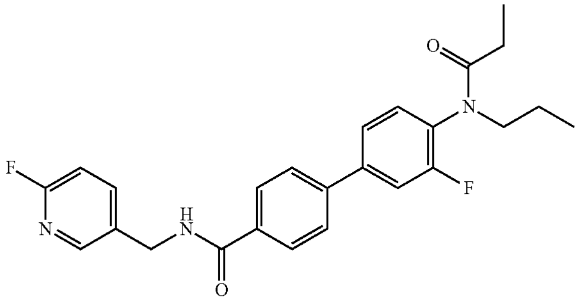
I-T 1595
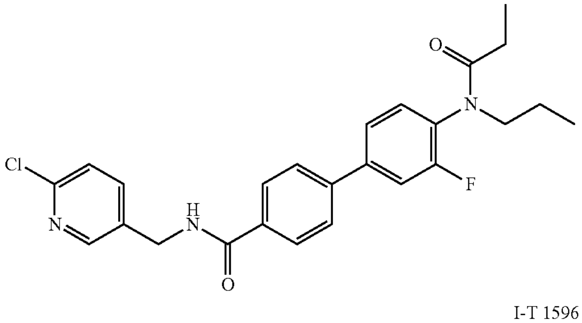
I-T 1596
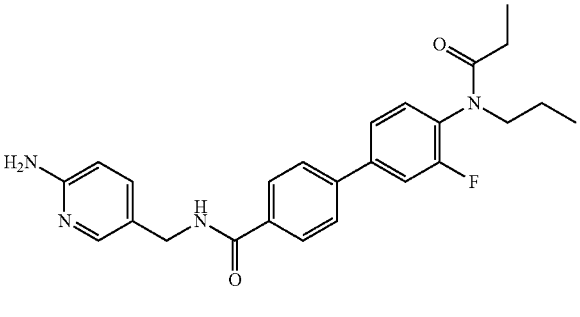
-continued
I-T 1597
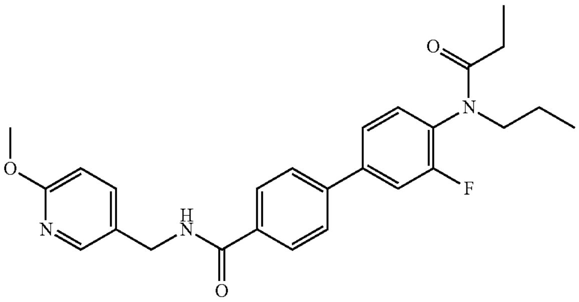
I-T 1598
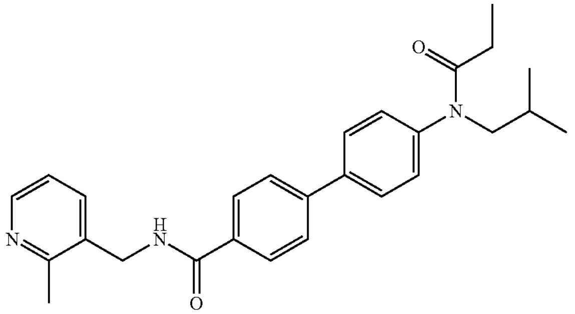
I-T 1599
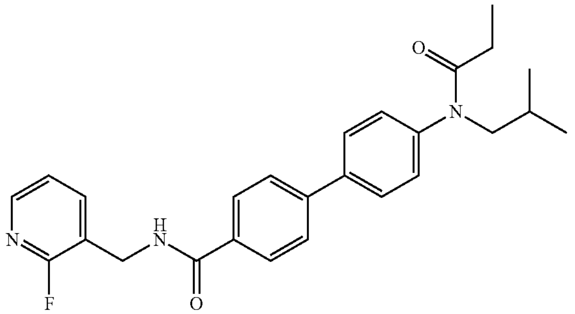
I-T 1600
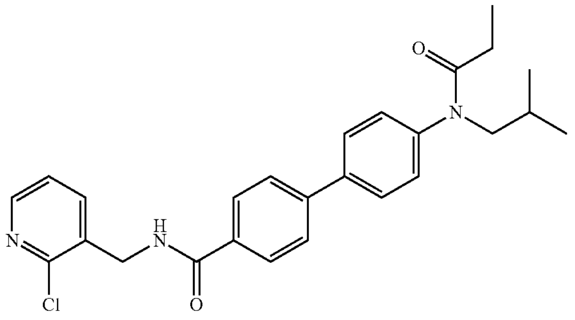

-continued
I-T 1601
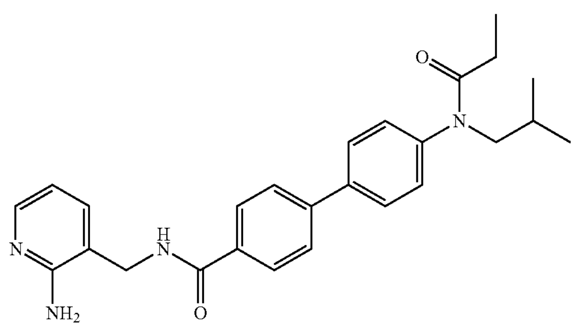
I-T 1602
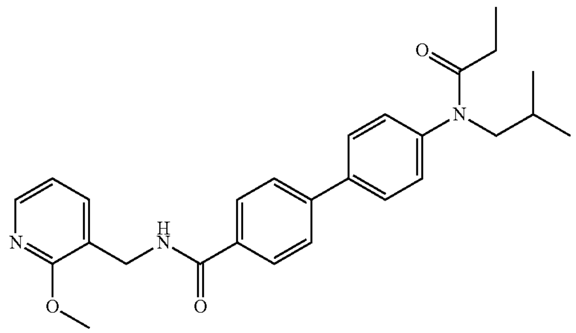
I-T 1603
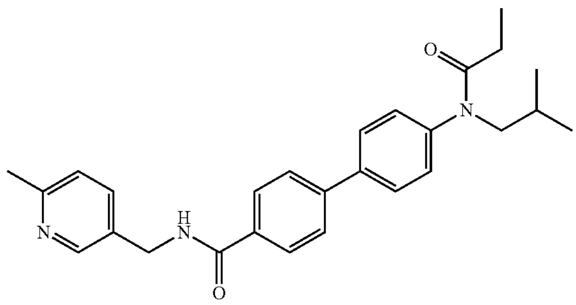
I-T 1604
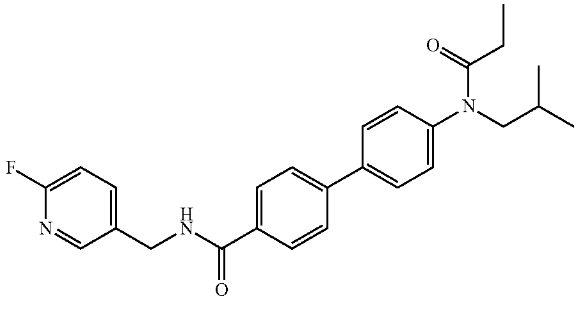
-continued
I-T 1605
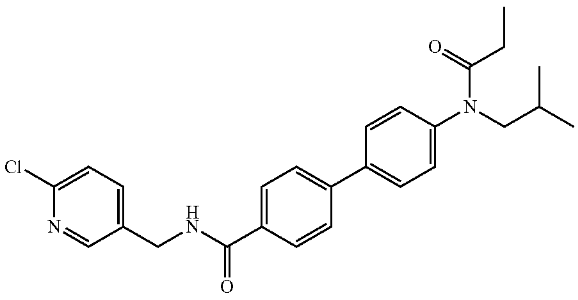
I-T 1606
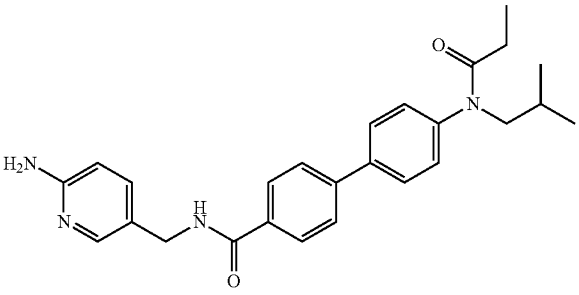
I-T 1607
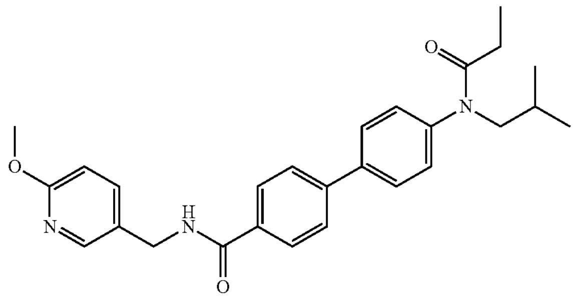
I-T 1608
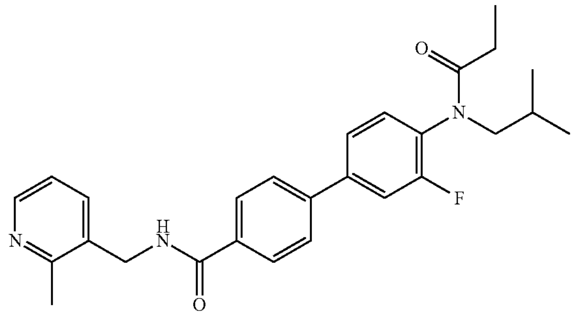
I-T 1609
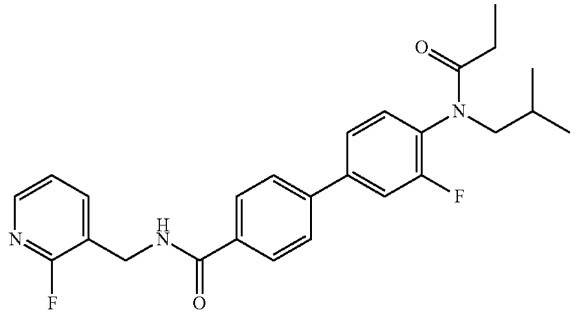

I-T 1610
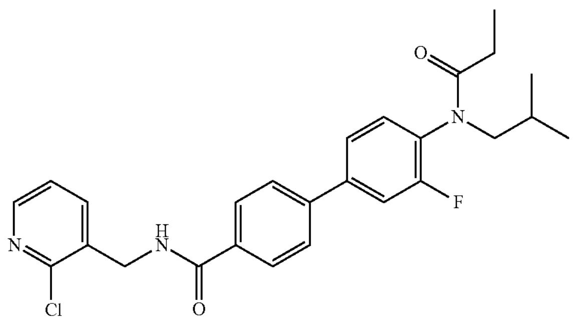
I-T 1611
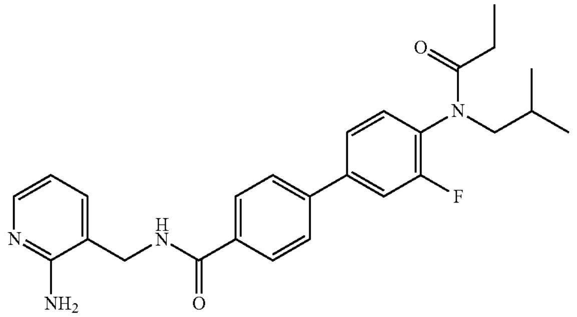
I-T 1612
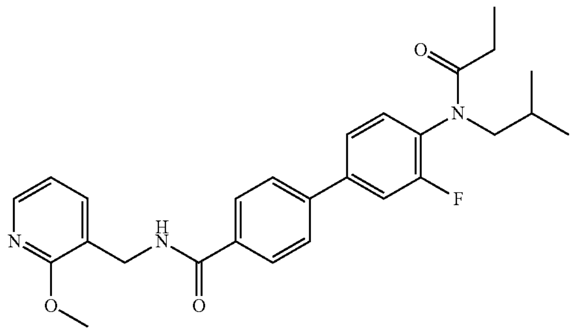
I-T 1613
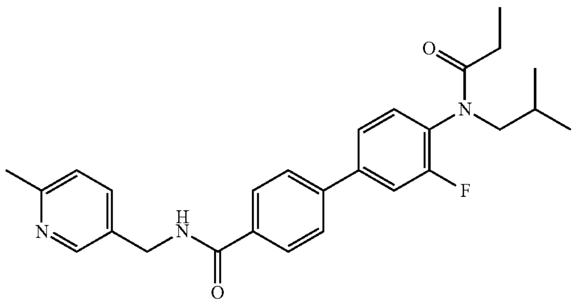
I-T 1614
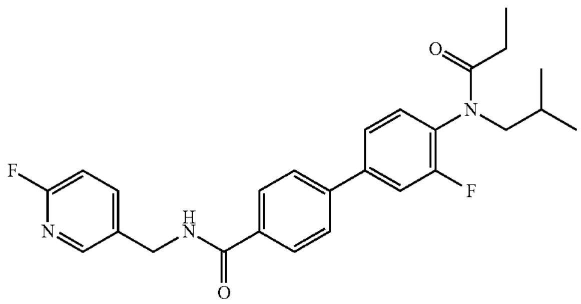
I-T 1615
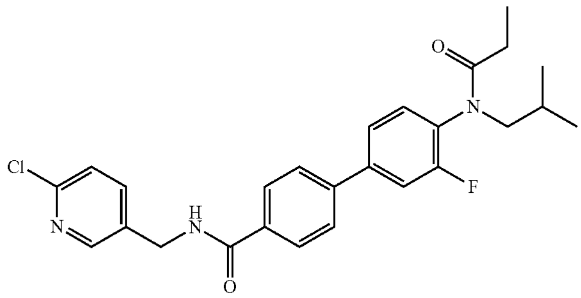
I-T 1616
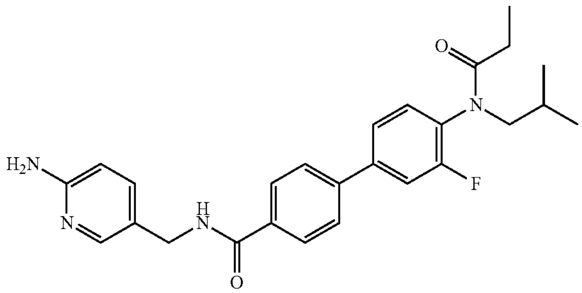
I-T 1617
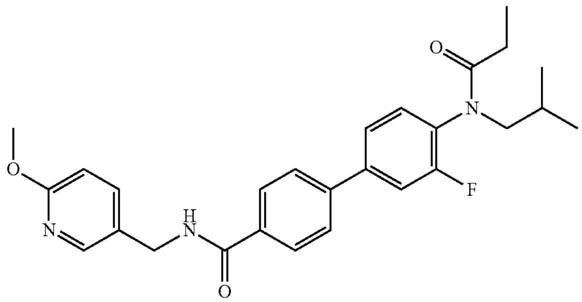
I-T 1618
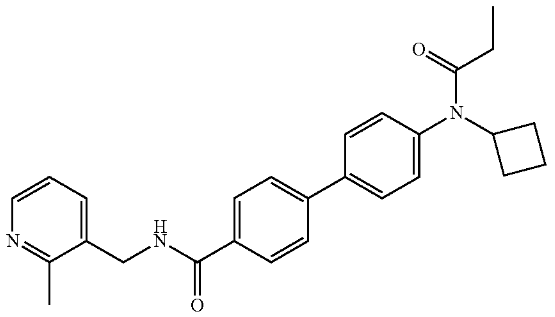

-continued
I-T 1619
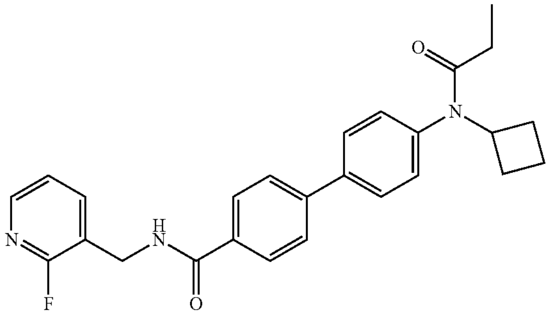
I-T 1620
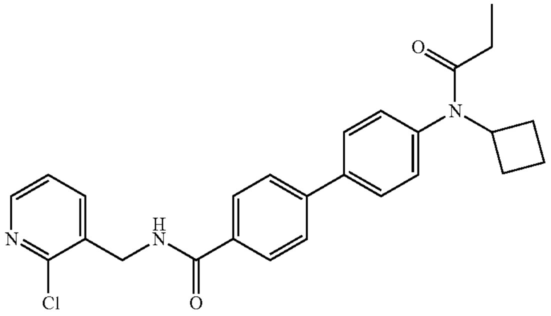
I-T 1621
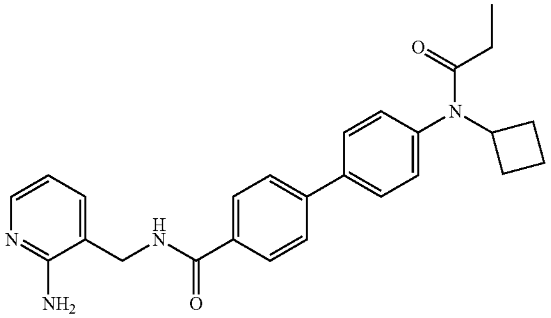
I-T 1622
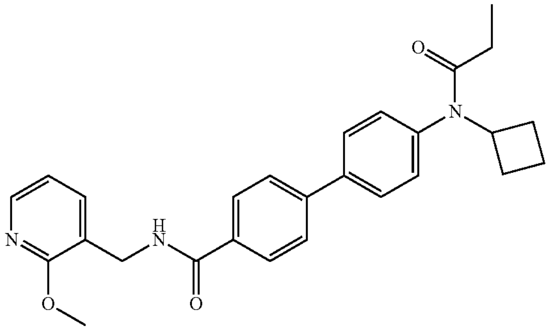
-continued
I-T 1623
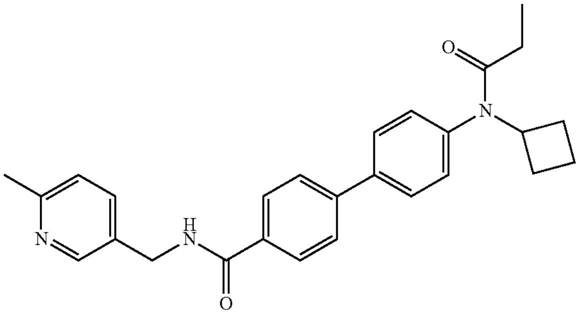
I-T 1624
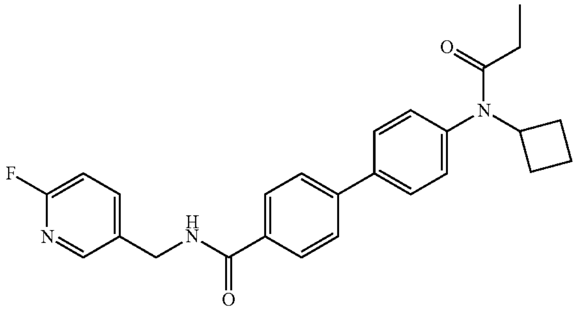
I-T 1625
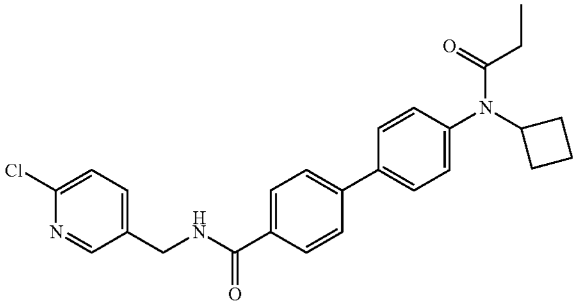
I-T 1626
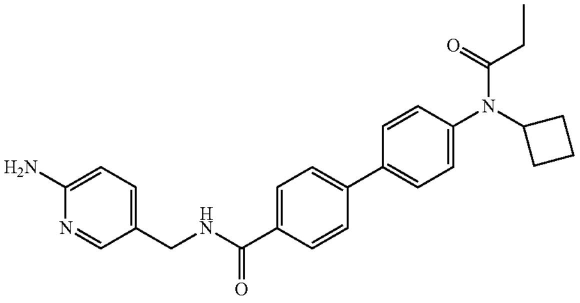

-continued
I-T 1627
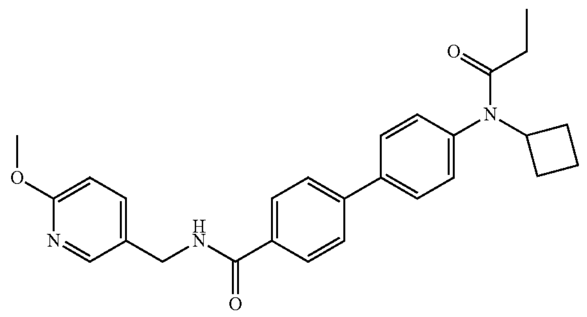
I-T 1628
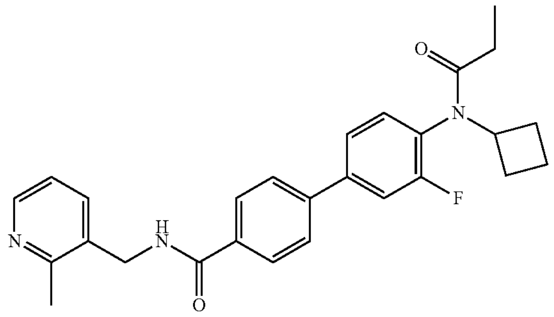
I-T 1629
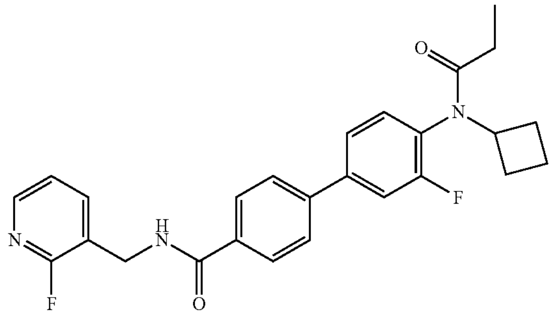
I-T 1630
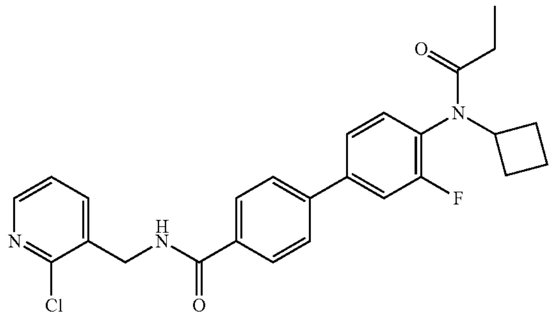
-continued
I-T 1631
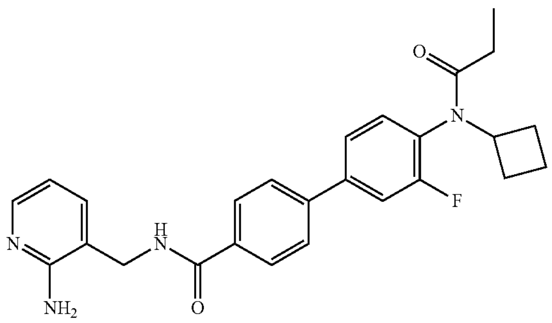
I-T 1632
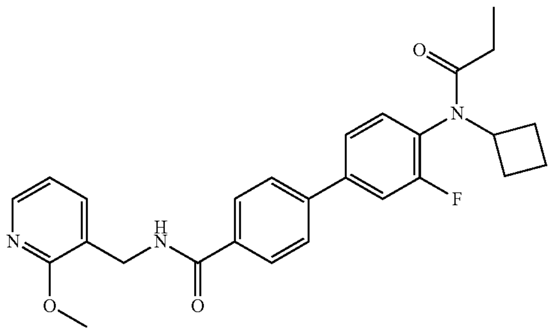
I-T 1633
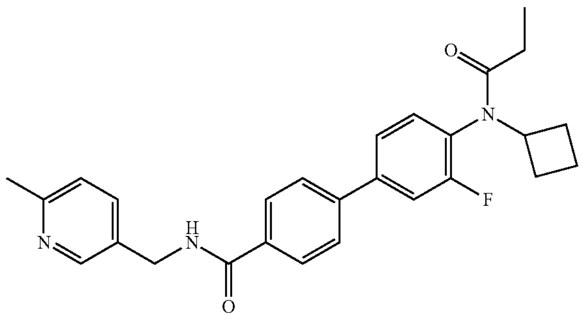
I-T 1634
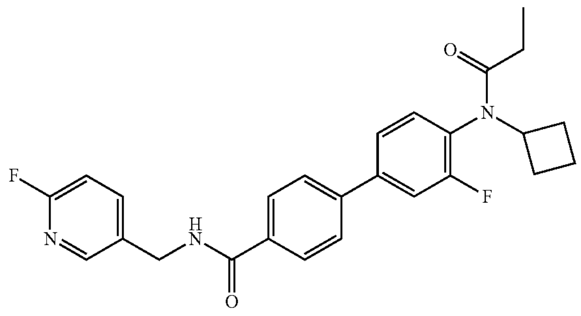

-continued
I-T 1635
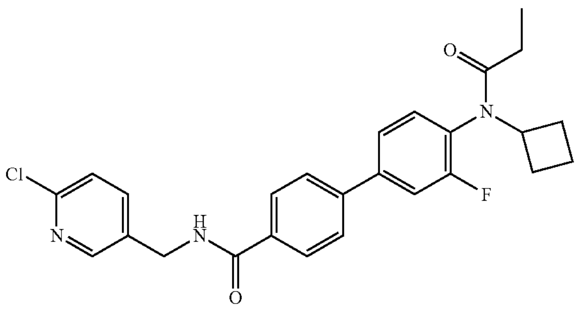
I-T 1636
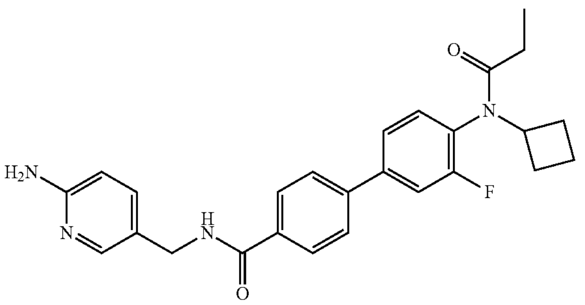
I-T 1637
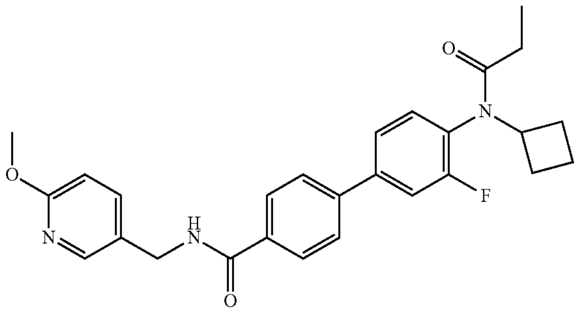
I-T 1638
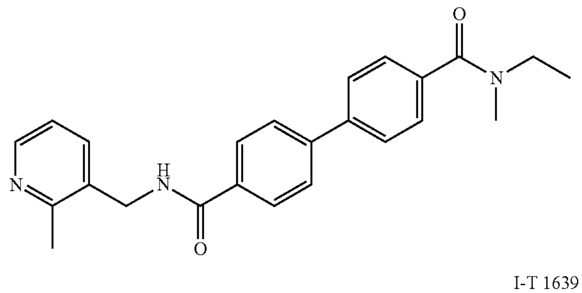
I-T 1639
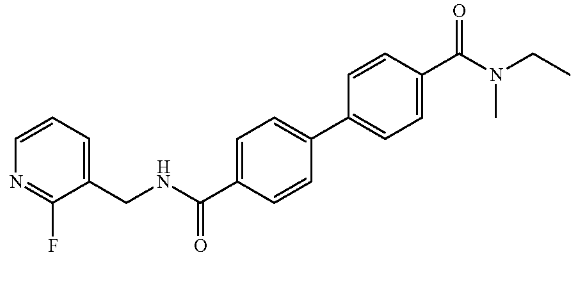
-continued
I-T 1640
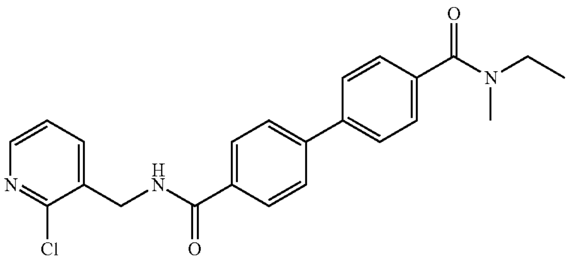
I-T 1641
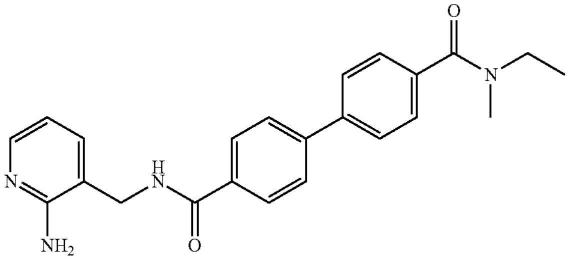
I-T 1642
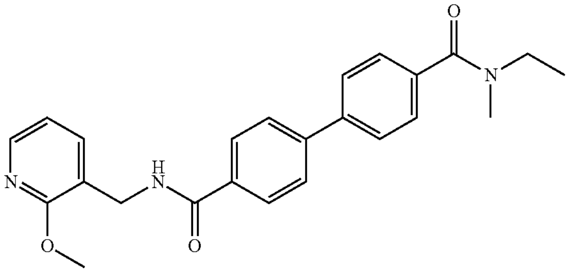
I-T 1643
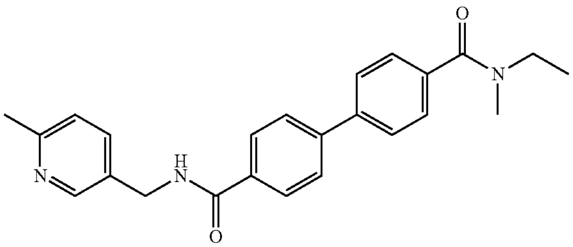
I-T 1644
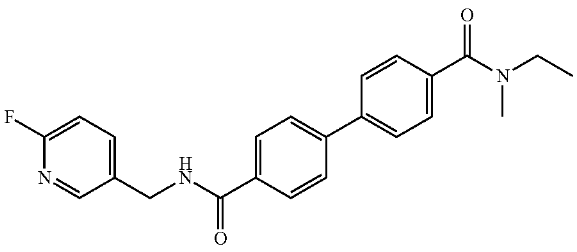

-continued
I-T 1645
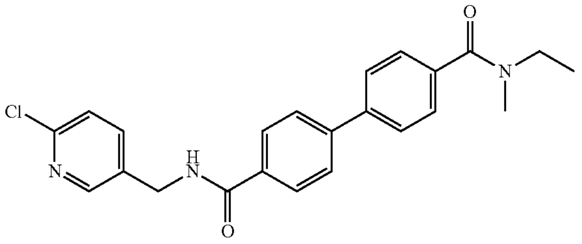
I-T 1646
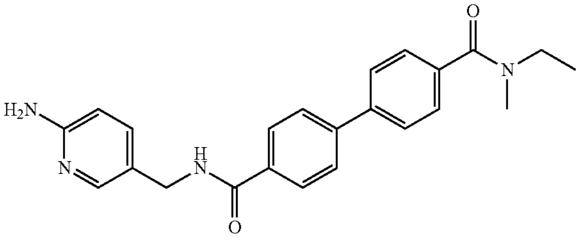
I-T 1647
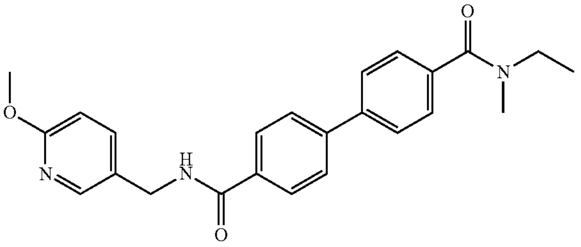
I-T 1648
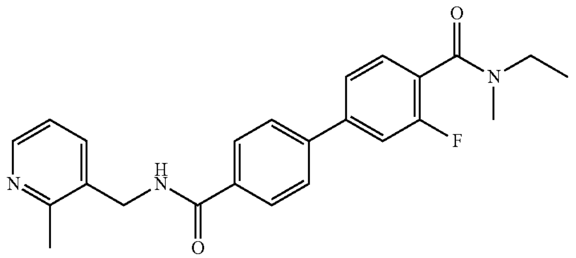
I-T 1649
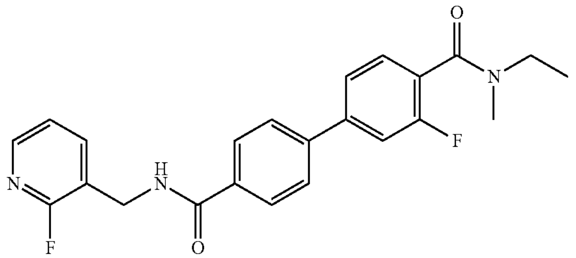
-continued
I-T 1650
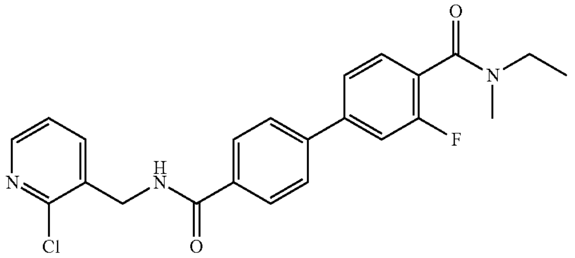
I-T 1651
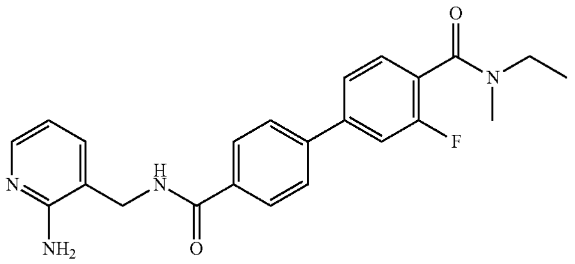
I-T 1652
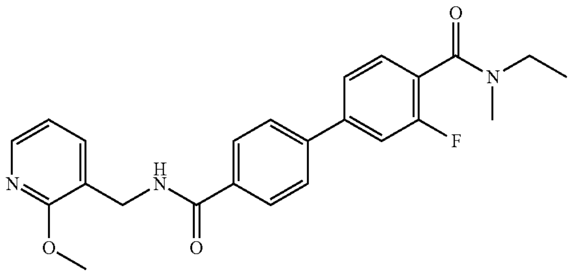
I-T 1653
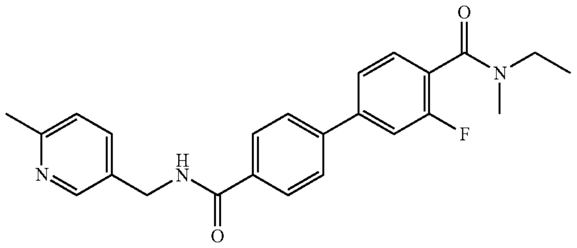
I-T 1654
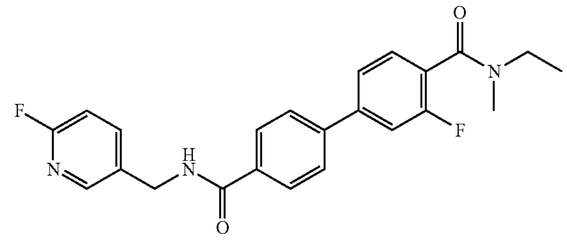

-continued
I-T 1655
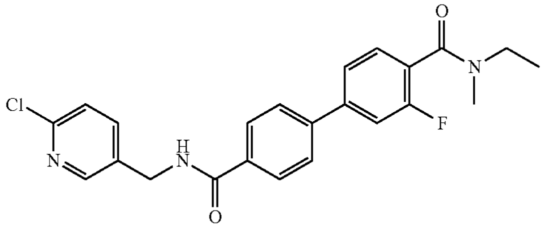
I-T 1656
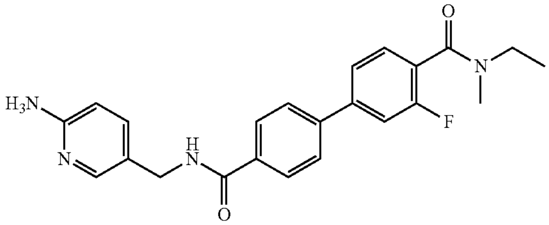
I-T 1657
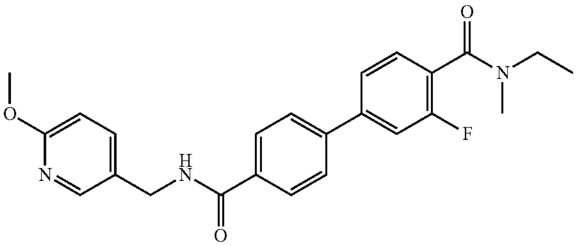
I-T 1658
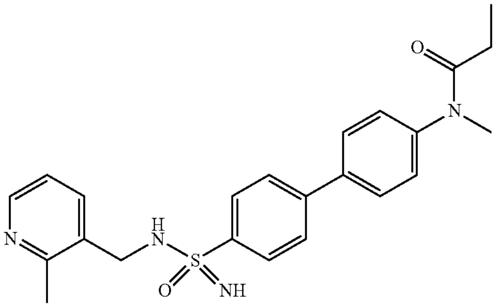
I-T 1659
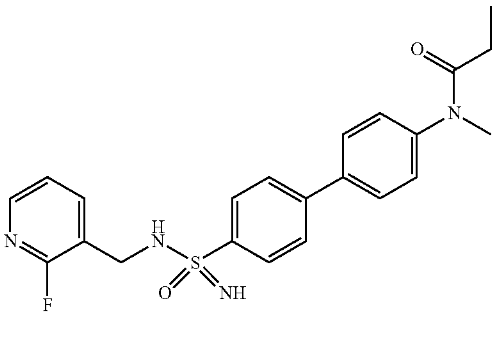
-continued
I-T 1660
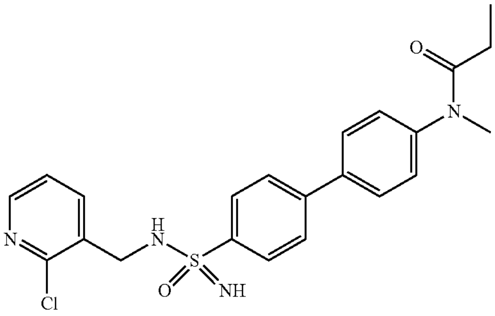
I-T 1661
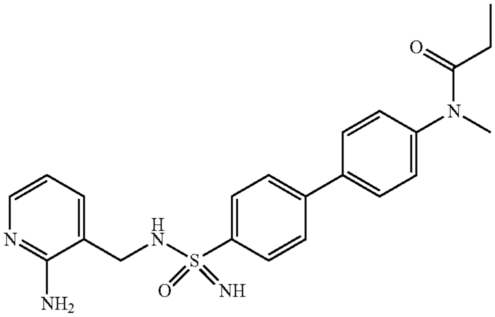
I-T 1662
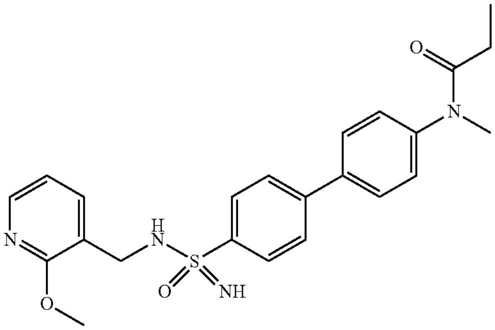
I-T 1663
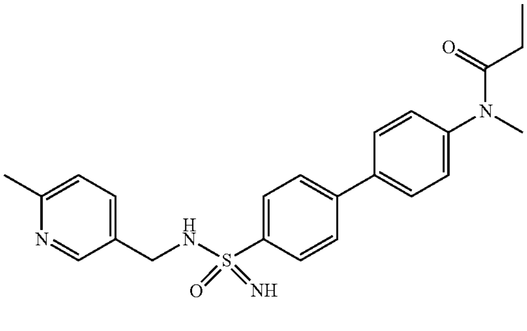

-continued
I-T 1664
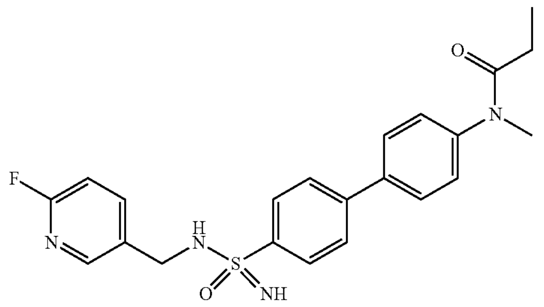
I-T 1665
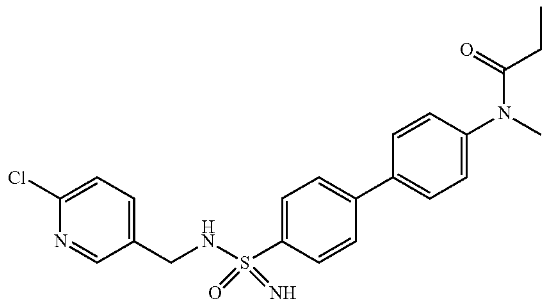
I-T 1666
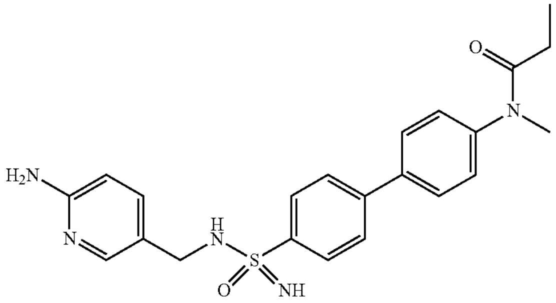
I-T 1667
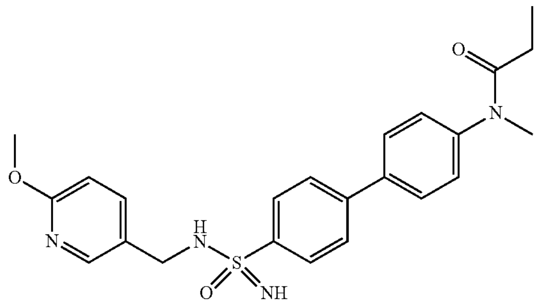
I-T 1668
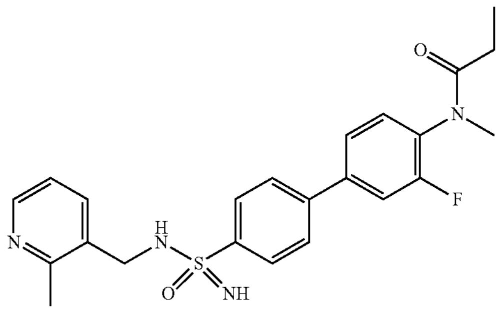
-continued
I-T 1669
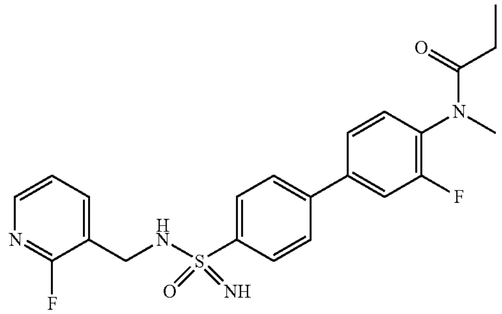
I-T 1670
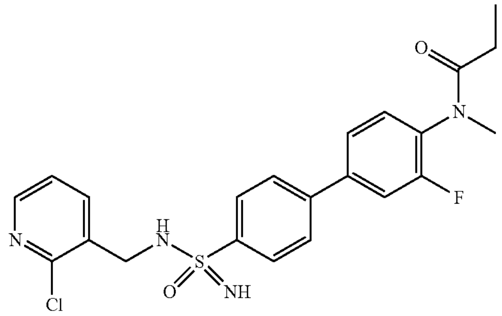
I-T 1671
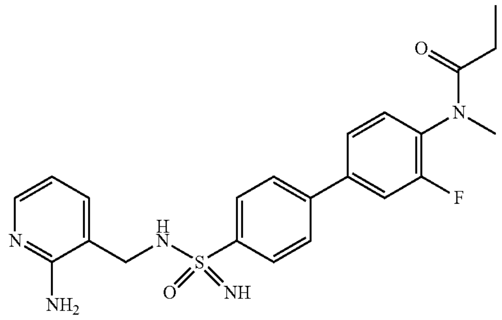
I-T 1672
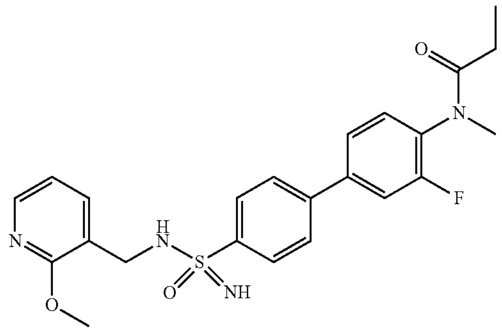

-continued
I-T 1673
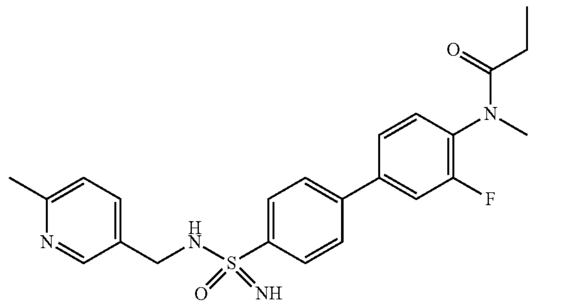
I-T 1674
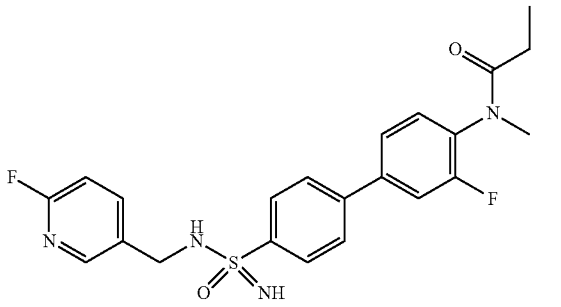
I-T 1675
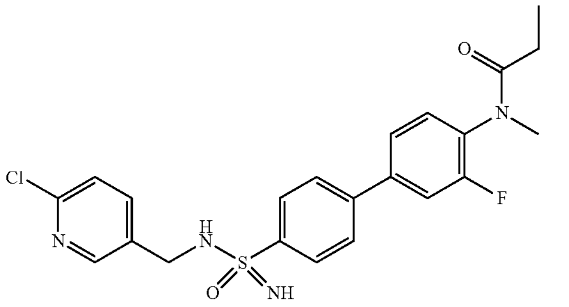
I-T 1676
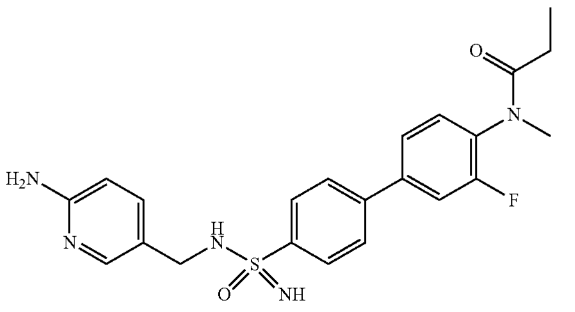
I-T 1677
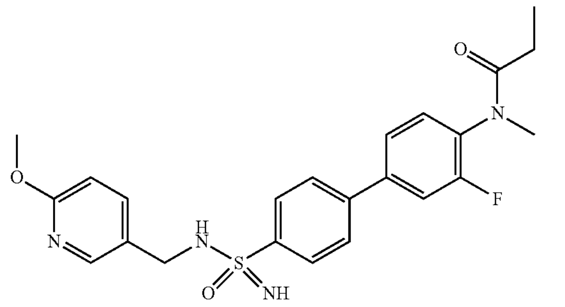
-continued
I-T 1678
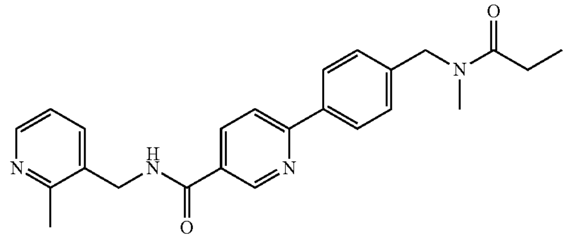
I-T 1679
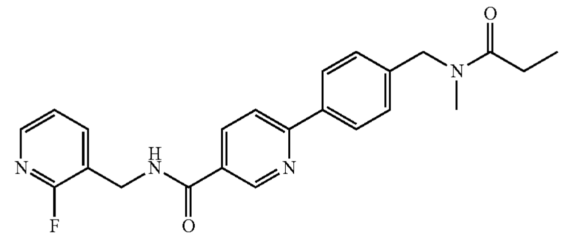
I-T 1680
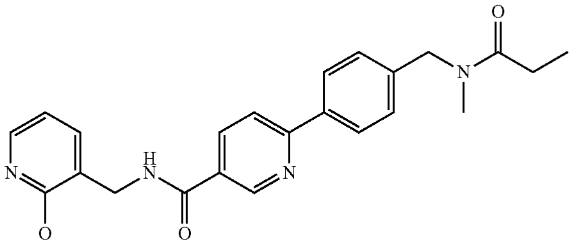
I-T 1681
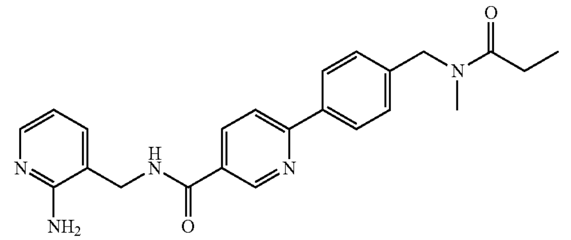
I-T 1682
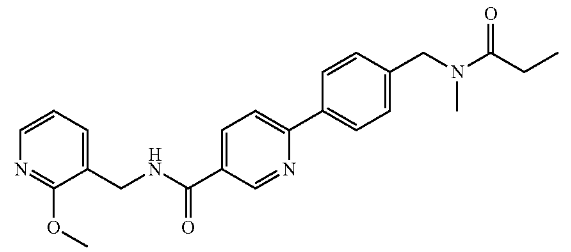
I-T 1683
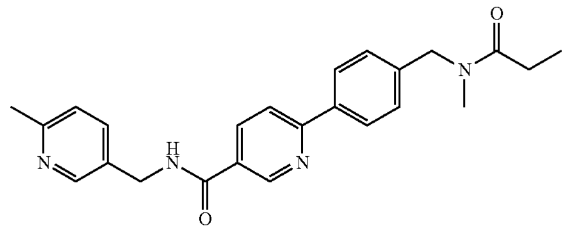

-continued
I-T 1684
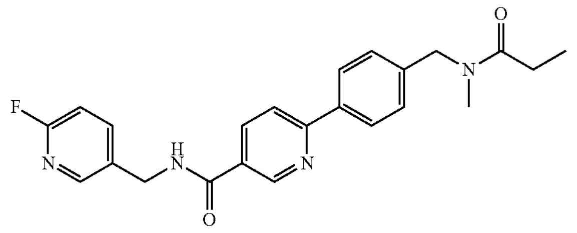
I-T 1685
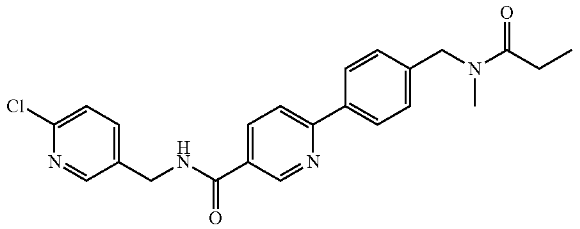
I-T 1686
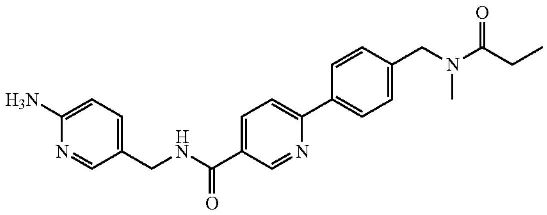
I-T 1687
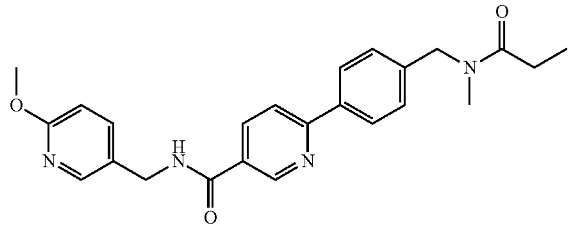
I-T 1688
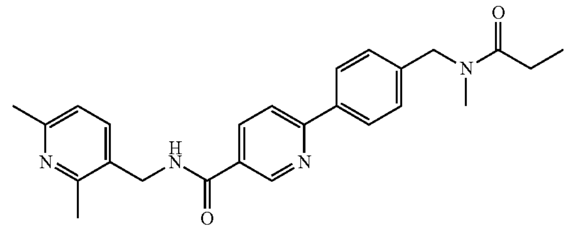
I-T 1689
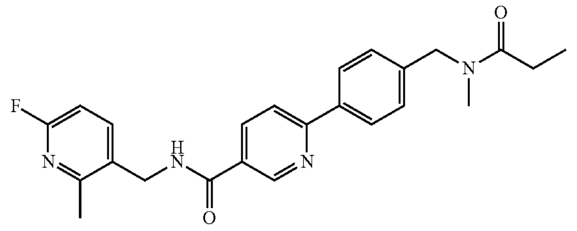
-continued
I-T 1690
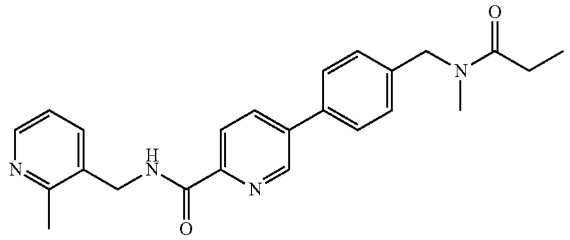
I-T 1691
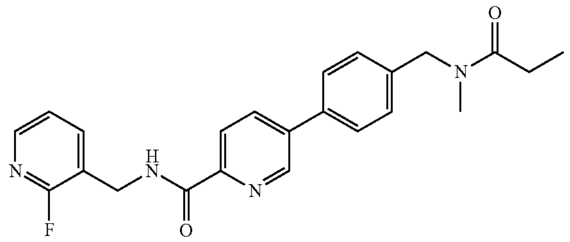
I-T 1692
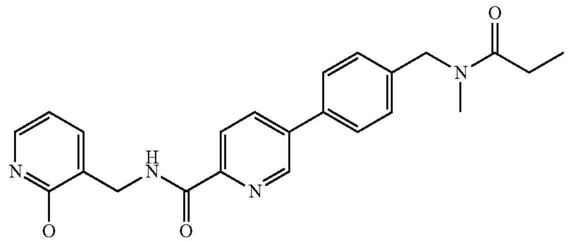
I-T 1693
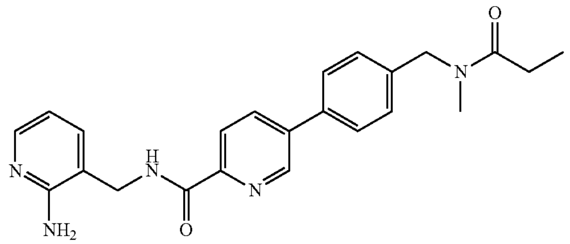
I-T 1694
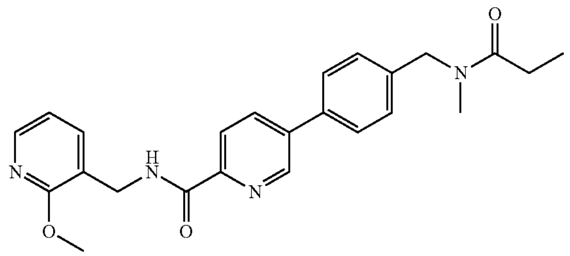
I-T 1695
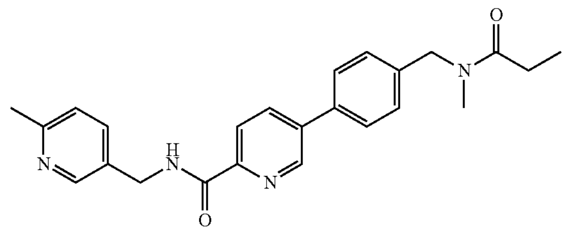

-continued
I-T 1696
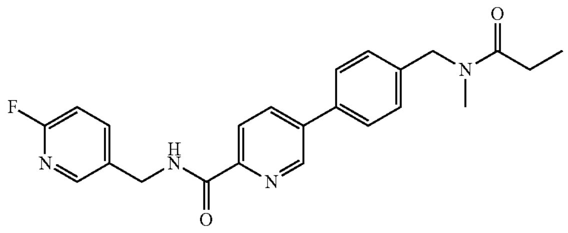
I-T 1697
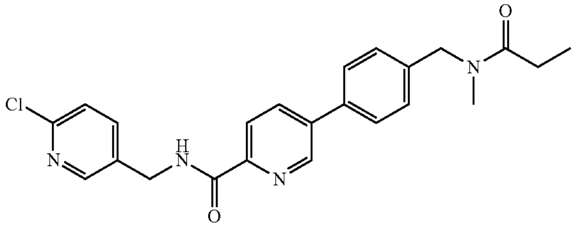
I-T 1698
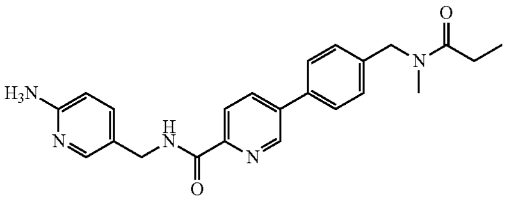
I-T 1699
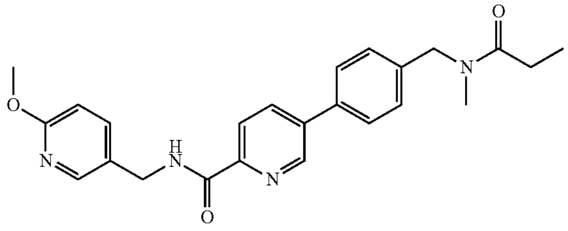
I-T 1700
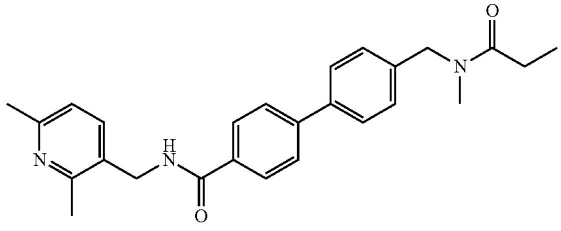
I-T 1701
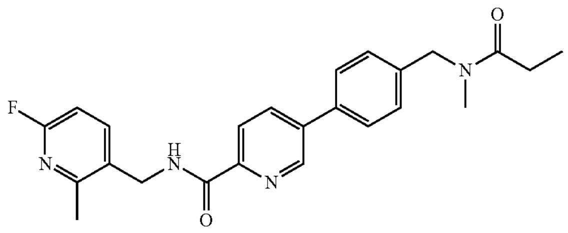
-continued
I-T 1702
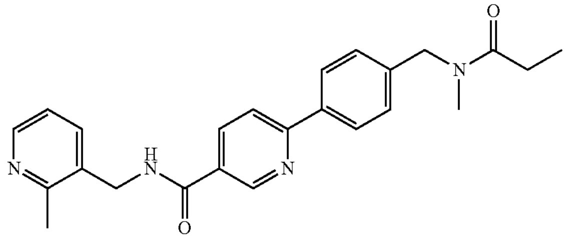
I-T 1703
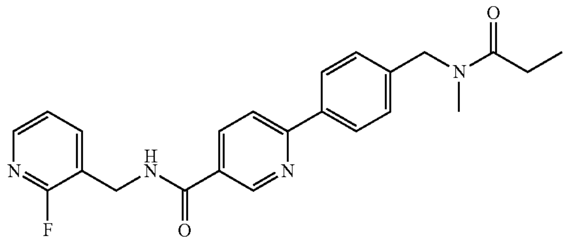
I-T 1704
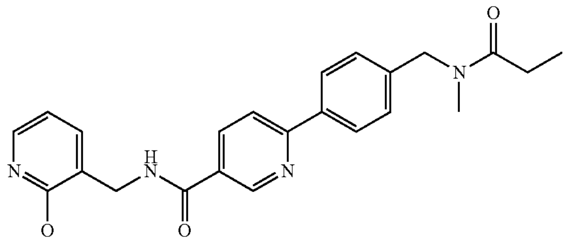
I-T 1705
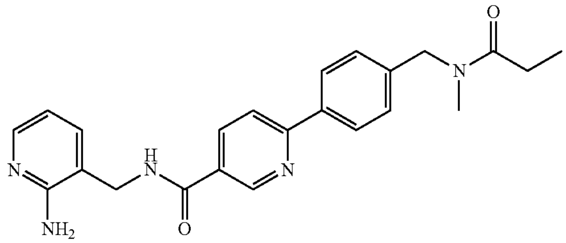
I-T 1706
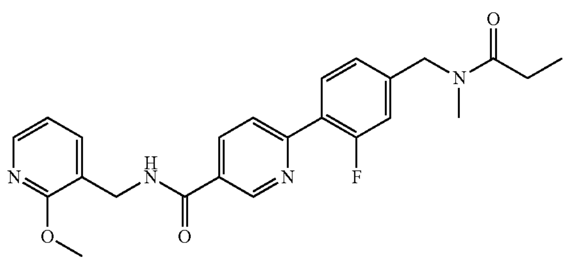
I-T 1707
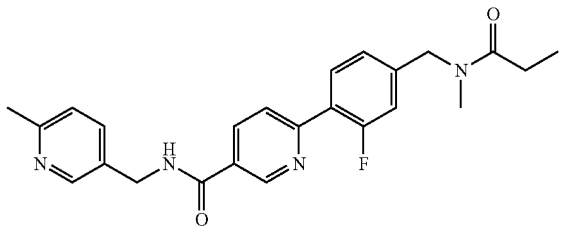

-continued
I-T 1708
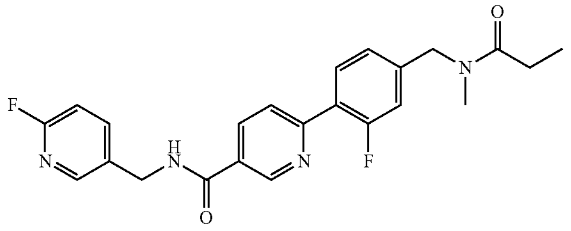
I-T 1709
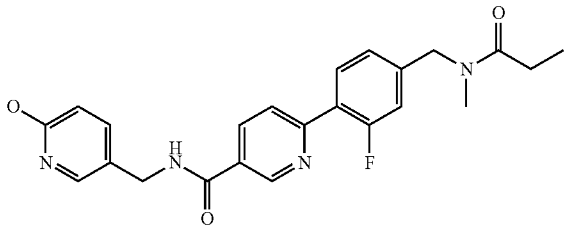
I-T 1710
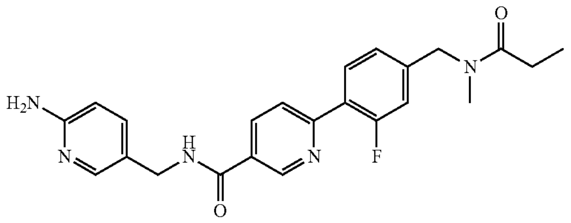
I-T 1711
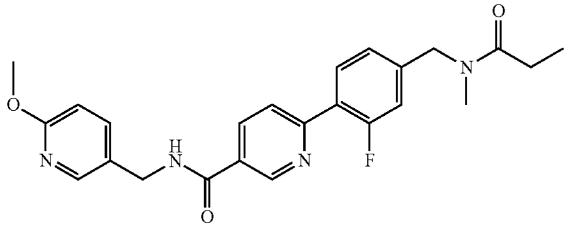
I-T 1712
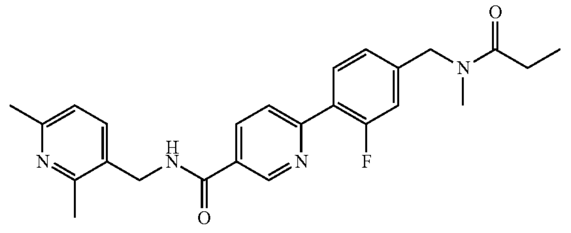
I-T 1713
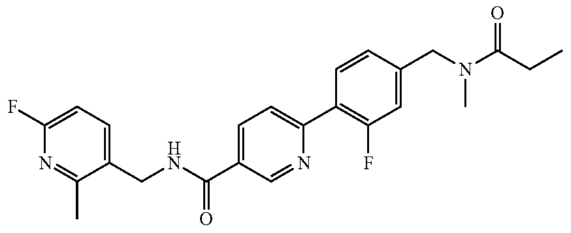
-continued
I-T 1714
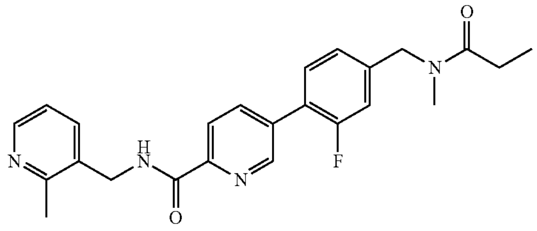
I-T 1715
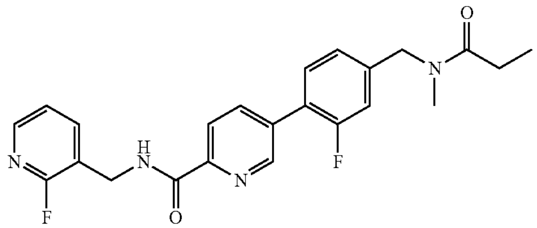
I-T 1716
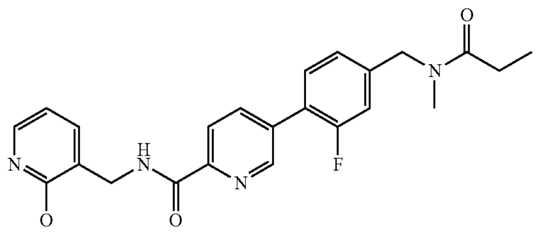
I-T 1717
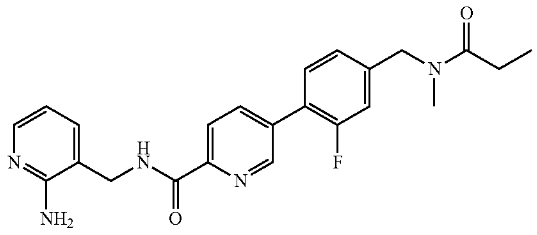
I-T 1718
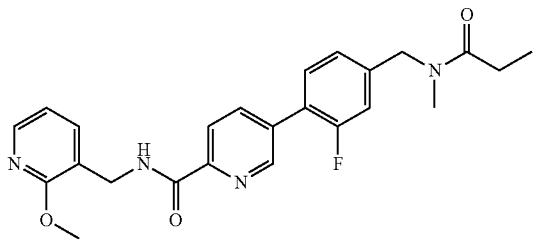
I-T 1719
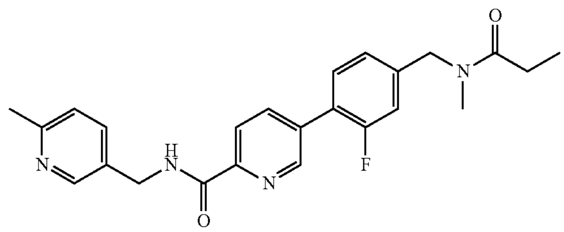

-continued
I-T 1720
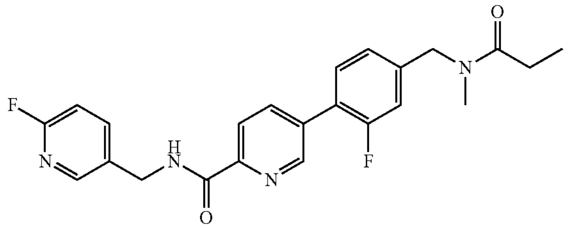
I-T 1721
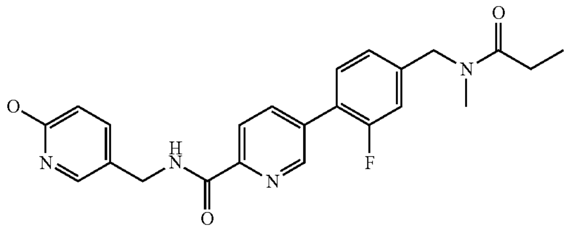
I-T 1722
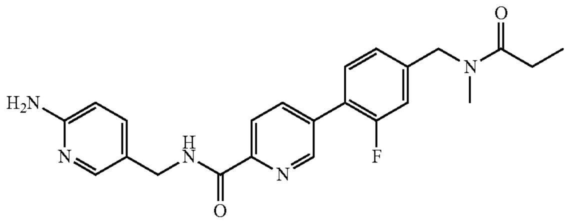
I-T 1723
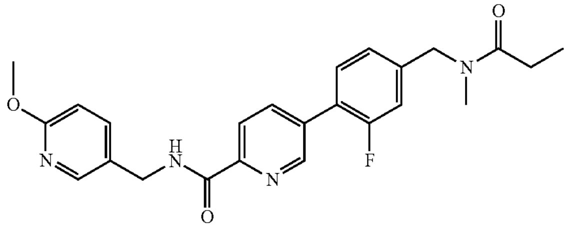
I-T 1724
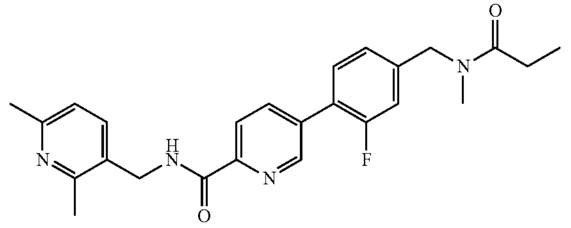
I-T 1725
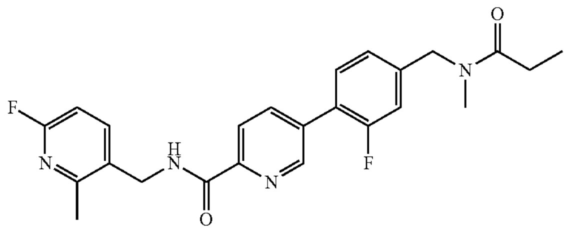
-continued
I-T 1726
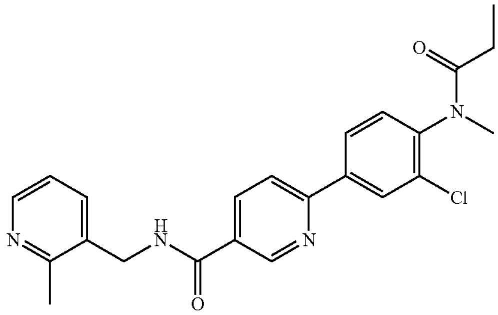
I-T 1727
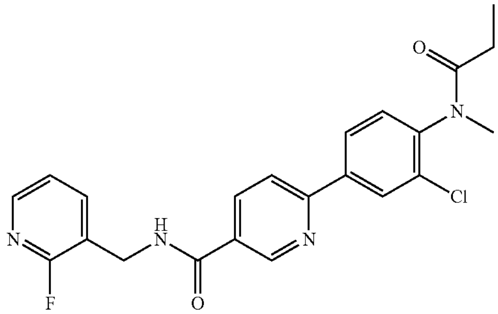
I-T 1728
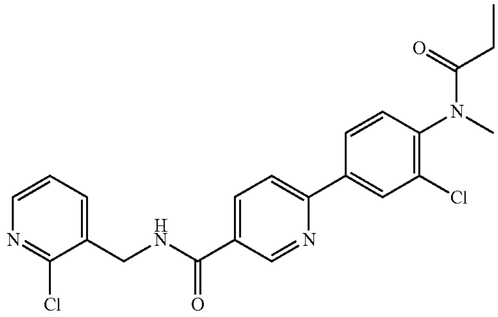
I-T 1729
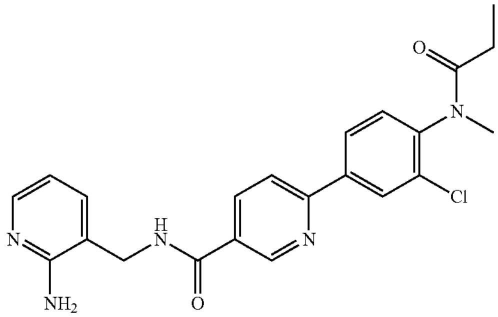

-continued
I-T 1730
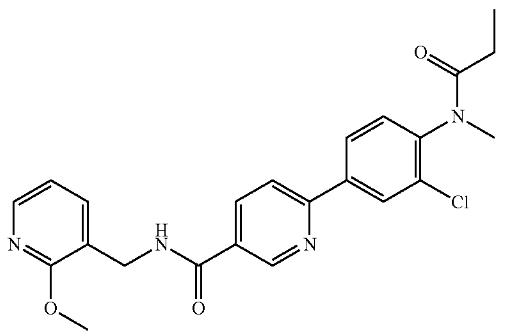
I-T 1731
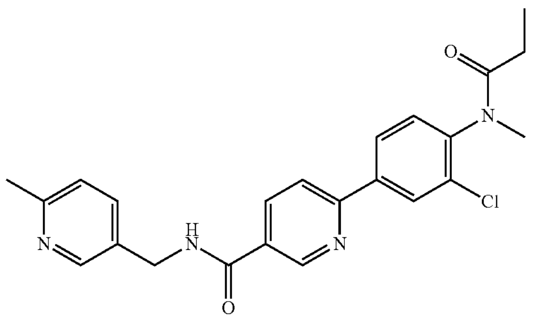
I-T 1732
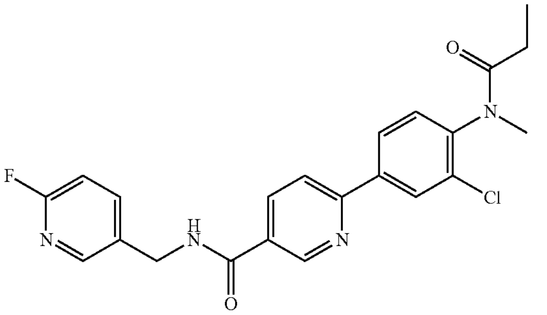
I-T 1733
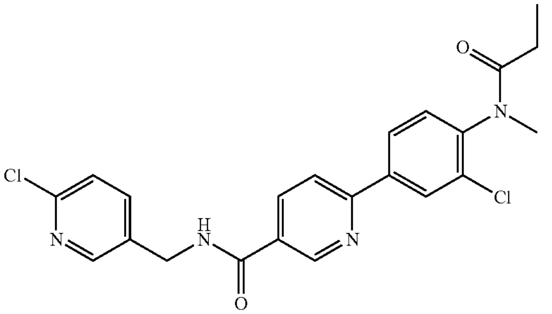
-continued
I-T 1734
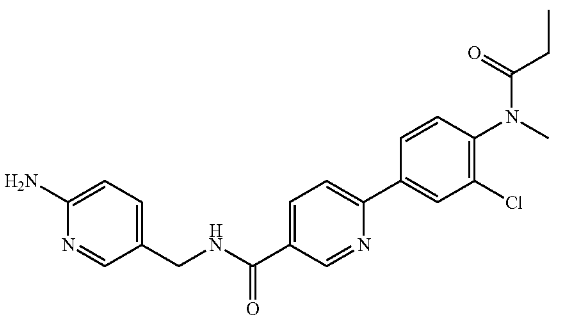
I-T 1735
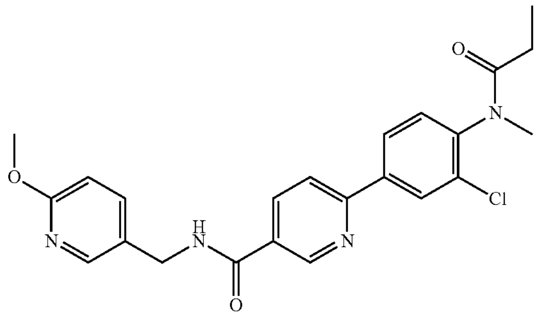
I-T 1736
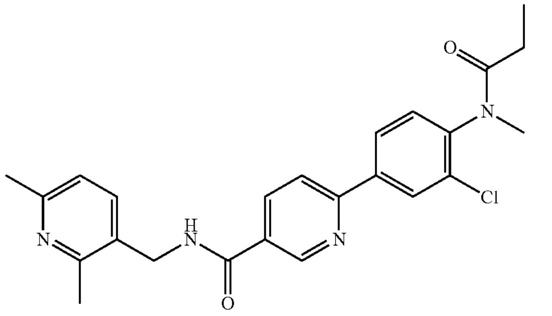
I-T 1737
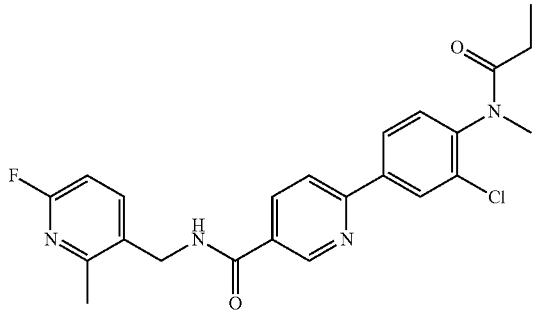

-continued
I-T 1738
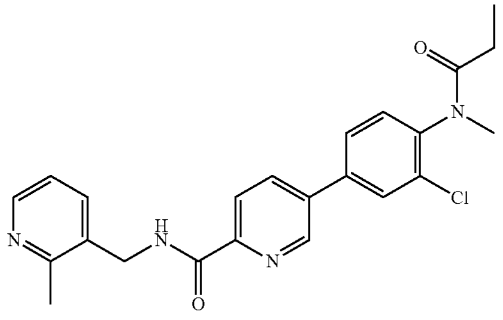
I-T 1739
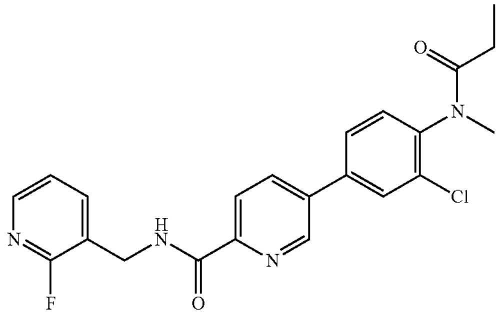
I-T 1740
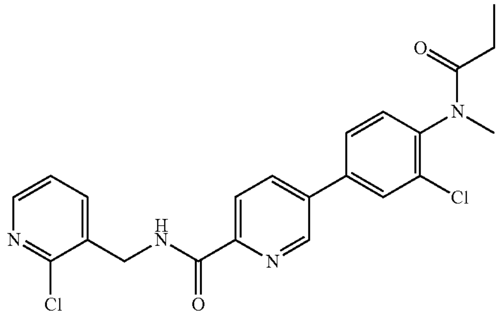
I-T 1741
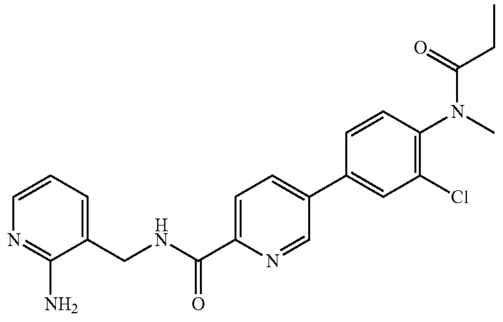
-continued
I-T 1742
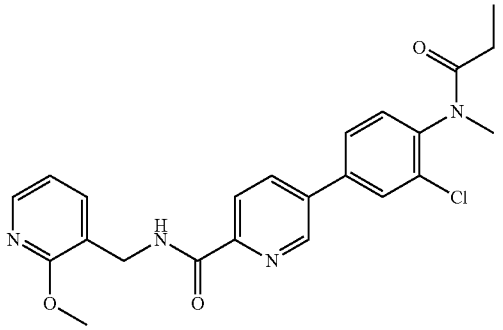
I-T 1743
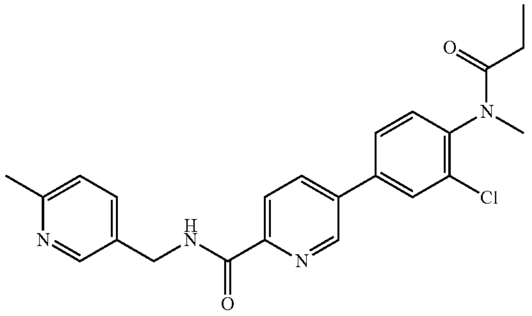
I-T 1744
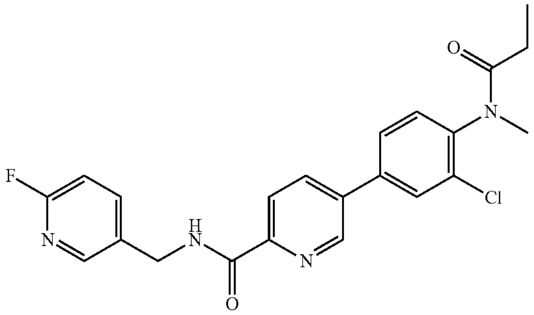
I-T 1745
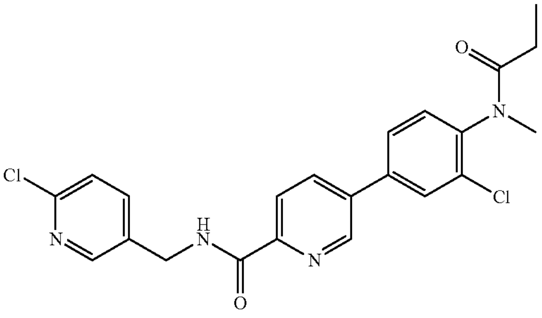

I-T 1746
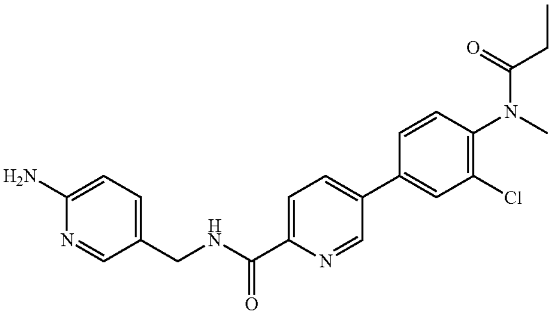
I-T 1747
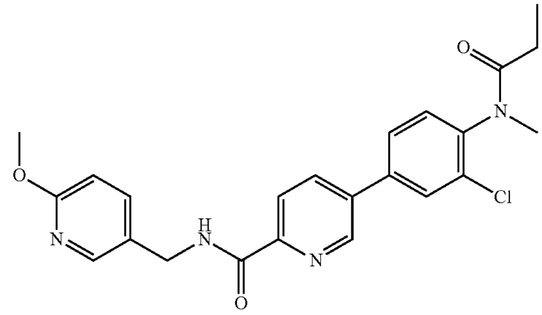
I-T 1748
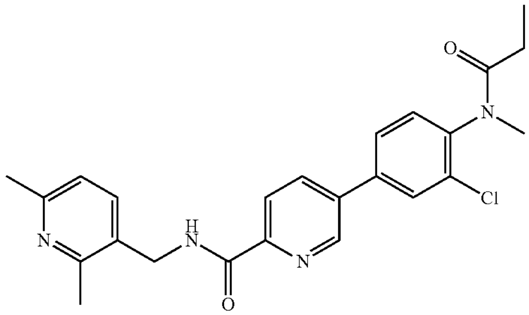
I-T 1749
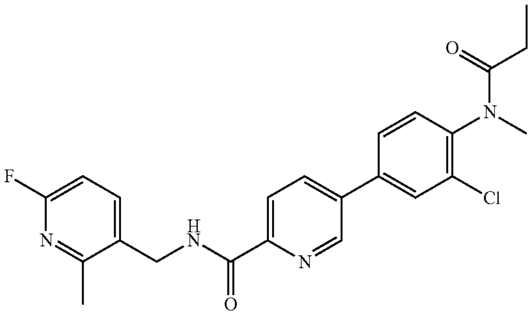
I-T 1750
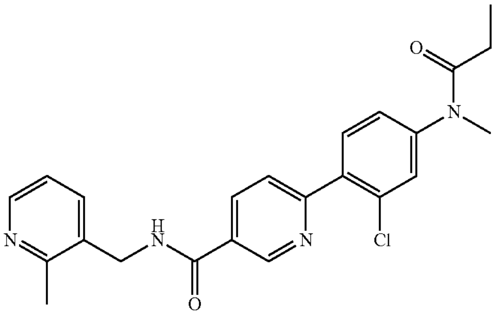
I-T 1751
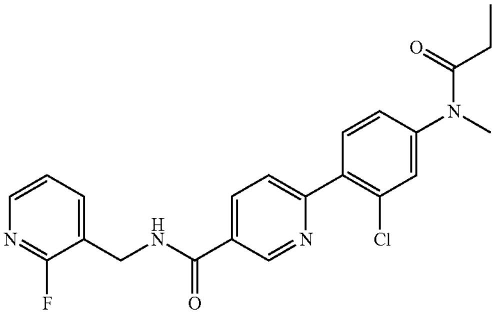
I-T 1752
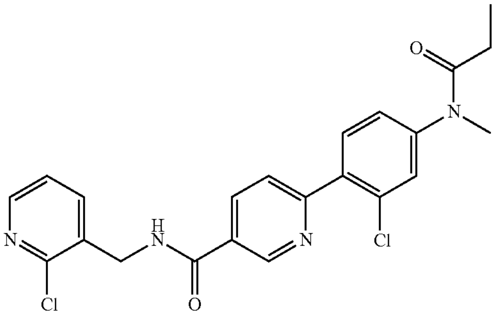
I-T 1753
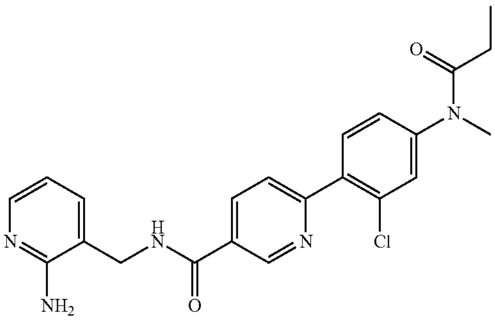

-continued
I-T 1754
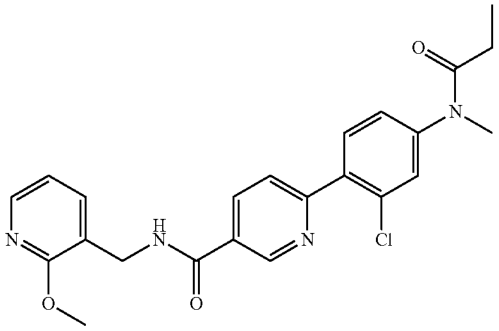
I-T 1755
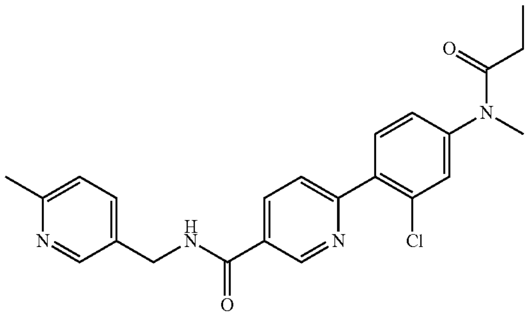
I-T 1756
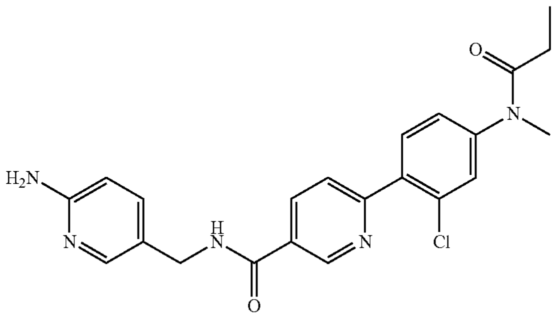
I-T 1757
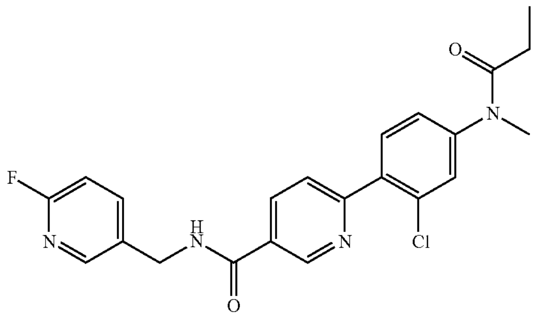
-continued
I-T 1758
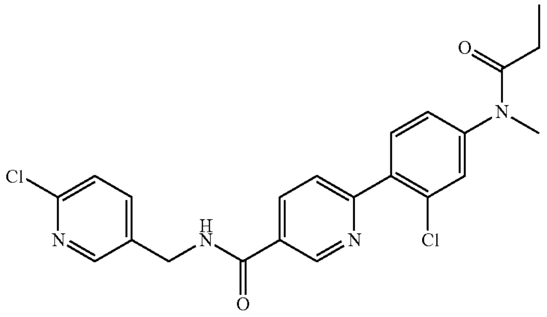
I-T 1759
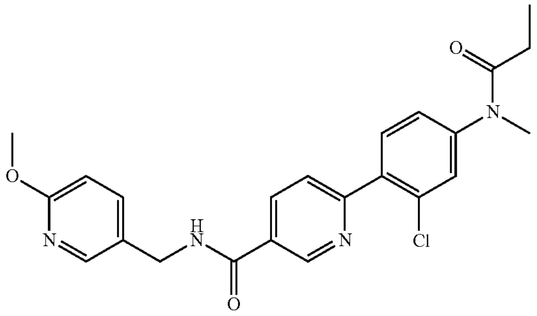
I-T 1760
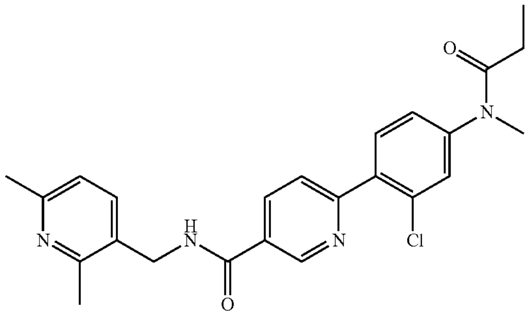
I-T 1761
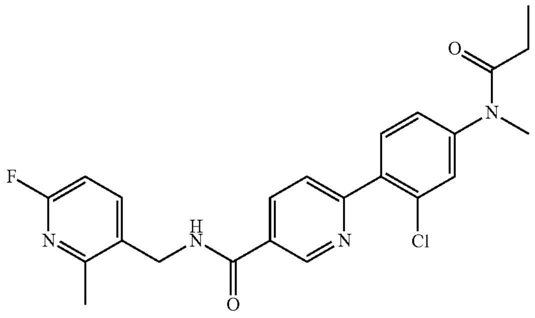

-continued
I-T 1762
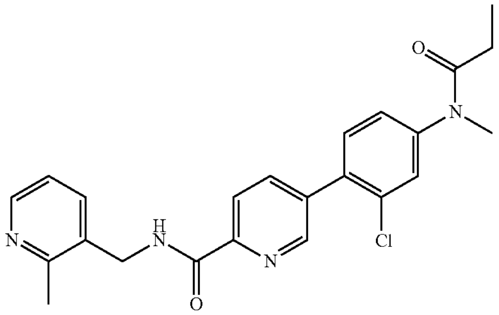
I-T 1763
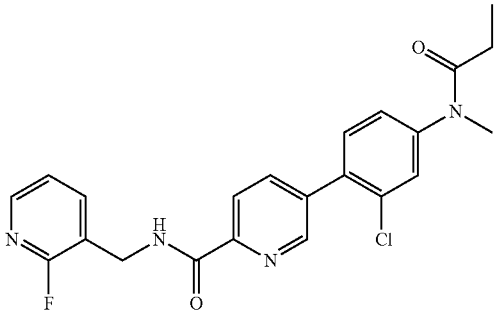
I-T 1764
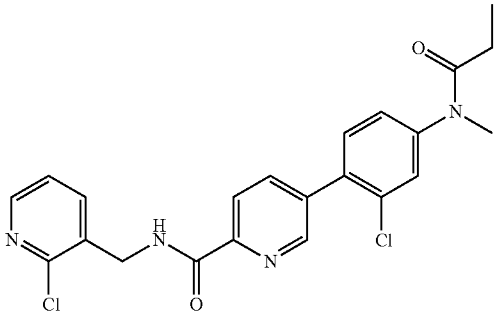
I-T 1765
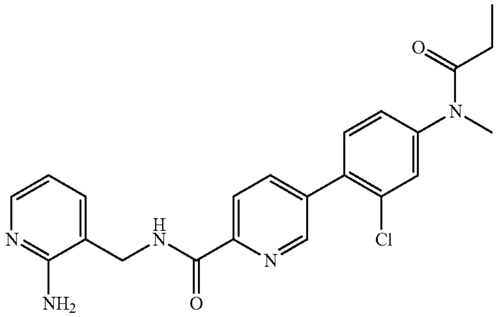
-continued
I-T 1766
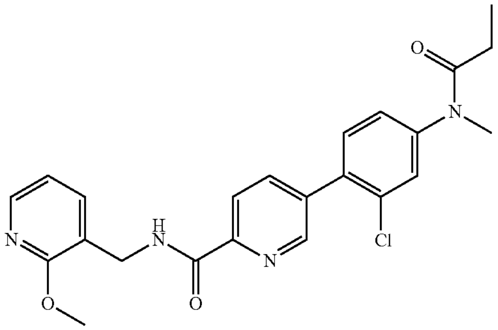
I-T 1767
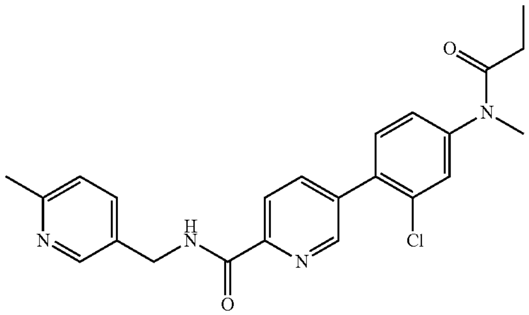
I-T 1768
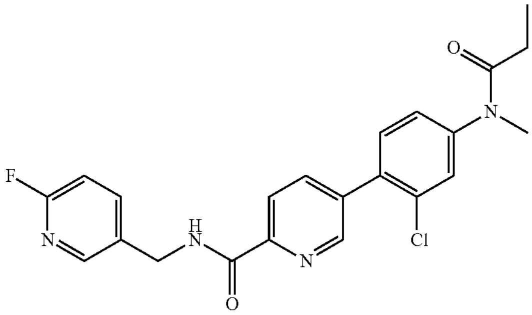
I-T 1769
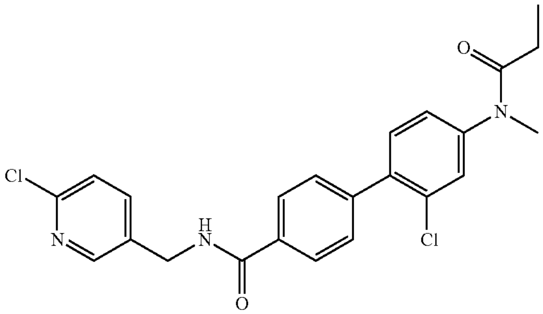

-continued
I-T 1770
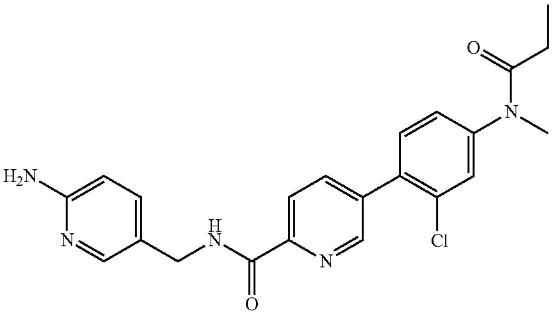
I-T 1771
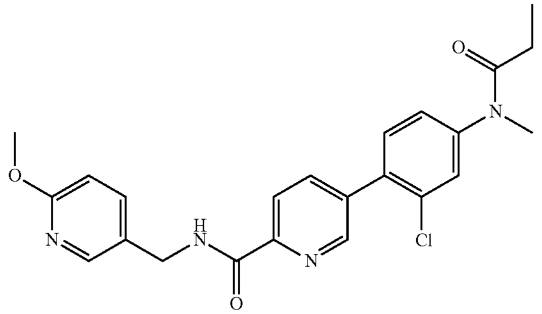
I-T 1772
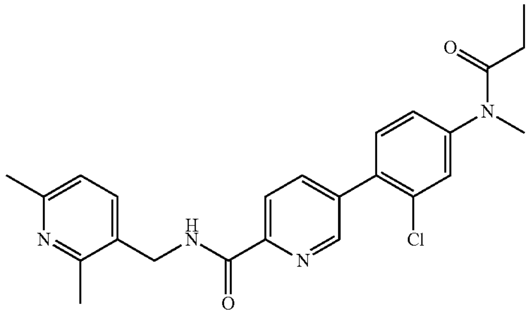
I-T 1773
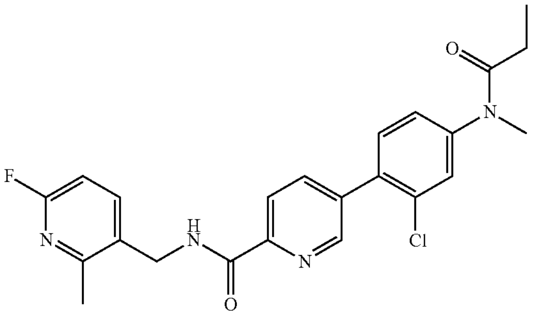
-continued
I-T 1774
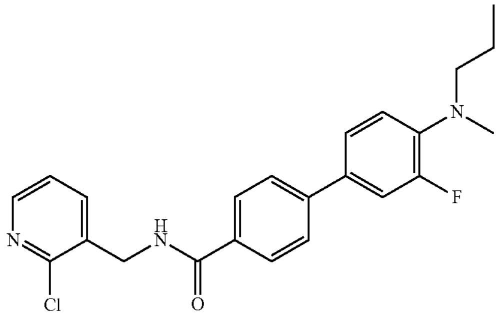
I-T 1775
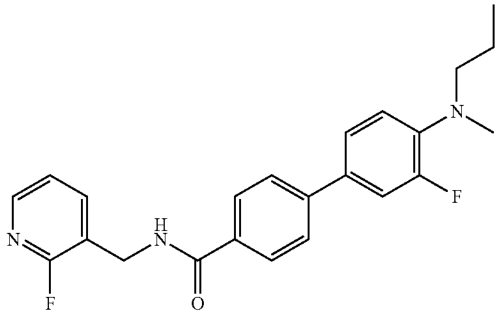
I-T 1776
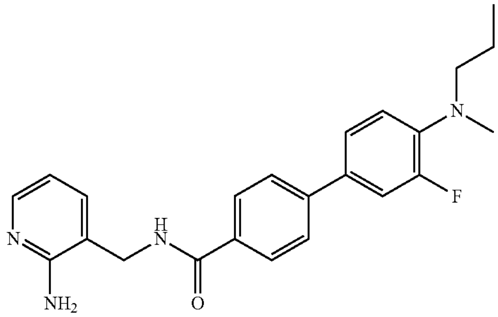
I-T 1777
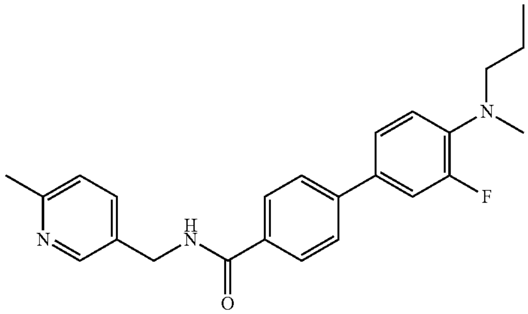

-continued
I-T 1778
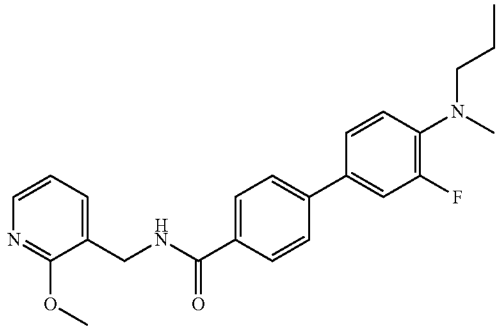
TABLE A
| Compound Structure | Compound Name |
|---|---|
| 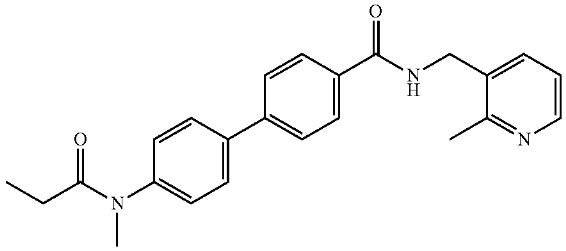 [SMILES: CCC(=O)N(C)c1ccc(-c2ccc(C(=O)NCc3cccnc3C)cc2)cc1] | I-252 |
| 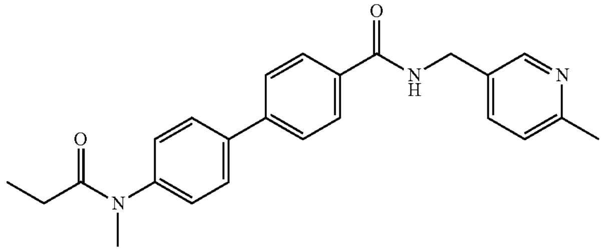 [SMILES: CCC(=O)N(C)c1ccc(-c2ccc(C(=O)NCc3ccc(C)nc3)cc2)cc1] | I-253 |
| 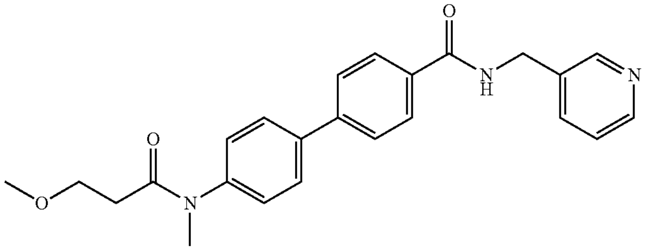 [SMILES: COCCC(=O)N(C)c1ccc(-c2ccc(C(=O)NCc3cccnc3)cc2)cc1] | I-256 |
| 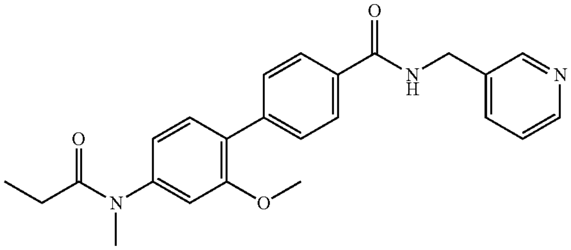 [SMILES: CCC(=O)N(C)c1ccc(-c2ccc(C(=O)NCc3cccnc3)cc2)c(OC)c1] | I-257 |

TABLE A-continued
| Compound Structure | Compound Name |
|---|---|
| 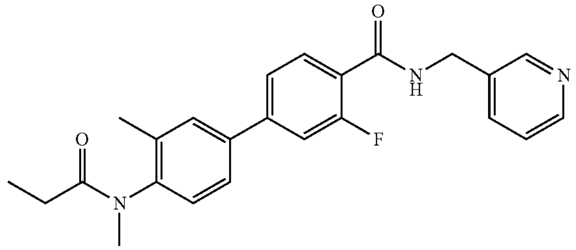 [SMILES: CCC(=O)N(C)c1ccc(-c2ccc(C(=O)NCc3cccnc3)c(F)c2)cc1C] | I-258 |
| 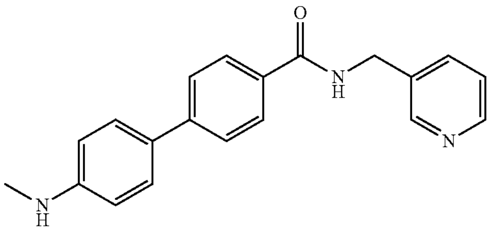 [SMILES: CNc1ccc(-c2ccc(C(=O)NCc3cccnc3)cc2)cc1] | I-259 |
| 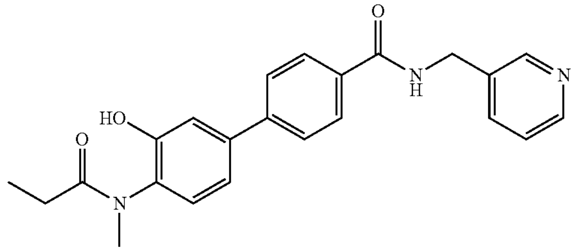 [SMILES: CCC(=O)N(C)c1ccc(-c2ccc(C(=O)NCc3cccnc3)cc2)cc1O] | I-260 |
| 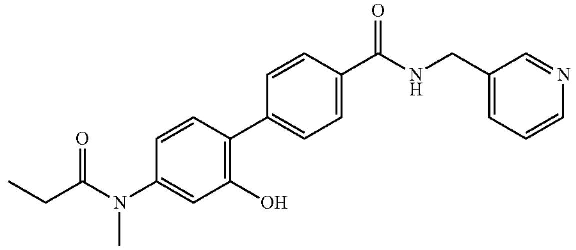 [SMILES: CCC(=O)N(C)c1ccc(-c2ccc(C(=O)NCc3cccnc3)cc2)c(O)c1] | I-263 |
| 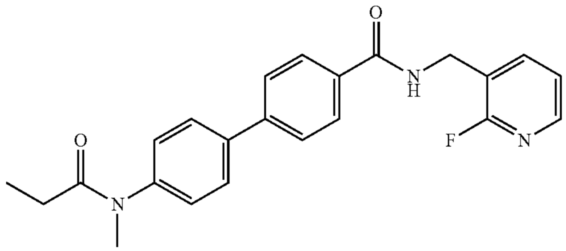 [SMILES: CCC(=O)N(C)c1ccc(-c2ccc(C(=O)NCc3cccnc3F)cc2)cc1] | I-264 |
| 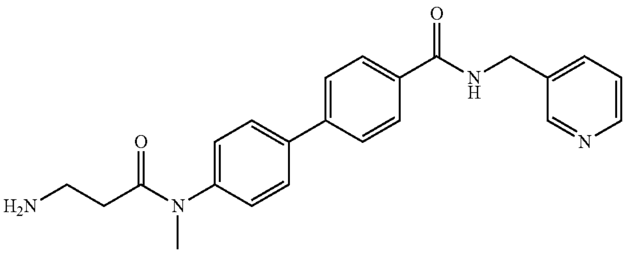 [SMILES: CN(C(=O)CCN)c1ccc(-c2ccc(C(=O)NCc3cccnc3)cc2)cc1] | I-266 |

TABLE A-continued
| Compound Structure | Compound Name |
|---|---|
| 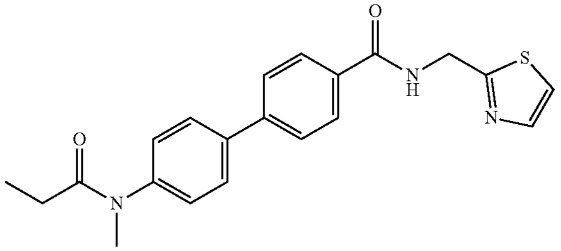 [SMILES: CCC(=O)N(C)c1ccc(-c2ccc(C(=O)NCc3nccs3)cc2)cc1] | I-267 |
| 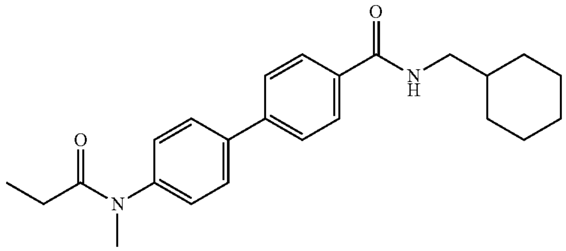 [SMILES: CCC(=O)N(C)c1ccc(-c2ccc(C(=O)NCC3CCCCC3)cc2)cc1] | I-268 |
| 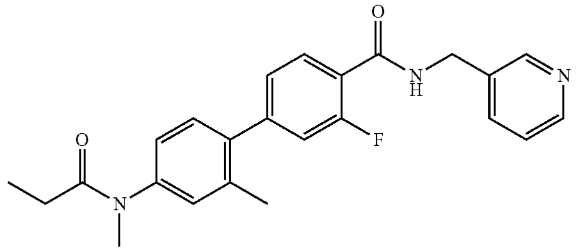 [SMILES: CCC(=O)N(C)c1ccc(-c2ccc(C(=O)NCc3cccnc3)c(F)c2)c(C)c1] | I-271 |
| 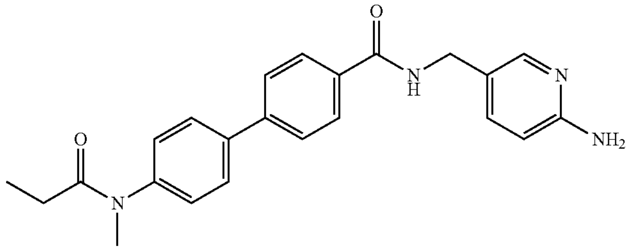 [SMILES: CCC(=O)N(C)c1ccc(-c2ccc(C(=O)NCc3ccc(N)nc3)cc2)cc1] | I-272 |
| 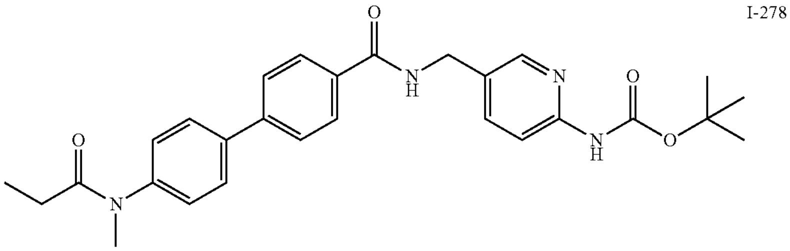 | I-278 |
| 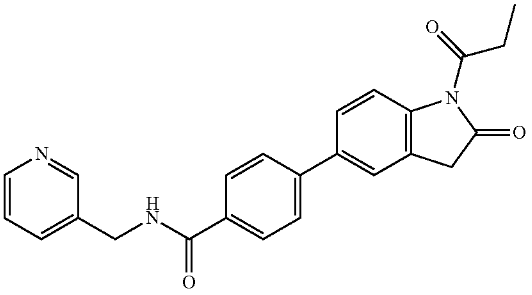 [SMILES: CCC(=O)N1C(=O)Cc2cc(-c3ccc(C(=O)NCc4cccnc4)cc3)ccc21] | I-T52 |

TABLE A-continued
| Compound Structure | Compound Name |
|---|---|
| 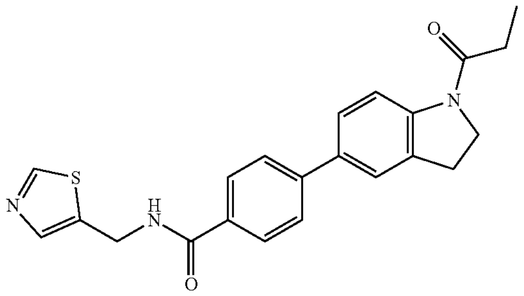 [SMILES: CCC(=O)N1CCc2cc(-c3ccc(C(=O)NCc4cncs4)cc3)ccc21] | I-T197 |
| 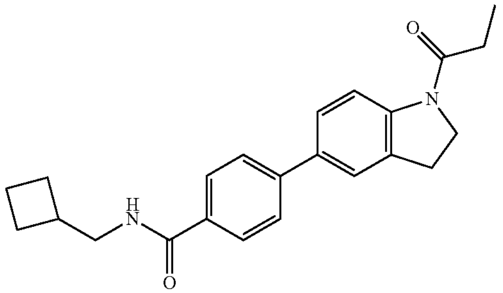 [SMILES: CCC(=O)N1CCc2cc(-c3ccc(C(=O)NCC4CCC4)cc3)ccc21] | I-T202 |
| 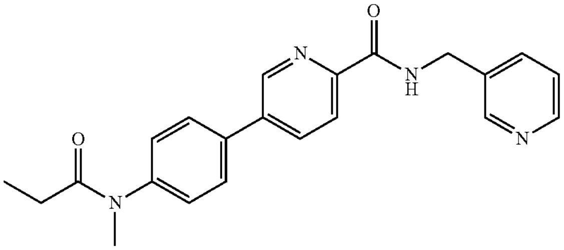 [SMILES: CCC(=O)N(C)c1ccc(-c2ccc(C(=O)NCc3cccnc3)nc2)cc1] | I-T214 |
| 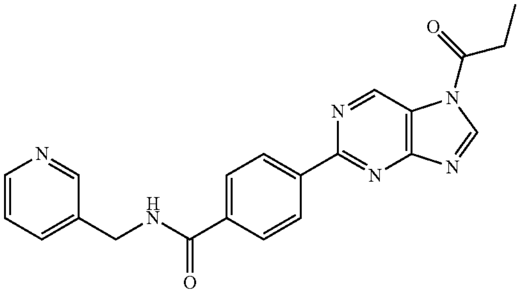 [SMILES: CCC(=O)n1cnc2nc(-c3ccc(C(=O)NCc4cccnc4)cc3)ncc21] | I-T216 |
| 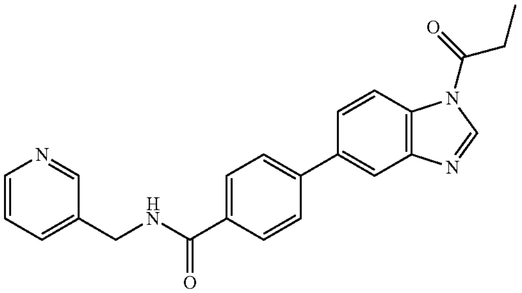 [SMILES: CCC(=O)n1cnc2cc(-c3ccc(C(=O)NCc4cccnc4)cc3)ccc21] | I-T218 |

TABLE A-continued
| Compound Structure | Compound Name |
|---|---|
| 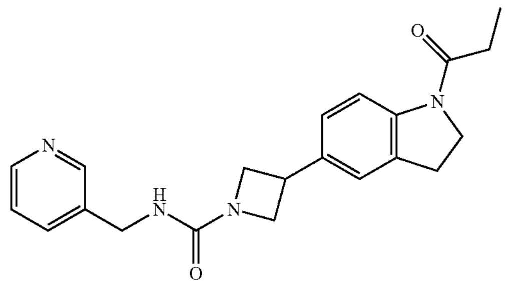 [SMILES: CCC(=O)N1CCc2cc(C3CN(C(=O)NCc4cccnc4)C3)ccc21] | I-T221 |
| 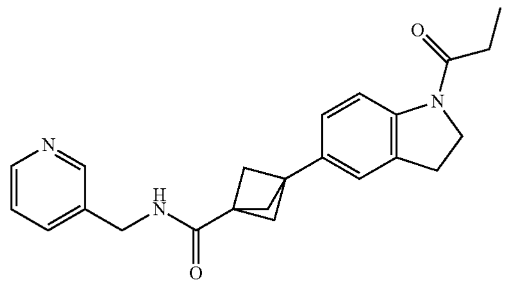 [SMILES: CCC(=O)N1CCc2cc(C34CC(C(=O)NCc5cccnc5)(C3)C4)ccc21] | I-T222 |
| 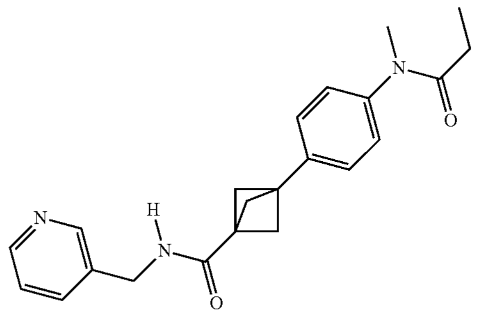 [SMILES: CCC(=O)N(C)c1ccc(C23CC(C(=O)NCc4cccnc4)(C2)C3)cc1] | I-T234 |
| 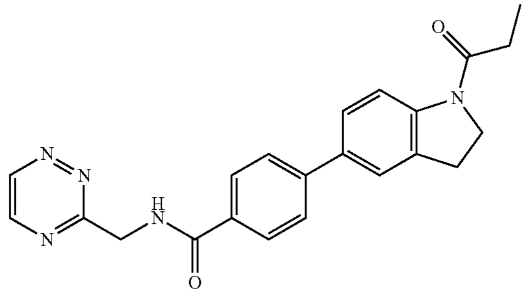 [SMILES: CCC(=O)N1CCc2cc(-c3ccc(C(=O)NCc4nccnn4)cc3)ccc21] | I-T235 |
| 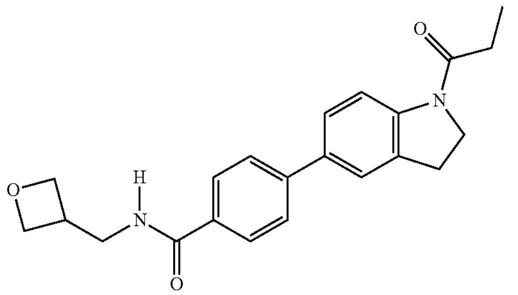 [SMILES: CCC(=O)N1CCc2cc(-c3ccc(C(=O)NCC4COC4)cc3)ccc21] | I-T236 |

TABLE A-continued
| Compound Structure | Compound Name |
| --- | --- |
| 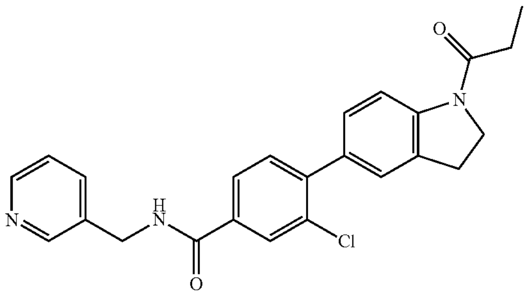 [SMILES: CCC(=O)N1CCc2cc(-c3ccc(C(=O)NCc4cccnc4)cc3Cl)ccc21] | I-T253 |
| 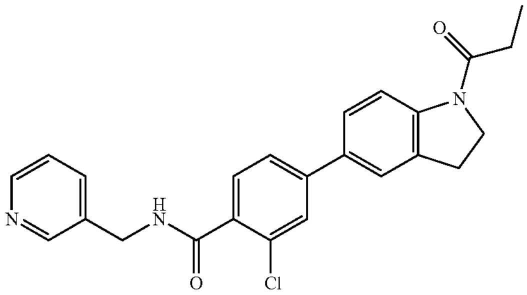 [SMILES: CCC(=O)N1CCc2cc(-c3ccc(C(=O)NCc4cccnc4)c(Cl)c3)ccc21] | I-T254 |
| 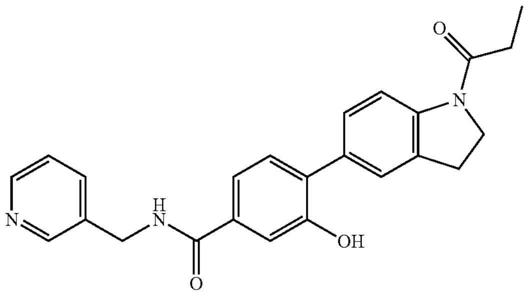 [SMILES: CCC(=O)N1CCc2cc(-c3ccc(C(=O)NCc4cccnc4)cc3O)ccc21] | I-T255 |
| 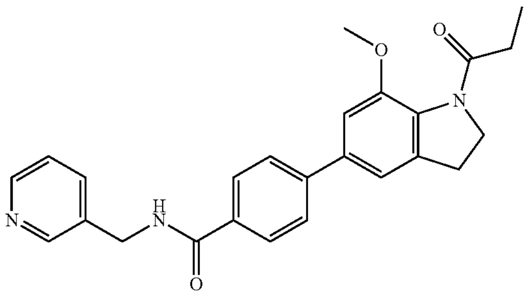 [SMILES: CCC(=O)N1CCc2cc(-c3ccc(C(=O)NCc4cccnc4)cc3)cc(OC)c21] | I-T257 |
| 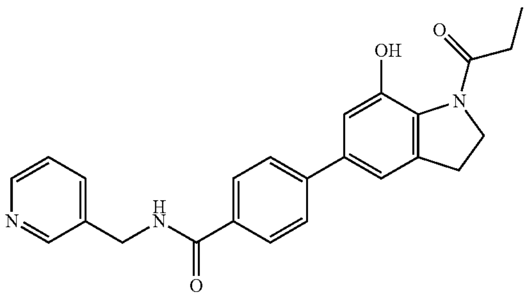 [SMILES: CCC(=O)N1CCc2cc(-c3ccc(C(=O)NCc4cccnc4)cc3)cc(O)c21] | I-T258 |

TABLE A-continued
| Compound Structure | Compound Name |
|---|---|
| 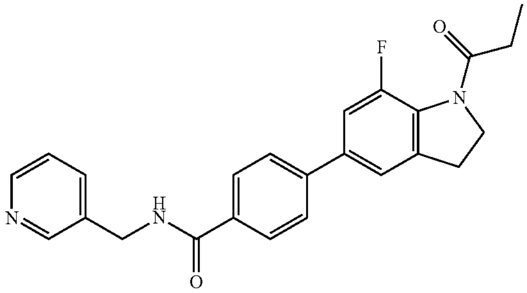 [SMILES: CCC(=O)N1CCc2cc(-c3ccc(C(=O)NCc4cccnc4)cc3)cc(F)c21] | I-T259 |
| 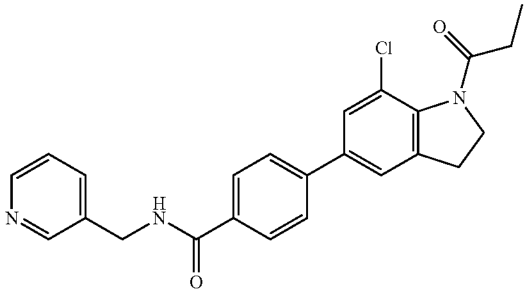 [SMILES: CCC(=O)N1CCc2cc(-c3ccc(C(=O)NCc4cccnc4)cc3)cc(Cl)c21] | I-T260 |
| 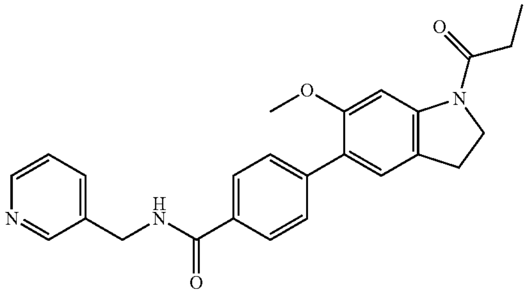 [SMILES: CCC(=O)N1CCc2cc(-c3ccc(C(=O)NCc4cccnc4)cc3)c(OC)cc21] | I-T261 |
| 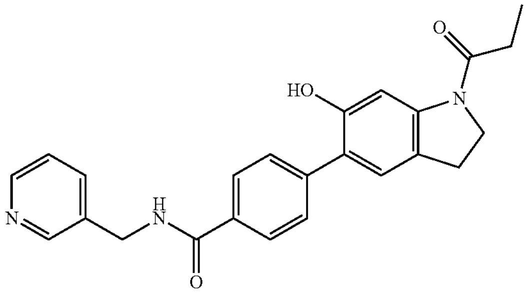 [SMILES: CCC(=O)N1CCc2cc(-c3ccc(C(=O)NCc4cccnc4)cc3)c(O)cc21] | I-T262 |
| 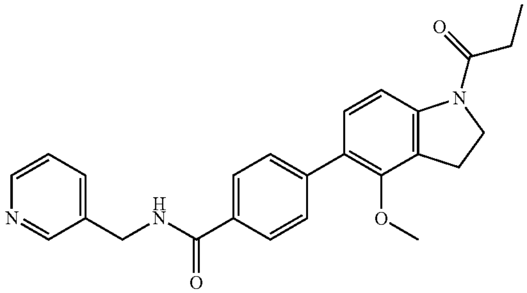 [SMILES: CCC(=O)N1CCc2c1ccc(-c1ccc(C(=O)NCc3cccnc3)cc1)c2OC] | I-T265 |

TABLE A-continued
| Compound Structure | Compound Name |
|---|---|
| 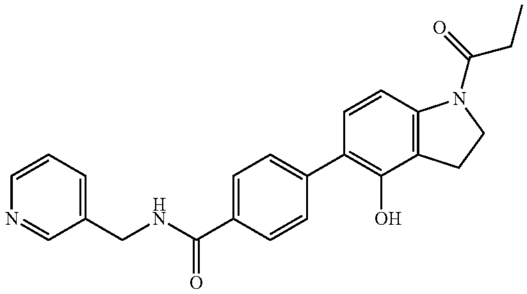 [SMILES: CCC(=O)N1CCc2c1ccc(-c1ccc(C(=O)NCc3cccnc3)cc1)c2O] | I-T266 |
| 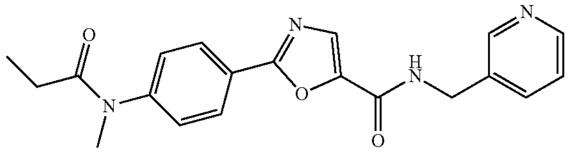 [SMILES: CCC(=O)N(C)c1ccc(-c2ncc(C(=O)NCc3cccnc3)o2)cc1] | I-T278 |
| 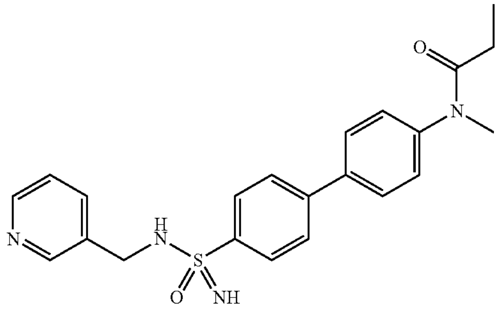 [SMILES: CCC(=O)N(C)c1ccc(-c2ccc(S(=N)(=O)NCc3cccnc3)cc2)cc1] | I-T302 |
| 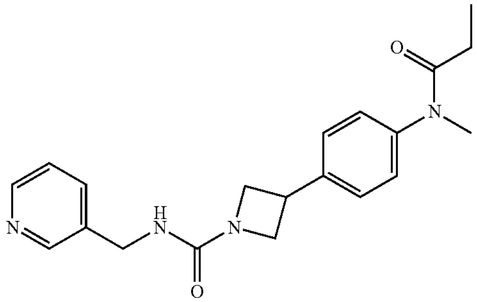 [SMILES: CCC(=O)N(C)c1ccc(C2CN(C(=O)NCc3cccnc3)C2)cc1] | I-T305 |
| 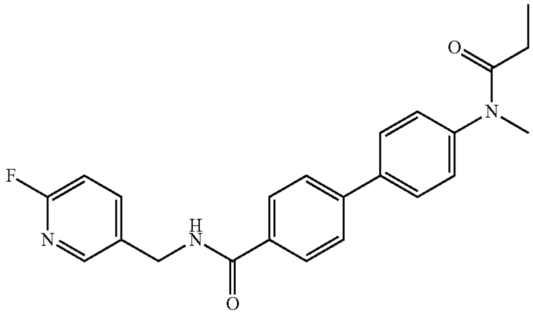 [SMILES: CCC(=O)N(C)c1ccc(-c2ccc(C(=O)NCc3ccc(F)nc3)cc2)cc1] | I-T310 |

TABLE A-continued
| Compound Structure | Compound Name |
| --- | --- |
| 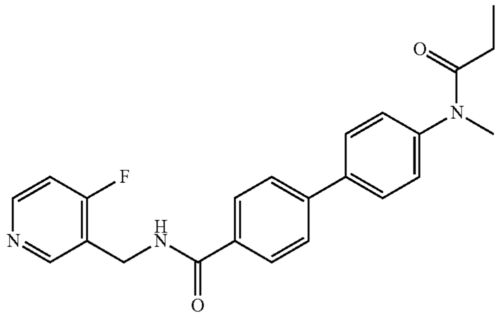 | I-T312 |
| 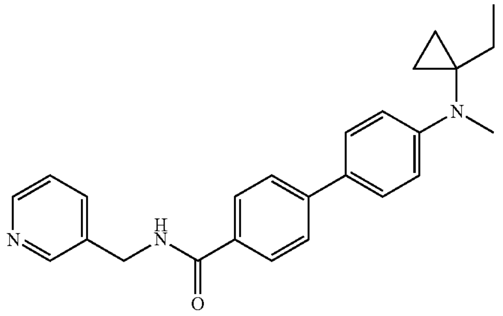 [SMILES: CCC1(N(C)c2ccc(-c3ccc(C(=O)NCc4cccnc4)cc3)cc2)CC1] | I-T314 |
| 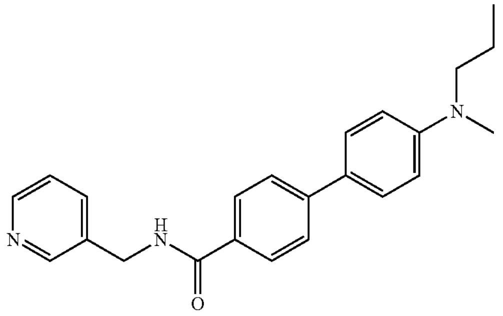 [SMILES: CCCN(C)c1ccc(-c2ccc(C(=O)NCc3cccnc3)cc2)cc1] | I-T317 |
| 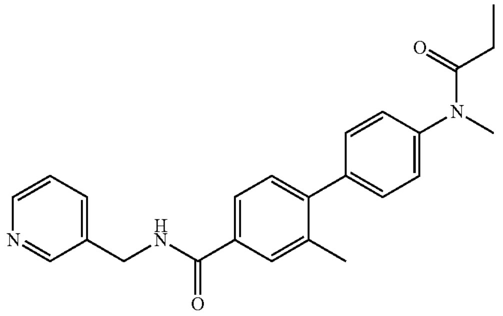 [SMILES: CCC(=O)N(C)c1ccc(-c2ccc(C(=O)NCc3cccnc3)cc2C)cc1] | I-T323 |

TABLE A-continued
| Compound Structure | Compound Name |
|---|---|
| 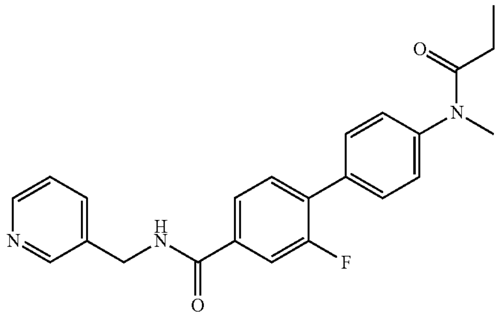 [SMILES: CCC(=O)N(C)c1ccc(-c2ccc(C(=O)NCc3cccnc3)cc2F)cc1] | I-T324 |
| 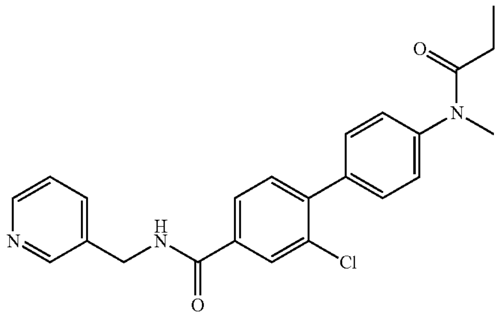 [SMILES: CCC(=O)N(C)c1ccc(-c2ccc(C(=O)NCc3cccnc3)cc2Cl)cc1] | I-T325 |
| 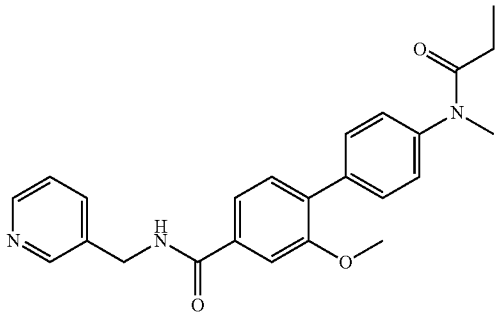 [SMILES: CCC(=O)N(C)c1ccc(-c2ccc(C(=O)NCc3cccnc3)cc2OC)cc1] | I-T326 |
| 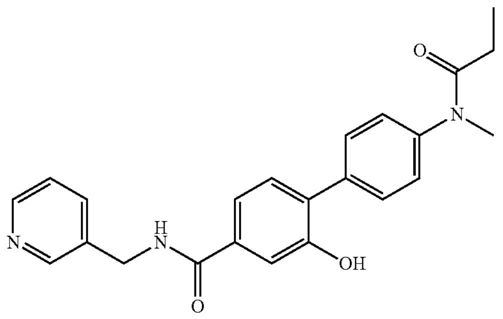 [SMILES: CCC(=O)N(C)c1ccc(-c2ccc(C(=O)NCc3cccnc3)cc2O)cc1] | I-T327 |

TABLE A-continued
| Compound Structure | Compound Name |
|---|---|
| 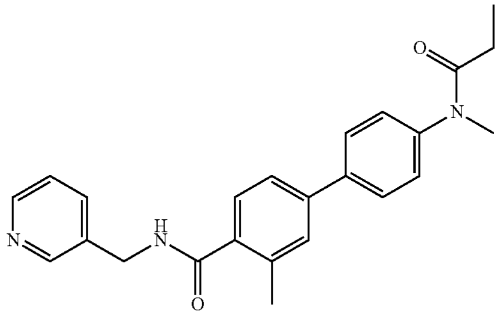 [SMILES: CCC(=O)N(C)c1ccc(-c2ccc(C(=O)NCc3cccnc3)c(C)c2)cc1] | I-T328 |
| 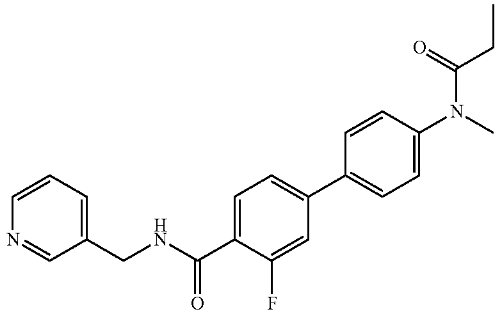 | I-T329 |
| 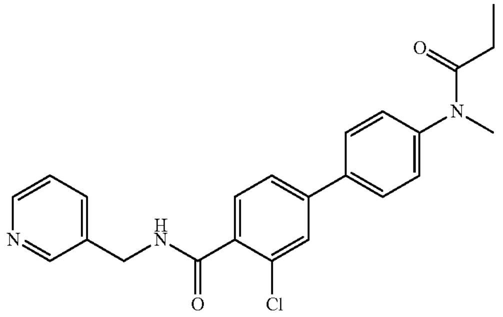 [SMILES: CCC(=O)N(C)c1ccc(-c2ccc(C(=O)NCc3cccnc3)c(Cl)c2)cc1] | I-T330 |
| 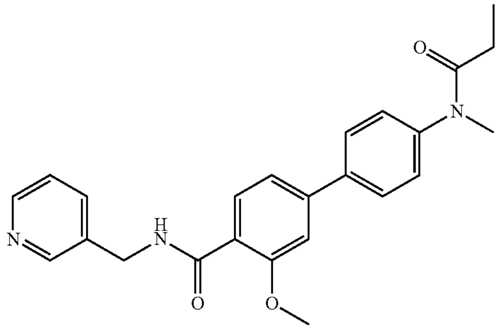 [SMILES: CCC(=O)N(C)c1ccc(-c2ccc(C(=O)NCc3cccnc3)c(OC)c2)cc1] | I-T331 |

TABLE A-continued
| Compound Structure | Compound Name |
|---|---|
| 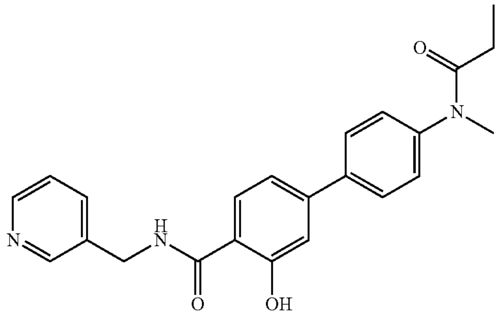 [SMILES: CCC(=O)N(C)c1ccc(-c2ccc(C(=O)NCc3cccnc3)c(O)c2)cc1] | I-T332 |
| 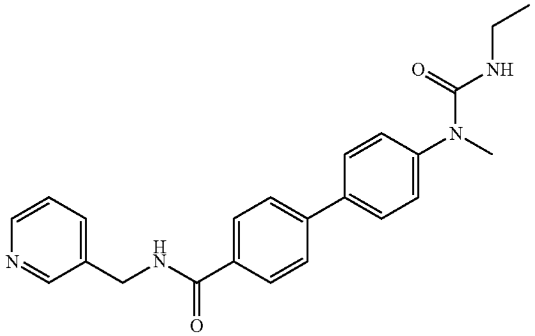 [SMILES: CCNC(=O)N(C)c1ccc(-c2ccc(C(=O)NCc3cccnc3)cc2)cc1] | I-T334 |
| 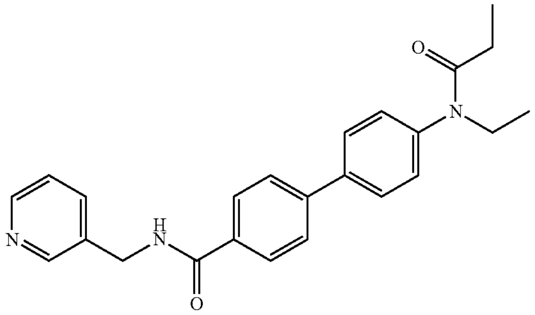 [SMILES: CCC(=O)N(CC)c1ccc(-c2ccc(C(=O)NCc3cccnc3)cc2)cc1] | I-T335 |
| 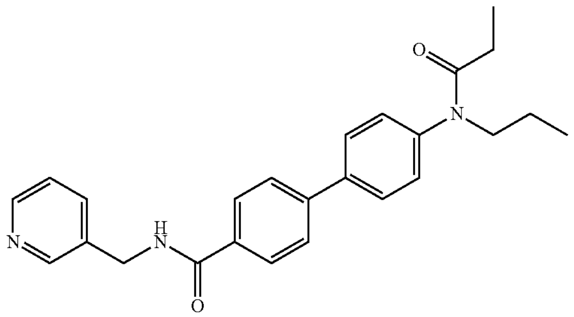 [SMILES: CCCN(C(=O)CC)c1ccc(-c2ccc(C(=O)NCc3cccnc3)cc2)cc1] | I-T336 |

TABLE A-continued
| Compound Structure | Compound Name |
|---|---|
| 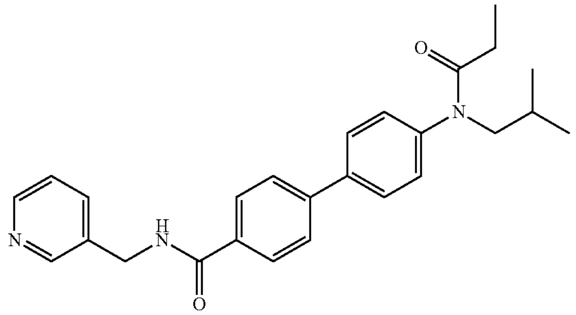 [SMILES: CCC(=O)N(CC(C)C)c1ccc(-c2ccc(C(=O)NCc3cccnc3)cc2)cc1] | I-T337 |
| 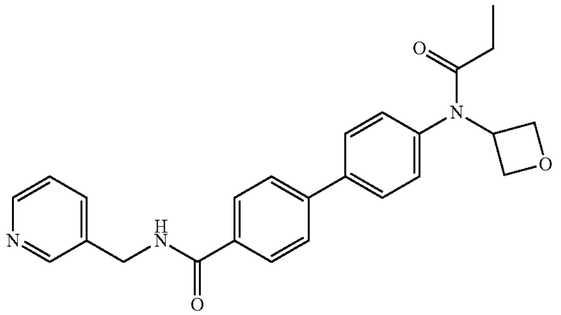 [SMILES: CCC(=O)N(c1ccc(-c2ccc(C(=O)NCc3cccnc3)cc2)cc1)C1COC1] | I-T338 |
| 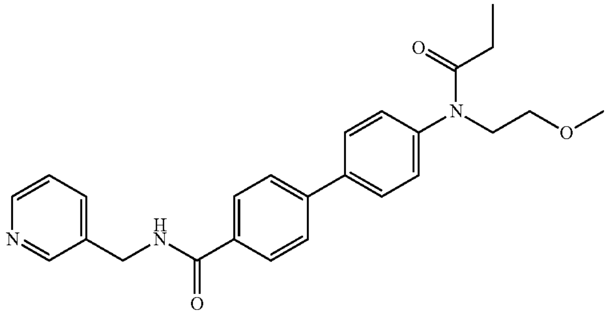 [SMILES: CCC(=O)N(CCOC)c1ccc(-c2ccc(C(=O)NCc3cccnc3)cc2)cc1] | I-T339 |
| 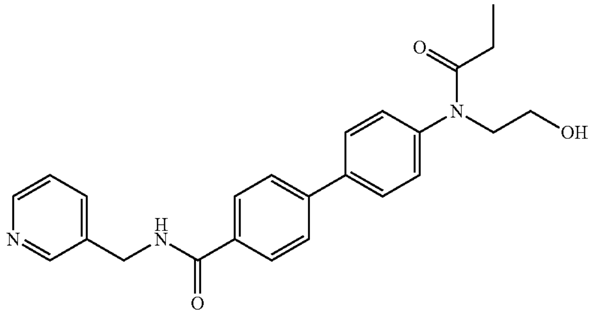 [SMILES: CCC(=O)N(CCO)c1ccc(-c2ccc(C(=O)NCc3cccnc3)cc2)cc1] | I-T340 |

TABLE A-continued
| Compound Structure | Compound Name |
| --- | --- |
| 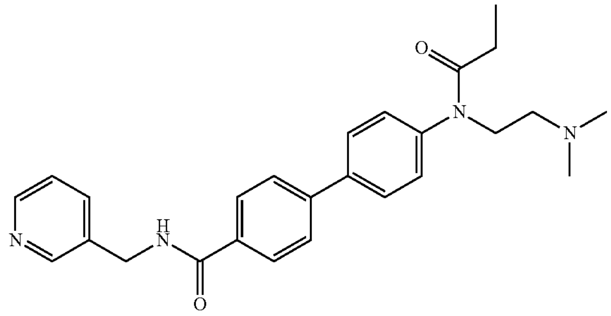 [SMILES: CCC(=O)N(CCN(C)C)c1ccc(-c2ccc(C(=O)NCc3cccnc3)cc2)cc1] | I-T341 |
| 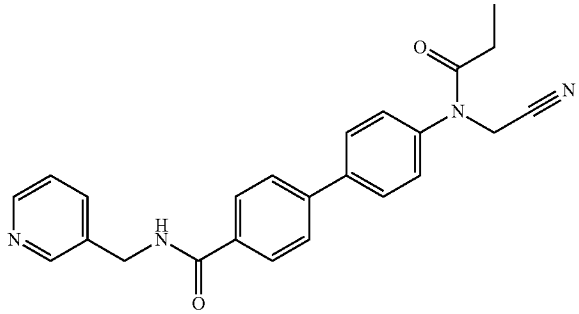 [SMILES: CCC(=O)N(CC#N)c1ccc(-c2ccc(C(=O)NCc3cccnc3)cc2)cc1] | I-T342 |
| 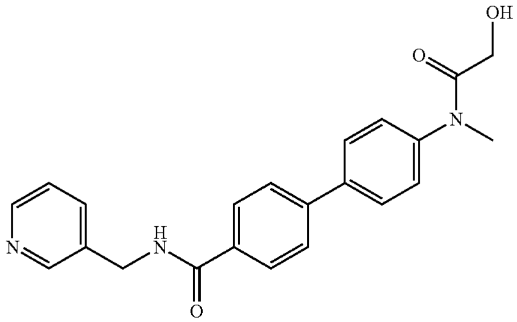 [SMILES: CN(C(=O)CO)c1ccc(-c2ccc(C(=O)NCc3cccnc3)cc2)cc1] | I-T345 |
| 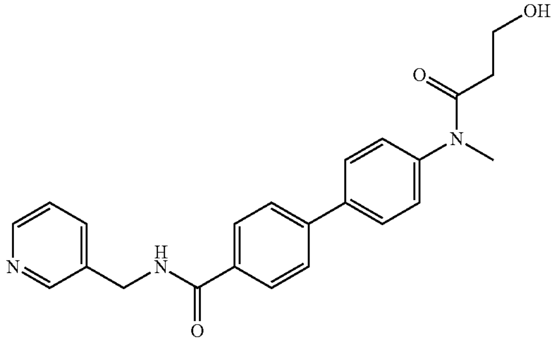 [SMILES: CN(C(=O)CCO)c1ccc(-c2ccc(C(=O)NCc3cccnc3)cc2)cc1] | I-T347 |

TABLE A-continued
| Compound Structure | Compound Name |
|---|---|
| 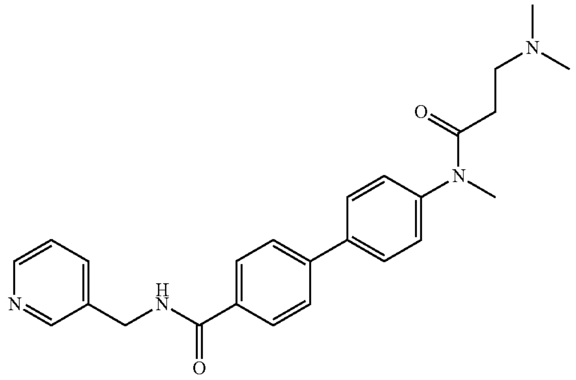 [SMILES: CN(C)CCC(=O)N(C)c1ccc(-c2ccc(C(=O)NCc3cccnc3)cc2)cc1] | I-T348 |
| 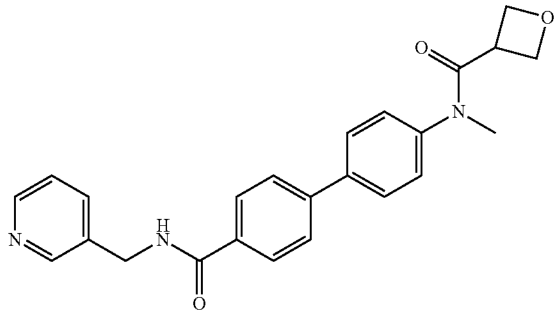 [SMILES: CN(C(=O)C1COC1)c1ccc(-c2ccc(C(=O)NCc3cccnc3)cc2)cc1] | I-T350 |
| 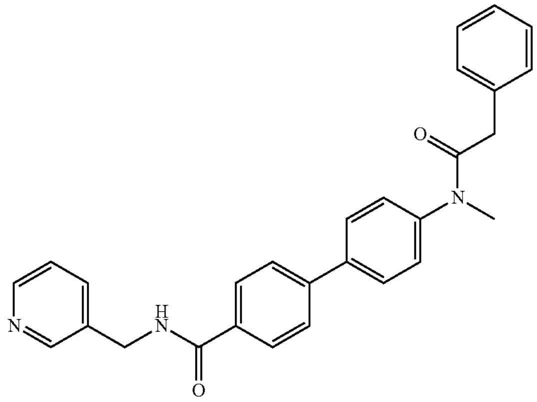 [SMILES: CN(C(=O)Cc1ccccc1)c1ccc(-c2ccc(C(=O)NCc3cccnc3)cc2)cc1] | I-T352 |
| 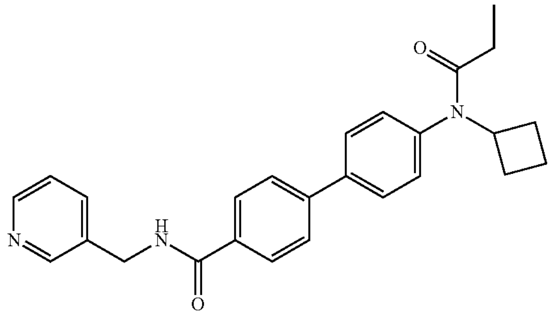 [SMILES: CCC(=O)N(c1ccc(-c2ccc(C(=O)NCc3cccnc3)cc2)cc1)C1CCC1] | I-T360 |

TABLE A-continued
| Compound Structure | Compound Name |
|---|---|
| 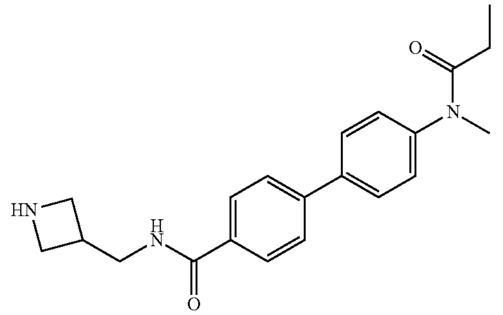 [SMILES: CCC(=O)N(C)c1ccc(-c2ccc(C(=O)NCC3CNC3)cc2)cc1] | I-T378 |
| 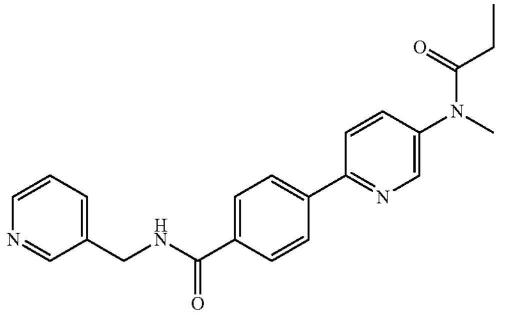 [SMILES: CCC(=O)N(C)c1ccc(-c2ccc(C(=O)NCc3cccnc3)cc2)nc1] | I-T383 |
| 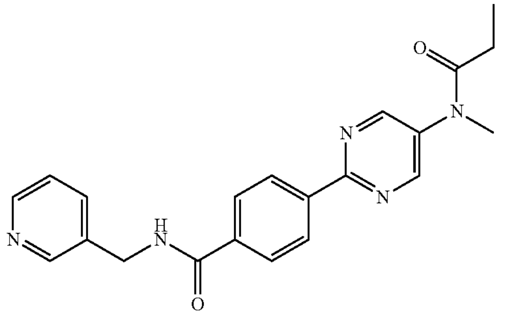 [SMILES: CCC(=O)N(C)c1cnc(-c2ccc(C(=O)NCc3cccnc3)cc2)nc1] | I-T384 |
| 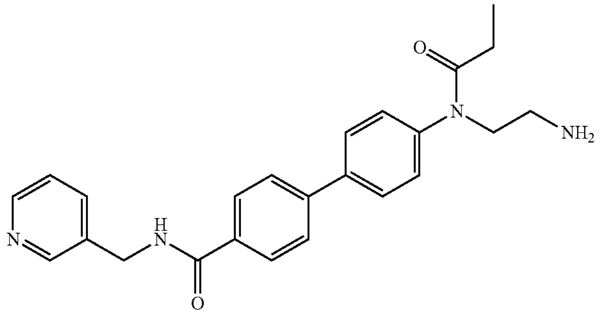 [SMILES: CCC(=O)N(CCN)c1ccc(-c2ccc(C(=O)NCc3cccnc3)cc2)cc1] | I-T395 |

TABLE A-continued
| Compound Structure | Compound Name |
| --- | --- |
| 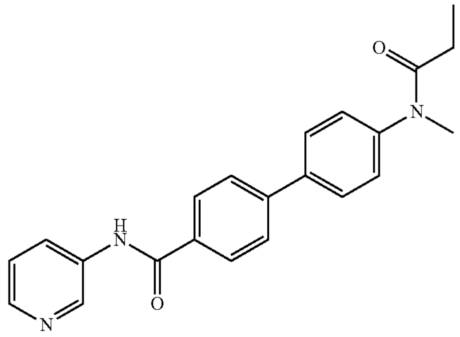 [SMILES: CCC(=O)N(C)c1ccc(-c2ccc(C(=O)Nc3cccnc3)cc2)cc1] | I-T396 |
| 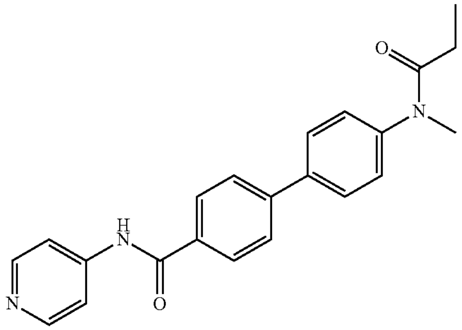 [SMILES: CCC(=O)N(C)c1ccc(-c2ccc(C(=O)Nc3ccncc3)cc2)cc1] | I-T397 |
| 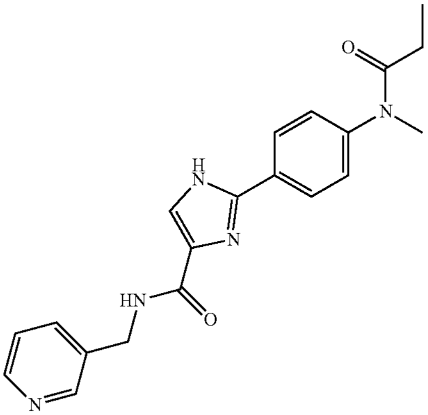 [SMILES: CCC(=O)N(C)c1ccc(-c2nc(C(=O)NCc3cccnc3)c[nH]2)cc1] | I-T399 |
| 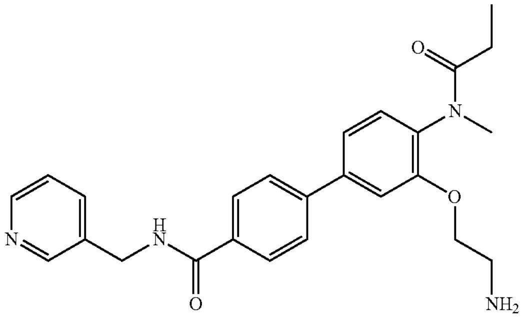 [SMILES: CCC(=O)N(C)c1ccc(-c2ccc(C(=O)NCc3cccnc3)cc2)cc1OCCN] | I-T401 |

TABLE A-continued
| Compound Structure | Compound Name |
|---|---|
| 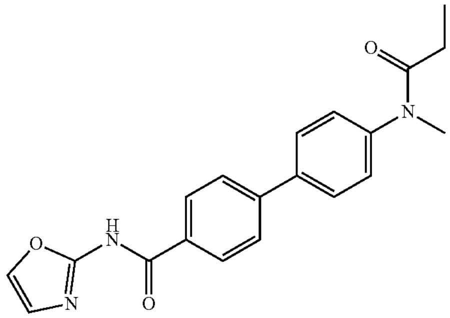 [SMILES: CCC(=O)N(C)c1ccc(-c2ccc(C(=O)Nc3ncco3)cc2)cc1] | I-T402 |
| 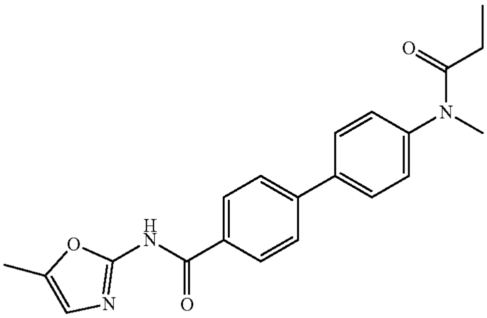 [SMILES: CCC(=O)N(C)c1ccc(-c2ccc(C(=O)Nc3ncc(C)o3)cc2)cc1] | I-T403 |
| 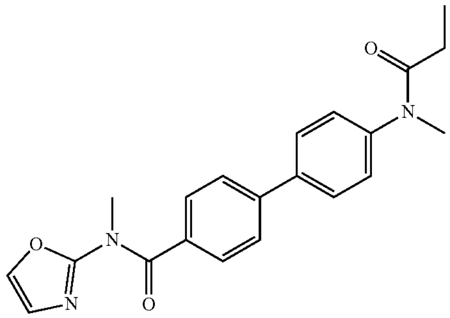 [SMILES: CCC(=O)N(C)c1ccc(-c2ccc(C(=O)N(C)c3ncco3)cc2)cc1] | I-T404 |
| 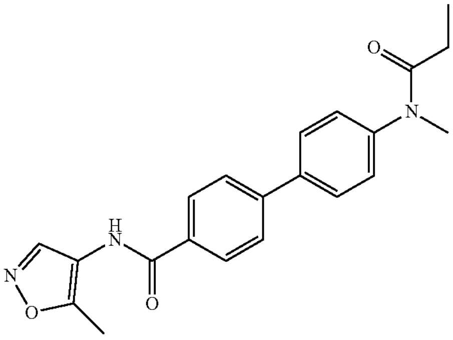 [SMILES: CCC(=O)N(C)c1ccc(-c2ccc(C(=O)Nc3cnoc3C)cc2)cc1] | I-T405 (I-281) |

TABLE A-continued
| Compound Structure | Compound Name |
|---|---|
| 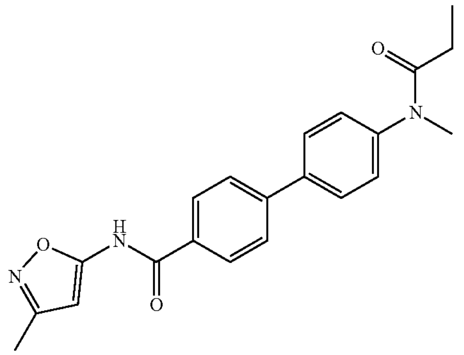 [SMILES: CCC(=O)N(C)c1ccc(-c2ccc(C(=O)Nc3cc(C)no3)cc2)cc1] | I-T406 |
| 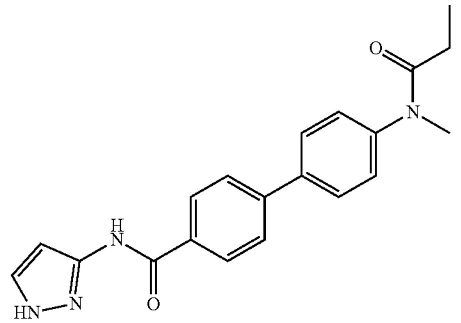 [SMILES: CCC(=O)N(C)c1ccc(-c2ccc(C(=O)Nc3cc[nH]n3)cc2)cc1] | I-T407 |
| 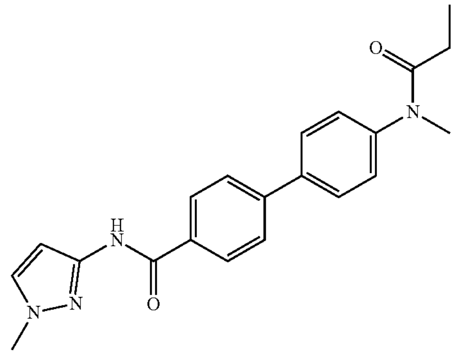 [SMILES: CCC(=O)N(C)c1ccc(-c2ccc(C(=O)Nc3ccn(C)n3)cc2)cc1] | I-T408 (I-282) |
| 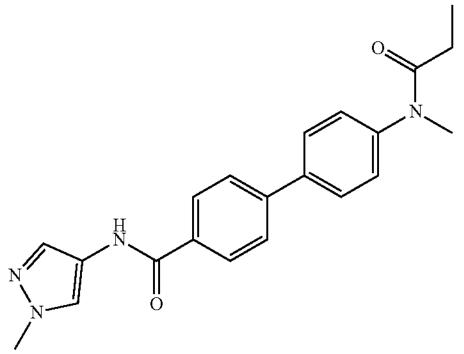 [SMILES: CCC(=O)N(C)c1ccc(-c2ccc(C(=O)Nc3cnn(C)c3)cc2)cc1] | I-T409 |

TABLE A-continued
| Compound Structure | Compound Name |
|---|---|
| 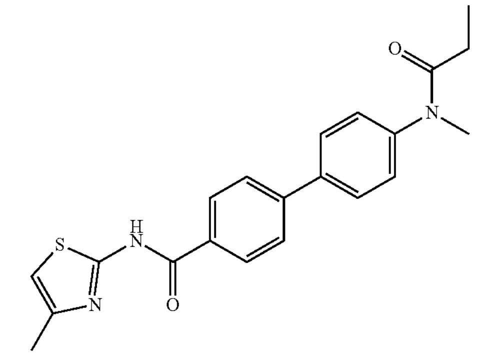 [SMILES: CCC(=O)N(C)c1ccc(-c2ccc(C(=O)Nc3nc(C)cs3)cc2)cc1] | I-T410 (I-283) |
| 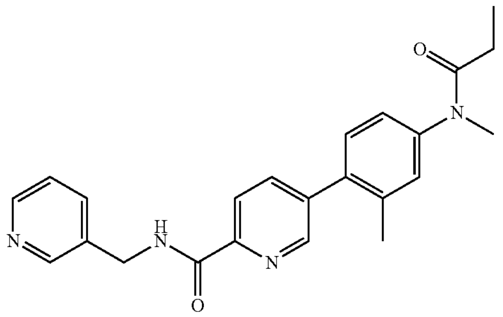 [SMILES: CCC(=O)N(C)c1ccc(-c2ccc(C(=O)NCc3cccnc3)nc2)c(C)c1] | I-T411 |
| 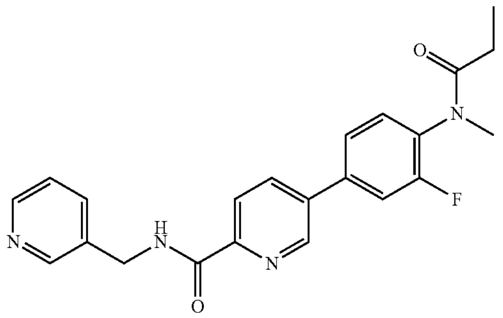 [SMILES: CCC(=O)N(C)c1ccc(-c2ccc(C(=O)NCc3cccnc3)nc2)cc1F] | I-284 |
| 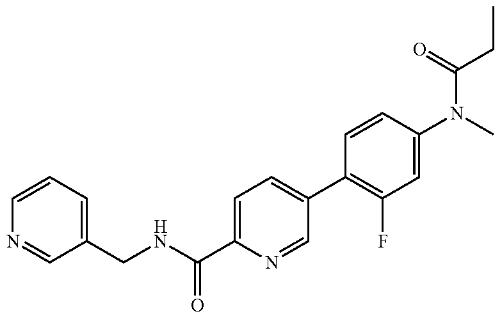 | I-296 |

TABLE A-continued
| Compound Structure | Compound Name |
|---|---|
| 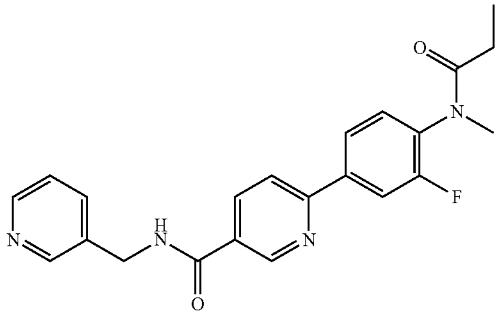 [SMILES: CCC(=O)N(C)c1ccc(-c2ccc(C(=O)NCc3cccnc3)cn2)cc1F] | I-T418 |
| 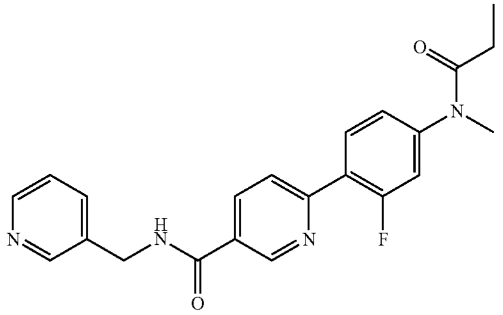 | I-T419 |
| 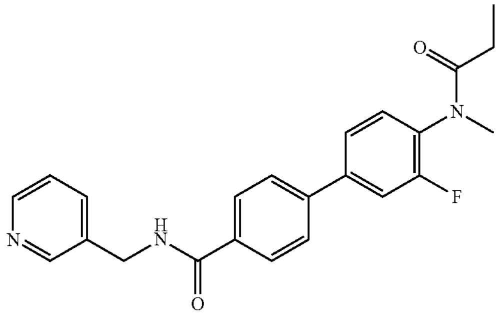 [SMILES: CCC(=O)N(C)c1ccc(-c2ccc(C(=O)NCc3cccnc3)cc2)cc1F] | I-T420 |
| 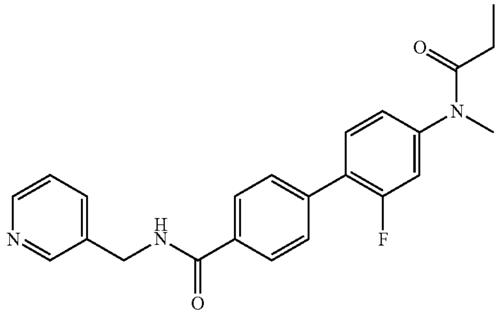 [SMILES: CCC(=O)N(C)c1ccc(-c2ccc(C(=O)NCc3cccnc3)cc2)c(F)c1] | I-T421 |
| 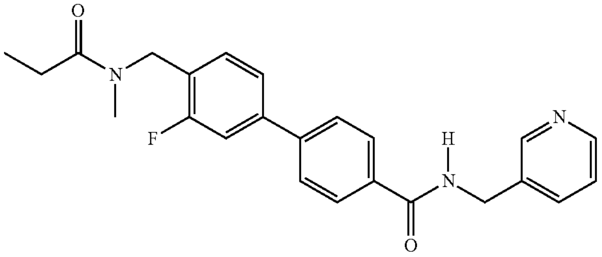 [SMILES: CCC(=O)N(C)Cc1ccc(-c2ccc(C(=O)NCc3cccnc3)cc2)cc1F] | I-285 |

TABLE A-continued
| Compound Structure | Compound Name |
|---|---|
| 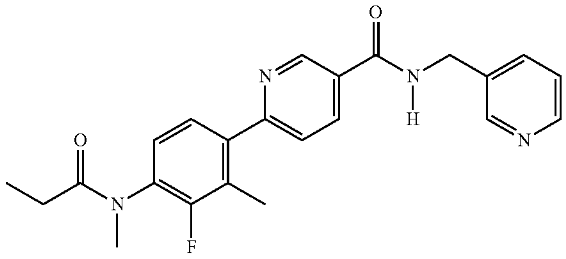 [SMILES: CCC(=O)N(C)c1ccc(-c2ccc(C(=O)NCc3cccnc3)cn2)c(C)c1F] | I-T428 |
| 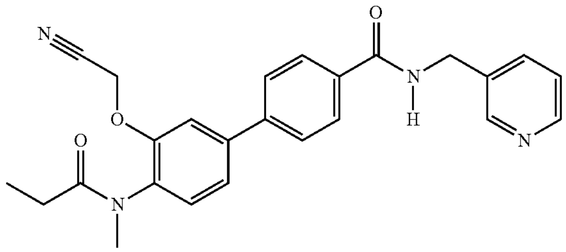 [SMILES: CCC(=O)N(C)c1ccc(-c2ccc(C(=O)NCc3cccnc3)cc2)cc1OCC#N] | I-T429 |
| 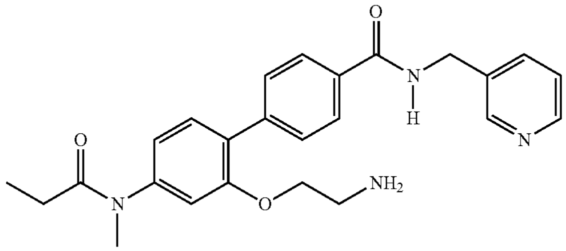 [SMILES: CCC(=O)N(C)c1ccc(-c2ccc(C(=O)NCc3cccnc3)cc2)c(OCCN)c1] | I-T432 |
| 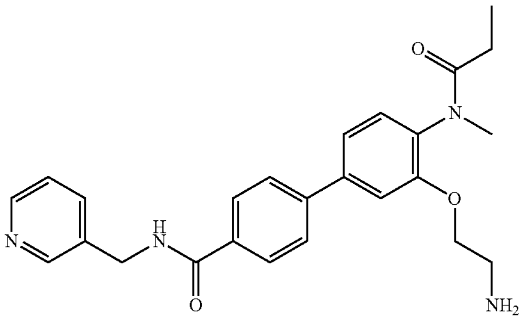 [SMILES: CCC(=O)N(C)c1ccc(-c2ccc(C(=O)NCc3cccnc3)cc2)cc1OCCN] | I-T434 |
| 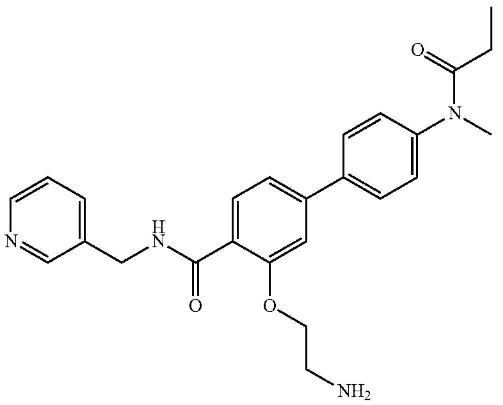 [SMILES: CCC(=O)N(C)c1ccc(-c2ccc(C(=O)NCc3cccnc3)c(OCCN)c2)cc1] | I-T435 |

TABLE A-continued
| Compound Structure | Compound Name |
|---|---|
| 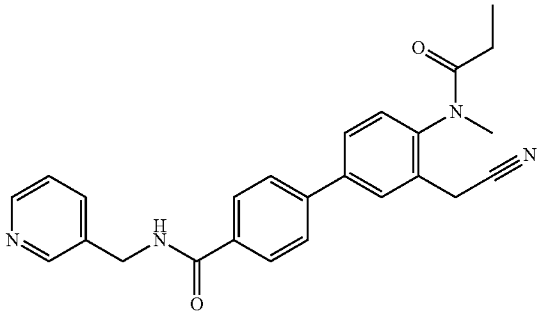 [SMILES: CCC(=O)N(C)c1ccc(-c2ccc(C(=O)NCc3cccnc3)cc2)cc1CC#N] | I-T445 |
| 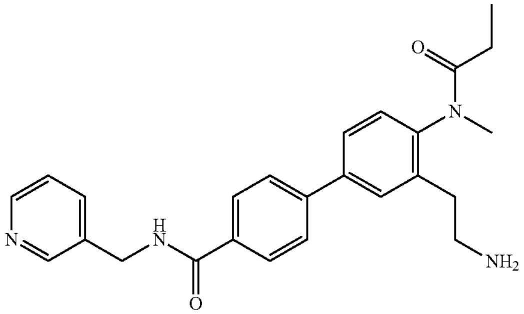 [SMILES: CCC(=O)N(C)c1ccc(-c2ccc(C(=O)NCc3cccnc3)cc2)cc1CCN] | I-T446 |
| 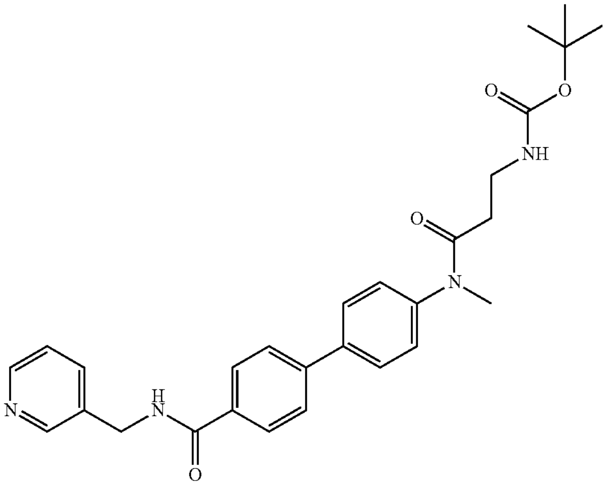 [SMILES: CN(C(=O)CCNC(=O)OC(C)(C)C)c1ccc(-c2ccc(C(=O)NCc3cccnc3)cc2)cc1] | I-T448 |
| 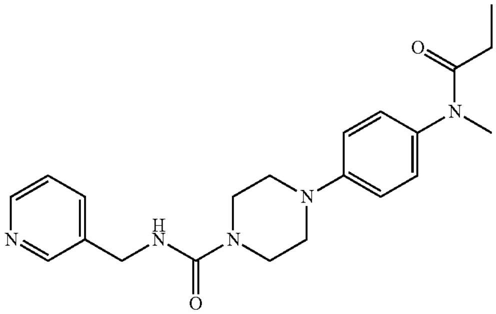 [SMILES: CCC(=O)N(C)c1ccc(N2CCN(C(=O)NCc3cccnc3)CC2)cc1] | I-T456 |

TABLE A-continued
| Compound Structure | Compound Name |
|---|---|
| 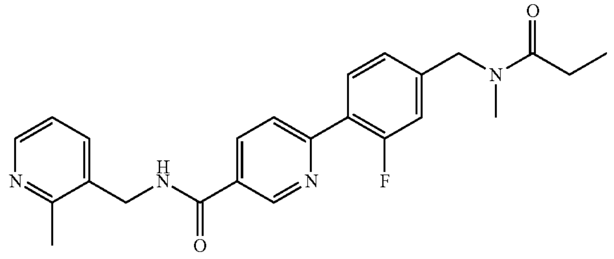 [SMILES: CCC(=O)N(C)Cc1ccc(-c2ccc(C(=O)NCc3cccnc3C)cn2)c(F)c1] | I-T1702A |
| 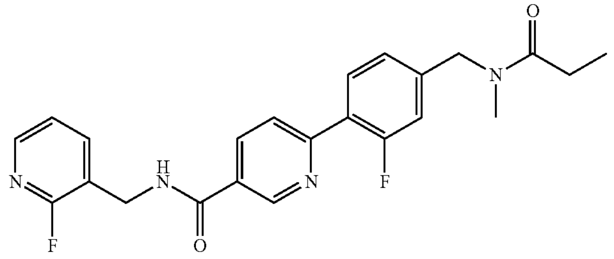 [SMILES: CCC(=O)N(C)Cc1ccc(-c2ccc(C(=O)NCc3cccnc3F)cn2)c(F)c1] | I-T1703A |
| 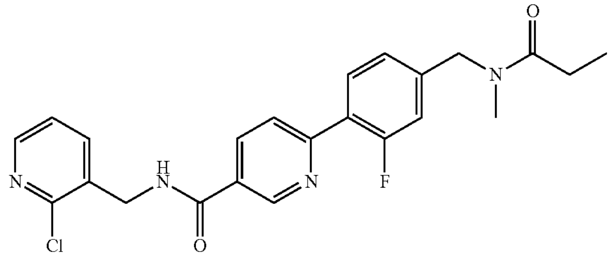 [SMILES: CCC(=O)N(C)Cc1ccc(-c2ccc(C(=O)NCc3cccnc3Cl)cn2)c(F)c1] | I-T1704A |
| 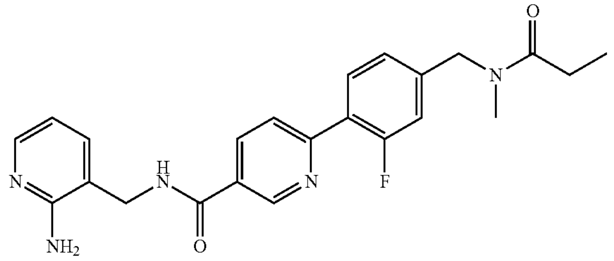 [SMILES: CCC(=O)N(C)Cc1ccc(-c2ccc(C(=O)NCc3cccnc3N)cn2)c(F)c1] | I-T1705A |
| 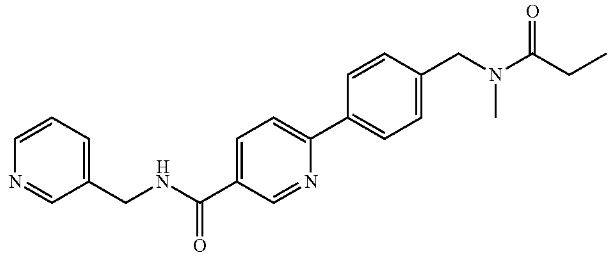 [SMILES: CCC(=O)N(C)Cc1ccc(-c2ccc(C(=O)NCc3cccnc3)cn2)cc1] | I-T1779 |
| 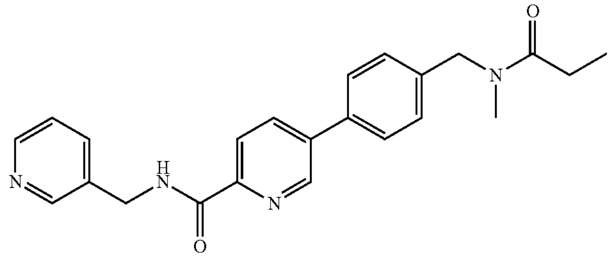 [SMILES: CCC(=O)N(C)Cc1ccc(-c2ccc(C(=O)NCc3cccnc3)nc2)cc1] | I-T1780 |

TABLE A-continued
| Compound Structure | Compound Name |
| --- | --- |
| 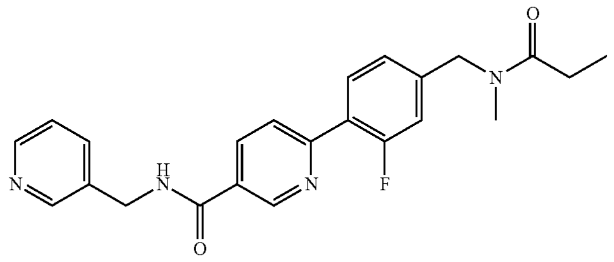 [SMILES: CCC(=O)N(C)Cc1ccc(-c2ccc(C(=O)NCc3cccnc3)cn2)c(F)c1] | I-T1781 |
| 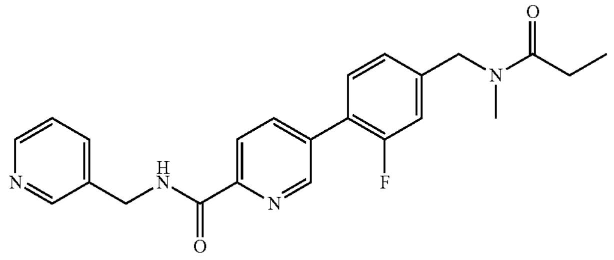 [SMILES: CCC(=O)N(C)Cc1ccc(-c2ccc(C(=O)NCc3cccnc3)nc2)c(F)c1] | I-T1782 |
| 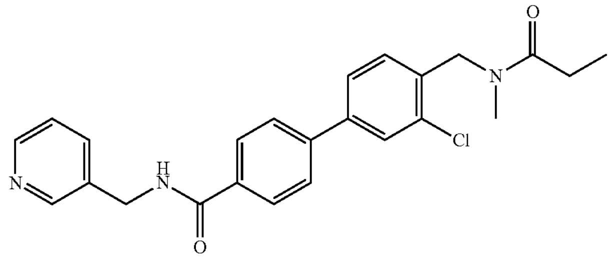 | I-T1783 |
| 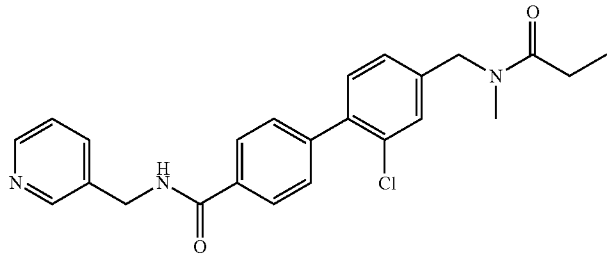 [SMILES: CCC(=O)N(C)Cc1ccc(-c2ccc(C(=O)NCc3cccnc3)cc2)c(Cl)c1] | I-T1784 |
| 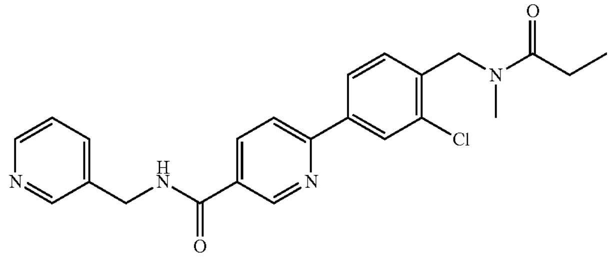 [SMILES: CCC(=O)N(C)Cc1ccc(-c2ccc(C(=O)NCc3cccnc3)cn2)cc1Cl] | I-T1785 |

TABLE A-continued
| Compound Structure | Compound Name |
| --- | --- |
| 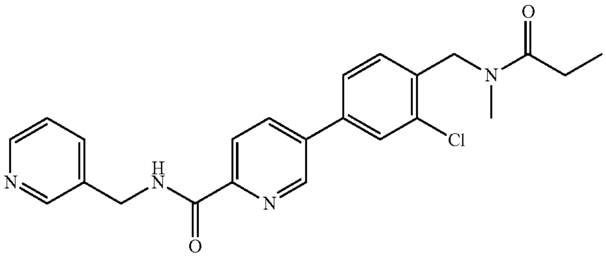 [SMILES: CCC(=O)N(C)Cc1ccc(-c2ccc(C(=O)NCc3cccnc3)nc2)cc1Cl] | I-T1786 |
| 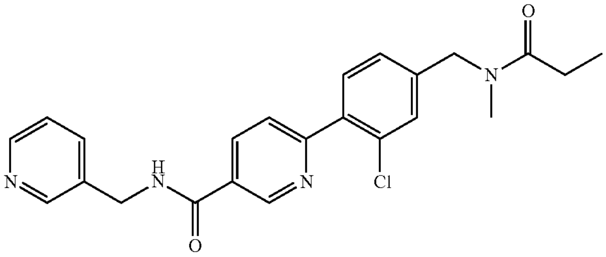 | I-T1787 |
| 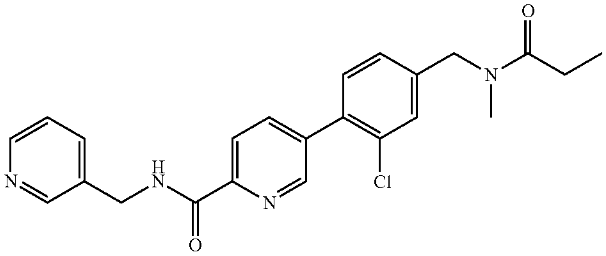 | I-T1788 |
| 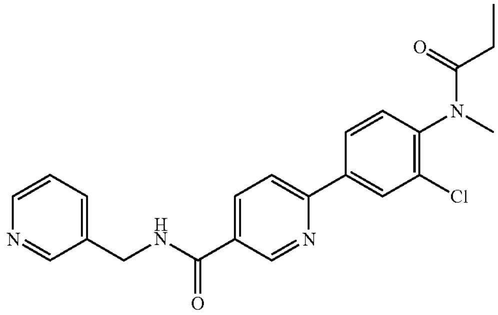 [SMILES: CCC(=O)N(C)c1ccc(-c2ccc(C(=O)NCc3cccnc3)cn2)cc1Cl] | I-T1789 |
| 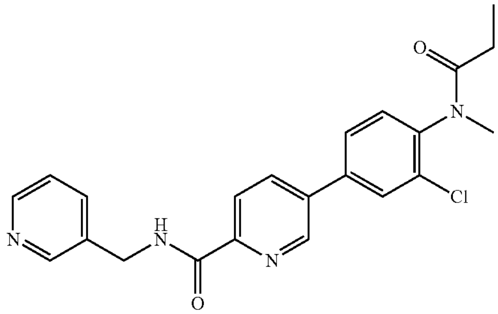 [SMILES: CCC(=O)N(C)c1ccc(-c2ccc(C(=O)NCc3cccnc3)nc2)cc1Cl] | I-T1790 |

TABLE A-continued

| Compound Structure | Compound Name |
|---|---|
| 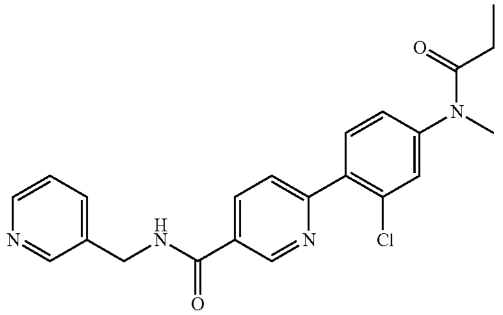 | I-T1791 |
| 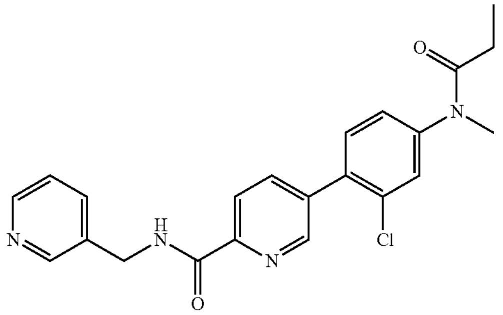 | I-T1792 |

Compositions and Kits

The present disclosure provides compositions (e.g., pharmaceutical compositions) comprising a compound of the disclosure, and an excipient (e.g., pharmaceutically acceptable excipient). In certain embodiments, the composition is a pharmaceutical composition. In certain embodiments, the excipient is a pharmaceutically acceptable excipient.

Compositions described herein can be prepared by any method known in the art. In general, such preparatory methods include bringing a compound of the disclosure described herein into association with an excipient and may include one or more agents or accessory ingredients, and then, if necessary and/or desirable, shaping, and/or packaging the product into a desired single- or multi-dose unit. In certain embodiments, the agent is a pharmaceutical agent.

In certain embodiments, the compound of the disclosure is in the form of a pharmaceutically acceptable salt, solvate, hydrate, polymorph, co-crystal, tautomer, stereoisomer, isotopically labeled derivative, or prodrug.

Compositions can be prepared, packaged, and/or sold in bulk, as a single unit dose, and/or as a plurality of single unit doses. A "unit dose" is a discrete amount of the composition comprising a predetermined amount of the agent. The amount of the agent is generally equal to the dosage of the agent which would be administered to a subject and/or a convenient fraction of such a dosage, such as one-half or one-third of such a dosage.

Relative amounts of the compound of the disclosure, excipient, agent, and/or any additional ingredients in a composition described herein will vary, depending upon the identity, size, and/or condition of the subject treated and further depending upon the route by which the composition is to be administered. The composition may comprise between 0.1% and 100% (w/w) agent.

Excipients and accessory ingredients used in the manufacture of provided compositions include inert diluents, dispersing and/or granulating agents, surface active agents and/or emulsifiers, disintegrating agents, binding agents, preservatives, buffering agents, lubricating agents, and/or oils. Excipients and accessory ingredients, such as cocoa butter, PEGylated lipids, phospholipids, suppository waxes, coloring agents, coating agents, sweetening, flavoring, and perfuming agents, may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan monostearate (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *Litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

In certain embodiments, the compositions, further comprise an agent, and are useful for delivering said agent (e.g., to a subject or cell). In certain embodiments, the compositions are pharmaceutical compositions which are useful for treating a disease in a subject in need thereof. In certain embodiments, the disease is cancer. In certain embodiments, the cancer is colorectal cancer (e.g., colon cancer or rectal cancer). In certain embodiments, the cancer is gastric cancer.

In certain embodiments, the cancer is gastrointestinal stromal tumor. In certain embodiments, the cancer is ovarian cancer (e.g., ovarian adenocarcinoma). In certain embodiments, the cancer is lung cancer (e.g., small cell lung cancer). In certain embodiments, the cancer is non-small cell lung cancer. In certain embodiments, the cancer is breast cancer. In certain embodiments, the cancer is pancreatic cancer (e.g., pancreatic carcinoma or pancreatic adenocarcinoma). In certain embodiments, the cancer is prostate cancer (e.g., prostate adenocarcinoma). In certain embodiments, the cancer is testicular cancer. In certain embodiments, the cancer is liver cancer. In certain embodiments, the cancer is endometrial cancer (e.g., uterine cancer). In certain embodiments, the cancer is lymphoma, such as non-Hodgkin's lymphoma (e.g., B-cell non-Hodgkin's lymphoma). In certain embodiments, the cancer is B-cell lymphoma (e.g., Burkitt's B-cell lymphoma, large B-cell lymphoma). In certain embodiments, the cancer is T-cell lymphoma. In certain embodiments, the cancer is Burkitt's lymphoma (e.g., Burkitt's B-cell lymphoma). In certain embodiments, the cancer is large cell immunoblastic lymphoma. In certain embodiments, the cancer is leukemia. In certain embodiments, the cancer is acute monocytic leukemia or acute lymphocytic leukemia (e.g., B-cell acute lymphocytic leukemia). In certain embodiments, the cancer is acute lymphoblastic leukemia (e.g., B-cell acute lymphoblastic leukemia or T-cell acute lymphoblastic leukemia). In certain embodiments, the cancer is multiple myeloma (e.g., B-cell myeloma).

A composition, as described herein, can be administered in combination with one or more additional agents. In certain embodiments, the agents are organic molecules. In certain embodiments, the agents are inorganic molecules. In certain embodiments, the agents are targeting agents. In certain embodiments, the agents are isotopically labeled chemical compounds. In certain embodiments, the agents are agents useful in bioprocessing. In certain embodiments, the agents are pharmaceutical agents (e.g., therapeutically and/or prophylactically active agents). Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, polynucleotides, lipids, hormones, vitamins, vaccines, immunological agents, and cells.

In certain embodiments, the compound of the disclosure described herein is provided in an effective amount in the composition. In certain embodiments, the effective amount is a therapeutically effective amount. In certain embodiments, the effective amount is an amount effective for treating cancer in a subject in need thereof. In certain embodiments, the effective amount is an amount effective for inhibiting the signaling pathway required for metastasis in a subject or cell.

In certain embodiments, the cell is in vitro. In certain embodiments, the cell is ex vivo.

Compositions may be formulated into liquid dosage forms for oral and parenteral administration include pharmaceutically acceptable emulsions, microemulsions, solutions, suspensions, syrups and elixirs. In addition to the agents, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the compositions described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the disclosure, it is often desirable to slow the absorption of the compound from subcutaneous or intramuscular injection. This can be accomplished by the use of a liquid suspension of crystalline or amorphous material with poor water solubility. The rate of absorption of the compound then depends upon its rate of dissolution, which, in turn, may depend upon crystal size and crystalline form. Alternatively, delayed absorption of a parenterally administered drug form may be accomplished by dissolving or suspending the compound in an oil vehicle.

Compositions for rectal or vaginal administration are typically suppositories which can be prepared by mixing the compositions described herein with suitable non-irritating excipients or carriers such as cocoa butter, polyethylene glycol, or a suppository wax which are solid at ambient temperature but liquid at body temperature and therefore melt in the rectum or vaginal cavity and release the compound of the disclosure.

Compositions may be formulated into solid dosage forms for oral administration include capsules, tablets, pills, powders, and granules. In such solid dosage forms, the compound of the disclosure is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the compound of the disclosure only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The compound of the disclosure can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the compound of the disclosure can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the compound of the disclosure only, or preferentially, in a certain part of the intestinal tract, optionally, in a delayed manner. Examples of encapsulating agents which can be used include polymeric substances and waxes.

Dosage forms for topical and/or transdermal administration of a composition described herein may include ointments, pastes, creams, lotions, gels, powders, solutions, sprays, inhalants, and/or patches. Generally, the compound of the disclosure is admixed under sterile conditions with a pharmaceutically acceptable carrier or excipient and/or any needed preservatives and/or buffers as can be required.

Suitable devices for use in delivering intradermal compositions described herein include short needle devices. Intradermal compositions can be administered by devices which limit the effective penetration length of a needle into the skin. Alternatively, or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the polymer in powder form through the outer layers of the skin to the dermis are suitable.

Formulations suitable for topical administration include liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 100% (w/w) compound of the disclosure, although the concentration of the compound of the disclosure can be as high as the solubility limit of the compound of the disclosure in the solvent. Formulations for topical administration may further comprise one or more of the additional ingredients described herein.

A composition described herein can be prepared, packaged, and/or sold in a formulation suitable for pulmonary administration via the buccal cavity. Such a formulation may comprise dry particles which comprise the compound of the disclosure. Such compositions are conveniently in the form of dry powders for administration using a device comprising a dry powder reservoir to which a stream of propellant can be directed to disperse the powder and/or using a self-propelling solvent/powder dispensing container such as a device comprising the agent dissolved and/or suspended in a low-boiling propellant in a sealed container. Dry powder compositions may include a solid fine powder diluent such as sugar and are conveniently provided in a unit dose form.

Low boiling propellants generally include liquid propellants having a boiling point of below 65° F. at atmospheric pressure. Generally, the propellant may constitute 50 to 99.9% (w/w) of the composition, and the compound of the disclosure may constitute 0.1 to 100% (w/w) of the composition. The propellant may further comprise additional ingredients such as a liquid non-ionic and/or solid anionic surfactant and/or a solid diluent.

Compositions described herein formulated for pulmonary delivery may provide the compound of the disclosure in the form of droplets of a solution and/or suspension. Such formulations can be prepared, packaged, and/or sold as aqueous and/or dilute alcoholic solutions and/or suspensions, optionally sterile, comprising the compound of the disclosure, and may conveniently be administered using any nebulization and/or atomization device. Such formulations may further comprise one or more additional ingredients including a flavoring agent such as saccharin sodium, a volatile oil, a buffering agent, a surface active agent, and/or a preservative such as methylhydroxybenzoate.

Formulations described herein as being useful for pulmonary delivery are useful for intranasal delivery of a pharmaceutical composition described herein. Another formulation suitable for intranasal administration is a coarse powder comprising the compound of the disclosure. Such a formulation is administered by rapid inhalation through the nasal passage from a container of the powder held close to the nares.

Formulations for nasal administration may, for example, comprise from about as little as 0.1% (w/w) to as much as 100% (w/w) of the compound of the disclosure, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) agent, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the compound of the disclosure.

A composition described herein can be prepared, packaged, and/or sold in a formulation for ophthalmic administration. Such formulations may, for example, be in the form of eye drops including, for example, a 0.1-100% (w/w) solution and/or suspension of the compound of the disclosure in an aqueous or oily liquid carrier or excipient. Such drops may further comprise buffering agents, salts, and/or one or more other of the additional ingredients described herein. Other opthalmically-administrable formulations which are useful include those which comprise the compound of the disclosure in microcrystalline form and/or in a liposomal preparation. Ear drops and/or eye drops are also contemplated as being within the scope of this disclosure.

Although the descriptions of compositions provided herein are principally directed to compositions which are suitable for administration to humans, it will be understood by the skilled artisan that such compositions are generally suitable for administration to animals of all sorts. Modification of compositions suitable for administration to humans in order to render the compositions suitable for administration to various animals is well understood, and the ordinarily skilled veterinary pharmacologist can design and/or perform such modification with ordinary experimentation.

Compositions provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the cancer being treated and the severity of the cancer; the activity of the specific compound of the disclosure employed; the specific composition employed; the age, body weight, general health, sex, and diet of the subject; the time of administration, route of administration, and rate of excretion of the specific compound of the disclosure employed; the duration of the treatment; drugs used in combination or coincidental with the specific compound of the disclosure employed; and like factors well known in the medical arts.

The compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically, contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the compound of the disclosure (e.g., its stability in the environment of the gastrointestinal tract), and/or the condition of the subject (e.g., whether the subject is able to tolerate oral administration). In certain embodiments, the composition described herein is suitable for topical administration to the eye of a subject.

In some embodiments, administration of any of the compositions described herein occurs at least one hour prior to treatment with another cancer therapy.

The compositions can be administered in combination with additional agents that improve their activity (e.g., potency and/or efficacy) in treating a disease or disorder (e.g., cancer) in a subject in need thereof and/or in inhibiting the signaling pathway in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a composition described herein, including a compound of the disclosure described herein, and an agent show a synergistic effect that is absent in a composition including one of the compounds of the disclosure or the agent, but not both.

The composition can be administered concurrently with, prior to, or subsequent to one or more additional agents, which are different from the composition and may be useful as, e.g., combination therapies. Each additional pharmaceutical agent may be administered at a dose and/or on a time schedule determined for that pharmaceutical agent. The additional pharmaceutical agents may also be administered together with each other and/or with the compound of the disclosure or composition described herein in a single dose or administered separately in different doses. The particular combination to employ in a regimen will take into account compatibility of the compound of the disclosure described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include anti-proliferative agents, anti-cancer agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is a chemotherapeutic agent. In certain embodiments, the additional pharmaceutical agent is an anti-viral agent. In certain embodiments, the additional pharmaceutical agent is a binder or inhibitor of a protein kinase. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compound of the disclosures described herein or pharmaceutical compositions can be administered in combination with an anti-cancer therapy including surgery, radiation therapy, transplantation (e.g., stem cell transplantation, bone marrow transplantation), immunotherapy, and chemotherapy. In some embodiments, the subject is administered concurrently with, prior to, or subsequent to one or more additional agents, such as one or more additional cancer therapies. In some embodiments, the one or more additional cancer therapy includes an immunotherapy. In general, immunotherapy, also called biologic therapy, is a type of cancer treatment that boosts a subject's natural defenses to treat cancer. In certain embodiments, the immunotherapy utilizes compounds biologically produced by the subject. In certain embodiments, the immunotherapy utilizes compounds not biologically produced by the subject. In certain embodiments, the immunotherapy utilizes cells from the subject. In certain embodiments, the immunotherapy utilizes cells not from the subject. In certain embodiments, the immunotherapy utilizes compounds biologically produced by an organism that is not the subject. In certain embodiments, the immunotherapy utilizes cells biologically produced by an organism that is not the subject. In certain embodiments, the immunotherapy includes at least one chemical modification to compounds or cells from the subject. In certain embodiments, the immunotherapy includes at least one chemical modification to compounds or cells not from the subject.

In some embodiments, the immunotherapy may involve one of more of the following steps: preventing or inhibiting the growth of cancer cells; preventing cancer from spreading to other parts of the body; and improving the ability and activity of the immune system to kill cancer cells. Non-limiting examples of immunotherapies include: monoclonal antibodies, checkpoint inhibitors, non-specific immunotherapies, oncolytic virus therapy, T cell therapies, and cancer vaccines.

In certain embodiments, the immunotherapy utilizes monoclonal antibodies. In some embodiments, the monoclonal antibodies target (bind to) and/or block an abnormal protein on a cancer cell.

In certain embodiments, the immunotherapy utilizes checkpoint inhibitors. In certain embodiments, the immune checkpoint inhibitors are monoclonal antibodies. Immune checkpoints are regulators of immune activation by maintaining immune homeostasis and preventing autoimmunity. In cancer cells, immune checkpoint mechanisms are often activated to suppress the nascent anti-cancer immune response. In some embodiments, the checkpoint inhibitor is an inhibitor of PD-1 (programmed cell death protein 1). In some embodiments, the checkpoint inhibitor is an inhibitor of PD-L1 (programmed death-ligand 1). In some embodiments, the checkpoint inhibitor is an inhibitor of CTLA-4 (cytotoxic T-lymphocyte-associated protein 4). Examples of immune checkpoint inhibitors include, without limitation, Ipilimumab (Yervoy), Nivolumab (Opdivo), Pembrolizumab (Keytruda), Atezolizumab (Tecentriq), Avelumab (Bavencio), and Durvalumab (Imfinzi).

In certain embodiments, the immunotherapy is non-specific immunotherapy (e.g., interferons or interleukins). In certain embodiments, the immunotherapy is an oncolytic virus therapy.

In certain embodiments, the immunotherapy is a T cell therapy. In some embodiments, the T cell therapy is chimeric antigen receptor (CAR) T cell therapy.

In certain embodiments, the immunotherapy is an anti-cancer vaccine.

Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. Herceptin (trastuzumab), T-DM1, AVASTIN (bevacizumab), ERBITUX (cetuximab), Vectibix (panitumumab), Rituxan (rituximab), Bexxar (tositumomab)). Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent) docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonuclotide reductase inhibitors (e.g. hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g. 1-methyl-4-phenylpyridinium ion), cell cycle inhibitors (e.g., staurosporine), actinomycin (e.g. actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe), and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In some embodiments, the composition is substantially soluble in water (e.g., hydrophilic). In some embodiments, the composition is substantially insoluble in water (e.g., hydrophobic). In some embodiments, the composition is substantially insoluble in water and greater than about 10,000 parts water are required to dissolve 1 part compound of the disclosure.

In some embodiments, the percentage of the composition that comprise a compound of the disclosure is between about 1 and about 100% (e.g., about 1%, about 2%, about 3%, about 4%, about 5%, about 10%, about 15%, about 20%, about 30%, about 40%, about 50%, about 60%, about 70%, about 80%, about 90%, or about 100%). In some embodiments, the percentage of the composition that comprise a compound of the disclosure is less than about 50%, e.g., less than about 40%, less than about 35%, less than about 30%, less than about 25%, less than about 20%, less than about 15%, or less than about 10%. In some embodiments, the percentage of the composition that comprise a compound of the disclosure is between about 5% and about 50%, about 5% and about 40%, about 5% and about 30%, about 5% and about 25%, or about 5% and about 20%. In some embodiments, the percentage of the composition that comprise a compound of the disclosure is between about 5% and 90%. In some embodiments, the percentage of the composition that comprise a compound of the disclosure is between about 5% and about 75%. In some embodiments, the composition that comprise a compound of the disclosure is between about 5% and about 50%. In some embodiments, the percentage of the composition that comprise a compound of the disclosure is between about 10% and about 25%.

In some embodiments, the total amount of the compound of the disclosure present in the composition is greater than about 1% (e.g., about 1%, about 2%, about 3%, about 4%, about 5%, about 6%, about 7%, about 8%, about 9%, about 10%, about 12%, about 15%, about 20%, about 25%, about 30%, or more) of the total size or weight of the composition. In some embodiments, the total amount of the compound of the disclosure present in the composition is greater than about 10% (e.g., about 12%, about 15%, about 20%, about 25%, about 30%, or more) of the total size or weight of the composition.

Without being bound by theory, the compositions disclosed herein may improve the efficiency of a compound of the disclosure by one or more of increasing the localization and/or release (e.g., preferential release) of the compound of the disclosure to a target cell (e.g., a cancer or a fibrotic cell; a cell associated with a hypoxic environment), or increasing the half life of the compound of the disclosure, thus resulting in a significantly higher amount of a released compound of the disclosure at a target site (e.g., a tumor or liver (e.g., cirrhotic cell). Accordingly, the compositions disclosed herein can be more effective therapeutically than the free compound (e.g., due to enhanced drug uptake in the target tissue) and/or allow for a lower therapeutic dose of the compound of the disclosure, e.g., without substantially compromising the resulting drug concentration at a target tissue. In some embodiments, the compositions disclosed herein can reduce the adverse effect associated with systemic administration of a compound in free form.

In some embodiments, the compound of the disclosure is incorporated into a composition at a dose that is less than the dose or amount of said compound in free form to have a desired effect (e.g., a desired therapeutic effect). In certain embodiments, the composition increases the amount of the compound of the disclosure delivered to a tissue or cell in need thereof and reduces the amount of the compound of the disclosure exposed to a non-target tissue or cell, as compared to the free compound.

In another aspect, provided are kits comprising a compound of the disclosure; or a pharmaceutical composition as described herein; and instructions for using the compound of the disclosure or pharmaceutical composition.

In certain embodiments, the instructions of the kit may also include information as required by a regulatory agency such as the U.S. Food and Drug Administration (FDA). In certain embodiments, the information included in the kits is prescribing information. In certain embodiments, the kits and instructions provide for delivering a compound of the disclosure. In certain embodiments, the kits and instructions provide for delivering a composition. In certain embodiments, the kits and instructions provide for treating cancer in a subject in need thereof. In certain embodiments, the kits and instructions provide for inhibiting the signaling pathway in a subject or cell.

Methods of Treatment and Prevention & Uses

Some aspects of the invention relate to methods, uses, compositions, and kits for administration to a subject in need thereof. In some embodiments, the subject is a subject having, suspected of having, or at risk of developing a disease or disorder (e.g., cancer). As used herein, "subject," "individual," and "patient" may be used interchangeably. In some embodiments, the subject is a mammalian subject, including but not limited to a dog, cat, horse, cow, pig, sheep, goat, chicken, rodent, or primate. In some embodiments, the subject is a human subject, such as a patient. The human subject may be a pediatric or adult subject.

As used herein "treating" includes amelioration, cure, prevent it from becoming worse, slow the rate of progression, to prevent the disorder from re-occurring (i.e., to prevent a relapse), or to prevent or slow the rate of metastasis. An effective amount of a composition refers to an amount of the composition that results in a therapeutic effect. For example, in methods or uses for treating cancer in a subject, an effective amount of a chemotherapeutic agent is any amount that provides an anti-cancer effect, such as reduces or prevents proliferation of a cancer cell or is cytotoxic towards a cancer cell.

The methods and uses disclosed herein involve administering any of the compounds of the disclosure or compositions described herein in an effective amount to a subject having a proliferative disease. In some embodiments, the proliferative disease is cancer. In some embodiments, the proliferative disease is benign neoplasms.

Methods and uses disclosed herein involve administering any of the compounds of the disclosure or compositions described herein in an effective amount to a subject having cancer or at risk of having cancer. In some embodiments, the cancer is characterized by the presence of cancer stem cells. In some embodiments, the cancer comprises, involves, or is associated with stem cells. In some embodiments, the subject has undergone or is currently undergoing a cancer therapy (e.g. chemotherapeutic, immunotherapeutic, surgery, radiation). Whether a subject is deemed "at risk" of having a disease or disorder, such as cancer, may be determined by a skilled practitioner.

In certain embodiments, the cancer is colorectal cancer. Colorectal cancer is a cancer that starts in the colon or the rectum. These cancers may also be referred to as colon cancer or rectal cancer, depending on where the cancer begins. Colon cancer and rectal cancer are often grouped together due to several shared features. Most colorectal cancers start as a growth on the inner lining of the colon or rectum. The colorectal cancer (CRC) Subtyping Consortium has unified six independent molecular classification systems, based on gene expression data, into a single consensus system with four distinct groups, known as the Consensus Molecular Subtypes (CMS). The CMS were determined and correlated with epigenomic, transcriptomic, microenvironmental, genetic, prognostic and clinical characteristics. The CMS1 subtype is immunogenic and hypermutated. CMS2 tumors are activated by the WNT-β-catenin pathway and generally are associated with higher overall survival rates. CMS3 feature a metabolic cancer phenotype. CMS4 cancers are associated with the lowest survival rates and have a strong stromal gene signature. Molecular subtypes CMS2 and CMS4 exhibit the highest levels of embryonic signaling.[11]

In certain embodiments, the cancer is gastric cancer. Gastric cancer is a cancer that begins in the stomach. Stomach cancers tend to develop slowly over many years. Before a true cancer develops, pre-cancerous changes often occur in the inner lining (mucosa) of the stomach. These early changes rarely cause symptoms and therefore often go undetected. The types of stomach cancer include adenocarcinoma, lymphoma, gastrointestinal stromal tumor (GIST), carcinoid tumor, squamous cell carcinoma, small cell carcinoma, and leiomyocarcoma. The Cancer Genome Atlas (TCGA) project recently uncovered four molecular subtypes of gastric cancer: Epstein-Barr virus (EBV), microsatellite instability (MSI), genomically stable (GS), and chromosomal instability (CIN). The GS (genomically stable) and CIN (chromosomal instability) molecular subtypes exhibit the highest levels embryonic signaling, as measured by comprehensive analysis of gene expression patterns across gastric cancer subtypes.[12,13]

In certain embodiments, the subject has been administered an additional therapy. In certain embodiments, the subject is further administered (co-administration) an additional therapy (e.g., before, concurrently with, and/or after the administration of a compound or composition described herein). The additional therapy is different from a compound or composition described herein. In certain embodiments, the additional therapy alone is ineffective, or less effective as compared with co-administration with (e.g., before, concurrently with, and/or after) a compound or composition described herein, in a method or use described herein.

The exact amount of a compound of the disclosure required to achieve an effective amount will vary from subject to subject, depending, for example, on species, age, and general condition of a subject, severity of the side effects or disorder, identity of the particular compound of the disclosure, mode of administration, and the like.

An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of an agent described herein.

In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks or longer. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell.

Any of the compositions described herein may be administered in a therapeutically effective amount. In some embodiments, the methods and uses involve administering a composition comprising any of the compounds described herein to achieve a desired amount (e.g., a therapeutically effective amount) of the compound at a particular site in the subject. In some embodiments, the methods and uses involve administering a composition comprising any of the compounds described herein to achieve a desired amount (e.g., a therapeutically effective amount) of the compound at the site of a tumor in the subject.

Dosage may be adjusted appropriately to achieve a desired local level of the compound.

"Dose" and "dosage" are used interchangeably herein. In some embodiments, the amount of the compound administered to a subject is about 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound of the disclosure described herein. In certain embodiments, a dose described herein includes independently between 1 mg and 3 mg, inclusive, of a compound of the disclosure described herein. In certain embodiments, a dose described herein includes independently between 3 mg and 10 mg, inclusive, of a compound of the disclosure described herein. In certain embodiments, a dose described herein includes independently between 10 mg and 30 mg, inclusive, of a compound of the disclosure described herein. In certain embodiments, a dose described herein includes independently between 30 mg and 100 mg, inclusive, of a compound of the disclosure described herein.

In some embodiments, the subject is administered an initial dose of any one of the compositions described herein, followed by one or more additional doses of any of the compositions described herein. In some embodiments, the initial dose may contain a different amount of any of the compounds described herein as compared to the one or more additional doses. In some embodiments, the initial dose is a higher dose (e.g., contains more of any one of the compounds described herein) as compared to the one or more additional doses.

Dose ranges as described herein provide guidance for the administration of provided compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

Efficacy in treating cancer, for example, can be measured by determining the growth, replication, proliferation, metastasis, and/or gene expression profile of one or more cancer cells. An effective amount, therefore, is an amount that is deemed by the clinician to be toxicologically tolerable, yet efficacious.

Without being bound to a particular theory, the compounds disclosed herein are thought to induce the differentiation of embryonic cells and/or cells exhibiting characteristics of embryonic cells. In some embodiments, the methods and uses disclosed herein involve administering any of the compositions described herein in an effective amount to a subject in need of regenerative medicine or regenerative therapy. In some embodiments, the subject is in need of restoring or improving one or more biological function of a cell, tissue, and/or organ that is dysfunctional or impaired. In some embodiments, the subject is in need of tissue engineering and organ regeneration. In some embodiments, the compositions described herein regenerate or differentiate cells, tissues, and/or organs that may be damaged. In some embodiments, the subject has experienced brain injury (e.g., injury or damage to the brain tissue or cells) and/or injury to the central nervous system (e.g., injury or damage to the tissue or cells of the central nervous system) and is in need of repair of said tissue or cells. In some embodiments, the subject has experienced heart injury (e.g., injury or damage to the heart tissue or cells) and is in need of repair of said tissue or cells.

In some embodiments, the administration of any of the compositions described herein is by oral administration, intravenous administration (e.g., systemic intravenous injection), parental administration, subcutaneous administration, intramuscular administration, mucosal administration, transdermal administration, intradermal administration, intravaginal administration, intraperitoneal administration, topical administration, nasal administration, buccal administration, sublingual administration; by intratracheal regional administration via blood and/or lymph supply, and/or direct administration to an affected site.

The present disclosure provides methods for treating cancer comprising administering to a subject a therapeutically effective amount of a compound of Formula (0):

(0)

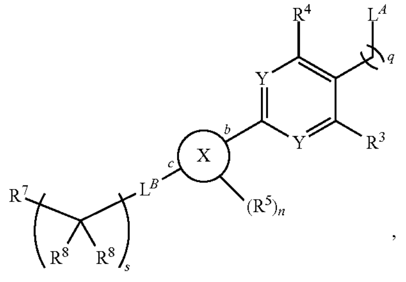

, or a pharmaceutically acceptable salt, solvate, hydrate, polymorph, co-crystal, tautomer, stereoisomer, isotopically labeled derivative, or prodrug thereof, wherein:

$L^A$ is —$N(R^2)(L^1R^1)$ or —$C(=O)NR^1R^2$;

$L^1$ is a single bond or —$C(=O)$—;

when $L^1$ is a single bond, $R^1$ is hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, or substituted or unsubstituted, 5- to 11-membered, monocyclic or bicyclic heteroaryl;

when $L^1$ is —$C(=O)$—, $R^1$ is substituted or unsubstituted $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, or substituted or unsubstituted, 5- to 11-membered, monocyclic or bicyclic heteroaryl;

$R^2$ is hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 5- to 11-membered, monocyclic or bicyclic heteroaryl, or a nitrogen protecting group;

$R^3$ is hydrogen, halogen, substituted or unsubstituted, $C_{1-6}$ alkyl, —$OR^a$, —$N(R^a)_2$, or —CN;

each instance of $R^a$ is independently hydrogen, substituted or unsubstituted, $C_{1-6}$ alkyl, an oxygen protecting group when attached to an oxygen atom, or a nitrogen protecting group when attached to a nitrogen atom;

or $R^2$ and $R^3$ are joined with their intervening atoms to form substituted or unsubstituted, 5-membered or 6-membered, monocyclic, heterocyclyl or heteroaryl;

q is 0 or 1;

each instance of Y is independently N or $CR^4$;

each instance of $R^4$ is independently hydrogen, halogen, substituted or unsubstituted, $C_{1-6}$ alkyl, —$OR^a$, —$N(R^a)_2$, or —CN;

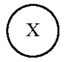

is phenyl, pyridinyl, pyridazinyl, pyrimidinyl, pyrazinyl, imidazolyl, oxazolyl, thizaolyl, piperidinyl, piperazinyl, morpholinyl, thiomorpholinyl, azetidinyl, —C≡C—, or

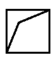;

bond b and bond c are meta or para to each other when

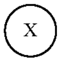

is phenyl, pyridinyl, pyridazinyl, pyrimidinyl, or pyrazinyl;

each instance of $R^5$ is independently hydrogen, halogen, substituted or unsubstituted, $C_{1-6}$ alkyl, —$OR^a$, —$N(R^a)_2$, or —CN;

n is 0, 1, 2, 3, or 4, as valency permits, wherein when n is 1, 2, 3, or 4, no instance of $R^5$ is attached to a nitrogen atom;

$L^B$ is —$N(R^6)L^2$-, or -$L^2N(R^6)$—;

$L^2$ is —C(═O)—,

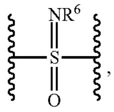

or —$S(═O)_2$—;

each $R^6$ is independently hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, substituted or unsubstituted, 5- to 11-membered, monocyclic or bicyclic heteroaryl, or a nitrogen protecting group;

s is 0 or 1;

$R^7$ is substituted or unsubstituted, 3- to 7-membered, monocyclic carbocyclyl, substituted or unsubstituted, 3- to 7-membered, monocyclic heterocyclyl, substituted or unsubstituted phenyl, or substituted or unsubstituted, 5- or 6-membered, monocyclic heteroaryl; and each instance of $R^8$ is independently hydrogen, halogen, substituted or unsubstituted, $C_{1-6}$ alkyl, —$OR^a$, —$N(R^a)_2$, or —CN.

In certain aspects, the present disclosure further provides methods for treating cancer comprising administering to a subject a therapeutically effective amount of a compound of Formula (0'):

(0')

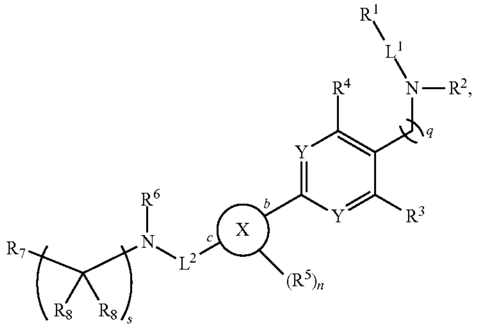

or a pharmaceutically acceptable salt, solvate, hydrate, polymorph, co-crystal, tautomer, stereoisomer, isotopically labeled derivative, or prodrug thereof, wherein:

$L^1$ is a single bond or —C(═O)—;

when $L^1$ is a single bond, $R^1$ is hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, or substituted or unsubstituted, 5- to 11-membered, monocyclic or bicyclic heteroaryl;

when $L^1$ is —C(═O)—, $R^1$ is substituted or unsubstituted $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, or substituted or unsubstituted, 5- to 11-membered, monocyclic or bicyclic heteroaryl;

$R^2$ is hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 5- to 11-membered, monocyclic or bicyclic heteroaryl, or a nitrogen protecting group;

$R^3$ is hydrogen, halogen, substituted or unsubstituted, $C_{1-6}$ alkyl, —$OR^a$, —$N(R^a)_2$, or —CN;

each instance of $R^a$ is independently hydrogen, substituted or unsubstituted, $C_{1-6}$ alkyl, an oxygen protecting group when attached to an oxygen atom, or a nitrogen protecting group when attached to a nitrogen atom;

or $R^2$ and $R^3$ are joined with their intervening atoms to form substituted or unsubstituted, 5-membered or 6-membered, monocyclic, heterocyclyl or heteroaryl;

q is 0 or 1;

each instance of Y is independently N or $CR^4$;

each instance of $R^4$ is independently hydrogen, halogen, substituted or unsubstituted, $C_{1-6}$ alkyl, —$OR^a$, —$N(R^a)_2$, or —CN;

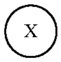

is phenyl, pyridinyl, pyridazinyl, pyrimidinyl, pyrazinyl, imidazolyl, oxazolyl, thizaolyl, piperidinyl, piperazinyl, morpholinyl, thiomorpholinyl, azetidinyl, —C≡C—, or

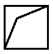;

bond b and bond c are meta or para to each other when

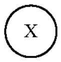

is phenyl, pyridinyl, pyridazinyl, pyrimidinyl, or pyrazinyl;

each instance of $R^5$ is independently hydrogen, halogen, substituted or unsubstituted, $C_{1-6}$ alkyl, —$OR^a$, —$N(R^a)_2$, or —CN;

n is 0, 1, 2, 3, or 4, as valency permits, wherein when n is 1, 2, 3, or 4, no instance of $R^5$ is attached to a nitrogen atom;

$L^2$ is —C(=O)—,

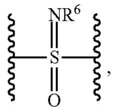

or $—S(=O)_2—$;

each $R^6$ is independently hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, substituted or unsubstituted, 5- to 11-membered, monocyclic or bicyclic heteroaryl, or a nitrogen protecting group;

s is 0 or 1;

$R^7$ is substituted or unsubstituted, 3- to 7-membered, monocyclic carbocyclyl, substituted or unsubstituted, 3- to 7-membered, monocyclic heterocyclyl, substituted or unsubstituted phenyl, or substituted or unsubstituted, 5- or 6-membered, monocyclic heteroaryl; and each instance of $R^8$ is independently hydrogen, halogen, substituted or unsubstituted, $C_{1-6}$ alkyl, $—OR^a$, $—N(R^a)_2$, or —CN.

The present disclosure also provides methods for treating cancer comprising administering to a subject a therapeutically effective amount of a compound of Formula (I):

(I)

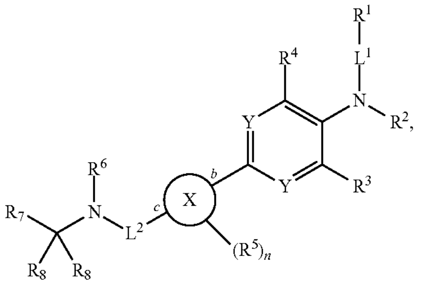

or a pharmaceutically acceptable salt, solvate, hydrate, polymorph, co-crystal, tautomer, stereoisomer, isotopically labeled derivative, or prodrug thereof, wherein:

$L^1$ is a single bond or —C(=O)—;

when $L^1$ is a single bond, $R^1$ is hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, or substituted or unsubstituted, 5- to 11-membered, monocyclic or bicyclic heteroaryl;

when $L^1$ is —C(=O)—, $R^1$ is substituted or unsubstituted $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, or substituted or unsubstituted, 5- to 11-membered, monocyclic or bicyclic heteroaryl;

$R^2$ is hydrogen, substituted or unsubstituted, $C_{1-6}$ alkyl, or a nitrogen protecting group;

$R^3$ is hydrogen, halogen, substituted or unsubstituted, $C_{1-6}$ alkyl, $—OR^a$, $—N(R^a)_2$, or —CN;

each instance of $R^a$ is independently hydrogen, substituted or unsubstituted, $C_{1-6}$ alkyl, an oxygen protecting group when attached to an oxygen atom, or a nitrogen protecting group when attached to a nitrogen atom;

or $R^2$ and $R^3$ are joined with their intervening atoms to form substituted or unsubstituted, 5-membered or 6-membered, monocyclic, heterocyclyl or heteroaryl;

each instance of Y is independently N or $CR^4$;

each instance of $R^4$ is independently hydrogen, halogen, substituted or unsubstituted, $C_{1-6}$ alkyl, $—OR^a$, $—N(R^a)_2$, or —CN;

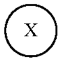

is phenyl, pyridinyl, pyridazinyl, pyrimidinyl, pyrazinyl, imidazolyl, oxazolyl, azetidinyl, —C≡C—, or

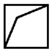;

bond b and bond c are meta or para to each other;

each instance of $R^5$ is independently hydrogen, halogen, substituted or unsubstituted, $C_{1-6}$ alkyl, $—OR^a$, $—N(R^a)_2$, or —CN;

n is 0, 1, 2, 3, or 4, as valency permits, wherein when n is 1, 2, 3, or 4, no instance of $R^5$ is attached to a nitrogen atom;

$L^2$ is —C(=O)— or $—S(=O)_2—$;

$R^6$ is hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, substituted or unsubstituted, 5- to 11-membered, monocyclic or bicyclic heteroaryl, or a nitrogen protecting group;

$R^7$ is substituted or unsubstituted, 3- to 7-membered, monocyclic carbocyclyl, substituted or unsubstituted, 3- to 7-membered, monocyclic heterocyclyl, substituted or unsubstituted phenyl, or substituted or unsubstituted, 5- or 6-membered, monocyclic heteroaryl; and each instance of $R^8$ is independently hydrogen, halogen, substituted or unsubstituted, $C_{1-6}$ alkyl, $—OR^a$, $—N(R^a)_2$, or —CN.

In certain embodiments of the Methods of Treatment and Prevention:

$L^1$ is a single bond or —C(=O)—;

when $L^1$ is a single bond, $R^1$ is hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, or substituted or unsubstituted, 5- to 11-membered, monocyclic or bicyclic heteroaryl;

when $L^1$ is —C(=O)—, $R^1$ is substituted or unsubstituted $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, or substituted or unsubstituted, 5- to 11-membered, monocyclic or bicyclic heteroaryl;

$R^2$ is hydrogen, substituted or unsubstituted, $C_{1-6}$ alkyl, or a nitrogen protecting group;

$R^3$ is hydrogen, halogen, substituted or unsubstituted, $C_{1-6}$ alkyl, —$OR^a$, —$N(R^a)_2$, or —CN;

each instance of $R^a$ is independently hydrogen, substituted or unsubstituted, $C_{1-6}$ alkyl, an oxygen protecting group when attached to an oxygen atom, or a nitrogen protecting group when attached to a nitrogen atom;

or $R^2$ and $R^3$ are joined with their intervening atoms to form substituted or unsubstituted, 5-membered or 6-membered, monocyclic, heterocyclyl or heteroaryl;

each instance of Y is independently N or $CR^4$;

each instance of $R^4$ is independently hydrogen, halogen, substituted or unsubstituted, $C_{1-6}$ alkyl, —$OR^a$, —$N(R^a)_2$, or —CN;

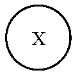

is phenyl, pyridinyl, pyridazinyl, pyrimidinyl, or pyrazinyl;

bond b and bond c are meta or para to each other;

each instance of $R^5$ is independently hydrogen, halogen, substituted or unsubstituted, $C_{1-6}$ alkyl, —$OR^a$, —$N(R^a)_2$, or —CN;

n is 0, 1, 2, 3, or 4, as valency permits, wherein when n is 1, 2, 3, or 4, no instance of $R^5$ is attached to a nitrogen atom;

$L^2$ is —C(=O)— or —$S(=O)_2$—;

$R^6$ is hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, substituted or unsubstituted, 5- to 11-membered, monocyclic or bicyclic heteroaryl, or a nitrogen protecting group;

$R^7$ is substituted or unsubstituted, 3- to 7-membered, monocyclic carbocyclyl, substituted or unsubstituted, 3- to 7-membered, monocyclic heterocyclyl, substituted or unsubstituted phenyl, or substituted or unsubstituted, 5- or 6-membered, monocyclic heteroaryl; and each instance of $R^8$ is independently hydrogen, halogen, substituted or unsubstituted, $C_{1-6}$ alkyl, —$OR^a$, —$N(R^a)_2$, or —CN.

In certain aspects, the present disclosure provides a method of treating cancer comprising administering to a subject a therapeutically effective amount of a compound of Formula (I):

(I)

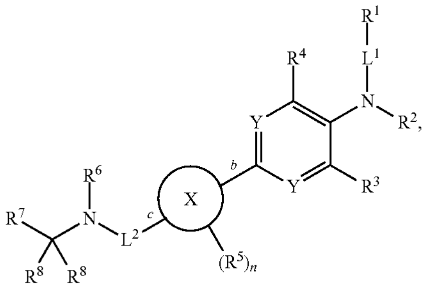

or a pharmaceutically acceptable salt, solvate, hydrate, polymorph, co-crystal, tautomer, stereoisomer, isotopically labeled derivative, or prodrug thereof, wherein:

$L^1$ is a single bond or —C(=O)—;

when $L^1$ is a single bond, $R^1$ is hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, or substituted or unsubstituted, 5- to 11-membered, monocyclic or bicyclic heteroaryl;

when $L^1$ is —C(=O)—, $R^1$ is substituted or unsubstituted $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, or substituted or unsubstituted, 5- to 11-membered, monocyclic or bicyclic heteroaryl;

$R^2$ is hydrogen, substituted or unsubstituted, $C_{1-6}$ alkyl, or a nitrogen protecting group;

$R^3$ is hydrogen, halogen, substituted or unsubstituted, $C_{1-6}$ alkyl, —$OR^a$, —$N(R^a)_2$, or —CN;

each instance of $R^a$ is independently hydrogen, substituted or unsubstituted, $C_{1-6}$ alkyl, an oxygen protecting group when attached to an oxygen atom, or a nitrogen protecting group when attached to a nitrogen atom;

or $R^2$ and $R^3$ are joined with their intervening atoms to form substituted or unsubstituted, 5-membered or 6-membered, monocyclic, heterocyclyl or heteroaryl;

each instance of Y is independently N or $CR^4$;

each instance of $R^4$ is independently hydrogen, halogen, substituted or unsubstituted, $C_{1-6}$ alkyl, —$OR^a$, —$N(R^a)_2$, or —CN;

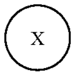

is phenyl, pyridinyl, pyridazinyl, pyrimidinyl, or pyrazinyl;

bond b and bond c are meta or para to each other;

each instance of $R^5$ is independently hydrogen, halogen, substituted or unsubstituted, $C_{1-6}$ alkyl, —$OR^a$, —$N(R^a)_2$, or —CN;

n is 0, 1, 2, 3, or 4, as valency permits, wherein when n is 1, 2, 3, or 4, no instance of $R^5$ is attached to a nitrogen atom;

$L^2$ is —C(=O)— or —$S(=O)_2$—;

$R^6$ is hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, substituted or unsubstituted, 5- to 11-membered, monocyclic or bicyclic heteroaryl, or a nitrogen protecting group;

$R^7$ is substituted or unsubstituted, 3- to 7-membered, monocyclic carbocyclyl, substituted or unsubstituted, 3- to 7-membered, monocyclic heterocyclyl, substituted or unsubstituted phenyl, or substituted or unsubstituted, 5- or 6-membered, monocyclic heteroaryl; and each instance of $R^8$ is independently hydrogen, halogen, substituted or unsubstituted, $C_{1-6}$ alkyl, —$OR^a$, —$N(R^a)_2$, or —CN.

In certain embodiments of the Methods of Treatment and Prevention & Uses section, $L^1$, $R^1$, $R^2$, $R^3$, $R^a$, $R^4$, Y,

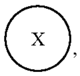, bond b and bond c, $R^5$, n, $L^2$, $R^6$, $R^7$, and $R^8$ are as described in the Compounds section.

In certain embodiments of the Methods of Treatment and Prevention & Uses section, when $L^1$ is a single bond, $R^1$ is hydrogen. In certain embodiments of the Methods of Treatment and Prevention & Uses section, when $L^1$ is —C(=O)—, $R^1$ is substituted $C_{1-6}$ alkyl. In certain embodiments of the Methods of Treatment and Prevention & Uses section, when $L^1$ is —C(=O)—, $R^1$ is unsubstituted $C_{1-6}$ alkyl (e.g., Me or Et).

In certain embodiments of the Methods of Treatment and Prevention & Uses section, $R^3$ is hydrogen.

In certain embodiments of the Methods of Treatment and Prevention & Uses section, $R^2$ and $R^3$ are joined with their intervening atoms to form substituted or unsubstituted, 6-membered, monocyclic, heterocyclyl or heteroaryl. In certain embodiments of the Methods of Treatment and Prevention & Uses section, $R^2$ and $R^3$ are joined with their intervening atoms to form unsubstituted, 6-membered, monocyclic, heterocyclyl. In certain embodiments of the Methods of Treatment and Prevention & Uses section

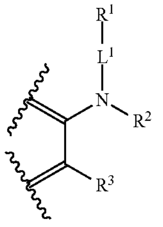

is

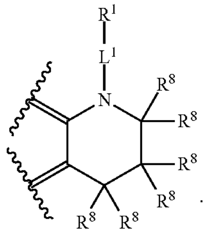.

In certain embodiments of the Methods of Treatment and Prevention & Uses section, the compound of Formula (I) is of the formula

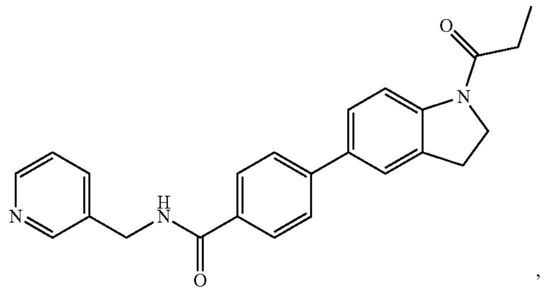 [SMILES: CCC(=O)N1CCc2cc(-c3ccc(C(=O)NCc4cccnc4)cc3)ccc21], or a pharmaceutically acceptable salt, solvate, hydrate, polymorph, co-crystal, tautomer, stereoisomer, isotopically labeled derivative, or prodrug thereof.

In certain embodiments of the Methods of Treatment and Prevention & Uses section, the compound of Formula (I) is of the formula

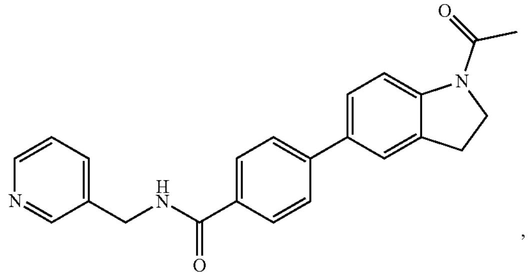 [SMILES: CC(=O)N1CCc2cc(-c3ccc(C(=O)NCc4cccnc4)cc3)ccc21], or a pharmaceutically acceptable salt, solvate, hydrate, polymorph, co-crystal, tautomer, stereoisomer, isotopically labeled derivative, or prodrug thereof.

Additional Methods

The present disclosure also provides methods for contacting a cell with an effective amount of a compound of the disclosure. The present disclosure also provides uses for contacting a cell with an effective amount of a compound of the disclosure.

In some embodiments, any of the compounds described herein are contacted with a cell in vivo, e.g. in an organism. In some embodiments, any of the compounds described herein are contacted with a cell in vitro, e.g., in cell culture. In some embodiments, any of the compounds described herein are contacted with a cell ex vivo, meaning the cell is removed from an organism prior to the contacting. As will be evident to one of skill in the art, the term cell may be used to refer to a single cell as well as a population of cells. In some embodiments, the populations cells are contacted with any of the compounds described herein to regenerate or differentiate one or more cell in the population of cells. In some embodiments, the populations cells are contacted with any of the compounds described herein for use in personalized medicine, for example for diagnostic and/or therapeutic purposes.

In general, any cells known in the art may be used in the methods and uses described herein. In some embodiments, the cell is of a cell line. In some embodiments, the cell is obtained from an organism, such as a subject. In some embodiments, the cell is a cancer cell (e.g., a cancer stem cell). In some embodiments, the cell is a stem cell. In some embodiments, the cell is an embryonic stem cell. In some embodiments, the cell is an induced pluripotent stem cell. In some embodiments, the cell is a neural cell, such as a neural stem cell. In some embodiments, the cell is an adult stem cell, such as a stomach stem cell or intestinal stem cell.

In some embodiments, the methods and uses further comprise inhibiting the growth of cells. In other embodiments, the methods and uses comprise killing cells. In some embodiments, the cells are stem cells. In some embodiments, the cells are selected from the group consisting of a cancer stem cell, an embryonic stem cell, an induced pluripotent stem cell, a neural stem cell, or an adult stem cell. In certain embodiments, the cells are cancer stem cells. In certain embodiments, the cells are embryonic stem cells. In certain embodiments, the disclosure provides methods and uses of inhibiting the growth of cells and/or killing cells with an effective amount of a compound of the disclosure. In certain aspects, inhibiting the growth of cells and/or killing cells is useful in the treatment of proliferative diseases including cancer.

In some embodiments, the methods and uses further comprise measuring or assessing the level of one or more embryonic properties of the cell. In some embodiments, the level of one or more embryonic properties of the cell is assessed following contacting the cell with any of the compositions described herein. In some embodiments, the level of one or more embryonic properties following contacting the cell with any of the compositions described herein is compared to the level of one or more embryonic properties in a reference sample or prior to contacting the cell with the composition. In some embodiments, the contacting the cell with any of the compositions described herein reduces one or more embryonic properties of the cell. In some aspects, the methods and uses described herein may be used to determine whether a cell is susceptible to treatment with the compositions described herein. In some embodiments, if the level of one or more embryonic properties is reduced following contacting the cell with any of the compositions described herein, the cell is determined to be susceptible to treatment with the composition. In some embodiments, if the level of one or more embryonic properties is reduced following contacting the cell with any of the compositions described herein, the composition is determined to be a candidate for a disease or disorder associated with the cell.

In some embodiments, the methods and uses described herein may be used for regenerative medicine. In some embodiments, a cell is contacted with any of the compositions described herein to promote differentiation and/or loss of one or more embryonic properties of the cell. In some embodiments, a cell is contacted with any of the compositions described herein to promote regenerative capacity of the cell. In some embodiments, contacting the cell with any of the compositions described herein enhances the regenerative capacity of the cell. In some embodiments, contacting the cell with any of the compositions described herein regenerates a population of cells, such as a tissue or an organ. In some embodiments, the regenerated population of cells, such as a tissue or an organ may be administered or implanted into a subject. In some embodiments, the subject is the same subject from which a cell was obtained. In some embodiments, the subject is a different subject from which a cell was obtained (e.g., autotransplantation). In some embodiments, the subject is a different subject from which a cell was obtained but belongs to the same species (e.g., allotransplantation). In some embodiments, the subject is a different subject from which a cell was obtained and belongs to a different species (e.g., xenotransplantation).

EXAMPLES

In order that the present disclosure may be more fully understood, the following examples are set forth. The synthetic and biological examples described in this application are offered to illustrate the compounds, pharmaceutical compositions, methods, and uses provided herein and are not to be construed in any way as limiting their scope.

Example 1. Kinetic Cell Viability with AGS Cells

Approximately 50,000 AGS cells were seeded per well of a 96-well plate in media containing NanoLuc Luciferase and MT Cell Viability Substrate provided on the RealTime Glo MT Cell Viability Assay Kit from PROMEGA. Four hours after plating, cells were treated with DMSO alone (no drug treatment) or decreasing concentrations of a compound of the disclosure to achieve final concentrations of 20, 10, 5, and 2.5 μM. Luminescence Units (RLU) were measured every 16-20 hours using a SynergyHTX plate reader with a 30 msec integration (see FIG. 1).

Example 2. Human Microarray Studies

AGS human gastric adenocarcinoma cells were treated with compound I-1, or DMSO alone (as a negative control) for two days. After two days, RNA was isolated from compound I-1 treated cells and DMSO treated cells, in duplicate, and subjected to microarray analysis using AFFYMETRIX CLARIOM S microarrays. Data were represented as fold change relative to the compound I-1 treated cells, negative values represented genes that were on higher in compound I-1 treated cells than in DMSO treated cells, and positive values represented genes that were on higher in DMSO treated cells than in compound I-1 treated cells. Values were averaged for the duplicate samples. We included data for the genes whose expression was altered by more than 3 fold, either up or down, in response to compound I-1.

Table 1 shows the list of genes upregulated upon treatment of AGS human gastric cancer cell line with compound I-1 (shown below). Negative numbers indicate fold upregulation upon drug treatment. Positive numbers indicate fold downregulation upon drug treatment. Overall, these data represented a reactivation of tumor suppressor genes, and a decrease in expression in tumor promoting genes. For example, DUSP10, NR1D1 and Perl were all shown to have tumor suppressor activity in preventing out of control cell proliferation, and the expression of all three of these genes was greatly increased by compound I-1 treatment. In addition, Chac1, PCK2, and SLC7A11 were all shown to have a tumor promoting activity and to be associated with the more dangerous and lethal forms of cancer, and these three genes were the three most strongly repressed genes measured in this analysis. There were other examples in the data that supported this model, but the overall model was that compound I-1 increased the expression of tumor suppressor genes, and decreased the expression of tumor promoting genes.

I-1

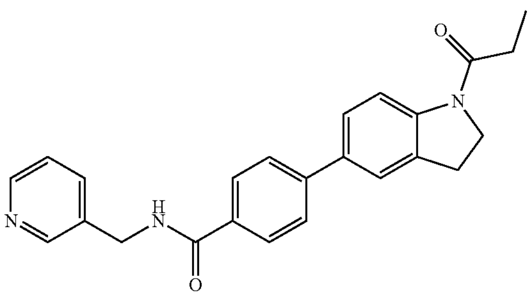

TABLE 1

| Gene Symbol | I-1-Fold Change |
|---|---|
| DUSP10 | −27.17 |
| NR1D1 | −23.3 |
| AKR1C1 | −16.86 |
| PERI; MIR6883 | −16.75 |
| ABHD4 | −15.57 |
| HMOX1 | −14.23 |
| FGA | −13.67 |
| MICB | −12.71 |
| DBP | −10.5 |
| HMGCS1 | −9.9 |
| MSMO1 | −9.47 |
| DHCR7 | −8.77 |
| AKR1C3 | −8.57 |
| INSIG1 | −8.5 |
| ACSS2 | −8.4 |
| BHLHE40 | −7.94 |
| FDFT1 | −7.56 |
| ZNF114 | −7.07 |
| AKR1C2 | −6.95 |
| ARHGEF3 | −6.93 |
| PDGFRL | −6.65 |
| RBM26 | −6.5 |
| TEF | −6.45 |
| HK1 | −6.34 |
| STK17B | −6.26 |
| MXD1 | −6.23 |
| ARRDC3 | −5.99 |
| RASSF5 | −5.9 |
| FASN | −5.82 |
| IDI1 | −5.77 |
| SLN | −5.63 |
| CREBRF | −5.55 |
| ACAT2 | −5.41 |
| HSPA1A; HSPA1B | −5.34 |
| RND1 | −5.3 |
| EFNA1 | −5.15 |
| TMPRSS2 | −5.06 |
| HSPA1B; HSPA1A | −5.04 |
| NFKBIA | −4.97 |
| GRHL3 | −4.96 |
| NEU1 | −4.89 |
| SLC20A1 | −4.87 |
| SLC30A1 | −4.84 |
| GDF15 | −4.83 |
| LY6D | −4.81 |
| HMGCR | −4.8 |
| FAM46A | −4.76 |
| CYP51A1 | −4.74 |
| HSPB8 | −4.71 |
| RHOV | −4.66 |
| TIAL1 | −4.62 |
| PRSS22 | −4.6 |
| EPHA4 | −4.56 |
| TMEM2 | −4.49 |
| LNX1 | −4.32 |
| SQLE | −4.32 |
| SQSTM1 | −4.27 |
| AKR1B10 | −4.25 |

TABLE 1-continued

| Gene Symbol | I-1-Fold Change |
|---|---|
| UGDH | −4.16 |
| TNFSF13B | −4.12 |
| FGG | −4.11 |
| CA5B | −4.1 |
| CXCL17 | −4.1 |
| LYPD3 | −4.09 |
| IL1RN | −4.04 |
| OVOL1 | −4.01 |
| DNMBP | −4 |
| BCL2L11 | −4 |
| SAT2 | −3.99 |
| MYLIP; MIR4639 | −3.88 |
| FAM160A1 | −3.86 |
| TGFBR3 | −3.86 |
| SEC24D | −3.84 |
| DNAJB5 | −3.84 |
| MVD | −3.82 |
| RAB30 | −3.82 |
| PCDH7 | −3.81 |
| EYA3 | −3.81 |
| CDA | −3.79 |
| KAT6B | −3.77 |
| PGM2L1 | −3.76 |
| CDC42EP4 | −3.75 |
| PLPP3 | −3.74 |
| SLC25A25 | −3.73 |
| PIM1 | −3.7 |
| EBP | −3.69 |
| CNNM2 | −3.68 |
| MICA | −3.66 |
| LIPG | −3.65 |
| OSGIN1 | −3.63 |
| YBX1 | −3.62 |
| RSRP1 | −3.61 |
| JAK2 | −3.6 |
| FAM46C | −3.6 |
| HHLA2 | −3.59 |
| CCNG2 | −3.58 |
| GATSL2 | −3.58 |
| PVRL1 | −3.57 |
| TKT | −3.56 |
| SQSTM1 | −3.5 |
| PADI1 | −3.48 |
| SUSD6 | −3.48 |
| DHCR24 | −3.44 |
| TAF5 | −3.41 |
| MTSS1L | −3.41 |
| NEURL3 | −3.41 |
| SC5D | −3.39 |
| RYBP | −3.38 |
| F2RL1 | −3.37 |
| NFAT5 | −3.32 |
| PVRL4 | −3.32 |
| JAG1 | −3.31 |
| CSF1 | −3.31 |
| OTUD1 | −3.29 |
| NSDHL | −3.29 |
| ZSWIM6 | −3.28 |
| SPATA5 | −3.26 |
| MID1 | −3.25 |
| CBFA2T2 | −3.24 |
| LPIN1; MIR548S | −3.22 |
| OCLM | −3.22 |
| GNE | −3.21 |
| ILF2 | −3.2 |
| PSCA | −3.18 |
| GALM | −3.17 |
| LEMD1 | −3.16 |
| ANO6 | −3.15 |
| AVPI1 | −3.14 |
| POLR2L | −3.14 |
| ZNRF3 | −3.14 |
| PLK2 | −3.13 |
| INPP5D | −3.12 |
| MVK | −3.11 |
| G6PD | −3.11 |
| CDKN1A | −3.11 |
| DNAJB4 | −3.09 |

TABLE 1-continued

| Gene Symbol | I-1-Fold Change |
|---|---|
| PRDM1 | −3.06 |
| AKR1B15 | −3.05 |
| REG1A | −3.05 |
| MT1E | −3.03 |
| RRAGC | −3.01 |
| NR1D2 | −3.01 |
| BCL6 | −3.01 |
| TRIM24 | −3.01 |
| TMEM263 | −3.01 |
| MT1L | −3 |
| EDN2 | −3 |

Table 2 shows the list of genes downregulated upon treatment of AGS human gastric cancer cell line with compound I-1.

TABLE 2

| Gene Symbol | I-1-Fold Change |
|---|---|
| STAMBPL1 | 3 |
| NCOA5 | 3 |
| FAM216A | 3 |
| NPIPA7; NPIPA8; PKD1P1 | 3.01 |
| CDC7 | 3.01 |
| HIST1H4D | 3.02 |
| YAE1D1 | 3.02 |
| SLC38A1 | 3.03 |
| HIST1H3A | 3.04 |
| REG4 | 3.04 |
| DEPTOR | 3.05 |
| MINA | 3.05 |
| RBBP9 | 3.05 |
| HIST1H2BE | 3.05 |
| NPIPA2 | 3.06 |
| LGALS4 | 3.06 |
| HIST1H2BK | 3.06 |
| CDX2 | 3.07 |
| CCDC138 | 3.07 |
| HIST2H2AA4; HIST2H2AA3 | 3.08 |
| FAIM | 3.09 |
| HIST1H2BB | 3.09 |
| HIST1H2BH | 3.09 |
| GRB10 | 3.1 |
| LMO4 | 3.1 |
| NEDD4 | 3.11 |
| AARS | 3.12 |
| NPIPA5 | 3.15 |
| CTNS | 3.16 |
| KLHL5 | 3.17 |
| NPIPA3 | 3.17 |
| THOC1 | 3.18 |
| FAM86C1 | 3.18 |
| MIR17HG; MIR17; MIR18A; MIR19A; MIR19B1; MIR20A; MIR92A1 | 3.18 |
| RASGRP3 | 3.19 |
| SLC7A1 | 3.19 |
| ZNF780B | 3.19 |
| ZNF780B | 3.19 |
| NPIPA8 | 3.2 |
| NCOA7 | 3.2 |
| HIST2H2AA3; HIST2H2AA4 | 3.2 |
| SYNPO | 3.2 |
| RASIP1 | 3.21 |
| SHMT2 | 3.22 |
| GARS | 3.24 |
| HIST1H4H | 3.25 |
| GSTM2 | 3.25 |
| XPA | 3.25 |
| DMBT1 | 3.25 |
| MTHFD2 | 3.26 |
| CEBPG | 3.29 |
| IARS | 3.29 |
| ZFAND1 | 3.29 |
| TMEM218 | 3.29 |
| ORAOV1 | 3.3 |

TABLE 2-continued

| Gene Symbol | I-1-Fold Change |
|---|---|
| UNC93A | 3.31 |
| CCDC125 | 3.31 |
| SETMAR | 3.32 |
| ERICH2 | 3.35 |
| PKD1; MIR6511B2; MIR6511B1 | 3.36 |
| DCLRE1A | 3.36 |
| TADA2A | 3.37 |
| AKTIP | 3.39 |
| GEN1 | 3.39 |
| C12orf4 | 3.45 |
| FAM111B | 3.46 |
| FUT1 | 3.48 |
| PDK1 | 3.5 |
| TSEN15 | 3.5 |
| XRCC2 | 3.5 |
| HIST1H2AK | 3.52 |
| KIF21B | 3.52 |
| FAM86B1 | 3.53 |
| LYRM7 | 3.58 |
| IRAK1BP1 | 3.59 |
| H1F0 | 3.59 |
| SLCO1B3 | 3.61 |
| WBP4 | 3.63 |
| SLC16A4 | 3.65 |
| KIF15 | 3.66 |
| EFHC1 | 3.67 |
| EXOSC8 | 3.68 |
| HAX1 | 3.68 |
| C14orf79 | 3.68 |
| C4BPB | 3.69 |
| GPX8 | 3.7 |
| FILIP1L | 3.7 |
| HIST1H2AL; HIST1H2BN | 3.72 |
| PYROXD1 | 3.74 |
| PHLDB2; PLCXD2 | 3.75 |
| HIST1H1E | 3.75 |
| HIST1H2BF | 3.75 |
| DDIT3 | 3.76 |
| PKD2 | 3.76 |
| HIST1H2AJ | 3.77 |
| MARS; MIR6758 | 3.79 |
| HIST2H4B; HIST2H4A | 3.79 |
| HIST1H2BG | 3.8 |
| LRRC8D | 3.82 |
| PKDCC | 3.89 |
| ZCCHC8 | 3.9 |
| PTER | 3.93 |
| HIST2H4A; HIST2H4B | 3.94 |
| RNF170; MIR4469 | 3.95 |
| PTPRB | 3.96 |
| STPG1 | 3.97 |
| EEF2KMT | 4.01 |
| GSTM4 | 4.02 |
| SLC1A5 | 4.04 |
| ZC3H8 | 4.04 |
| ZNF518A | 4.12 |
| RFXAP | 4.14 |
| HIST2H3D | 4.21 |
| BRCA1 | 4.22 |
| PSPH | 4.23 |
| HIST1H1C | 4.26 |
| GTPBP2 | 4.3 |
| C17orf80 | 4.3 |
| RBCK1 | 4.36 |
| S100P | 4.36 |
| FAM27E3 | 4.39 |
| METTL4 | 4.39 |
| C5orf28 | 4.4 |
| PRIM1 | 4.42 |
| HIST1H3I | 4.49 |
| SH2B3 | 4.5 |
| IZUMO1 | 4.5 |
| ZBED8 | 4.58 |
| HMMR | 4.62 |
| IFT88 | 4.63 |
| MB21D2 | 4.66 |
| CDH11 | 4.69 |
| ARHGEF2 | 4.73 |

TABLE 2-continued

| Gene Symbol | I-1-Fold Change |
|---|---|
| IL20RB | 4.75 |
| ST6GALNAC3 | 4.78 |
| HIST1H3D; HIST1H2AD | 4.82 |
| HIST1H2BJ | 4.83 |
| ZNF302 | 4.83 |
| FIGNL1 | 4.84 |
| WARS | 4.85 |
| HIST1H1B | 4.91 |
| JDP2 | 4.94 |
| BTC | 5.04 |
| MAT2A | 5.04 |
| HIST1H2AG | 5.06 |
| HIST1H1D | 5.18 |
| IGF2BP3 | 5.34 |
| SLC46A1 | 5.39 |
| HIST1H2BL | 5.51 |
| CARS | 5.53 |
| HOXB9 | 5.66 |
| HIST1H4A | 5.75 |
| NUPR1 | 5.76 |
| HIST1H2AI | 5.81 |
| TUBE1 | 5.83 |
| MOCOS | 5.87 |
| HIST1H2AE | 5.92 |
| HIST1H3B | 5.94 |
| NOX1 | 6.01 |
| SERPINB8 | 6.07 |
| IFRD1 | 6.11 |
| HIST1H3F | 6.21 |
| ATF5; MIR4751 | 6.55 |
| EIF4EBP1 | 6.66 |
| HIST1H2AB | 6.88 |
| HIST1H2AM; HIST1H3J | 6.91 |
| SLC7A5 | 7.31 |
| ASS1 | 7.34 |
| CRNDE | 7.6 |
| HIST1H3H | 7.63 |
| SLC6A9 | 7.78 |
| PSAT1 | 7.92 |
| HIST1H2BI | 8.02 |
| TNFRSF9 | 8.19 |
| SLC43A1 | 8.25 |
| SLC1A4 | 8.26 |
| AJUBA | 8.65 |
| HIST2H3A; HIST2H3C | 8.95 |
| HIST1H3G | 9.34 |
| HIST2H3A | 10.31 |
| TFF1 | 11.81 |
| CTH | 12.23 |
| HIST1H2BM | 12.33 |
| CYP1A1 | 12.34 |
| INHBE | 12.74 |
| ASNS | 12.78 |
| DDIT4 | 14.73 |
| SLC7A11 | 15.27 |
| PCK2 | 17.83 |
| CHAC1 | 43.64 |

Example 3. Kinetic Cell Viability with AGS Cells

We tested the ability of compound I-1 to inhibit the growth of 12 additional cell lines, derived from a variety of different types of human cancer. In addition to its potent inhibition of the growth of gastric adenocarcinoma and gastrointestinal stromal cells (data for gastric adenocarcinoma shown in Example 1, data for gastrointestinal stromal tumor shown in Table 3), compound I-1 had the most potent effect on non-Hodgkin's lymphoma, small cell lung cancer, pancreatic carcinoma, gastrointestinal stroma and ovarian adenocarcinoma cells. Exemplary results are shown in Table 3. Results are listed as $IC_{50}$ values, the lowest concentration of compound I-1 that resulted in a 50% inhibition of growth of the cancer cells.

TABLE 3

| Cell Line | Cancer Type | $IC_{50}$ (μM) |
|---|---|---|
| IGROV-1 | ovarian adenocarcinoma | 4.54 |
| NCI-H69 | small cell lung cancer | 1.50 |
| RL | non-Hodgkin's lymphoma | 0.13 |
| MCF-7 | breast cancer | 6.00 |
| Colo205 | Dukes' type D, colorectal adenocarcinoma | >10 |
| DLD-1 | Dukes' type C, colorectal adenocarcinoma | >10 |
| MiaPaca-2 | pancreatic carcinoma | 3.38 |
| PC-3 | prostate adenocarcinoma | 5.52 |
| A549 | lung adenocarcinoma | >10 |
| CFPAC-1 | pancreatic adenocarcinoma | 8.24 |
| UACC-62 | melanoma | >10 |
| A498 | kidney carcinoma | >10 |
| GIST T1 | gastrointestinal stromal tumor | 0.98 |

General Methods Employed in Examples 4 to 10 and 11

Unless otherwise provided, Examples 4 to 10 and 11 were performed according to the General Methods described in this sub-section.

RT-qPCR

Approximately $2.5\times10^5$ AGS cells were treated for 4 days with DMSO alone (no drug treatment) or 10 μM compound I-1 in DMSO. Cells were lysed and RNA was extracted using Zymo's Quick RNA-Microprep following manufacturer instructions. 100 ng of RNA were reverse transcribed using MuLV reverse transcriptase (New England Biolabs, USA). qPCR was performed using 2 ul of cDNA and Luna Universal qPCR Master Mix from NEB in a Stratagene Mx3005P.

Hepatocyte Toxicity Assay

Fresh Primary CD-1 mouse hepatocytes were obtained from XenoTech in 96-well plates the day after perfusion. After 24 hrs of recovery at 37° C. using OptiCulture Hepatocyte Media, medium was replaced containing either DMSO alone (no drug treatment) or 10 μM of compound I-1 daily for 4 days. Cell viability was measured using CellTiter Glo 2.0 Kit from PROMEGA, following manufacturer instructions. Luminescence was measured using a SynergyHTX plate reader with a 1 sec integration.

Kinetic Cell Viability

Approximately 50,000 AGS cells were seeded per well of a 96-well plate in media containing NanoLuc Luciferase and MT Cell Viability Substrate provided on the RealTime Glo MT Cell Viability Assay Kit from PROMEGA. Four hours after plating, cells were treated with DMSO alone (no drug treatment) or decreasing concentrations of compound I-1 to achieve final concentrations of 20, 10, 5, and 2.5 μM. Luminescence Units (RLU) were measured every 16-20 hrs using a SynergyHTX plate reader with a 30 msec integration.

Absorption, Distribution, Metabolism, and Excretion (ADME) Profiling

Plasma Stability. Plasma stability was determined by QuintaraBio's stability assay using samples supplied in DMSO solution. Briefly, compounds at a final concentration of 1 μM were incubated in duplicate at 37° C. in the presence of mouse plasma. At four different time points, 300 μL of quench solution (50% acetonitrile, 50% methanol, and 0.05% formic acid, warmed up at 37° C.) containing internal standards were added to each well. Plates were sealed, vortexed, and centrifuged at 4° C. for 15 minutes at 4000 rpm. The supernatants were transferred to fresh plates for LC/MS/MS analysis. All samples were analyzed on LC/MS/

MS using an AB Sciex API 4000 instrument, coupled to a Shimadzu LC-20AD LC Pump system. The extent of metabolism was calculated as the disappearance of the test compound, compared to the 0-min control reaction incubations. Initial rates were calculated for the compound concentration and used to determine $t_{1/2}$ values.

Microsomal Stability.

Microsomal stability was determined by QuintaraBio's stability assay using samples supplied in DMSO solution. Briefly, the assay was carried out in 96-well microtiter plates at 37° C. Reaction mixtures (25 μL) were incubated containing a final concentration of 1 M test compound, 0.5 mg/mL liver microsomes protein, and 1 mM NADPH and/or 1 mM uridine 5'-diphospho-α-D-glucuronic acid (UDPGA) (with alamethicin) in 100 mM potassium phosphate, pH 7.4 buffer with 3 mM $MgCl_2$. At each time point (0.25, 0.5, 1, 2, 4, 6, 8, and 24 minutes), 150 μL of quench solution (100% acetonitrile with 0.1% formic acid) with internal standard was transferred to each well. Plates were sealed and centrifuged at 4° C. for 15 minutes at 4000 rpm. The supernatant was transferred to fresh plates for LC/MS/MS analysis. All samples were analyzed on LC/MS/MS using an AB Sciex API 4000 instrument, coupled to a Shimadzu LC-20AD LC Pump system. The extent of metabolism was calculated as the disappearance of the test compound, compared to the 0-min time incubation. Initial rates were calculated for the compound concentration and used to determine $t_{1/2}$ values and subsequently, the intrinsic clearance, CLint=(0.693)(1/$t_{1/2}$ (min))(g of liver/kg of body weight)(mL incubation/mg of microsomal protein)(45 mg of microsomal protein/g of liver weight).

Kinetic solubility.

Solubility was determined by QuintaraBio's solubility assay using samples supplied in DMSO solution. Briefly, compound I-1 at 10 mM was diluted with the appropriate amount of buffer (PBS, pH 7.4) and mixed by shaking for 1.5 hours followed by vacuum filtration. The sample was then assayed via reverse phase HPLC with UV detection. Quantitation was achieved by the reference to a three-point standard curve constructed via serial dilution of drug substance dissolved in 100% DMSO.

Pharmacokinetic Profile

The pharmacokinetic profile of compound I-1 was determined after oral gavage of 100 mg/kg in male CD1 mice (n=3), using freshly prepared formulations. Approximately 0.025 mL of blood were collected from the dorsal metatarsal vein at 15 min, 30 min, and 1, 2, 4, 6, 8, and 24 hr post dosing. Plasma concentrations of the drug were analyzed by LC/MS/MS method.

Maximum Tolerated Dose Studies

The maximum tolerated dose profile of compound I-1 was determined after oral gavage of either vehicle control (n=3) or compound I-1 (n=9) in female BALB/c nude mice, using freshly prepared formulations. Animals were dose with 50 mg/kg (n=3), 25 mg/kg (n=3), or 12 mg/kg (n=3) for 5 consecutive days and followed for another 5 days for clinical observations.

Example 4

Figure 2:
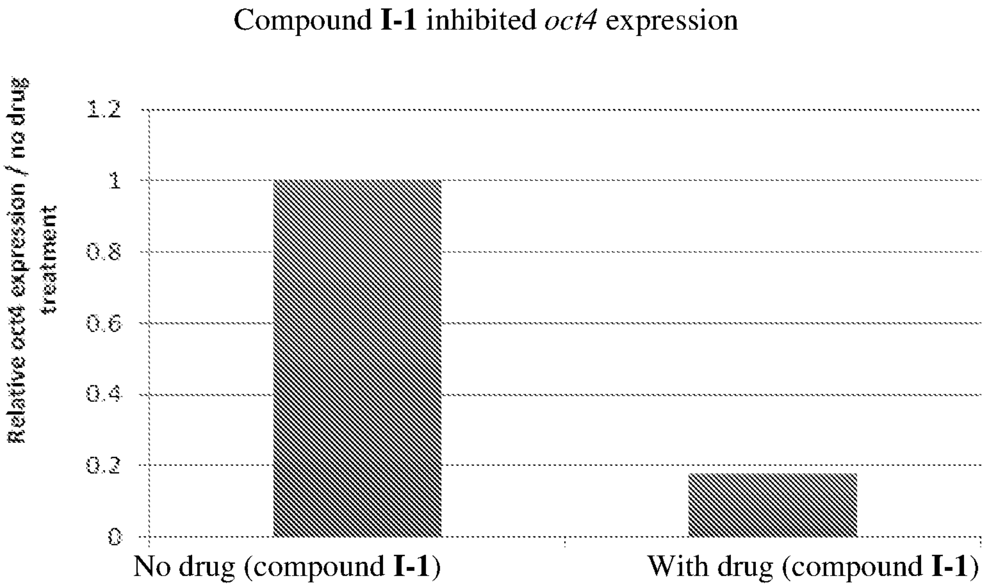
FIG. 2 shows that compound I-1 decreased oct4 expression in gastric cancer cells.

AGS gastric cancer cells were treated with either DMSO alone (no drug treatment) or compound I-1 at 10 M for 4 days. RNA was isolated and oct4 RNA levels were measured by RT-qPCR. Exemplary results are shown in FIG. 2.

Example 5

Figure 3:
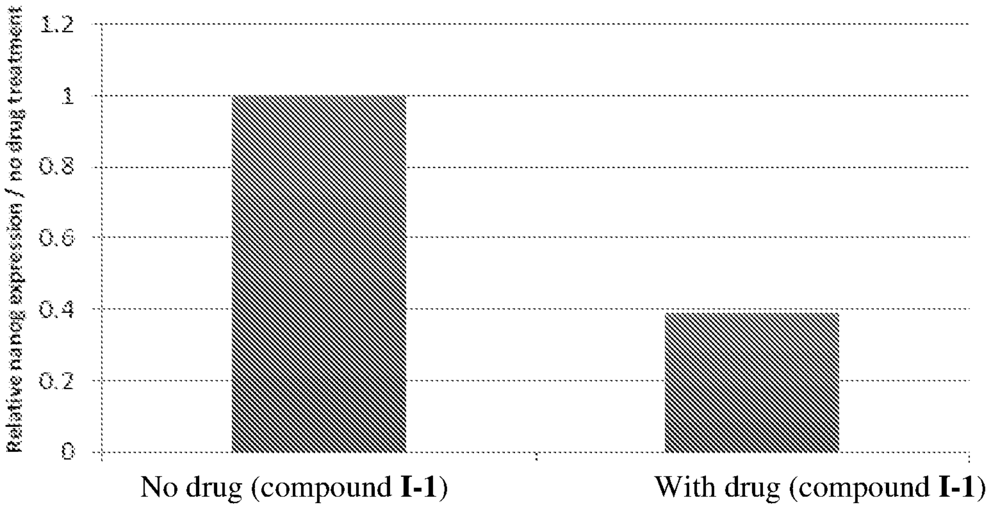
FIG. 3 shows that compound I-1 decreased nanog expression in gastric cancer cells.

AGS gastric cancer cells were treated with either DMSO alone (no drug treatment) or 10 M of compound I-1 for 4 days. RNA was isolated and nanog RNA levels were measured by RT-qPCR. Exemplary results are shown in FIG. 3.

Example 6

Figure 4:
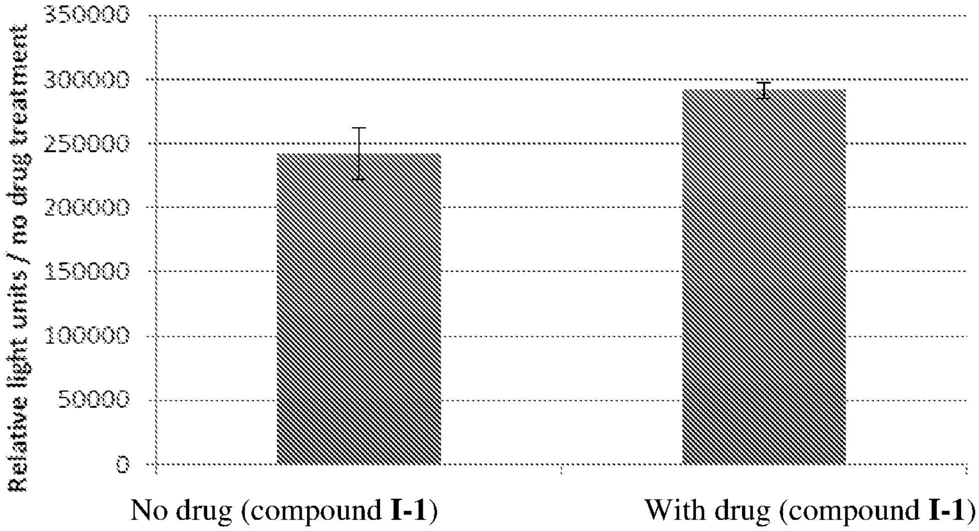
FIG. 4 shows that compound I-1 exhibited no toxicity to healthy hepatocytes.

Normal, healthy mouse hepatocytes were treated with DMSO alone (no drug treatment) or 10 M of compound I-1 for 4 days. Cell health was measured using CELLTITER GLO reagent, which provided a luminescence readout as a measurement of total ATP concentration. Exemplary results are shown in FIG. 4.

Example 7

Figures 5, 6:
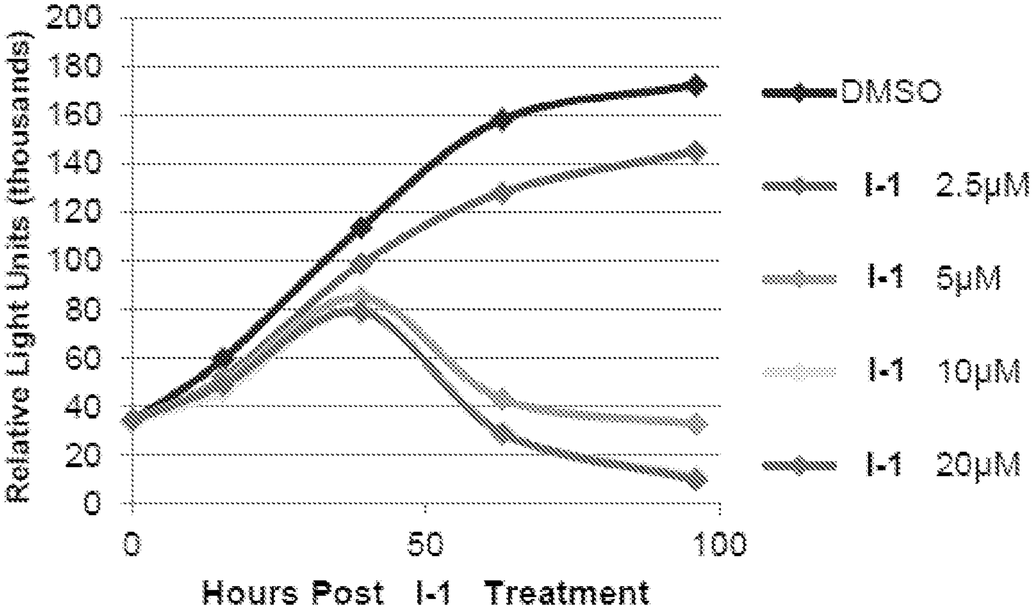
FIG. 5 shows that compound I-1 inhibited growth of gastric cancer cells.
FIG. 6 shows in vitro properties (e.g., solubility, microsomal stability, and plasma stability) of compound I-1.

AGS gastric cancer cells were treated with either DMSO alone (no drug treatment) or various concentrations of compound I-1 (including 2.5 M, 5 M, 10 M, and 20 M) for 4 days. Cell health and replication were measured using REALTIME-GLO MT Cell Viability Assay, which provided a luminescence readout as a measurement of cell number and health. Exemplary results are shown in FIG. 5.

Example 8

Select chemical properties were measured for compound I-1. Solubility was measured in aqueous solution at either pH 1.2 or 7.4. Mouse liver microsomal stability is listed as the measured half-life ($ti/_2$, in minutes), and plasma stability was listed as the percentage of compound I-1 that remained after 4 hours in mouse plasma. Exemplary results are shown in FIG. 6.

Example 9

Figure 7:
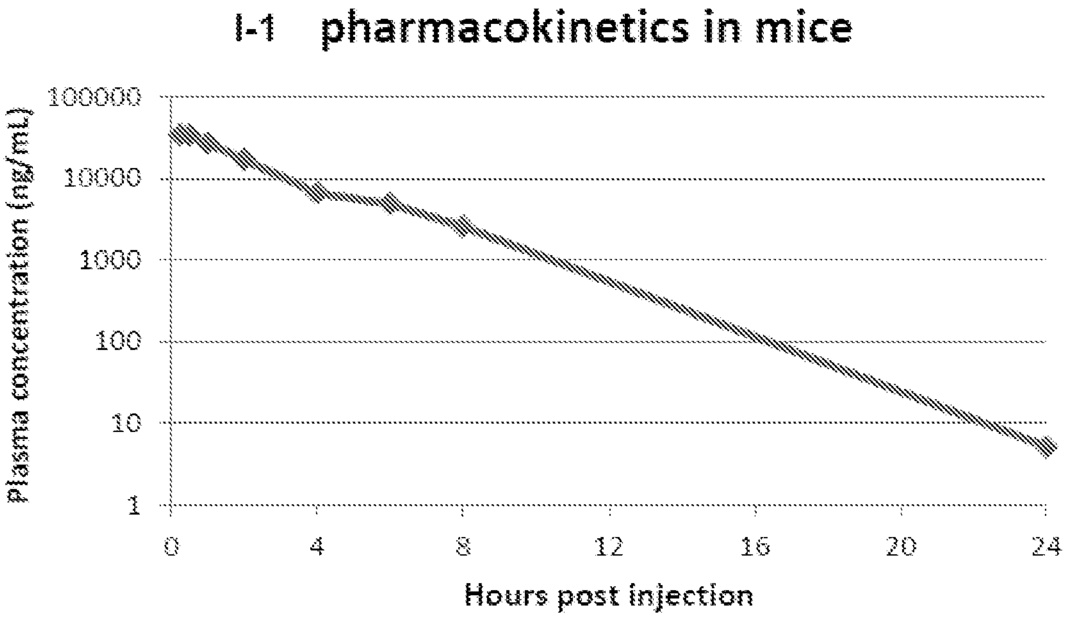
FIG. 7 shows the pharmacokinetics of compound I-1 in mice.

Following a single PO (oral) injection in mice at 100 mg/kg, the concentration of compound I-1 was measured in the plasma over 24 hours. Exemplary results are shown in FIG. 7. The half life was approximately 6 hours.

Example 10

Figure 8:
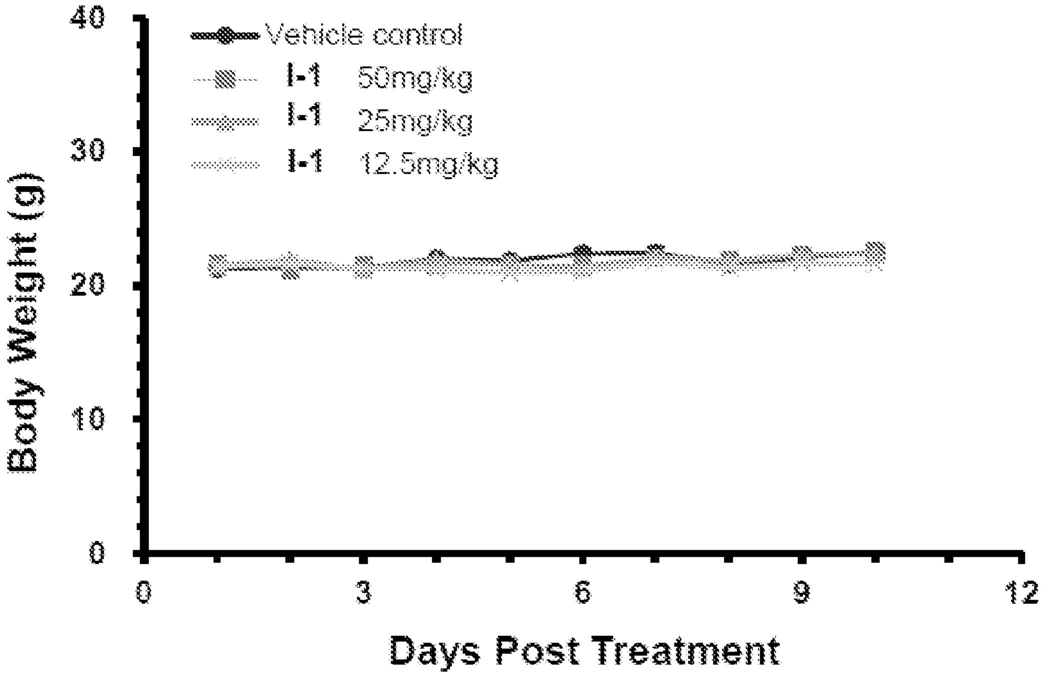
FIG. 8 shows the mouse tolerability results of compound I-1.

Nude BALB/c mice were treated once daily (orally) with either the vehicle control or 50 mg/kg of compound I-1, 25 mg/kg of compound I-1, or 12.5 mg/kg of compound I-1, for 5 days, 3 mice for vehicle control and 3 mice for compound I-1. Mice were monitored for a total of 10 days, and their body weight was measured to assess overall health. Exemplary results are shown in FIG. 8.

Example 11. Kinetic Cell Viability with AGS Cells

We tested the ability of compound I-1 to inhibit the growth of 11 additional cell lines, derived from a variety of different types of human cancer. Exemplary results are shown in Table 4. Results are listed as $IC_{50}$ values, the lowest concentration of compound I-1 that resulted in a 50% inhibition of growth of the cancer cells.

TABLE 4

| Cell Line | Cancer Type | $IC_{50}$ (μM) |
|---|---|---|
| SW620 | Colon | 2.79 |
| MM.1R | Hematopoietic-B-cell myeloma | 5.44 |
| Ramos (RA 1) | Hematopoietic-Burkitt's B-cell lymphoma | 3.41 |
| SU-DHL-10 | Hematopoietic-large B-cell lymphoma | 2.61 |
| HepG2 | Liver | 4.02 |
| NCI-H520 | NSCLC | 3.66 |

TABLE 4-continued

| Cell Line | Cancer Type | $IC_{50}$ (μM) |
|---|---|---|
| RL95-2 | Uterus/endometrium | 2.5 |
| Thp1 | Heme (acute monocytic leukemia) | 5.17 |
| NALM-6 | Heme (B-cell precursor leukemia, ALL) | 0.675 |
| Raji | Heme (Burkitt's lymphoma) | 2.52 |
| SR | Heme (large cell immunoblastic lymphoma-unknown B or T cell origin) | 0.489 |

Example 12. Preparation of Exemplary Compounds

Compounds I-152, I-156, I-157, I-160, I-168, I-171, I-174, I-175, I-176, I-178, I-179, I-180, and I-181 were purchased through commercial vendors.

The following LC-MS Methods (analytical) were used in the preparation of compounds I-215, I-224, I-225, I-227, I-228, I-230, I-231, I-232, I-241, I-246, I-248, I-252, I-257, I-258, I-260, I-263, I-264, I-271, I-272, I-284, I-285, and I-296.

Method 1 (LC-MS) 2 min_low_3_97_BEH:

LC/MS System: Acquity UPLC coupled with SQD mass spectrometer; Column: Acquity UPLC BEH C18 (50 mm×2.1 mm i.d., 1.7 μm packing diameter); mobile phase A: 0.1% formic acid in water, mobile phase B: 0.1% formic acid in acetonitrile; gradient: 0.0 min 97% A, 3% B, flow rate 0.9 ml/min; 1.5 min 3% A, 97% B, flow rate 0.9 ml/min; 1.9 min 3% A, 97% B, flow rate 0.9 ml/min; 2.0 min 97% A, 3% B, flow rate 0.05 ml/min; column temperature: 40° C.; UV detection: from 210 nm to 350 nm; MS conditions: Ionization Mode: alternate-scan Positive and Negative Electrospray (ES+/ES−); Scan Range: 100 to 1000 AMU.

Method 2 (LC-MS): 2 min_high_3_97_BEH:

LC/MS System: Acquity UPLC coupled with SQD mass spectrometer; Column: Acquity UPLC BEH C18 (50 mm×2.1 mm i.d., 1.7 m packing diameter); mobile phase A: 10 mM aqueous solution of ammonium bicarbonate (adjusted to pH 10 with ammonia), mobile phase B: acetonitrile; gradient: 0.0 min 97% A, 3% B, flow rate 0.9 ml/min; 1.5 min 3% A, 97% B, flow rate 0.9 ml/min; 1.9 min 3% A, 97% B, flow rate 0.9 ml/min; 2.0 min 97% A, 3% B, flow rate 0.05 ml/min; column temperature: 40° C.; UV detection: from 210 nm to 350 nm; MS conditions: Ionization Mode: alternate-scan Positive and Negative Electrospray (ES+/ES−); Scan Range: 100 to 1500 AMU.

Method 5 (LC-MS): 12 min_low_3_97_BEH:

LC/MS System: Acquity UPLC coupled with SQD mass spectrometer; Column: Acquity UPLC BEH C18 (50 mm×2.1 mm i.d., 1.7 m packing diameter); mobile phase A: 0.1% formic acid in water, mobile phase B: 0.1% formic acid in acetonitrile; gradient: 0.0 min 97% A, 3% B, flow rate 0.9 ml/min; 1.5 min 97% A, 3% B, flow rate 0.9 ml/min; 11.5 min 3% A, 97% B, flow rate 0.9 ml/min; 12.0 min 97% A, 3% B, flow rate 0.05 ml/min; column temperature: 40° C.; UV detection: from 210 nm to 350 nm; MS conditions: Ionization Mode: alternate-scan Positive and Negative Electrospray (ES+/ES−); Scan Range: 100 to 1500 AMU.

Method 6 (LC-MS): 12 min_high_3_97_BEH:

LC/MS System: Acquity UPLC coupled with SQD mass spectrometer; Column: Acquity UPLC BEH C18 (50 mm×2.1 mm i.d., 1.7 m packing diameter); mobile phase A: 10 mM aqueous solution of ammonium bicarbonate (adjusted to pH 10 with ammonia), mobile phase B: acetonitrile; gradient: 0.0 min 97% A, 3% B, flow rate 0.9 ml/min; 1.5 min 97% A, 3% B, flow rate 0.9 ml/min; 11.5 min 3% A, 97% B, flow rate 0.9 ml/min; 12.0 min 97% A, 3% B, flow rate 0.05 ml/min; column temperature: 40° C.; UV detection: from 210 nm to 350 nm; MS conditions: Ionization Mode: alternate-scan Positive and Negative Electrospray (ES+/ES−); Scan Range: 100 to 1500 AMU.

Synthesis of 4-(1-acetylindolin-5-yl)-N-(pyridin-3-ylmethyl) benzamide (Compound I-42)

Preparation of tert-butyl 5-bromoindoline-1-carboxylate

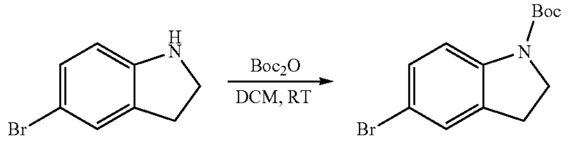 [SMILES: "Boc2O" ; Brc1ccc2c(c1)CCN2 ; CC(C)(C)OC(=O)N1CCc2cc(Br)ccc21]

Procedure A: To a mixture of 5-bromoindoline (10.0 g, 50.8 mmol) in DCM (80 mL), was added a solution of di-tert-butyl dicarbonate (11.2 g, 51.3 mmol) in DCM (20 mL). The reaction mixture was stirred at RT for 2 h and concentrated in vacuo to give tert-butyl 5-bromoindoline-1-carboxylate as a yellow oil (18.0 g, quantitative yield). LC-MS (ESI): m/z $(M)^+$=297.12/299.33.

Preparation of tert-butyl 5-(4-(methoxycarbonyl)phenyl) indoline-1-carboxylate

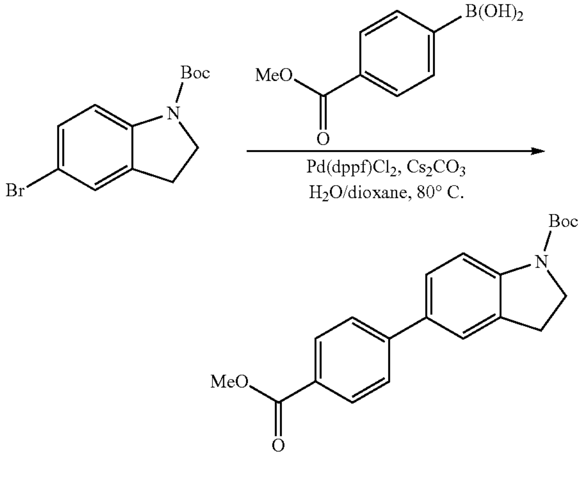

Procedure B: To a mixture of tert-butyl 5-bromoindoline-1-carboxylate (18.0 g, 50.8 mmol) in dioxane/$H_2O$ (135 mL), were added (4-(methoxycarbonyl)phenyl)boronic acid (13.2 g, 76.2 mmol), Pd(dppf)$Cl_2$ (4.2 g, 5.1 mmol) and $Cs_2CO_3$ (49.4 g, 152 mmol). The reaction mixture was stirred at 80° C. for 20 h, then diluted with DCM, and washed with brine. The organic layer was dried over anhydrous $Na_2SO_4$, filtered and concentrated under reduced pressure. The residue was purified by flash column chromatography over silica gel (PE/EA 4:1, v/v) to give tert-butyl 5-(4-(methoxycarbonyl)phenyl) indoline-1-carboxylate as a yellow solid (11.2 g, 62%). LC-MS (ESI): m/z $(M-56)^+$=298.14.

Preparation of 4-(1-(tert-butoxycarbonyl)indolin-5-yl) benzoic acid

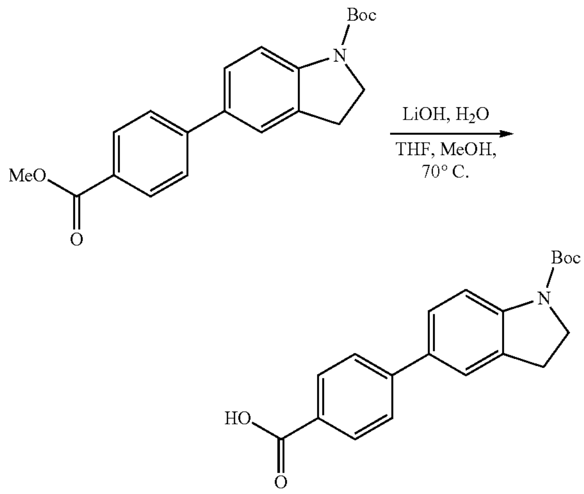

Procedure C: To a mixture of tert-butyl 5-(4-(methoxycarbonyl)phenyl) indoline-1-carboxylate (5.0 g, 14.2 mmol) in MeOH/THF 1:1 (60 mL), was added LiGH (1N, 30 ml). The reaction mixture was stirred at 70° C. for 3 h. It was then concentrated in vacuo and acidified with aq. HCl (1N). After filtration, the solid was dried to give 4-(1-(tert-butoxycarbonyl)indolin-5-yl) benzoic acid as a white solid (5.6 g, quantitative yield). LC-MS (ESI): m/z $(M-56)^+$=284.09.

Preparation of tert-butyl 5-(4-((pyridin-3-ylmethyl) carbamoyl) phenyl) indoline-1-carboxylate

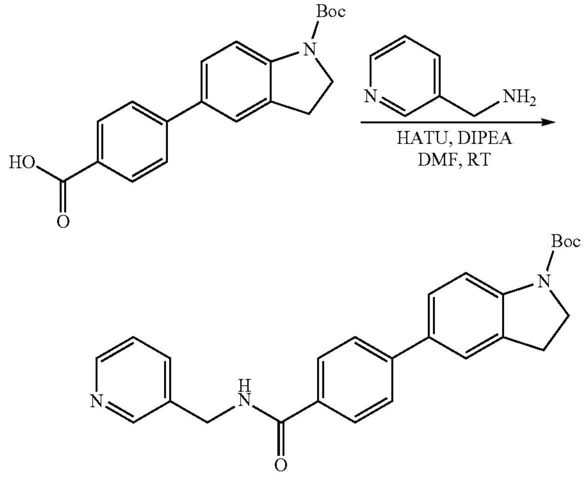

Procedure D: To a mixture of 4-(1-(tert-butoxycarbonyl) indolin-5-yl) benzoic acid (3.0 g, 8.8 mmol) in DMF, were added pyridin-3-ylmethanamine (1.1 g, 10.6 mmol), HATU (5.0 g, 13.2 mmol) and DIPEA (3.4 g, 26.4 mmol). The reaction mixture was stirred at RT for 20 h. It was then diluted with DCM and washed with water and brine. The organic layer was dried over anhydrous $Na_2SO_4$, filtered, and concentrated under reduced pressure. The residue was purified by flash column chromatography over silica gel (DCM/MeOH 9:1, v/v) to give tert-butyl 5-(4-((pyridin-3-ylmethyl) carbamoyl) phenyl) indoline-1-carboxylate as a solid (3.2 g, 85%). LC-MS (ESI): m/z $(M+1)^+$=430.28.

Preparation of 4-(indolin-5-yl)-N-(pyridin-3-ylmethyl) benzamide

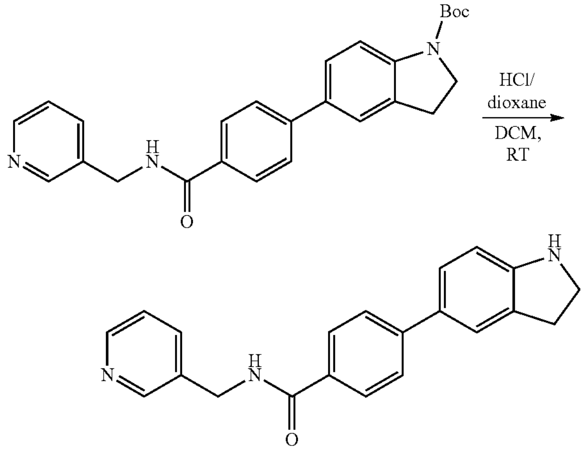

Procedure E: To a mixture of tert-butyl 5-(4-((pyridin-3-ylmethyl)carbamoyl)phenyl) indoline-1-carboxylate (2.0 g, 4.7 mmol) in DCM (5 mL), was added HCl in dioxane (4N, 20 mL). The reaction mixture was stirred at RT for 18 h, then concentrated under reduced pressure to give a red solid (2.4 g). The residue (100 mg) was purified by prep-HPLC (C18, 40-100% MeCN in $H_2O$ with 0.1% formic acid) to give 4-(indolin-5-yl)-N-(pyridin-3-ylmethyl) benzamide as a white solid (27 mg, 35%).

Preparation of 4-(1-acetylindolin-5-yl)-N-(pyridin-3-ylmethyl) benzamide (Compound I-42)

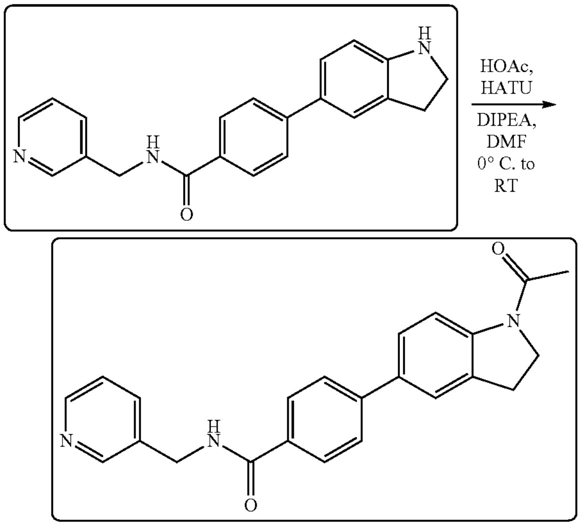

Procedure D was followed starting from 4-(indolin-5-yl)-N-(pyridin-3-ylmethyl) benzamide (200 mg, 0.5 mmol) and HOAc (36 mg, 0.6 mmol), In this case, the reagents were added at 0° C. and the reaction mixture was allowed to warm up to RT. (1-acetylindolin-5-yl)-N-(pyridin-3-ylmethyl) benzamide was isolated as a white solid (47 mg, 25%). LC-MS (ESI): m/z $(M+H)^+$=372.21. $^1H$ NMR (400 MHz, DMSO-$d_6$) δ 9.12 (t, J=5.9 Hz, 1H), 8.57 (d, J=1.8 Hz, 1H), 8.46 (dd, J=4.7, 1.5 Hz, 1H), 8.15-8.06 (m, J=8.4 Hz, 1H), 7.98-7.92 (m, J=8.4 Hz, 2H), 7.78-7.71 (m, J=9.0, 5.1 Hz, 3H), 7.63 (s, 1H), 7.57-7.52 (m, J=8.4 Hz, 1H), 7.39-7.34 (m, J=7.8, 4.8 Hz, 1H), 4.51 (d, J=5.9 Hz, 2H), 4.14 (t, J=8.5 Hz, 2H), 3.21 (t, J=8.5 Hz, 2H), 2.18 (s, 3H).

Synthesis of 4-(1-propionylindolin-5-yl)-N-(pyridin-3-ylmethyl) benzamide (Compound I-43)

3.4.1 Preparation of 4-(1-propionylindolin-5-yl)-N-(pyridin-3-ylmethyl) benzamide (Compound I-43)

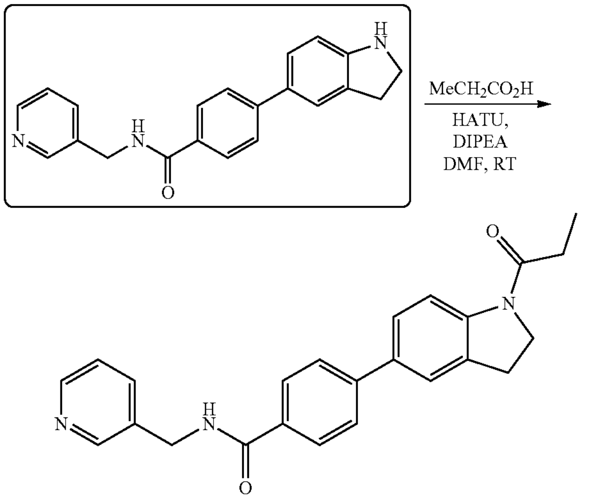

Following general Procedure D, starting from 4-(indolin-5-yl)-N-(pyridin-3-ylmethyl) benzamide (1.5 g, 5.0 mmol) and propionic acid (340 mg, 6.0 mmol), 4-(1-propionylindolin-5-yl)-N-(pyridin-3-ylmethyl)benzamide was isolated as a white solid (690 mg, 36%). LC-MS (ESI): m/z $(M+H)^+$=386.23. $^1H$ NMR (400 MHz, DMSO-$d_6$) δ 9.17-9.09 (m, J=5.9 Hz, 1H), 8.57 (d, J=1.7 Hz, 1H), 8.47 (dd, J=4.7, 1.5 Hz, 1H), 8.22-8.11 (m, 1H), 7.99-7.92 (m, 2H), 7.80-7.71 (m, 5.2 Hz, 3H), 7.63 (s, 1H), 7.58-7.53 (m, 1H), 7.40-7.31 (m, 1H), 4.52 (d, J=5.8 Hz, 2H), 4.12 (t, J=8.5 Hz, 2H), 3.21 (t, J=8.4 Hz, 2H), 2.50-2.44 (m, 2H), 1.08 (t, J=7.3 Hz, 3H).

Synthesis of 4'-propionamido-N-(pyridin-3-ylmethyl)-[1,1'-biphenyl]-4-Carboxamide (Compound I-44)

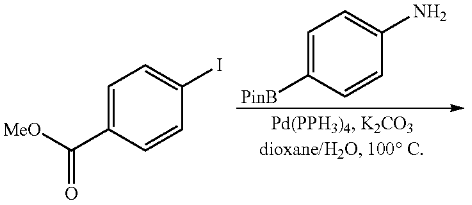

-continued

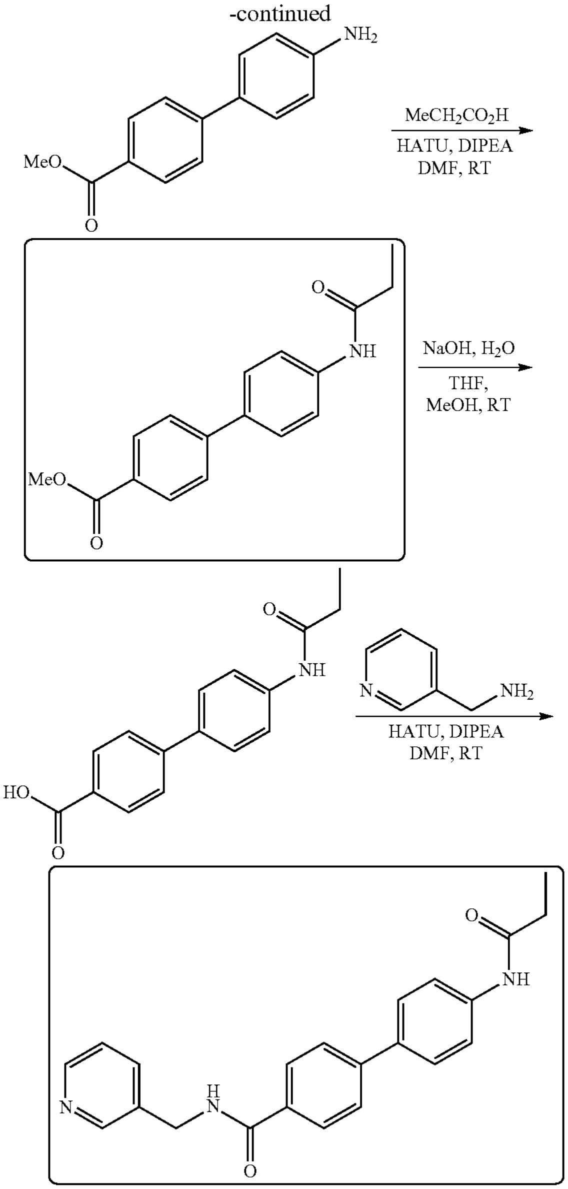

To a solution of methyl 4-iodobenzoate (3.0 g, 11.5 mmol), 4-(4,4,5,5-tetramethyl-1,3,2-dioxaborolan-2-yl)aniline (3.03 g, 13.8 mmol), and $K_2CO_3$ (3.2 g, 23.0 mmol) in dioxane/$H_2O$ (25/5 mL), was added $Pd(PPh_3)_4$ (1.33 g, 1.15 mmol) in one portion. The mixture was stirred at 100° C. for 10 h. It was then extracted with EA, the combined organic layers were washed with brine, dried over $Na_2SO_4$, concentrated, and purified by flash chromatography to give the methyl 4'-amino-[1,1'-biphenyl]-4-carboxylate as a white solid (2.5 g, quantitative yield), LC-MS (ESI): m/z $(M+H)^+$=220.19.

Following general Procedure D, starting from methyl 4'-amino-[1,1'-biphenyl]-4-carboxylate (2.4 g, 10.6 mmol) and propionic acid (1.18 g, 15.9 mmol), methyl 4'-propionamido-[1,1'-biphenyl]-4-carboxylate was isolated as a white solid (2.1 g, 70%). LC-MS (ESI): m/z (M+H)=284.14.

To a solution of methyl 4'-propionamido-[1,1'-biphenyl]-4-carboxylate (200 mg, 0.7 mmol) in MeOH/THF (2/2 mL), was added NaOH (3.5 mL, 3.5 mmol). The mixture was stirred at RT for 12 h. It was acidified with HCl 4N and extracted with EA. The combined organic layers were washed with brine, dried over $Na_2SO_4$, concentrated, and purified by flash chromatography to give 4'-propionamido-[1,1'-biphenyl]-4-carboxylic acid as a white solid (150 mg, 79%). LC-MS (ESI): m/z (M+H)=270.09.

Compound I-44 was prepared following general Procedure D, starting from 4'-propionamido-[1,1'-biphenyl]-4-carboxylic acid (150 mg, 0.56 mmol) and pyridin-3-ylmethanamine (91 mg, 0.84 mmol). Purification by prep-HPLC yielded 4'-propionamido-N-(pyridin-3-ylmethyl)-[1,1'-biphenyl]-4-carboxamide as a white solid (32 mg, 16%). LC-MS (ESI): m/z $(M+H)^+$=360.25. $^1$H NMR (400 MHz, DMSO-$d_6$) δ 10.00 (s, 1H), 9.13 (t, J=5.9 Hz, 1H), 8.57 (d, J=1.5 Hz, 1H), 8.47 (dd, J=4.7, 1.4 Hz, 1H), 7.96 (d, J=8.4 Hz, 2H), 7.81-7.65 (m, 7H), 7.40-7.33 (m, 1H), 4.52 (d, J=5.8 Hz, 2H), 2.35 (q, J=7.5 Hz, 2H), 1.10 (t, J=7.5 Hz, 3H).

Synthesis of 4'-(N-methylpropionamido)-N-(pyridin-3-ylmethyl)-[1,1'-biphenyl]-4-carboxamide (Compound I-45)

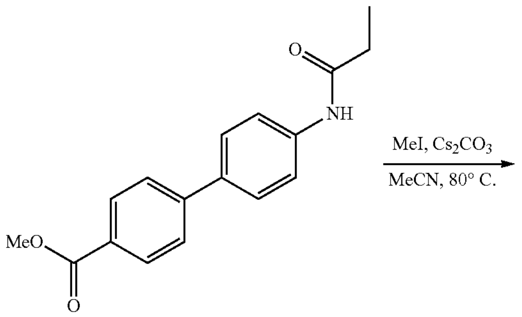

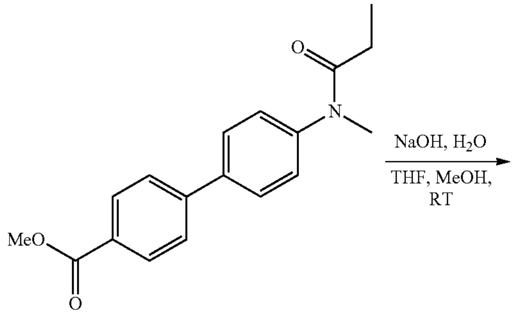

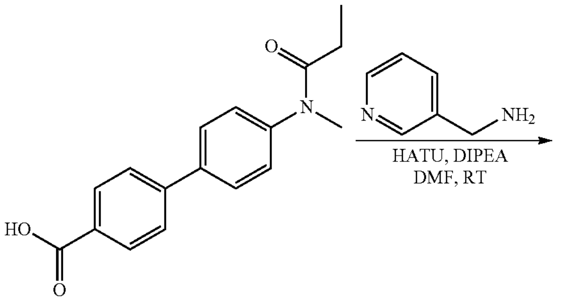

-continued

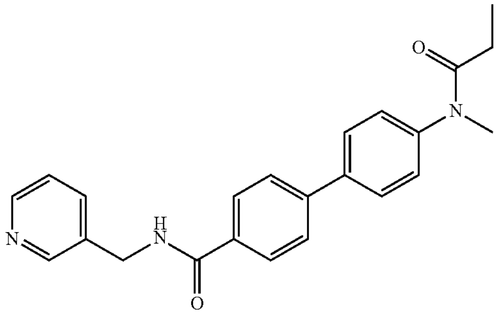

To a solution of methyl 4'-propionamido-[1,1'-biphenyl]-4-carboxylate (500 mg, 1.77 mmol) and $Cs_2CO_3$ (1.36 g, 3.54 mmol) in MeCN (10 mL), was added MeI (0.22 mL, 3.54 mmol) in one portion. The mixture was stirred at 80° C. for 10 h. It was then extracted with EA, the combined organic layers were washed with brine, dried over $Na_2SO_4$, concentrated, and purified by flash chromatography to give methyl 4'-(N-methylpropionamido)-[1,1'-biphenyl]-4-carboxylate as a white solid (475 mg, 90%). LC-MS (ESI): m/z $(M+H)^+$=298.14.

To a solution of methyl 4'-(N-methylpropionamido)-[1,1'-biphenyl]-4-carboxylate (200 mg, 0.68 mmol) in MeOH/THF (2/2 mL), was added NaOH (3.4 mL, 3.4 mmol) in one portion. The mixture was stirred at RT for 12 h. It was then acidified with HCl 4N and extracted with EA. The combined organic layers were washed with brine, dried over $Na_2SO_4$, concentrated and purified by flash chromatography to give 4'-(N-methylpropionamido)-[1,1'-biphenyl]-4-carboxylic acid as a white solid (140 mg, 73%). LC-MS (ESI): m/z $(M+H)^+$=284.14.

Following general Procedure D, starting from 4'-(N-methylpropionamido)-[1,1'-biphenyl]-4-carboxylic acid (140 mg, 0.50 mmol) and pyridin-3-ylmethanamine (82 mg, 0.75 mmol), 4'-(N-methylpropionamido)-N-(pyridin-3-ylmethyl)-[1,1'-biphenyl]-4-carboxamide was isolated as a white solid (30 mg, 16%). LC-MS (ESI): m/z $(M+H)^+$=374.30. $^1$H NMR (400 MHz, DMSO-$d_6$) δ 9.17 (t, 1H), 8.58 (s, 1H), 8.47 (d, J=3.7 Hz, 1H), 8.00 (d, J=8.3 Hz, 2H), 7.90-7.66 (m, 5H), 7.44 (d, J=8.3 Hz, 2H), 7.40-7.31 (m, 1H), 4.53 (d, J=5.8 Hz, 2H), 3.20 (s, 3H), 2.32-1.89 (m, 2H), 0.95 (t, J=7.3 Hz, 3H).

Synthesis of 4-(1-acetyl-1,2,3,4-tetrahydroquinolin-6-yl)-N-(pyridin-3-ylmethyl)benzamide (Compound I-46)

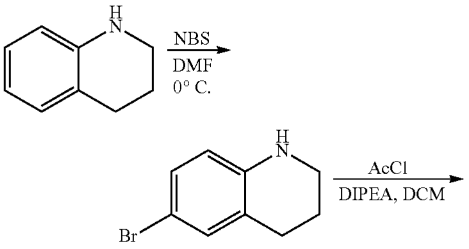

-continued

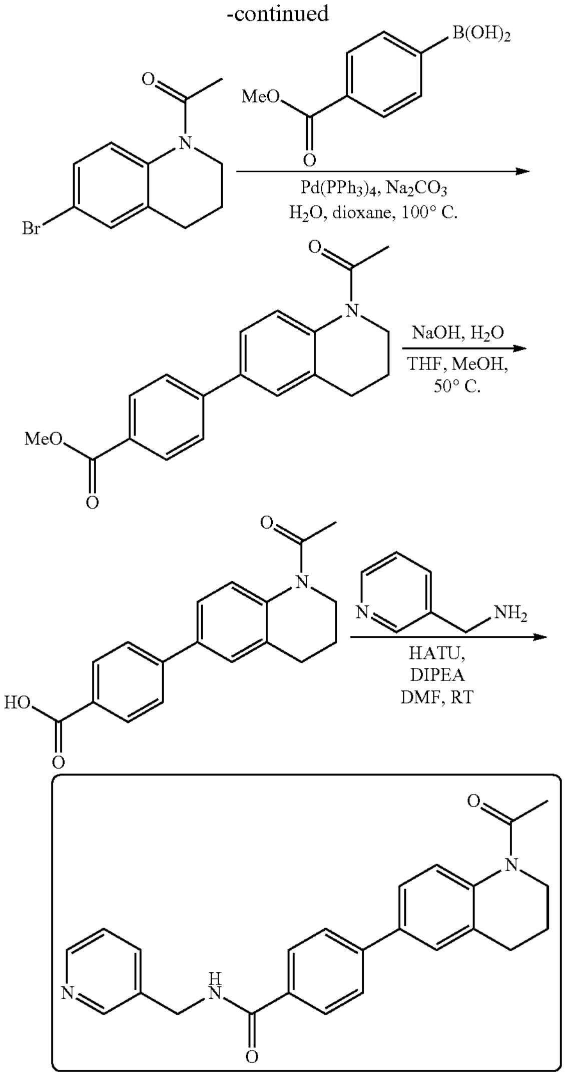

To a solution of 1,2,3,4-tetrahydroquinoline (2.0 g, 15.0 mmol) in DMF (20 mL), was added NBS (2.67 g, 15.0 mmol) in one portion. The mixture was stirred at 0° C. for 1 h. It was then extracted with EA, the combined organic layers were washed with brine, dried over $Na_2SO_4$, concentrated and purified by flash chromatography to give 6-bromo-1,2,3,4-tetrahydroquinoline as a yellow oil (3.1 g, 97%). LC-MS (ESI): m/z (M+H)=212.08/214.08.

To a solution of 6-bromo-1,2,3,4-tetrahydroquinoline (13.1 g, 14.6 mmol) and DIPEA (6.5 mL, 36.5 mmol) in DCM (30 mL) at 0° C., was added AcCl (1.72 g, 21.9 mmol) in one portion. The reaction mixture was stirred at RT for 4 h, then quenched with water. It was extracted with EA, the combined organic layers were washed with brine, dried over $Na_2SO_4$, and concentrated to give 1-(6-bromo-3,4-dihydroquinolin-1(2H)-yl)ethan-1-one as a light-yellow oil (3.33 g, 90%). LC-MS (ESI): m/z $(M+H)^+$=254.06/256.06.

To a solution of 1-(6-bromo-3,4-dihydroquinolin-1(2H)-yl)ethan-1-one (1.0 g, 4.0 mmol), (4-(methoxycarbonyl) phenyl) boronic acid (1.08 g, 6.0 mmol), and $Na_2CO_3$ (850 mg, 8.0 mmol) in dioxane/$H_2O$ (10/2 mL), was added $Pd(PPh_3)_4$ (466 mg, 0.4 mmol). The mixture was stirred at 100° C. for 10 h. It was then extracted with EA, the combined organic layers were washed with brine, dried over $Na_2SO_4$, concentrated, and purified by flash chromatography to give methyl 4-(1-acetyl-1,2,3,4-tetrahydroquinolin-6-yl)benzoate as a white solid (1.25 g, 100%). LC-MS (ESI): m/z $(M+H)^+$=310.13.

Procedure F: To a solution of methyl 4-(1-acetyl-1,2,3,4-tetrahydroquinolin-6-yl)benzoate (500 mg, 1.62 mmol) in MeOH (10 mL), was added NaOH (2.1 mL, 8.1 mmol). The mixture was stirred at 50° C. for 12 h, acidified with HCl (4N), and then extracted with EA. The combined organic layers were washed with brine, dried over $Na_2SO_4$, concentrated and purified by flash chromatography to give 4-(1-acetyl-1,2,3,4-tetrahydroquinolin-6-yl)benzoic acid as a white solid (445 mg, 93%). LC-MS (ESI): m/z $(M+H)^+$ =296.15.

Following general Procedure D, starting from 4-(1-acetyl-1,2,3,4-tetrahydroquinolin-6-yl)benzoic acid (150 mg, 0.51 mmol) and pyridin-3-ylmethanamine (66 mg, 0.61 mmol), 4-(1-acetyl-1,2,3,4-tetrahydroquinolin-6-yl)-N-(pyridin-3-ylmethyl)benzamide was isolated as a white solid (53 mg, 27%). LC-MS (ESI): m/z $(M+H)^+$=386.25. $^1H$ NMR (400 MHz, DMSO-$d_6$) δ 9.17 (t, J=5.9 Hz, 1H), 8.51 (d, J=5.5 Hz, 2H), 8.00 (d, J=8.3 Hz, 2H), 7.80 (d, J=8.3 Hz, 2H), 7.66-7.48 (m, 3H), 7.32 (d, J=5.5 Hz, 2H), 4.52 (d, J=5.8 Hz, 2H), 3.71 (t, J=6.3 Hz, 2H), 2.80 (t, J=6.5 Hz, 2H), 2.21 (s, 3H), 1.94-1.87 (m, 2H).

Synthesis of 4-(1-(2-hydroxyacetyl)indolin-5-yl)-N-(pyridin-3-ylmethyl) benzamide (Compound I-47)

Preparation of 4-(1-(2-(benzyloxy) acetyl) indolin-5-yl)-N-(pyridin-3-ylmethyl) benzamide

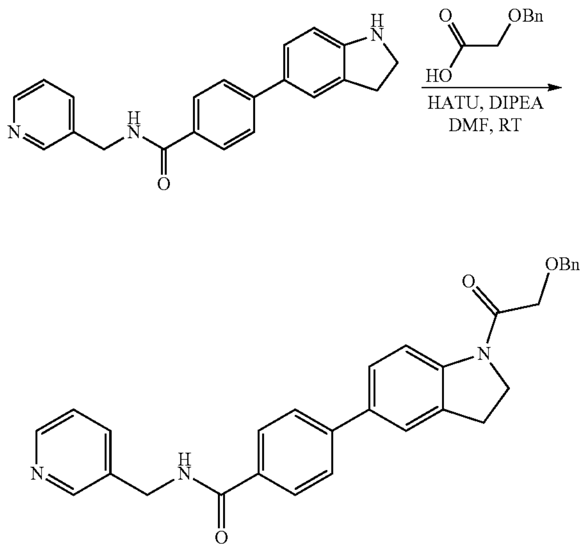

Following general Procedure D, starting from 4-(indolin-5-yl)-N-(pyridin-3-ylmethyl) benzamide (150 mg, 0.45 mmol) and 2-(benzyloxy)acetic acid (60 mg, 0.54 mmol), 4-(1-(2-(benzyloxy) acetyl) indolin-5-yl)-N-(pyridin-3-ylmethyl) benzamide was obtained as a white solid (140 mg, 65%). LC-MS (ESI): m/z $(M-56)^+$=478.32.

Preparation of 4-(1-(2-hydroxyacetyl)indolin-5-yl)-N-(pyridin-3-ylmethyl)benzamide (Compound I-47)

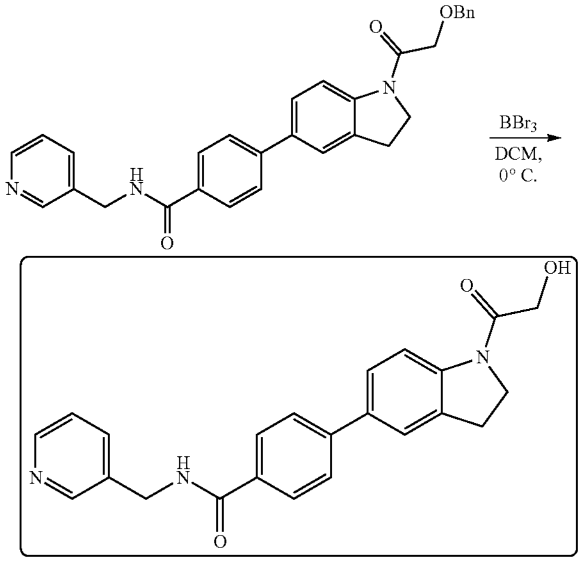

To a solution of 4-(1-(2-(benzyloxy) acetyl) indolin-5-yl)-N-(pyridin-3-ylmethyl) benzamide (100 mg, 0.209 mmol) in DCM (5 mL), was added $BBr_3$ (262 mg, 1.05 mmol). The reaction mixture was stirred at 0° C. for 2 h under $N_2$. After quenching with aq. $NaHCO_3$, the mixture was extracted with DCM, and washed with brine. The organic layer was dried over anhydrous $Na_2SO_4$, filtered, and concentrated under reduced pressure. The residue was purified by prep-HPLC (C18, 40-100% MeCN in $H_2O$ with 0.1% formic acid) to give to 4-(1-(2-hydroxyacetyl)indolin-5-yl)-N-(pyridin-3-ylmethyl)benzamide as a white solid (15 mg, 18%). LC-MS (ESI): m/z $(M+H)^+$=388.61. $^1H$ NMR (400 MHz, DMSO-$d_6$) δ 9.14 (t, J=5.9 Hz, 1H), 8.57 (d, J=1.6 Hz, 1H), 8.47 (dd, J=4.7, 1.4 Hz, 1H), 8.15 (d, J=8.3 Hz, 1H), 7.96 (d, J=8.4 Hz, 2H), 7.82-7.70 (m, 3H), 7.65 (s, 2H), 7.59 (d, J=8.4 Hz, 1H), 7.37 (dd, J=7.7, 4.8 Hz, 1H), 4.94 (s, 1H), 4.52 (d, J=5.8 Hz, 2H), 4.21 (s, 2H), 4.06 (t, J=8.5 Hz, 2H), 3.22 (t, J=8.3 Hz, 2H).

Synthesis of 4-(1-propionylindolin-5-yl)-N-(pyridin-3-ylmethyl) benzenesulfonamide (Compound I-48)

Preparation of 1-(5-bromoindolin-1-yl) propan-1-one

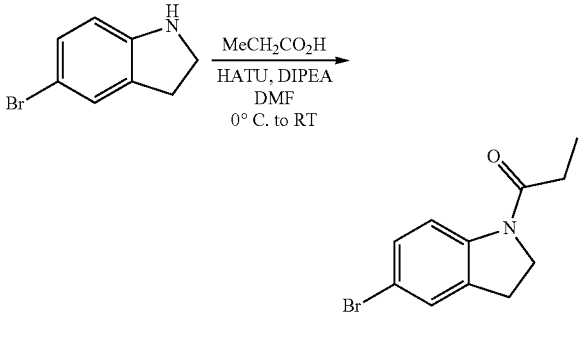

General Procedure D was followed starting from 5-bromoindoline (3.0 g, 15.2 mmol) and propionic acid (1.37 g, 18.3 mmol). In this case, the reagents were added at 0° C. and the reaction mixture was allowed to warm up to RT. 1-(5-bromoindolin-1-yl) propan-1-one was isolated as a white solid (3.0 g, 78%). LC-MS (ESI): m/z $(M)^+$=253.01, 255.52.

Preparation of 1-(5-(4,4,5,5-tetramethyl-1,3,2-dioxaborolan-2-yl) indolin-1-yl) propan-1-one

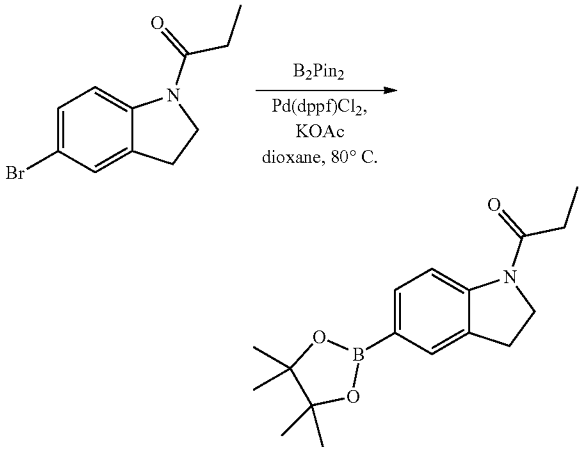

Procedure G: To a mixture of 1-(5-bromoindolin-1-yl) propan-1-one (1.5 g, 5.9 mmol) in dioxane (15 mL), were added $B_2Pin_2$ (1.65 g, 6.5 mmol), Pd(dppf)$Cl_2$ (240 mg, 0.3 mmol), and KOAc (1.7 g, 17.7 mmol). The reaction mixture was stirred at 80° C. for 20 h. It was then diluted with DCM, and washed with water and brine. The organic layer was dried over anhydrous $Na_2SO_4$, filtered and concentrated under reduced pressure. The residue was purified by flash column chromatography over silica gel (PE/EA 4:1, v/v) to give 1-(5-(4,4,5,5-tetramethyl-1,3,2-dioxaborolan-2-yl) indolin-1-yl) propan-1-one as a yellow solid (800 mg, 45%). LC-MS (ESI): m/z $(M-56)^+$=254.20.

Preparation of 4-bromo-N-(pyridin-3-ylmethyl) benzenesulfonamide

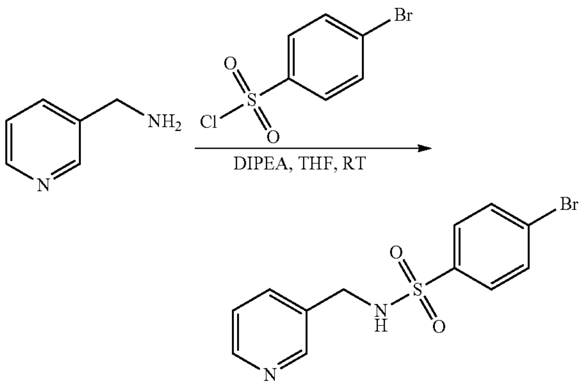

To a mixture of 4-bromo-N-(pyridin-3-ylmethyl) benzenesulfonamide (200 mg, 0.783 mmol) in THF (5 mL), were added pyridin-3-ylmethanamine (92.9 mg, 0.861 mmol) and DIPEA (303.1 mg, 2.349 mmol). The reaction mixture was stirred at RT for 2 h. It was quenched with water, washed with brine, and extracted with EA. The organic layer was dried over anhydrous $Na_2SO_4$, filtered, and concentrated under reduced pressure. The residue was purified by flash column chromatography over silica gel (PE/EA 4:1, v/v) to give 4-bromo-N-(pyridin-3-ylmethyl) benzenesulfonamide as a yellow solid (140 mg, 55%). LC-MS (ESI): m/z $(M)^+$=326.02, 328.33.

Preparation of 4-(1-propionylindolin-5-yl)-N-(pyridin-3-ylmethyl)benzenesulfonamide (Compound I-48)

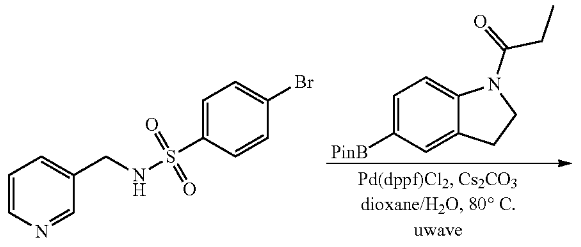

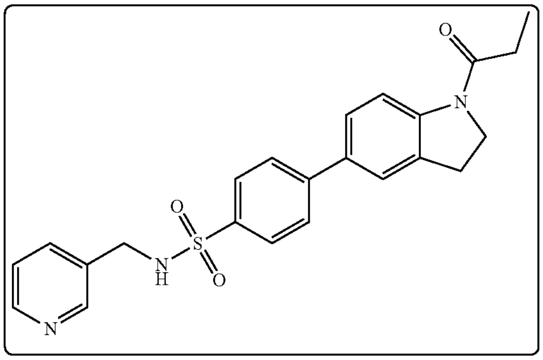

Procedure B was followed starting from 4-bromo-N-(pyridin-3-ylmethyl) benzenesulfonamide (100 mg, 0.31 mmol) and 1-(5-(4,4,5,5-tetramethyl-1,3,2-dioxaborolan-2-yl) indolin-1-yl) propan-1-one. In this case, the reaction mixture was stirred at 80° C. in the microwave for 1 h. Purification by prep-HPLC (C18, 40-100% MeCN in $H_2O$ with 0.1% formic acid) afforded 4-(1-propionylindolin-5-yl)-N-(pyridin-3-ylmethyl)benzenesulfonamide as a white solid (18 mg, 13%). LC-MS (ESI): m/z $(M+1)^+$=422.23. $^1H$ NMR (400 MHz, DMSO-$d_6$) δ 8.47-8.40 (m, 2H), 8.31-8.25 (m, J=15.9 Hz, 1H), 8.21-8.13 (m, J=8.3 Hz, 1H), 7.83 (s, 4H), 7.68-7.61 (m, J=11.3, 3.2 Hz, 2H), 7.59-7.54 (m, J=8.4 Hz, 1H), 7.32-7.27 (m, J=7.8, 4.8 Hz, 1H), 4.15 (t, J=8.5 Hz, 2H), 4.07 (d, J=3.5 Hz, 2H), 3.23 (t, J=8.4 Hz, 3H), 2.50-2.46 (m, 2H), 1.09 (t, J=7.3 Hz, 3H).

Synthesis of 4-(1-propionylindolin-5-yl)-N-(pyridin-4-ylmethyl) benzamide (Compound I-49)

Preparation of methyl 4-(indolin-5-yl) benzoate

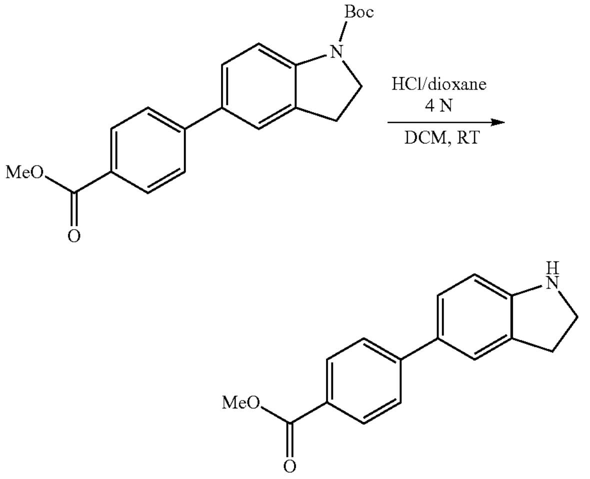

Following procedure E, methyl 4-(indolin-5-yl) benzoate was obtained as a solid (1.5 g, 95%). LC-MS (ESI): m/z $(M-56)^+$=254.14.

Preparation of methyl 4-(1-propionylindolin-5-yl) benzoate

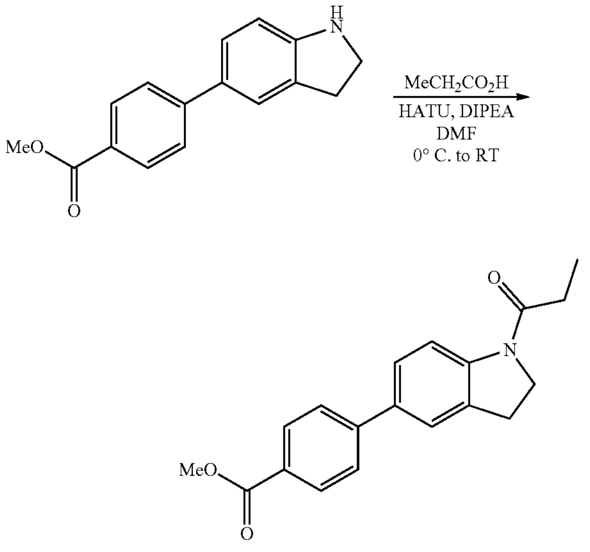

General Procedure D was followed starting from methyl 4-(indolin-5-yl) benzoate (4.8 g, 19.0 mmol) and propionic acid (1.7 g, 22.7 mmol). In this case, the reagents were added at 0° C. and the reaction mixture was allowed to warm up to RT. Methyl 4-(1-propionylindolin-5-yl) benzoate was isolated as a solid (4.4 g, 75%). LC-MS (ESI): m/z $(M+1)^+$=310.14.

Preparation of 4-(1-propionylindolin-5-yl) benzoic acid

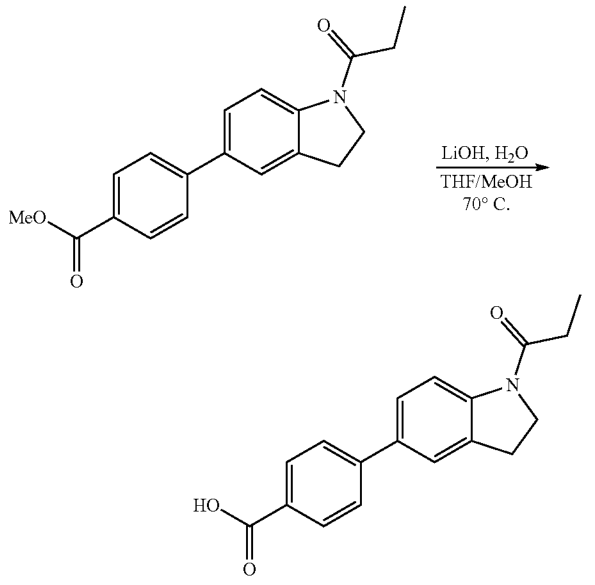

Following Procedure C, 4-(1-propionylindolin-5-yl) benzoic acid (Intermediate B) was obtained as a white solid (1.3 g, 76%) from methyl 4-(1-propionylindolin-5-yl) benzoate (1.8 g, 5.8 mmol). LC-MS (ESI): m/z $(M+1)^+$=296.09.

Preparation of 4-(1-propionylindolin-5-yl)-N-(pyridin-4-ylmethyl)benzamide (Compound I-49)

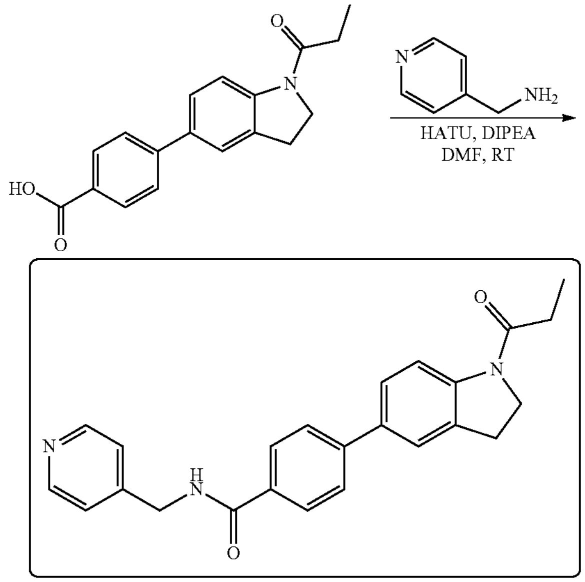

Following general Procedure D, starting from 4-(1-propionylindolin-5-yl) benzoic acid (100 mg, 0.34 mmol) and pyridin-4-ylmethanamine (44 mg, 0.41 mmol), 4-(1-propionylindolin-5-yl)-N-(pyridin-4-ylmethyl)benzamide was isolated as a white solid (70 mg, 53%). LC-MS (ESI): m/z $(M+H)^+$=386.22. $^1$H NMR (400 MHz, DMSO-$d_6$) δ 9.16 (t, J=6.0 Hz, 1H), 8.55-8.45 (m, J=4.5, 1.6 Hz, 2H), 8.16 (d, J=8.4 Hz, 1H), 8.02-7.93 (m, J=8.5 Hz, 2H), 7.81-7.73 (m, J=8.5 Hz, 2H), 7.64 (s, 1H), 7.60-7.54 (m, J=8.4 Hz, 1H), 7.32 (d, J=5.9 Hz, 2H), 4.52 (d, J=5.9 Hz, 2H), 4.13 (t, J=8.5 Hz, 2H), 3.21 (t, J=8.4 Hz, 2H), 1.08 (t, J=7.3 Hz, 3H).

Synthesis of 4-(1-propionylindolin-5-yl)-N-(pyrimidin-5-ylmethyl)benzamide (Compound I-51)

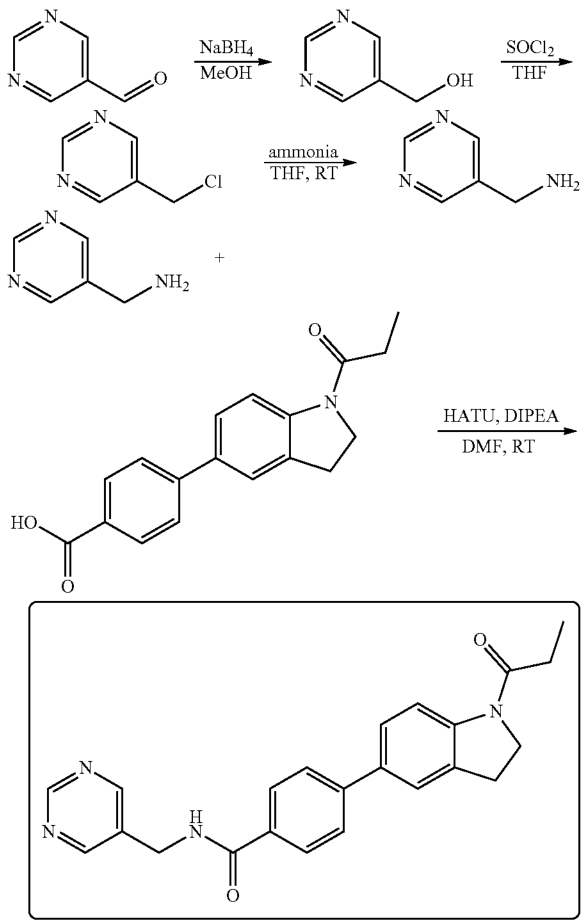

To a solution of pyrimidine-5-carbaldehyde (500 mg, 4.6 mmol) in MeOH (10 mL) at 0° C., was added $NaBH_4$ (262 mg, 6.9 mmol) in one portion. The mixture was stirred at RT for 4 h. It was then washed with brine and extracted with EA. The combined organic layers were washed with brine, dried over $Na_2SO_4$, and concentrated to give pyrimidin-5-ylmethanol as a white solid (456 mg, 89%). LC-MS (ESI): m/z (M+H)=111.13.

To a solution of pyrimidin-5-ylmethanol (410 mg, 3.7 mmol) in THF (10 mL) at 0° C., was added $SOCl_2$ (1.33 g, 11.1 mmol) in one portion. The mixture was stirred at RT for 4 h. It was then quenched with $Na_2CO_3$, the mixture was extracted with EA, the combined organic layers were washed with brine, dried over $Na_2SO_4$, and concentrated to give 5-(chloromethyl)pyrimidine as a white solid (456 mg, 95%). LC-MS (ESI): m/z (M+H)=129.02/131.07.

To a solution of 5-(chloromethyl)pyrimidine (200 mg, 1.56 mmol) in THF, was added $NH_3$—$H_2O$ (4 mL). The mixture was stirred at RT for 30 min. Then the reaction mixture was concentrated and purified by flash chromatography to give (pyrimidin-5-ylmethanamine as a white solid (130 mg, 38%). LC-MS (ESI): m/z (M+H)=110.13.

Following general Procedure D, starting from 4-(1-propionylindolin-5-yl)benzoic acid (238 mg, 0.8 mmol) and pyrimidin-5-ylmethanamine (130 mg, 1.2 mmol), 4-(1-propionylindolin-5-yl)-N-(pyrimidin-5-ylmethyl)benzamide was isolated as a white solid (38 mg, 12%). LC-MS (ESI): m/z (M+H)=387.24. $^1$H NMR (400 MHz, DMSO-$d_6$) δ 9.21-9.06 (m, 2H), 8.80 (s, 2H), 8.16 (d, J=6.2 Hz, 1H), 7.95 (d, J=6.6 Hz, 2H), 7.76 (d, J=6.4 Hz, 2H), 7.67-7.52 (m, 2H), 4.61-4.48 (m, 2H), 4.19-4.06 (m, 2H), 3.28-3.14 (m, 2H), 2.50-2.39 (m, 2H), 1.13-1.02 (m, 3H).

Synthesis of 4-(1-propionylindolin-5-yl)-N-(pyridazin-4-ylmethyl)benzamide (Compound I-52)

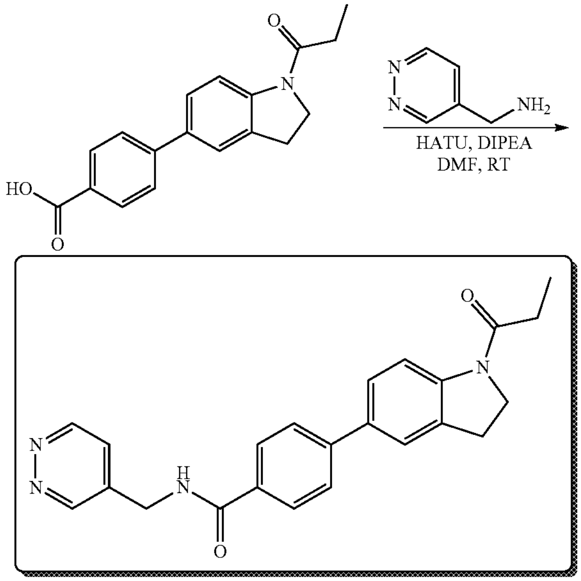

Following general Procedure D, starting from 4-(1-propionylindolin-5-yl)benzoic acid (106 mg, 0.36 mmol) and pyridazin-4-ylmethanamine (50 mg, 0.33 mmol), 4-(1-propionylindolin-5-yl)-N-(pyridazin-4-ylmethyl) benzamide was isolated as a white solid (59 mg, 42%). LC-MS (ESI): m/z $(M+H)^+$=387.22. $^1$H NMR (400 MHz, DMSO-$d_6$) δ 9.29-9.24 (m, 1H), 9.22 (s, 1H), 9.16 (dd, J=5.3, 1.0 Hz, 1H), 8.20-8.13 (m, 1H), 8.01-7.96 (m, 2H), 7.80-7.75 (m, 2H), 7.64 (s, 1H), 7.60-7.54 (m, 2H), 4.55 (d, J=5.8 Hz, 2H), 4.13 (t, J=8.5 Hz, 2H), 3.21 (t, J=8.3 Hz, 2H), 2.50-2.44 (m, 2H), 1.08 (t, J=7.3 Hz, 3H).

Synthesis of 4-(1-propionylindolin-5-yl)-N-(1-(pyridin-3-yl)ethyl)benzamide (Compound I-57)

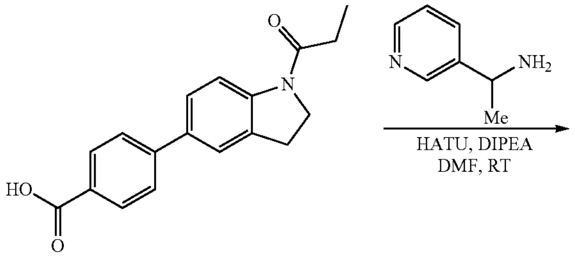

-continued

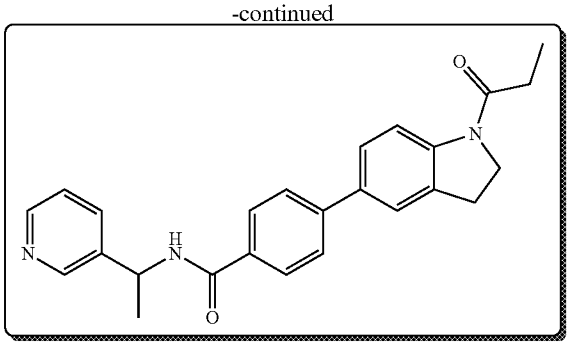

Following general Procedure D, starting from 4-(1-propionylindolin-5-yl) benzoic acid (100 mg, 0.34 mmol) and 1-(pyridin-3-yl)ethan-1-amine (38 mg, 0.31 mmol), 4-(1-propionylindolin-5-yl)-N-(1-(pyridin-3-yl)ethyl) benzamide was isolated as a white solid (50 mg, 40%). LC-MS (ESI): m/z $(M+H)^+$=400.20. $^1$H NMR (400 MHz, DMSO-$d_6$) δ 8.90 (d, J=7.8 Hz, 1H), 8.62 (d, J=2.0 Hz, 1H), 8.45 (dd, J=4.7, 1.5 Hz, 1H), 8.16 (d, J=8.4 Hz, 1H), 7.95 (d, J=8.4 Hz, 2H), 7.83-7.78 (m, 1H), 7.75 (d, J=8.4 Hz, 2H), 7.62 (s, 1H), 7.55 (d, J=8.4 Hz, 1H), 7.39-7.34 (m, 1H), 5.26-5.18 (m, 1H), 4.13 (t, J=8.5 Hz, 2H), 3.21 (t, J=8.3 Hz, 2H), 2.50-2.44 (m, 2H), 1.53 (d, J=7.1 Hz, 3H), 1.08 (t, J=7.3 Hz, 3H).

Synthesis of 4-(1-propionylindolin-5-yl)-N-(2-(pyridin-3-yl)propan-2-yl)benzamide (Compound I-58)

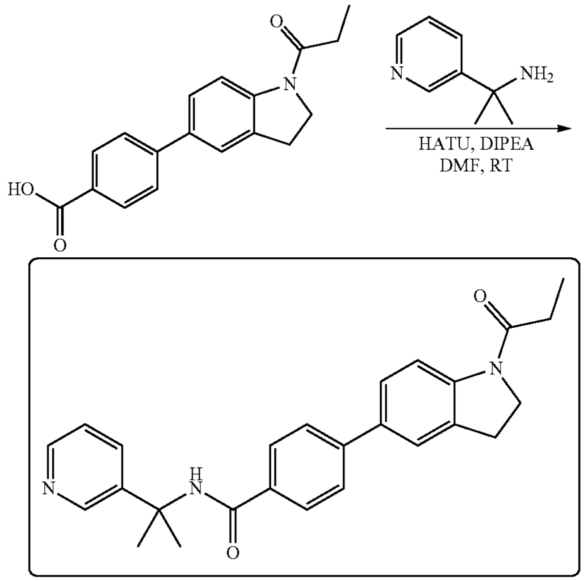

Following general Procedure D, starting from 4-(1-propionylindolin-5-yl) benzoic acid (80 mg, 0.271 mmol) and 2-(pyridin-3-yl)propan-2-amine (40 mg, 0.298 mmol), 4-(1-propionylindolin-5-yl)-N-(2-(pyridin-3-yl)propan-2-yl)benzamide was isolated as a white solid (63 mg, 56%). LC-MS (ESI): m/z $(M+H)^+$=414.32. $^1$H NMR (400 MHz, DMSO-$d_6$) δ 8.62 (d, J=2.2 Hz, 1H), 8.56 (s, 1H), 8.39 (dd, J=4.7, 1.4 Hz, 1H), 8.16 (d, J=8.3 Hz, 1H), 7.91 (d, J=8.4 Hz, 2H), 7.77-7.71 (m, 3H), 7.62 (s, 1H), 7.55 (d, J=8.3 Hz, 1H), 7.33-7.29 (m, 1H), 4.13 (t, J=8.5 Hz, 2H), 3.21 (t, J=8.5 Hz, 2H), 2.50-2.46 (m, 2H), 1.71 (s, 6H), 1.08 (t, J=7.3 Hz, 3H).

Synthesis of N-((6-methylpyridin-3-yl)methyl)-4-(1-propionylindolin-5-yl) benzamide (Compound I-59)

Preparation of (6-methylpyridin-3-yl) methanamine

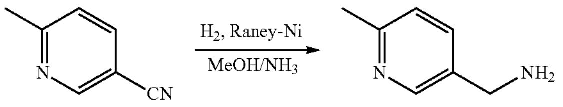

Procedure H: To a mixture of 6-methylnicotinonitrile (300 mg, 2.54 mmol) in MeOH/$NH_3$ (7N, 10 mL), was added Raney Ni (50 mg). The reaction mixture was stirred at RT for 3 h under $H_2$. It was then filtered, and the filtrate concentrated in vacuo to give 6-methylpyridin-3-yl) methanamine as a yellow oil (280 mg, 90%). LC-MS (ESI): m/z (M+1)+=123.30.

Preparation of N-((6-methylpyridin-3-yl)methyl)-4-(1-propionylindolin-5-yl) benzamide (Compound I-59)

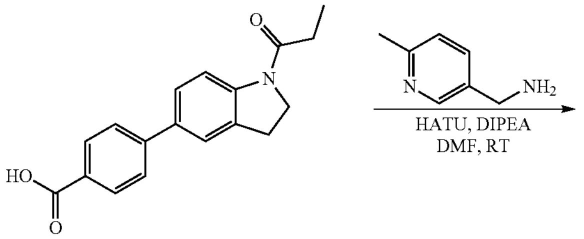

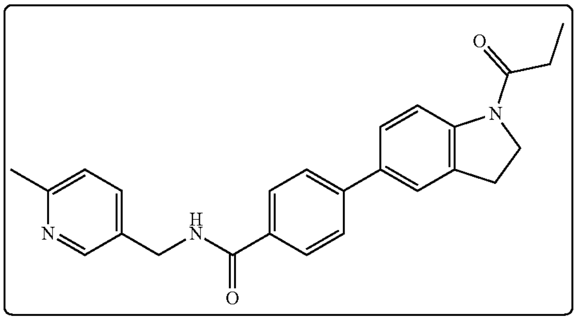

Following general Procedure D, starting from 4-(1-propionylindolin-5-yl)benzoic acid (100 mg, 0.34 mmol) and (6-methylpyridin-3-yl) methanamine (50 mg, 0.41 mmol), N-((6-methylpyridin-3-yl)methyl)-4-(1-propionylindolin-5-yl) benzamide was isolated as a white solid (50 mg, 36%). LC-MS (ESI): m/z $(M+H)^+$=400.32. $^1H$ NMR (400 MHz, DMSO-$d_6$) δ 9.08 (t, J=5.8 Hz, 1H), 8.42 (d, J=1.9 Hz, 1H), 8.15 (d, J=8.4 Hz, 1H), 7.94 (d, J=8.4 Hz, 2H), 7.75 (d, J=8.4 Hz, 2H), 7.65-7.59 (m, 2H), 7.56 (d, J=8.4 Hz, 1H), 7.21 (d, J=8.0 Hz, 1H), 4.46 (d, J=5.8 Hz, 2H), 4.13 (t, J=8.4 Hz, 2H), 3.21 (t, J=8.4 Hz, 2H), 2.50-2.47 (m, 2H), 2.44 (s, 3H), 1.07 (t, J=7.3 Hz, 3H).

Synthesis of N-((2,6-dimethylpyridin-3-yl)methyl)-4-(1-propionylindolin-5-yl) benzamide (Compound I-60)

Preparation of 2,6-dimethylnicotinonitrile

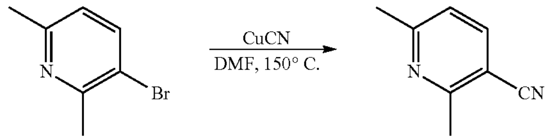

Procedure I: To a mixture of 3-bromo-2,6-dimethylpyridine (500 mg, 2.69 mmol) in DMF (5 mL), was added CuCN (480 mg, 5.38 mmol). The reaction mixture was stirred at 150° C. for 12 h. It was then diluted with DCM and washed with aq. $NH_4Cl$ (85%)/$NH_3 \cdot H_2O$ (15%), water and brine. The organic layer was dried over anhydrous $Na_2SO_4$, filtered, and concentrated under reduced pressure. The residue was purified by flash column chromatography over silica gel (DCM/MeOH 10:1, v/v) to give 2,6-dimethylnicotinonitrile as a yellow solid (210 mg, 59%). LC-MS (ESI): m/z $(M+1)^+$=133.17.

Preparation of (2,6-dimethylpyridin-3-yl)methanamine

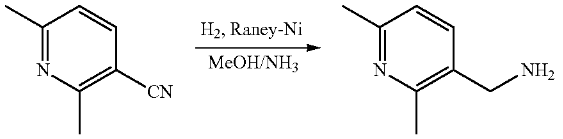

Following Procedure H, (2,6-dimethylpyridin-3-yl) methanamine was obtained as a yellow oil (60 mg, 58%) from 2,6-dimethylnicotinonitrile (100 mg, 0.176 mmol). LC-MS (ESI): m/z $(M+1)^+$=137.20.

Preparation of N-((2,6-dimethylpyridin-3-yl) methyl)-4-(1-propionylindolin-5-yl)benzamide (Compound I-60)

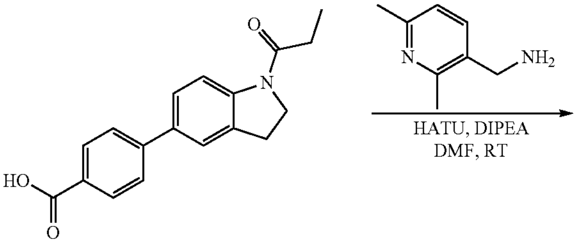

-continued

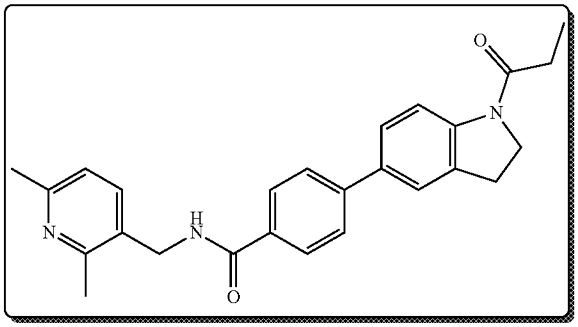

Following general Procedure D, starting from 4-(1-propionylindolin-5-yl)benzoic acid (100 mg, 0.34 mmol) and (2,6-dimethylpyridin-3-yl) methanamine (50 mg, 0.41 mmol), N-((2,6-dimethylpyridin-3-yl)methyl)-4-(1-propionylindolin-5-yl)benzamide was isolated as a white solid (41 mg, 29%). LC-MS (ESI): m/z $(M+H)^+$=414.32. $^1H$ NMR (400 MHz, DMSO-$d_6$) δ 8.96 (t, J=5.5 Hz, 1H), 8.18-8.14 (m, 1H), 7.96 (d, J=8.3 Hz, 2H), 7.75 (d, J=8.3 Hz, 2H), 7.62 (s, 1H), 7.55 (d, J=8.3 Hz, 1H), 7.49 (d, J=7.8 Hz, 1H), 7.04 (d, J=7.7 Hz, 1H), 4.44 (d, J=5.5 Hz, 2H), 4.13 (t, J=8.4 Hz, 2H), 3.21 (t, J=8.4 Hz, 2H), 2.50-2.45 (m, 5H), 2.39 (s, 3H), 1.08 (t, J=7.2 Hz, 3H).

Synthesis of N-((2-methylpyridin-3-yl)methyl)-4-(1-propionylindolin-5-yl) benzamide (Compound I-61)

Preparation of 2-methylnicotinonitrile

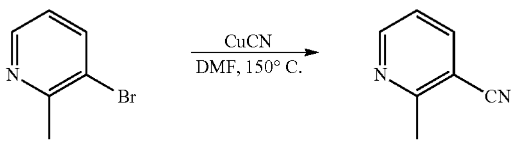

Following Procedure I, 2-methylnicotinonitrile was obtained as a yellow solid (110 mg, 32%) from 3-bromo-2-methylpyridine (500 mg, 2.9 mmol). LC-MS (ESI): m/z $(M+1)^+$=119.20.

Preparation of (2-methylpyridin-3-yl) methanamine

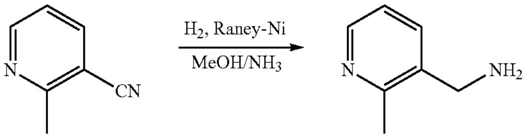

Following Procedure H: (2-methylpyridin-3-yl) methanamine was obtained as a yellow solid (80 mg, 77%) from 2-methylnicotinonitrile (100 mg, 0.85 mmol). LC-MS (ESI): m/z $(M+1)^+$=123.71.

Preparation of N-((2-methylpyridin-3-yl)methyl)-4-(1-propionylindolin-5-yl)benzamide (Compound I-61)

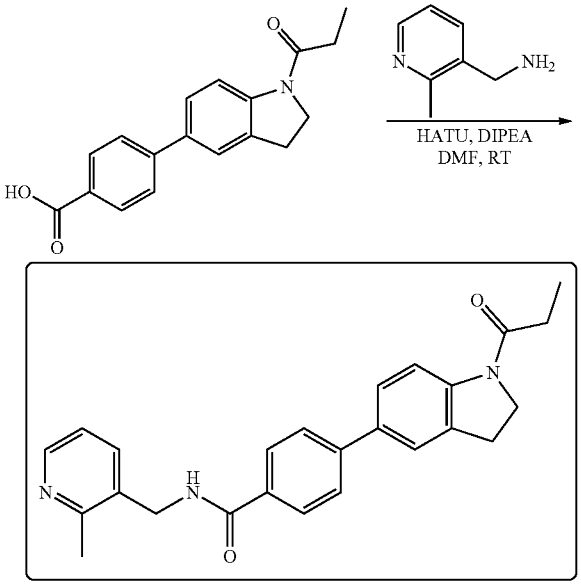

Following general Procedure D, starting from 4-(1-propionylindolin-5-yl)benzoic acid (145 mg, 0.49 mmol) and (2-methylpyridin-3-yl) methanamine (60 mg, 0.49 mmol), N-((2-methylpyridin-3-yl)methyl)-4-(1-propionylindolin-5-yl)benzamide was obtained as a white solid (41 mg, 29%). LC-MS (ESI): m/z $(M+H)^+$=400.31. $^1H$ NMR (400 MHz, DMSO-$d_6$) δ 9.02 (t, J=5.6 Hz, 1H), 8.33 (d, J=3.9 Hz, 1H), 8.16 (d, J=8.4 Hz, 1H), 7.97 (d, J=8.3 Hz, 2H), 7.75 (d, J=8.3 Hz, 2H), 7.65-7.52 (m, 3H), 7.20 (dd, J=7.5, 4.9 Hz, 1H), 4.49 (d, J=5.5 Hz, 2H), 4.13 (t, J=8.4 Hz, 2H), 3.21 (t, J=8.3 Hz, 3H), 2.53 (s, 3H), 2.48 (t, 2H), 1.08 (t, J=7.2 Hz, 3H).

Synthesis of N-methyl-4-(1-propionylindolin-5-yl)-N-(pyridin-3-ylmethyl)benzamide (Compound I-62)

Preparation of N-(pyridin-3-ylmethyl) formamide

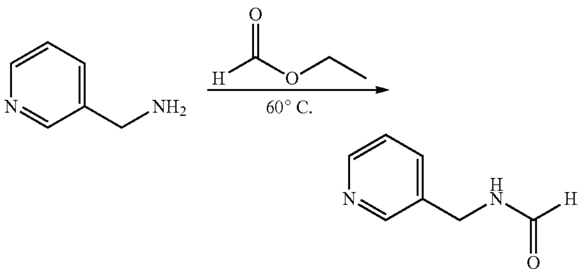

A mixture of pyridin-3-ylmethanamine (1.0 g, 9.2 mmol) in ethyl formate (10 mL) was stirred at 60° C. for 4 h. It was then concentrated under reduced pressure to give N-(pyridin-3-ylmethyl) formamide as a colorless oil (1.0 g, 79%). LC-MS (ESI): m/z $(M+1)^+$=137.06.

Preparation of N-methyl-1-(pyridin-3-yl) methanamine

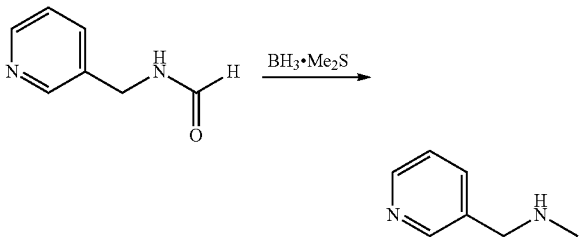

To a solution of N-(pyridin-3-ylmethyl) formamide (500 mg, 3.6 mmol) in THF (20 mL), was added $BH_3$·MeS in THF (10N, 3 mL). The reaction mixture was stirred at 60° C. for 4 h. It was then diluted with DCM and washed with aq. $NH_4Cl$ and brine. The organic layer was concentrated under reduced pressure and the residue was purified by prep-HPLC (C18, 40-100% MeCN in $H_2O$ with 0.1% formic acid) to give to N-methyl-1-(pyridin-3-yl)methanamine as a yellow oil (600 mg, quantitative yield). LC-MS (ESI): m/z $(M+H)^+$=151.31.

Preparation of N-methyl-4-(1-propionylindolin-5-yl)-N-(pyridin-3-ylmethyl)benzamide (Compound I-62)

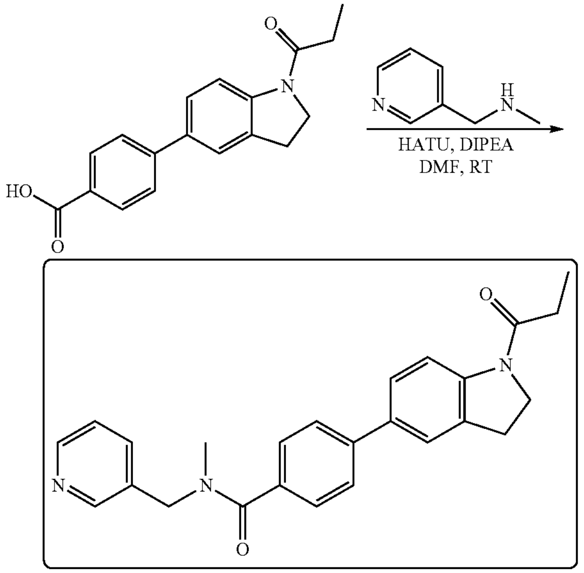

Following general Procedure D, starting from 4-(1-propionylindolin-5-yl)benzoic acid (100 mg, 0.34 mmol) and N-methyl-1-(pyridin-3-yl)methanamine (62 mg, 0.41 mmol), N-methyl-4-(1-propionylindolin-5-yl)-N-(pyridin-3-ylmethyl)benzamide was obtained as a yellow solid (36 mg, 26%). LC-MS (ESI): m/z $(M+H)^+$=400.31. $^1H$ NMR (400 MHz, DMSO-$d_6$) δ 8.90-8.68 (m, 2H), 8.44-8.25 (m, 1H), 8.18-8.13 (m, 1H), 7.92-7.81 (m, 1H), 7.72 (d, J=7.2 Hz, 2H), 7.66-7.47 (m, 4H), 4.89-4.71 (m, 2H), 4.13 (t, J=8.2 Hz, 2H), 3.21 (t, J=8.2 Hz, 2H), 2.99 (s, 3H), 2.49-2.45 (m, 2H), 1.08 (t, J=7.2 Hz, 3H).

Synthesis of N-(piperidin-3-ylmethyl)-4-(1-propionylindolin-5-yl)benzamide (Compound I-63)

Preparation of piperidin-3-ylmethanamine

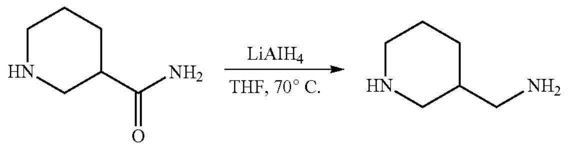

To a solution of 4 piperidine-3-carboxamide (500 mg, 3.9 mmol) in THF (20 mL) at 0° C., was added $LiAlH_4$ (300 mg, 7.8 mmol). The reaction mixture was then stirred at 70° C. for 12 h. Water (0.3 mL) was added, followed by NaOH (10%, 0.3 mL). The reaction mixture was filtered, and the filtrate was concentrated under reduced pressure to give piperidin-3-ylmethanamine as a colorless oil (200 mg, 44%). LC-MS (ESI): m/z $(M+H)^+$=115.20.

Preparation of N-(piperidin-3-ylmethyl)-4-(1-propionylindolin-5-yl)benzamide (Compound I-63)

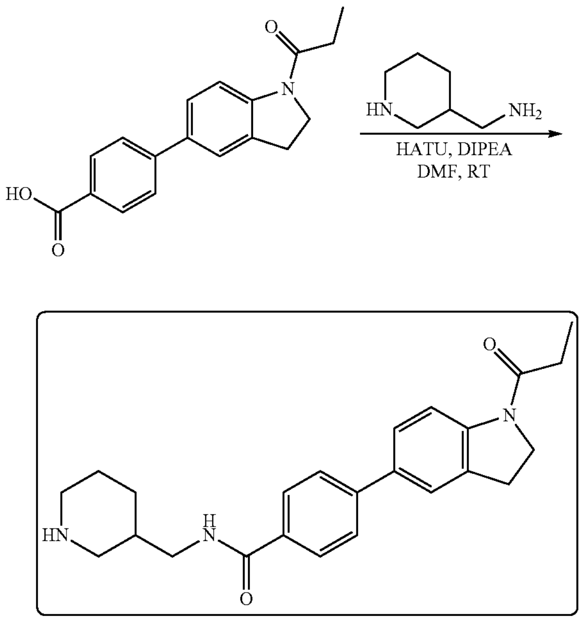

Following general Procedure D, starting from 4-(1-propionylindolin-5-yl)benzoic acid (100 mg, 0.34 mmol) and piperidin-3-ylmethanamine (43 mg, 0.38 mmol), N-(piperidin-3-ylmethyl)-4-(1-propionylindolin-5-yl) benzamide was isolated as a white solid (31 mg, 23%). LC-MS (ESI): m/z $(M+H)^+$=392.33. $^1H$ NMR (400 MHz, DMSO-$d_6$) δ 8.15 (d, J=8.3 Hz, 1H), 7.90 (d, J=8.4 Hz, 2H), 7.72 (d, J=8.4 Hz, 2H), 7.62 (s, 1H), 7.55 (d, J=8.3 Hz, 1H), 4.13 (t, J=8.5 Hz, 2H), 3.21 (t, J=8.4 Hz, 2H), 3.12 (t, J=6.3 Hz, 2H), 2.96-2.90 (m, 1H), 2.86-2.80 (m, 1H), 2.48-2.40 (m, 3H), 2.24-2.16 (m, 1H), 1.79-1.26 (m, 6H), 1.08 (t, J=7.3 Hz, 3H).

Synthesis of 4-(1-propionylindolin-5-yl)-N-((1,2,3,6-tetrahydropyridin-4-yl)methyl)benzamide (Compound I-69)

Preparation of tert-butyl (pyridin-4-ylmethyl)carbamate

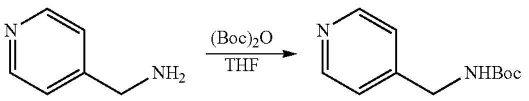 [SMILES: "(Boc)2O" ; NCc1ccncc1 ; CC(C)(C)OC(=O)NCc1ccncc1 ; "THF"]

To a mixture of pyridin-4-ylmethanamine (1.0 g, 9.3 mmol) in THF (30 mL), was added a solution of di-tert-butyl dicarbonate (2.1 g, 9.4 mmol) in DCM (20 mL). The reaction mixture was stirred at RT for 10 h. It was then concentrated in vacuo to give tert-butyl (pyridin-4-ylmethyl) carbamate as a colorless oil (crude 1.9 g, quantitative yield). LC-MS (ESI): m/z $(M+1)^+$=209.33.

Preparation of 1-benzyl-4-(((tert-butoxycarbonyl) amino)methyl) pyridin-1-ium bromide

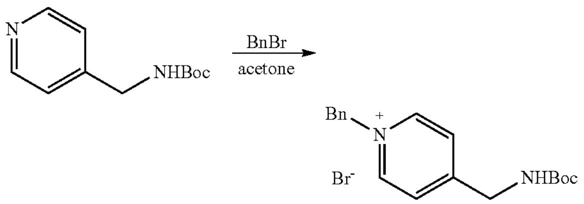

To a mixture of tert-butyl (pyridin-4-ylmethyl)carbamate (1.9 g, 9.3 mmol) in acetone (40 mL), was added solution of BnBr (2.4 g, 14.1 mmol). The reaction mixture was stirred at RT for 15 h. It was then diluted with DCM and washed with brine. The organic layer was dried over anhydrous $Na_2SO_4$, filtered and concentrated under reduced pressure to give 1-benzyl-4-(((tert-butoxycarbonyl)amino)methyl) pyridin-1-ium bromide as a blue oil (crude 2.5 g, quantitative yield). LC-MS (ESI): m/z $(M+1)^+$=299.24.

Preparation of tert-butyl ((1-benzyl-1,2,3,6-tetrahydropyridin-4-yl)methyl)carbamate

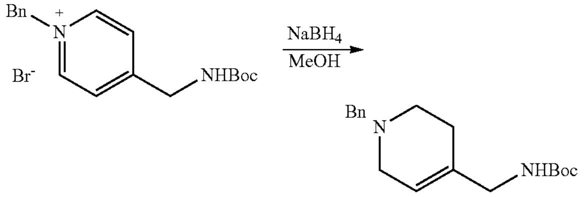

To a mixture of -benzyl-4-(((tert-butoxycarbonyl)amino) methyl) pyridin-1-ium bromide (crude 2.5 g, 9.3 mmol) in MeOH (15 mL) at 0° C., was added $NaBH_4$ (1.0 g, 21.9 mmol). The reaction mixture was stirred at 0° C. for 3 h. It was then diluted with EA, and washed with brine. The organic layer was dried over anhydrous $Na_2SO_4$, filtered and concentrated under reduced pressure. The residue was purified by flash column chromatography over silica gel (DCM/MeOH 3:1, v/v) to give tert-butyl ((1-benzyl-1,2,3,6-tetrahydropyridin-4-yl) methyl)carbamate as a yellow oil (1.7 g, 60%). LC-MS (ESI): m/z $(M-56)^+$=304.29.

Preparation of (1-benzyl-1,2,3,6-tetrahydropyridin-4-yl)methanamine

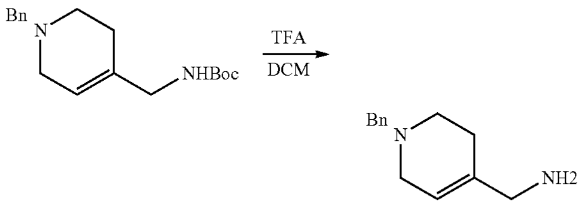 [SMILES: CC(C)(C)OC(=O)NCC1=CCNCC1 ; NCC1=CCNCC1 ; "Bn" ; "Bn"]

To a mixture of tert-butyl ((1-benzyl-1,2,3,6-tetrahydropyridin-4-yl) methyl)carbamate (200 mg, 0.66 mmol) in DCM (10 mL) was added TFA (5 mL), then the reaction mixture was stirred at RT for 0.5 h. The reaction mixture was concentrated in vacuo to give (1-benzyl-1,2,3,6-tetrahydropyridin-4-yl)methanamine as a purple solid (crude 250 mg, quantitative yield). LC-MS (ESI): m/z $(M+1)^+$=204.50.

Preparation of N-((1-benzyl-1,2,3,6-tetrahydropyridin-4-yl)methyl)-4-(1-propionylindolin-5-yl)benzamide

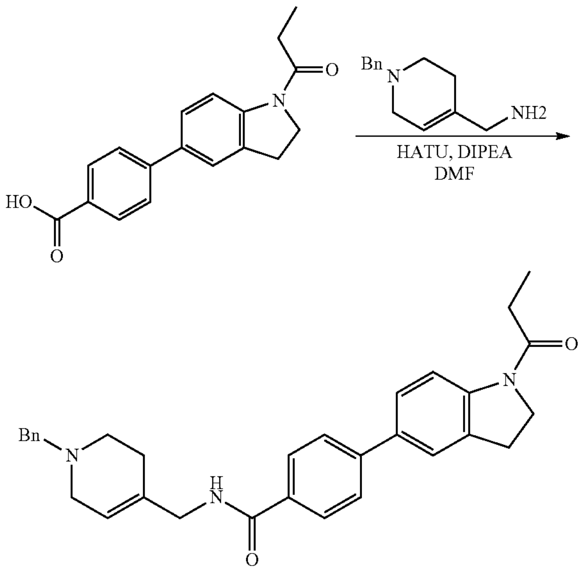 [SMILES: CCC(=O)N1CCc2cc(-c3ccc(C(=O)O)cc3)ccc21 ; NCC1=CCNCC1 ; CCC(=O)N1CCc2cc(-c3ccc(C(=O)NCC4=CCN(Cc5ccccc5)CC4)cc3)ccc21 ; "Bn"]

Following general Procedure D, starting from 4-(1-propionylindolin-5-yl)benzoic acid (233 mg, 0.79 mmol) and (1-benzyl-1,2,3,6-tetrahydropyridin-4-yl)methanamine (crude 250 mg, 0.66 mmol), N-((1-benzyl-1,2,3,6-tetrahydropyridin-4-yl)methyl)-4-(1-propionylindolin-5-yl)benzamide was obtained as a solid (230 mg, 72%). LC-MS (ESI): m/z $(M+1)^+$=480.30.

Preparation of Monoformate 4-(1-propionylindolin-5-yl)-N-((1,2,3,6-tetrahydropyridin-4-yl)methyl) benzamide (Monoformate of Compound I-69)

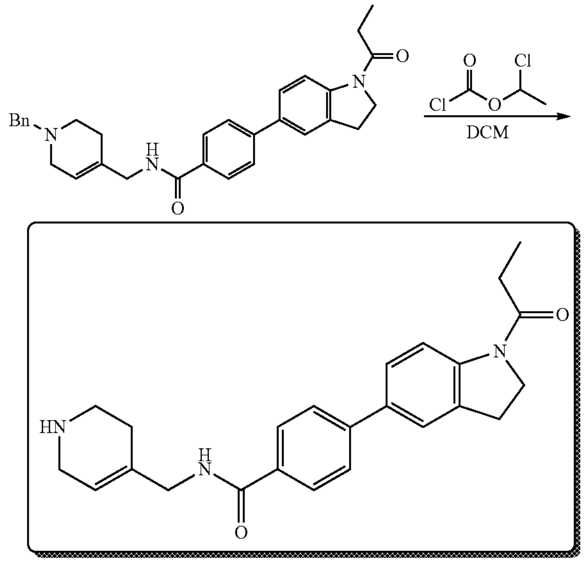

To a solution of N-((1-benzyl-1,2,3,6-tetrahydropyridin-4-yl) methyl)-4-(1-propionylindolin-5-yl)benzamide (100 mg, 0.21 mmol) in DCM (3 mL), was added 1-chloroethyl carbonochloridate (44 mg, 0.31 mmol). The reaction mixture was stirred at RT for 12 h, then filtered. The filtrate was concentrated under reduced pressure and the residue was purified by prep-HPLC (C18, 40-100% MeCN in $H_2O$ with 0.1% formic acid) to give to 4-(1-propionylindolin-5-yl)-N-((1,2,3,6-tetrahydropyridin-4-yl)methyl)benzamide as a white solid (11 mg, 13%). LC-MS (ESI): m/z $(M+H)^+$=390.22. $^1H$ NMR (400 MHz, DMSO-$d_6$) δ 8.74 (t, J=5.8 Hz, 1H), 8.39 (s, 1H), 8.16 (d, J=8.4 Hz, 1H), 7.95 (d, J=8.4 Hz, 2H), 7.74 (d, J=8.4 Hz, 2H), 7.62 (s, 1H), 7.55 (d, J=8.4 Hz, 1H), 5.55 (s, 1H), 4.39 (s, 2H), 4.12 (t, J=8.5 Hz, 2H), 3.86 (d, J=4.4 Hz, 3H), 3.41 (s, 2H), 3.21 (t, J=8.3 Hz, 2H), 3.02 (t, J=5.5 Hz, 2H), 2.50-2.44 (m, 1H), 2.14 (s, 2H), 1.08 (t, J=7.3 Hz, 3H).

Synthesis of N-(piperidin-4-ylmethyl)-4-(1-propionylindolin-5-yl) benzamide (Compound I-70)

Preparation of tert-butyl 4-((4-(1-propionylindolin-5-yl)benzamido)methyl) piperidine-1-carboxylate

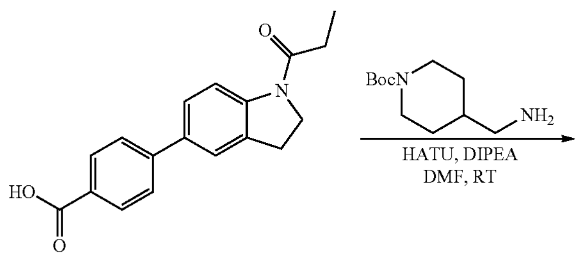

-continued

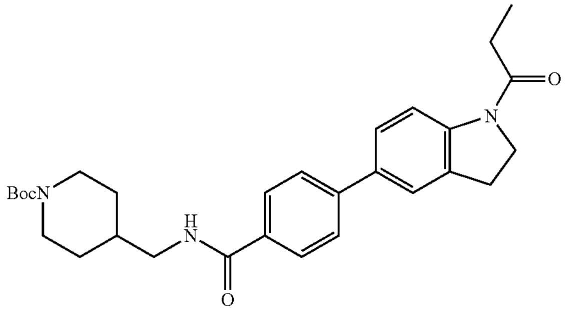

Following general Procedure D, starting from 4-(1-propionylindolin-5-yl)benzoic acid (120 mg, 0.41 mmol) and tert-butyl 4-(aminomethyl) piperidine-1-carboxylate (105 mg, 0.49 mmol), tert-butyl 4-((4-(1-propionylindolin-5-yl) benzamido)methyl)piperidine-1-carboxylate was obtained as a white solid (200 mg, 99%). LC-MS (ESI): m/z $(M+1)^+$ =436.36.

Preparation of N-(piperidin-4-ylmethyl)-4-(1-propionylindolin-5-yl)benzamide (Compound I-70)

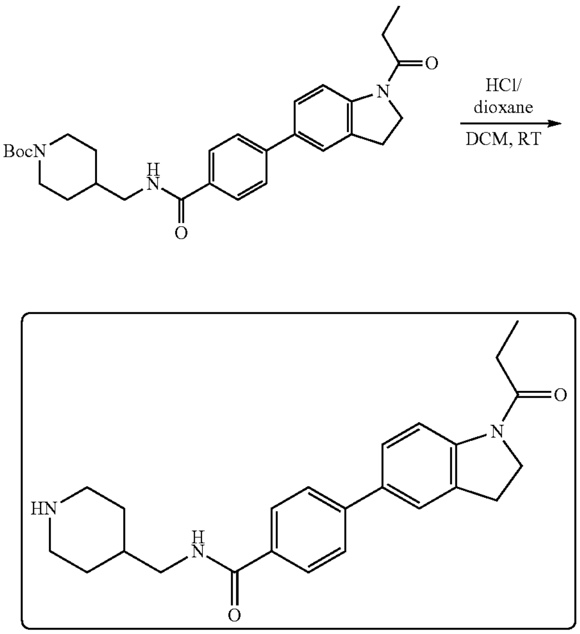

Procedure E was followed starting from tert-butyl 4-((4-(1-propionylindolin-5-yl) benzamido)methyl)piperidine-1-carboxylate (200 mg, 0.40 mmol). Purification by prep-HPLC (C18, 40-100% MeCN in $H_2O$ with 0.1% formic acid) afforded N-(piperidin-4-ylmethyl)-4-(1-propionylindolin-5-yl)benzamide as a white solid (76 mg, 48%). LC-MS (ESI): m/z $(M+H)^+$=392.31. $^1H$ NMR (400 MHz, DMSO-$d_6$) δ 8.56 (t, J=5.8 Hz, 1H), 8.15 (d, J=8.4 Hz, 1H), 7.91 (d, J=8.4 Hz, 2H), 7.73 (d, J=8.4 Hz, 2H), 7.62 (s, 1H), 7.55 (d, J=8.4 Hz, 1H), 4.13 (t, J=8.5 Hz, 3H), 3.24-3.13 (m, 6H), 2.69 (t, J=11.4 Hz, 2H), 2.49-2.46 (m, 2H), 1.77-1.72 (m, 3H), 1.33-1.25 (m, 2H), 1.08 (t, J=7.3 Hz, 3H).

Synthesis of N-((1H-pyrazol-4-yl)methyl)-4-(1-propionylindolin-5-yl) benzamide (Compound I-72)

Preparation of (H-pyrazol-4-yl)methanamine

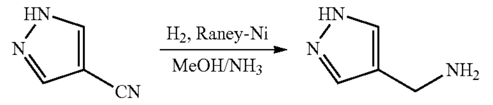 [SMILES: N#Cc1cn[nH]c1 ; NCc1cn[nH]c1]

Following Procedure H, (1H-pyrazol-4-yl)methanamine was obtained as a yellow oil (60 mg, 66%) from 1H-pyrazole-4-carbonitrile (100 mg, 0.93 mmol). LC-MS (ESI): m/z $(M+1)^+=98.20$.

Preparation of N-((1H-pyrazol-4-yl)methyl)-4-(1-propionylindolin-5-yl)benzamide (Compound I-72)

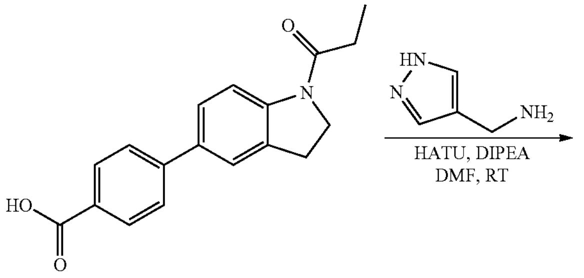

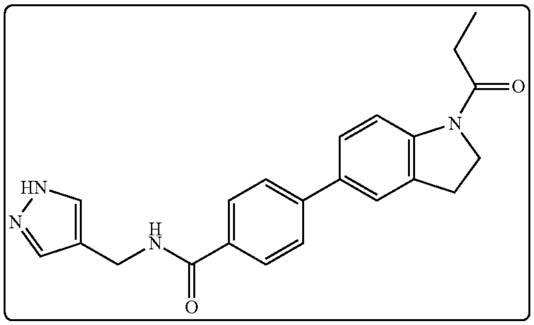

Following general Procedure D, starting from 4-(1-propionylindolin-5-yl)benzoic acid (182 mg, 0.62 mmol) and (1H-pyrazol-4-yl) methanamine (60 mg, 0.62 mmol), N-((1H-pyrazol-4-yl)methyl)-4-(1-propionylindolin-5-yl) benzamide was obtained as a white solid (28 mg, 16%). LC-MS (ESI): m/z $(M+H)^+=375.30$. $^1H$ NMR (400 MHz, DMSO-$d_6$) δ 12.66 (s, 1H), 8.82 (t, J=5.7 Hz, 1H), 8.15 (d, J=8.4 Hz, 1H), 7.92 (d, J=8.5 Hz, 2H), 7.72 (d, J=8.5 Hz, 2H), 7.66-7.47 (m, 4H), 4.35 (d, J=5.6 Hz, 2H), 4.12 (t, J=8.5 Hz, 2H), 3.20 (t, J=8.3 Hz, 2H), 2.50-2.45 (m, 2H), 1.07 (t, J=7.3 Hz, 3H).

Synthesis of 4-(1-propionylindolin-5-yl)-N-((1,2,3,6-tetrahydropyridin-4-yl)methyl)benzamide (Compound I-73)

Preparation of tert-butyl (oxazol-5-ylmethyl)carbamate

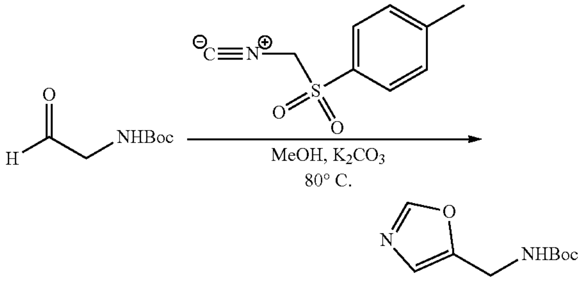

To a mixture of tert-butyl (pyridin-4-ylmethyl) carbamate (200 mg, 1.26 mmol) in MeOH (5 mL), were added $K_2CO_3$ (521 mg, 3.77 mmol) and 1-((isocyanomethyl)sulfonyl)-4-methylbenzene (250 mg, 1.26 mmol). The reaction mixture was stirred at 80° C. for 2 h. It was then diluted with EA and washed with brine. The organic layer was dried over anhydrous $Na_2SO_4$, filtered, and concentrated under reduced pressure to give tert-butyl (oxazol-5-ylmethyl)carbamate as a colorless oil (crude 80 g, 64%). LC-MS (ESI): m/z $(M+1)^+=199.20$ Preparation of oxazol-5-ylmethanamine Hydrochloride

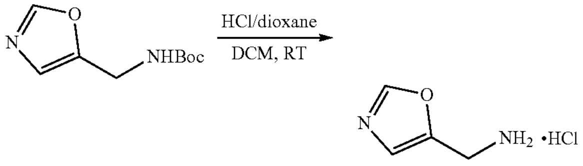

Following Procedure E, starting from tert-butyl (oxazol-5-ylmethyl)carbamate (100 mg, 0.34 mmol), oxazol-5-ylmethanamine hydrochloride was obtained as a yellow solid (crude 40 mg, quantitative yield). LC-MS (ESI): m/z (M+1)+99.20.

Preparation of N-(oxazol-5-ylmethyl)-4-(1-propionylindolin-5-yl)benzamide (Compound I-73)

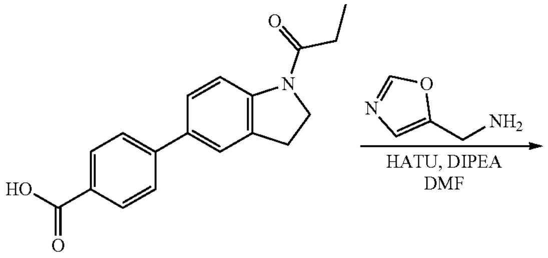

-continued

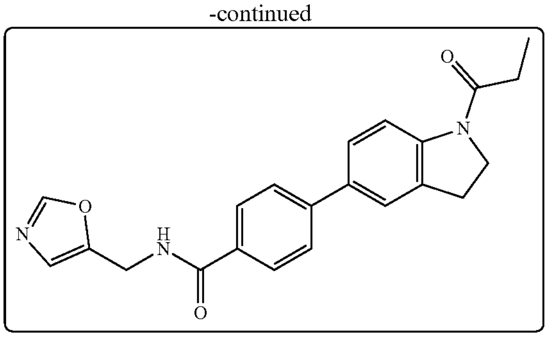

Following general Procedure D, starting from 4-(1-propionylindolin-5-yl)benzoic acid (100 mg, 0.34 mmol) and oxazol-5-ylmethanamine hydrochloride (40 mg, 0.40 mmol), N-(oxazol-5-ylmethyl)-4-(1-propionylindolin-5-yl)benzamide was isolated as a white solid (12 mg, 9%). LC-MS (ESI): m/z $(M+H)^+$=376.25. $^1H$ NMR (400 MHz, DMSO-$d_6$) δ 9.04 (t, J=5.6 Hz, 1H), 8.29 (s, 1H), 8.15 (d, J=8.4 Hz, 1H), 7.93 (d, J=8.5 Hz, 2H), 7.75 (d, J=8.5 Hz, 2H), 7.63 (s, 1H), 7.55 (dd, J=8.5, 1.7 Hz, 1H), 7.06 (s, 1H), 4.55 (d, J=5.4 Hz, 2H), 4.13 (t, J=8.5 Hz, 2H), 3.21 (t, J=8.4 Hz, 2H), 2.49-2.43 (m, 2H), 1.08 (t, J=7.3 Hz, 3H).

Synthesis of 4-(1-propionylindolin-5-yl)-N-(pyridin-2-ylmethyl)benzamide (Compound I-185)

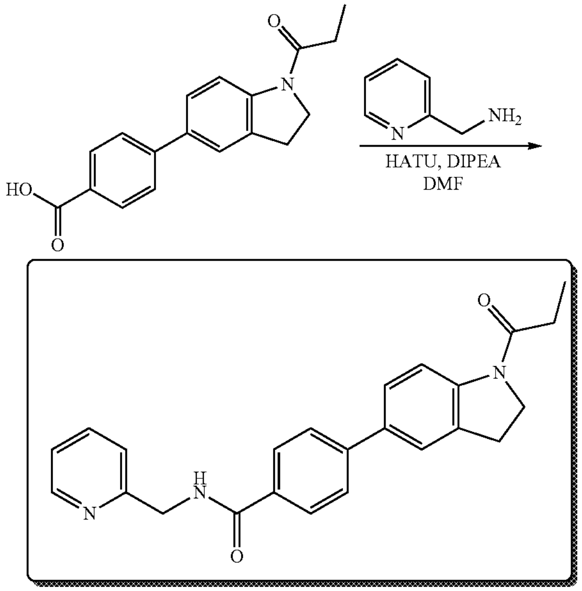

Following general Procedure D, starting from 4-(1-propionylindolin-5-yl)benzoic acid (100 mg, 0.34 mmol) and pyridin-2-ylmethanamine (48 mg, 0.44 mmol), 4-(1-propionylindolin-5-yl)-N-(pyridin-2-ylmethyl)benzamide was obtained as a white solid (65 mg, 49%). LC-MS (ESI): m/z $(M+1)^+$=386.18. $^1H$ NMR (400 MHz, DMSO-$d_6$) δ 9.14 (t, J=6.0 Hz, 1H), 8.52 (d, J=4.0 Hz, 1H), 8.16 (d, J=8.4 Hz, 1H), 7.99 (d, J=8.5 Hz, 2H), 7.83-7.71 (m, 3H), 7.64 (s, 1H), 7.57 (d, J=8.4 Hz, 1H), 7.34 (d, J=7.9 Hz, 1H), 7.29-7.24 (m, 1H), 4.59 (d, J=5.9 Hz, 2H), 4.13 (t, J=8.5 Hz, 2H), 3.21 (t, J=8.5 Hz, 2H), 2.49-2.46 (m, 2H), 1.08 (t, J=7.3 Hz, 3H).

Synthesis of N-(cyclohexylmethyl)-4-(1-propionylindolin-5-yl)benzamide (Compound I-186)

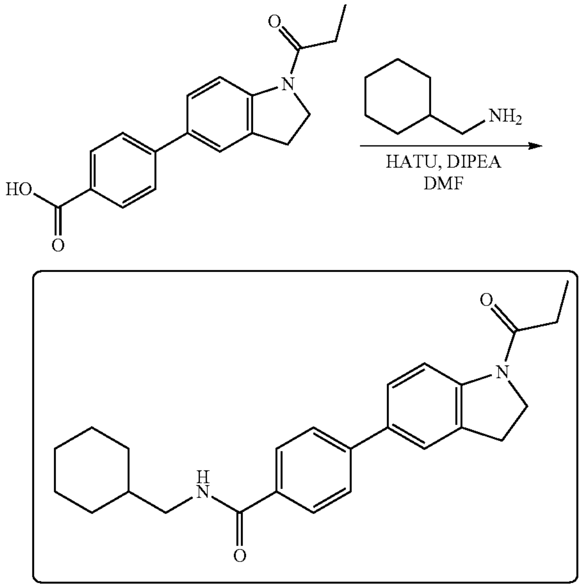

Following general Procedure D, starting from 4-(1-propionylindolin-5-yl)benzoic acid (100 mg, 0.34 mmol) and cyclohexylmethanamine (50 mg, 0.44 mmol), N-(cyclohexylmethyl)-4-(1-propionylindolin-5-yl)benzamide was obtained as a white solid (45 mg, 34%). LC-MS (ESI): m/z $(M+1)^+$=391.17. $^1H$ NMR (400 MHz, DMSO-$d_6$) δ 8.44 (t, J=5.7 Hz, 1H), 8.15 (d, J=8.4 Hz, 1H), 7.90 (d, J=8.3 Hz, 2H), 7.72 (d, J=8.3 Hz, 2H), 7.61 (s, 1H), 7.54 (d, J=8.3 Hz, 1H), 4.13 (t, J=8.5 Hz, 2H), 3.21 (t, J=8.3 Hz, 2H), 3.12 (t, J=6.3 Hz, 2H), 2.49-2.46 (m, 2H), 1.76-1.56 (m, 6H), 1.25-1.14 (m, 3H), 1.08 (t, J=7.3 Hz, 3H), 0.99-0.88 (m, 2H).

Synthesis of N-((4-methylpyridin-3-yl)methyl)-4-(1-propionylindolin-5-yl)benzamide (Compound I-188)

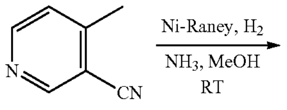

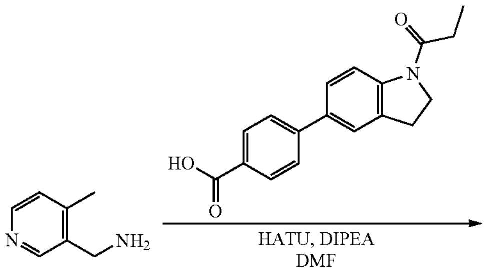

-continued

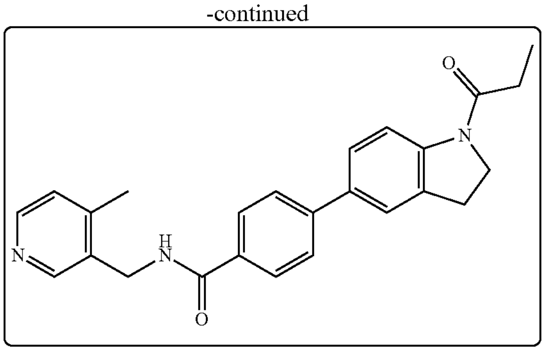

Preparation of (4-methylpyridin-3-yl)methanamine

Following Procedure H, starting from 4-methylnicotinonitrile (300 mg, 2.54 mmol), (4-methylpyridin-3-yl)methanamine was obtained as a colorless oil (400 mg, quantitative yield).

Preparation of N-((4-methylpyridin-3-yl)methyl)-4-(1-propionylindolin-5-yl)benzamide Following general Procedure D, starting from 4-(1-propionylindolin-5-yl)benzoic acid (300 mg, 1.02 mmol) and (4-methylpyridin-3-yl)methanamine (250 mg, 2.03 mmol), N-((4-methylpyridin-3-yl)methyl)-4-(1-propionylindolin-5-yl)benzamide was obtained as a white solid (30 mg, 7%). LC-MS (ESI): m/z $(M+1)^+$=400.30. $^1H$ NMR (400 MHz, DMSO-$d_6$) δ 8.96 (t, J=5.5 Hz, 1H), 8.43 (s, 1H), 8.33 (d, J=4.9 Hz, 1H), 8.15 (d, J=8.4 Hz, 1H), 7.95 (d, J=8.4 Hz, 2H), 7.74 (d, J=8.4 Hz, 2H), 7.62 (s, 1H), 7.55 (d, J=8.5 Hz, 1H), 7.20 (d, J=4.9 Hz, 1H), 4.51 (d, J=5.5 Hz, 2H), 4.13 (t, J=8.5 Hz, 2H), 3.21 (t, J=8.5 Hz, 2H), 2.49-2.44 (m, 2H), 2.36 (s, 3H), 1.08 (t, J=7.3 Hz, 3H).

Synthesis of 4-(1-propionylindolin-5-yl)-N-((tetrahydro-2H-pyran-4-yl)methyl)benzamide (Compound I-191)

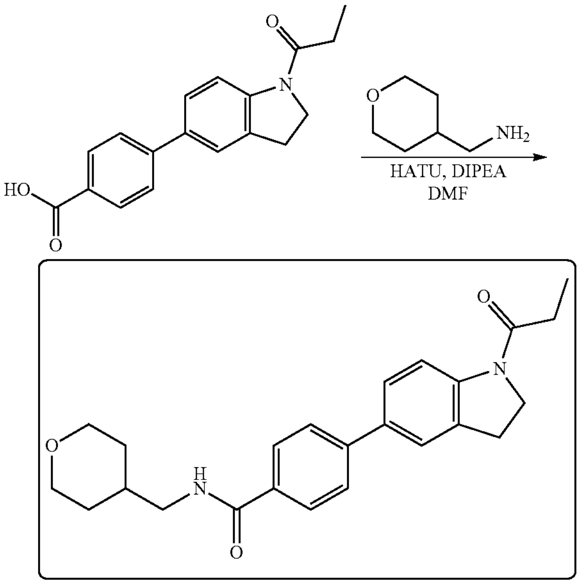

Following general Procedure D, starting from 4-(1-propionylindolin-5-yl)benzoic acid (100 mg, 0.34 mmol) and (tetrahydro-2H-pyran-4-yl)methanamine (51 mg, 0.44 mmol), 4-(1-propionylindolin-5-yl)-N-((tetrahydro-2H-pyran-4-yl)methyl)benzamide was obtained as a white solid (47 mg, 35%). LC-MS (ESI): m/z $(M+1)^+$=393.32. $^1H$ NMR (400 MHz, DMSO-$d_6$) δ 8.50 (t, J=5.7 Hz, 1H), 8.15 (d, J=8.4 Hz, 1H), 7.91 (d, J=8.4 Hz, 2H), 7.73 (d, J=8.4 Hz, 2H), 7.62 (s, 1H), 7.54 (d, J=8.3 Hz, 1H), 4.13 (t, J=8.5 Hz, 2H), 3.85 (dd, J=11.3, 2.5 Hz, 2H), 3.30-3.15 (m, 6H), 2.49-2.46 (m, 2H), 1.84-1.76 (m, 1H), 1.64-1.56 (m, 2H), 1.25-1.16 (m, 2H), 1.08 (t, J=7.3 Hz, 3H).

Synthesis of 4-(1-propionylindolin-5-yl)-N-(pyridazin-3-ylmethyl) benzamide (Compound I-197)

Preparation of pyridazine-3-carbonitrile

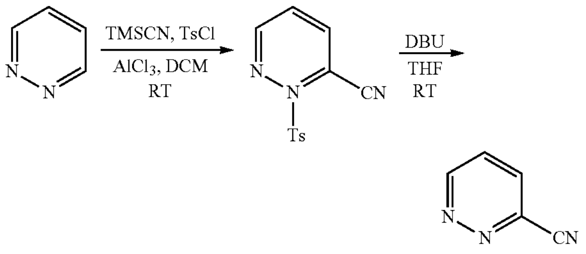

To a solution of pyridazine (2.0 g, 25.0 mmol) in DCM (300 mL), were added trimethylsilyl cyanide (6 mL, 45 mmol) and aluminum chloride (10 mg, 0.075 mmol). After stirring the reaction mixture at RT for 10 minutes, a solution of 4-methylbenzenesulfonyl chloride (8.2 g, 43 mmol) in DCM (10 mL) was added dropwise via an addition funnel over 30 minutes. The resulting light orange solution was left stirring at RT overnight. The reaction mixture was concentrated to give a light brown solid. To this material, was added EtOH (50 mL). A white precipitate was seen, it was filtered and washed with ethanol to give 2-tosyl-2,3-dihydropyridazine-3-carbonitrile (crude 6.0 g, quantitative yield). LC-MS (ESI): m/z (M+H)=262.

To a solution of 2-tosyl-2,3-dihydropyridazine-3-carbonitrile (crude 6.0 g, 25 mmol) in anhydrous THF (30 mL), was added DBU (4 mL, 26.3 mmol). The resulting solution was stirred at RT for 30 minutes. The reaction was quenched by the addition of saturated ammonium chloride solution (20 mL). The resulting mixture was diluted with water (30 mL) and extracted with ethyl acetate. The organic layer was washed with brine, dried over anhydrous sodium sulfate, filtered, and concentrated under reduced pressure to give pyridazine-3-carbonitrile as a white solid (1.4 g, 53%). LC-MS (ESI): m/z $(M)^+$=106.13.

Preparation of pyridazin-3-ylmethanamine Hydrochloride

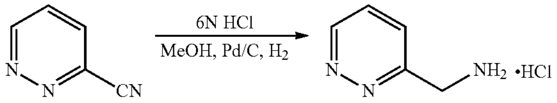

To a solution of pyridazine-3-carbonitrile (500 mg, 4.7 mmol) in MeOH (10 mL), was added HCl 6N (2 mL, 12 mmol) followed by Pd/C (50 mg). The reaction mixture was kept on a Parr shaker for 2 hours at 40 psig hydrogen. The reaction mixture was filtered through Celite® (diatomaceous earth), washed with 100 mL of MeOH, and the filtrate was concentrated. The residue was azeotroped several times with toluene to give pyridazin-3-ylmethanamine hydrochloride as a dark brown solid (crude 500 mg, quantitative yield). LC-MS (ESI): m/z (M+H)=110.15.

Preparation of 4-(1-propionylindolin-5-yl)-N-(pyridazin-3-ylmethyl)benzamide (Compound I-197)

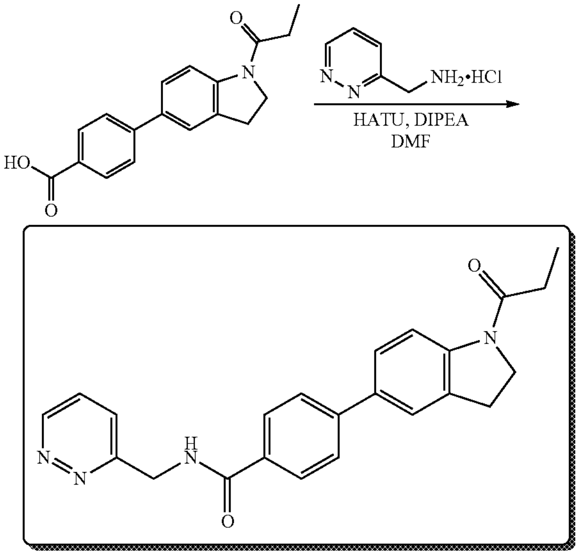

Following general Procedure D, starting from 4-(1-propionylindolin-5-yl)benzoic acid (150 mg, 0.51 mmol) and pyridazin-3-ylmethanamine hydrochloride (88 mg, 0.61 mmol), 4-(1-propionylindolin-5-yl)-N-(pyridazin-3-ylmethyl)benzamide was obtained as a white solid (35 mg, 18%). LC-MS (ESI): m/z $(M+H)^+$=387.28. $^1H$ NMR (400 MHz, DMSO-$d_6$) δ9.27 (t, J=5.9 Hz, 1H), 9.15 (dd, J=4.7, 1.8 Hz, 1H), 8.16 (d, J=8.4 Hz, 1H), 7.98 (d, J=8.5 Hz, 2H), 7.77 (d, J=8.5 Hz, 2H), 7.69-7.61 (m, 3H), 7.56 (dd, J=8.4, 1.4 Hz, 1H), 4.78 (d, J=5.9 Hz, 2H), 4.13 (t, J=8.5 Hz, 2H), 3.21 (t, J=8.4 Hz, 2H), 2.49-2.43 (m, 2H), 1.08 (t, J=7.3 Hz, 3H).

Synthesis of N-((5-methylpyridin-3-yl)methyl)-4-(1-propionylindolin-5-yl) benzamide (Compound I-198)

Preparation of (5-methylpyridin-3-yl)methanamine

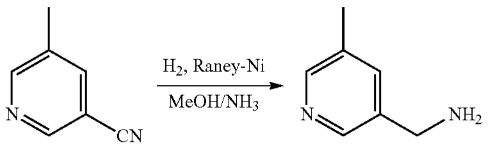

Following Procedure H, (5-methylpyridin-3-yl)methanamine was obtained as a yellow solid (70 mg, 67%) from 5-methylnicotinonitrile (100 mg, 0.85 mmol). LC-MS (ESI): m/z $(M+1)^+$=123.12.

Preparation of N-((5-methylpyridin-3-yl)methyl)-4-(1-propionylindolin-5-yl)benzamide (Compound I-198)

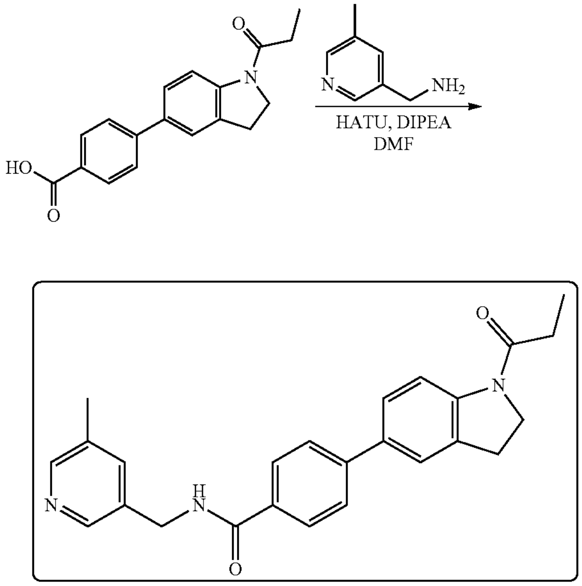

Following general Procedure D, starting from 4-(1-propionylindolin-5-yl)benzoic acid (100 mg, 0.34 mmol) and (5-methylpyridin-3-yl)methanamine (75 mg, 0.61 mmol), N-((5-methylpyridin-3-yl)methyl)-4-(1-propionylindolin-5-yl)benzamide was obtained as a white solid (60 mg, 29%). LC-MS (ESI): m/z $(M+H)^+$=400.38. $^1H$ NMR (400 MHz, DMSO-$d_6$) δ 9.09 (t, J=5.6 Hz, 1H), 8.36 (s, 1H), 8.30 (s, 1H), 8.16 (d, J=8.3 Hz, 1H), 7.95 (d, J=8.2 Hz, 2H), 7.75 (d, J=8.2 Hz, 2H), 7.63 (s, 1H), 7.57-7.52 (m, 2H), 4.48 (d, J=5.7 Hz, 2H), 4.13 (t, J=8.3 Hz, 2H), 3.21 (t, J=8.2 Hz, 2H), 2.49-2.44 (m, 2H), 2.29 (s, 3H), 1.08 (t, J=7.2 Hz, 3H).

Synthesis of N-((1H-imidazol-5-yl)methyl)-4-(1-propionylindolin-5-yl) benzamide (Compound I-199)

Preparation of (H-imidazol-5-yl)methanamine

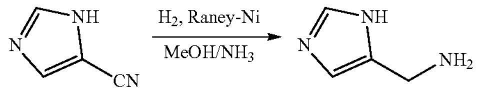 [SMILES: N#Cc1cnc[nH]1 ; NCc1cnc[nH]1]

Following Procedure H, (1H-imidazol-5-yl)methanamine was obtained as a yellow solid (100 mg, quantitative yield) from 1H-imidazole-5-carbonitrile (100 mg, 1.1 mmol). LC-MS (ESI): m/z $(M+1)^+$=98.22.

Preparation of N-((1H-imidazol-5-yl)methyl)-4-(1-propionylindolin-5-yl)benzamide (Compound I-199)

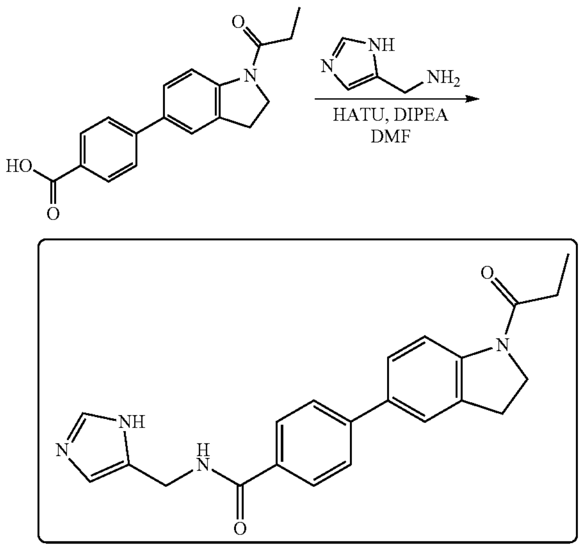

Following general Procedure D, starting from 4-(1-propionylindolin-5-yl)benzoic acid (150 mg, 0.51 mmol) and (1H-imidazol-5-yl)methanamine (60 mg, 0.61 mmol), N-((1H-imidazol-5-yl)methyl)-4-(1-propionylindolin-5-yl) benzamide was obtained as a white solid (7.8 mg, 4%). LC-MS (ESI): m/z $(M+H)^+$=375.14. $^1H$ NMR (400 MHz, DMSO-$d_6$) δ 11.86 (s, 1H), 8.79 (s, 1H), 8.15 (d, J=8.3 Hz, 1H), 7.94 (d, J=8.4 Hz, 2H), 7.73 (d, J=8.3 Hz, 2H), 7.62 (s, 1H), 7.58-7.51 (m, 2H), 6.95 (s, 1H), 4.45-4.34 (m, 2H), 4.13 (t, J=8.4 Hz, 2H), 3.21 (t, J=8.3 Hz, 2H), 2.49-2.43 (m, 2H), 1.08 (t, J=7.3 Hz, 3H).

Synthesis of N-(azetidin-3-ylmethyl)-4-(1-propionylindolin-5-yl)benzamide (Compound I-200)

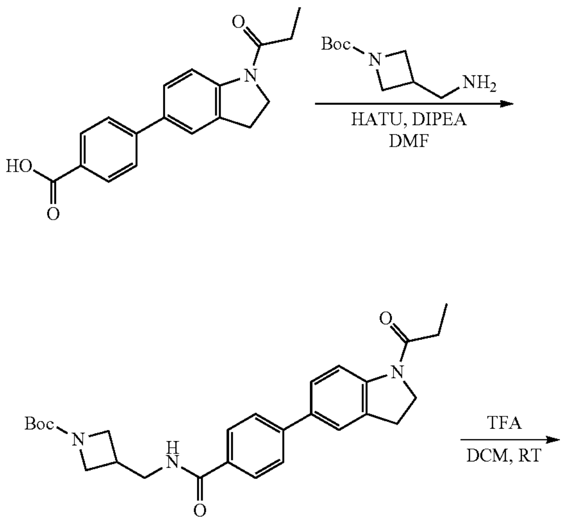

-continued

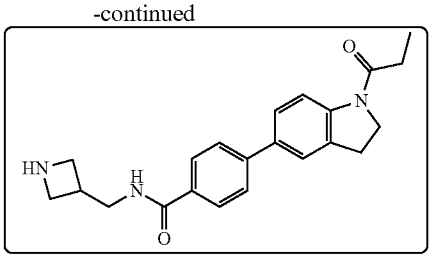

Preparation of tert-butyl 3-((4-(1-propionylindolin-5-yl)benzamido)methyl)azetidine-1-carboxylate Following general Procedure D, starting from 4-(1-propionylindolin-5-yl)benzoic acid (100 mg, 0.34 mmol) and tert-butyl 3-(aminomethyl)azetidine-1-carboxylate (82 mg, 0.44 mmol), tert-butyl 3-((4-(1-propionylindolin-5-yl)benzamido)methyl)azetidine-1-carboxylate was obtained as a white solid (120 mg, 75%).

Preparation of N-(azetidin-3-ylmethyl)-4-(1-propionylindolin-5-yl)benzamide (Compound I-200)

To a solution of tert-butyl 3-((4-(1-propionylindolin-5-yl) benzamido)methyl)azetidine-1-carboxylate (100 mg, 0.22 mmol) in DCM (5 mL), was added TFA (2 mL). The resulting mixture was stirred at RT for 4 h. LC-MS showed the reaction was complete. The mixture was concentrated in vacuo and purified by prep-HPLC (C18, 10~100% acetonitrile in water with 0.1% formic acid) to give N-(azetidin-3-ylmethyl)-4-(1-propionylindolin-5-yl)benzamide as a white solid (12.9 mg, 16%). LC-MS (ESI): m/z $(M+1)^+$=364.22. $^1H$ NMR (400 MHz, DMSO-$d_6$) δ 8.77-8.69 (m, 1H), 8.43 (s, 1H), 8.15 (d, J=8.4 Hz, 1H), 7.93 (d, J=8.3 Hz, 2H), 7.74 (d, J=8.3 Hz, 2H), 7.62 (s, 1H), 7.55 (d, J=8.4 Hz, 1H), 4.13 (t, J=8.5 Hz, 2H), 3.91-3.81 (m, 2H), 3.74-3.64 (m, 2H), 3.51-3.44 (m, 2H), 3.21 (t, J=8.3 Hz, 2H), 3.04-2.95 (m, 1H), 2.50-2.44 (m, 2H), 1.08 (t, J=7.3 Hz, 3H).

Synthesis of 4-(1-propionylindolin-5-yl)-N-(pyrimidin-4-ylmethyl)benzamide (Compound I-204)

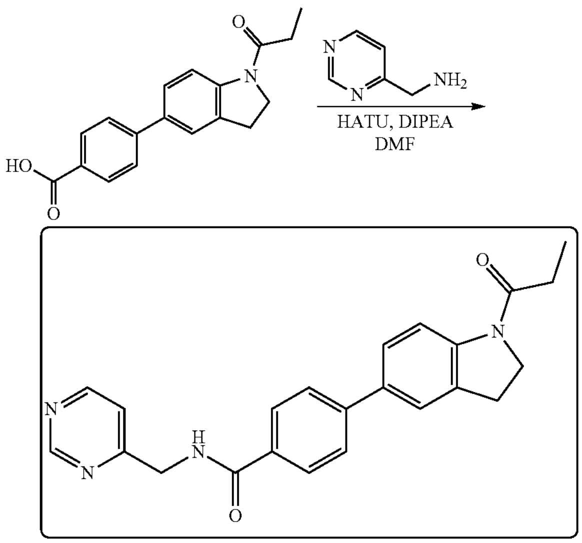

Following general Procedure D, starting from 4-(1-propionylindolin-5-yl)benzoic acid (150 mg, 0.51 mmol) and pyrimidin-4-ylmethanamine (61 mg, 0.56 mmol), 4-(1-propionylindolin-5-yl)-N-(pyrimidin-4-ylmethyl)benzamide was obtained as a white solid (33 mg, 16%). LC-MS (ESI): m/z $(M+H)^+$=387.23. $^1H$ NMR (400 MHz, DMSO-$d_6$) δ 9.22 (t, J=5.9 Hz, 1H), 9.12 (d, J=1.3 Hz, 1H), 8.74 (d, J=5.2 Hz, 1H), 8.16 (d, J=8.4 Hz, 1H), 7.99 (d, J=8.5 Hz, 2H), 7.78 (d, J=8.5 Hz, 2H), 7.64 (s, 1H), 7.57 (dd, J=8.4, 1.7 Hz, 1H), 7.44 (dd, J=5.2, 1.2 Hz, 1H), 4.57 (d, J=5.9 Hz, 2H), 4.13 (t, J=8.5 Hz, 2H), 3.22 (t, J=8.4 Hz, 2H), 2.49-2.47 (m, 2H), 1.08 (t, J=7.3 Hz, 3H).

Synthesis of 4-(1-propionyl-1H-indol-5-yl)-N-(pyridin-3-ylmethyl) benzamide (Compound I-90)

Preparation of 4-(1-propionyl-1H-indol-5-yl)benzoic acid

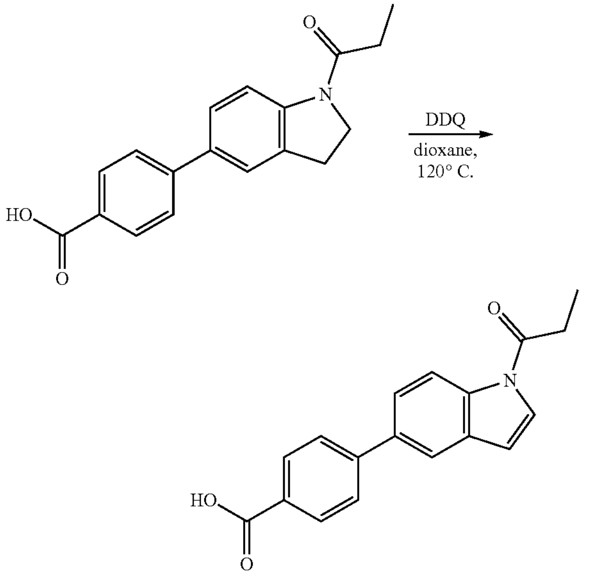

To a mixture of 4-(1-propionylindolin-5-yl)benzoic acid (200 mg, 0.68 mmol) in dioxane (10 mL), was added DDQ (310 mg, 1.36 mmol). The reaction mixture was stirred at 120° C. for 40 h. It was then diluted with DCM and washed with brine. The organic layer was dried over anhydrous $Na_2SO_4$, filtered, and concentrated under reduced pressure to give 4-(1-propionyl-1H-indol-5-yl)benzoic acid as a red solid (150 mg, 75%). LC-MS (ESI): m/z (M)+=294.13.

Preparation of 4-(1-propionyl-1H-indol-5-yl)-N-(pyridin-3-ylmethyl)benzamide (Compound I-90)

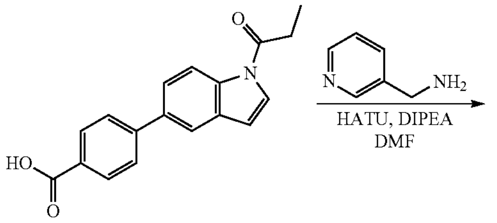

-continued

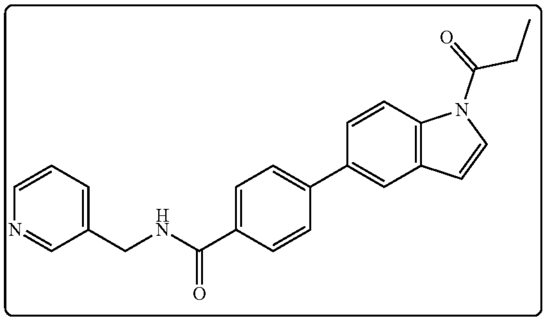

Following general Procedure D, starting from 4-(1-propionylindolin-5-yl)benzoic acid (100 mg, 0.34 mmol) and oxazol4-(1-propionyl-1H-indol-5-yl)benzoic acid, 4-(1-propionyl-1H-indol-5-yl)-N-(pyridin-3-ylmethyl) benzamide was obtained as a white solid (24 mg, 18%). LC-MS (ESI): m/z $(M+H)^+$=382.00. $^1H$ NMR (400 MHz, DMSO-$d_6$) δ 9.24 (t, J=5.8 Hz, 1H), 8.78 (d, J=1.3 Hz, 1H), 8.69 (d, J=4.3 Hz, 1H), 8.45 (d, J=8.7 Hz, 1H), 8.22 (d, J=8.0 Hz, 1H), 8.04-7.94 (m, 4H), 7.85 (d, J=8.5 Hz, 2H), 7.77 (dd, J=7.9, 5.4 Hz, 1H), 7.71 (dd, J=8.7, 1.8 Hz, 1H), 6.81 (d, J=3.6 Hz, 1H), 4.62 (d, J=5.7 Hz, 2H), 3.10 (q, J=7.2 Hz, 2H), 1.20 (t, J=7.2 Hz, 3H).

Synthesis of 3-(1-propionylindolin-5-yl)-N-(pyridin-3-ylmethyl) benzamide (Compound I-50)

Preparation of 3-bromo-N-(pyridin-3-ylmethyl)benzamide

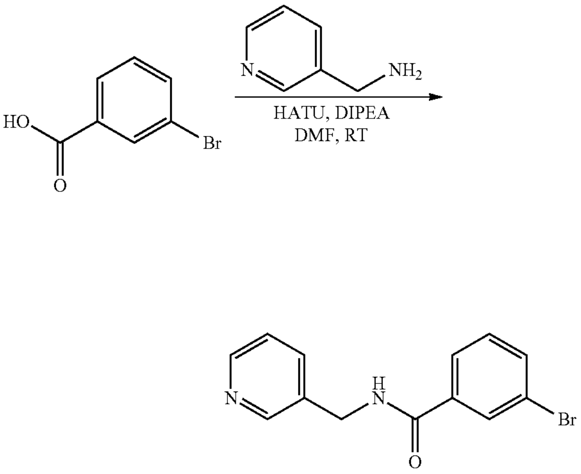

Following general Procedure D, starting from 3-bromobenzoic acid (300 mg, 1.49 mmol) and pyridin-3-ylmethanamine (146 mg, 1.36 mmol), 3-bromo-N-(pyridin-3-ylmethyl) benzamide was obtained as a colorless oil (600 mg, quantitative yield). LC-MS (ESI): m/z $(M)^+$=290.20, 292.33.

Preparation of 3-(1-propionylindolin-5-yl)-N-(pyridin-3-ylmethyl)benzamide (Compound I-50)

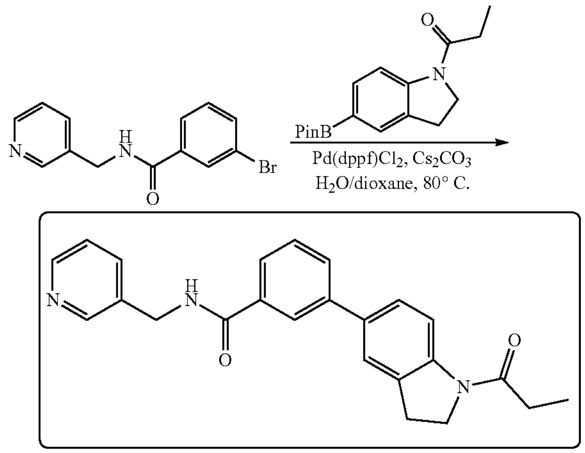

Procedure B was followed starting from 3-bromo-N-(pyridin-3-ylmethyl) benzamide (150 mg, 0.52 mmol) and 1-(5-(4,4,5,5-tetramethyl-1,3,2-dioxaborolan-2-yl) indolin-1-yl) propan-1-one (233 mg, 0.78 mmol). In this case, the reaction mixture was stirred at 80° C. in the microwave for 1 h. After purification by prep-HPLC (C18, 40-100% MeCN in $H_2O$ with 0.1% formic acid), 3-(1-propionylindolin-5-yl)-N-(pyridin-3-ylmethyl)benzamide was obtained as a white solid (17 mg, 8%). LC-MS (ESI): m/z $(M+1)^+$=386.22.

Synthesis of 4-(1-(2-methoxyethyl)indolin-5-yl)-N-(pyridin-3-ylmethyl) benzamide (Compound I-53)

Preparation of 2-methoxyacetaldehyde

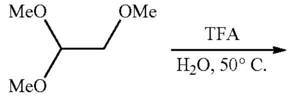

To a solution of 1,1,2-trimethoxyethane (132 mg, 0.46 mmol) in $H_2O$ (1 mL), was added TFA (1 mL). The reaction mixture was stirred at 50° C. for 5 min. The resulting colorless solution was used as such in the following step.

Preparation of 4-(1-(2-methoxyethyl)indolin-5-yl)-N-(pyridin-3-ylmethyl)benzamide (Compound I-53)

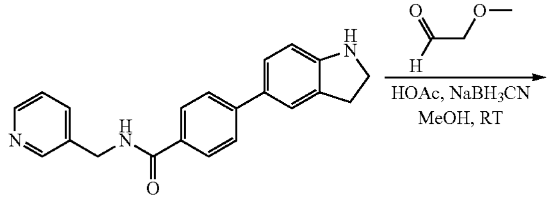

-continued

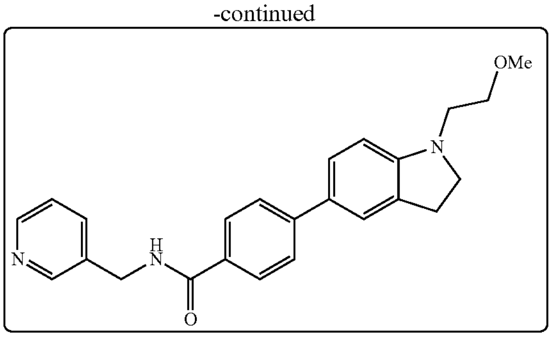

21

To a solution of 4-(indolin-5-yl)-N-(pyridin-3-ylmethyl) benzamide (190 mg, 0.58 mmol) in MeOH (5 mL), was added AcOH (34 mg, 0.58 mmol) followed by the solution of 2-methoxyacetaldehyde (0.46 mmol) obtained above. The reaction mixture was stirred at RT for 5 min and cooled to 0° C. before the addition of $NaBH_3CN$. The mixture was stirred at 0° C. for 1 h. After quenching with aq. $NaHCO_3$, the mixture was extracted with DCM and washed with brine. The organic layer was dried over anhydrous $Na_2SO_4$, filtered, and concentrated under reduced pressure. The residue was purified by prep-HPLC (C18, 40-100% MeCN in $H_2O$ with 0.1% formic acid) to give to 4-(1-(2-methoxyethyl) indolin-5-yl)-N-(pyridin-3-ylmethyl)benzamide as a white solid (20 mg, 8%). LC-MS (ESI): m/z $(M+H)^+$=388.25. $^1$H NMR (400 MHz, DMSO-$d_6$) δ 9.09-9.01 (m, 1H), 8.56 (d, J=1.7 Hz, 1H), 8.46 (dd, J=4.7, 1.5 Hz, 1H), 7.93-7.86 (m, 2H), 7.75-7.70 (m, 1H), 7.69-7.60 (m, 2H), 7.44-7.32 (m, 3H), 6.61-6.54 (m, 1H), 4.50 (d, J=5.9 Hz, 2H), 3.61-3.52 (m, 2H), 3.50-3.40 (m, 2H), 3.32-3.26 (m, 5H), 2.96 (t, J=8.4 Hz, 2H).

Synthesis of 6-(1-propionylindolin-5-yl)-N-(pyridin-3-ylmethyl) nicotinamide (Compound I-54)

Preparation of 6-chloro-N-(pyridin-3-ylmethyl) nicotinamide

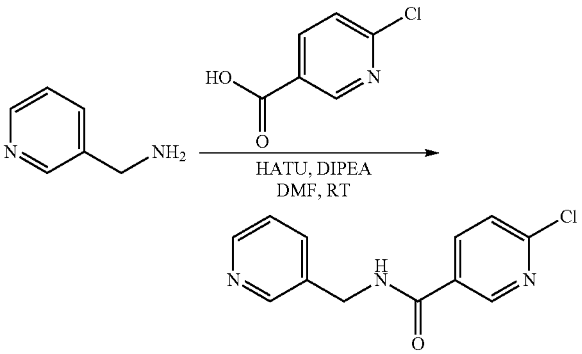

Following general Procedure D, starting from 6-chloronicotinic acid (300 mg, 1.9 mmol) and pyridin-3-ylmethanamine (226 mg, 2.1 mmol), 6-chloro-N-(pyridin-3-ylmethyl) nicotinamide was obtained as a white solid (320 mg, 68%). LC-MS (ESI): m/z $(M)^+$=247.20, 249.33

Preparation of 6-(1-propionylindolin-5-yl)-N-(pyridin-3-ylmethyl)nicotinamide (Compound I-54)

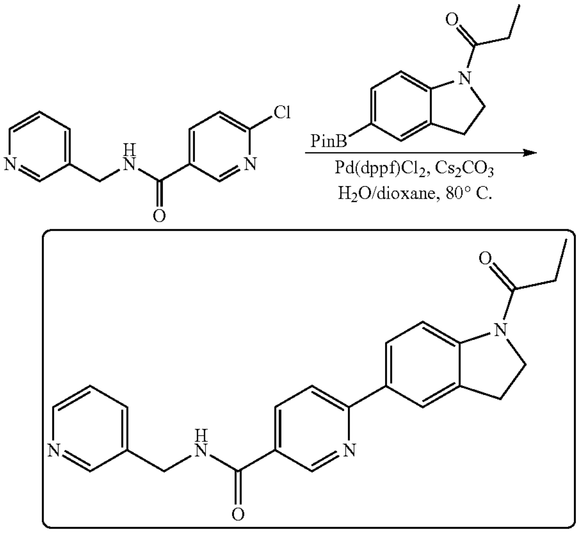

Procedure B was followed starting from 6-chloro-N-(pyridin-3-ylmethyl) nicotinamide (136 mg, 0.55 mmol) and 1-(5-(4,4,5,5-tetramethyl-1,3,2-dioxaborolan-2-yl) indolin-1-yl) propan-1-one (200 mg, 0.66 mmol). In this case, the reaction mixture was stirred 80° C. in the microwave for 1 h. After purification by prep-HPLC (C18, 40-100% MeCN in $H_2O$ with 0.1% formic acid), 6-(1-propionylindolin-5-yl)-N-(pyridin-3-ylmethyl)nicotinamide was obtained as a white solid (20 mg, 9%). LC-MS (ESI): m/z (M+1)+ =387.20. $^1$H NMR (400 MHz, DMSO-$d_6$) δ 9.29 (t, J=5.8 Hz, 1H), 9.08 (d, J=1.9 Hz, 1H), 8.58 (d, J=1.5 Hz, 1H), 8.48 (d, J=3.5 Hz, 1H), 8.27 (dd, J=8.4, 2.2 Hz, 1H), 8.17 (d, J=8.4 Hz, 1H), 8.10-7.97 (m, 3H), 7.76 (d, J=7.8 Hz, 1H), 7.38 (dd, J=7.7, 4.8 Hz, 1H), 4.54 (d, J=5.7 Hz, 2H), 4.14 (t, J=8.5 Hz, 2H), 3.22 (t, J=8.4 Hz, 2H), 2.47 (t, 2H), 1.08 (t, J=7.3 Hz, 3H).

Synthesis of 5-(1-propionylindolin-5-yl)-N-(pyridin-3-ylmethyl) picolinamide (Compound I-55)

Preparation of 5-bromo-N-(pyridin-3-ylmethyl) picolinamide

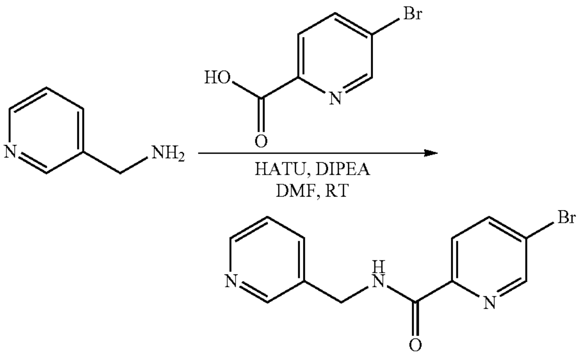

Following general Procedure D, starting from 5-bromopicolinic acid (300 mg, 1.49 mmol) and pyridin-3-ylmethanamine (147 mg, 1.36 mmol), 5-bromo-N-(pyridin-3-ylmethyl) picolinamide was obtained as a solid (220 mg, 55%). LC-MS (ESI): m/z (M)$^+$=291.99, 293.98.

Preparation of 5-(1-propionylindolin-5-yl)-N-(pyridin-3-ylmethyl)picolinamide (Compound I-55)

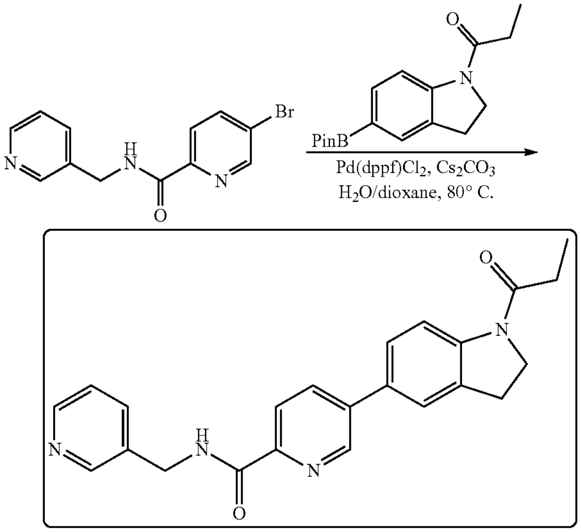

Procedure B was followed starting from 5-bromo-N-(pyridin-3-ylmethyl) picolinamide (160 mg, 0.55 mmol) and 1-(5-(4,4,5,5-tetramethyl-1,3,2-dioxaborolan-2-yl) indolin-1-yl) propan-1-one (200 mg, 0.66 mmol). In this case, the reaction mixture was stirred at 80° C. in the microwave for 1 h. After purification by prep-HPLC (C18, 40-100% MeCN in $H_2O$ with 0.1% formic acid), 5-(1-propionylindolin-5-yl)-N-(pyridin-3-ylmethyl)picolinamide was obtained as a white solid (35 mg, 16%). LC-MS (ESI): m/z (M+1)$^+$=387.12. $^1$H NMR (400 MHz, CDCl3) δ 8.73 (d, J=1.3 Hz, 1H), 8.65 (s, 1H), 8.55 (d, J=3.9 Hz, 1H), 8.43 (t, J=5.6 Hz, 1H), 8.35 (d, J=8.3 Hz, 1H), 8.25 (d, J=8.1 Hz, 1H), 8.01 (dd, J=8.1, 1.9 Hz, 1H), 7.74 (d, J=7.8 Hz, 1H), 7.49-7.41 (m, 2H), 7.33-7.27 (m, 1H), 4.71 (d, J=6.2 Hz, 2H), 4.12 (t, J=8.4 Hz, 2H), 3.29 (t, J=8.3 Hz, 2H), 2.49 (dd, J=14.3, 7.0 Hz, 2H), 1.26 (t, J=7.1 Hz, 3H).

Synthesis of 4-(1-propionyl-1H-indazol-5-yl)-N-(pyridin-3-ylmethyl)benzamide (Compound I-56)

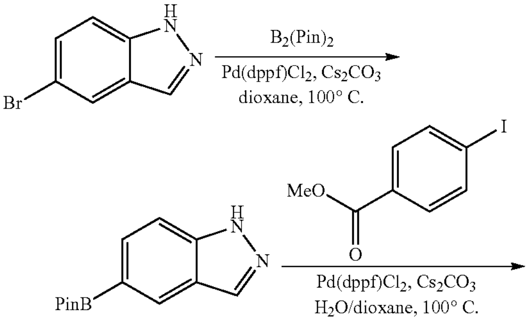

-continued

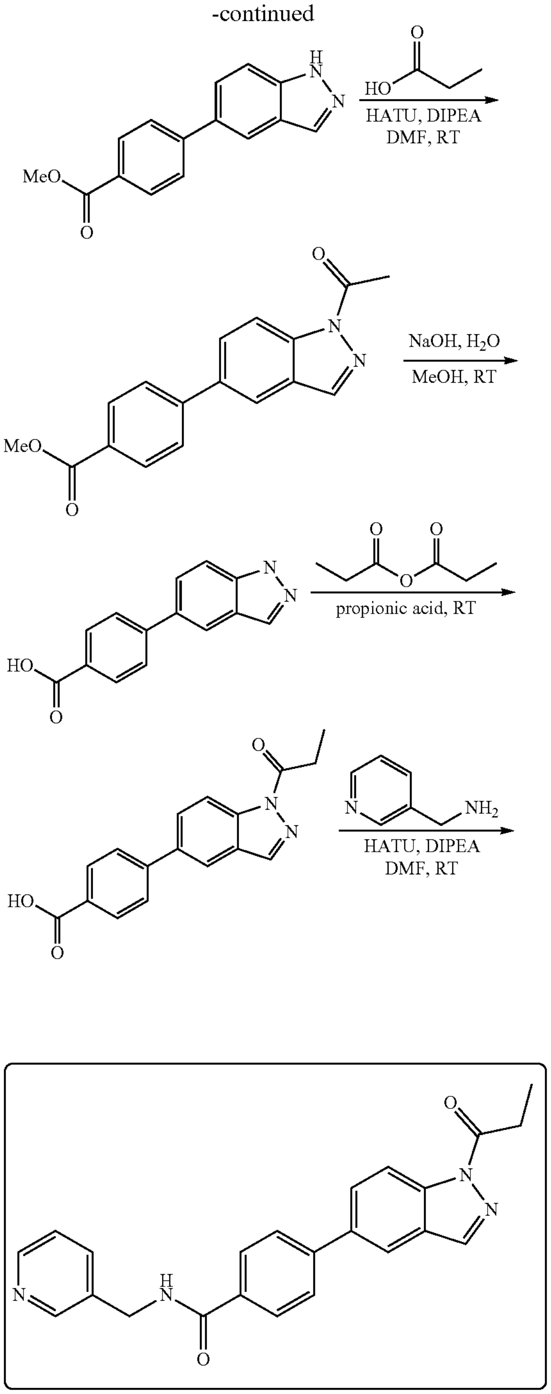

To a solution of 5-bromo-1H-indazole (3.0 g, 15.2 mmol), Bis(pinacolato)diboron (7.7 g, 30.4 mmol) and $Cs_2CO_3$ (9.9 g, 30.4 mmol) in dioxane (30 mL), was added $Pd(dppf)Cl_2$ (1.24 g, 1.52 mmol) in one portion. The mixture was stirred at 100° C. for 10 h, then washed with brine and extracted with EA. The combined organic layer was dried over $Na_2SO_4$, filtered and concentrated to give 5-(4,4,5,5-tetramethyl-1,3,2-dioxaborolan-2-yl)-1H-indazole as a white solid (quantitative yield). The crude was used as such in the next step. LC-MS (ESI): m/z (M+H)=245.37.

Procedure J: To a solution of 5-(4,4,5,5-tetramethyl-1,3,2-dioxaborolan-2-yl)-1H-indazole (3.7 g, 15.2 mmol), methyl 4-iodobenzoate (4.4 g, 16.7 mmol), $Cs_2CO_3$ (850 mg, 8.0 mmol) in dioxane/$H_2O$ (40/8 mL), was added $Pd(dppf)Cl_2$ (1.24 g, 1.52 mmol) in one portion. The mixture was stirred at 100° C. for 10 h. It was extracted with EA, the combined organic layer was washed with brine, dried over $Na_2SO_4$, concentrated, and purified by flash chromatography to give methyl 4-(1H-indazol-5-yl)benzoate as a white solid (2.8 g, 73%). LC-MS (ESI): m/z (M+H)=253.46.

Following general Procedure D, starting from methyl 4-(1H-indazol-5-yl)benzoate (2.8 g, 11.0 mmol) and propionic acid (1.3 g, 16.5 mmol), methyl 4-(1-propionyl-1H-indazol-5-yl)benzoate was obtained as a white solid (1.2 g, 35%). LC-MS (ESI): m/z (M+H)=309.33.

To a solution of methyl 4-(1-propionyl-1H-indazol-5-yl) benzoate (700 mg, 2.27 mmol) in MeOH (10 mL), was added NaOH 4N (2.8 mL, 11.4 mmol). The mixture was stirred at 50° C. for 12 h and was then acidified with HCl 4N. The crude was extracted with EA, the combined organic layer was washed with brine, dried over $Na_2SO_4$, filtered, concentrated, and the residue purified by flash chromatography to give 4-(1H-indazol-5-yl)benzoic acid as a white solid (470 mg, 86%). LC-MS (ESI): m/z (M+H)=239.33.

To a solution of 4-(1H-indazol-5-yl)benzoic acid (450 mg, 1.9 mmol) in propionic acid (10 mL), was added propionic anhydride (495 mg, 3.8 mmol) in one portion. The mixture was stirred at RT for 12 h. It was then concentrated and purified by flash chromatography to give 4-(1-propionyl-1H-indazol-5-yl)benzoic acid as a white solid (370 mg, 67%). LC-MS (ESI): m/z (M+H)=295.57.

Following general Procedure D, starting from 4-(1-propionyl-1H-indazol-5-yl)benzoic acid (100 mg, 0.34 mmol) and pyridin-3-ylmethanamine (74 mg, 0.68 mmol), 4-(1-propionyl-1H-indazol-5-yl)-N-(pyridin-3-ylmethyl)benzamide was obtained as a white solid (30 mg, 23%). LC-MS (ESI): m/z (M+H)=385.33. $^1H$ NMR (400 MHz, DMSO-$d_6$) δ 9.18 (t, J=5.9 Hz, 1H), 8.58 (d, J=1.8 Hz, 1H), 8.53 (d, J=0.6 Hz, 1H), 8.47 (dd, J=4.7, 1.5 Hz, 1H), 8.42 (d, J=8.7 Hz, 1H), 8.26 (d, J=1.0 Hz, 1H), 8.05-7.99 (m, 3H), 7.87 (d, J=8.5 Hz, 2H), 7.78-7.73 (m, 1H), 7.39-7.35 (m, 1H), 4.53 (d, J=5.8 Hz, 2H), 3.22 (q, J=7.4 Hz, 2H), 1.23 (t, J=7.4 Hz, 3H).

Synthesis of 5-(1-propionylindolin-5-yl)-N-(pyridin-3-ylmethyl)pyrimidine-2-carboxamide (Compound I-65)

Preparation of methyl 5-(1-propionylindolin-5-yl) pyrimidine-2-carboxylate

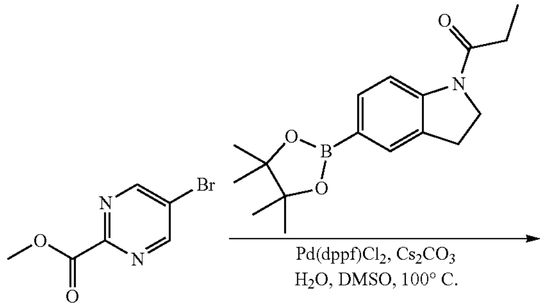

-continued

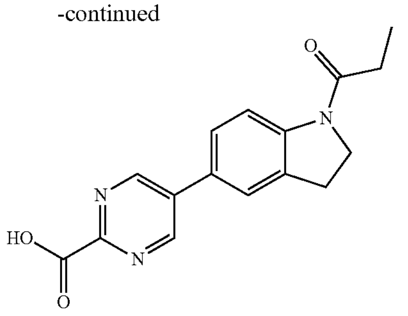

To a mixture of 4 methyl 5-bromopyrimidine-2-carboxylate (100 mg, 0.46 mmol) in DMSO/$H_2O$, were added 1-(5-(4,4,5,5-tetramethyl-1,3,2-dioxaborolan-2-yl) indolin-1-yl)propan-1-one (138 mg, 0.46 mmol), Pd(dppf)$Cl_2$ (41 mg, 0.05 mmol), and $Cs_2CO_3$ (450 mg, 1.38 mmol). The reaction mixture was stirred at 100° C. in the microwave for 40 min. It was then diluted with DCM and washed with water and brine. The organic layer was dried over anhydrous $Na_2SO_4$, filtered, and concentrated under reduced pressure. The residue was purified by flash column chromatography over silica gel (DCM/MeOH 4:1, v/v) to give 5-(1-propionylindolin-5-yl)pyrimidine-2-carboxylic acid as a yellow solid (190 mg, quantitative yield). LC-MS (ESI): m/z $(M)^+$=298.35.

Preparation of 5-(1-propionylindolin-5-yl)-N-(pyridin-3-ylmethyl) pyrimidine-2-carboxamide (Compound I-65)

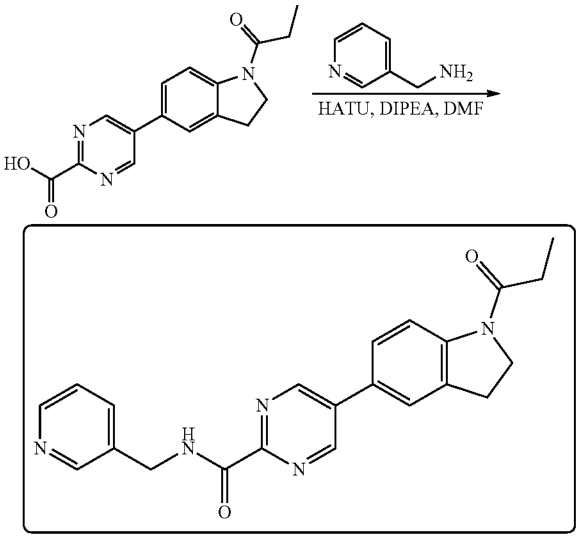

Following general Procedure D, starting from 4-(1-propionylindolin-5-yl)benzoic acid (100 mg, 0.34 mmol) and pyridin-3-ylmethanamine (43 mg, 0.40 mmol), 5-(1-propionylindolin-5-yl)-N-(pyridin-3-ylmethyl)pyrimidine-2-carboxamide was obtained as a white solid (37 mg, 28%). LC-MS (ESI): m/z $(M+H)^+$=388.59. $^1$H NMR (400 MHz, DMSO-d) δ 9.58 (t, J=6.2 Hz, 1H), 9.25 (s, 2H), 8.58 (s, 1H), 8.47 (d, J=3.8 Hz, 1H), 8.22 (d, J=8.4 Hz, 1H), 7.81 (s, 1H), 7.79-7.70 (m, 2H), 7.40-7.33 (m, 1H), 4.53 (d, J=6.2 Hz, 2H), 4.15 (t, J=8.3 Hz, 2H), 3.23 (t, 2H), 2.56-2.51 (m, 2H), 1.08 (t, J=7.2 Hz, 3H).

Synthesis of 2-(1-propionylindolin-5-yl)-N-(pyridin-3-ylmethyl)pyrimidine-5-carboxamide (Compound I-66)

Preparation of methyl 2-(1-propionylindolin-5-yl) pyrimidine-5-carboxylate

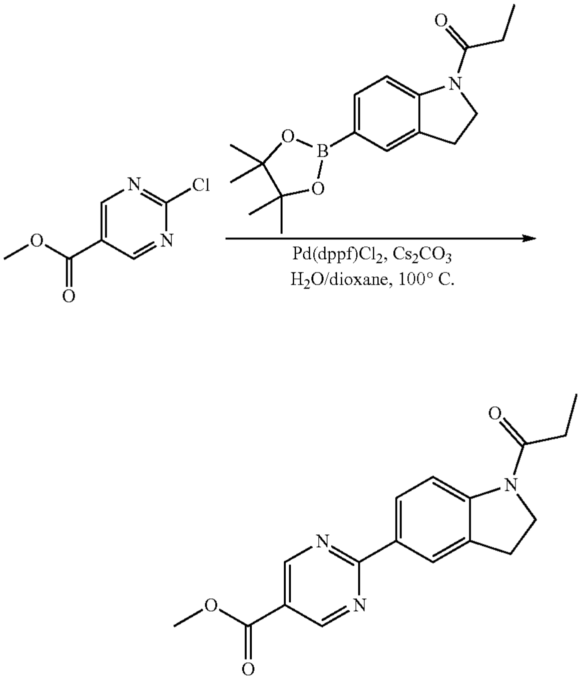

Procedure J was followed starting from methyl 2-chloropyrimidine-5-carboxylate (300 mg, 1.32 mmol) and 1-(5-(4,4,5,5-tetramethyl-1,3,2-dioxaborolan-2-yl) indolin-1-yl) propan-1-one (398 mg, 1.32 mmol). In this case, the reaction mixture was stirred at 100° C. in the microwave for 1 h. After purification by flash column chromatography over silica gel (DCM/MeOH 4:1, v/v), methyl 2-(1-propionylindolin-5-yl)pyrimidine-5-carboxylate was obtained as a yellow solid (50 mg, 12%). LC-MS (ESI): m/z $(M)^+$=312.13.

Preparation of 2-(1-propionylindolin-5-yl)pyrimidine-5-carboxylic acid

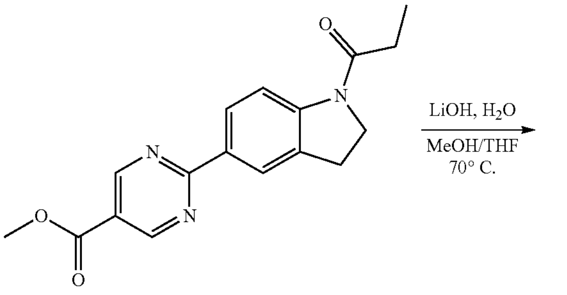

-continued

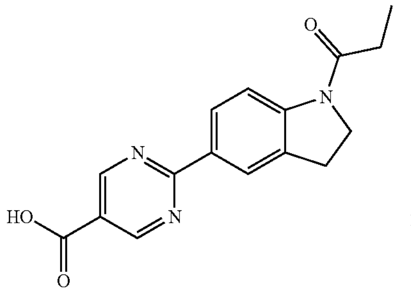

Following Procedure C, 2-(1-propionylindolin-5-yl)pyrimidine-5-carboxylic acid was obtained as a yellow solid (40 mg, 84%) from methyl 2-(1-propionylindolin-5-yl)pyrimidine-5-carboxylate (50 mg, 0.16 mmol). LC-MS (ESI): m/z $(M+1)^+$=298.14.

Preparation of 2-(1-propionylindolin-5-yl)-N-(pyridin-3-ylmethyl) pyrimidine-5-carboxamide (Compound I-66)

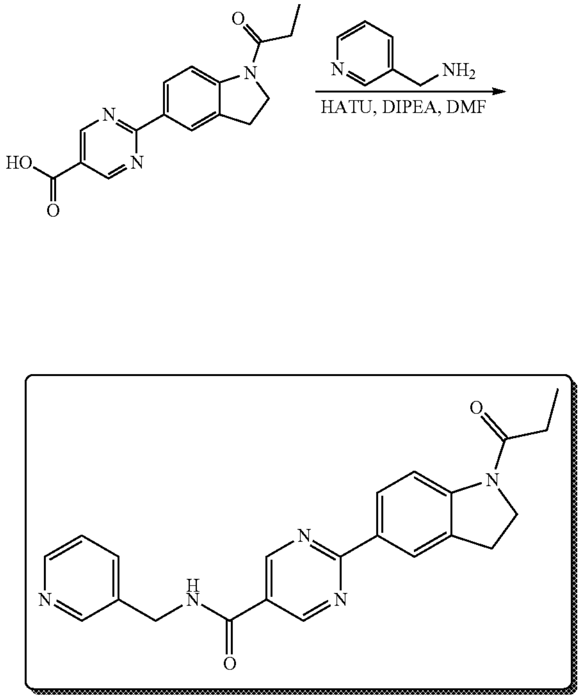

Following general Procedure D, starting from 2-(1-propionylindolin-5-yl)pyrimidine-5-carboxylic acid and pyridin-3-ylmethanamine (16.2 mg, 0.15 mmol), 2-(1-propionylindolin-5-yl)-N-(pyridin-3-ylmethyl) pyrimidine-5-carboxamide was obtained as a white solid (11 mg, 22%). LC-MS (ESI): m/z $(M+H)^+$=388.77. $^1$H NMR (400 MHz, DMSO-d) δ 9.39 (t, J=5.8 Hz, 1H), 9.23 (s, 2H), 8.60 (d, J=1.5 Hz, 1H), 8.48 (d, J=3.6 Hz, 1H), 8.33-8.27 (m, 2H), 8.24-8.14 (m, 1H), 7.78 (d, J=7.9 Hz, 1H), 7.40-7.36 (m, 1H), 4.56 (d, J=5.7 Hz, 2H), 4.16 (t, J=8.5 Hz, 2H), 3.23 (t, J=8.4 Hz, 2H), 2.56-2.51 (m, 2H), 1.08 (t, J=7.3 Hz, 3H).

Synthesis of 4-(1-(2-hydroxy-2-methylpropanoyl) indolin-5-yl)-N-(pyridin-3-ylmethyl)benzamide (Compound I-68)

Preparation of 1-(5-bromoindolin-1-yl)propane-1,2-dione

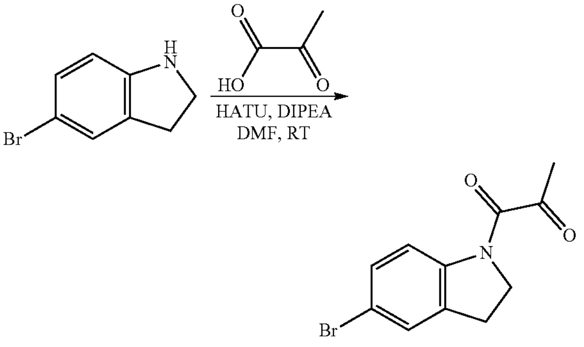

Following general Procedure D, starting from 5-bromoindoline (1.5 g, 7.6 mmol) and 2-oxopropanoic acid (800 mg, 9.0 mmol), 1-(5-bromoindolin-1-yl)propane-1,2-dione was obtained as a white solid (250 mg, 20%). LC-MS (ESI): m/z $(M-56)^+$=268.00.

Preparation of I-(5-bromoindolin-1-yl)propane-1,2-dione

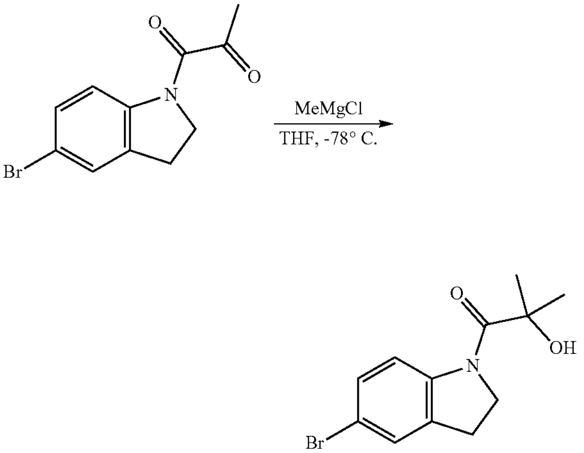

To a mixture of 1-(5-bromoindolin-1-yl)propane-1,2-dione (1.2 g, 4.5 mmol) in THF (10 mL) at −78° C., was added MeMgCl in THF (3M, 2.3 mL, 6.98 mmol). The reaction mixture was stirred at −78° C. for 5 h. After quenching with aq. $NH_4C_1$, the reaction mixture was extracted with EA and washed with brine. The organic layer was dried over anhydrous $Na_2SO_4$, filtered, and concentrated under reduced pressure. The residue was purified by flash column chromatography over silica gel (PE/EA 4:1, v/v) to give 1-(5-bromoindolin-1-yl)propane-1,2-dione as a white solid (1.0 g, 77%). LC-MS (ESI): m/z $(M-56)^+$=284.12.

Preparation of methyl 4-(1-(2-hydroxy-2-methylpropanoyl)indolin-5-yl) benzoate

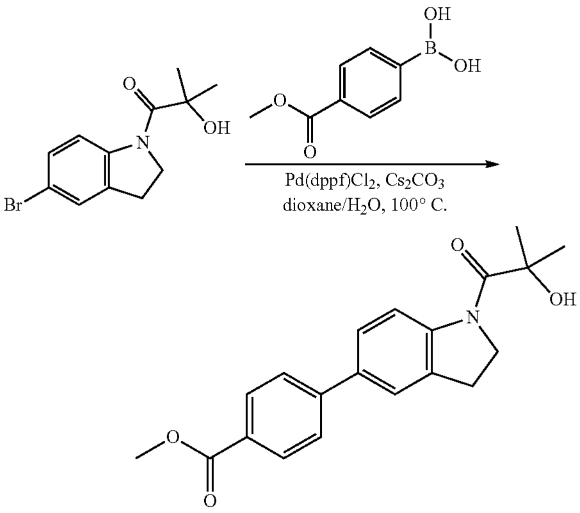

Procedure J was followed starting from 1-(5-bromoindolin-1-yl)propane-1,2-dione (300 mg, 1.06 mmol) and (4-(methoxycarbonyl)phenyl)boronic acid (286 mg, 1.59 mmol). After flash column chromatography over silica gel (PE/EA 4:1, v/v), methyl 4-(1-(2-hydroxy-2-methylpropanoyl)indolin-5-yl)benzoate was obtained as a yellow solid (200 mg, 55%). LC-MS (ESI): m/z $(M+1)^+$=340.25.

Preparation of 4-(1-(2-hydroxy-2-methylpropanoyl) indolin-5-yl) benzoic acid

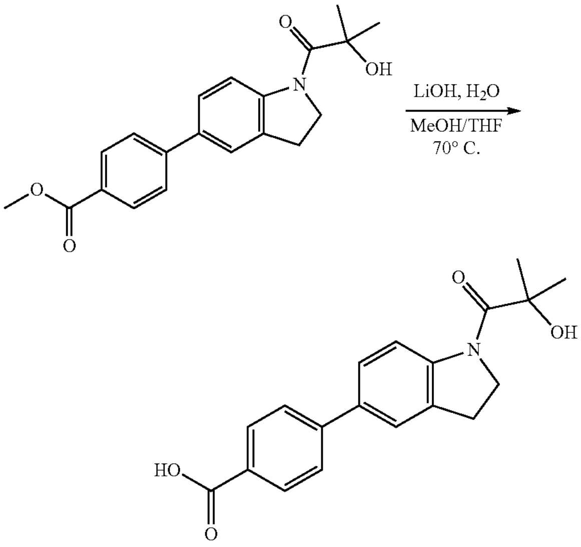

Following Procedure C, 4-(1-(2-hydroxy-2-methylpropanoyl)indolin-5-yl) benzoic acid was obtained as a white solid (200 mg, quantitative yield) from methyl 4-(1-(2-hydroxy-2-methylpropanoyl)indolin-5-yl) benzoate (200 mg, 0.59 mmol) LC-MS (ESI): m/z $(M+1)^+$=326.41.

Preparation of 4-(1-(2-hydroxy-2-methylpropanoyl) indolin-5-yl)-N-(pyridin-3-ylmethyl)benzamide (Compound I-68)

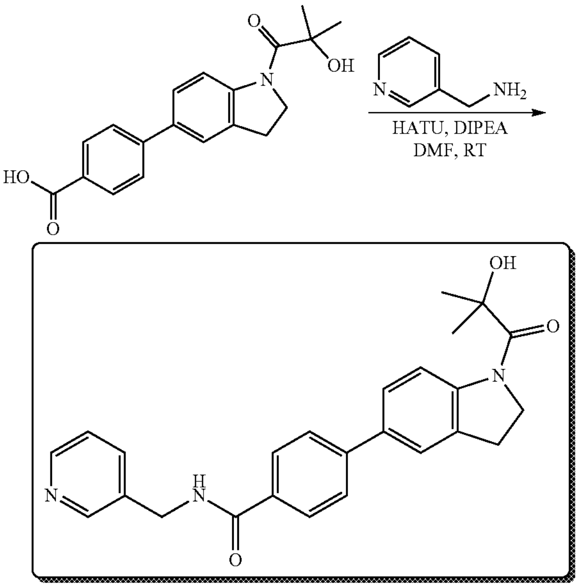

Following general Procedure D, starting from 4-(1-(2-hydroxy-2-methylpropanoyl)indolin-5-yl) benzoic acid (200 mg, 0.62 mmol) and pyridin-3-ylmethanamine (80 mg, 0.74 mmol), 4-(1-(2-hydroxy-2-methylpropanoyl)indolin-5-yl)-N-(pyridin-3-ylmethyl)benzamide was obtained as a white solid (15 mg, 6%). LC-MS (ESI): m/z $(M+H)^+$=416.30. $^1$H NMR (400 MHz, DMSO-$d_6$) δ 9.13 (t, J=5.9 Hz, 1H), 8.57 (d, J=1.7 Hz, 1H), 8.46 (dd, J=4.8, 1.6 Hz, 1H), 8.18 (d, J=8.5 Hz, 1H), 7.96 (d, J=8.5 Hz, 2H), 7.78-7.72 (m, 3H), 7.65 (s, 1H), 7.56 (dd, J=8.5, 1.9 Hz, 1H), 7.39-7.34 (m, 1H), 5.50 (s, 1H), 4.53-4.44 (m, 4H), 3.16 (t, J=8.3 Hz, 2H), 1.42 (s, 6H).

Synthesis of 4-(1-propionyl-2,3-dihydro-1H-pyrrolo [3,2-b]pyridin-5-yl)-N-(pyridin-3-ylmethyl)benzamide (Compound I-71)

Preparation of tert-butyl 1H-pyrrolo[3,2-b]pyridine-1-carboxylate

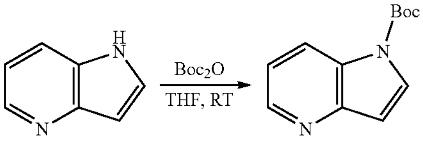 [SMILES: "Boc2O" ; c1cnc2cc[nH]c2c1 ; CC(C)(C)OC(=O)n1ccc2ncccc21]

To a mixture of 1H-pyrrolo[3,2-b]pyridine (1.0 g, 9.0 mmol) in THF (30 mL), was added a solution of di-tert-butyl dicarbonate (2.1 g, 9.4 mmol) in DCM (20 mL). The reaction mixture was stirred at RT for 10 h. It was then concentrated in vacuo to give tert-butyl 5-bromoindoline-1-carboxylate as a yellow oil (1.9 g, quantitative yield). LC-MS (ESI): m/z $(M+1)^+$=209.23.

Preparation of tert-butyl 2,3-dihydro-1H-pyrrolo[3,2-b]pyridine-1-carboxylate

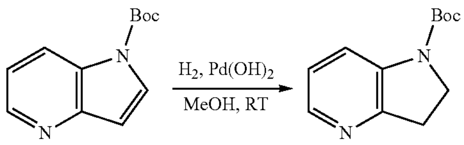 [SMILES: CC(C)(C)OC(=O)n1ccc2ncccc21 ; CC(C)(C)OC(=O)N1CCc2ncccc21]

To a mixture of tert-butyl 5-bromoindoline-1-carboxylate (crude 5.0 g, 22.9 mmol) in EtOH (20 mL), was added $Pd(OH)_2$ (200 mg). The reaction mixture was stirred at RT for 12 h under $H_2$. It was then filtered and the filtrate concentrated in vacuo to give tert-butyl 2,3-dihydro-1H-pyrrolo[3,2-b]pyridine-1-carboxylate as a black oil (crude 5.0 g, quantitative yield). LC-MS (ESI): m/z $(M+1)^+$=221.19.

Preparation of 2,3-dihydro-1H-pyrrolo[3,2-b]pyridine

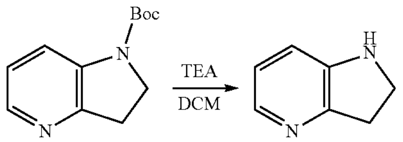 [SMILES: CC(C)(C)OC(=O)N1CCc2ncccc21 ; c1cnc2c(c1)NCC2]

To a mixture of 2,3-dihydro-1H-pyrrolo[3,2-b]pyridine-1-carboxylate (crude 5.0 g, 22.9 mmol) in DCM (15 mL), was added TFA (5 mL). The reaction mixture was stirred at RT for 2 h and concentrated in vacuo. Aq. $NaHCO_3$ and MeOH were added and the reaction mixture was stirred at RT for 30 min and filtered. The filtrate was concentrated under reduced pressure to give 2,3-dihydro-1H-pyrrolo[3,2-b]pyridine as a red oil (crude 5.0 g, quantitative yield). LC-MS (ESI): m/z $(M-56)^+$=121.12.

Preparation of 5-bromo-2,3-dihydro-1H-pyrrolo[3,2-b]pyridine

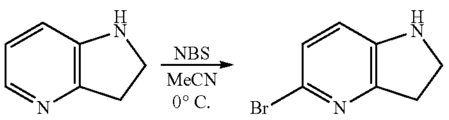

Procedure K: To a mixture of 4 2,3-dihydro-1H-pyrrolo[3,2-b]pyridine (crude 5.0 g, 22.9 mmol) in THF (20 mL) at 0° C., was added NBS (25.2 mg, 1.1 mmol) within 20 min. The reaction mixture was stirred at RT for 10 h. It was then diluted with IPA and washed with water and brine. The organic layer was dried over anhydrous $Na_2SO_4$, filtered, and concentrated under reduced pressure. The residue was purified by silica gel column chromatography (PE/EA 4:1, v/v) to give 5-bromo-2,3-dihydro-1H-pyrrolo[3,2-b]pyridine as a red solid (1.5 g, 33%). LC-MS (ESI): m/z $(M)^+$=199.07, 201.06.

Preparation of I-(5-bromo-2,3-dihydro-1H-pyrrolo[3,2-b]pyridin-1-yl) propan-1-one

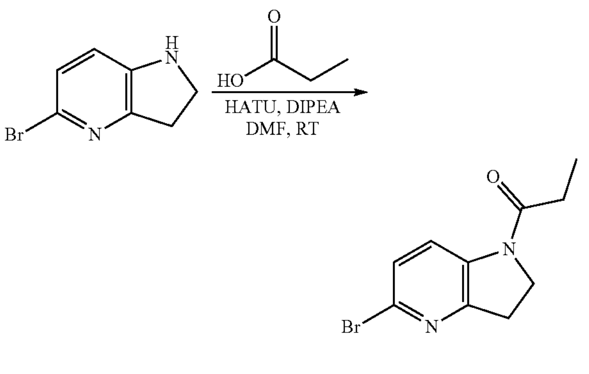

Following general Procedure D, starting from 5-bromo-2,3-dihydro-1H-pyrrolo[3,2-b]pyridine (500 mg, 2.5 mmol) and propionic acid (222 mg, 3.0 mmol), 1-(5-bromo-2,3-dihydro-1H-pyrrolo[3,2-b]pyridin-1-yl) propan-1-one was obtained as a reddish solid (400 mg, 63%). LC-MS (ESI): m/z $(M)^+$=255.04, 257.04.

Preparation of methyl 4-(1-propionyl-2,3-dihydro-1H-pyrrolo[3,2-b]pyridin-5-yl)benzoate

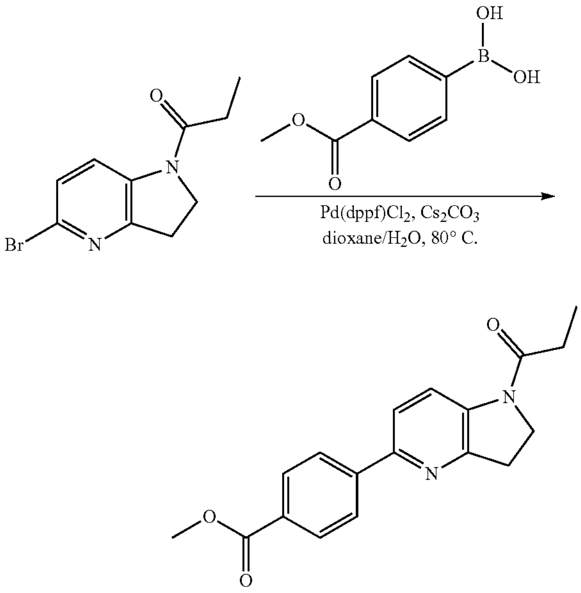

Procedure B was followed starting from 1-(5-bromo-2,3-dihydro-1H-pyrrolo[3,2-b]pyridin-1-yl) propan-1-one (150 mg, 0.59 mmol) and (4-(methoxycarbonyl)phenyl)boronic acid (128 mg, 0.71 mmol). In this case, the reaction mixture was stirred at 80° C. in the microwave for 1 h. was After purification by flash column chromatography over silica gel (DCM/MeOH 4:1, v/v), 4-(1-propionyl-2,3-dihydro-1H-pyrrolo[3,2-b] pyridin-5-yl)benzoate was obtained as a white solid (90 mg, 50%). LC-MS (ESI): m/z $(M+1)^+$=311.23.

Preparation of 4-(1-propionyl-2,3-dihydro-1H-pyrrolo[3,2-b]pyridin-5-yl) benzoic acid

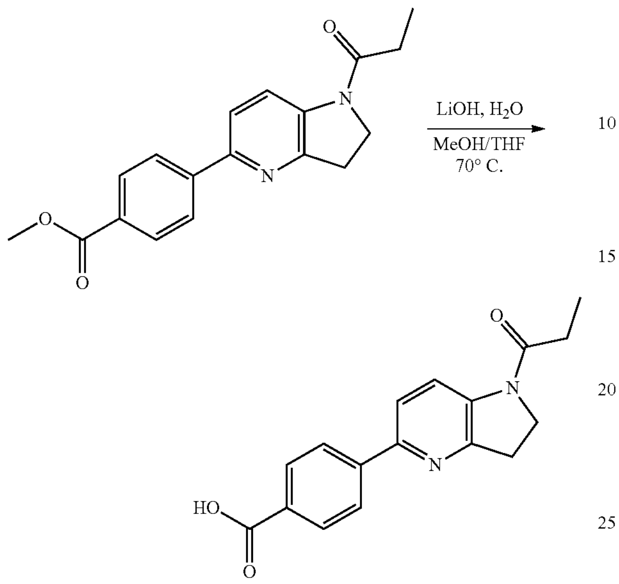

Following Procedure C, 4-(1-propionyl-2,3-dihydro-1H-pyrrolo[3,2-b]pyridin-5-yl)benzoic acid was obtained as a white solid (50 mg, 58%) from 4-(1-propionyl-2,3-dihydro-1H-pyrrolo[3,2-b] pyridin-5-yl) benzoate (90 mg, 0.29 mmol). LC-MS (ESI): m/z $(M+1)^+$=297.14.

Preparation of 4-(1-propionyl-2,3-dihydro-1H-pyrrolo[3,2-b]pyridin-5-yl)-N-(pyridin-3-ylmethyl)benzamide (Compound I-71)

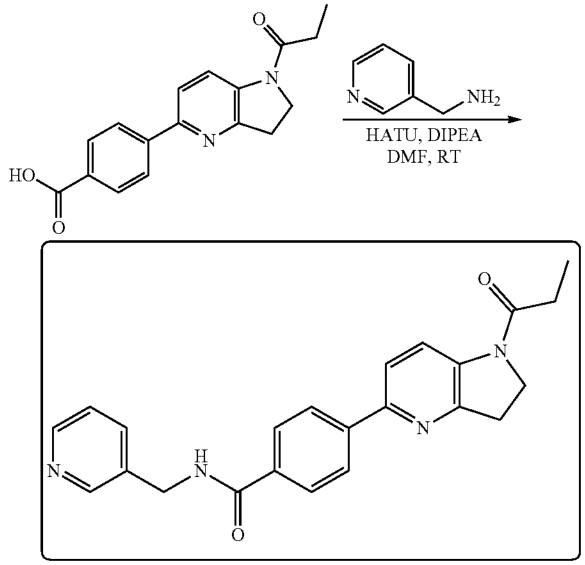

Following Procedure D, starting from 4-(1-propionyl-2,3-dihydro-1H-pyrrolo [3,2-b]pyridin-5-yl) benzoic acid (50 mg, 0.169 mmol) and pyridin-3-ylmethanamine (22 mg, 0.203 mmol), 4-(1-propionyl-2,3-dihydro-1H-pyrrolo[3,2-b]pyridin-5-yl)-N-(pyridin-3-ylmethyl) benzamide was isolated as a white solid (20 mg, 30%). LC-MS (ESI): m/z $(M+H)^+$=387.33. $^1$H NMR (400 MHz, DMSO-$d_6$)) δ 9.19 (t, J=5.8 Hz, 1H), 8.65 (s, 1H), 8.56 (d, J=4.5 Hz, 1H), 8.32 (d, J=8.5 Hz, 1H), 8.13 (d, J=8.4 Hz, 2H), 7.97 (d, J=8.5 Hz, 2H), 7.93 (d, J=7.9 Hz, 1H), 7.86 (d, J=8.5 Hz, 1H), 7.53 (dd, J=7.7, 5.1 Hz, 1H), 4.55 (d, J=5.8 Hz, 2H), 4.18 (t, J=8.6 Hz, 2H), 3.31 (t, 2H), 2.56-2.51 (m, 2H), 1.08 (t, J=7.3 Hz, 3H).

Synthesis of 4-(1-methylindolin-5-yl)-N-(pyridin-3-ylmethyl)benzamide (Compound I-75)

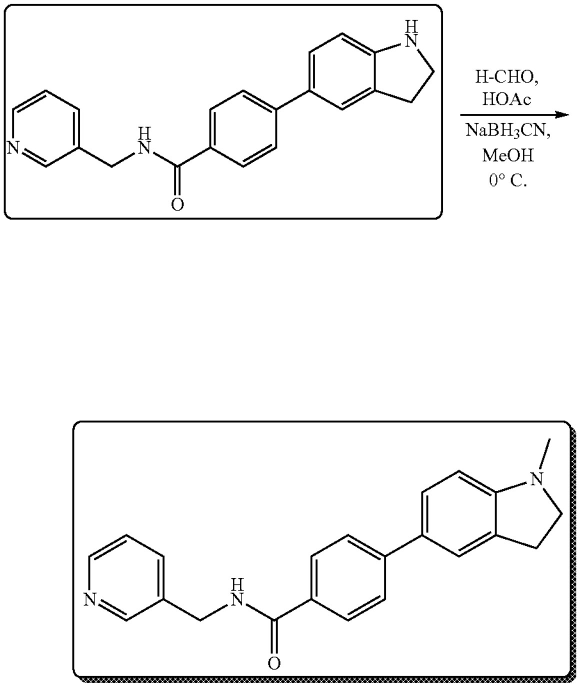

To a solution of 4-(indolin-5-yl)-N-(pyridin-3-ylmethyl) benzamide (200 mg, 0.5 mmol) in MeOH (10 mL) at 0° C., were added formaldehyde (22 mg, 0.6 mmol) and HOAc (30 mg, 0.5 mmol). The reaction mixture was stirred at 0° C. for 10 min. $NaBH_3CN$ was then added. The mixture was stirred at 0° C. for another 30 min. It was then quenched with aq. $NaHCO_3$ and the mixture was extracted with DCM and then washed with brine. The organic layer was dried over anhydrous $Na_2SO_4$, filtered, and concentrated under reduced pressure. The residue was purified by prep-HPLC (C18, 40-100% MeCN in $H_2O$ with 0.1% formic acid) to give to 4-(1-methylindolin-5-yl)-N-(pyridin-3-ylmethyl)benzamide as a white solid (31 mg, 18%). LC-MS (ESI): m/z $(M+H)^+$=344.20. $^1$H NMR (400 MHz, DMSO-$d_6$) δ 9.11-9.03 (m, J=5.9 Hz, 1H), 8.56 (d, J=1.7 Hz, 1H), 8.46 (dd, J=4.7, 1.5 Hz, 1H), 7.94-7.86 (m, J=8.5 Hz, 2H), 7.75-7.70 (m, J=7.8, 1.9 Hz, 1H), 7.70-7.63 (m, J=8.5 Hz, 2H), 7.47-7.39 (m, J=10.6, 2.4 Hz, 2H), 7.38-7.33 (m, J=7.6, 4.5 Hz, 1H), 6.61-6.55 (m, J=8.1 Hz, 1H), 4.50 (d, J=5.9 Hz, 2H), 3.32-3.28 (m, J=8.1 Hz, 2H), 2.94 (t, J=8.2 Hz, 2H), 2.75 (s, 3H).

Synthesis of 4-(7-methyl-1-propionylindolin-5-yl)-N-(pyridin-3-ylmethyl)benzamide (Compound I-17)

Preparation of tert-butyl 7-methylindoline-1-carboxylate

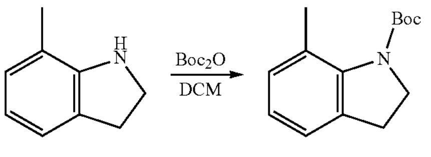

Following Procedure A, starting from 7-methylindoline (5.2 g, 39.1 mmol), tert-butyl 7-methylindoline-1-carboxylate was obtained as a white solid (6.0 g, 66%). LC-MS (ESI): m/z $(M+1)^+$=134.17.

Preparation of tert-butyl 5-bromo-7-methylindoline-1-carboxylate

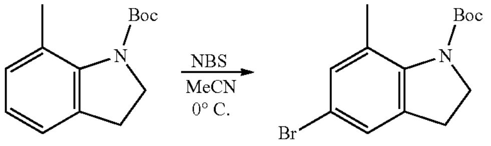

Following Procedure K, tert-butyl 5-bromo-7-methylindoline-1-carboxylate was obtained as a yellow solid (11.0 g, quantitative yield) from tert-butyl 7-methylindoline-1-carboxylate (crude, 25.8 mmol). LC-MS (ESI): m/z $(M+1)^+$=313.33, 315.22.

Preparation of tert-butyl 5-(4-(methoxycarbonyl)phenyl)-7-methylindoline-1-carboxylate

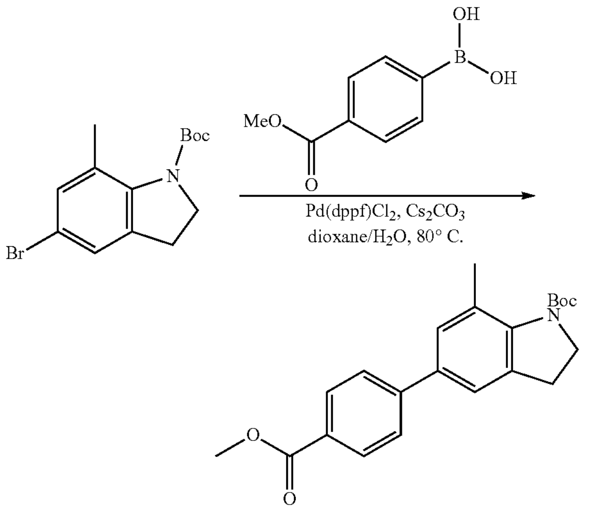

Following Procedure B, tert-butyl 5-(4-(methoxycarbonyl)phenyl)-7-methylindoline-1-carboxylate was obtained as a white solid (1.8 g, 76%) from tert-butyl 5-bromo-7-methylindoline-1-carboxylate (2.0 g, 6.4 mmol) and (4-(methoxycarbonyl)phenyl) boronic acid (1.7 g, 9.6 mmol). LC-MS (ESI): m/z $(M-100)^+$=268.21.

Preparation of methyl 4-(7-methylindolin-5-yl)benzoate

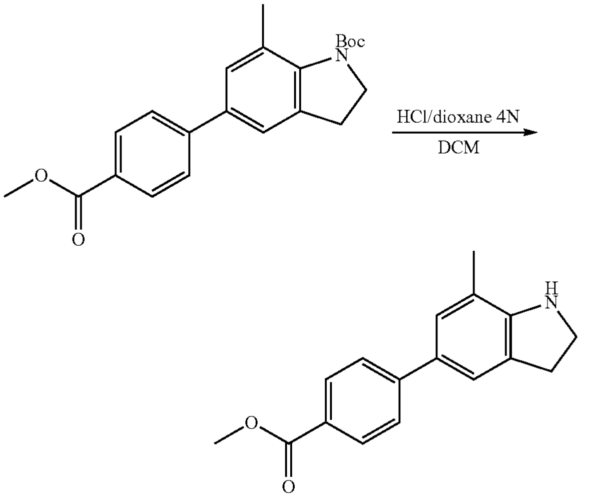

Following procedure E, starting from tert-butyl 5-(4-(methoxycarbonyl)phenyl)-7-methylindoline-1-carboxylate (1.0 g, 2.7 mmol), methyl 4-(7-methylindolin-5-yl)benzoate was obtained as a yellow solid (800 mg, quantitative yield). LC-MS (ESI): m/z $(M+1)^+$=268.32.

Preparation of methyl 4-(7-methyl-1-propionylindolin-5-yl)benzoate

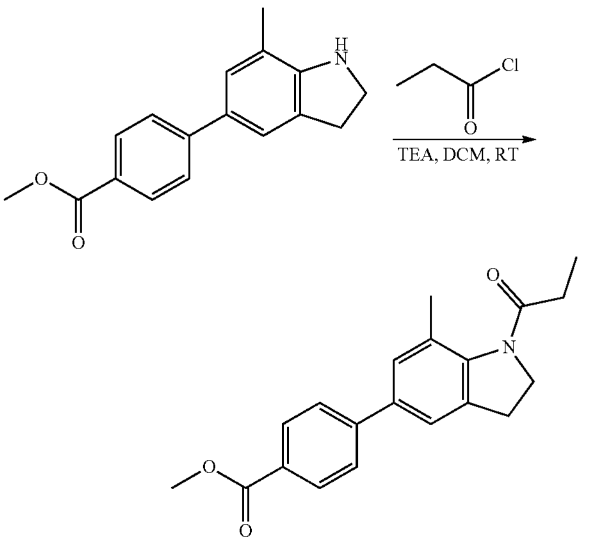

Procedure L: To a solution of methyl 4-(7-methylindolin-5-yl)benzoate (500 mg, 2.7 mmol) in DCM (10 mL) were added TEA (880 mg, 8.2 mmol), and then a solution of propionyl chloride (380 mg, 4.1 mmol) in DCM (5 mL). The reaction mixture was stirred at RT for 10 h. The mixture was extracted with DCM and washed with brine. The organic layer was dried over anhydrous $Na_2SO_4$, filtered and concentrated under reduced pressure. The residue was purified by flash column chromatography over silica gel (DCM/MeOH 4:1, v/v) to give methyl 4-(7-methyl-1-propionylindolin-5-yl)benzoate as a white solid (900 mg, quantitative yield). LC-MS (ESI): m/z $(M)^+$=324.22.

Preparation of 4-(7-methyl-1-propionylindolin-5-yl)benzoic acid

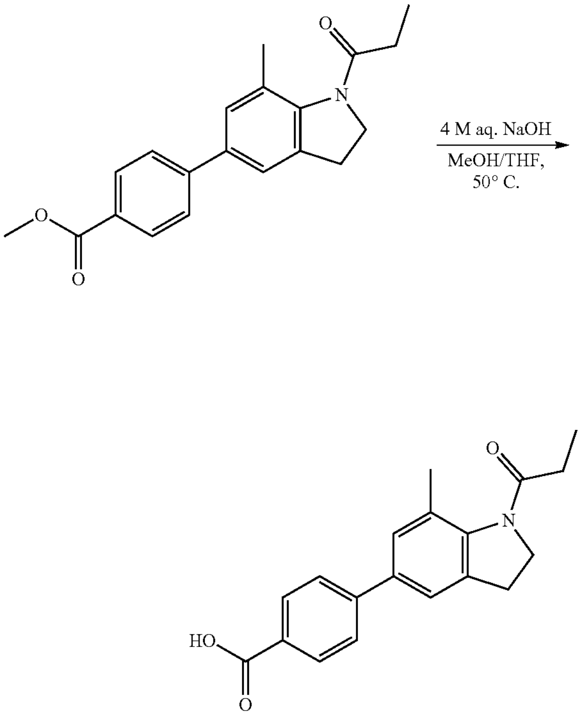 [SMILES: CCC(=O)N1CCc2cc(-c3ccc(C(=O)OC)cc3)cc(C)c21 ; CCC(=O)N1CCc2cc(-c3ccc(C(=O)O)cc3)cc(C)c21]

Following procedure F, starting from methyl 4-(7-methyl-1-propionylindolin-5-yl)benzoate (500 mg, 1.55 mmol), 4-(7-methyl-1-propionylindolin-5-yl)benzoic acid was obtained as a white solid (421 mg, 88%). LC-MS (ESI): m/z $(M+1)^+$=310.21.

Preparation of 4-(7-methyl-1-propionylindolin-5-yl)-N-(pyridin-3-ylmethyl)benzamide (Compound I-17)

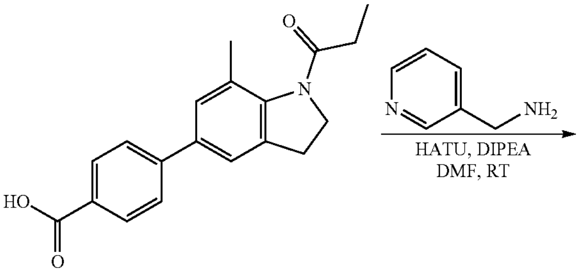

-continued

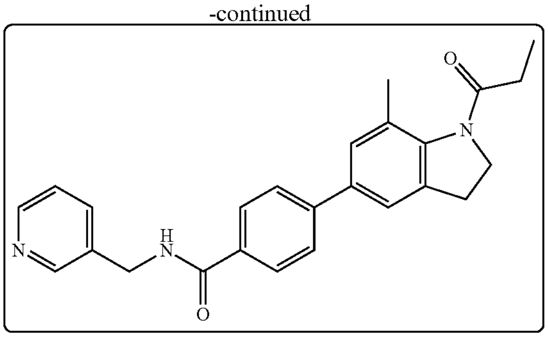

Following general Procedure D, starting from 4-(7-methyl-1-propionylindolin-5-yl)benzoic acid (220 mg, 0.715 mmol) and pyridin-3-ylmethanamine (92 mg, 0.854 mmol), 4-(7-methyl-1-propionylindolin-5-yl)-N-(pyridin-3-ylmethyl) benzamide was obtained as a white solid (21 mg, 7%). LC-MS (ESI): m/z $(M+H)^+$=400.38. $^1$H NMR (400 MHz, DMSO-d) δ 9.14 (t, J=5.6 Hz, 1H), 8.57 (s, 1H), 8.47 (d, J=3.8 Hz, 1H), 7.96 (d, J=8.3 Hz, 2H), 7.79-7.70 (m, 3H), 7.47 (s, 1H), 7.41-7.32 (m, 2H), 4.52 (d, J=5.6 Hz, 2H), 4.10 (t, J=7.5 Hz, 2H), 3.06 (t, J=7.4 Hz, 2H), 2.58-2.52 (m, 2H), 2.22 (s, 3H), 1.11 (t, J=7.4 Hz, 3H).

Synthesis of 4-(4-methyl-1-propionylindolin-5-yl)-N-(pyridin-3-ylmethyl)benzamide (Compound I-80)

Preparation of 4-methylindoline

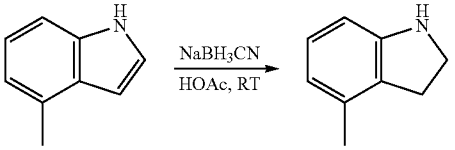

To a mixture of 4-methyl-1H-indole (5.0 g, 38.1 mmol) in AcOH (50 mL), was added $NaBH_3CN$ (4.8 g, 76.2 mmol) at 0° C. The reaction mixture was stirred at RT for 2 h. It was then diluted with DCM and washed with brine. The organic layer was dried over anhydrous $Na_2SO_4$, filtered, and concentrated under reduced pressure to give 4-methylindoline as a white solid (5.1 g, 99%). LC-MS (ESI): m/z $(M)^+$=134.12.

Preparation of tert-butyl 4-methylindoline-1-carboxylate

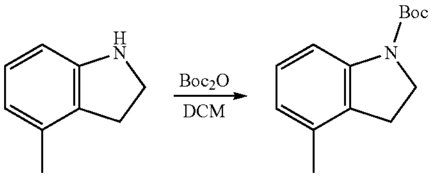

Following Procedure A, tert-butyl 4-methylindoline-1-carboxylate was obtained as a yellow oil (4.6 g, quantitative yield) starting from 4-methylindoline (2.5 g, 19.0 mmol). LC-MS (ESI): m/z $(M+1)^+$=234.12.

Preparation of tert-butyl 5-bromo-4-methylindoline-1-carboxylate

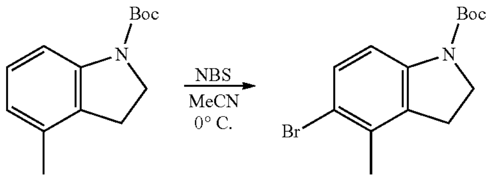

Following Procedure K, tert-butyl 5-bromo-4-methylindoline-1-carboxylate was obtained as a white solid (4.3 g, 70%) starting from tert-butyl 4-methylindoline-1-carboxylate (crude 4.6 g, 19.0 mmol). LC-MS (ESI): m/z $(M)^+$=156.16, 258.11.

Preparation of tert-butyl 5-bromo-4-methylindoline-1-carboxylate

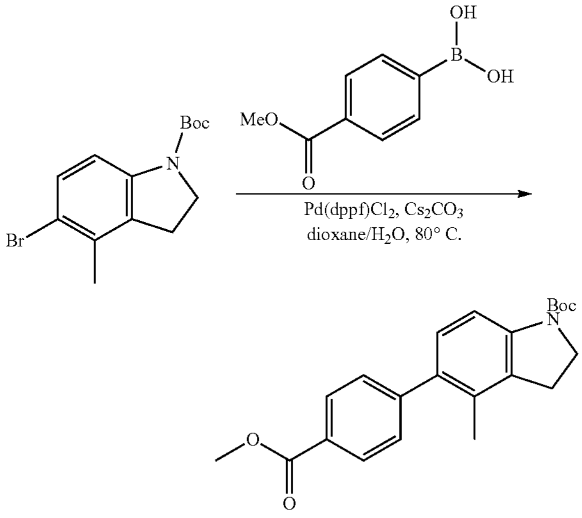

Following Procedure B, tert-butyl 5-bromo-4-methylindoline-1-carboxylate was obtained as a white solid (1.7 g, 72%) from tert-butyl 5-bromo-4-methylindoline-1-carboxylate (2.0 g, 6.4 mmol). LC-MS (ESI): m/z $(M+1)^+$=368.42.

Preparation of methyl 4-(4-methylindolin-5-yl)benzoate

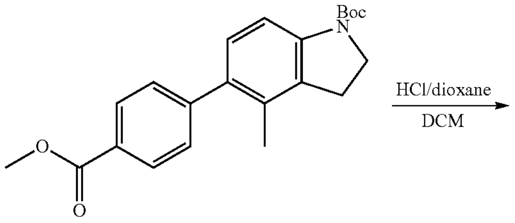

-continued

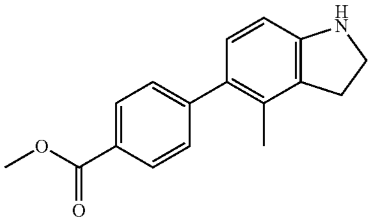

Following procedure E, methyl 4-(4-methylindolin-5-yl)benzoate was obtained as a yellow solid (1.0 g, quantitative yield) from tert-butyl 5-bromo-4-methylindoline-1-carboxylate (1.0 g, 2.7 mmol). LC-MS (ESI): m/z $(M+1)^+$=268.32.

Preparation of methyl 4-(4-methyl-1-propionylindolin-5-yl)benzoate

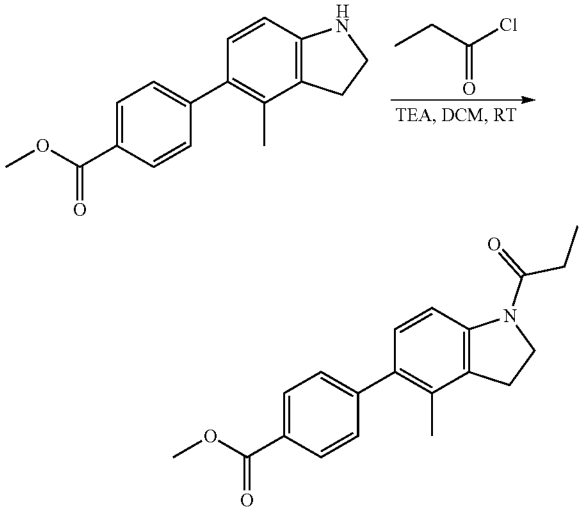

Following Procedure L, methyl 4-(4-methyl-1-propionylindolin-5-yl)benzoate was obtained as a white solid (1.0 g, quantitative yield) from methyl 4-(4-methylindolin-5-yl)benzoate (720 mg, 2.5 mmol). LC-MS (ESI): m/z $(M)^+$=324.39.

Preparation of 4-(4-methyl-1-propionylindolin-5-yl)benzoic acid

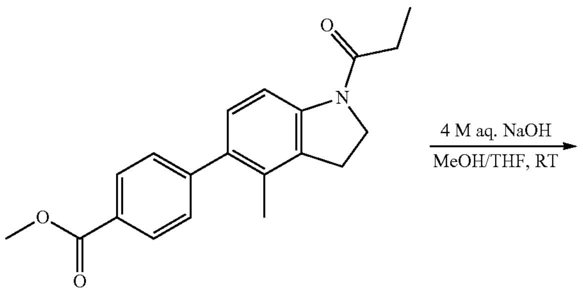

-continued

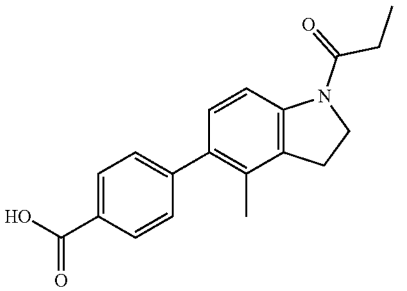

Following Procedure F, 4-(4-methyl-1-propionylindolin-5-yl)benzoic acid was obtained as a white solid (465 mg, 50%) from methyl 4-(4-methyl-1-propionylindolin-5-yl) benzoate (1.0 g, 3.0 mmol). LC-MS (ESI): m/z $(M+1)^+$=310.26.

Preparation of 4-(4-methyl-1-propionylindolin-5-yl)-N-(pyridin-3-ylmethyl)benzamide (Compound I-80)

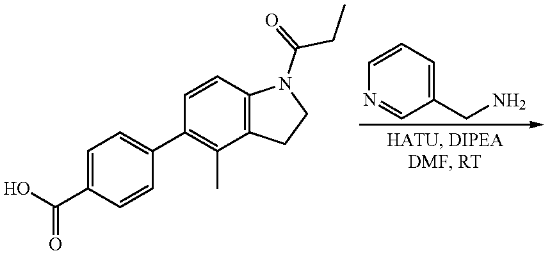

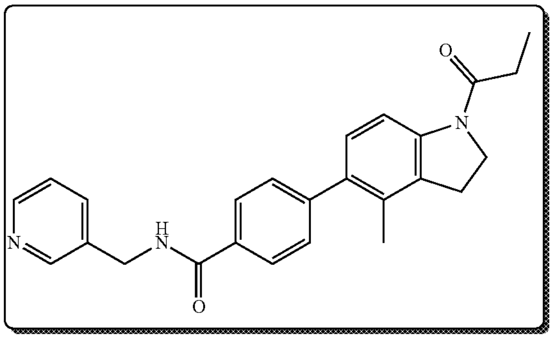

Following general Procedure D, starting from 4-(4-methyl-1-propionylindolin-5-yl)benzoic acid (220 mg, 0.712 mmol) and pyridin-3-ylmethanamine (92 mg, 0.854 mmol), 4-(4-methyl-1-propionylindolin-5-yl)-N-(pyridin-3-ylmethyl)benzamide was obtained as a white solid (66 mg, 23%). LC-MS (ESI): m/z $(M+H)^+$=400.22. $^1H$ NMR (400 MHz, DMSO-d) δ 9.39 (t, J=5.8 Hz, 1H), 9.23 (s, 2H), 8.60 (d, J=1.5 Hz, 1H), 8.48 (d, J=3.6 Hz, 1H), 8.33-8.27 (m, 2H), 8.24-8.14 (m, 1H), 7.78 (d, J=7.9 Hz, 1H), 7.40-7.36 (m, 1H), 4.56 (d, J=5.7 Hz, 2H), 4.16 (t, J=8.5 Hz, 2H), 3.23 (t, J=8.4 Hz, 2H), 2.56-2.51 (m, 2H), 1.08 (t, J=7.3 Hz, 3H).

Synthesis of 3-methyl-4-(1-propionylindolin-5-yl)-N-(pyridin-3-ylmethyl) benzamide (Compound I-91)

Preparation of methyl 3-methyl-4-(4,4,5,5-tetramethyl-1,3,2-dioxaborolan-2-yl)benzoate

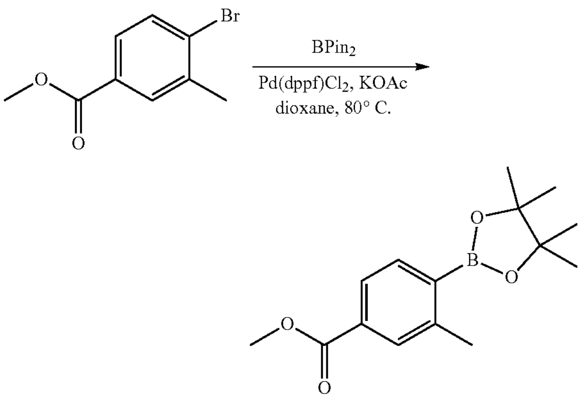

Following Procedure G, methyl 3-methyl-4-(4,4,5,5-tetramethyl-1,3,2-dioxaborolan-2-yl)benzoate was obtained as a yellow solid (2.1 g, 87%) from methyl 4-bromo-3-methylbenzoate (2.0 g, 8.7 mmol). LC-MS (ESI): m/z $(M+1)^+$=277.21.

Preparation of methyl 3-methyl-4-(1-propionylindolin-5-yl)benzoate

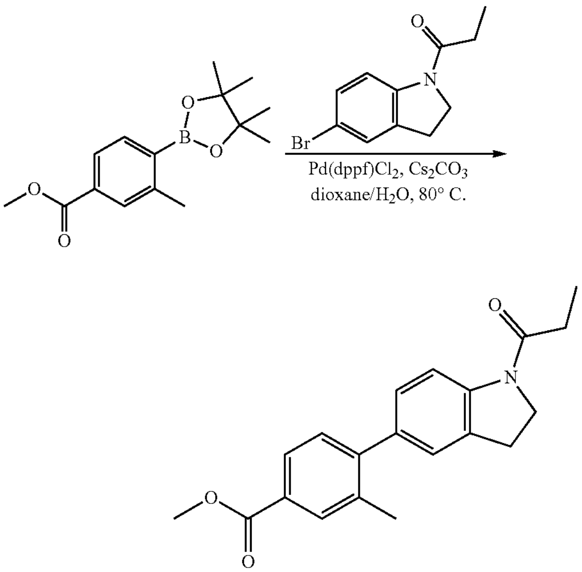

Following Procedure B, methyl 3-methyl-4-(1-propionylindolin-5-yl)benzoate was isolated as a white solid (700 mg, 73%) from 3-methyl-4-(4,4,5,5-tetramethyl-1,3,2-dioxaborolan-2-yl) benzoate (817 mg, 2.96 mmol). LC-MS (ESI): m/z $(M+1)^+$=324.33.

Preparation of 3-methyl-4-(1-propionylindolin-5-yl)benzoic acid

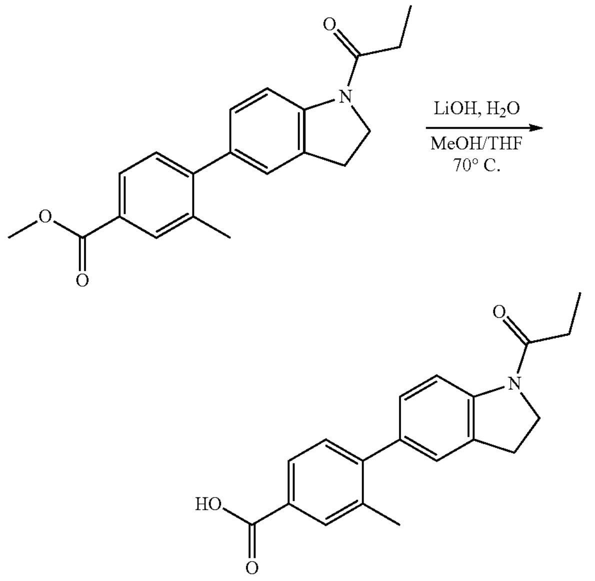

Following Procedure C, 3-methyl-4-(1-propionylindolin-5-yl)benzoic acid was obtained as a white solid (171 mg, 88%) from methyl 3-methyl-4-(1-propionylindolin-5-yl) benzoate (200 mg, 0.62 mmol). LC-MS (ESI): m/z $(M+1)^+$=310.26.

Preparation of 3-methyl-4-(1-propionylindolin-5-yl)-N-(pyridin-3-ylmethyl)benzamide (Compound I-91)

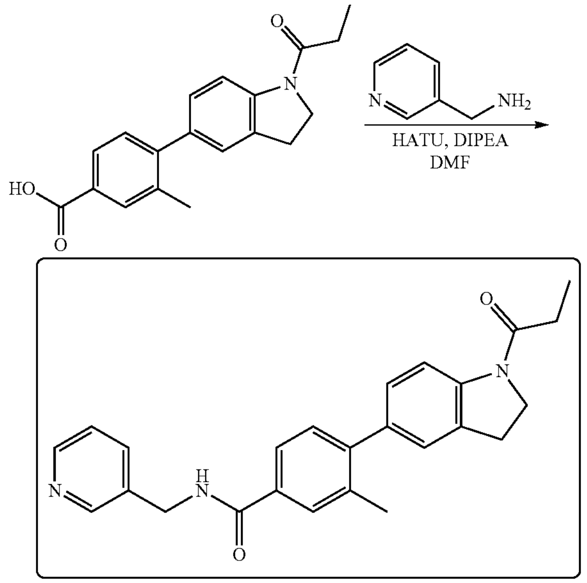

Following general Procedure D, starting from 3-methyl-4-(1-propionylindolin-5-yl) benzoic acid (80 mg, 0.26 mmol) and pyridin-3-ylmethanamine (33 mg, 0.31 mmol), 3-methyl-4-(1-propionylindolin-5-yl)-N-(pyridin-3-ylmethyl)benzamide was obtained in the form of 2 atropisomers. Both are white solids (43 mg, 41%). LC-MS (ESI): m/z $(M+H)^+$=400.33. Isomer 1: $^1$H NMR (400 MHz, DMSO-$d_6$) δ 9.09 (t, J=5.9 Hz, 1H), 8.56 (d, J=1.6 Hz, 1H), 8.46 (dd, J=4.7, 1.4 Hz, 1H), 8.14 (d, J=8.2 Hz, 1H), 7.81 (s, 1H), 7.77-7.70 (m, 2H), 7.36 (dd, J=7.7, 4.8 Hz, 1H), 7.28 (d, J=7.9 Hz, 1H), 7.23 (s, 1H), 7.14 (d, J=8.1 Hz, 1H), 4.51 (d, J=5.8 Hz, 2H), 4.12 (t, J=8.4 Hz, 2H), 3.19 (t, J=8.3 Hz, 2H), 2.49-2.43 (m, 2H), 2.29 (s, 3H), 1.08 (t, J=7.3 Hz, 3H). Isomer 2: $^1$H NMR (400 MHz, DMSO-$d_6$) δ 9.20 (t, J=5.8 Hz, 1H), 8.81 (s, 1H), 8.73 (d, J=5.1 Hz, 1H), 8.30 (d, J=8.0 Hz, 1H), 8.14 (d, J=7.5 Hz, 1H), 7.90-7.80 (m, 2H), 7.76 (d, J=7.9 Hz, 1H), 7.30 (d, J=8.0 Hz, 1H), 7.23 (s, 1H), 7.14 (d, J=8.2 Hz, 1H), 4.63 (d, J=5.7 Hz, 2H), 4.13 (t, J=8.4 Hz, 2H), 3.19 (t, J=8.3 Hz, 2H), 2.50-2.44 (m, 4H), 2.30 (s, 3H), 1.08 (t, J=7.3 Hz, 3H).

Synthesis of 2-methyl-4-(1-propionylindolin-5-yl)-N-(pyridin-3-ylmethyl) benzamide (Compound I-93)

Preparation of methyl 2-methyl-4-(4,4,5,5-tetramethyl-1,3,2-dioxaborolan-2-yl)benzoate

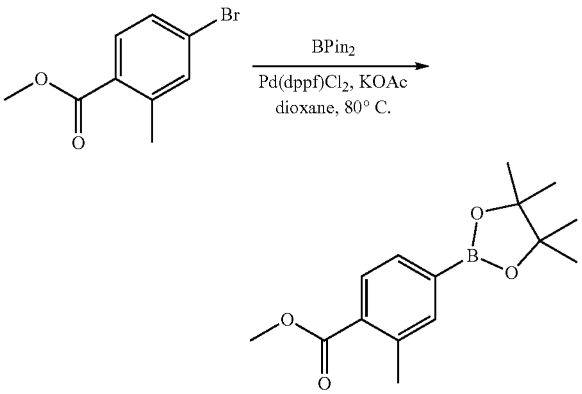

Following Procedure G, methyl 2-methyl-4-(4,4,5,5-tetramethyl-1,3,2-dioxaborolan-2-yl)benzoate was obtained as a yellow solid (2.5 g, quantitative yield) from methyl 4-bromo-2-methylbenzoate (2.0 g, 8.7 mmol). LC-MS (ESI): m/z $(M+1)^+$=277.21.

Preparation of methyl 2-methyl-4-(1-propionylindolin-5-yl)benzoate

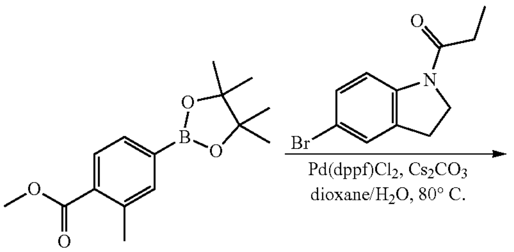

-continued

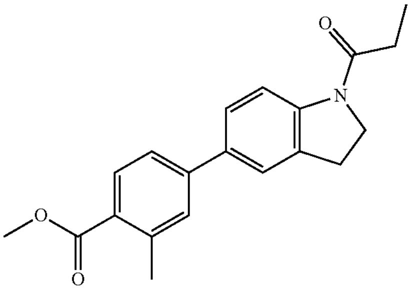

Following Procedure B, methyl 2-methyl-4-(1-propionylindolin-5-yl)benzoate was obtained as a white solid (450 mg, 47%) from methyl 2-methyl-4-(4,4,5,5-tetramethyl-1,3,2-dioxaborolan-2-yl)benzoate (817 mg, 2.96 mmol). LC-MS (ESI): m/z $(M+1)^+$=324.40.

Preparation of 2-methyl-4(1-propionylindolin-5-yl)benzoic acid

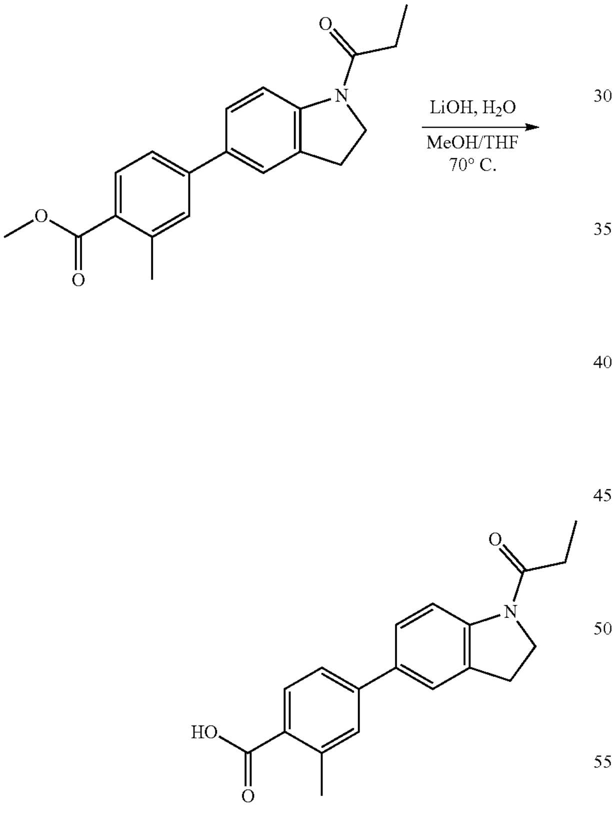

Following Procedure C, 2-methyl-4-(1-propionylindolin-5-yl)benzoic acid was obtained as a white solid (130 mg, 91%) from methyl 2-methyl-4-(1-propionylindolin-5-yl) benzoate (150 mg, 0.46 mmol). LC-MS (ESI): m/z $(M+1)^+$=310.26.

Preparation of 2-methyl-4-(1-propionylindolin-5-yl)-N-(pyridin-3-ylmethyl)benzamide (Compound I-93)

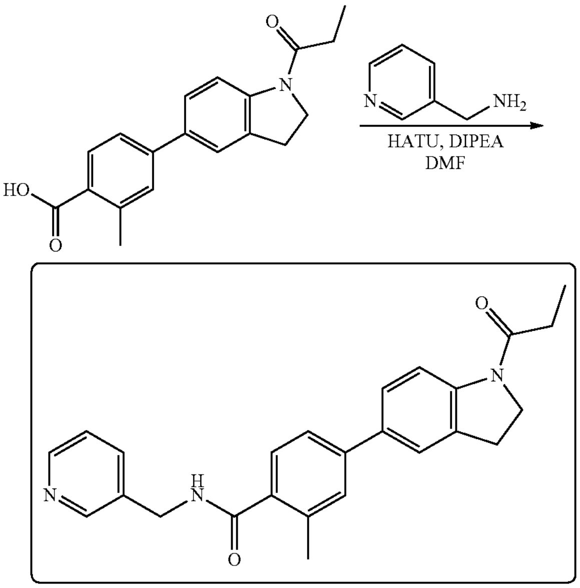

Following general Procedure D, starting from 2-methyl-4-(1-propionylindolin-5-yl)benzoic acid (80 mg, 0.26 mmol) and pyridin-3-ylmethanamine (33 mg, 0.31 mmol), 2-methyl-4-(1-propionylindolin-5-yl)-N-(pyridin-3-ylmethyl)benzamide was isolated in the form of 2 atropisomers. Both are white solids (56 mg, 54%). LC-MS (ESI): m/z $(M+H)^+$=400.33. Isomer 1: $^1H$ NMR (400 MHz, DMSO-$d_6$) δ 8.87 (t, J=6.0 Hz, 1H), 8.57 (d, J=1.8 Hz, 1H), 8.48 (dd, J=4.8, 1.6 Hz, 1H), 8.14 (d, J=8.4 Hz, 1H), 7.79-7.72 (m, 1H), 7.58 (s, 1H), 7.55-7.47 (m, 3H), 7.44 (d, J=7.9 Hz, 1H), 7.41-7.37 (m, 1H), 4.47 (d, J=6.0 Hz, 2H), 4.12 (t, J=8.5 Hz, 2H), 3.20 (t, J=8.4 Hz, 2H), 2.49-2.44 (m, 2H), 2.39 (s, 3H), 1.07 (t, J=7.3 Hz, 3H). Isomer 2: $^1H$ NMR (400 MHz, DMSO-$d_6$) δ8.97 (t, J=5.9 Hz, 1H), 8.81 (d, J=1.4 Hz, 1H), 8.74 (dd, J=5.3, 1.0 Hz, 1H), 8.31 (d, J=8.0 Hz, 1H), 8.14 (d, J=8.4 Hz, 1H), 7.87 (dd, J=7.9, 5.5 Hz, 1H), 7.66-7.45 (m, 5H), 4.59 (d, J=5.8 Hz, 2H), 4.12 (t, J=8.5 Hz, 2H), 3.20 (t, J=8.4 Hz, 2H), 2.49-2.44 (m, 2H), 2.40 (s, 3H), 1.08 (t, J=7.3 Hz, 3H).

Synthesis of 3-methoxy-4-(1-propionylindolin-5-yl)-N-(pyridin-3-ylmethyl) benzamide (Compound I-94)

Preparation of methyl 4-bromo-3-methoxybenzoate

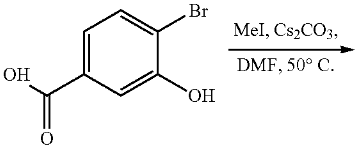

-continued

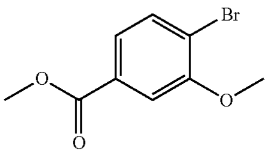

Procedure M: To a mixture of 2-4-bromo-3-hydroxybenzoic acid (2.5 g, 23.0 mmol) in DMF (10 mL), were added $Cs_2CO_3$ (12.0 g, 69.0 mmol) and methyl iodide (4.1 g, 57.5 mmol). The reaction mixture was stirred at 50° C. for 12 h. It was then diluted with DCM and washed with water and brine. The organic layer was dried over anhydrous $Na_2SO_4$, filtered, and concentrated under reduced pressure. The residue was purified by flash column chromatography over silica gel (DCM/MeOH 4:1, v/v) to give methyl 4-bromo-3-methoxybenzoate as a white solid (2.4 g, 85%). LC-MS (ESI): m/z $(M)^+$=245.11, 247.16.

Preparation of methyl 3-methoxy-4-(1-propionylindolin-5-yl)benzoate

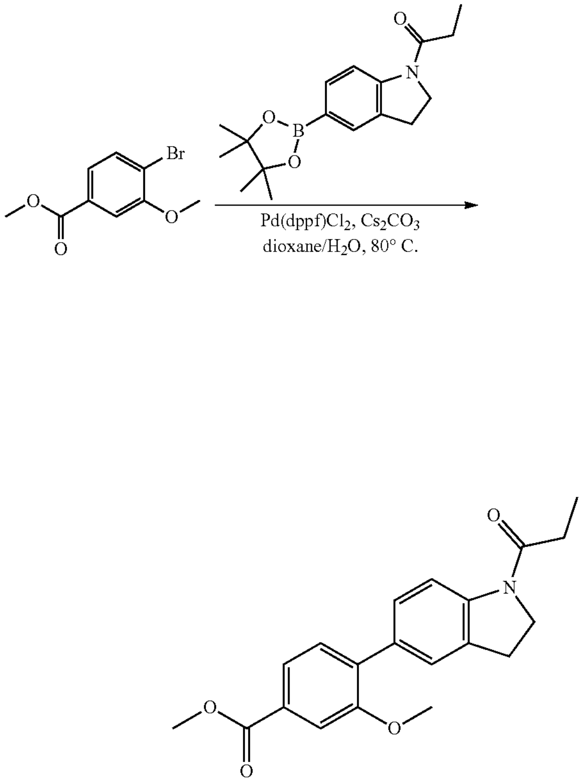

Following Procedure B, methyl 3-methoxy-4-(1-propionylindolin-5-yl) benzoate was obtained as a white solid (385 mg, 82%) from methyl 4-bromo-3-methoxybenzoate (340 mg, 1.38 mmol) and 1-(5-(4,4,5,5-tetramethyl-1,3,2-dioxaborolan-2-yl)indolin-1-yl)propan-1-one (500 mg, 1.66 mmol). LC-MS (ESI): m/z $(M+1)^+$=340.22.

Preparation of 3-methoxy-4-(1-propionylindolin-5-yl)benzoic acid

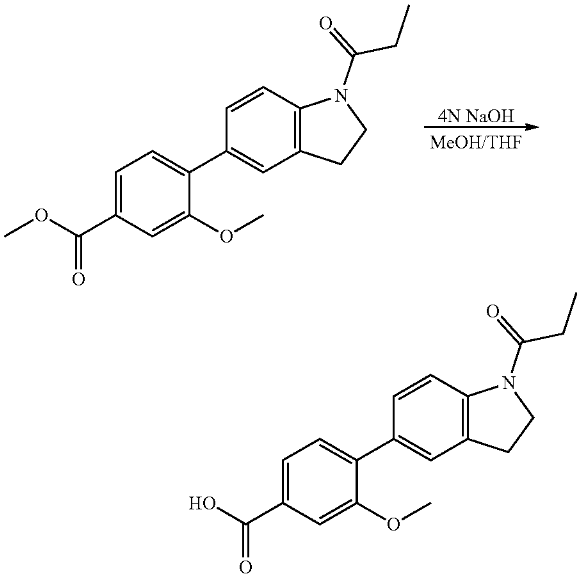

Following Procedure F, starting from methyl 3-methoxy-4-(1-propionylindolin-5-yl) benzoate (200 mg, 0.59 mmol), 3-methoxy-4-(1-propionylindolin-5-yl)benzoic acid was obtained as a white solid (160 mg, 83%). LC-MS (ESI): m/z $(M+1)^+$=326.26.

Preparation of 3-methoxy-4-(1-propionylindolin-5-yl)-N-(pyridin-3-ylmeth yl)benzamide (Compound I-94)

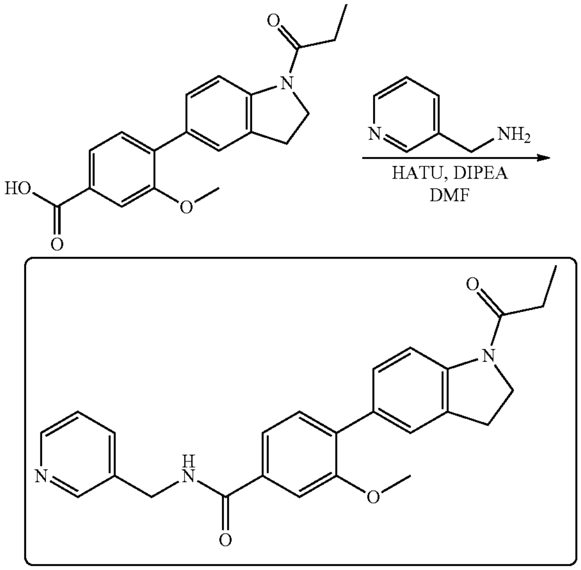

Following general Procedure D, starting from 3-methoxy-4-(1-propionylindolin-5-yl)benzoic acid (100 mg, 0.31 mmol) and pyridin-3-ylmethanamine (40 mg, 0.37 mmol), 3-methoxy-4-(1-propionylindolin-5-yl)-N-(pyridin-3-ylmeth yl)benzamide was obtained in the form of 2 atropisomers. Both are white solids (32 mg, 25%). LC-MS (ESI): m/z $(M+H)^+$=416.39. Isomer 1: $^1H$ NMR (400 MHz, DMSO-$d_6$) δ 9.14 (t, J=5.9 Hz, 1H), 8.57 (d, J=1.7 Hz, 1H), 8.47 (dd, J=4.8, 1.6 Hz, 1H), 8.10 (d, J=8.4 Hz, 1H), 7.76-7.72 (m, 1H), 7.58-7.53 (m, 2H), 7.40-7.34 (m, 3H), 7.29 (d, J=8.0 Hz, 1H), 4.52 (d, J=5.8 Hz, 2H), 4.11 (t, J=8.5 Hz, 2H), 3.82 (s, 3H), 3.17 (t, J=8.3 Hz, 2H), 2.47 (d, J=7.2 Hz, 2H), 1.08 (t, J=7.3 Hz, 3H). Isomer 2: $^1H$ NMR (400 MHz, DMSO-$d_6$) δ 9.25 (t, J=5.8 Hz, 1H), 8.81 (d, J=1.2 Hz, 1H), 8.73 (d, J=4.6 Hz, 1H), 8.30 (d, J=8.0 Hz, 1H), 8.11 (d, J=8.3 Hz, 1H), 7.86 (dd, J=7.9, 5.5 Hz, 1H), 7.61-7.54 (m, 2H), 7.39 (d, J=7.6 Hz, 2H), 7.30 (d, J=8.3 Hz, 1H), 4.64 (d, J=5.7 Hz, 2H), 4.11 (t, J=8.5 Hz, 2H), 3.83 (s, 3H), 3.18 (t, J=8.3 Hz, 2H), 2.49-2.42 (m, 2H), 1.08 (t, J=7.3 Hz, 3H).

Synthesis of 2-methoxy-4-(1-propionylindolin-5-yl)-N-(pyridin-3-ylmethyl) benzamide (Compound I-96)

Preparation of methyl 4-bromo-2-methoxybenzoate

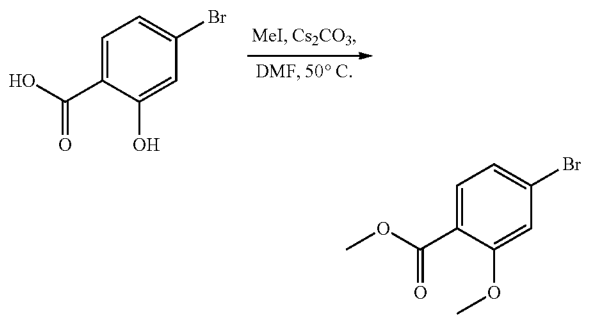

Following Procedure M, methyl 4-bromo-2-methoxybenzoate was obtained as a white solid (4.4 g, 78%) from 4-bromo-2-hydroxybenzoic acid (5.0 g, 23.0 mmol). LC-MS (ESI): m/z $(M)^+$=245.01, 247.01.

Preparation of methyl 2-methoxy-4-(4,4,5,5-tetramethyl-1,3,2-dioxaborolan-2-yl)benzoate

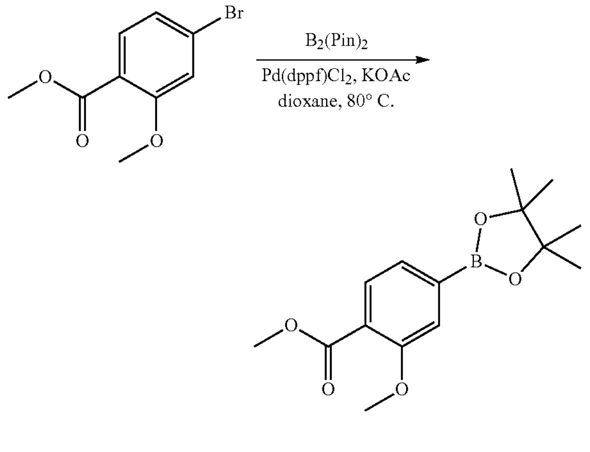

Following Procedure G, methyl 2-methoxy-4-(4,4,5,5-tetramethyl-1,3,2-dioxaborolan-2-yl)benzoate was obtained as a yellow solid (2.1 g, 84%) from methyl 4-bromo-2-methoxybenzoate (2.0 g, 8.2 mmol). LC-MS (ESI): m/z $(M+1)^+$=293.16.

Preparation of methyl 2-methoxy-4-(1-propionylindolin-5-yl)benzoate

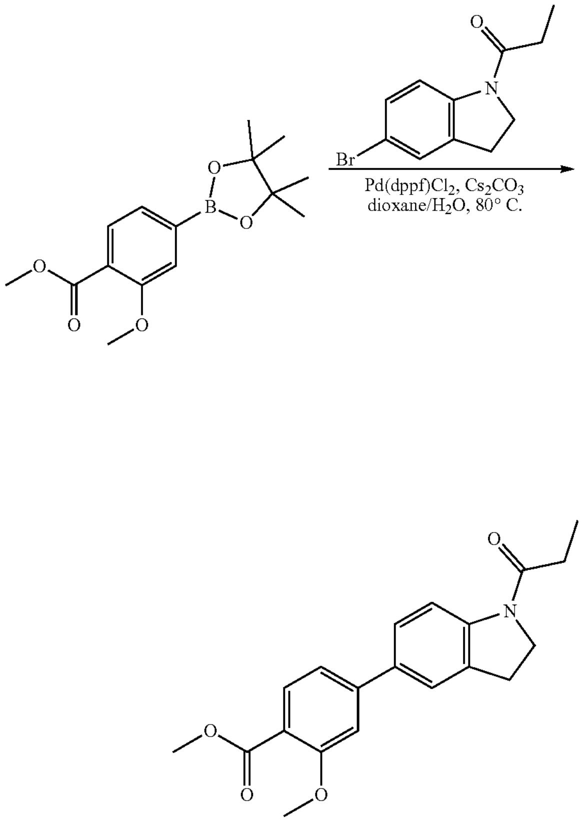

Following Procedure B, methyl 2-methoxy-4-(1-propionylindolin-5-yl)benzoate was obtained as a white solid (700 mg, quantitative yield) from methyl 2-methoxy-4-(4,4,5,5-tetramethyl-1,3,2-dioxaborolan-2-yl) benzoate (500 mg, 1.71 mmol). LC-MS (ESI): m/z $(M+1)^+$=340.22.

Preparation of 2-methoxy-4-(1-propionylindolin-5-yl)benzoic acid

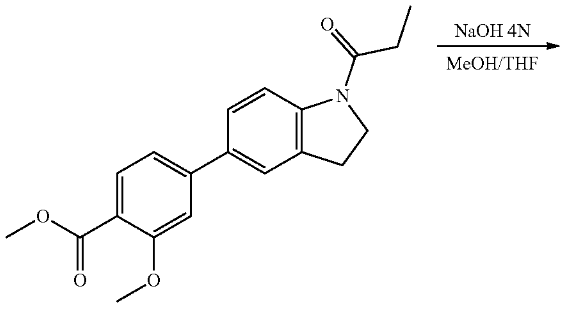

-continued

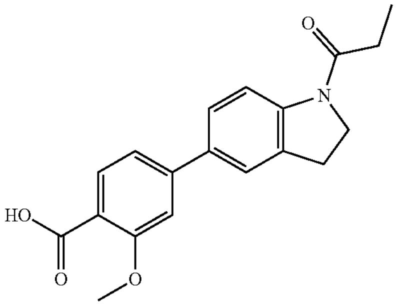

Following Procedure F, starting from methyl 2-methoxy-4-(1-propionylindolin-5-yl)benzoate (300 mg, 0.88 mmol), 2-methoxy-4-(1-propionylindolin-5-yl)benzoic acid was obtained as a white solid (220 mg, 76%) from. LC-MS (ESI): m/z $(M+1)^+$=326.33.

Preparation of 2-methoxy-4-(1-propionylindolin-5-yl)-N-(pyridin-3-ylmethyl)benzamide (Compound I-96)

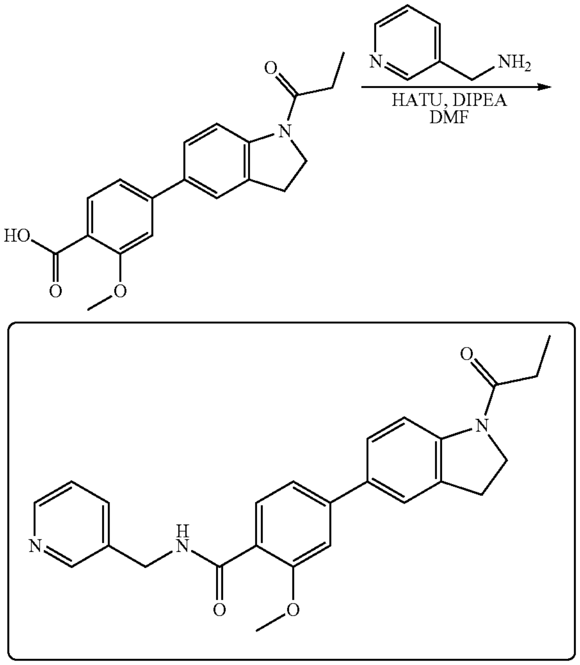

Following general Procedure D, starting from 2-methoxy-4-(1-propionylindolin-5-yl)benzoic acid (100 mg, 0.31 mmol) and pyridin-3-ylmethanamine (40 mg, 0.37 mmol), 2-methoxy-4-(1-propionylindolin-5-yl)-N-(pyridin-3-ylmethyl)benzamide was obtained as a white solid (33 mg, 25%). LC-MS (ESI): m/z $(M+H)^+$=416.21. $^1$H NMR (400 MHz, DMSO-d) δ 8.79 (t, J=6.1 Hz, 1H), 8.56 (d, J=1.7 Hz, 1H), 8.45 (dd, J=4.7, 1.5 Hz, 1H), 8.15 (d, J=8.4 Hz, 1H), 7.82 (d, J=8.0 Hz, 1H), 7.76-7.72 (m, 1H), 7.66 (s, 1H), 7.58 (d, J=8.4 Hz, 1H), 7.38-7.29 (m, 3H), 4.53 (d, J=6.1 Hz, 2H), 4.13 (t, J=8.5 Hz, 2H), 4.00 (s, 3H), 3.21 (t, J=8.3 Hz, 2H), 2.49-2.46 (m, 2H), 1.08 (t, J=7.3 Hz, 3H).

Synthesis of 3-fluoro-4-(1-propionylindolin-5-yl)-N-(pyridin-3-ylmethyl) benzamide (Compound I-97)

Preparation of methyl 4-bromo-3-fluorobenzoate

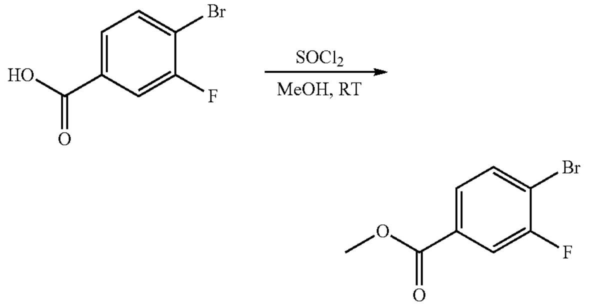

Procedure N: To a mixture of 4-bromo-3-fluorobenzoic acid (2.5 g, 11.4 mmol) in MeOH (20 mL), was added $SOCl_2$ (4.0 g, 34.2 mmol). The reaction mixture was stirred at RT for 10 h and was then concentrated under reduced pressure. It was diluted with DCM and washed with aq. $NaHCO_3$ and brine. The organic layer was dried over anhydrous $Na_2SO_4$, filtered, and concentrated under reduced pressure to give methyl 4-bromo-3-fluorobenzoate as a yellow solid (2.6 g, 98%). LC-MS (ESI): m/z $(M+1)^+$=233.01.

Preparation of methyl 3-fluoro-4-(1-propionylindolin-5-yl)benzoate

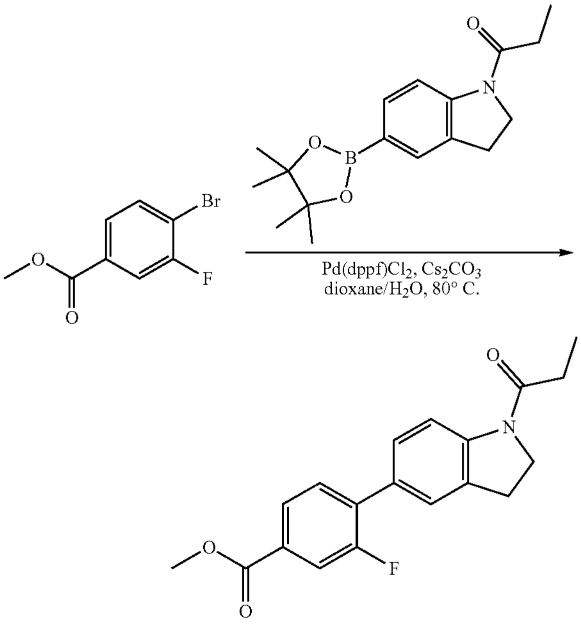

Following Procedure B, methyl 3-fluoro-4-(1-propionylindolin-5-yl)benzoate was obtained as a white solid (320 mg, 97%) from methyl 4-bromo-3-fluorobenzoate (321 mg, 1.38 mmol). LC-MS (ESI): m/z $(M+1)^+$=328.27.

Preparation of 3-fluoro-4-(1-propionylindolin-5-yl)benzoic acid

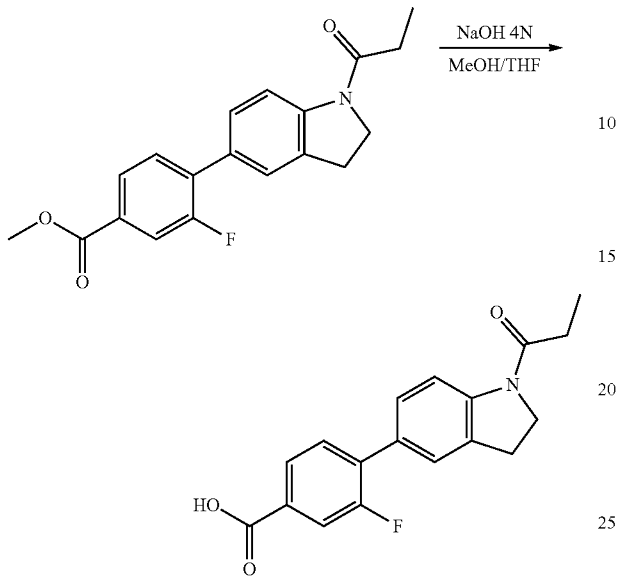

Following Procedure F, starting from 3-fluoro-4-(1-propionylindolin-5-yl)benzoate (320 mg, 0.98 mmol), 3-fluoro-4-(1-propionylindolin-5-yl)benzoic acid was obtained as a white solid (220 mg, 70%). LC-MS (ESI): m/z $(M+1)^+$=314.41.

Preparation of 3-fluoro-4-(1-propionylindolin-5-yl)-N-(pyridin-3-ylmethyl) benzamide (Compound I-97)

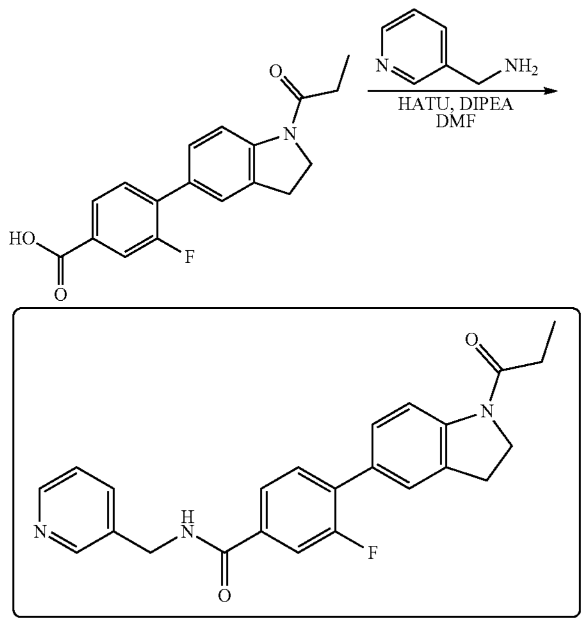

Following general Procedure D, starting from 3-fluoro-4-(1-propionylindolin-5-yl) benzoic acid (100 mg, 0.31 mmol) and pyridin-3-ylmethanamine (41 mg, 0.38 mmol), 3-fluoro-4-(1-propionylindolin-5-yl)-N-(pyridin-3-ylmethyl)benzamide was obtained as a white solid (35 mg, 27%). LC-MS (ESI): m/z $(M+H)^+$=404.33. $^1$H NMR (400 MHz, DMSO-$d_6$) δ 9.25 (t, J=5.8 Hz, 1H), 8.81 (d, J=1.2 Hz, 1H), 8.73 (d, J=4.6 Hz, 1H), 8.30 (d, J=8.0 Hz, 1H), 8.11 (d, J=8.3 Hz, 1H), 7.86 (dd, J=7.9, 5.5 Hz, 1H), 7.61-7.54 (m, 2H), 7.39 (d, J=7.6 Hz, 2H), 7.30 (d, J=8.3 Hz, 1H), 4.64 (d, J=5.7 Hz, 2H), 4.11 (t, J=8.5 Hz, 2H), 3.83 (s, 3H), 3.18 (t, J=8.3 Hz, 2H), 2.49-2.42 (m, 2H), 1.08 (t, J=7.3 Hz, 3H).

Synthesis of 2-fluoro-4-(1-propionylindolin-5-yl)-N-(pyridin-3-ylmethyl) benzamide (Compound I-98)

Preparation of methyl 4-bromo-2-fluorobenzoate

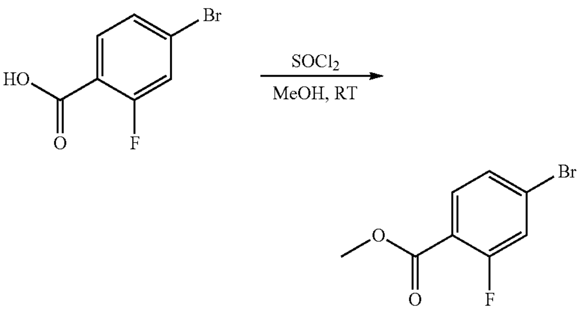

Following Procedure N, methyl 4-bromo-2-fluorobenzoate was obtained as a yellow solid (4.5 g, 85%) from 4-bromo-2-fluorobenzoic acid (5.0 g, 22.8 mmol). LC-MS (ESI): m/z $(M+1)^+$=233.11, 235.02.

Preparation of methyl 2-fluoro-4-(4,4,5,5-tetramethyl-1,3,2-dioxaborolan-2-yl)benzoate

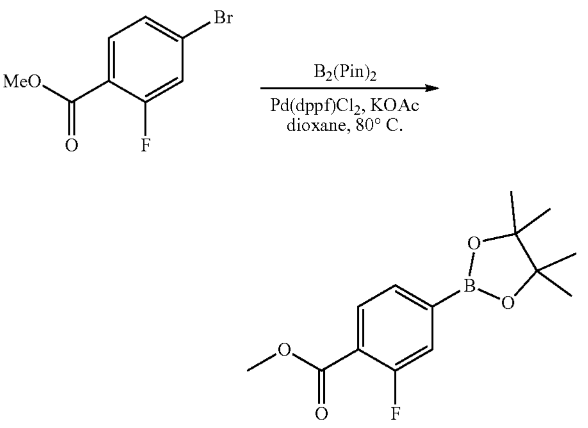

Following Procedure G, methyl 2-fluoro-4-(4,4,5,5-tetramethyl-1,3,2-dioxaborolan-2-yl)benzoate was obtained as a yellow solid (2.2 g, 91%) from methyl 4-bromo-2-fluorobenzoate (2.0 g, 8.6 mmol). LC-MS (ESI): m/z $(M+1)^+$=281.16.

Preparation of methyl 2-fluoro-4-(1-propionylindolin-5-yl)benzoate

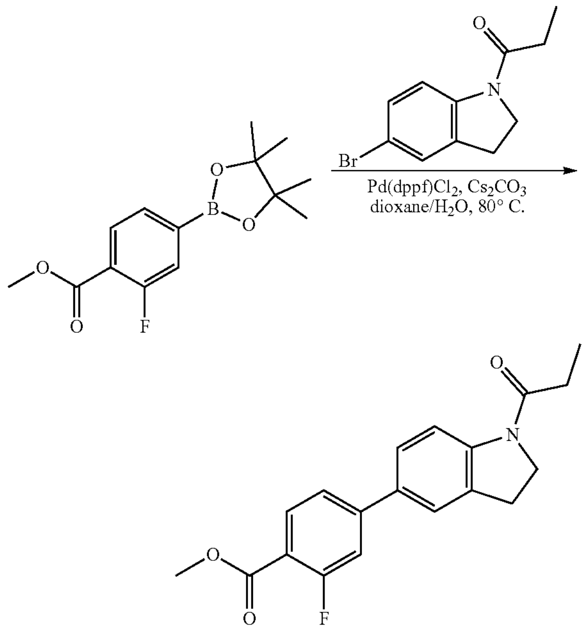

Following Procedure B, methyl 2-fluoro-4-(1-propionylindolin-5-yl)benzoate was obtained as a white solid (500 mg, quantitative yield) from methyl 2-fluoro-4-(4,4,5,5-tetramethyl-1,3,2-dioxaborolan-2-yl)benzoate (500 mg, 1.79 mmol) and 1-(5-bromoindolin-1-yl)propan-1-one (378 mg, 1.49 mmol). LC-MS (ESI): m/z $(M+1)^+$=328.17.

Preparation of 2-fluoro-4-(1-propionylindolin-5-yl)benzoic acid

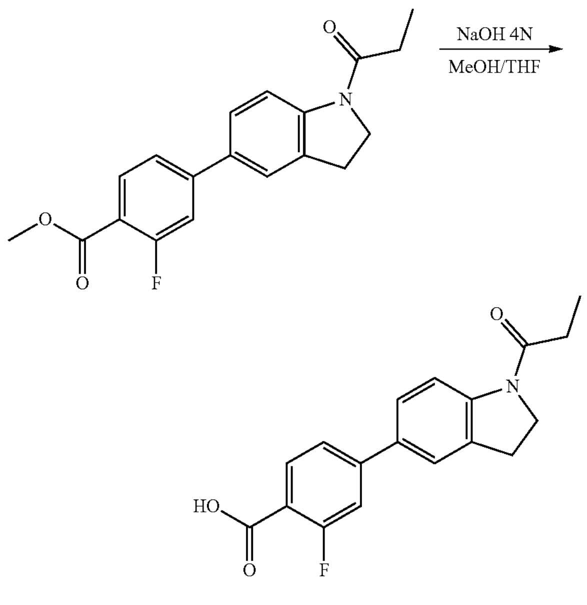

Following Procedure F, starting from methyl 2-fluoro-4-(1-propionylindolin-5-yl)benzoate (250 mg, 0.76 mmol), 2-fluoro-4-(1-propionylindolin-5-yl)benzoic acid was obtained as a white solid (180 mg, 76%). LC-MS (ESI): m/z $(M+1)^+$=314.33.

Preparation of 2-fluoro-4-(1-propionylindolin-5-yl)-N-(pyridin-3-ylmethyl) benzamide (Compound I-98)

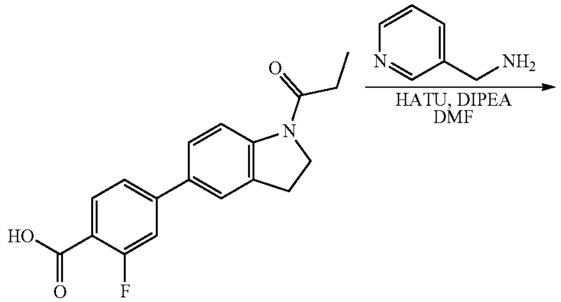

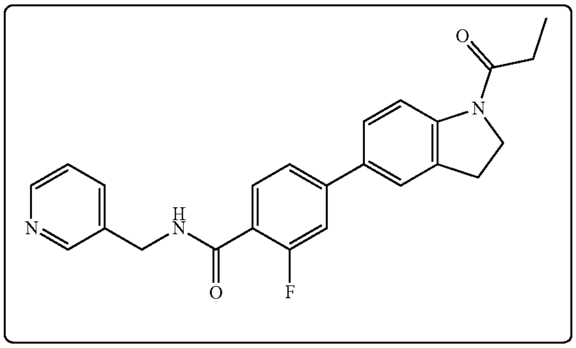

Following general Procedure D, starting from 2-fluoro-4-(1-propionylindolin-5-yl) benzoic acid (100 mg, 0.32 mmol) and pyridin-3-ylmethanamine (41 mg, 0.38 mmol), 2-fluoro-4-(1-propionylindolin-5-yl)-N-(pyridin-3-ylmethyl) benzamide was obtained as a white solid (38 mg, 29%). LC-MS (ESI): m/z $(M+H)^+$=404.74. $^1$H NMR (400 MHz, DMSO-d$_6$) δ 9.22 (t, J=5.8 Hz, 1H), 8.57 (d, J=1.7 Hz, 1H), 8.47 (dd, J=4.7, 1.5 Hz, 1H), 8.17 (d, J=8.4 Hz, 1H), 7.82-7.76 (m, 2H), 7.74 (d, J=7.9 Hz, 1H), 7.64 (t, J=8.2 Hz, 1H), 7.48 (s, 1H), 7.42-7.35 (m, 2H), 4.52 (d, J=5.8 Hz, 2H), 4.13 (t, J=8.5 Hz, 2H), 3.21 (t, J=8.4 Hz, 2H), 2.49-2.45 (m, 2H), 1.08 (t, J=7.3 Hz, 3H).

Synthesis of 2-(1-propionylindolin-5-yl)-N-(pyridin-3-ylmethyl)oxazole-4-carboxamide (Compound I-187)

Preparation of methyl 2-(1-propionylindolin-5-yl)oxazole-4-carboxylate

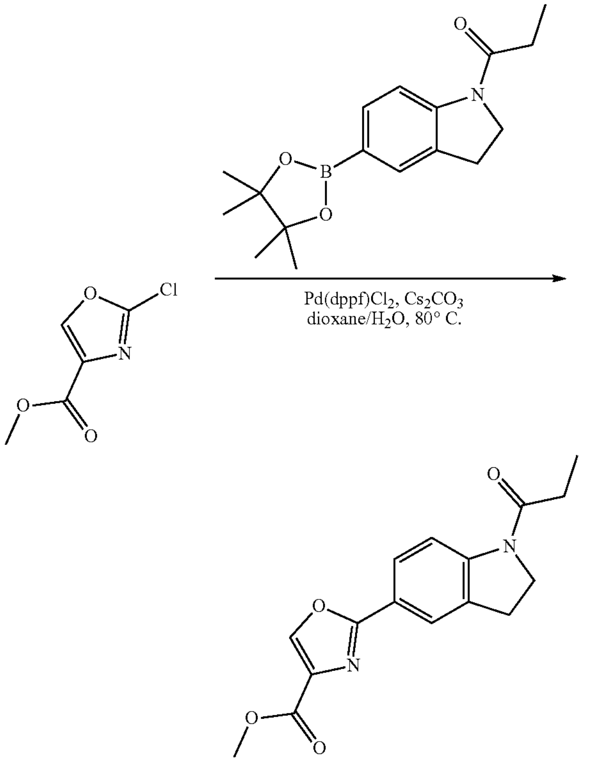

Following Procedure B, methyl 2-(1-propionylindolin-5-yl)oxazole-4-carboxylate was obtained as a white solid (340 mg, 74%) from methyl 2-chlorooxazole-4-carboxylate (250 mg, 1.46 mmol) and 1-(5-(4,4,5,5-tetramethyl-1,3,2-dioxaborolan-2-yl)indolin-1-yl)propan-1-one (500 mg, 1.72 mmol). LC-MS (ESI): m/z $(M+1)^+$=315.33.

Preparation of 2-(1-propionylindolin-5-yl)oxazole-4-carboxylic acid

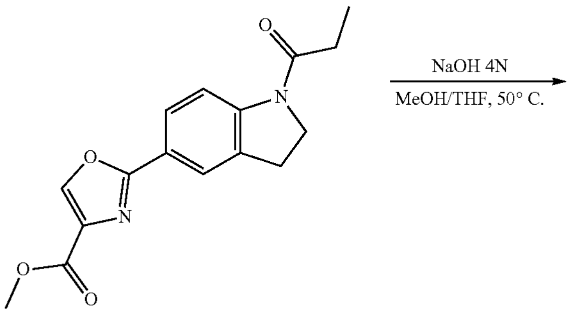

-continued

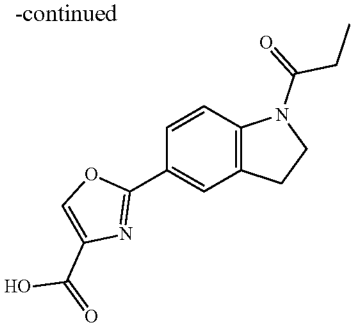

Following Procedure F, starting from methyl 2-(1-propionylindolin-5-yl)oxazole-4-carboxylate (150 mg, 0.47 mmol), 2-(1-propionylindolin-5-yl)oxazole-4-carboxylic acid was obtained as a white solid (286 mg, 66%). LC-MS (ESI): m/z $(M+1)^+$=287.22.

Preparation of 2-(1-propionylindolin-5-yl)-N-(pyridin-3-ylmethyl)oxazole-4-carboxamide (Compound I-187)

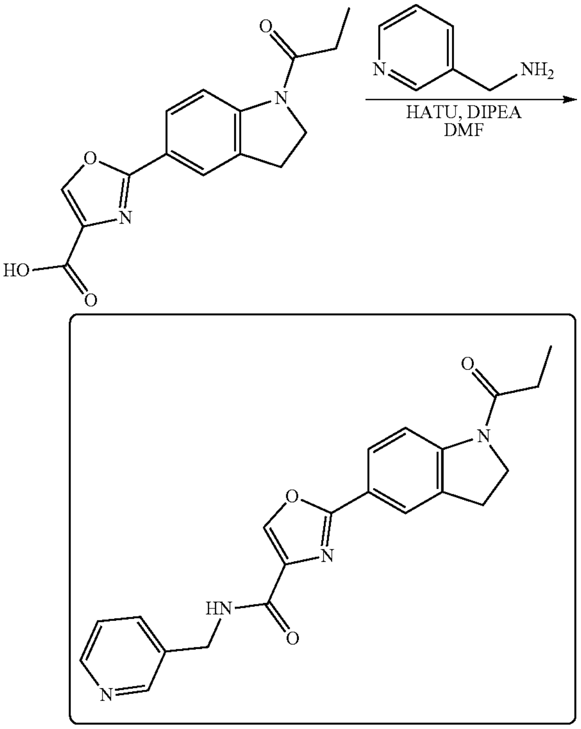

Following general Procedure D, starting from 2-(1-propionylindolin-5-yl)oxazole-4-carboxylic acid (90 mg, 0.31 mmol) and pyridin-3-ylmethanamine (41 mg, 0.38 mmol), 2-(1-propionylindolin-5-yl)-N-(pyridin-3-ylmethyl)oxazole-4-carboxamide was obtained as a white solid (50 mg, 43%). LC-MS (ESI): m/z $(M+H)^+$=377.33. $^1$H NMR (400 MHz, DMSO-d) δ 8.96 (t, J=6.1 Hz, 1H), 8.66 (s, 1H), 8.56 (s, 1H), 8.46 (d, J=4.3 Hz, 1H), 8.21 (d, J=8.1 Hz, 1H), 7.85 (d, J=10.1 Hz, 2H), 7.73 (d, J=7.7 Hz, 1H), 7.36 (dd, J=7.7, 4.8 Hz, 1H), 4.47 (d, J=6.2 Hz, 2H), 4.15 (t, J=8.4 Hz, 2H), 3.22 (t, J=8.2 Hz, 2H), 2.50-2.45 (m, 2H), 1.07 (t, J=7.2 Hz, 3H).

Synthesis of 3-(1-propionylindolin-5-yl)-N-(pyridin-3-ylmethyl)propiolamide (Compound I-201)

Preparation of 1-(5-iodoindolin-1-yl)propan-1-one

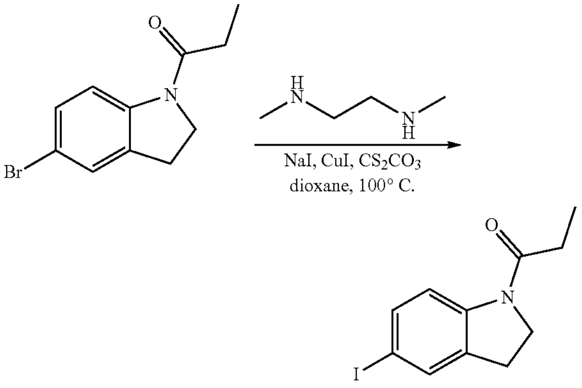

To a mixture of 1-(5-bromoindolin-1-yl)propan-1-one (1.2 g, 4.7 mmol) in dioxane, were added N,N'-dimethylethylenediamine (124 mg, 1.4 mmol), NaI (2.1 g, 14.0 mmol), CuI (2.6 g, 14.0 mmol) and $Cs_2CO_3$ (1.4 g, 4.29 mmol). The reaction mixture was stirred at 100° C. for 50 h. It was then diluted with DCM/IPA and washed with water and brine. The organic layer was dried over anhydrous $Na_2SO_4$, filtered, and concentrated under reduced pressure. The residue was purified by flash column chromatography over silica gel (DCM/MeOH 4:1, v/v) to give 1-(5-iodoindolin-1-yl)propan-1-one as a white solid (1.3 g, 91%). LC-MS (ESI): m/z $(M+1)^+$=301.11.

Preparation of 3-(1-propionylindolin-5-yl)propiolic acid

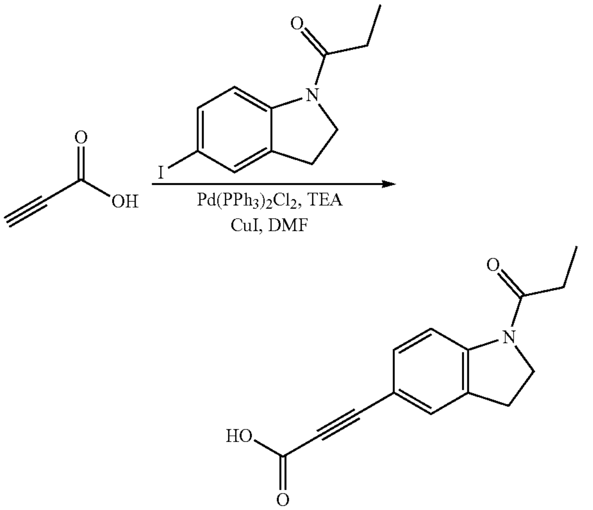

To a mixture of 1-(5-iodoindolin-1-yl)propan-1-one (105 mg, 1.5 mmol) in DMF/TEA (1:1, 4 mL), were added CuI (2.6 g, 14.0 mmol) and $Pd(PPh_3)_2Cl_2$ (21 mg, 0.03 mmol). The reaction mixture was stirred at RT for 0.5 h. It was then diluted with DCM/IPA and washed with water and brine. The organic layer was dried over anhydrous $Na_2SO_4$, filtered and concentrated under reduced pressure to give 3-(1-propionylindolin-5-yl)propiolic acid as a yellow solid (crude 200 mg, quantitative yield). LC-MS (ESI): m/z $(M+1)^+$=244.12.

Preparation of 3-(1-propionylindolin-5-yl)-N-(pyridin-3-ylmethyl)propiolamide (Compound I-201)

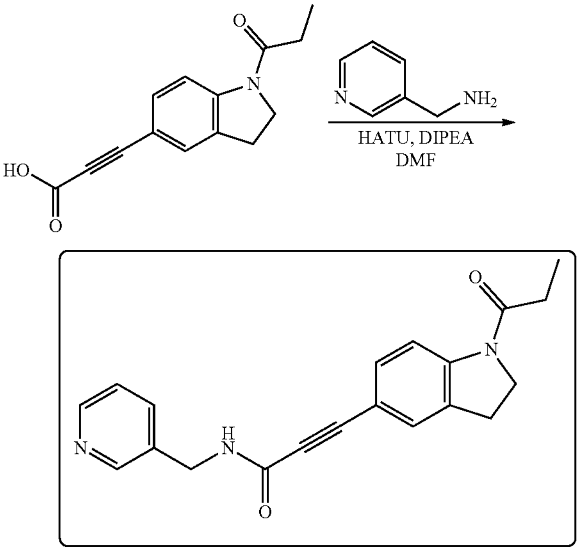

Following general Procedure D, starting from 3-(1-propionylindolin-5-yl)propiolic acid (150 mg, 0.62 mmol) and pyridin-3-ylmethanamine (80 mg, 0.74 mmol), 3-(1-propionylindolin-5-yl)-N-(pyridin-3-ylmethyl) propiolamide was obtained as a white solid (5.9 mg, 3%). LC-MS (ESI): m/z $(M+H)^+$=334.22. $^1H$ NMR (400 MHz, DMSO-$d_6$) δ 9.27 (t, J=6.0 Hz, 1H), 8.51 (d, J=1.8 Hz, 1H), 8.48 (dd, J=4.8, 1.6 Hz, 1H), 8.10 (d, J=7.9 Hz, 1H), 7.71-7.67 (m, 1H), 7.42-7.35 (m, 3H), 4.36 (d, J=6.0 Hz, 2H), 4.11 (t, J=8.6 Hz, 2H), 3.14 (t, J=8.5 Hz, 2H), 2.49-2.40 (m, 2H), 1.06 (t, J=7.3 Hz, 3H).

Synthesis of 5-(4-(N-methylacetamido)phenyl)-N-(pyridin-3-ylmethyl) picolinamide (Compound I-202)

Preparation of N-(4-(4,4,5,5-tetramethyl-1,3-dioxolan-2-yl)phenyl) acetamide

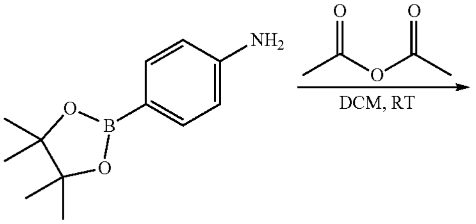

-continued

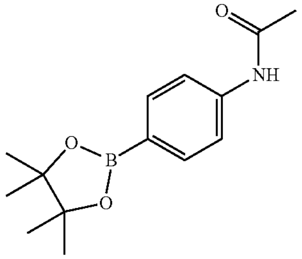

To a mixture of 4-(4,4,5,5-tetramethyl-1,3,2-dioxaborolan-2-yl)aniline (3.0 g, 13.7 mmol) in DCM (70 mL), was added acetic anhydride (7.0 g, 68.5 mmol). The reaction mixture was stirred at RT for 10 h. It was then concentrated under reduced pressure and the resulting residue was purified by flash column chromatography over silica gel (PE/EA 1:1, v/v) to give N-(4-(4,4,5,5-tetramethyl-1,3-dioxolan-2-yl)phenyl) acetamide as a yellow solid (3.1 g, 87%). LC-MS (ESI): m/z $(M+1)^+=262.31$.

Preparation of N-(4-(4,4,5,5-tetramethyl-1,3-dioxolan-2-yl)phenyl) acetamide

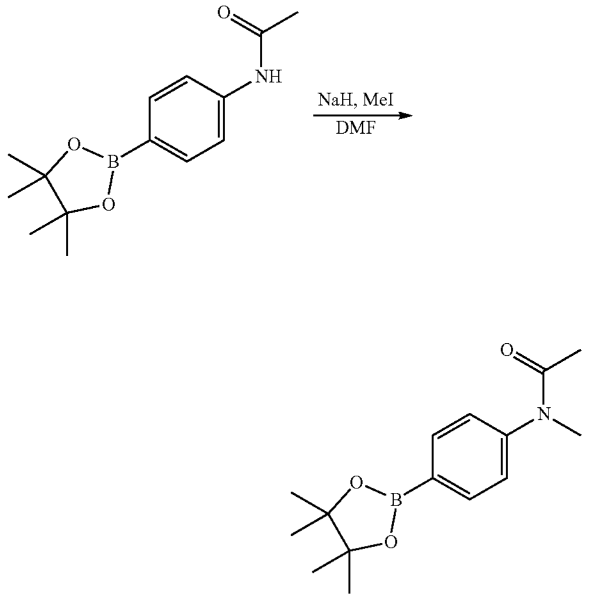

To a mixture of N-(4-(4,4,5,5-tetramethyl-1,3-dioxolan-2-yl)phenyl) acetamide (1.5 g, 5.7 mmol) in THF (20 mL), was added NaH (60%, 344 mg, 8.6 mmol). The reaction mixture was stirred at 0° C. for 5 min. Me (6.5 g, 46.0 mmol) was then added. The reaction mixture was stirred at RT for 10 h. It was diluted with DCM and washed with aq. $NH_4Cl$ and brine. The organic layer was dried over anhydrous $Na_2SO_4$, filtered, and concentrated under reduced pressure. The resulting residue was purified by flash column chromatography over silica gel (DCM/MeOH 4:1, v/v) to give N-methyl-N-(4-(4,4,5,5-tetramethyl-1,3-dioxolan-2-yl)phenyl)acetamide as a white solid (1.7 g, quantitative yield). LC-MS (ESI): m/z $(M)^+=276.22$.

Preparation of methyl 5-(4-(N-methylacetamido)phenyl)picolinate

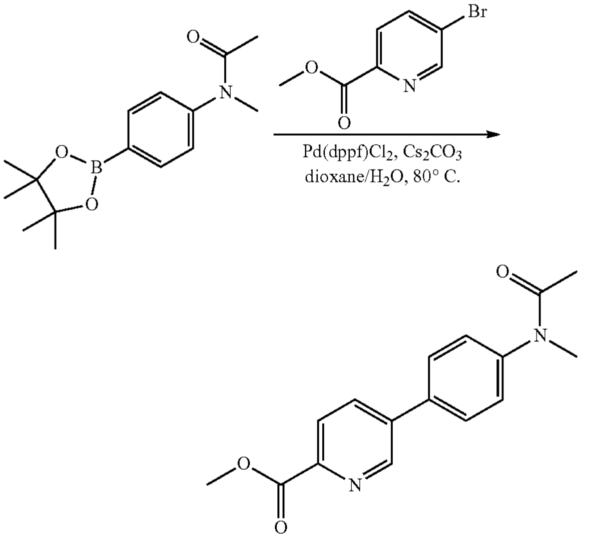

Following Procedure B, methyl 5-(4-(N-methylacetamido)phenyl)picolinate was obtained as a white solid (800 mg, quantitative yield) from N-methyl-N-(4-(4,4,5,5-tetramethyl-1,3-dioxolan-2-yl)phenyl) acetamide (500 mg, 1.82 mmol). LC-MS (ESI): m/z $(M-100)^+=285.33$.

Preparation of 5-(4-(N-methylacetamido)phenyl)picolinic acid

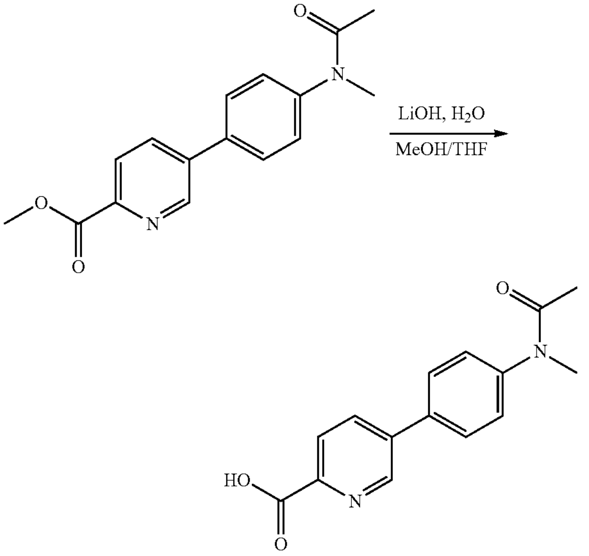

Following Procedure C, 5-(4-(N-methylacetamido)phenyl)picolinic acid was obtained as a white solid (crude 800 mg, quantitative yield) from 5-(4-(N-methylacetamido)phenyl)picolinate (800 mg, 2.8 mmol). LC-MS (ESI): m/z $(M+1)^+=271.29$.

Preparation of 5-(4-(N-methylacetamido)phenyl)-N-(pyridin-3-ylmethyl)picolinamide (Compound I-202)

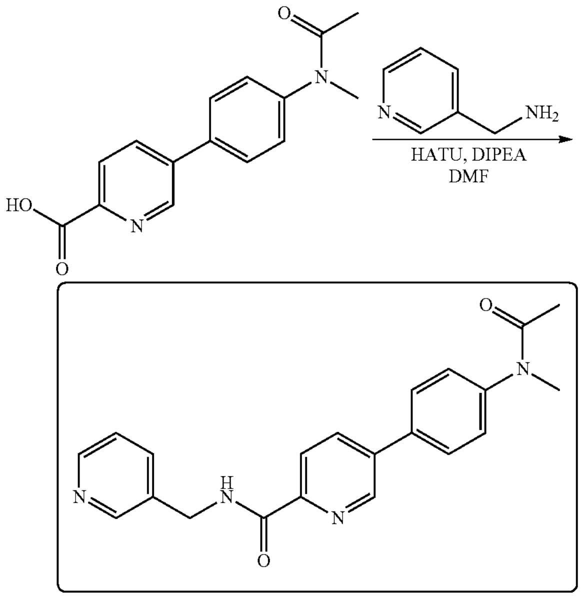

Following general Procedure D, starting from 5-(4-(N-methylacetamido)phenyl)picolinic acid (150 mg, 0.56 mmol) and pyridin-3-ylmethanamine (72 mg, 0.67 mmol), 5-(4-(N-methylacetamido)phenyl)-N-(pyridin-3-ylmethyl) picolinamide was obtained as a white solid (46.7 mg, 23%). LC-MS (ESI): m/z $(M+H)^+=361.27$. $^1H$ NMR (400 MHz, DMSO-$d_6$) δ 9.52 (t, J=6.3 Hz, 1H), 8.99 (d, J=1.8 Hz, 1H), 8.58 (d, J=1.7 Hz, 1H), 8.46 (dd, J=4.7, 1.6 Hz, 1H), 8.32 (dd, J=8.2, 2.3 Hz, 1H), 8.12 (dd, 1H), 7.89 (d, J=8.2 Hz, 2H), 7.77-7.73 (m, 1H), 7.51 (d, J=8.3 Hz, 2H), 7.37-7.33 (m, 1H), 4.54 (d, J=6.4 Hz, 2H), 3.21 (s, 3H), 1.87 (s, 3H).

Synthesis of 4-(6-methyl-1-propionylindolin-5-yl)-N-(pyridin-3-ylmethyl)benzamide (Compound I-203)

Preparation of 6-methylindoline

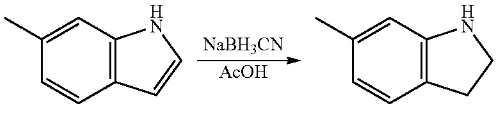

To a mixture of 6-methyl-1H-indole (2.0 g, 15.25 mmol) in AcOH (20 mL) at 0° C., was added $NaBH_3CN$ (1.9 g, 30.5 mmol). The reaction mixture was stirred at RT for 4 h. LC-MS showed the reaction was complete, it was neutralized by NaOH, extracted with EtOAc, the combined organic layers were washed with brine, dried over anhydrous $Na_2SO_4$, filtered, and concentrated under reduced pressure to give 6-methylindoline as a colorless oil (2.09 g, quantitative yield). LC-MS (ESI): m/z $(M+1)^+=134.15$.

Preparation of tert-butyl 6-methylindoline-1-carboxylate

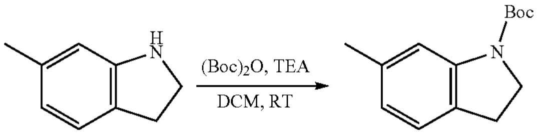

To a solution of 6-methylindoline (2.09 g, 15.7 mmol) in $CH_2Cl_2$ (30 mL), were added $(Boc)_2O$ (5.14 g, 23.5 mmol) and $Et_3N$ (4.36 mL, 31.4 mmol). The reaction mixture was stirred at RT for 16 h. TLC showed the reaction was complete and then the reaction was washed with brine. The organic layer was dried over anhydrous $Na_2SO_4$, filtered, and concentrated under reduced pressure. The resulting residue was purified by flash column chromatography over silica gel (EtOAc in PE 10-20%, v/v) to give tert-butyl 6-methylindoline-1-carboxylate as a white solid (3.92 g, quantitative yield).

Preparation of tert-butyl 5-bromo-6-methylindoline-1-carboxylate

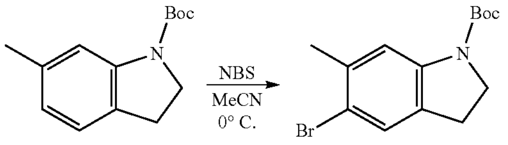

Following Procedure K, tert-butyl 5-bromo-6-methylindoline-1-carboxylate was obtained as a yellow solid (6.0 g, quantitative yield) from tert-butyl 6-methylindoline-1-carboxylate (3.0 g, 12.9 mmol). $^1H$ NMR (400 MHz, $CDCl_3$) δ 7.76 (s, 1H), 7.26 (s, 1H), 3.96 (t, J=8.6 Hz, 2H), 3.04 (t, J=8.7 Hz, 2H), 2.35 (s, 3H), 1.53 (s, 9H).

Preparation of 5-bromo-6-methylindoline

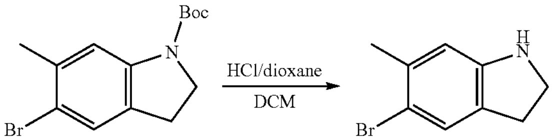 [SMILES: Cc1cc2c(cc1Br)CCN2C(=O)OC(C)(C)C ; Cc1cc2c(cc1Br)CCN2]

Procedure E was followed starting from tert-butyl 5-bromo-6-methylindoline-1-carboxylate (6.0 g, 19.2 mmol). The reaction mixture was concentrated and used as such in the next step. LC-MS (ESI): m/z $(M+1)+/(M+2)^+=212.11/214.16$.

Preparation of I-(5-bromo-6-methylindolin-1-yl)propan-1-one

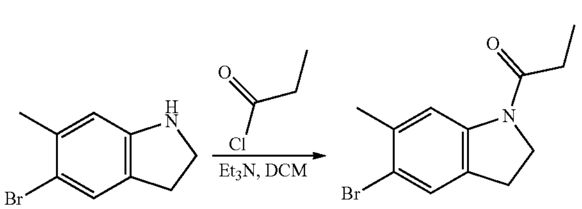

Following Procedure L, starting from 5-bromo-6-methylindoline (3.68 g, 17.4 mmol), 1-(5-bromo-6-methylindolin-1-yl)propan-1-one was obtained as a white solid (2.3 g, 49%). LC-MS (ESI): m/z $(M+1)^+/(M+2)^+$=268.11/270.11.

Preparation of methyl 4-(6-methyl-1-propionylindolin-5-yl)benzoate

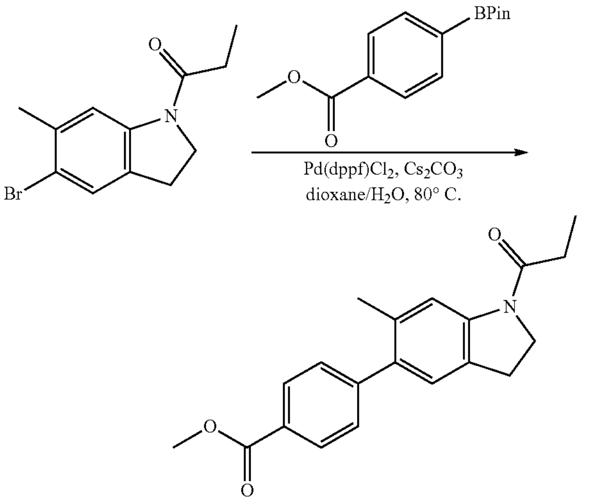

Following Procedure B, methyl 4-(6-methyl-1-propionylindolin-5-yl)benzoate was obtained as a light yellow solid (2.36 g, 85%) from 1-(5-bromo-6-methylindolin-1-yl) propan-1-one (2.3 g, 8.58 mmol) and methyl 4-(4,4,5,5-tetramethyl-1,3,2-dioxaborolan-2-yl)benzoate (2.3 g, 12.87 mmol). LC-MS (ESI): m/z $(M+H)^+$=324.22.

Preparation of 4-(6-methyl-1-propionylindolin-5-yl)benzoic acid

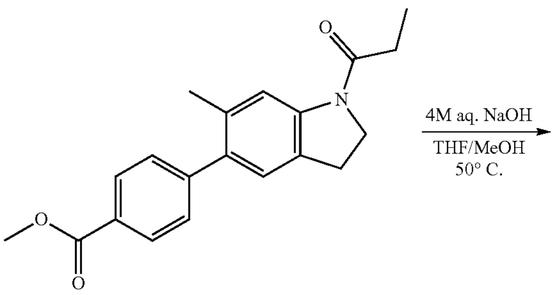

-continued

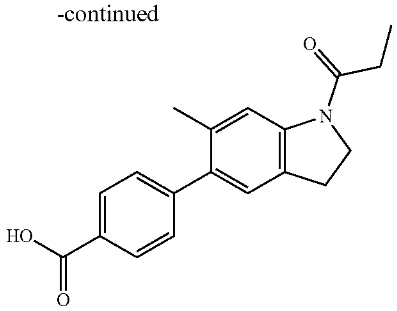

To a solution of methyl 4-(6-methyl-1-propionylindolin-5-yl)benzoate (2.36 g, 7.30 mmol) in MeOH/THF (20/20 mL), was added 4 N NaOH (5 mL). The reaction mixture was stirred at 50° C. overnight. LC-MS showed the reaction was complete. The mixture was cooled to RT and neutralized with HCl, then filtered. The filtrate was concentrated under reduced pressure to give 4-(6-methyl-1-propionylindolin-5-yl)benzoic acid as a white solid (610 mg, 23%). LC-MS (ESI): m/z $(M+1)^+$=310.21.

Preparation of 4-(6-methyl-1-propionylindolin-5-yl)-N-(pyridin-3-ylmethyl)benzamide (Compound I-203)

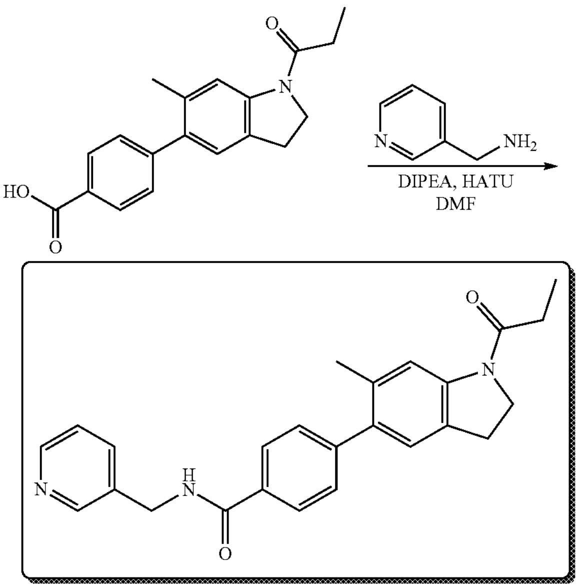

Procedure D was followed starting from 4-(6-methyl-1-propionylindolin-5-yl)benzoic acid (150 mg, 0.48 mmol) and pyridin-3-ylmethanamine (78 mg, 0.73 mmol). Purification by prep-HPLC (C18, 10~100% acetonitrile in water with 0.1% formic acid) afforded 4-(6-methyl-1-propionylindolin-5-yl)-N-(pyridin-3-ylmethyl)benzamide in the form of 2 atropisomers as white solids (51.4 mg, 26% & 47.3 mg, 24%). LC-MS (ESI): m/z (M+1)+/m/z $(M+1)^+$=400.05/400.32. Isomer 1: $^1H$ NMR (400 MHz, DMSO-$d_6$) δ 9.14 (t, J=5.9 Hz, 1H), 8.57 (d, J=1.7 Hz, 1H), 8.47 (dd, J=4.7, 1.5 Hz, 1H), 8.05 (s, 1H), 7.93 (d, J=8.3 Hz, 2H), 7.74 (d, J=7.9 Hz, 1H), 7.44-7.34 (m, 3H), 7.09 (s, 1H), 4.52 (d, J=5.8 Hz, 2H), 4.10 (t, J=8.4 Hz, 2H), 3.13 (t, J=8.2 Hz, 2H), 2.49-2.44 (m, 2H), 2.21 (s, 3H), 1.08 (t, J=7.3 Hz, 3H). Isomer 2: $^1H$ NMR δ 9.25 (t, J=5.8 Hz, 1H), 8.84 (d, J=1.4 Hz, 1H), 8.75 (d, J=4.5 Hz, 1H), 8.36 (d, J=8.0 Hz, 1H), 8.06 (s, 1H), 7.99-7.86 (m, 3H), 7.44 (d, J=8.3 Hz, 2H), 7.09 (s, 1H), 4.64 (d, J=5.7 Hz, 2H), 4.10 (t, J=8.4 Hz, 2H), 3.13 (t, J=8.2 Hz, 2H), 2.49-2.45 (m, 2H), 2.21 (s, 3H), 1.08 (t, J=7.3 Hz, 3H).

Synthesis of 2-(1-propionylindolin-5-yl)-N-(pyridin-3-ylmethyl)-1H-imidazole-4-carboxamide (Compound I-208)

Preparation of methyl 1-((2-(trimethylsilyl)ethoxy) methyl)-1H-imidazole-4-carboxylate

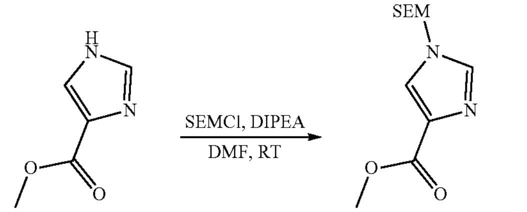

To a mixture of methyl 1H-imidazole-4-carboxylate (2.0 g, 15.9 mmol) in DMF (30 mL), were added DIPEA (4.1 g, 31.72 mmol), then SEM-Cl (4.0 g, 23.4 mmol) dropwise. The reaction mixture was stirred at RT for 16 h, then quenched with water and extracted with EtOAc. The combined organic layers were washed with brine, dried over anhydrous $Na_2SO_4$, filtered, and concentrated under reduced pressure. The resulting residue was purified by flash column chromatography over silica gel (EtOAc in PE 30-50%, v/v) to give methyl 1-((2-(trimethylsilyl)ethoxy)methyl)-1H-imidazole-4-carboxylate as a colorless oil (2.13 g, 52%). LC-MS (ESI): m/z $(M+1)^+$=257.21.

Preparation of methyl 2-bromo-1-((2-(trimethylsilyl)ethoxy)methyl)-1H-imidazole-4-carboxylate

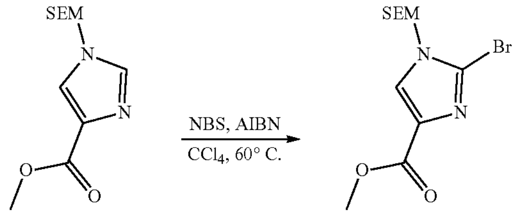 [SMILES: COC(=O)c1cn(COCC[Si](C)(C)C)cn1 ; COC(=O)c1cn(COCC[Si](C)(C)C)c(Br)n1]

To a mixture of methyl 1-((2-(trimethylsilyl)ethoxy) methyl)-1H-imidazole-4-carboxylate (1.0 g, 3.9 mmol) in $CCl_4$ (50 mL), were added NBS (649 mg, 3.9 mmol) and AIBN (cat.). The reaction mixture was stirred at 60° C. for 4 h. LC-MS showed the reaction was complete. It was cooled to RT, washed with sat. $NH_4Cl$ and extracted with $CH_2Cl_2$ (2×50 mL). The organic layer was dried over anhydrous $Na_2SO_4$, filtered, and concentrated under reduced pressure. The resulting residue was purified by flash column chromatography over silica gel (EtOAc in PE 40-60%, v/v) to give methyl 2-bromo-1-((2-(trimethylsilyl)ethoxy) methyl)-1H-imidazole-4-carboxylate as a light yellow solid (700 mg, 53%). $^1$H NMR (400 MHz, $CDCl_3$) δ 7.77 (s, 1H), 5.31 (s, 2H), 3.90 (s, 3H), 3.55 (dd, J=8.7, 7.7 Hz, 2H), 0.95-0.91 (m, 2H), 0.004 (s, 9H).

Preparation of methyl 2-(1-propionylindolin-5-yl)-1-((2-(trimethylsilyl)ethoxy)methyl)-1H-imidazole-4-carboxylate

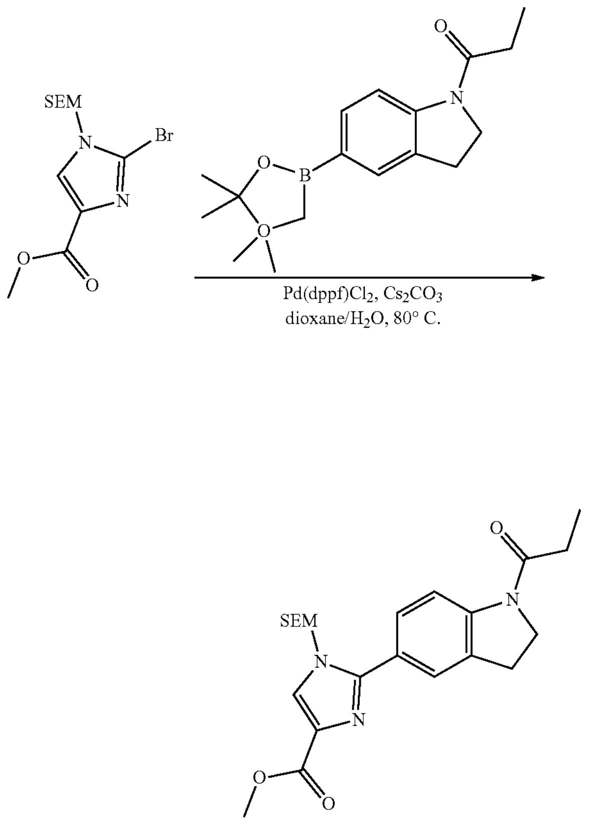

Following Procedure B, methyl 2-(1-propionylindolin-5-yl)-1-((2-(trimethylsilyl)ethoxy)methyl)-1H-imidazole-4-carboxylate was obtained as a white solid (135 mg, 27%), from methyl 2-bromo-1-((2-(trimethylsilyl)ethoxy)methyl)-1H-imidazole-4-carboxylate (380 mg, 1.13 mmol) and 1-(5-(4,4,5,5-tetramethyl-1,3,2-dioxaborolan-2-yl)indolin-1-yl) propan-1-one (340 mg, 1.13).

Preparation of 2-(1-propionylindolin-5-yl)-1-((2-(trimethylsilyl)ethoxy)methyl)-1H-imidazole-4-carboxylic acid

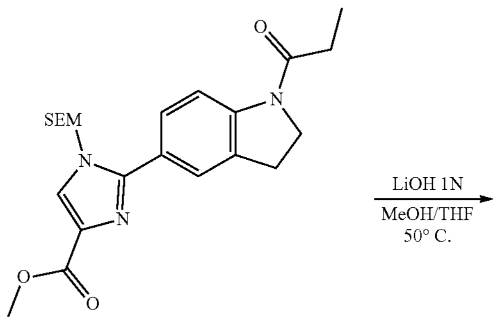

-continued

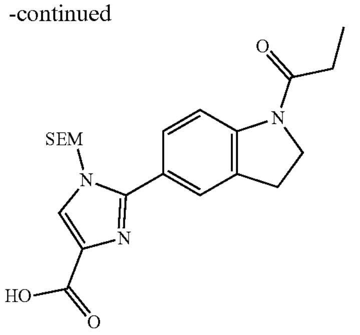

To a solution of methyl 2-(1-propionylindolin-5-yl)-1-((2-(trimethylsilyl)ethoxy)methyl)-1H-imidazole-4-carboxylate (135 mg, 0.31 mmol) in MeOH/THF (5/5 mL) was added LiOH 1N (1 mL). The mixture was stirred at 50° C. for 2 h. TLC showed the reaction was complete. It was cooled to RT, neutralized with HCl, and extracted with EtOAc. The combined organic layers were washed with brine, dried over anhydrous $Na_2SO_4$, filtered, and concentrated under reduced pressure to give 2-(1-propionylindolin-5-yl)-1-((2-(trimethylsilyl)ethoxy)methyl)-1H-imidazole-4-carboxylic acid as a white solid (120 mg, 93%).

Preparation of 2-(1-propionylindolin-5-yl)-N-(pyridin-3-ylmethyl)-1-((2-(trimethylsilyl)ethoxy)methyl)-1H-imidazole-4-carboxamide

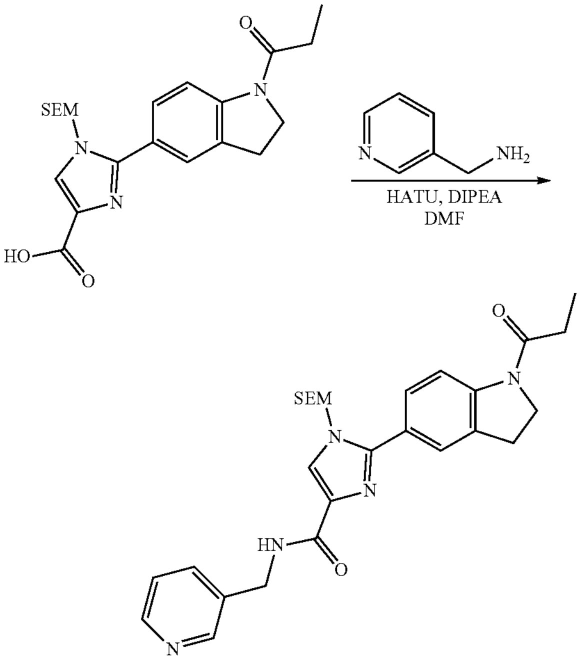

Following general Procedure D, starting from 2-(1-propionylindolin-5-yl)-1-((2-(trimethylsilyl)ethoxy)methyl)-1H-imidazole-4-carboxylic acid (120 mg, 0.29 mmol) and pyridin-3-ylmethanamine (40 mg, 0.35 mmol), 2-(1-propionylindolin-5-yl)-N-(pyridin-3-ylmethyl)-1-((2-(trimethylsilyl)ethoxy)methyl)-1H-imidazole-4-carboxamide was obtained as a white solid (130 mg, 89%). LC-MS (ESI): m/z $(M+1)^+$=506.31.

Preparation of 2-(1-propionylindolin-5-yl)-N-(pyridin-3-ylmethyl)-1H-imidazole-4-carboxamide (Compound I-208)

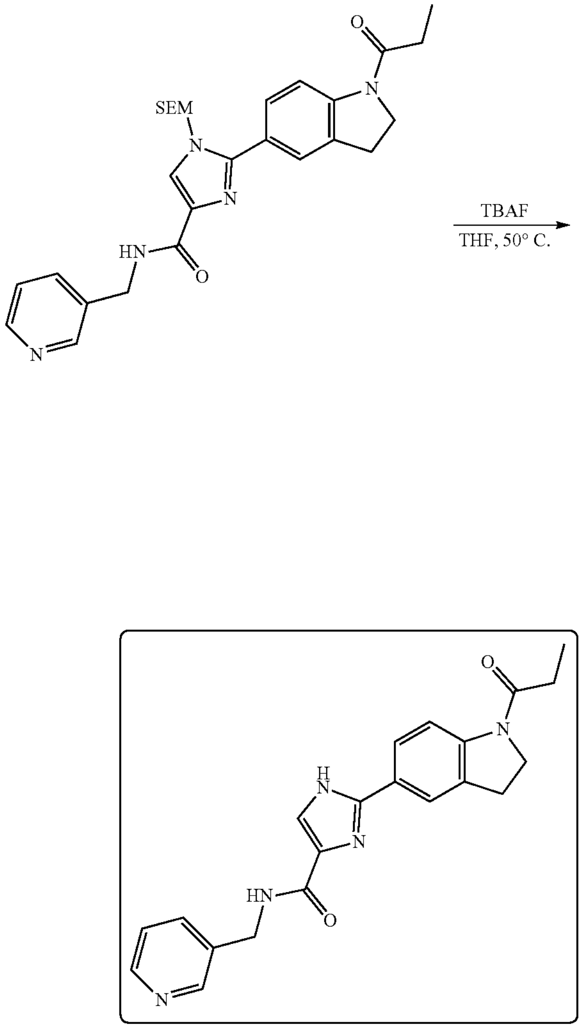

To a solution of 2-(1-propionylindolin-5-yl)-N-(pyridin-3-ylmethyl)-1-((2-(trimethylsilyl)ethoxy)methyl)-1H-imidazole-4-carboxamide (130 mg, 0.26 mmol) in THF (10 mL), was added TBAF/THF (5 mL). The mixture was stirred at 50° C. for 16 h. LC-MS showed the reaction was complete. It was cooled to RT and purified by prep-HPLC (C18, 10~100% acetonitrile in water with 0.1% formic acid) to afford 2-(1-propionylindolin-5-yl)-N-(pyridin-3-ylmethyl)-1-((2-(trimethylsilyl)ethoxy)methyl)-1H-imidazole-4-carboxamide as a white solid (3.4 mg, 26%). LC-MS (ESI): m/z (M+1)+/(M+1)+/2=376.23/188.62. $^{1}$H NMR (400 MHz, DMSO-$d_6$) δ 12.84 (s, 1H), 8.56 (t, J=7.1 Hz, 2H), 8.45 (dd, J=4.7, 1.3 Hz, 1H), 8.13 (d, J=8.2 Hz, 1H), 7.87 (s, 1H), 7.79 (d, J=7.9 Hz, 1H), 7.72 (dd, J=7.4, 5.5 Hz, 2H), 7.35 (dd, J=7.7, 4.8 Hz, 1H), 4.47 (d, J=6.2 Hz, 2H), 4.12 (t, J=8.4 Hz, 2H), 3.19 (t, J=8.3 Hz, 2H), 2.46 (d, J=7.2 Hz, 2H), 1.07 (t, J=7.3 Hz, 3H).

Synthesis of I-(1-propionylindolin-5-yl)-N-(pyridin-3-ylmethyl)azetidine-3-carboxamide (Compound I-209)

Preparation of I-(5-(4,4,5,5-tetramethyl-1,3,2-dioxaborolan-2-yl)indolin-1-yl)propan-1-one

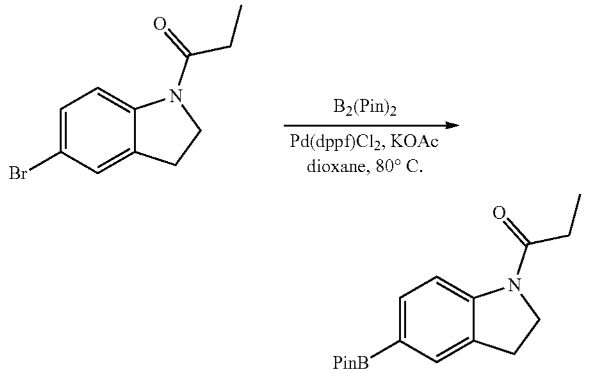

Following Procedure G, 1-(5-(4,4,5,5-tetramethyl-1,3,2-dioxaborolan-2-yl)indolin-1-yl)propan-1-one was obtained as a white solid (1.24 g, quantitative yield) from 1-(5-bromoindolin-1-yl)propan-1-one (1.0 g, 3.93 mmol) and 4,4,4',4',5,5,5',5'-octamethyl-2,2'-bi(1,3,2-dioxaborolane) (1.5 g, 5.90 mmol). LC-MS (ESI): m/z $(M+1)^+$=302.26.

Preparation of (1-propionylindolin-5-yl)boronic acid

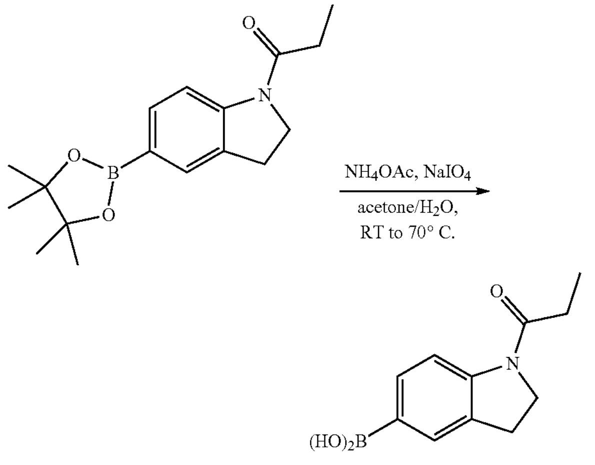

To a mixture of 1-(5-(4,4,5,5-tetramethyl-1,3,2-dioxaborolan-2-yl)indolin-1-yl)propan-1-one (500 mg, 1.66 mmol) in acetone/water (10/10 mL), were added $NaIO_4$ (800 mg, 3.74) and $NH_4OAc$ (288 mg, 3.74 mmol) The reaction mixture was stirred at RT for 16 h, then at 70° C. for 4 h. It was concentrated under reduced pressure. The resulting residue was washed with EtOH, filtered, and concentrated under reduced pressure to give (1-propionylindolin-5-yl) boronic acid as a white solid (260 mg, 70%). LC-MS (ESI): m/z $(M+1)^+$=220.21.

Preparation of methyl 1-(1-propionylindolin-5-yl)azetidine-3-carboxylate

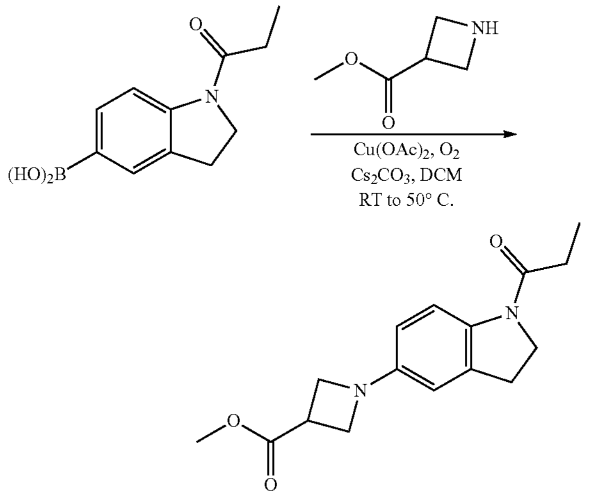

To a mixture of (1-propionylindolin-5-yl)boronic acid (100 mg, 0.46 mmol) in $CH_2Cl_2$ (5 mL), were added methyl azetidine-3-carboxylate (106 mg, 0.93), $Et_3N$ (94 mg, 0.93 mmol) and $Cu(OAc)_2$ (10 mg, 0.05 mmol). The reaction mixture was stirred at RT for 16 h under 02, then at 50° C. for 2 h. It was then purified by flash column chromatography over silica gel (EtOAc in PE 30-50%, v/v) to give methyl 1-(1-propionylindolin-5-yl)azetidine-3-carboxylate as a white solid (70 mg, 53%). LC-MS (ESI): m/z $(M+1)^+$ =289.16.

Preparation of 1-(1-propionylindolin-5-yl)azetidine-3-carboxylic acid

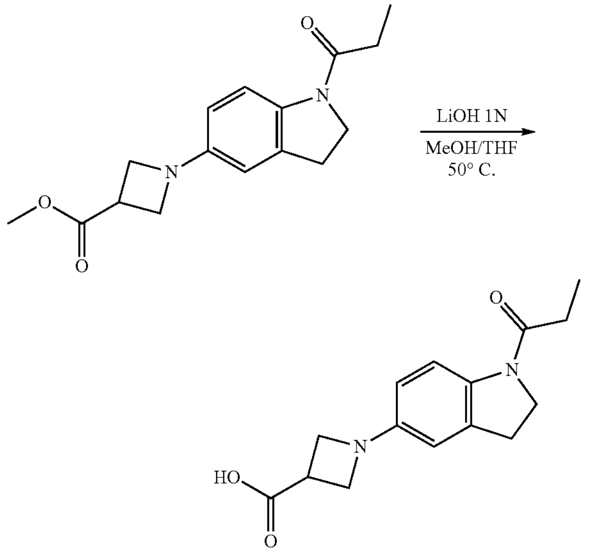

To a solution of methyl 1-(1-propionylindolin-5-yl)azetidine-3-carboxylate (70 mg, 0.24 mmol) in MeOH/THF (5/5 mL), was added LiOH 1N (1 mL). The reaction mixture was stirred at 50° C. overnight. It was then cooled to RT, neutralized with HCl 1 N, and concentrated under reduced pressure to give 1-(1-propionylindolin-5-yl)azetidine-3-carboxylic acid as a white solid (60 mg, 90%). LC-MS (ESI): m/z $(M+1)^+=274.16$.

Preparation of 1-(1-propionylindolin-5-yl)-N-(pyridin-3-ylmethyl)azetidine-3-carboxamide (Compound I-209)

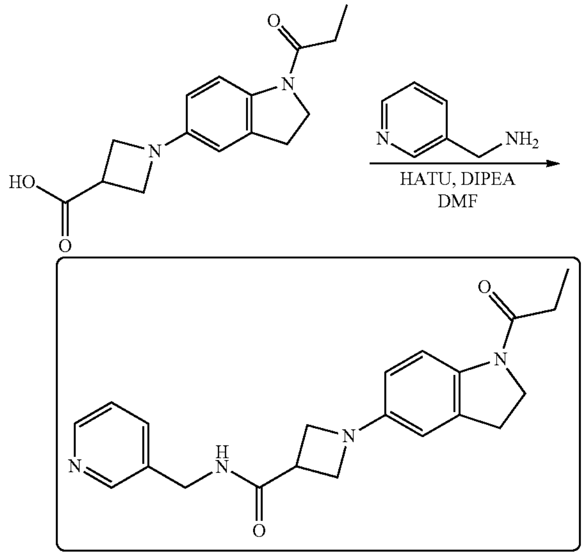

Following general Procedure D, starting from 1-(1-propionylindolin-5-yl)azetidine-3-carboxylic acid (60 mg, 0.22 mmol) and pyridin-3-ylmethanamine (36 mg, 0.44 mmol), 1-(1-propionylindolin-5-yl)-N-(pyridin-3-ylmethyl)azetidine-3-carboxamide was obtained as a white solid (2.87 mg, 3%) LC-MS (ESI): m/z $(M+1)^+=365.54$. $^1H$ NMR (400 MHz, DMSO-d) δ 8.66 (t, J=5.8 Hz, 1H), 8.50 (s, 1H), 8.45 (d, J=3.5 Hz, 1H), 7.82 (d, J=8.6 Hz, 1H), 7.66 (d, J=7.8 Hz, 1H), 7.34 (dd, J=7.7, 4.8 Hz, 1H), 6.46 (s, 1H), 6.37-6.31 (m, 1H), 5.78 (s, 1H), 5.69 (s, 1H), 5.47 (s, 1H), 4.36 (d, J=5.9 Hz, 2H), 3.97 (t, J=8.4 Hz, 2H), 3.88 (d, J=4.8 Hz, 2H), 3.01 (t, J=8.3 Hz, 2H), 2.37 (q, J=7.3 Hz, 2H), 1.03 (t, J=7.3 Hz, 3H).

Synthesis of 4'-((N-methylpropionamido)methyl)-N-(pyridin-3-ylmethyl)-[1,1'-biphenyl]-4-carboxamide (Compound I-228)

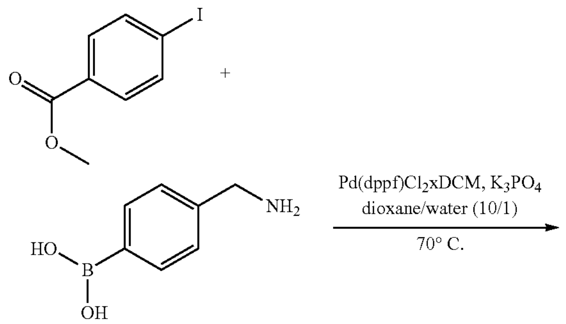

-continued

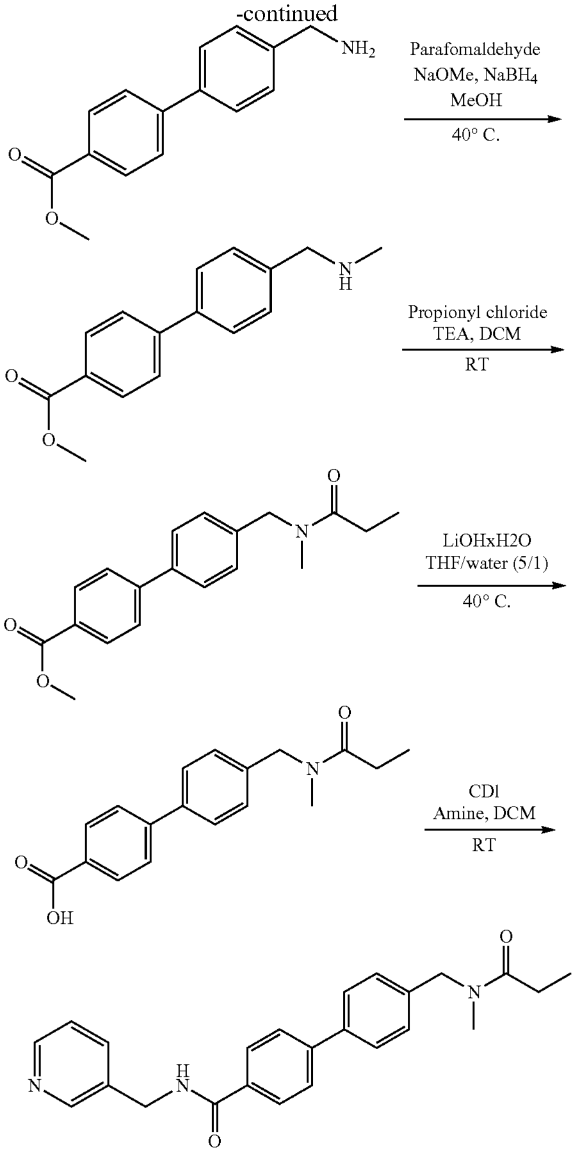

Preparation of methyl 4'-(aminomethyl)-[1,1'-biphenyl]-4-carboxylate PGP-51

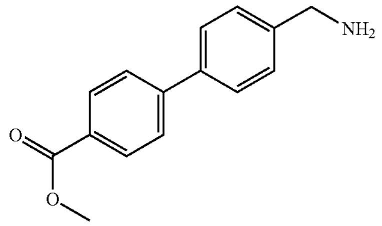 [SMILES: COC(=O)c1ccc(-c2ccc(CN)cc2)cc1]

To a solution of methyl 4-iodobenzoate (615 mg, 2.3 mmol) and (4-boronophenyl)methylammonium chloride (400 mg, 2.1 mmol) in a mixture of 1,4 dioxane (15 mL) and water (1.5 mL), was added K3PO4 (1.4 g, 6.4 mmol). The reaction mixture was degassed with Argon for 5 min when Pd(dppf)$Cl_2$xDCM (87 mg, 0.11 mmol) was added. The reaction mixture was heated to 70° C. and stirred overnight. After cooling to room temperature, water was added (15 ml). The aqueous layer was separated, and the organic layer was concentrated under reduced pressure. The remaining residue was dissolved in EtOAc, and washed with a saturated solution of $NaHCO_3$, then brine. The organic layer was concentrated under reduced pressure and the remaining residue was purified by flash chromatography (0-100% EtOAc in Cyclohexane, then 0-100% MeOH in DCM) to afford methyl 4'-(aminomethyl)-[1,1'-biphenyl]-4-carboxylate (389 mg, 76%). LC-MS (Method 2): $R_t$=1.50 min; m/z=242.03 $(M+H)^+$.

Preparation of methyl 4'-((methylamino)methyl)-[1,1'-biphenyl]-4-carboxylate

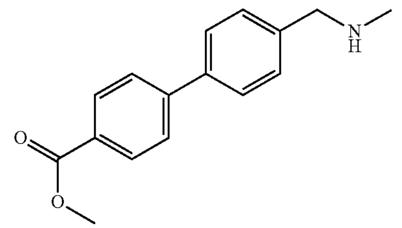 [SMILES: CNCc1ccc(-c2ccc(C(=O)OC)cc2)cc1]

To a suspension of NaOMe (333 mg, 6.2 mmol) in methanol (7.5 mL), were added paraformaldehyde (75 mg, 2.5 mmol) and methyl 4'-(aminomethyl)-[1,1'-biphenyl]-4-carboxylate (300 mg, 1.24 mmol). The reaction mixture was stirred at 40° C. overnight. $NaBH_4$ (141 mg, 3.7 mmol) was added and stirring was continued at 40° C. for 3 h. The reaction mixture was concentrated under reduced pressure. To the residue was added water, and it was extracted with DCM. The organic layer was concentrated under reduced pressure and the remaining residue was purified by flash chromatography (0-100% EtOAc in cyclohexane) to afford methyl 4'-((methylamino)methyl)-[1,1'-biphenyl]-4-carboxylate (35 mg, 9%). LC-MS (Method 2): $R_t$=0.94 min; m/z=256.07 $(M+H)^+$.

Preparation of methyl 4'-((N-methylpropionamido)methyl)-[1,1'-biphenyl]-4-carboxylate

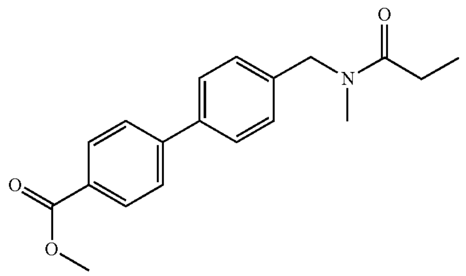 [SMILES: CCC(=O)N(C)Cc1ccc(-c2ccc(C(=O)OC)cc2)cc1]

To a solution of methyl 4'-((methylamino)methyl)-[1,1'-biphenyl]-4-carboxylate (35 mg, 0.127 mmol) in dry dichloromethane (3 mL) at 0° C., was added triethylamine (35 L, 0.25 mmol) followed by propionyl chloride (12.2 μL, 0.14 mmol). The resulting mixture was stirred at 0° C. for 5 min and then at room temperature overnight until complete conversion. The reaction mixture was washed with 0.1 M HCl (2×2 mL). Solvent was removed under reduced pressure to afford methyl 4'-((N-methylpropionamido)methyl)-[1,1'-biphenyl]-4-carboxylate (24 mg, 57%). The crude was used as such in the next step. LC-MS (Method 2): $R_t$=1.11 min; m/z=312.02 $(M+H)^+$.

Preparation of 4'-((N-methylpropionamido)methyl)-[1,1'-biphenyl]-4-carboxylic acid

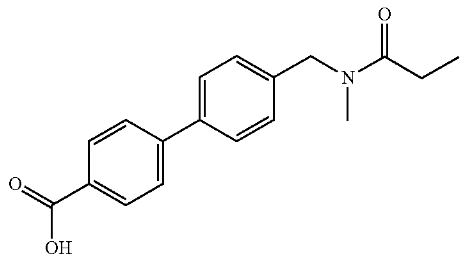 [SMILES: CCC(=O)N(C)Cc1ccc(-c2ccc(C(=O)O)cc2)cc1]

To a solution of methyl 4'-((N-methylpropionamido)methyl)-[1,1'-biphenyl]-4-carboxylate (24 mg, 0.077 mmol) in a mixture of tetrahydrofuran (5 mL) and water (1.0 mL), was added LiOH—$H_2O$ (10.7 mg, 0.44 mmol). The reaction mixture was stirred at room temperature overnight. THF was removed under reduced pressure. The aqueous layer was additionally diluted with water (4 ml) and then acidified with 1N HCl to pH=2. The resulting precipitate was collected by filtration, washed with diethyl ether and dried under reduced pressure to afford 4'-((N-methylpropionamido)methyl)-[1,1'-biphenyl]-4-carboxylic acid as a white solid (15 mg, 65%). LC-MS (Method 2): $R_t$=0.58 min; m/z=298.05 $(M+H)^+$.

Preparation of 4'-((N-methylpropionamido)methyl)-N-(pyridin-3-ylmethyl)-[1,1'-biphenyl]-4-carboxamide (Compound I-228)

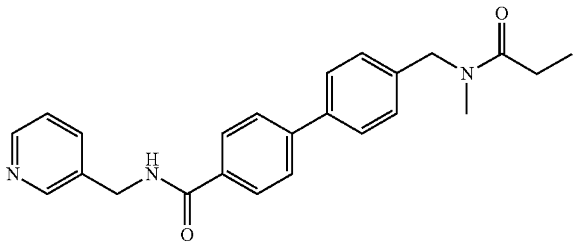 [SMILES: CCC(=O)N(C)Cc1ccc(-c2ccc(C(=O)NCc3cccnc3)cc2)cc1]

To a solution of 4'-((N-methylpropionamido)methyl)-[1,1'-biphenyl]-4-carboxylic acid (15 mg, 0.047 mmol) in dry dichloromethane (2 mL), were added DIPEA (17 μL, 0.095 mmol), HATU (22 mg, 0.057 mmol) and 3-pyridylmethanamine (4.8 μL, 0.047 mmol). The reaction mixture was stirred at room temperature for 3 h until complete conversion into the desired product. The reaction mixture was washed with water (2×5 ml). The organic layer was concentrated under reduced pressure, the remaining residue was purified by column chromatography (10% MeOH in DCM) to afford 4'-((N-methylpropionamido)methyl)-N-(pyridin-3-ylmethyl)-[1,1'-biphenyl]-4-carboxamide as a colorless oil (9 mg, 50%). LC-MS (Method 2): $R_t$=0.85 min; m/z=388.08 $(M+H)^+$. $^1H$-NMR (400 MHz, DMSO-$d_6$): δ [ppm]=1.03 (t, J=7.60 Hz, 3H) 2.39 (q, J=7.20 Hz, 2H) 2.84 (s, 2H) 2.92 (s, 3H) 4.51 (d, J=5.99 Hz, 2H) 7.27-7.33 (m, 3H) 7.68-7.80 (m, 5H) 7.95 (d, J=2.20 Hz, 2H) 8.45 (dd, J=4.65, 1.71 Hz, 1H) 8.55 (d, J=1.59 Hz, 1H) 9.13 (t, J=6.11 Hz, 1H).

Synthesis of 6-(2-methyl-4-(N-methylpropionamido)phenyl)-N-(pyridin-3-ylmethyl)nicotinamide (Compound I-285)

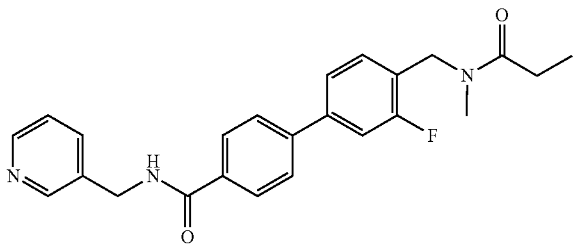 [SMILES: CCC(=O)N(C)Cc1ccc(-c2ccc(C(=O)NCc3cccnc3)cc2)cc1F]

Compound I-285 was synthesized in an essentially analogous manner to compound I-228 above. Appearance: white powder. LC-MS (Method 5): $R_t$=2.59 min; m/z=406.61 $(M+H)^+$. $^1$H-NMR (500 MHz, DMSO-$d_6$): δ [ppm]=1.04 (t, 3H), 2.38 (q, 2H), 2.94 (br. s, 3H), 4.52 (d, 2H), 4.61 (s, 2H), 7.32 (m, 2H), 7.53 (m, 2H), 7.80-7.70 (m, 3H), 7.96 (d, 2H), 8.45 (d, 1H), 8.57 (s, 1H), 8.87 (t, 1H).

Synthesis of N-((6-aminopyridin-3-yl)methyl)-4'-(N-methylpropionamido)-[1,1'-biphenyl]-4-carboxamide (Compound I-272)

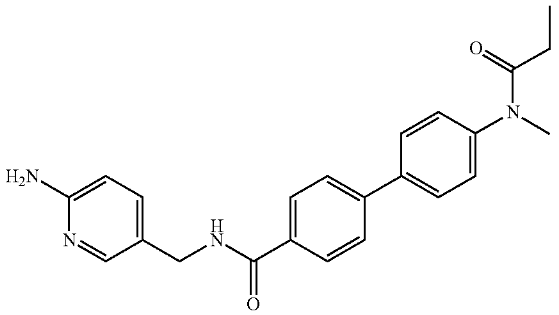 [SMILES: CCC(=O)N(C)c1ccc(-c2ccc(C(=O)NCc3ccc(N)nc3)cc2)cc1]

Compound I-272 was synthesized in an essentially analogous manner to compound I-228 above. Appearance: white powder. LC-MS (Method 6): $R_t$=2.93 min; m/z=389.58 $(M+H)^+$. $^1$H NMR (300 MHz, DMSO-$d_6$) δ ppm=0.93 (t, J=7.49 Hz, 3H) 2.10 (br. s., 2H) 3.19 (s, 3H) 4.28 (d, J=5.75 Hz, 2H) 6.40 (d, J=8.01 Hz, 2H) 7.33 (d, J=2.61 Hz, 1H) 7.36 (d, J=2.44 Hz, 1H) 7.42 (d, J=8.71 Hz, 2H) 7.78 (d, J=8.54 Hz, 4H) 7.87 (d, J=1.74 Hz, 1H) 7.95 (d, J=8.54 Hz, 2H) 8.89-8.98 (m, 1H).

Synthesis of 4'-(N-methylpropionamido)-N-((2-methylpyridin-3-yl)methyl)-[1,1'-biphenyl]-4-carboxamide (Compound I-252)

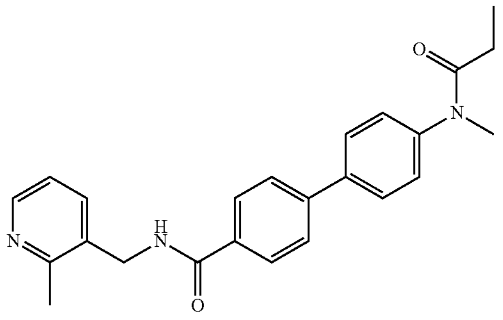 [SMILES: CCC(=O)N(C)c1ccc(-c2ccc(C(=O)NCc3cccnc3C)cc2)cc1]

Compound I-252 was synthesized in an essentially analogous manner to compound I-228 above. Appearance: white powder. LC-MS (Method 5): $R_t$=3.34 min; m/z=388.04 $(M+H)^+$. $^1$H-NMR (300 MHz, DMSO-$d_6$): δ [ppm]=0.93 (m, 3H), 2.10 (br. s, 2H), 2.55 (s, 3H), 3.19 (s, 3H), 4.49 (d, 2H), 7.28 (m, 1H), 7.43 (d, 2H), 7.70 (d, 1H), 7.75-7.84 (m, 4H), 8.00 (d, 2H), 8.37 (d, 1H), 9.08 (t, 1H).

Synthesis of ethyl methyl(4'-((pyridin-3-ylmethyl)carbamoyl)-[1,1'-biphenyl]-4-yl)carbamate (Compound I-231)

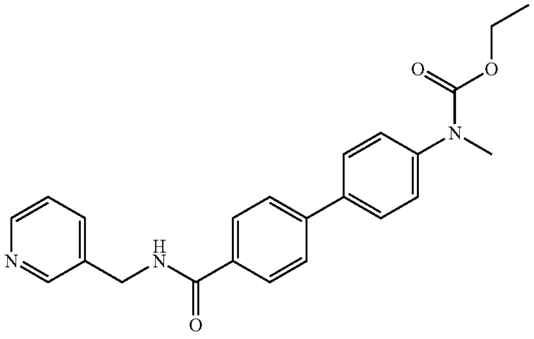 [SMILES: CCOC(=O)N(C)c1ccc(-c2ccc(C(=O)NCc3cccnc3)cc2)cc1]

Compound I-231 was synthesized in an essentially analogous manner to compound I-228 above. Appearance: white powder. LC-MS (Method 2): $R^t$=3.88 min; m/z=390.00 $(M+H)^+$. $^1$H-NMR (400 MHz, DMSO-$d_6$): δ [ppm]=1.18 (t, J=7.02 Hz, 3H) 3.26 (s, 3H) 4.10 (q, J=7.12 Hz, 2H) 4.52 (d, J=5.80 Hz, 2H) 7.36 (dd, J=7.63, 4.58 Hz, 1H) 7.42 (d, J=8.54 Hz, 2H) 7.71-7.75 (m, 3H) 7.98 (d, J=8.24 Hz, 2H) 8.46 (dd, J=4.58, 1.53 Hz, 1H) 8.57 (d, J=1.83 Hz, 1H) 9.15 (t, J=5.95 Hz, 1H).

Synthesis of 4'-(N-methylbutyramido)-N-(pyridin-3-ylmethyl)-[1,1'-biphenyl]-4-carboxamide (Compound I-230)

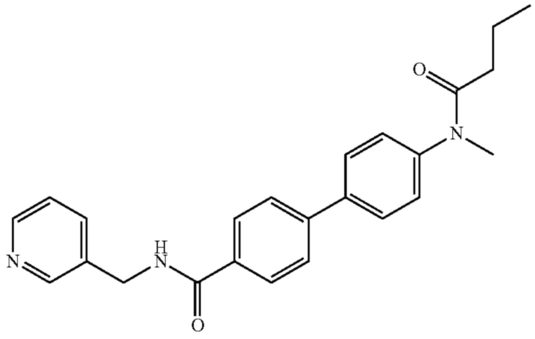 [SMILES: CCCC(=O)N(C)c1ccc(-c2ccc(C(=O)NCc3cccnc3)cc2)cc1]

Compound I-230 was synthesized in an essentially analogous manner to compound I-228 above. Appearance: brown oil. LC-MS (Method 6): $R_t$=3.52 min; m/z=388.04 $(M+H)^+$. $^1$H NMR (500 MHz, DMSO-$d_6$): δ [ppm]=0.79 (br. s., 3H) 1.49 (sxt, J=7.20 Hz, 2H) 2.07 (br. s., 2H) 3.20 (br. s., 3H) 4.52 (d, J=5.80 Hz, 2H) 7.37 (dd, J=7.78, 4.73 Hz, 1H) 7.42 (d, J=8.54 Hz, 2H) 7.72-7.76 (m, 1H) 7.77-7.85 (m, 4H) 7.99 (d, J=8.24 Hz, 2H) 8.47 (dd, J=4.88, 1.53 Hz, 1H) 8.57 (d, J=1.83 Hz, 1H) 9.16 (t, J=5.95 Hz, 1H).

Synthesis of 3'-methyl-4'-(N-methylpropionamido)-N-(pyridin-3-ylmethyl)-[1,1'-biphenyl]-4-carboxamide (Compound I-215)

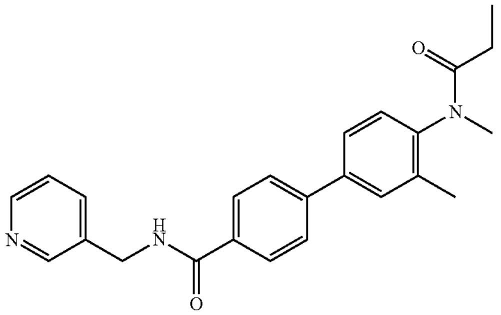 [SMILES: CCC(=O)N(C)c1ccc(-c2ccc(C(=O)NCc3cccnc3)cc2)cc1C]

Compound I-215 was synthesized in an essentially analogous manner to compound I-228 above. Appearance: white solid. LC-MS (Method 1): $R_t$=0.69 min; m/z=388.17 $(M+H)^+$. $^1$H NMR (500 MHz, DMSO-$d_6$) δ [ppm]=0.92 (t, J=7.48 Hz, 3H) 1.78-1.88 (m, 1H) 1.92-2.02 (m, 1H) 2.24 (s, 3H) 3.08 (s, 3H) 4.52 (d, J=5.80 Hz, 2H) 7.33-7.39 (m, 2H) 7.60-7.68 (m, 1H) 7.72-7.76 (m, 2H) 7.82 (d, J=8.24 Hz, 2H) 7.99 (d, J=8.54 Hz, 2H) 8.46 (d, J=4.58 Hz, 1H) 8.57 (s, 1H) 9.17 (t, J=5.95 Hz, 1H).

Synthesis of 2'-chloro-4'-(N-methylpropionamido)-N-(pyridin-3-ylmethyl)-[1,1'-biphenyl]-4-carboxamide (Compound I-224)

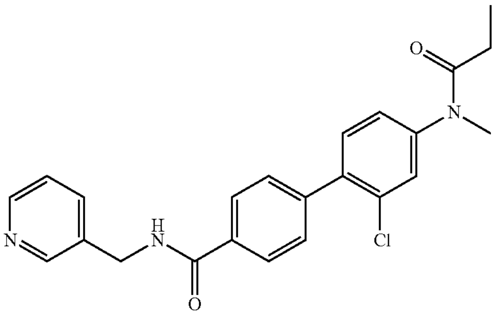 [SMILES: CCC(=O)N(C)c1ccc(-c2ccc(C(=O)NCc3cccnc3)cc2)c(Cl)c1]

Compound I-224 was synthesized in an essentially analogous manner to compound I-228 above. Appearance: white powder. LC-MS (Method 1): $R_t$=0.71 min; m/z=408.04 $(M+H)^+$. $^1$H-NMR (300 MHz, DMSO-$d_6$): δ [ppm]=0.97 (t, 3H), 2.18 (br. s, 2H), 3.22 (s, 3H), 4.53 (d, 2H), 7.38 (dd, 1H), 7.42 (dd, 1H), 7.50 (d, 1H), 7.57 (d, 2H), 7.66 (d, 1H), 7.75 (dt, 1H), 7.98 (d, 2H), 8.47 (dd, 1H), 8.58 (d, 1H), 9.20 (t, 1H).

Synthesis of 3'-chloro-4'-(N-methylpropionamido)-N-(pyridin-3-ylmethyl)-[1,1'-biphenyl]-4-carboxamide (Compound I-225)

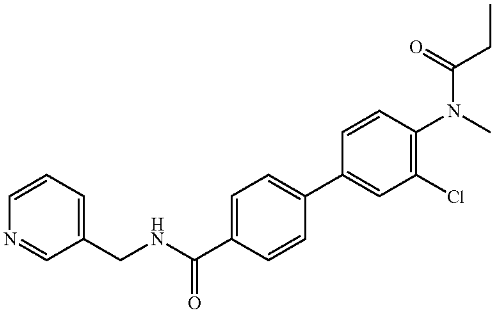 [SMILES: CCC(=O)N(C)c1ccc(-c2ccc(C(=O)NCc3cccnc3)cc2)cc1Cl]

Compound I-225 was synthesized in an essentially analogous manner to compound I-228 above. Appearance: white powder. LC-MS (Method 1): $R_t$=0.74 min; m/z=408.56 $(M+H)^+$. $^1$H-NMR (500 MHz, DMSO-$d_6$): δ [ppm]=0.94 (t, 3H), 1.83-2.06 (m, 2H), 3.11 (s, 3H), 4.52 (d, 2H), 7.37 (m, 1H), 7.65 (d, 1H), 7.74 (d, 1H), 7.83 (d, 1H), 7.88 (d, 2H), 7.97-8.06 (m, 3H), 8.47 (d, 1H), 8.57 (s, 1H), 9.21 (t, 1H).

Synthesis of N-((2-fluoropyridin-3-yl)methyl)-4'-(N-methylpropionamido)-[1,1'-biphenyl]-4-carboxamide (Compound I-264)

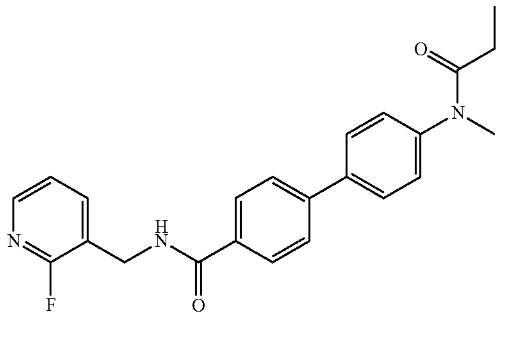 [SMILES: CCC(=O)N(C)c1ccc(-c2ccc(C(=O)NCc3cccnc3F)cc2)cc1]

Compound I-264 was synthesized in an essentially analogous manner to compound I-228 above. Appearance: white powder. LC-MS (Method 6): $R_t$=3.54 min; m/z=392.56 $(M+H)^+$. $^1$H NMR (300 MHz, DMSO-$d_6$) δ [ppm]: 0.93 (d, J=14.98 Hz, 3H) 2.11 (br. s., 2H) 3.19 (s, 3H) 4.51 (d, J=5.57 Hz, 2H) 7.34 (ddd, J=7.23, 5.14, 1.74 Hz, 1H) 7.43 (d, J=8.36 Hz, 2H) 7.80 (dd, J=8.45, 6.36 Hz, 4H) 7.89 (t, J=9.67 Hz, 1H) 7.99 (d, J=8.54 Hz, 2H) 8.13 (d, J=4.35 Hz, 1H) 9.15 (t, J=6.01 Hz, 1H).

Synthesis of 6-(3-methyl-4-(N-methylpropionamido)phenyl)-N-(pyridin-3-ylmethyl)nicotinamide (Compound I-232)

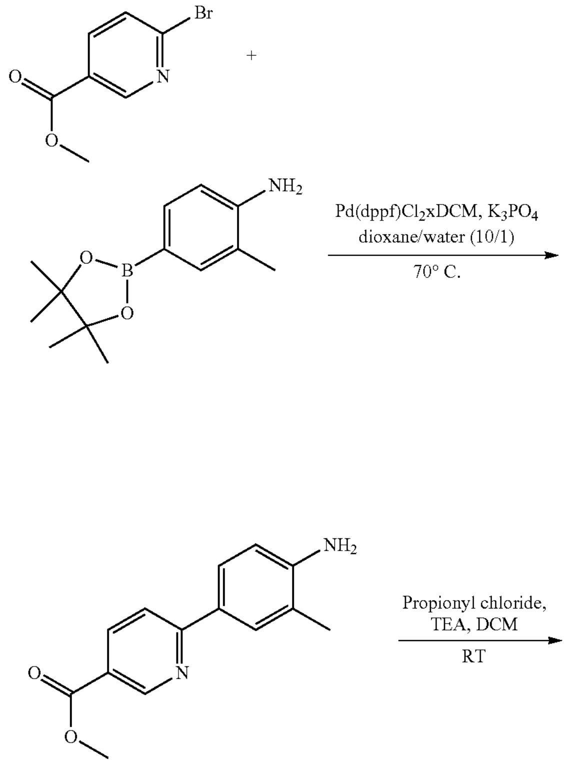

-continued

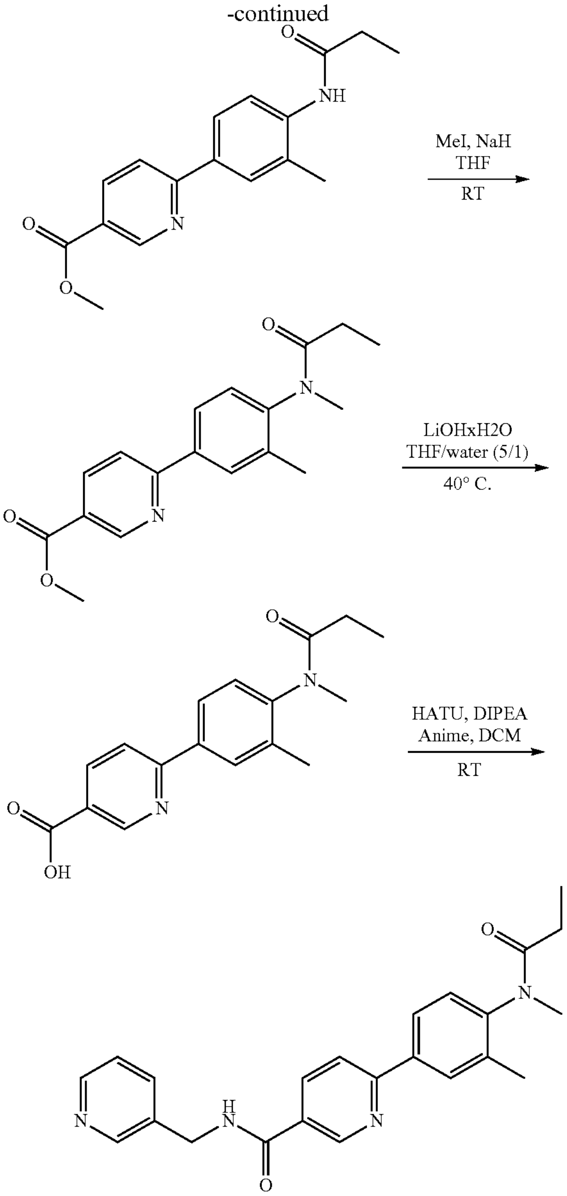

Preparation of methyl 6-(4-amino-3-methylphenyl)nicotinate

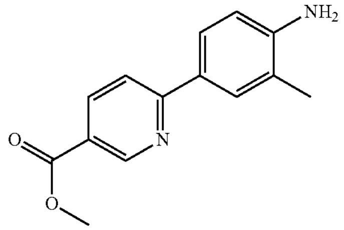 [SMILES: COC(=O)c1ccc(-c2ccc(N)c(C)c2)nc1]

To a solution of 2-methyl-4-(4,4,5,5-tetramethyl-1,3,2-dioxaborolan-2-yl)aniline (200 mg, 0.858 mmol) and methyl 6-bromopyridine-3-carboxylate (271 mg, 1.25 mmol) in a mixture of 1,4-dioxane (13 mL) and water (3 mL), was added $K_3PO4$ (728 mg, 3.43 mmol). The reaction mixture was degassed with Argon for 5 min when $Pd(dppf)Cl_2\times$ DCM (49 mg, 0.0601 mmol) was added. The reaction mixture was heated to 70° C. and stirred overnight. After cooling to room temperature, the organic layer was concentrated under reduced pressure. The remaining residue was dissolved in EtOAC (50 mL), and washed with a saturated solution of $NaHCO_3$ and brine. The organic layer was concentrated under reduced pressure to afford methyl 6-(4-amino-3-methylphenyl)nicotinate (105 mg, 45%). LC-MS (Method 2): $R_t$=0.93 min; m/z=243.07 $(M+H)^+$.

Preparation of methyl 6-(3-methyl-4-propionamidophenyl)nicotinate

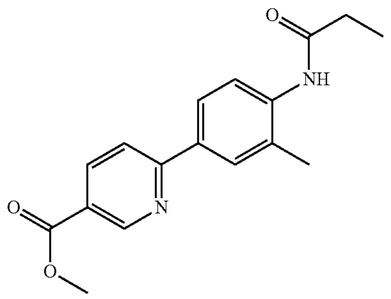 [SMILES: CCC(=O)Nc1ccc(-c2ccc(C(=O)OC)cn2)cc1C]

To a solution of methyl 6-(4-amino-3-methylphenyl)nicotinate (105 mg, 0.39 mmol) in dry dichloromethane (5 mL) at 0° C., was added triethylamine (110 μL, 0.77 mmol) followed by propionyl chloride (37 μL, 0.42 mmol). The resulting mixture was stirred at 0° C. for 5 min and then at room temperature for 3 h until complete conversion into target product. The reaction mixture was washed with 0.1 M HCl (2×2 mL). The solvent was removed under reduced pressure to afford methyl 6-(3-methyl-4-propionamidophenyl)nicotinate (113 mg, 95%) which was used as such in the next step. LC-MS (Method 2): $R_t$=0.92 min; m/z=299.05 $(M+H)^+$ Preparation of methyl 6-(3-methyl-4-(N-methylpropionamido)phenyl)nicotinate

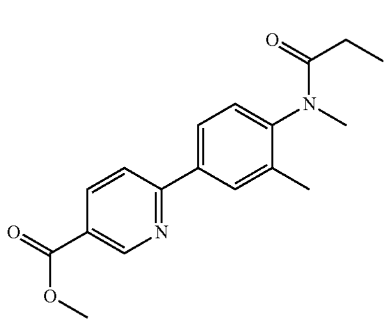 [SMILES: CCC(=O)N(C)c1ccc(-c2ccc(C(=O)OC)cn2)cc1C]

To a solution of methyl 6-(3-methyl-4-propionamidophenyl)nicotinate (113 mg, 97%, 0.12 mmol) in dry tetrahydrofuran (10 mL), was added NaH (16 mg, 0.40 mmol). The reaction mixture was stirred at room temperature for 10 min. Then MeI (86 μL, 0.44 mmol) was added and the reaction mixture was stirred at room temperature overnight. After removal of volatile components from the mixture, water was added and the mixture was extracted with DCM. The organic layers were combined, dried and filtered to afford methyl 6-(3-methyl-4-(N-methylpropionamido)phenyl)nicotinate (62 mg, 48%) as an orange oil that was used as such in the next step. LC-MS (Method 2): $R_t$=1.02 min; m/z=313.01 $(M+H)^+$.

Preparation of 6-(3-methyl-4-(N-methylpropionamido)phenyl)nicotinic acid

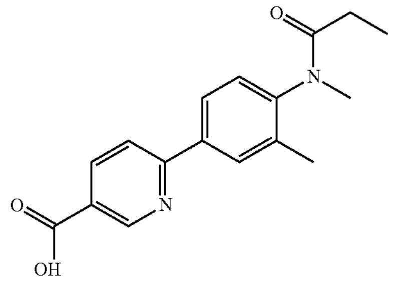 [SMILES: CCC(=O)N(C)c1ccc(-c2ccc(C(=O)O)cn2)cc1C]

To a solution of methyl 6-(3-methyl-4-(N-methylpropionamido)phenyl)nicotinate (62 mg, 0.17 mmol) in a mixture of tetrahydrofuran (5 mL) and water (1.0 mL), was added LiOH—$H_2O$ (26 mg, 1 mmol). The reaction mixture was stirred at room temperature overnight. THF was removed under reduced pressure. The aqueous layer was additionally diluted with water (4 ml) and acidified with 1N HCl to pH=2. The aqueous layer was extracted with EtOAc (2×20 ml). The organic layers were combined and evaporated to afford 6-(3-methyl-4-(N-methylpropionamido)phenyl)nicotinic acid (50 mg, 84%) that was used as such in the next step. LC-MS (Method 2): $R_t$=0.52 min; m/z=299.04 $(M+H)^+$.

Preparation of 6-(3-methyl-4-(N-methylpropionamido)phenyl)-N-(pyridin-3-ylmethyl)nicotinamide (Compound I-232)

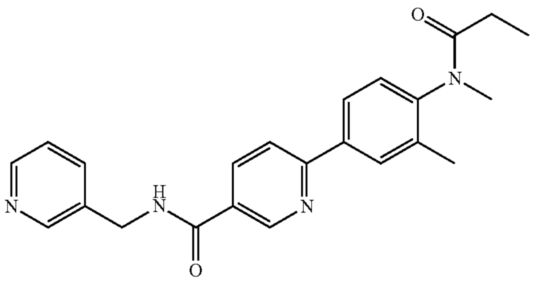 [SMILES: CCC(=O)N(C)c1ccc(-c2ccc(C(=O)NCc3cccnc3)cn2)cc1C]

To a solution of 6-(3-methyl-4-(N-methylpropionamido) phenyl)nicotinic acid (50 mg, 88%, 0.15 mmol) in dry dichloromethane (5 mL), were added DIPEA (51 μL, 0.29 mmol), HATU (67 mg, 0.18 mmol) and 3-pyridylmethanamine (15 μL, 0.15 mmol). The reaction mixture was stirred at room temperature for 3 h until complete conversion into the desired product. The reaction mixture was washed with water (2×5 ml). The organic layer was concentrated under reduced pressure, the remaining residue was purified by column chromatography (10% MeOH in DCM) to afford 6-(3-methyl-4-(N-methylpropionamido) phenyl)-

N-(pyridin-3-ylmethyl)nicotinamide as a colorless oil (23 mg, 39%). LC-MS (Method 6): $R_t$=2.89 min; m/z=389.00 $(M+H)^+$. $^1$H-NMR (400 MHz, DMSO-$d_6$): δ [ppm]=0.91 (t, J=7.46 Hz, 3H) 1.77-1.88 (m, 1H) 1.90-2.03 (m, 1H) 2.25 (s, 3H) 3.08 (s, 3H) 4.54 (d, J=5.87 Hz, 2H) 7.32-7.41 (m, 2H) 7.71-7.79 (m, 1H) 8.04 (dd, J=8.13, 1.77 Hz, 1H) 8.13 (td, J=8.25, 1.47 Hz, 2H) 8.32 (dd, J=8.38, 2.38 Hz, 1H) 8.47 (dd, J=4.83, 1.65 Hz, 1H) 8.54-8.62 (m, 1H) 9.12 (dd, J=2.32, 0.73 Hz, 1H) 9.31 (t, J=5.87 Hz, 1H).

Synthesis of 5-(2-fluoro-4-(N-methylpropionamido) phenyl)-N-(pyridin-3-ylmethyl)picolinamide (Compound I-296)

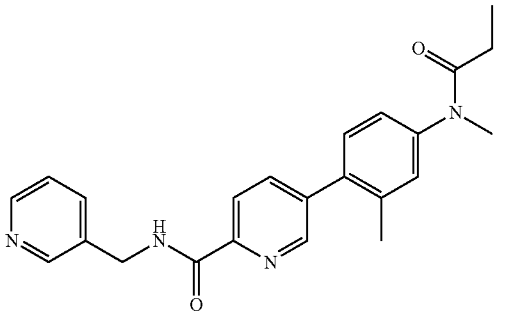 [SMILES: CCC(=O)N(C)c1ccc(-c2ccc(C(=O)NCc3cccnc3)nc2)c(C)c1]

Compound I-296 was synthesized in an essentially analogous manner to compound I-232 above. Appearance: yellow paste. LC-MS (Method 6): $R_t$=3.29 min; m/z=393.04 $(M+H)^+$. $^1$H-NMR (300 MHz, DMSO-$d_6$): δ [ppm]=0.95 (t, 3H) 2.20 (m, 2H) 3.22 (s, 3H) 4.56 (d, 2H) 7.36 (d, 1H) 7.52 (m, 2H), 7.73 (t, 1H), 7.95 (d, 1H), 8.08-8.25 (m, 2H), 8.85 (s, 1H), 9.58 (t, 1H).

Synthesis of 5-(3-fluoro-4-(N-methylpropionamido) phenyl)-N-(pyridin-3-ylmethyl)picolinamide (Compound I-284)

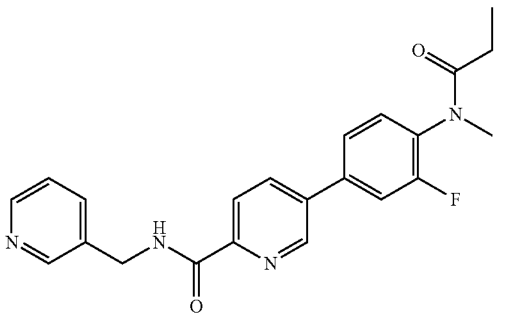 [SMILES: CCC(=O)N(C)c1ccc(-c2ccc(C(=O)NCc3cccnc3)nc2)cc1F]

Compound I-284 was synthesized in an essentially analogous manner to compound I-232 above. Appearance: white powder. LC-MS (Method 6): $R_t$=2.16 min; m/z=393.02 $(M+H)^+$. $^1$H-NMR (500 MHz, DMSO-$d_6$): δ [ppm]=0.94 (t, 3H), 2.03 (m, 2H), 3.15 (s, 3H), 4.53 (d, J=6.4 Hz, 2H), 7.34 (m, 1H), 7.63-7.78 (m, 3H), 7.93 (m, 1H), 8.12 (d, J=8.4 Hz, 1H,), 8.37 (d, J=8.4 Hz, 1H), 8.45 (dd, J=4.9, 1.8 Hz, 1H), 8.57 (d, J=1.8 Hz, 1H), 9.53 (t, J=6.4 Hz, 1H).

Synthesis of 6-(2-methyl-4-(N-methylpropionamido)phenyl)-N-(pyridin-3-ylmethyl)nicotinamide (Compound I-246)

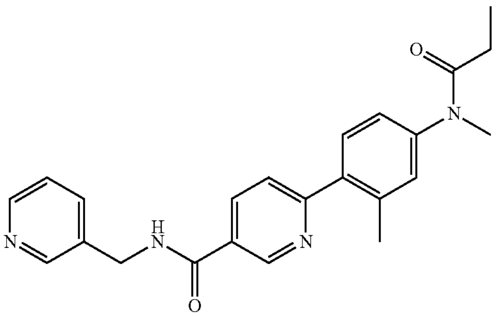 [SMILES: CCC(=O)N(C)c1ccc(-c2ccc(C(=O)NCc3cccnc3)cn2)c(C)c1]

Compound I-246 was synthesized in an essentially analogous manner to compound I-232 above. Appearance: white paste. LC-MS (Method 6): $R_t$=2.78 min; m/z=389.62 $(M+H)^+$. $^1$H-NMR (300 MHz, $CDCl_3$): δ [ppm]=1.04 (t, 3H), 1.87 (br. s, 3H), 2.12 (br. s, 2H), 2.35 (s, 3H), 3.15 (s, 3H), 4.69 (d, 2H), 6.80 (m, 1H), 7.09 (m, 1H), 7.29 (m, 1H), 7.42 (d, 1H), 7.50 (d, 1H), 7.75 (d, 1H), 8.23 (dd, 1H), 8.54 (d, 1H), 8.62 (s, 1H), 9.07 (t, 1H).

Synthesis of 2-(4-(N-methylpropionamido)phenyl)-N-(pyridin-3-ylmethyl)thiazole-4-carboxamide (Compound I-241)

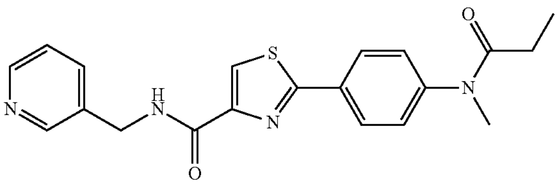 [SMILES: CCC(=O)N(C)c1ccc(-c2nc(C(=O)NCc3cccnc3)cs2)cc1]

Compound I-241 was synthesized in an essentially analogous manner to compound I-232 above. Appearance: white powder. LC-MS (Method 1): $R_t$=0.66 min; m/z=381.55 $(M+H)^+$. $^1$H-NMR (500 MHz, DMSO-$d_6$): δ [ppm]=0.94 (m, 3H), 2.14 (br. s, 2H), 3.21 (s, 3H), 4.52 (d, 2H), 7.36 (m, 1H), 7.49 (d, 2H), 7.75 (d, 1H), 8.11 (d, 2H), 8.35 (s, 1H), 8.46 (d, 1H), 8.57 (s, 1H), 9.21 (t, 1H).

Synthesis of 5-(3-methyl-4-(N-methylpropionamido)phenyl)-N-(pyridin-3-ylmethyl)picolinamide (Compound I-227)

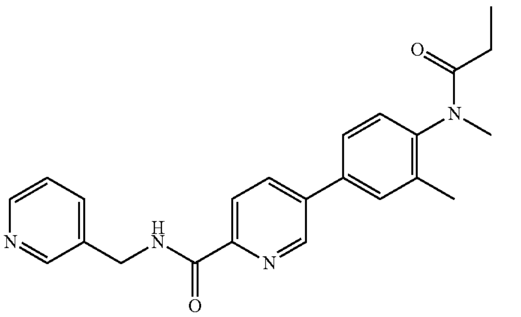

Compound I-227 was synthesized in an essentially analogous manner to compound I-232 above. Appearance: colorless oil. LC-MS (Method 2): $R_t$=0.85 min; m/z=388.08 $(M+H)^+$. $^1$H-NMR (400 MHz, DMSO-$d_6$): δ [ppm]=0.91 (d, J=14.9 Hz, 3H), 1.76-1.88 (m, 1H), 1.91-2.02 (m, 1H), 2.25 (s, 3H), 3.08 (s, 3H), 4.53 (d, J=6.2 4 Hz, 2H), 7.34 (dd, J=7.83, 4.77 Hz, 1H), 7.40 (d, J=8.19 Hz, 1H), 7.68-7.76 (m, 2H), 7.82 (d, J=2.08 Hz, 1H), 8.11 (dd, J=8.13, 0.67 Hz, 1H), 8.30 (dd, J=8.19, 2.32 Hz, 1H), 8.44 (dd, J=4.77, 1.71 Hz, 1H), 8.56 (d, J=1.83 Hz, 1H), 8.97 (dd, J=2.32, 0.73 Hz, 1H), 9.50 (t, J=6.36 Hz, 1H).

Synthesis of 3'-methoxy-4'-(N-methylpropionamido)-N-(pyridin-3-ylmethyl)-[1,1'-biphenyl]-4-carboxamide (Compound I-248)

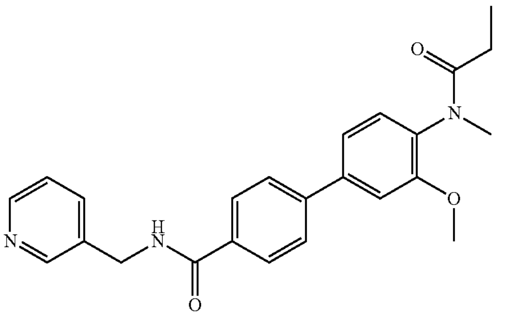 [SMILES: CCC(=O)N(C)c1ccc(-c2ccc(C(=O)NCc3cccnc3)cc2)cc1OC]

Compound I-248 was synthesized in an essentially analogous manner to compound I-232 above. Appearance: white powder. LC-MS (Method 6): $R_t$=3.30 min; m/z=404.01 $(M+H)^+$. $^1$H-NMR (300 MHz, DMSO-$d_6$): δ [ppm]=0.90 (t, 3H), 1.82-2.08 (m, 2H), 3.06 (s, 3H), 3.93 (s, 3H), 4.53 (d, 2H), 7.33-7.41 (m, 3H), 7.44 (s, 1H), 7.75 (dt, 1H), 7.86 (d, 2H), 8.00 (d, 2H), 8.47 (dd, 1H), 8.58 (d, 1H), 9.18 (t, 1H)

Synthesis of 3'-hydroxy-4'-(N-methylpropionamido)-N-(pyridin-3-ylmethyl)-[1,1'-biphenyl]-4-carboxamide (Compound I-260)

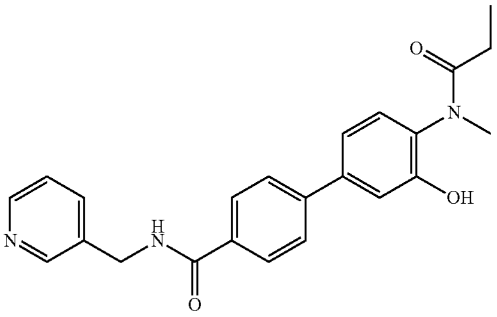

Compound I-260 was synthesized in an essentially analogous manner to compound I-232 above. Appearance: white powder. LC-MS (Method 6): $R_t$=2.43 min; m/z=390.00 $(M+H)^+$. $^1$H-NMR (500 MHz, DMSO-$d_6$): δ [ppm]=0.92 (t, 3H), 1.92-2.09 (m, 2H), 3.06 (s, 3H), 4.52 (d, 2H), 7.20 (dd, 1H), 7.25 (d, 1H), 7.29 (d, 1H), 7.37 (dd, 1H), 7.70-7.75 (m, 3H), 7.98 (d, 2H), 8.47 (dd, 1H), 8.57 (d, 1H), 9.15 (t, 1H), 10.06 (br. s, 1H).

Synthesis of 3-fluoro-2'-methyl-4'-(N-methylpropionamido)-N-(pyridin-3-ylmethyl)-[1,1'-biphenyl]-4-carboxamide (Compound I-271)

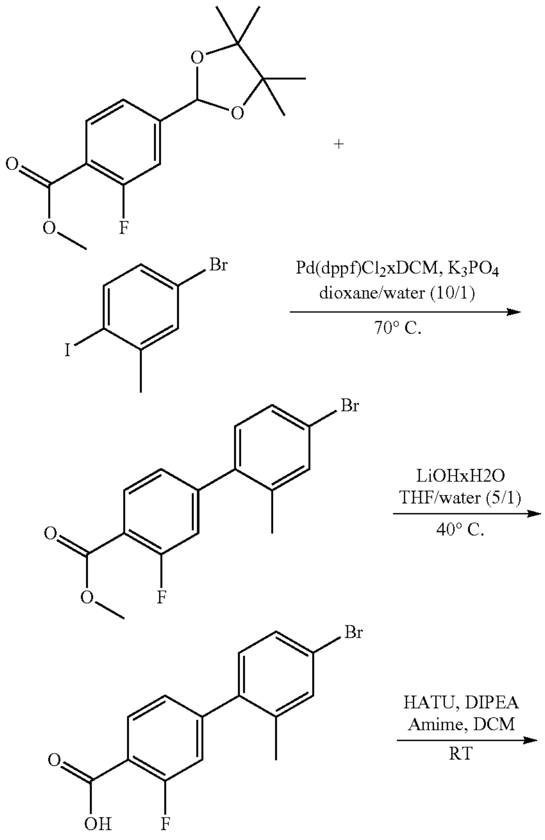

-continued

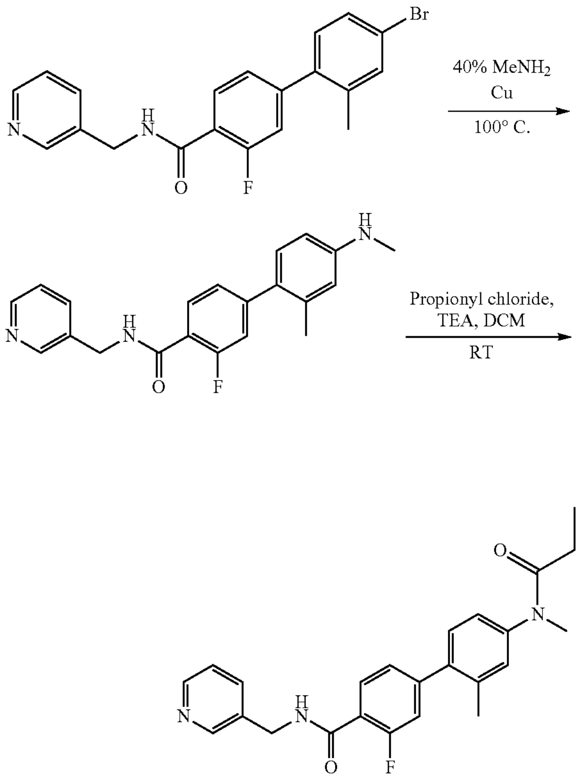

Preparation of methyl 4'-bromo-3-fluoro-2'-methyl-[1,1'-biphenyl]-4-carboxylate

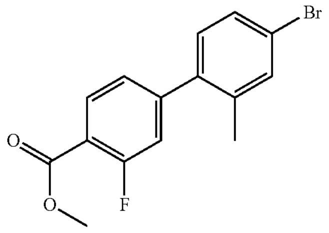 [SMILES: COC(=O)c1ccc(-c2ccc(Br)cc2C)cc1F]

To a solution of methyl 2-fluoro-4-(4,4,5,5-tetramethyl-1,3,2-dioxaborolan-2-yl)benzoate (200 mg, 0.71 mmol) and 4-bromo-1-iodo-2-methyl-benzene (110 μL, 0.79 mmol) in a mixture of 1,4-dioxane (11 mL) and water (1.1 mL), was added $K_3PO4$ (455 mg, 2.1 mmol). The reaction mixture was degassed with Argon for 5 min when Pd(dppf)$Cl_2$× DCM (29 mg, 0.036 mmol) was added. The reaction mixture was heated to 70° C. and stirred overnight. After cooling to room temperature, water was added (15 ml) and the aqueous layer was separated and removed. The organic layer was concentrated under reduced pressure. The remaining residue was dissolved in EtOAC, and washed with a saturated solution of $NaHCO_3$, then brine. The organic layer was concentrated under reduced pressure to afford methyl 4'-bromo-3-fluoro-2'-methyl-[1,1'-biphenyl]-4-carboxylate (300 mg) which was used as such in the next step. LC-MS (Method 1): $R_t$=1.46 min; m/z=no ionization seen $(M+H)^+$.

Preparation of 4'-bromo-3-fluoro-2'-methyl-[1,1'-biphenyl]-4-carboxylic acid

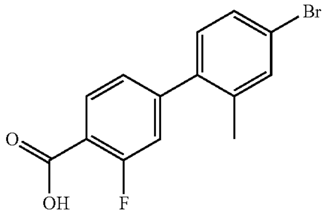 [SMILES: Cc1cc(Br)ccc1-c1ccc(C(=O)O)c(F)c1]

To a solution of methyl 4'-bromo-3-fluoro-2'-methyl-[1,1'-biphenyl]-4-carboxylate (500 mg, 2.1 mmol) in a mixture of tetrahydrofuran (30 mL) and water (3 mL), was added LiOH·$H_2O$ (304 mg, 12 mmol). The reaction solution was stirred at 40° C. for 4 h. THF was removed under reduced pressure. The aqueous layer was additionally diluted with water (4 ml) and acidified with 1N HCl to pH=2. The resulting precipitate was collected by filtration, washed with diethyl ether and dried under reduced pressure to afford 4'-bromo-3-fluoro-2'-methyl-[1,1'-biphenyl]-4-carboxylic acid as a white solid (250 mg, 73%). LC-MS (Method 1): $R_t$=1.25 min; m/z=309.35 $(M+H)^+$.

Preparation of 4'-bromo-3-fluoro-2'-methyl-N-(pyridin-3-ylmethyl)-[1,1'-biphenyl]-4-carboxamide

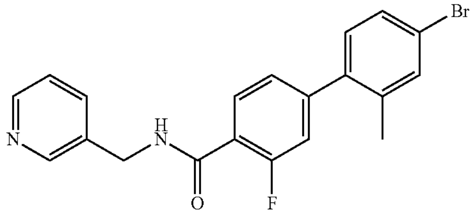 [SMILES: Cc1cc(Br)ccc1-c1ccc(C(=O)NCc2cccnc2)c(F)c1]

To a solution of 4'-bromo-3-fluoro-2'-methyl-[1,1'-biphenyl]-4-carboxylic acid (250 mg, 0.68 mmol) in dichloromethane, dry (20 mL), were added DIPEA (240 μL, 1.4 mmol), HATU (310 mg, 0.0.82 mmol) and 3-pyridylmethanamine (76 μL, 0.75 mmol). The reaction mixture was stirred at room temperature for 3 h until complete conversion into the desired product. The reaction mixture was washed with saturated $NaHCO_3$ (2×5 ml). The organic layer was concentrated under reduced pressure and dried to afford 4'-bromo-3-fluoro-2'-methyl-N-(pyridin-3-ylmethyl)-[1,1'-biphenyl]-4-carboxamide (310 mg, 98%). LC-MS (Method 1): $R_t$=1.06 min; m/z=401.43 $(M+H)^+$.

Preparation of 3-fluoro-2'-methyl-4'-(methylamino)-N-(pyridin-3-ylmethyl)-[1,1'-biphenyl]-4-carboxamide

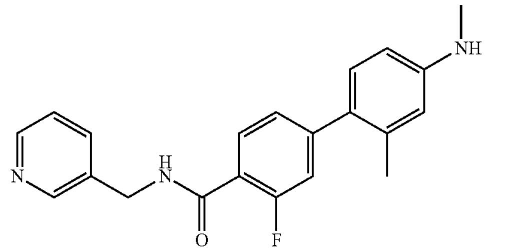 [SMILES: CNc1ccc(-c2ccc(C(=O)NCc3cccnc3)c(F)c2)c(C)c1]

A mixture of 4'-bromo-3-fluoro-2'-methyl-N-(pyridin-3-ylmethyl)-[1,1'-biphenyl]-4-carboxamide (44 mg, 0.115 mmol), 40% aqueous methylamine solution (1.11 mL, 12.9 mmol) and copper powder (0.366 mg, 0.00576 mmol) was stirred in a sealed tube at 100° C. overnight. After cooling to room temperature, the reaction mixture was diluted with water (10 ml) and extracted with EtOAc (3×5 ml). The combined organic layers was dried over $Na_2SO_4$ and concentrated under reduced pressure to afford 3-fluoro-2'-methyl-4'-(methylamino)-N-(pyridin-3-ylmethyl)-[1,1'-biphenyl]-4-carboxamide (175 mg, 30%). LC-MS (Method 1): $R_t$=0.72 min; m/z=333.57 $(M+H)^+$.

Synthesis of 3-fluoro-2'-methyl-4'-(N-methylpropionamido)-N-(pyridin-3-ylmethyl)-[1,1'-biphenyl]-4-carboxamide (Compound I-271)

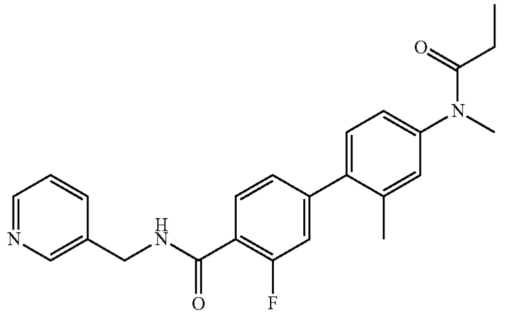 [SMILES: CCC(=O)N(C)c1ccc(-c2ccc(C(=O)NCc3cccnc3)c(F)c2)c(C)c1]

To a solution of 3-fluoro-2'-methyl-4'-(methylamino)-N-(pyridin-3-ylmethyl)-[1,1'-biphenyl]-4-carboxamide (175 mg, 0.25 mmol) in dichloromethane dry (3 mL) stirred at 0° C. (ice bath) was added triethylamine (70 µL, 0.50 mmol) followed by propionyl chloride (24 L, 0.27 mmol). The resulting mixture was stirred at 0° C. for 5 min and then at room temperature for 3 h until complete conversion into target product. The reaction mixture was washed with 0.1 M HCl (2×2 mL). The organic layer was concentrated under reduced pressure, the remaining residue was purified by column chromatography (10% MeOH in DCM) to afford 3-fluoro-2'-methyl-4'-(N-methylpropionamido)-N-(pyridin-3-ylmethyl)-[1,1'-biphenyl]-4-carboxamide as a yellow paste (20 mg, 10%). LC-MS (Method 2): $R_t$=0.73 min; m/z=406.61 $(M+H)^+$. $^1$H-NMR (500 MHz, DMSO-$d_6$): δ [ppm]=0.95 (m, 3H), 2.10 (br. s, 2H), 2.27 (s, 3H), 3.18 (s, 3H), 4.52 (d, 2H), 7.23 (d, 1H), 7.28-7.32 (m, 3H), 7.34-7.40 (m, 2H), 7.68-7.77 (m, 2H), 8.47 (d, 1H), 8.57 (s, 1H), 8.99 (t, 1H).

Synthesis of 2'-methoxy-4'-(N-methylpropionamido)-N-(pyridin-3-ylmethyl)-[1,1'-biphenyl]-4-carboxamide (Compound I-257)

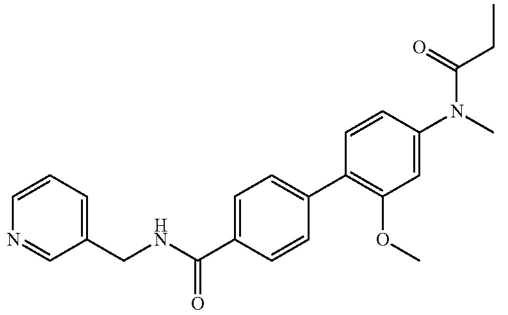 [SMILES: CCC(=O)N(C)c1ccc(-c2ccc(C(=O)NCc3cccnc3)cc2)c(OC)c1]

Compound I-257 was synthesized in an essentially analogous manner to compound I-271 above. Appearance: white powder. LC-MS (Method 2): $R_t$=3.29 min; m/z=404.04 $(M+H)^+$. $^1$H-NMR (400 MHz, DMSO-$d_6$): δ [ppm]=0.95 (t, J=7.40 Hz, 3H) 2.14 (br. s., 2H) 3.20 (s, 3H) 3.78 (s, 3H) 4.51 (d, J=5.99 Hz, 2H) 6.99 (d, J=7.95 Hz, 1H) 7.12 (s, 1H) 7.32-7.42 (m, 2H) 7.59 (d, J=7.82 Hz, 2H) 7.72 (d, J=7.82 Hz, 1H) 7.91 (d, J=8.07 Hz, 2H) 8.45 (d, J=4.65 Hz, 1H) 8.55 (s, 1H) 9.13 (t, J=5.93 Hz, 1H).

Synthesis of 3-fluoro-3'-methyl-4'-(N-methylpropionamido)-N-(pyridin-3-ylmethyl)-[1,1'-biphenyl]-4-carboxamide (Compound I-258)

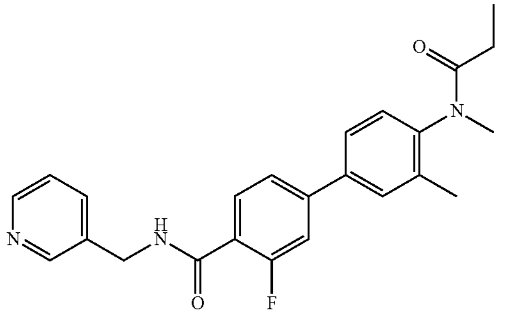 [SMILES: CCC(=O)N(C)c1ccc(-c2ccc(C(=O)NCc3cccnc3)c(F)c2)cc1C]

Compound I-258 was synthesized in an essentially analogous manner to compound I-271 above. Appearance: white powder. LC-MS (Method 6): $R_t$=3.59 min; m/z=406.03 $(M+H)^+$. $^1$H-NMR (400 MHz, DMSO-$d_6$): δ [ppm]=0.91 (t, J=7.21 Hz, 3H) 1.74-1.87 (m, 1H) 1.90-2.01 (m, 1H) 2.23 (br. s., 3H) 3.07 (br. s., 3H) 4.50 (br. s., 2H) 7.28-7.44 (m, 2H) 7.60-7.81 (m, 6H) 8.39-8.65 (m, 2H) 8.96 (br. s., 1H).

Synthesis of 2'-hydroxy-4'-(N-methylpropionamido)-N-(pyridin-3-ylmethyl)-[1,1'-biphenyl]-4-carboxamide (Compound I-263)

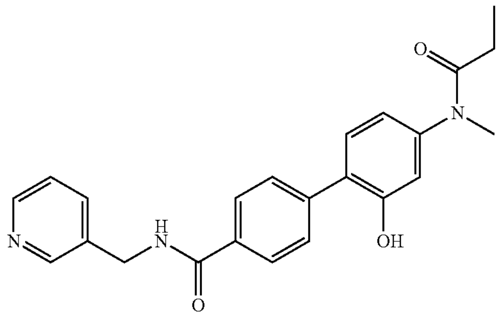 [SMILES: CCC(=O)N(C)c1ccc(-c2ccc(C(=O)NCc3cccnc3)cc2)c(O)c1]

Compound I-263 was synthesized in an essentially analogous manner to compound I-271 above. Appearance: white powder. LC-MS (Method 2): $R_t$=2.64 min; m/z=390.02 $(M+H)^+$. $^1$H-NMR (400 MHz, DMSO-$d_6$): δ [ppm]=0.96 (t, J=7.48 Hz, 3H) 2.09-2.17 (m, 2H) 3.16 (s, 3H) 4.52 (d, J=6.10 Hz, 2H) 6.84 (s, 2H) 6.86 (d, J=1.83 Hz, 2H) 7.65-7.68 (m, 2H) 7.73 (dt, J=8.09, 1.91 Hz, 1H) 7.92 (d, J=8.54 Hz, 2H) 8.46-8.56 (dd, J=4.58, 1.53 Hz, 1H) 8.56 (d, J=1.83 Hz, 1H) 9.11 (t, J=5.95 Hz, 1H) 10.00 (br. s., 1H).

Example 13. Cell Viability in AGS Cells

AGS cells were treated with DMSO (no drug control) or each compound in Table 5 in an 8-point dose response for 4 days. Cell viability was measured using CellTiter Glo2. The $IC_{50}$ of each compound was determined using CDD Vault. Exemplary results are shown in Table 5.

TABLE 5

| Compound structure | Compound number | AGS $IC_{50}$ (μM) |
|---|---|---|
| 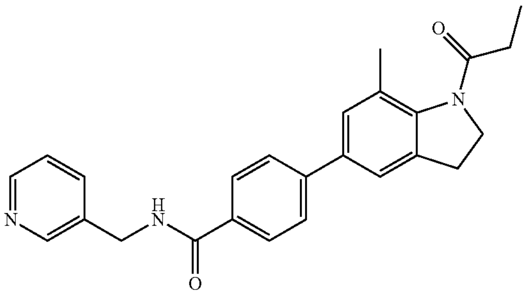 [SMILES: CCC(=O)N1CCc2cc(-c3ccc(C(=O)NCc4cccnc4)cc3)cc(C)c21] | I-17 | 1.05, 1.02 |
| 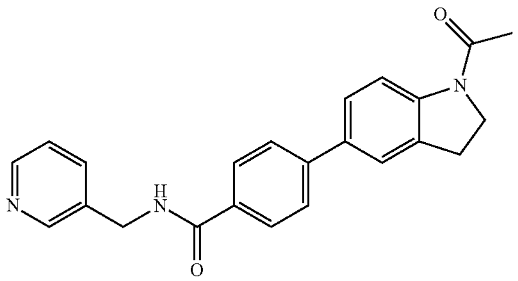 [SMILES: CC(=O)N1CCc2cc(-c3ccc(C(=O)NCc4cccnc4)cc3)ccc21] | I-42 | 3.83 |
| 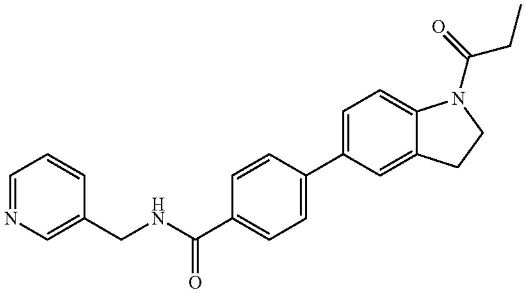 [SMILES: CCC(=O)N1CCc2cc(-c3ccc(C(=O)NCc4cccnc4)cc3)ccc21] | I-43 | 2.48, 2.36 |

TABLE 5-continued
| Compound structure | Compound number | AGS $IC_{50}$ (μM) |
|---|---|---|
| 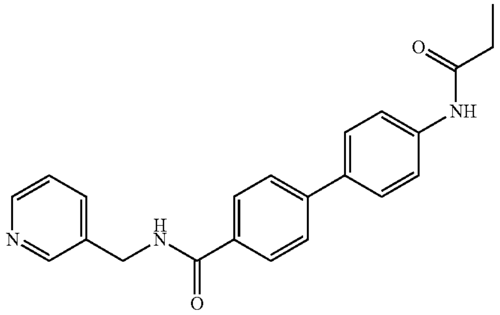 [SMILES: CCC(=O)Nc1ccc(-c2ccc(C(=O)NCc3cccnc3)cc2)cc1] | I-44 | >30.0 |
| 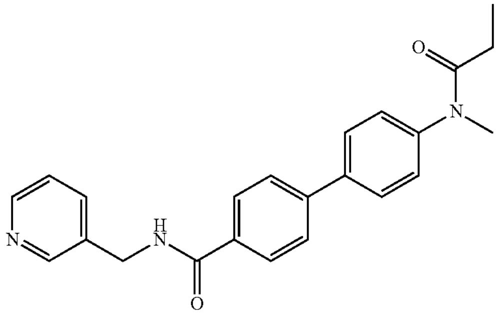 [SMILES: CCC(=O)N(C)c1ccc(-c2ccc(C(=O)NCc3cccnc3)cc2)cc1] | I-45 | 4.45, 4.29 |
| 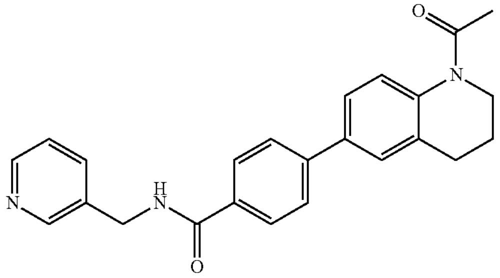 [SMILES: CC(=O)N1CCCc2cc(-c3ccc(C(=O)NCc4cccnc4)cc3)ccc21] | I-46 | >17.5, >18.3 |
| 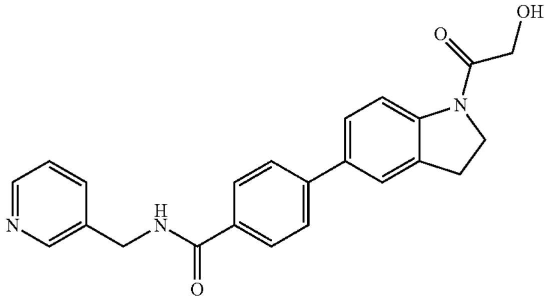 [SMILES: O=C(NCc1cccnc1)c1ccc(-c2ccc3c(c2)CCN3C(=O)CO)cc1] | I-47 | 3.22 |
| 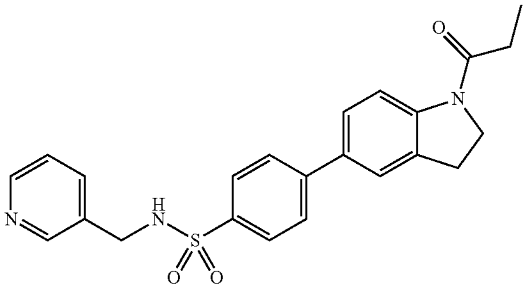 [SMILES: CCC(=O)N1CCc2cc(-c3ccc(S(=O)(=O)NCc4cccnc4)cc3)ccc21] | I-48 | 9.45 |

TABLE 5-continued
| Compound structure | Compound number | AGS $IC_{50}$ (μM) |
|---|---|---|
| 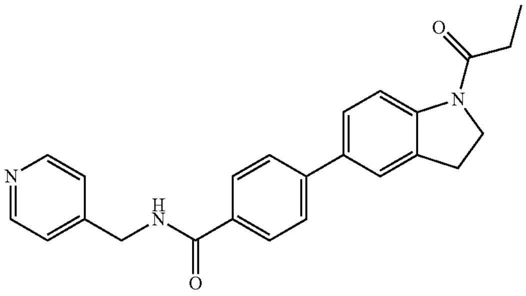 [SMILES: CCC(=O)N1CCc2cc(-c3ccc(C(=O)NCc4ccncc4)cc3)ccc21] | I-49 | >30.0 |
| 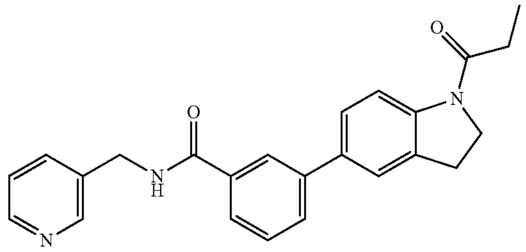 [SMILES: CCC(=O)N1CCc2cc(-c3cccc(C(=O)NCc4cccnc4)c3)ccc21] | I-50 | >30.0 |
| 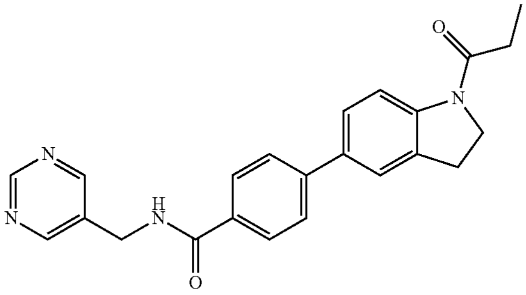 [SMILES: CCC(=O)N1CCc2cc(-c3ccc(C(=O)NCc4cncnc4)cc3)ccc21] | I-51 | >30.0 |
| 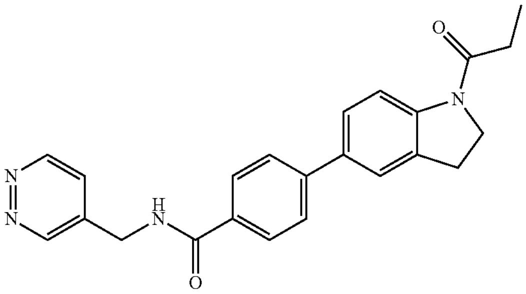 [SMILES: CCC(=O)N1CCc2cc(-c3ccc(C(=O)NCc4ccnnc4)cc3)ccc21] | I-52 | >10, >8.01 |
| 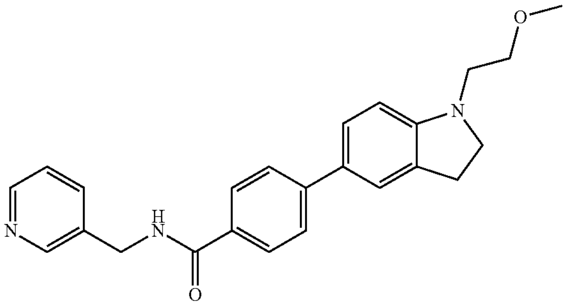 [SMILES: COCCN1CCc2cc(-c3ccc(C(=O)NCc4cccnc4)cc3)ccc21] | I-53 | 3.52 |

TABLE 5-continued
| Compound structure | Compound number | AGS $IC_{50}$ (μM) |
|---|---|---|
| 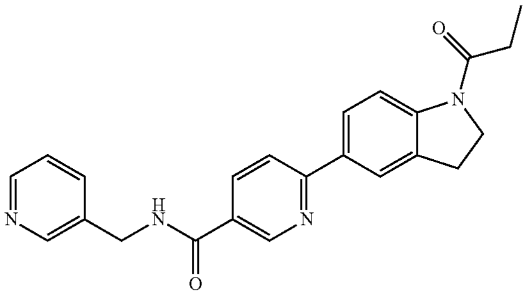 | I-54 | >17.0, >16.9 |
| 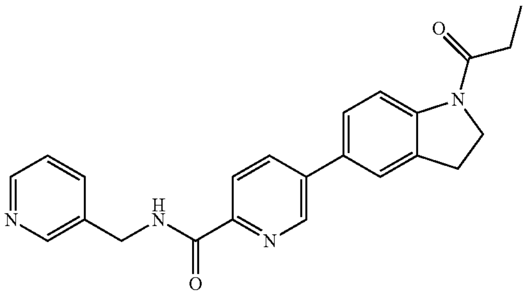 [SMILES: CCC(=O)N1CCc2cc(-c3ccc(C(=O)NCc4cccnc4)nc3)ccc21] | I-55 | 2.89, 3.66 |
| 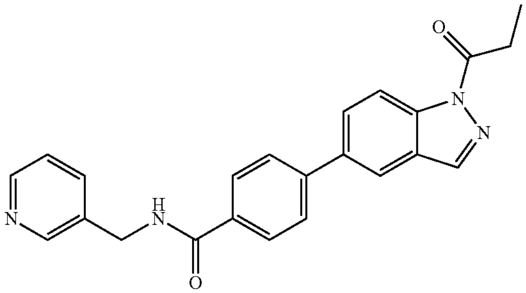 [SMILES: CCC(=O)n1ncc2cc(-c3ccc(C(=O)NCc4cccnc4)cc3)ccc21] | I-56 | 7.68 |
| 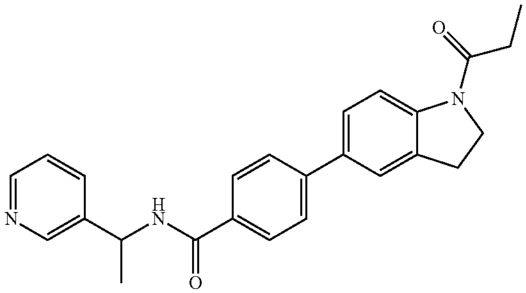 [SMILES: CCC(=O)N1CCc2cc(-c3ccc(C(=O)NC(C)c4cccnc4)cc3)ccc21] | I-57 | >28.2 |
| 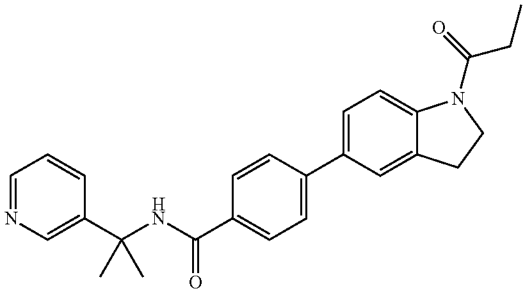 [SMILES: CCC(=O)N1CCc2cc(-c3ccc(C(=O)NC(C)(C)c4cccnc4)cc3)ccc21] | I-58 | >30.0 |

TABLE 5-continued
| Compound structure | Compound number | AGS $IC_{50}$ (μM) |
|---|---|---|
| 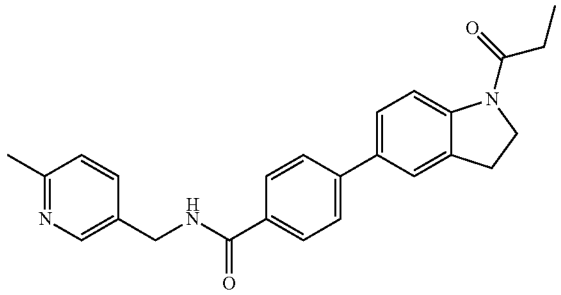 | I-59 | >30.0 |
| 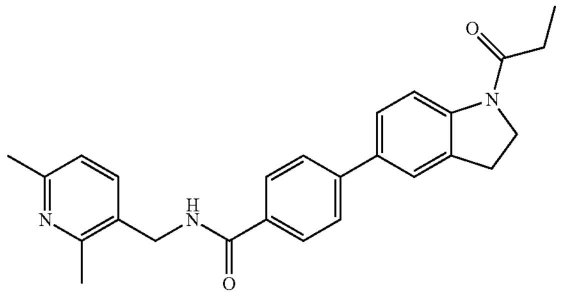 [SMILES: CCC(=O)N1CCc2cc(-c3ccc(C(=O)NCc4ccc(C)nc4C)cc3)ccc21] | I-60 | 0.344, 0.384 |
| 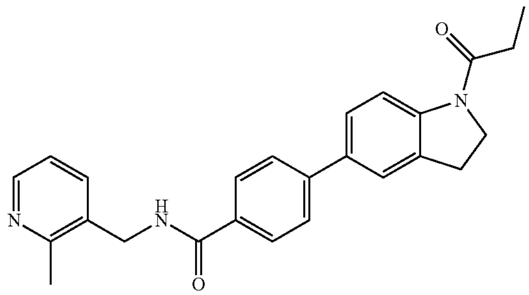 [SMILES: CCC(=O)N1CCc2cc(-c3ccc(C(=O)NCc4cccnc4C)cc3)ccc21] | I-61 | >30.0 |
| 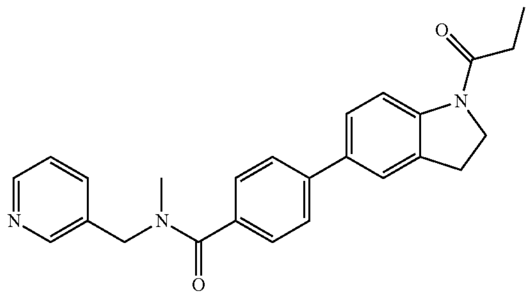 [SMILES: CCC(=O)N1CCc2cc(-c3ccc(C(=O)N(C)Cc4cccnc4)cc3)ccc21] | I-62 | 29.3 |
| 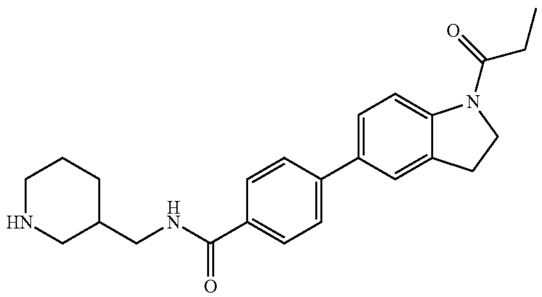 [SMILES: CCC(=O)N1CCc2cc(-c3ccc(C(=O)NCC4CCCNC4)cc3)ccc21] | I-63 | >30.0 |

TABLE 5-continued
| Compound structure | Compound number | AGS IC50 (μM) |
|---|---|---|
| 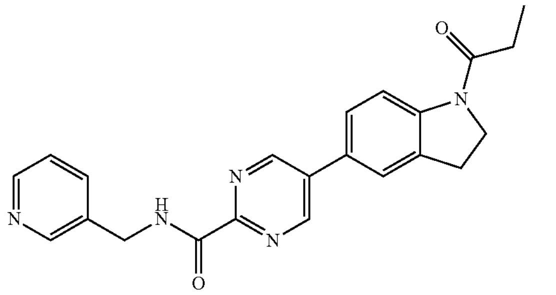 [SMILES: CCC(=O)N1CCc2cc(-c3cnc(C(=O)NCc4cccnc4)nc3)ccc21] | I-65 | 7.27 |
| 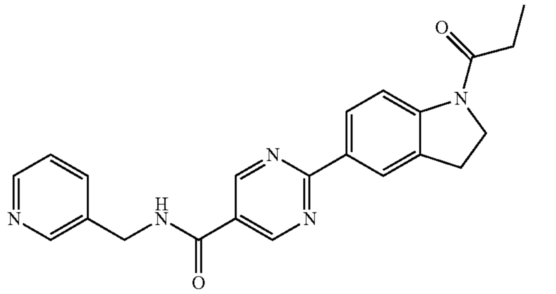 [SMILES: CCC(=O)N1CCc2cc(-c3ncc(C(=O)NCc4cccnc4)cn3)ccc21] | I-66 | >30.0 |
| 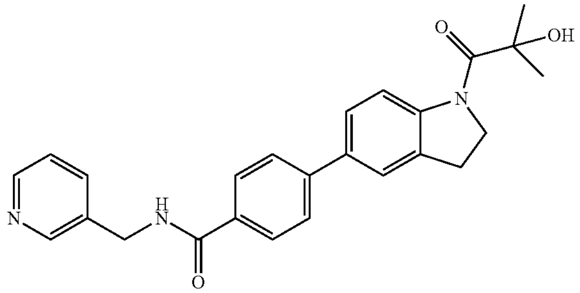 [SMILES: CC(C)(O)C(=O)N1CCc2cc(-c3ccc(C(=O)NCc4cccnc4)cc3)ccc21] | I-68 | 29.7 |
| 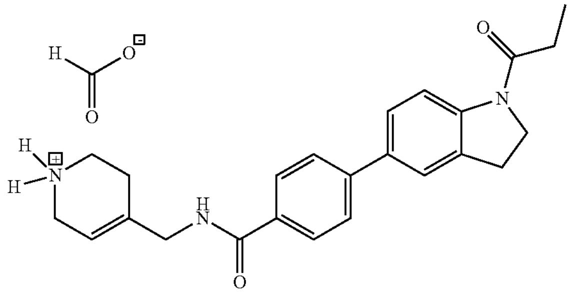 | Mono-formate of I-69 | >30.0 |
| 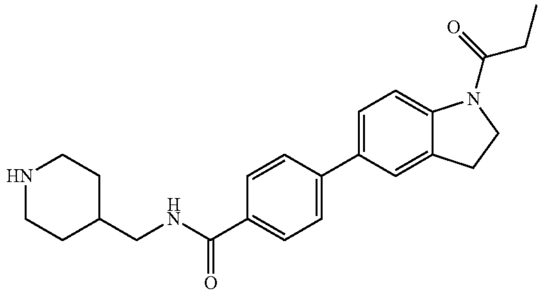 [SMILES: CCC(=O)N1CCc2cc(-c3ccc(C(=O)NCC4CCNCC4)cc3)ccc21] | I-70 | >30.0 |

TABLE 5-continued
| Compound structure | Compound number | AGS $IC_{50}$ (μM) |
|---|---|---|
| 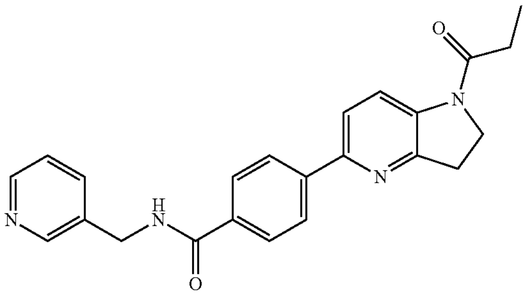 [SMILES: CCC(=O)N1CCc2nc(-c3ccc(C(=O)NCc4cccnc4)cc3)ccc21] | I-71 | 4.35 |
| 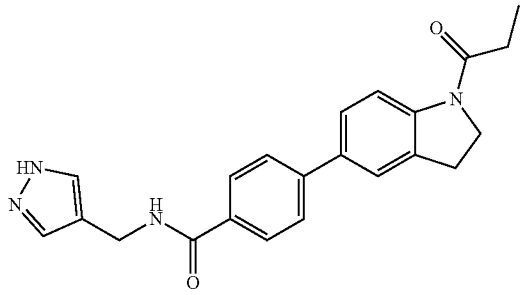 [SMILES: CCC(=O)N1CCc2cc(-c3ccc(C(=O)NCc4cn[nH]c4)cc3)ccc21] | I-72 | >30.0 |
| 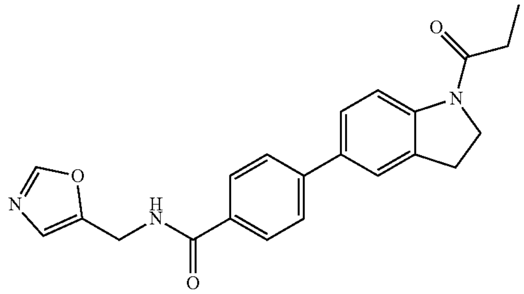 [SMILES: CCC(=O)N1CCc2cc(-c3ccc(C(=O)NCc4cnco4)cc3)ccc21] | I-73 | >30.0 |
| 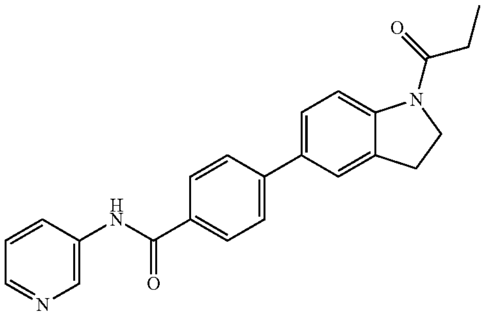 [SMILES: CCC(=O)N1CCc2cc(-c3ccc(C(=O)Nc4cccnc4)cc3)ccc21] | I-74 | 6.61 |
| 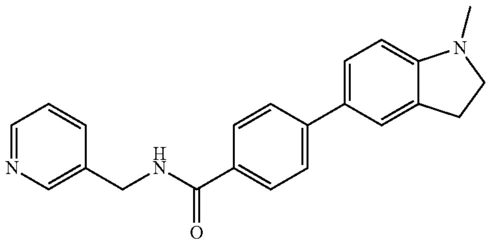 [SMILES: CN1CCc2cc(-c3ccc(C(=O)NCc4cccnc4)cc3)ccc21] | I-75 | >20.6 |

TABLE 5-continued
| Compound structure | Compound number | AGS IC50 (μM) |
|---|---|---|
| 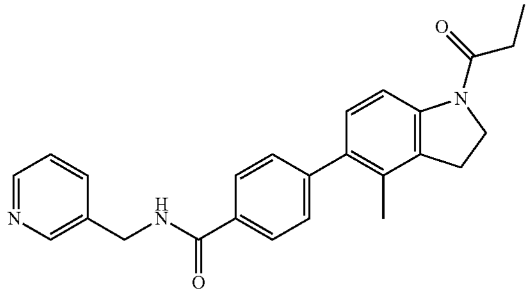 [SMILES: CCC(=O)N1CCc2c1ccc(-c1ccc(C(=O)NCc3cccnc3)cc1)c2C] | I-80 | 0.49, 0.653 |
| 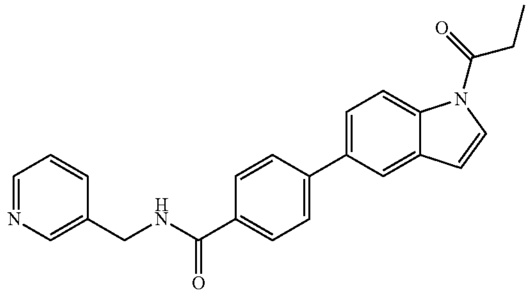 [SMILES: CCC(=O)n1ccc2cc(-c3ccc(C(=O)NCc4cccnc4)cc3)ccc21] | I-90 | >13.3 |
| 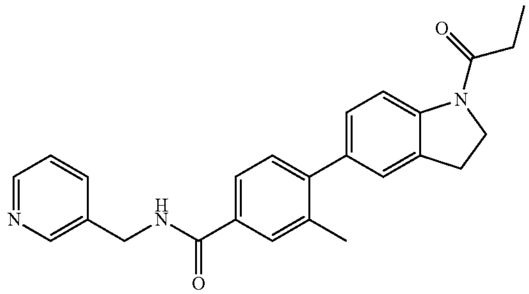 [SMILES: CCC(=O)N1CCc2cc(-c3ccc(C(=O)NCc4cccnc4)cc3C)ccc21] | I-91 | 2.03, 2.59 |
| 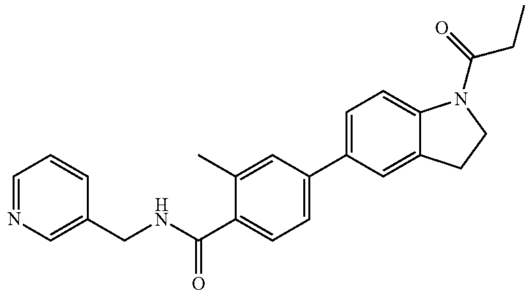 [SMILES: CCC(=O)N1CCc2cc(-c3ccc(C(=O)NCc4cccnc4)c(C)c3)ccc21] | I-93 | 7.44, >16.2 |
| 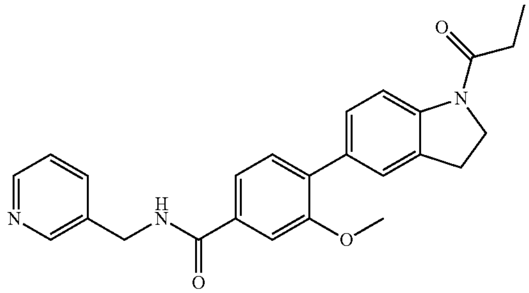 [SMILES: CCC(=O)N1CCc2cc(-c3ccc(C(=O)NCc4cccnc4)cc3OC)ccc21] | I-94 | 7.86, 8.71 |

TABLE 5-continued
| Compound structure | Compound number | AGS IC$_{50}$ (μM) |
|---|---|---|
| 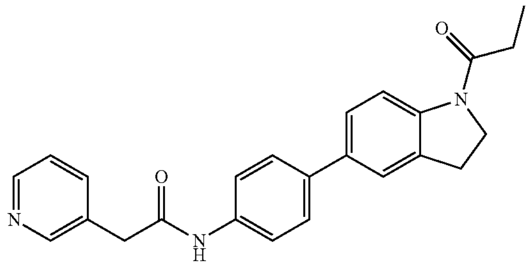 [SMILES: CCC(=O)N1CCc2cc(-c3ccc(NC(=O)Cc4cccnc4)cc3)ccc21] | I-95 | >30.0 |
| 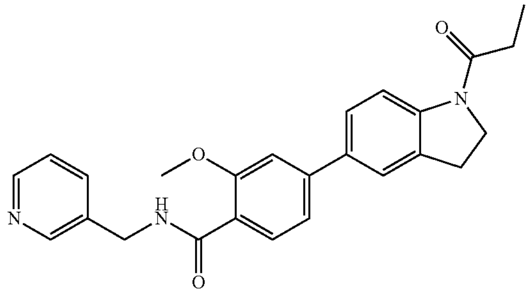 [SMILES: CCC(=O)N1CCc2cc(-c3ccc(C(=O)NCc4cccnc4)c(OC)c3)ccc21] | I-96 | >30.0 |
| 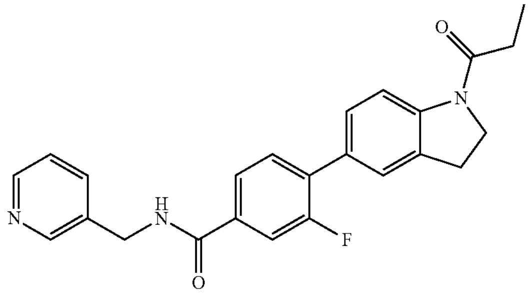 [SMILES: CCC(=O)N1CCc2cc(-c3ccc(C(=O)NCc4cccnc4)cc3F)ccc21] | I-97 | 3.17 |
| 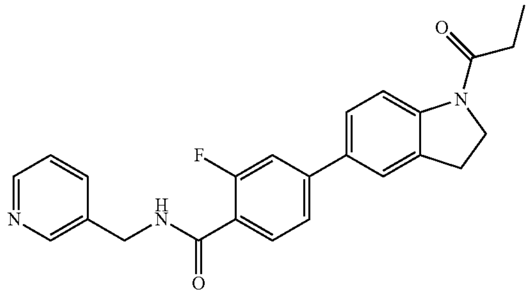 [SMILES: CCC(=O)N1CCc2cc(-c3ccc(C(=O)NCc4cccnc4)c(F)c3)ccc21] | I-98 | >30,<br>>6.76 |
| 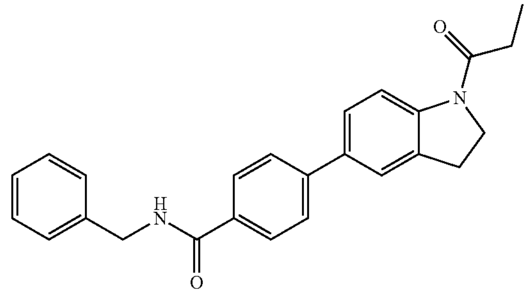 [SMILES: CCC(=O)N1CCc2cc(-c3ccc(C(=O)NCc4ccccc4)cc3)ccc21] | I-152 | >30.0 |

TABLE 5-continued
| Compound structure | Compound number | AGS $IC_{50}$ (μM) |
|---|---|---|
| 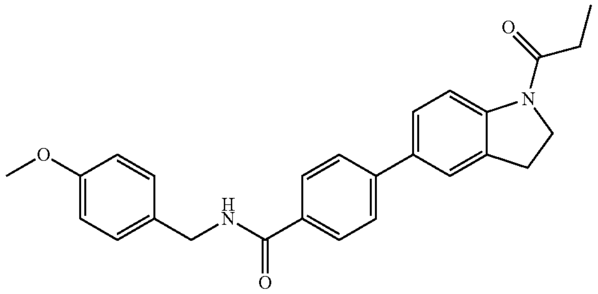 [SMILES: CCC(=O)N1CCc2cc(-c3ccc(C(=O)NCc4ccc(OC)cc4)cc3)ccc21] | I-156 | >30.0 |
| 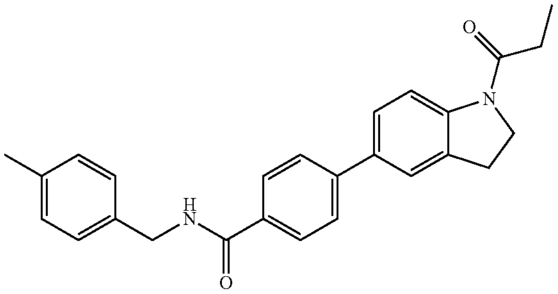 [SMILES: CCC(=O)N1CCc2cc(-c3ccc(C(=O)NCc4ccc(C)cc4)cc3)ccc21] | I-157 | >30.0 |
| 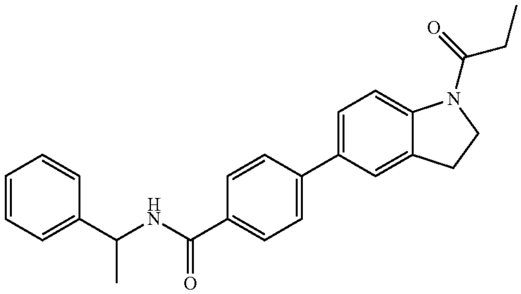 [SMILES: CCC(=O)N1CCc2cc(-c3ccc(C(=O)NC(C)c4ccccc4)cc3)ccc21] | I-160 | >30.0 |
| 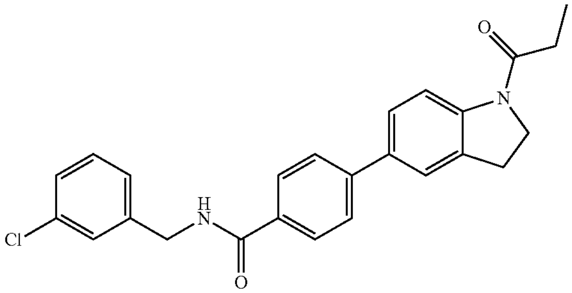 [SMILES: CCC(=O)N1CCc2cc(-c3ccc(C(=O)NCc4cccc(Cl)c4)cc3)ccc21] | I-168 | >30.0 |
| 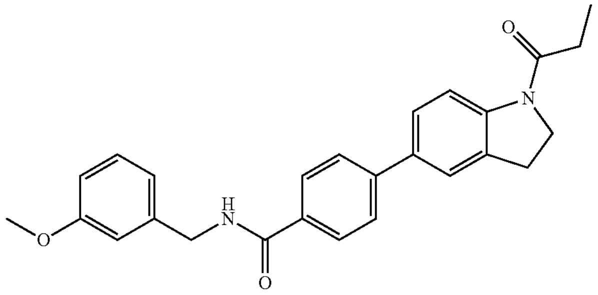 [SMILES: CCC(=O)N1CCc2cc(-c3ccc(C(=O)NCc4cccc(OC)c4)cc3)ccc21] | I-171 | >30.0 |

TABLE 5-continued
| Compound structure | Compound number | AGS $IC_{50}$ (μM) |
|---|---|---|
| 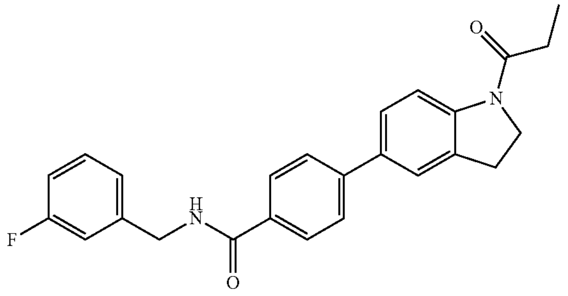 [SMILES: CCC(=O)N1CCc2cc(-c3ccc(C(=O)NCc4cccc(F)c4)cc3)ccc21] | I-174 | >30.0 |
| 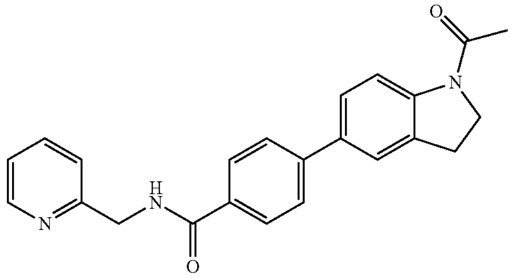 [SMILES: CC(=O)N1CCc2cc(-c3ccc(C(=O)NCc4ccccn4)cc3)ccc21] | I-175 | 5.14 |
| 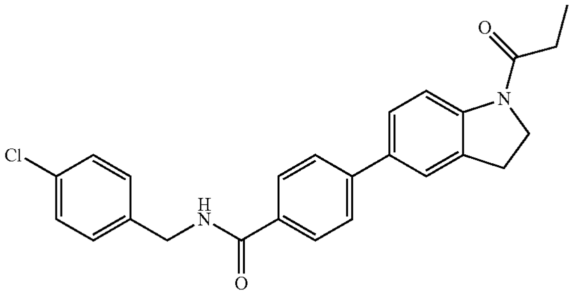 [SMILES: CCC(=O)N1CCc2cc(-c3ccc(C(=O)NCc4ccc(Cl)cc4)cc3)ccc21] | I-176 | 25.8 |
| 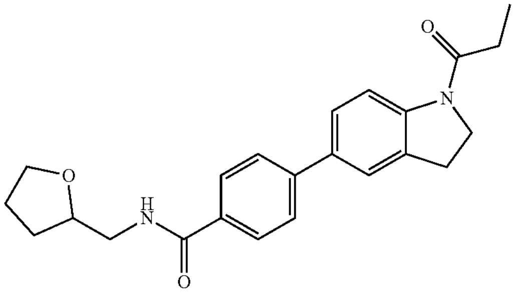 [SMILES: CCC(=O)N1CCc2cc(-c3ccc(C(=O)NCC4CCCO4)cc3)ccc21] | I-178 | >30.0 |
| 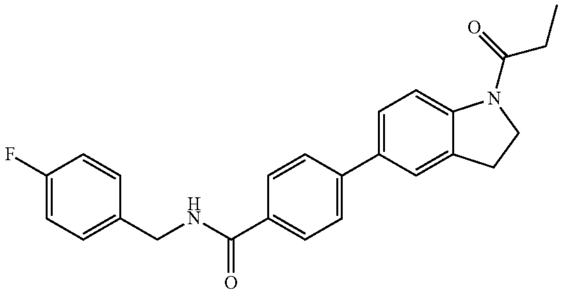 [SMILES: CCC(=O)N1CCc2cc(-c3ccc(C(=O)NCc4ccc(F)cc4)cc3)ccc21] | I-179 | >30.0 |

TABLE 5-continued
| Compound structure | Compound number | AGS $IC_{50}$ (μM) |
|---|---|---|
| 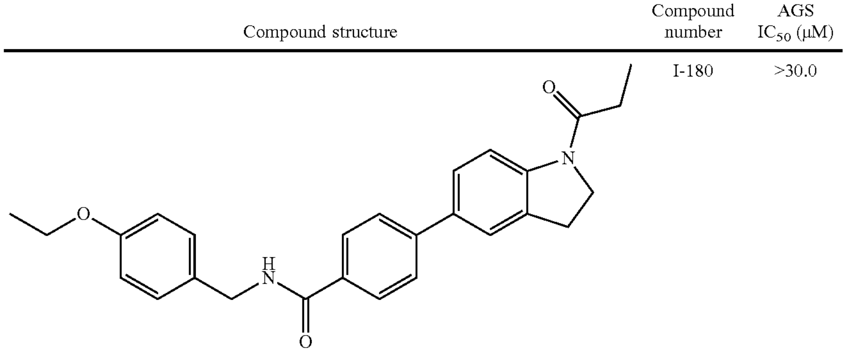 | I-180 | >30.0 |
| 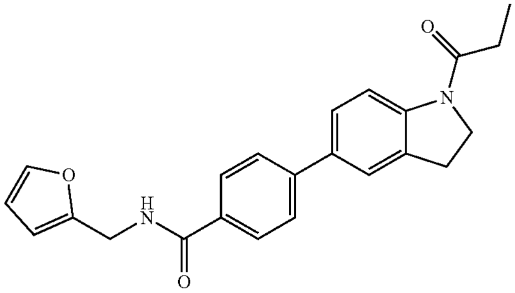 [SMILES: CCC(=O)N1CCc2cc(-c3ccc(C(=O)NCc4ccco4)cc3)ccc21] | I-181 | >30.0 |
| 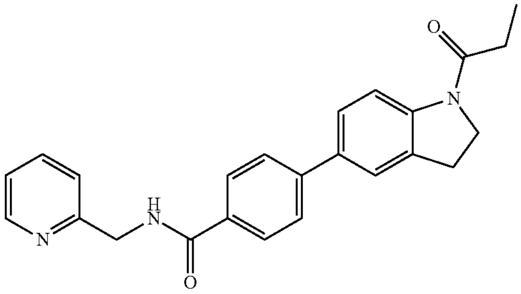 [SMILES: CCC(=O)N1CCc2cc(-c3ccc(C(=O)NCc4ccccn4)cc3)ccc21] | I-185 | 15.5, 21 |
| 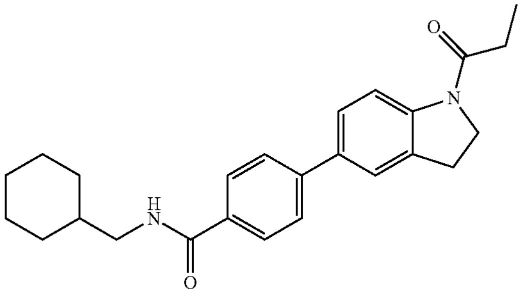 [SMILES: CCC(=O)N1CCc2cc(-c3ccc(C(=O)NCC4CCCCC4)cc3)ccc21] | I-186 | >30.0 |
| 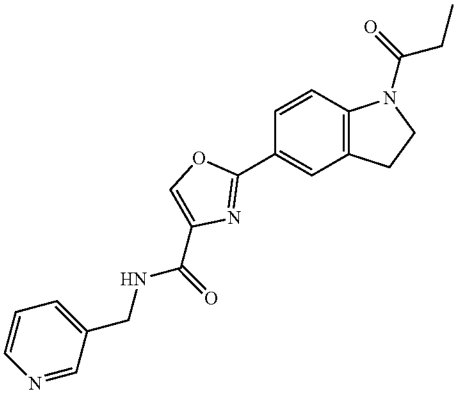 [SMILES: CCC(=O)N1CCc2cc(-c3nc(C(=O)NCc4cccnc4)co3)ccc21] | I-187 | 3.51, 16.3 |

TABLE 5-continued
| Compound structure | Compound number | AGS $IC_{50}$ (μM) |
|---|---|---|
| 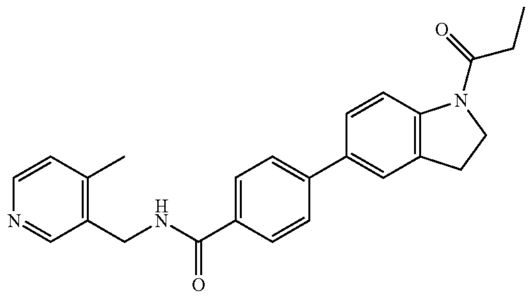 [SMILES: CCC(=O)N1CCc2cc(-c3ccc(C(=O)NCc4cnccc4C)cc3)ccc21] | I-188 | >30.0 |
| 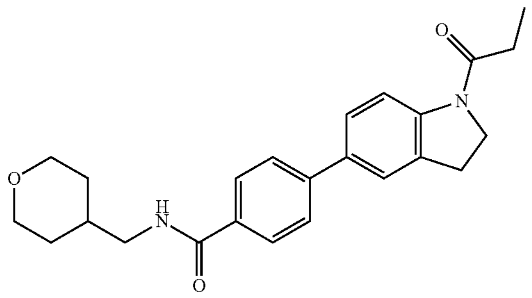 [SMILES: CCC(=O)N1CCc2cc(-c3ccc(C(=O)NCC4CCOCC4)cc3)ccc21] | I-191 | >30.0 |
| 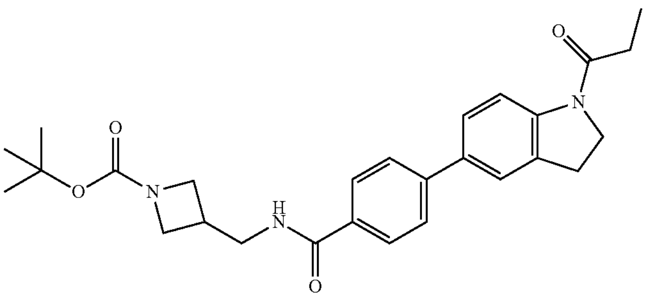 [SMILES: CCC(=O)N1CCc2cc(-c3ccc(C(=O)NCC4CN(C(=O)OC(C)(C)C)C4)cc3)ccc21] | I-196 | >30.0 |
| 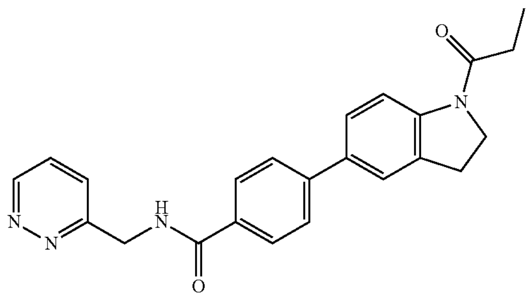 [SMILES: CCC(=O)N1CCc2cc(-c3ccc(C(=O)NCc4cccnn4)cc3)ccc21] | I-197 | 25.2 |
| 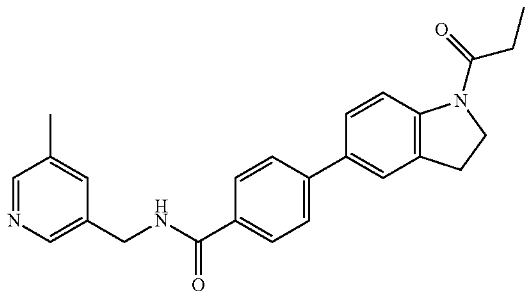 [SMILES: CCC(=O)N1CCc2cc(-c3ccc(C(=O)NCc4cncc(C)c4)cc3)ccc21] | I-198 | 1.06 |

TABLE 5-continued
| Compound structure | Compound number | AGS $IC_{50}$ (μM) |
|---|---|---|
| 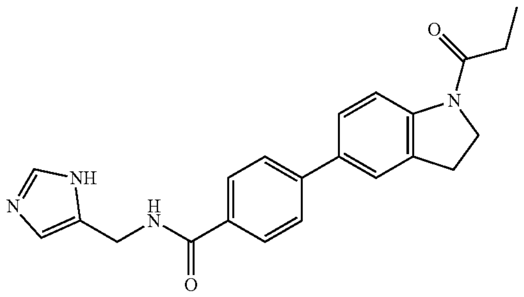 [SMILES: CCC(=O)N1CCc2cc(-c3ccc(C(=O)NCc4cnc[nH]4)cc3)ccc21] | I-199 | 29.9, 14.7 |
| 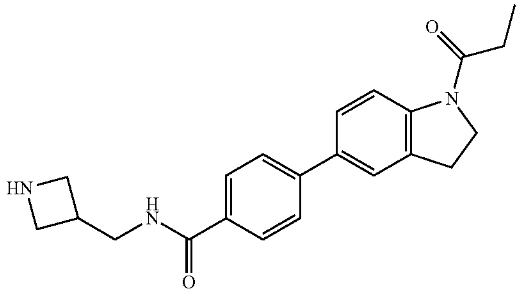 [SMILES: CCC(=O)N1CCc2cc(-c3ccc(C(=O)NCC4CNC4)cc3)ccc21] | I-200 | >30.0 |
| 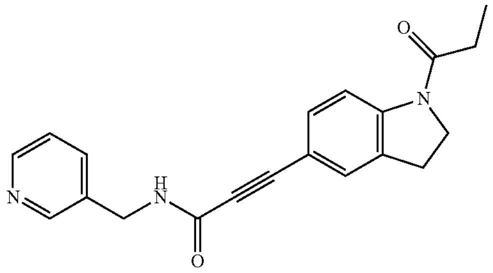 [SMILES: CCC(=O)N1CCc2cc(C#CC(=O)NCc3cccnc3)ccc21] | I-201 | 13.4, >100 |
| 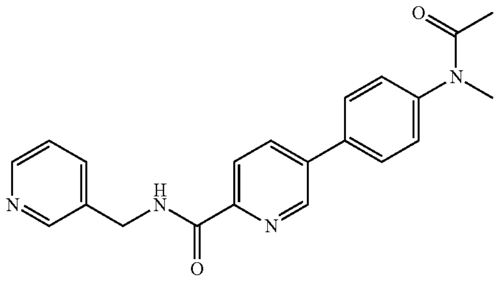 [SMILES: CC(=O)N(C)c1ccc(-c2ccc(C(=O)NCc3cccnc3)nc2)cc1] | I-202 | 10.3, 17.5 |
| 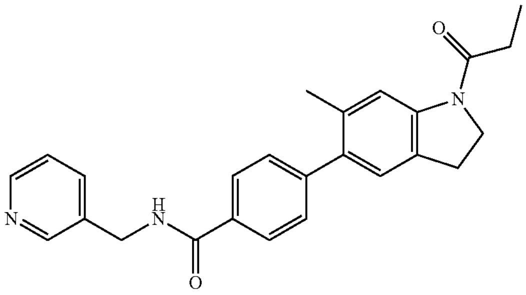 [SMILES: CCC(=O)N1CCc2cc(-c3ccc(C(=O)NCc4cccnc4)cc3)c(C)cc21] | I-203 | 1.54 |

TABLE 5-continued
| Compound structure | Compound number | AGS IC50 (μM) |
|---|---|---|
| 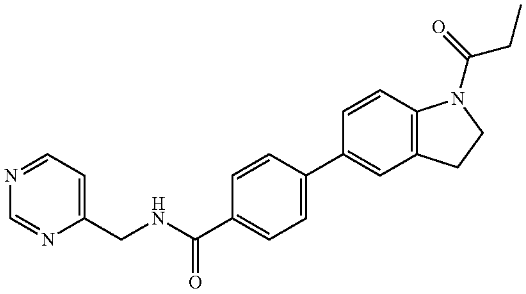 [SMILES: CCC(=O)N1CCc2cc(-c3ccc(C(=O)NCc4ccncn4)cc3)ccc21] | I-204 | >30 |
| 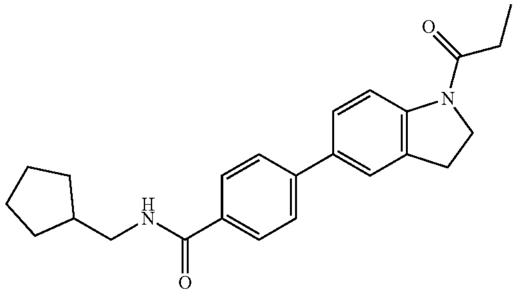 [SMILES: CCC(=O)N1CCc2cc(-c3ccc(C(=O)NCC4CCCC4)cc3)ccc21] | I-207 | >100 |
| 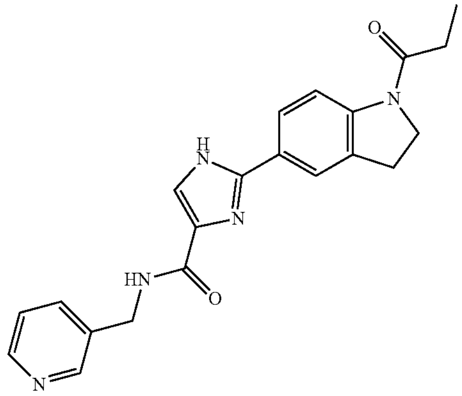 [SMILES: CCC(=O)N1CCc2cc(-c3nc(C(=O)NCc4cccnc4)c[nH]3)ccc21] | I-208 | >30.0, 15.1 |
| 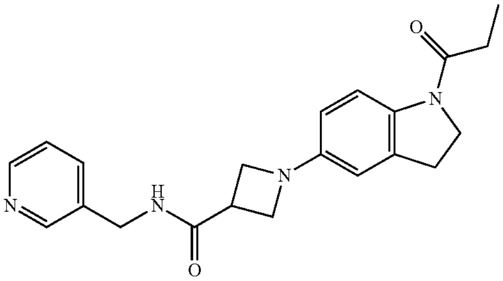 [SMILES: CCC(=O)N1CCc2cc(N3CC(C(=O)NCc4cccnc4)C3)ccc21] | I-209 | >30.0 |
| 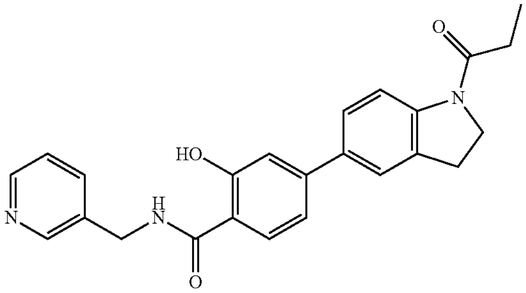 [SMILES: CCC(=O)N1CCc2cc(-c3ccc(C(=O)NCc4cccnc4)c(O)c3)ccc21] | I-210 | 3.02 |

TABLE 5-continued
| Compound structure | Compound number | AGS $IC_{50}$ (μM) |
|---|---|---|
| 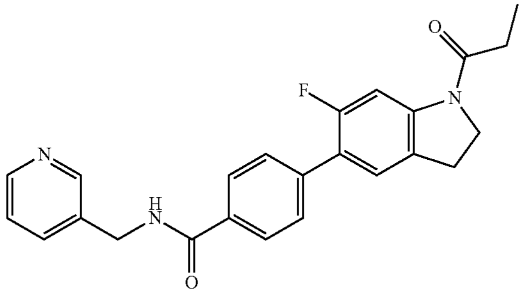 [SMILES: CCC(=O)N1CCc2cc(-c3ccc(C(=O)NCc4cccnc4)cc3)c(F)cc21] | I-211 | 1.16 |
| 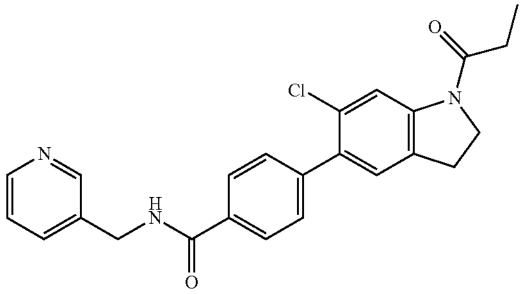 [SMILES: CCC(=O)N1CCc2cc(-c3ccc(C(=O)NCc4cccnc4)cc3)c(Cl)cc21] | I-212 | 1.35 |
| 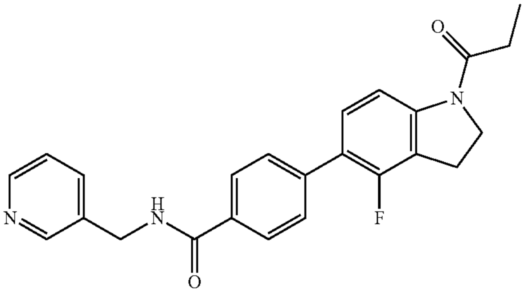 [SMILES: CCC(=O)N1CCc2c1ccc(-c1ccc(C(=O)NCc3cccnc3)cc1)c2F] | I-213 | 3.48 |
| 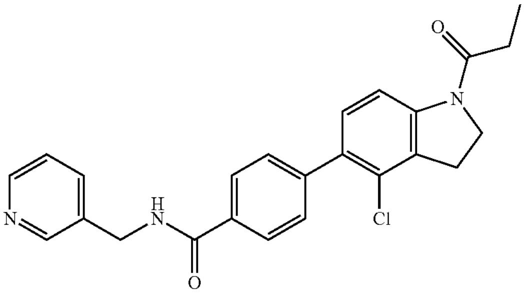 [SMILES: CCC(=O)N1CCc2c1ccc(-c1ccc(C(=O)NCc3cccnc3)cc1)c2Cl] | I-214 | 0.96 |
| 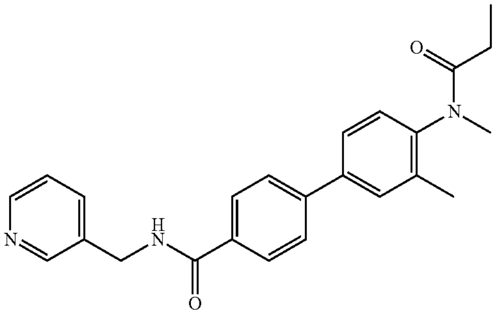 | I-215 | 1.82 |

TABLE 5-continued
| Compound structure | Compound number | AGS $IC_{50}$ (μM) |
|---|---|---|
| 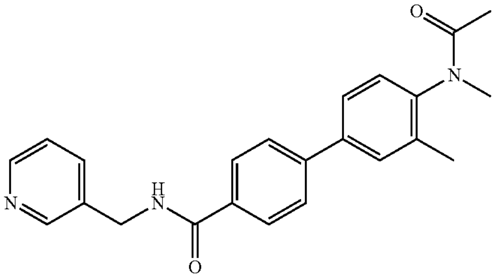 [SMILES: CC(=O)N(C)c1ccc(-c2ccc(C(=O)NCc3cccnc3)cc2)cc1C] | I-216 | 2.44 |
| 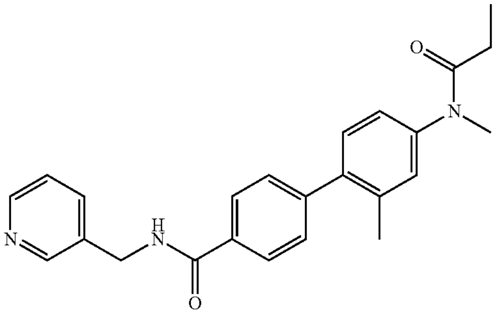 [SMILES: CCC(=O)N(C)c1ccc(-c2ccc(C(=O)NCc3cccnc3)cc2)c(C)c1] | I-217 | 1.85 |
| 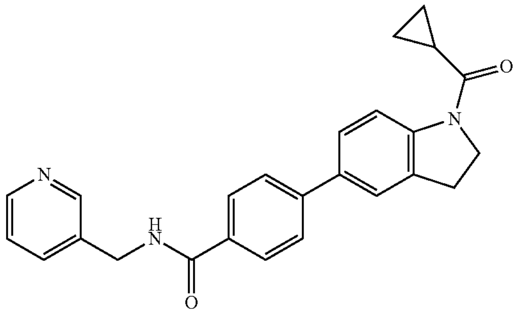 [SMILES: O=C(NCc1cccnc1)c1ccc(-c2ccc3c(c2)CCN3C(=O)C2CC2)cc1] | I-220 | 2.94 |
| 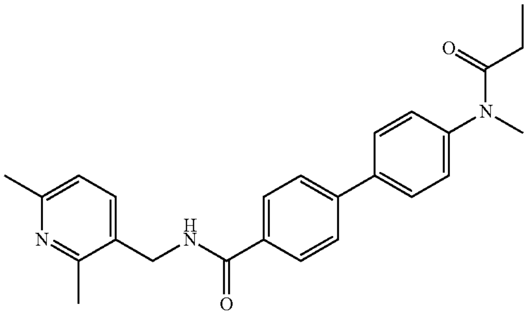 [SMILES: CCC(=O)N(C)c1ccc(-c2ccc(C(=O)NCc3ccc(C)nc3C)cc2)cc1] | I-221 | 0.607 |
| 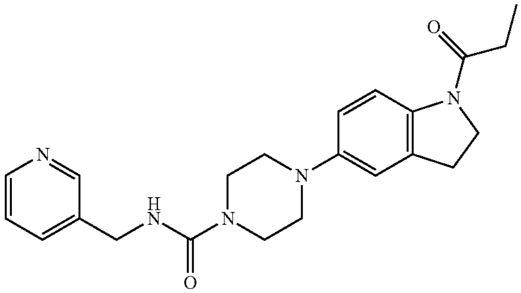 [SMILES: CCC(=O)N1CCc2cc(N3CCN(C(=O)NCc4cccnc4)CC3)ccc21] | I-223 | 4.54 |

TABLE 5-continued
| Compound structure | Compound number | AGS $IC_{50}$ (μM) |
|---|---|---|
| 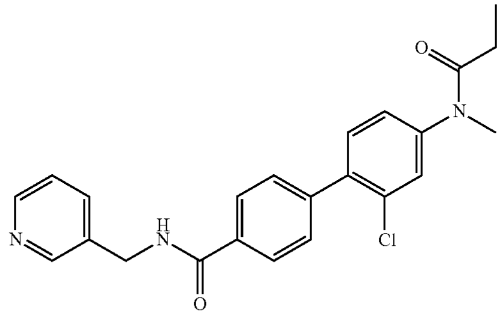 [SMILES: CCC(=O)N(C)c1ccc(-c2ccc(C(=O)NCc3cccnc3)cc2)c(Cl)c1] | I-224 | 1.48 |
| 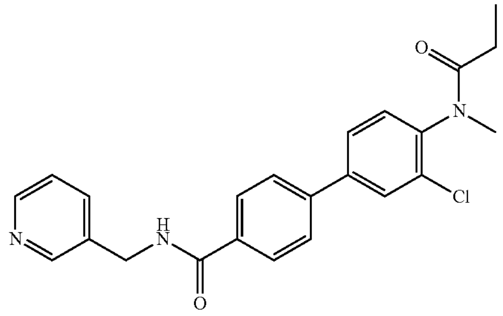 | I-225 | 1.09 |
| 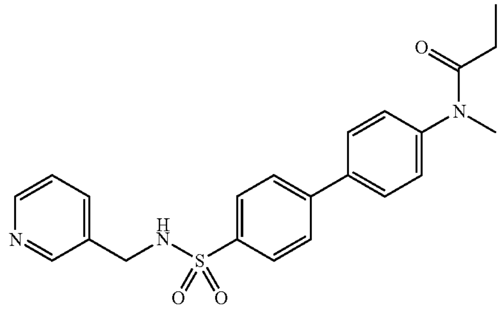 [SMILES: CCC(=O)N(C)c1ccc(-c2ccc(S(=O)(=O)NCc3cccnc3)cc2)cc1] | I-226 | 9.76 |
| 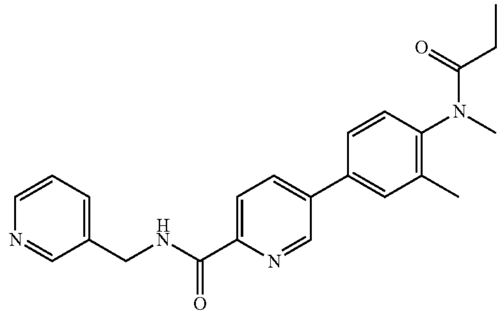 | I-227 | 5.22 |
| 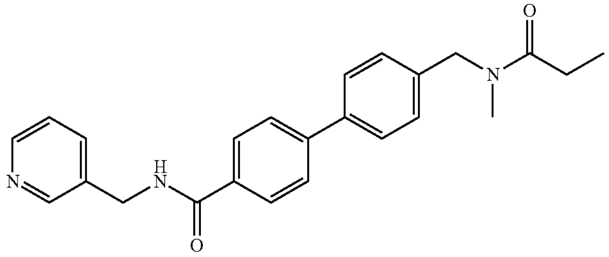 [SMILES: CCC(=O)N(C)Cc1ccc(-c2ccc(C(=O)NCc3cccnc3)cc2)cc1] | I-228 | 3.81 |

TABLE 5-continued
| Compound structure | Compound number | AGS IC$_{50}$ (μM) |
|---|---|---|
| 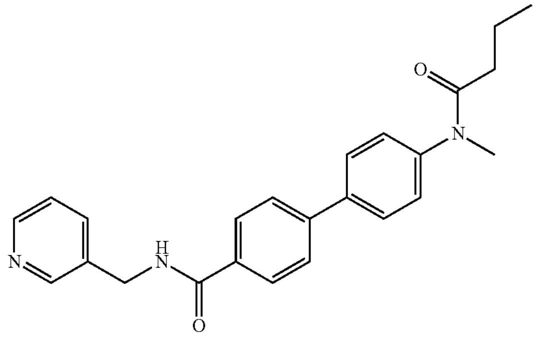 | I-230 | 4.57 |
| 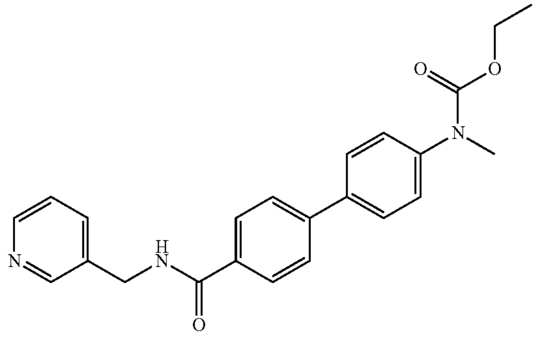 | I-231 | 3.41 |
| 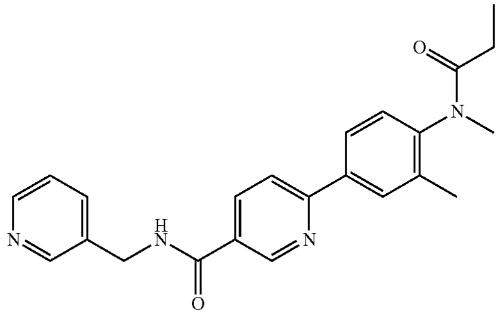 | I-232 | 1.28 |
| 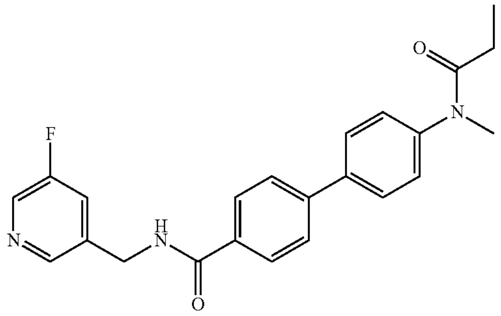 | I-234 | >30.0 |

TABLE 5-continued
| Compound structure | Compound number | AGS $IC_{50}$ (μM) |
|---|---|---|
| 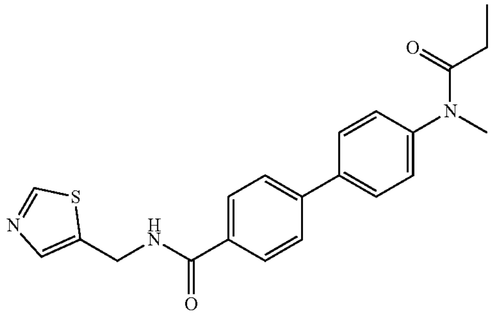 [SMILES: CCC(=O)N(C)c1ccc(-c2ccc(C(=O)NCc3cncs3)cc2)cc1] | I-235 | >30.0 |
| 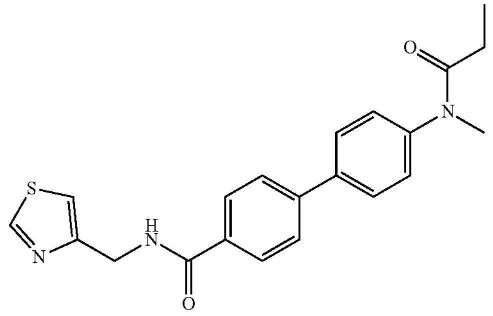 [SMILES: CCC(=O)N(C)c1ccc(-c2ccc(C(=O)NCc3cscn3)cc2)cc1] | I-236 | >30.0 |
| 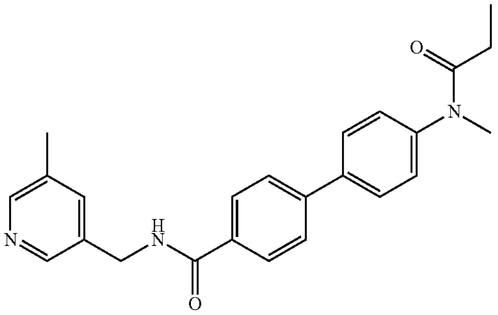 [SMILES: CCC(=O)N(C)c1ccc(-c2ccc(C(=O)NCc3cncc(C)c3)cc2)cc1] | I-237 | 6.69 |
| 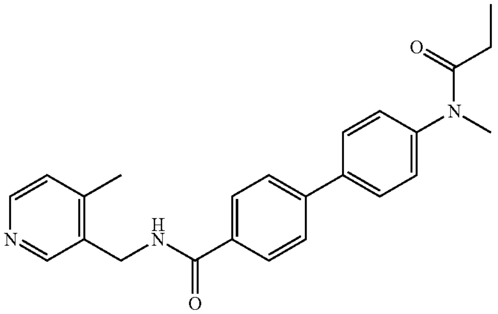 | I-238 | >30.0 |
| 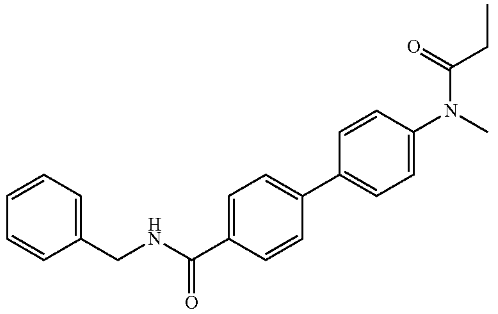 [SMILES: CCC(=O)N(C)c1ccc(-c2ccc(C(=O)NCc3ccccc3)cc2)cc1] | I-239 | >30.0 |

TABLE 5-continued
| Compound structure | Compound number | AGS IC$_{50}$ (μM) |
|---|---|---|
| 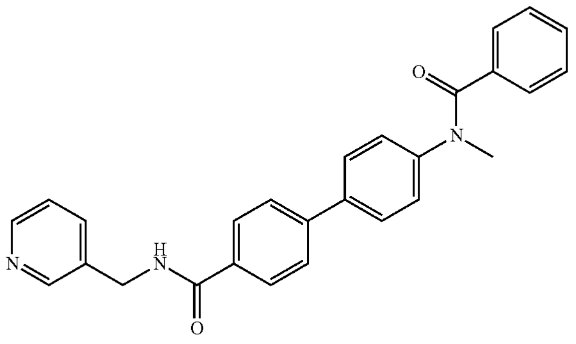 [SMILES: CN(C(=O)c1ccccc1)c1ccc(-c2ccc(C(=O)NCc3cccnc3)cc2)cc1] | I-240 | 5.11 |
| 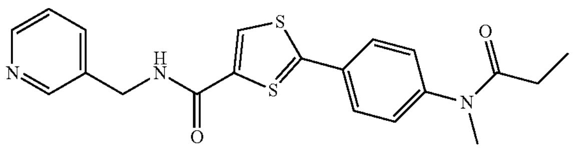 | I-241 | >30.0 |
| 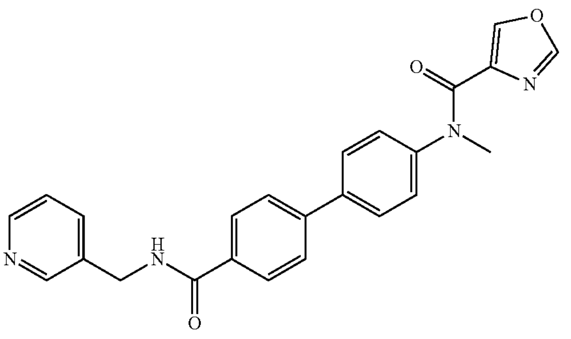 [SMILES: CN(C(=O)c1cocn1)c1ccc(-c2ccc(C(=O)NCc3cccnc3)cc2)cc1] | I-245 | 5.16 |
| 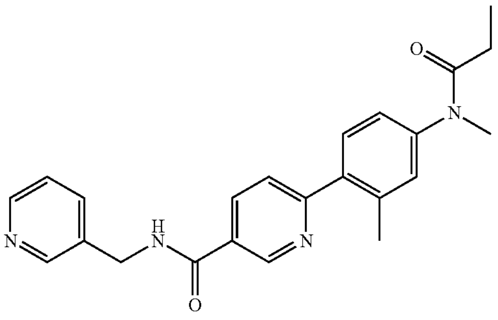 [SMILES: CCC(=O)N(C)c1ccc(-c2ccc(C(=O)NCc3cccnc3)cn2)c(C)c1] | I-246 | 12.1 |

TABLE 5-continued

| Compound structure | Compound number | AGS $IC_{50}$ (μM) |
|---|---|---|
| 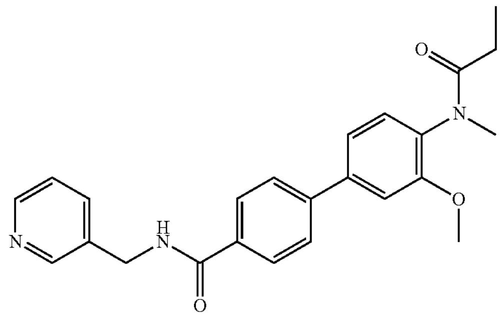 [SMILES: CCC(=O)N(C)c1ccc(-c2ccc(C(=O)NCc3cccnc3)cc2)cc1OC] | I-248 | 3.59 |
| 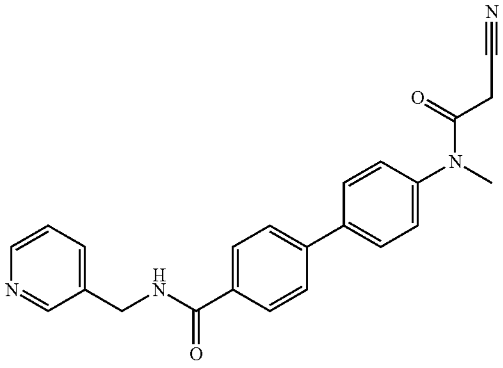 [SMILES: CN(C(=O)CC#N)c1ccc(-c2ccc(C(=O)NCc3cccnc3)cc2)cc1] | I-249 | >18.4 |
| 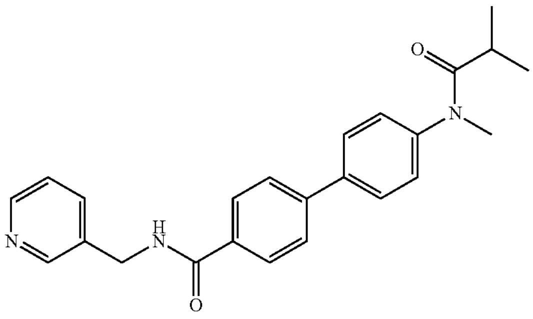 [SMILES: CC(C)C(=O)N(C)c1ccc(-c2ccc(C(=O)NCc3cccnc3)cc2)cc1] | I-250 | 1.87 |
| 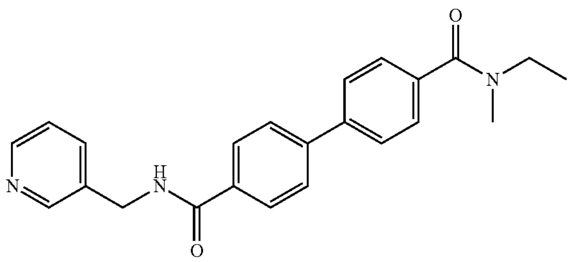 [SMILES: CCN(C)C(=O)c1ccc(-c2ccc(C(=O)NCc3cccnc3)cc2)cc1] | I-251 | 1.65 |

Example 14. Cell Viability in RS4;11 Cells and MV-4-11 Cells

Approximately 10,000 RS4;11 cells per well of a 96-well plate were treated with DMSO (no drug control) or each compound in Table 6 in an 8-point dose response for 4 days. Cell viability was measured using CellTiter Glo2. The $IC_{50}$ of each compound was determined using CDD Vault. Exemplary results are shown in Table 6.

Approximately 10,000 MV-4-11 cells per well of a 96-well plate were treated with DMSO (no drug control) or each compound in Table 6 in an 8-point dose response for 4 days. Cell viability was measured using CellTiter Glo2. The $IC_{50}$ of each compound was determined using CDD Vault. Exemplary results are shown in Table 6.

TABLE 6
| Compound Structure | Compound Number | MV-4-11 $IC_{50}$ (μM) | RS4;11 $IC_{50}$ (μM) |
|---|---|---|---|
| 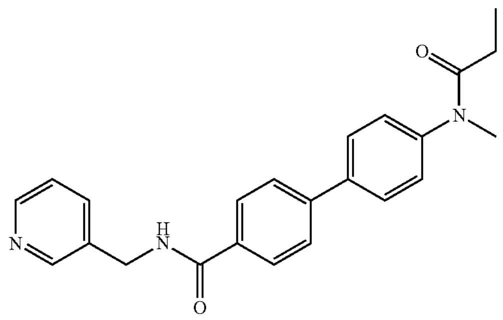 [SMILES: CCC(=O)N(C)c1ccc(-c2ccc(C(=O)NCc3cccnc3)cc2)cc1] | I-45 | 0.218 | 0.689 |
| 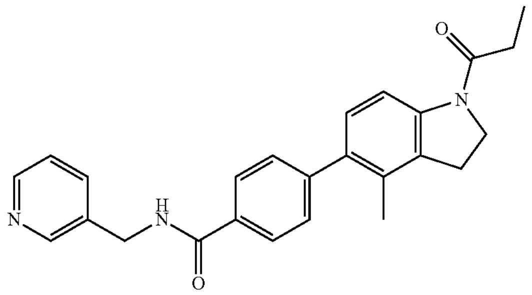 [SMILES: CCC(=O)N1CCc2c1ccc(-c1ccc(C(=O)NCc3cccnc3)cc1)c2C] | I-80 | 0.565 | 0.886 |
| 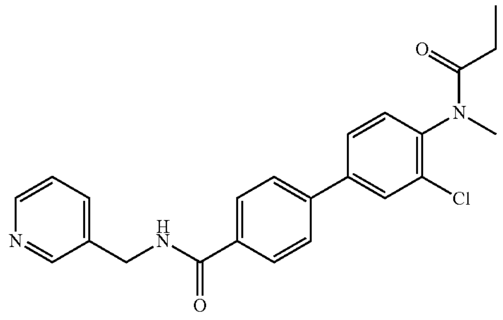 | I-225 | 0.613 | 0.237 |
| 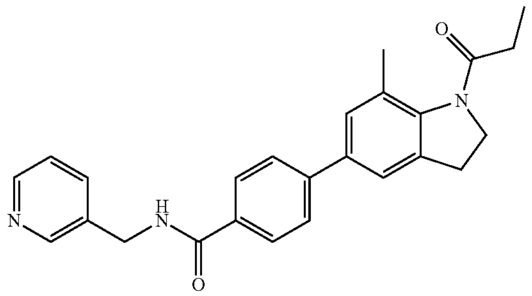 [SMILES: CCC(=O)N1CCc2cc(-c3ccc(C(=O)NCc4cccnc4)cc3)cc(C)c21] | I-17 | 0.67 | 0.27 |

TABLE 6-continued
| Compound Structure | Compound Number | MV-4-11 $IC_{50}$ (μM) | RS4;11 $IC_{50}$ (μM) |
|---|---|---|---|
| 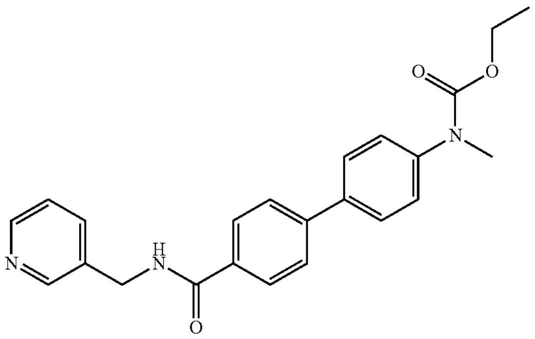 | I-231 | 0.741 | 2.92 |
| 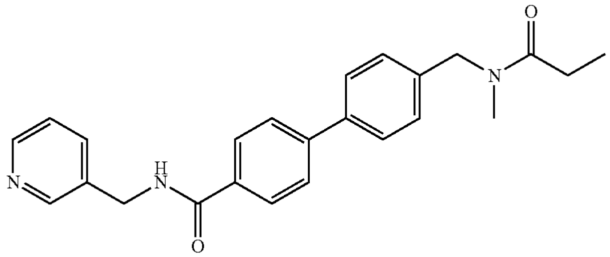 [SMILES: CCC(=O)N(C)Cc1ccc(-c2ccc(C(=O)NCc3cccnc3)cc2)cc1] | I-228 | 0.765 | 1.93 |
| 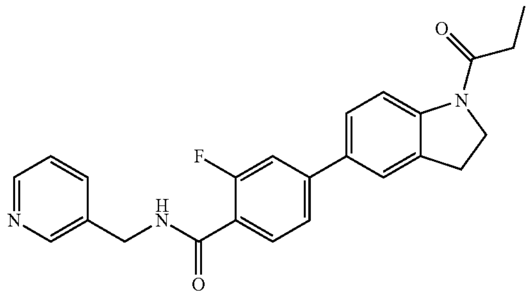 [SMILES: CCC(=O)N1CCc2cc(-c3ccc(C(=O)NCc4cccnc4)c(F)c3)ccc21] | I-98 | 0.845 | >30.0 |
| 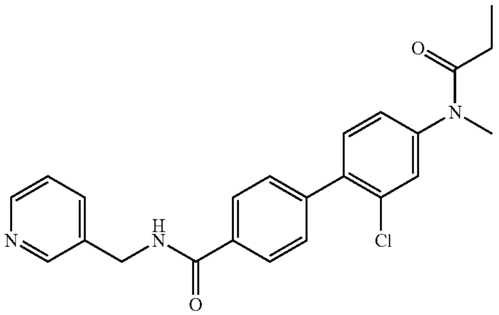 | I-224 | 1.1 | 5.32 |
| 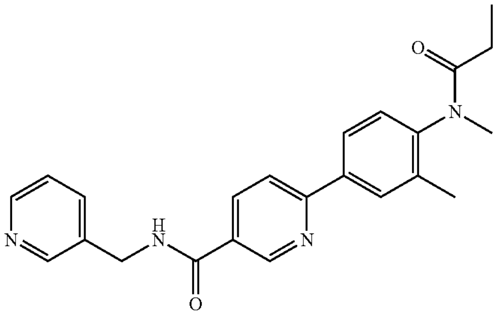 | I-232 | 1.22 | 0.231 |

TABLE 6-continued
| Compound Structure | Compound Number | MV-4-11 $IC_{50}$ (μM) | RS4;11 $IC_{50}$ (μM) |
|---|---|---|---|
| 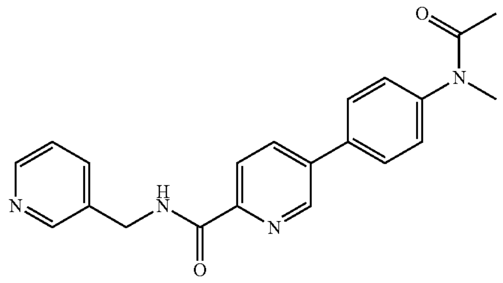 [SMILES: CC(=O)N(C)c1ccc(-c2ccc(C(=O)NCc3cccnc3)nc2)cc1] | I-202 | 1.47 | 2.55 |
| 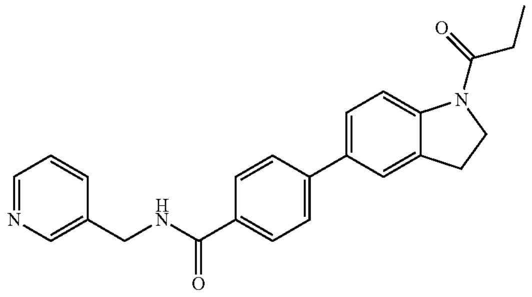 [SMILES: CCC(=O)N1CCc2cc(-c3ccc(C(=O)NCc4cccnc4)cc3)ccc21] | I-43 | 2.93 | 0.606 |
| 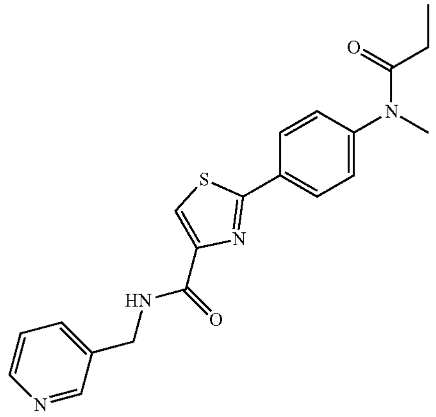 [SMILES: CCC(=O)N(C)c1ccc(-c2nc(C(=O)NCc3cccnc3)cs2)cc1] | I-241 | 3.92 | 10.5 |
| 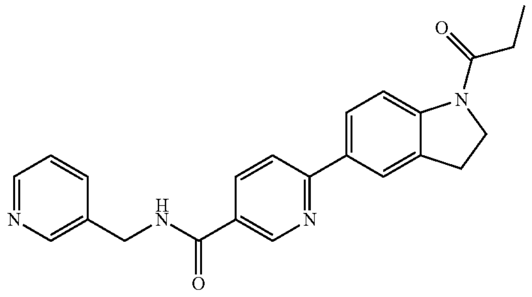 [SMILES: CCC(=O)N1CCc2cc(-c3ccc(C(=O)NCc4cccnc4)cn3)ccc21] | I-54 | 10.4 | 4.92 |

REFERENCES

1. American Cancer Society. 2017. Cancer Facts & Figures, 2017. Atlanta: American Cancer Society.
2. Stewart B W, Wild C P, editors. World cancer report 2014 Lyon: International Agency for Research on Cancer; 2014.
3. Taniguchi H, Moriya C, Igarashi H, Saitoh A, Yamamoto H, Adachi Y, Imai K. 2016. Cancer stem cells in human gastrointestinal cancer. *Cancer Sci* 107: 1556-1562.
4. Seyfried T and Huysentruyt L C. 2013. On the Origin of Cancer Metastasis. *Crit Rev Oncog.* 18(1-2): 43-73.
5. Bonnet D and Dick J E. 1997. Human acute myeloid leukemia is organized as a hierarchy that originates from a primitive hematopoietic cell. *Nat Med.* 3(7):730-7.
6. O'Brien C A, Pollett A, Gallinger S, Dick J E. 2007. A human colon cancer cell capable of initiating tumour growth in immunodeficient mice. *Nature.* 445(7123):106-10.
7. Saunders L R, Bankovich A J, Anderson W C, et al. 2015. A DLL3-targeted antibody-drug conjugate eradicates high-grade pulmonary neuroendocrine tumor-initiating cells in vivo. *Science translational medicine.* 7(302): 302ra136.
8. Chen J, Li Y, Yu T-S, et al. 2012. A restricted cell population propagates glioblastoma growth after chemotherapy. *Nature.* 488: 522-26.
9. Ben-Porath I, Thomson M W, Carey V J, Ge R, Bell G W, Regev A, Weinberg R A. 2008. An embryonic stem cell-like gene expression signature in poorly differentiated aggressive human. Nat Genet 40: 499-507.
10. Hadjimichael et al., *World J. Stem Cells,* 2015, 7(9): 1150-1184.
11. Guinney J, et al. 2015. The consensus molecular subtypes of colorectal cancer. *Nature Medicine.* 21:1350-1356.
12. The Cancer Genome Atlas Research Network. 2014. Comprehensive molecular characterization of gastric adenocarcinoma. *Nature* 513: 202-209.
13. Asciutti S, et al. 2011. Diverse Mechanisms of Wnt Activation and Effects of Pathway Inhibition on Proliferation of Human Gastric Carcinoma Cells. *Oncogene.* 24; 30(8): 956-966.
14. Laranjeira et al., *Expert Opin Drug Discov.,* 2016, 11, 1071-1080.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

(I)

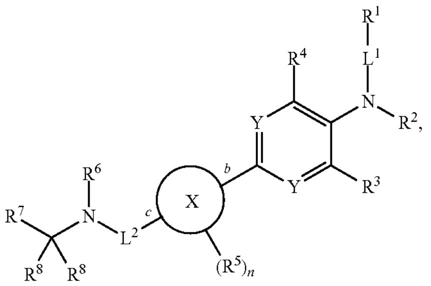

or a pharmaceutically acceptable salt, solvate, hydrate, polymorph, co-crystal, tautomer, stereoisomer, isotopically labeled derivative, or prodrug thereof, wherein:

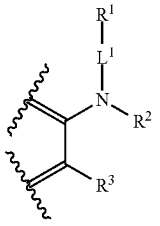 is 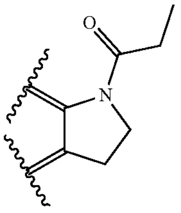 ;

each instance of $R^a$ is independently hydrogen, substituted or unsubstituted $C_{1-6}$ alkyl, an oxygen protecting group when attached to an oxygen atom, or a nitrogen protecting group when attached to a nitrogen atom;
each instance of Y is independently N or $CR^4$;
each instance of $R^4$ is independently hydrogen, halogen, substituted or unsubstituted $C_{1-6}$ alkyl, —$OR^a$, —$N(R^a)_2$, or —CN;

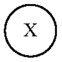

is phenyl, pyridinyl, pyridazinyl, pyrimidinyl, pyrazinyl, imidazolyl, oxazolyl, azetidinyl, —C≡C—, or

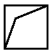 ;

bond b and bond c are meta or para to each other when

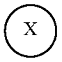

is phenyl, pyridinyl, pyridazinyl, pyrimidinyl, or pyrazinyl;
each instance of $R^5$ is independently hydrogen, halogen, substituted or unsubstituted $C_{1-6}$ alkyl, —$OR^a$, —$N(R^a)_2$, or —CN;
n is 0, 1, 2, 3, or 4, as valency permits, wherein when n is 1, 2, 3, or 4, no instance of $R^5$ is attached to a nitrogen atom;
$L^2$ is —C(=O)—;
$R^6$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, substituted or unsubstituted, 5- to 11-membered, monocyclic or bicyclic heteroaryl, or a nitrogen protecting group;
$R^7$ is substituted or unsubstituted, 3- to 7-membered, monocyclic carbocyclyl, substituted or unsubstituted, 3- to 7-membered, monocyclic heterocyclyl, unsubstituted phenyl, substituted or unsubstituted pyridinyl, substituted or unsubstituted pyrimidinyl, substituted or unsubstituted pyridazinyl, substituted or unsubstituted triazinyl, unsubstituted pyrazolyl, substituted or unsubstituted imidazolyl, substituted or unsubstituted oxazolyl, substituted or unsubstituted thiazolyl, or unsubstituted furyl; and
each instance of $R^8$ is independently hydrogen, halogen, substituted or unsubstituted $C_{1-6}$ alkyl, —$OR^a$, —$N(R^a)_2$, or —CN.

2. A pharmaceutical composition comprising:
a compound of claim 1, or a pharmaceutically acceptable salt, solvate, hydrate, polymorph, co-crystal, tautomer, stereoisomer, isotopically labeled derivative, or prodrug thereof; and optionally a pharmaceutically acceptable excipient.

3. A kit comprising:
a compound of claim 1, or a pharmaceutically acceptable salt, solvate, hydrate, polymorph, co-crystal, tautomer, stereoisomer, isotopically labeled derivative, or prodrug thereof; and
instructions for using the compound, pharmaceutically acceptable salt, solvate, hydrate, polymorph, co-crystal, tautomer, stereoisomer, isotopically labeled derivative, or prodrug.

4. The compound of claim 1, wherein each instance of Y is $CR^4$.

5. The compound of claim 1, wherein at least one Y is N.

6. The compound of claim 1, wherein $R^4$ is hydrogen, halogen, or substituted or unsubstituted $C_{1-6}$ alkyl.

7. The compound of claim 1, wherein

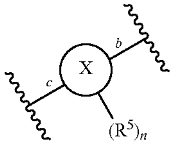 is 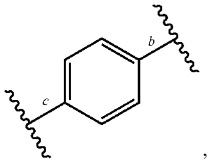 ,

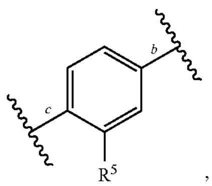 , or 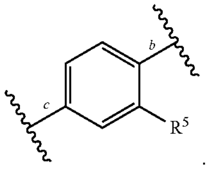 .

8. The compound of claim 1, wherein

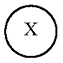

is pyridinyl, pyridazinyl, pyrimidinyl, or pyrazinyl.

9. The compound of claim 1, wherein each instance of $R^5$ is hydrogen.

10. The compound of claim 1, wherein $R^6$ is hydrogen.

11. The compound of claim 1, wherein each instance of $R^8$ is hydrogen.

12. The compound of claim 1, wherein $R^7$ is substituted or unsubstituted pyridinyl, substituted or unsubstituted pyrimidinyl, or substituted or unsubstituted pyridazinyl.

13. The compound of claim 1, wherein $R^7$ is

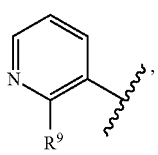 , 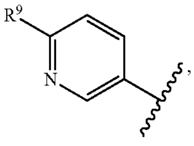 ,

-continued

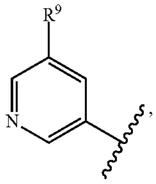

or

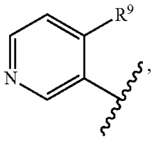

wherein $R^9$ is hydrogen, halogen, substituted or unsubstituted $C_{1-6}$ alkyl, —$OR^a$, —$N(R^a)_2$, or —CN.

14. The compound of claim 13, wherein each instance of $R^9$ is hydrogen.

15. The compound of claim 13, wherein at least one instance of $R^9$ is halogen, substituted or unsubstituted $C_{1-6}$ alkyl, or —$OR^a$.

16. The compound of claim 1, wherein the compound is of formula:

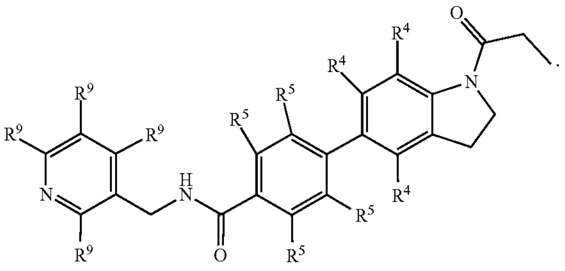

17. The compound of claim 1, wherein each instance of $R^4$ is hydrogen.

18. The compound of claim 1, wherein at least one instance of $R^5$ is halogen, substituted or unsubstituted $C_{1-6}$ alkyl, or —$OR^a$.

19. The compound of claim 1, wherein $R^7$ is unsubstituted phenyl.

20. The compound of claim 1, wherein $R^7$ is substituted or unsubstituted pyridinyl, substituted or unsubstituted pyrimidinyl, substituted or unsubstituted pyridazinyl, substituted or unsubstituted triazinyl, unsubstituted pyrazolyl, substituted or unsubstituted imidazolyl, substituted or unsubstituted oxazolyl, substituted or unsubstituted thiazolyl, or unsubstituted furyl.

21. The compound of claim 1, wherein $R^7$ is substituted or unsubstituted 3-pyridinyl.

22. The compound of claim 1, wherein $R^7$ is unsubstituted 3-pyridinyl.

23. The compound of claim 1, wherein the compound is of formula:

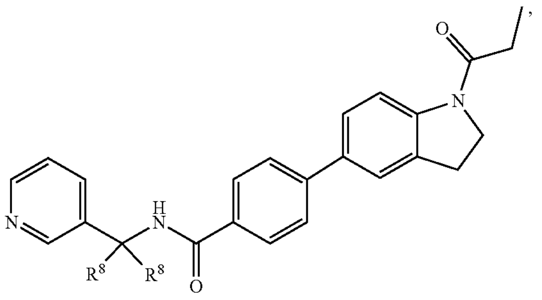

-continued

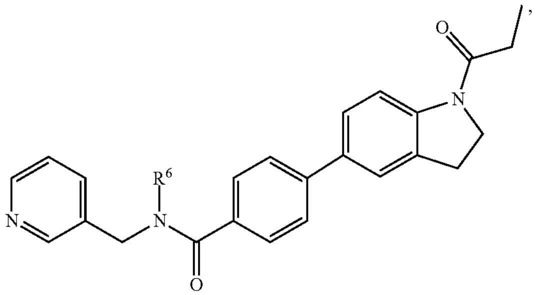

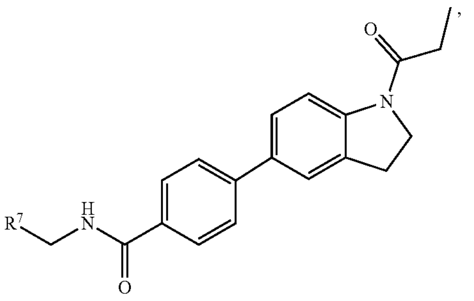

or

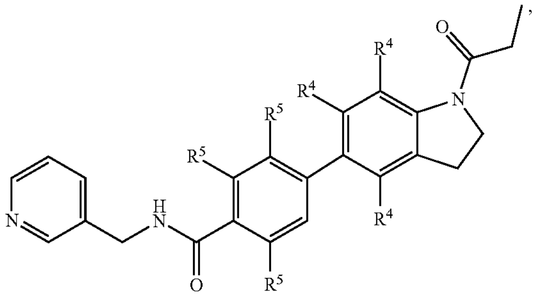

or a pharmaceutically acceptable salt, solvate, hydrate, polymorph, co-crystal, tautomer, stereoisomer, or isotopically labeled derivative thereof.

24. The compound of claim 1, wherein the compound is of formula:

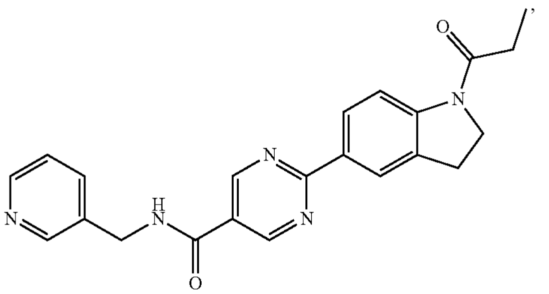

-continued
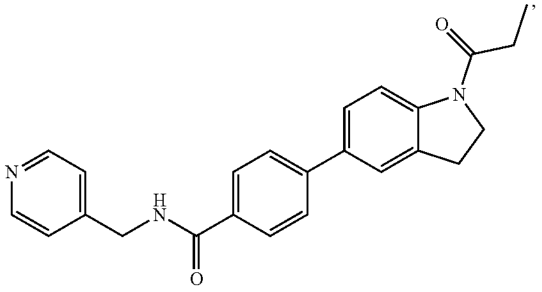
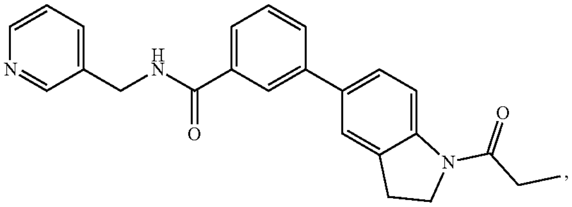
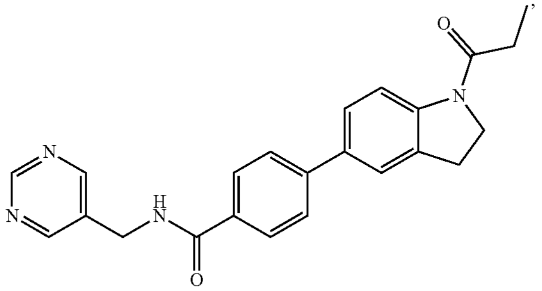
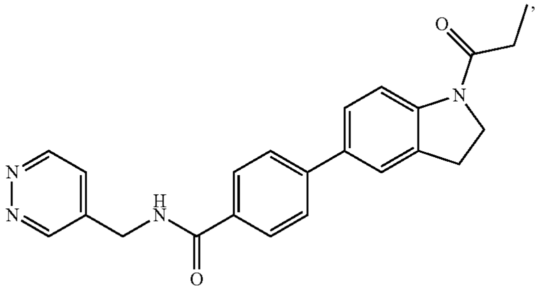
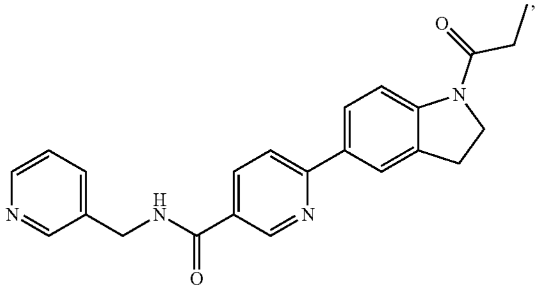
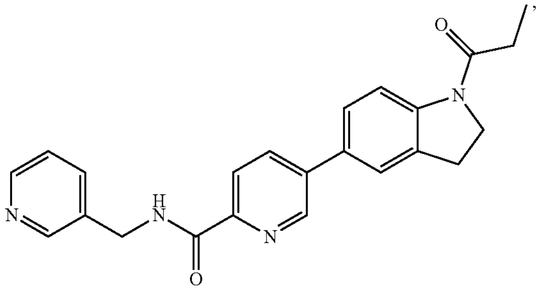
-continued
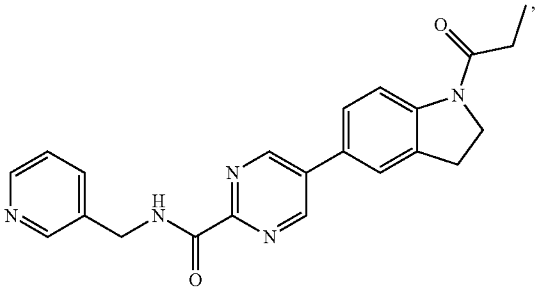
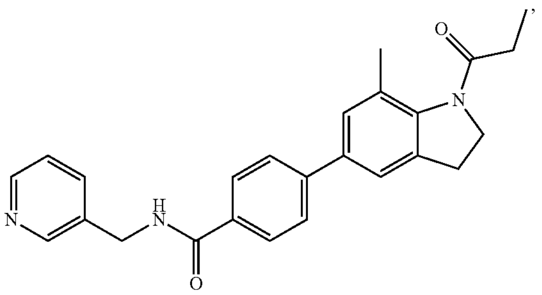
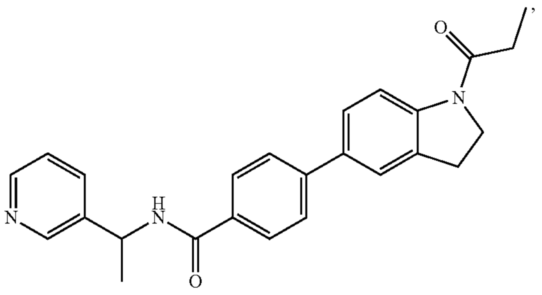
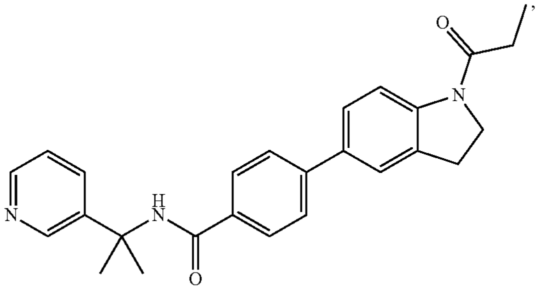
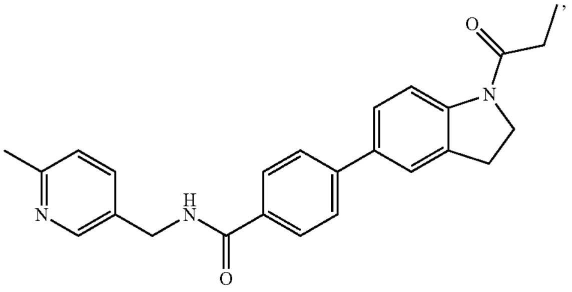

-continued
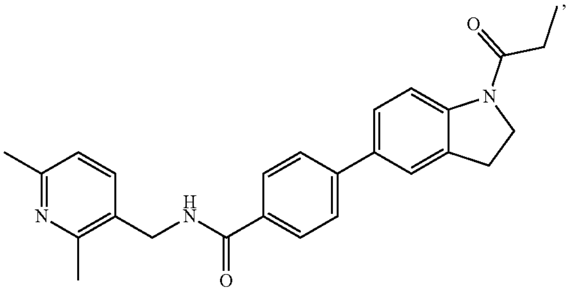
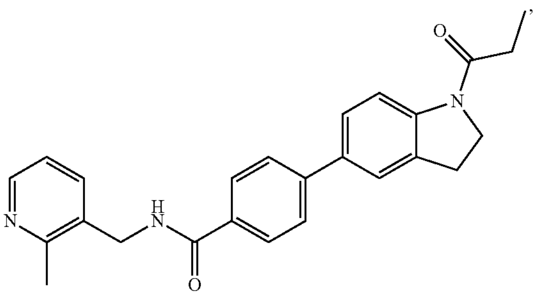
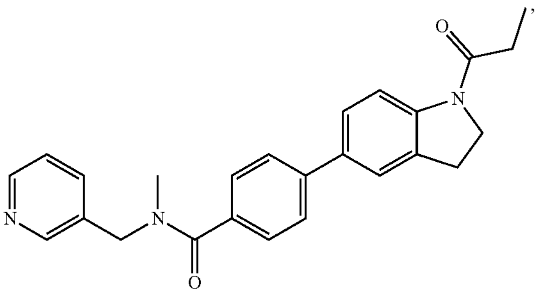
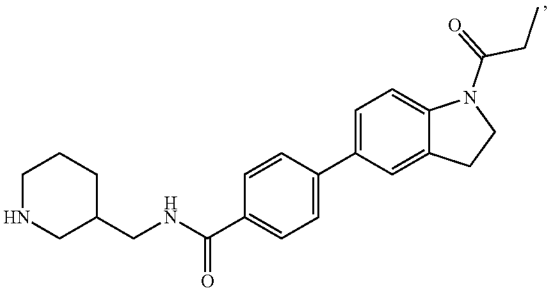
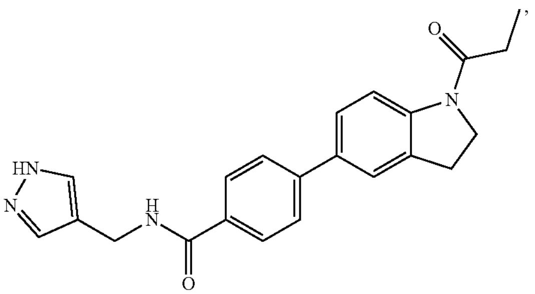
-continued
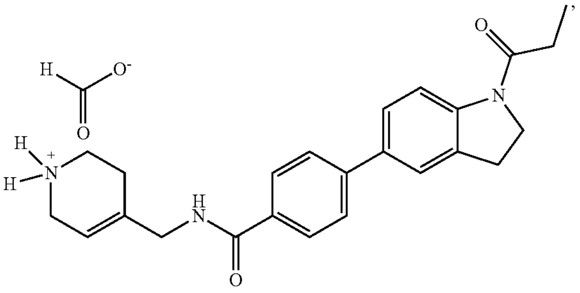
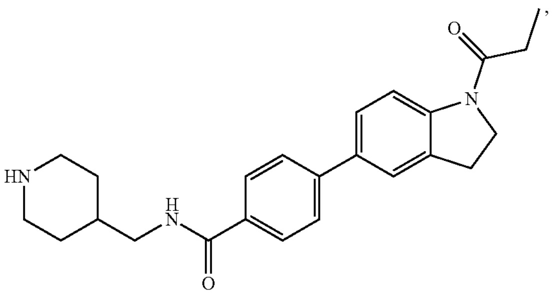
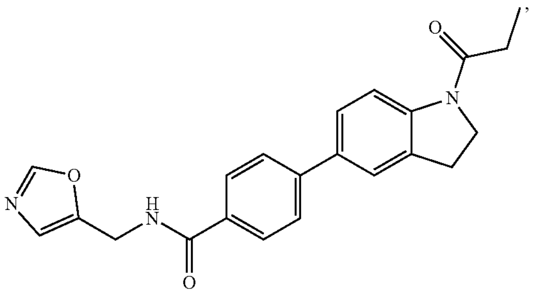
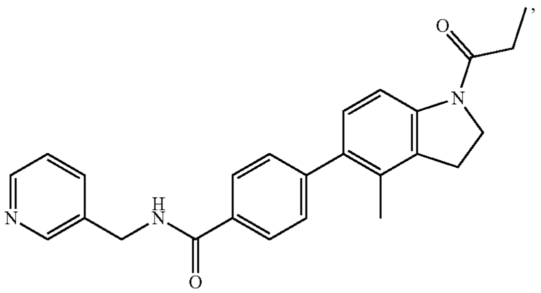
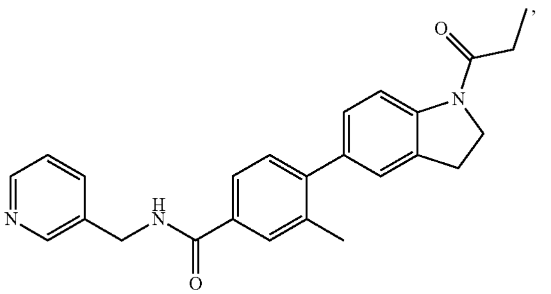

-continued
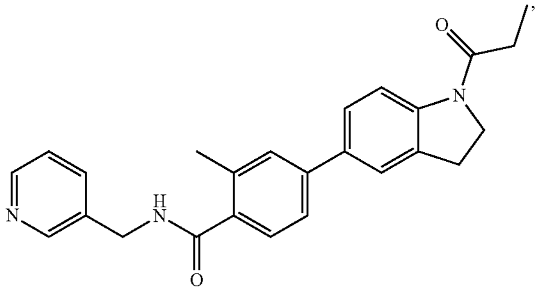
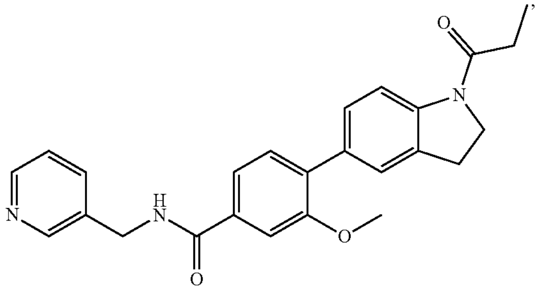
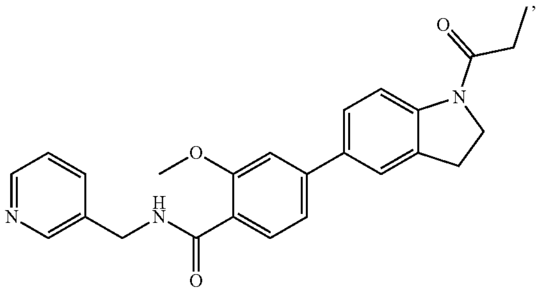
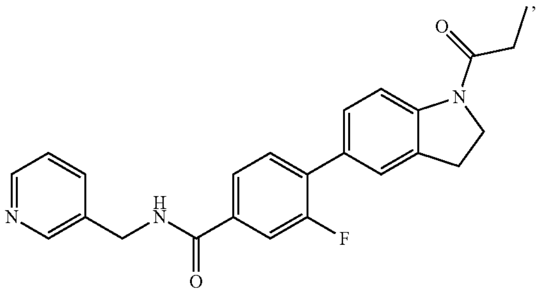
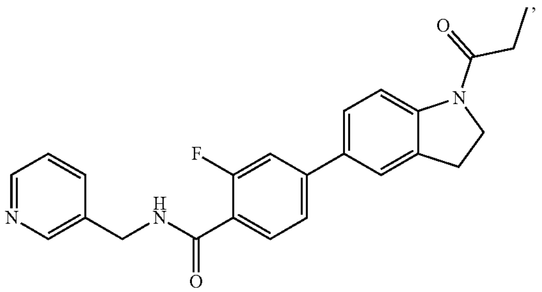
-continued
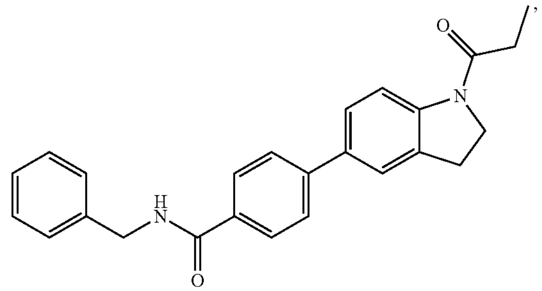
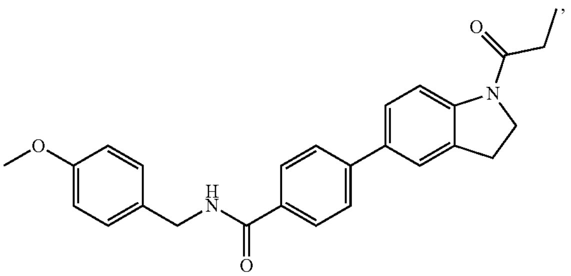
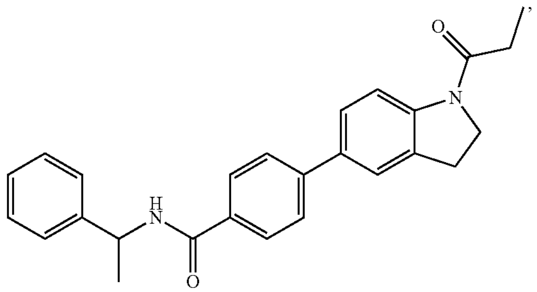 [SMILES: CCC(=O)N1CCc2cc(-c3ccc(C(=O)NC(C)c4ccccc4)cc3)ccc21]
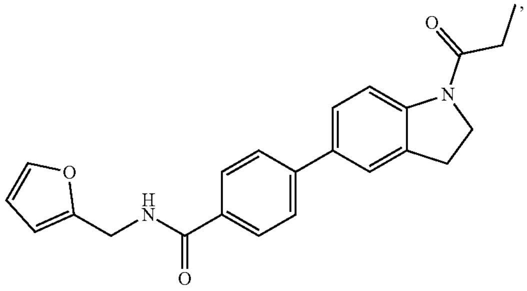
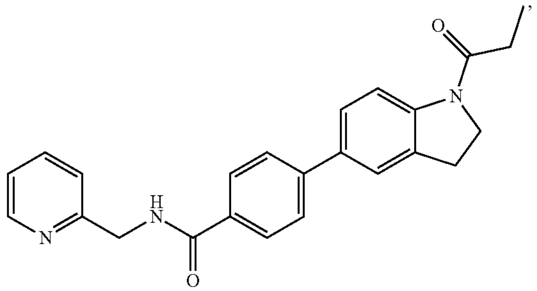

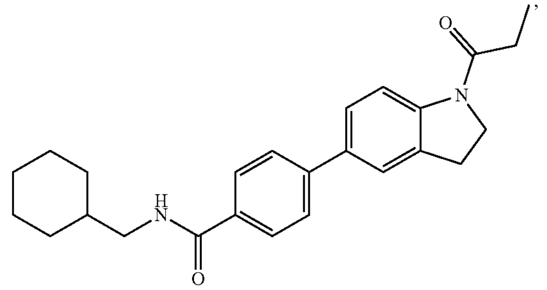
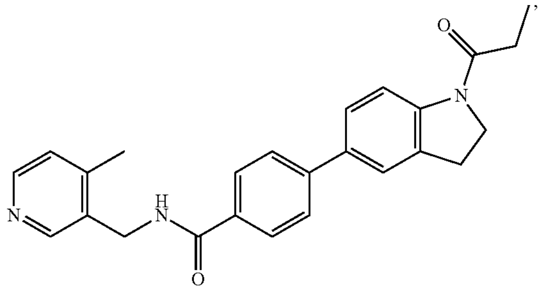
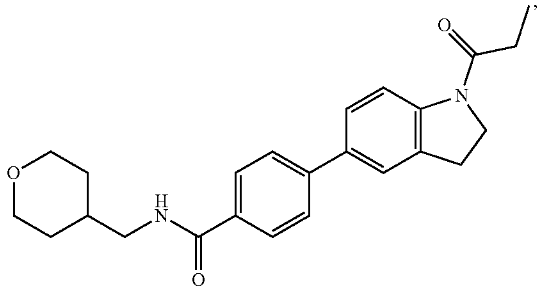
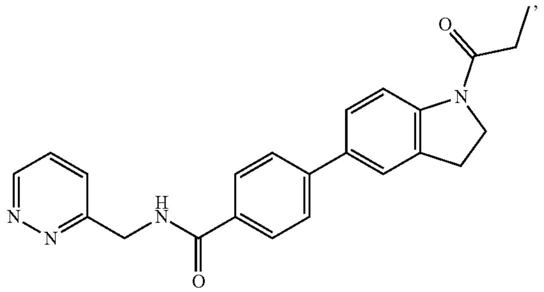
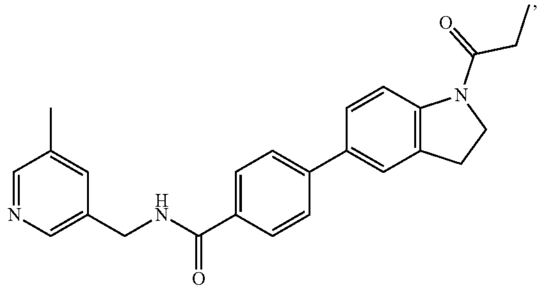
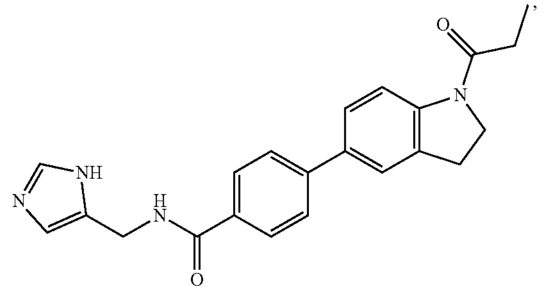
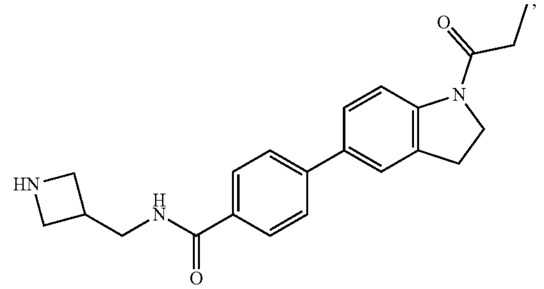
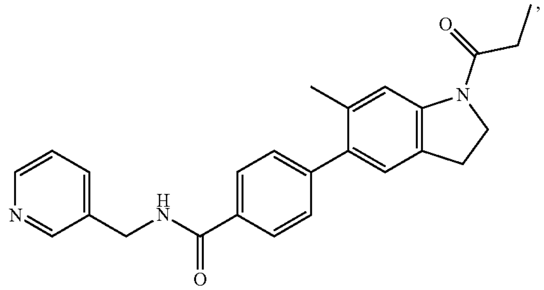
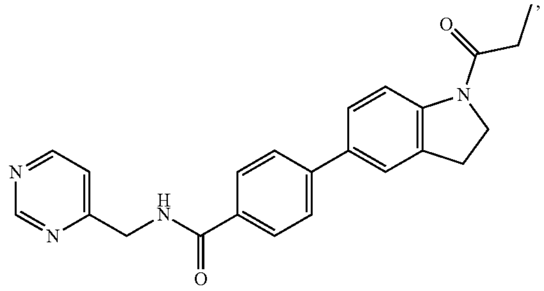
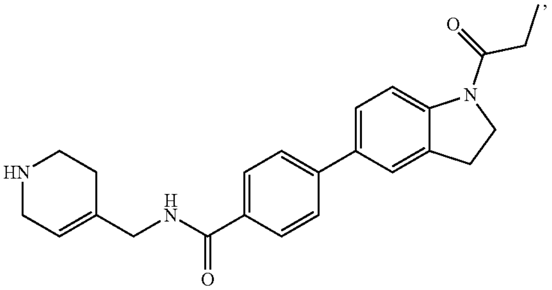

-continued
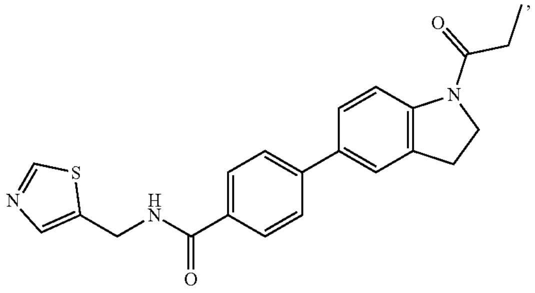
,
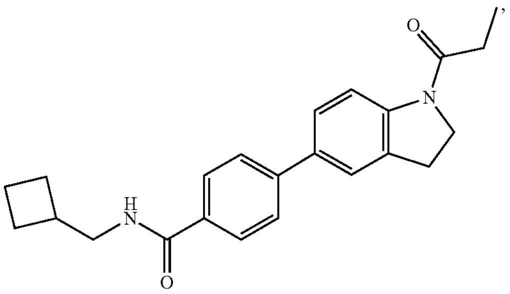
,
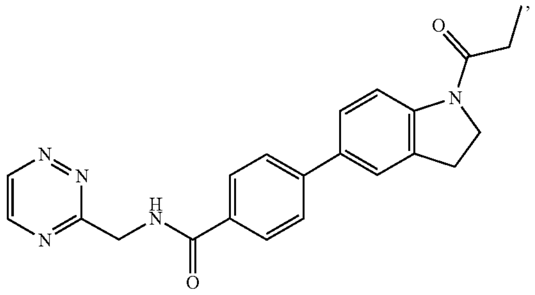
,
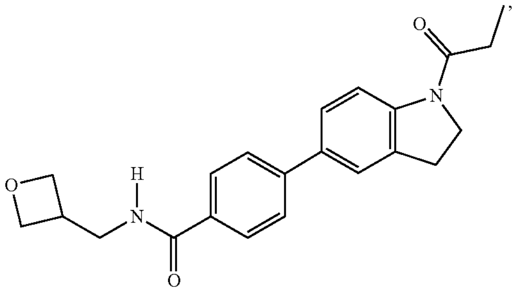
,
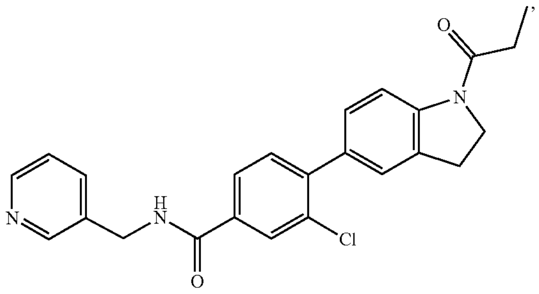
,
-continued
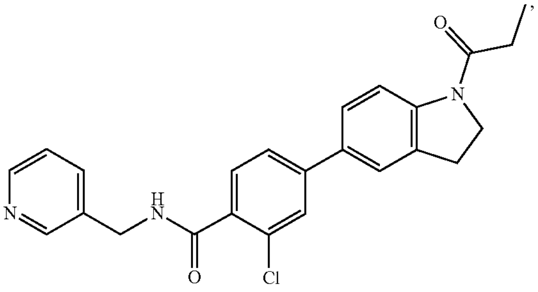
,
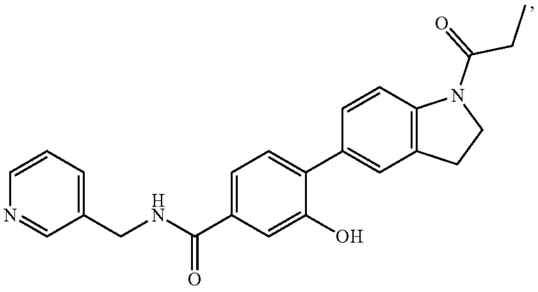
,
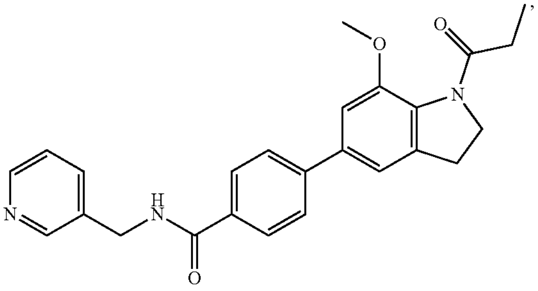
,
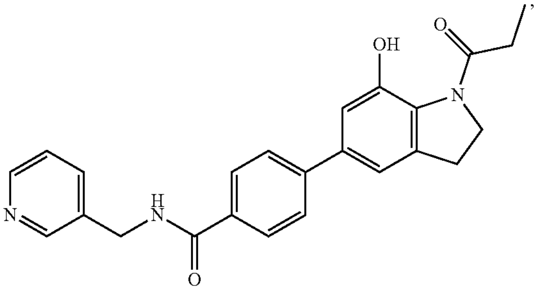
,
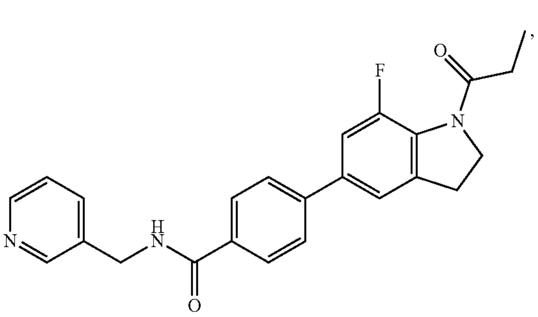
, -continued
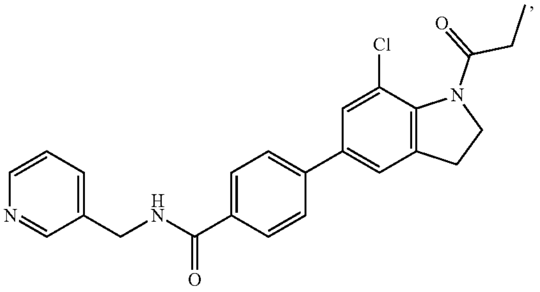
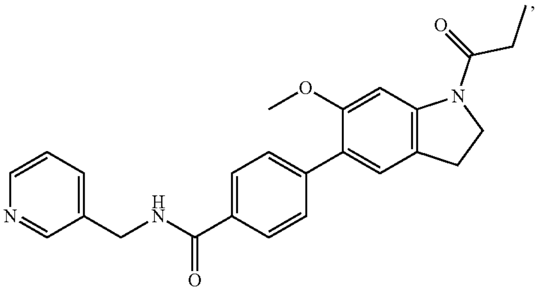
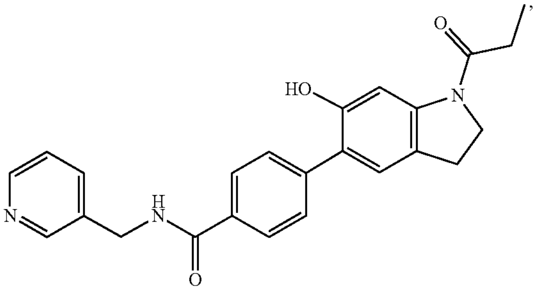
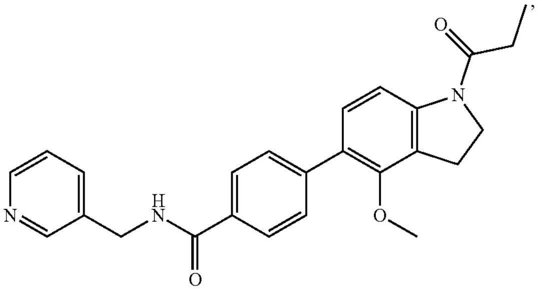
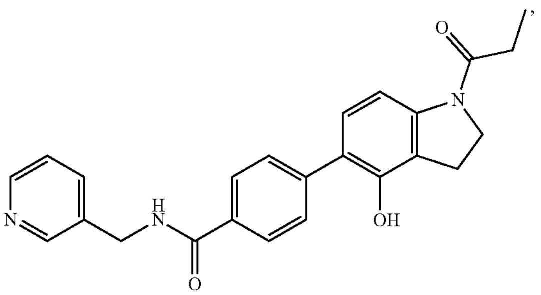
-continued
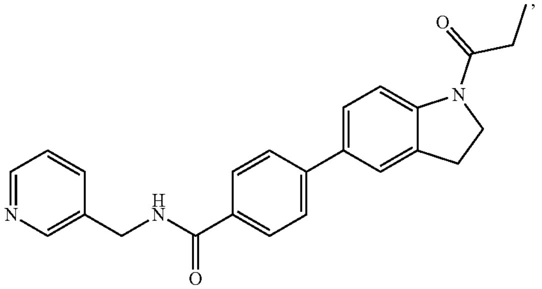
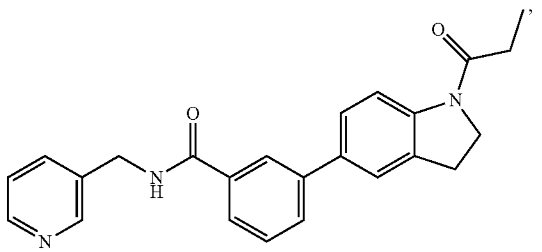
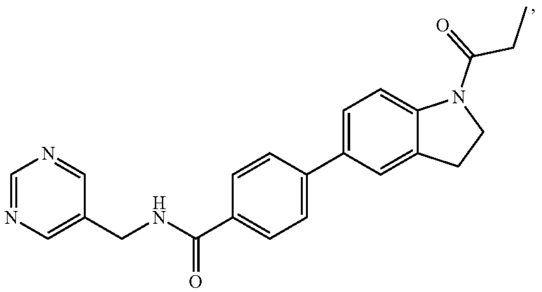
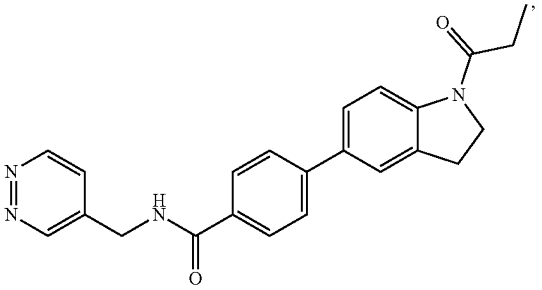
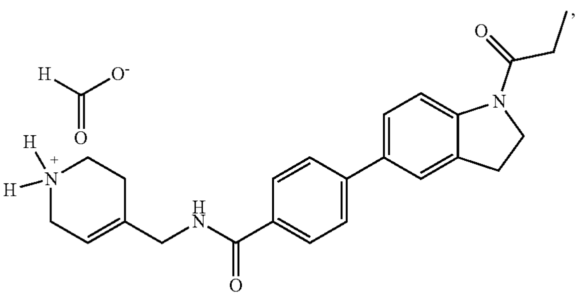

-continued
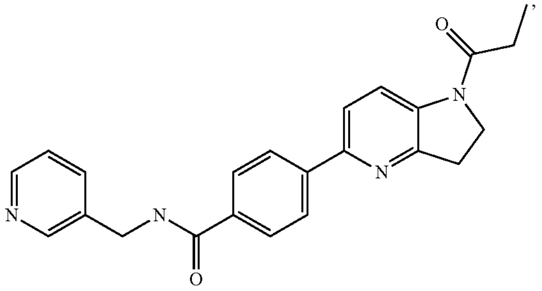
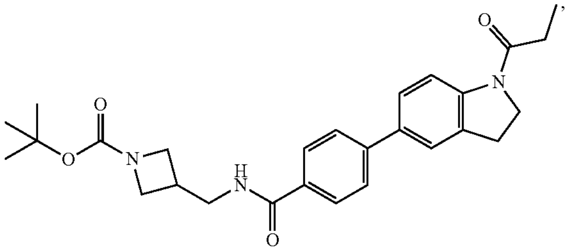
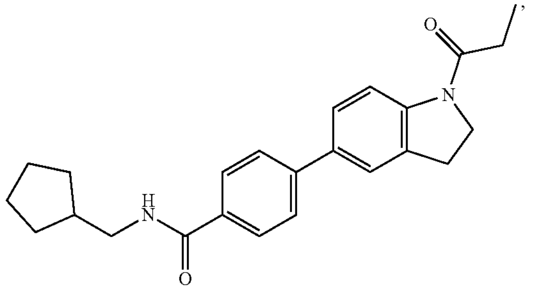
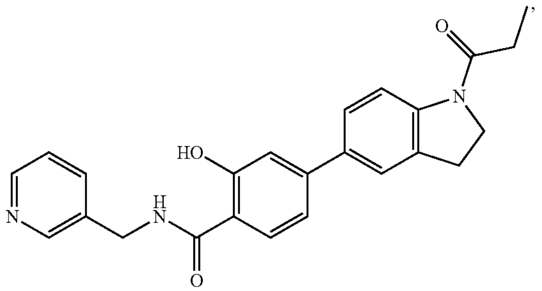
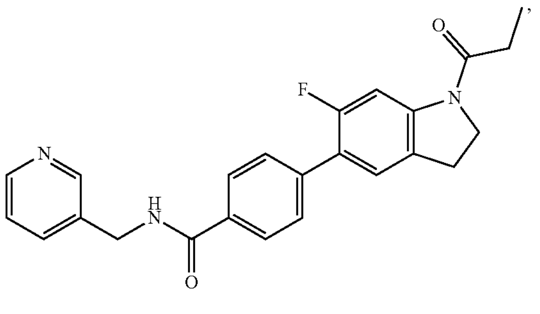
-continued
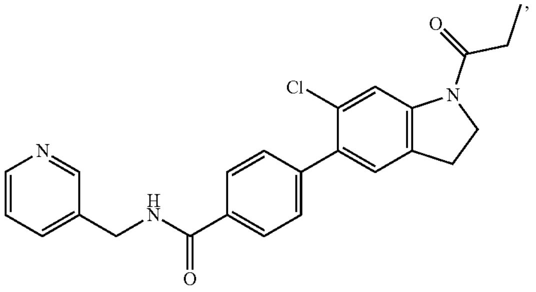
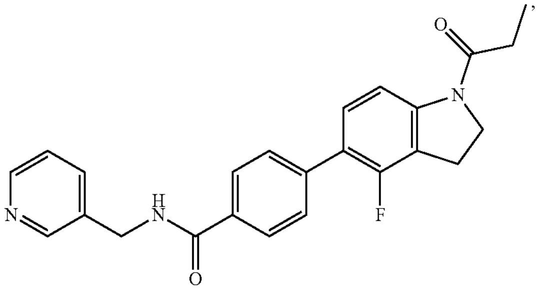
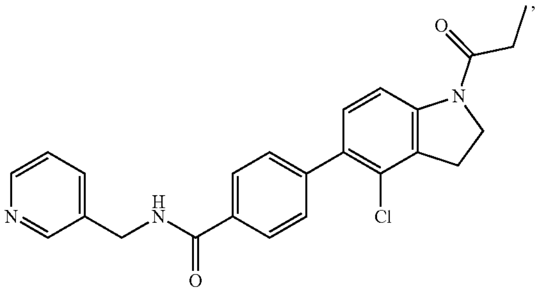
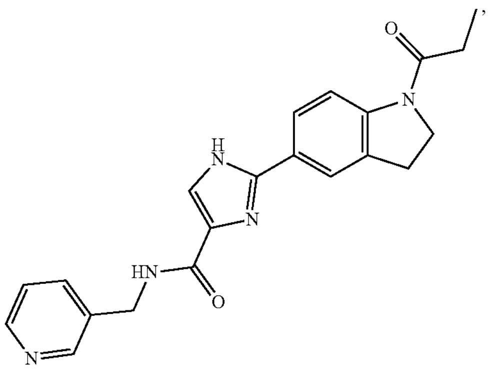
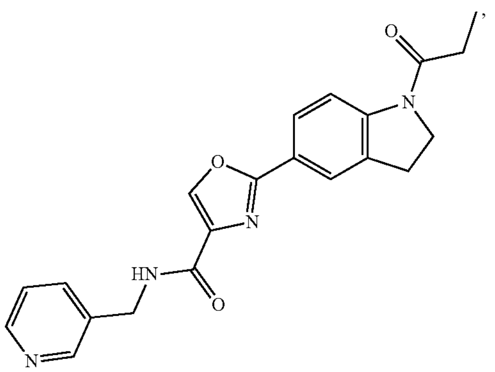

-continued
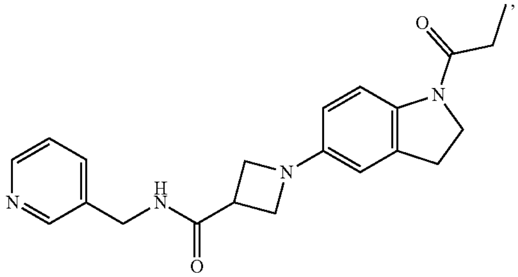
,
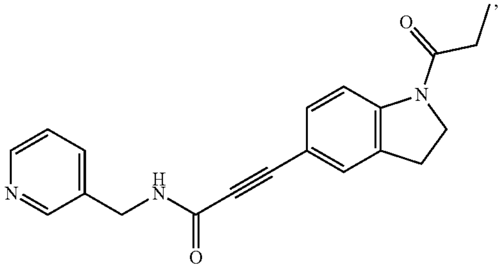
,
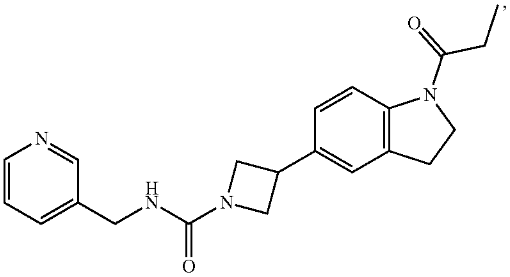
, or
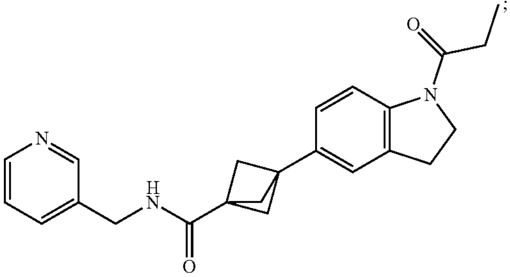
;
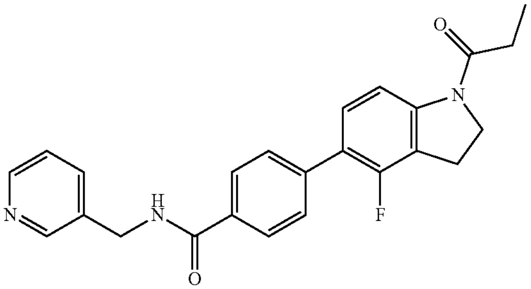
,
-continued
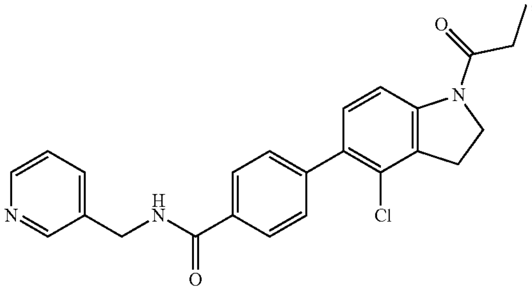
,
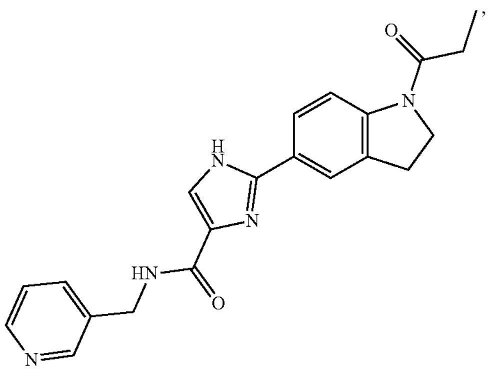
,
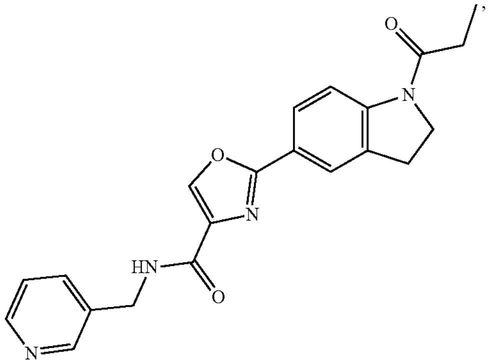
,
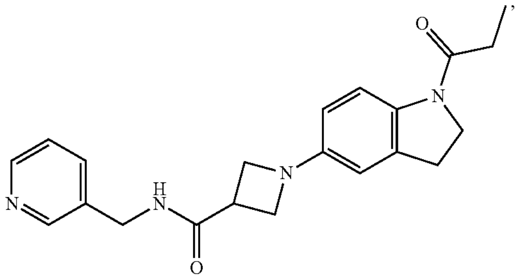
,
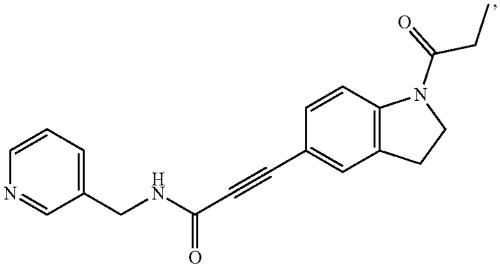
, -continued
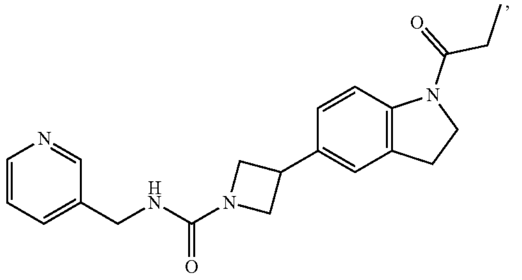
, or
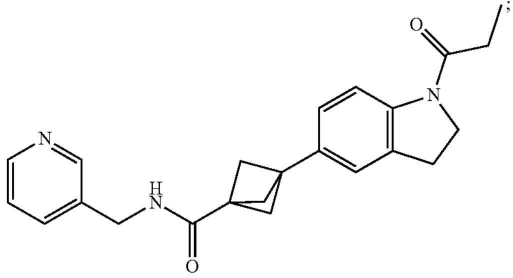
;
or a pharmaceutically acceptable salt, solvate, hydrate, polymorph, co-crystal, tautomer, stereoisomer, or isotopically labeled derivative thereof.
25. A pharmaceutically acceptable salt of the compound of claim 1.
* * * * *